(12) United States Patent
Hopkins et al.

(10) Patent No.: US 10,280,169 B2
(45) Date of Patent: May 7, 2019

(54) BIARYL BRUTON'S TYROSINE KINASE INHIBITORS

(71) Applicant: BIOGEN MA INC., Cambridge, MA (US)

(72) Inventors: Brian T. Hopkins, Newton, MA (US); Bin Ma, Arlington, MA (US); Timothy Raymond Chan, Newton, MA (US); Gnanasambandam Kumaravel, Westford, MA (US); Hua Miao, Newton, MA (US); Andrea Bertolotti-Ciarlet, Cambridge, MA (US); Kevin Otipoby, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 121 days.

(21) Appl. No.: 15/103,756

(22) PCT Filed: Dec. 11, 2014

(86) PCT No.: PCT/US2014/069839
§ 371 (c)(1),
(2) Date: Jun. 10, 2016

(87) PCT Pub. No.: WO2015/089327
PCT Pub. Date: Jun. 18, 2015

(65) Prior Publication Data
US 2016/0318935 A1     Nov. 3, 2016

Related U.S. Application Data

(60) Provisional application No. 61/914,891, filed on Dec. 11, 2013.

(51) Int. Cl.
| | | |
|---|---|---|
| *C07D 487/04* | (2006.01) |
| *C07D 473/00* | (2006.01) |
| *A61K 31/519* | (2006.01) |
| *A61K 31/522* | (2006.01) |
| *C07D 471/04* | (2006.01) |
| *C07D 513/04* | (2006.01) |
| *C07D 519/00* | (2006.01) |
| *G01N 33/573* | (2006.01) |

(52) U.S. Cl.
CPC ......... *C07D 487/04* (2013.01); *C07D 471/04* (2013.01); *C07D 473/00* (2013.01); *C07D 513/04* (2013.01); *C07D 519/00* (2013.01); *G01N 33/573* (2013.01); *G01N 2333/9121* (2013.01)

(58) Field of Classification Search
CPC .. C07D 487/04; C07D 473/00; A61K 31/519; A61K 31/522
USPC .................... 544/277, 280; 514/263.1, 265.1
See application file for complete search history.

(56) References Cited

U.S. PATENT DOCUMENTS

2015/0284394 A1* 10/2015 Bhagirath ............ C07D 487/04
514/210.18

FOREIGN PATENT DOCUMENTS

WO   WO 2007084667 A2 *  7/2007 ........... C07D 471/04
WO   WO-2009/045175 A1   4/2009

OTHER PUBLICATIONS

Meanwell, N.A. et al., Journal of Medicinal Chemistry vol. 54, pp. 2529-2591. Published 2011 (Year: 2011).*
Patani et al (Chem Rev vol. 96 pp. 3147-3176). Published 1996. (Year: 1996).*

* cited by examiner

*Primary Examiner* — Theodore R. West
*Assistant Examiner* — George W Kosturko
(74) *Attorney, Agent, or Firm* — McCarter & English, LLP; Steven G. Davis; Xin Zhang

(57) ABSTRACT

The present invention provides compounds and compositions thereof which are useful as inhibitors of Bruton's tyrosine kinase and which exhibit desirable characteristics for the same.

16 Claims, 6 Drawing Sheets

BIARYL BRUTON'S TYROSINE KINASE INHIBITORS

CROSS REFERENCE TO RELATED APPLICATIONS

The present invention is a 35 U.S.C. § 371 national stage filing of International Application No. PCT/US2014/069839, filed Dec. 11, 2014, which claims priority to U.S. provisional patent application No. 61/914,891, filed Dec. 11, 2013. The entire contents of each of the foregoing applications are hereby incorporated by reference.

BACKGROUND OF THE INVENTION

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk. The present invention fulfills these and other needs.

SUMMARY OF THE INVENTION

In certain embodiments, the present invention provides a compound of formula I:

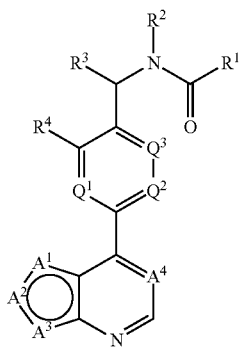

or a pharmaceutically acceptable salt thereof, wherein each of $R^1$, $R^2$, $R^3$, $R^4$, $Q^1$, $Q^2$, $Q^3$, $A^1$, $A^2$, $A^3$, and $A^4$ is as defined and described in classes and subclasses herein.

In some embodiments, the present invention also provides methods of using compounds of formula I. In some embodiments, the present invention provides methods of detecting Bruton's tyrosine kinase (Btk) activity in whole blood.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

DETAILED DESCRIPTION OF CERTAIN EMBODIMENTS

Figure 1:
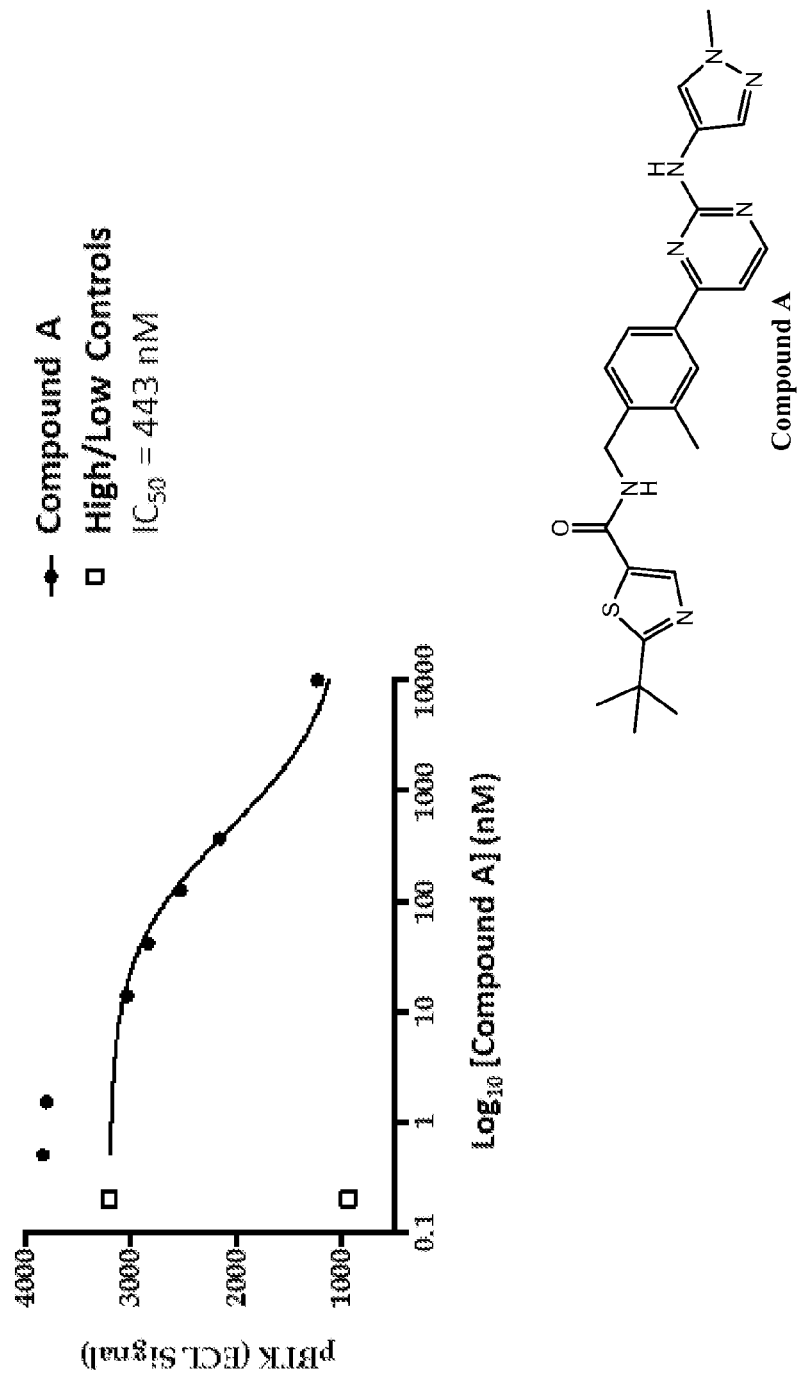
FIG. 1 is a graph of phosphorylated BTK in murine whole blood contacted with various concentrations of test agent Compound A (structure depicted).

In some embodiments, the present invention provides a compound of formula I:

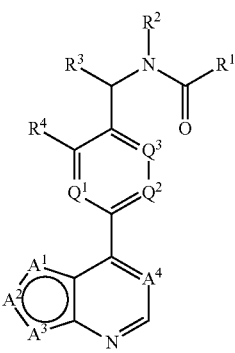

or a pharmaceutically acceptable salt thereof, wherein:
one of $A^1$ and $A^3$ is N—$R^5$, O, or S, and:
  i) $A^2$ is N, O, or S, and the other of $A^1$ and $A^3$ is CH; or
  ii) $A^2$ is C—$R^6$, and the other of $A^1$ and $A^3$ is selected from C—$R^5$ and N;
$A^4$ is selected from C—H and N;
$Q^1$ is selected from C—$R^7$ and N;
$Q^2$ is selected from C—$R^7$ and N;
$Q^3$ is selected from C—$R^7$ and N;
  wherein at most one of $Q^1$, $Q^2$, and $Q^3$ is N;
$R^1$ is —N(R)$_2$ or an optionally substituted group selected from phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and 8- to 10-membered bicyclic aryl;

$R^2$ is H or optionally substituted $C_{1-6}$ aliphatic, or $R^1$ and $R^2$, together with their intervening atoms, form an optionally substituted ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 7- to 10-membered bicyclic heteroaryl having 1-4 heteroatoms selected from oxygen, nitrogen;

$R^3$ is selected from H, halogen, —C(O)N(R)$_2$, —C(O)OR, —C(O)R, and optionally substituted $C_{1-6}$ aliphatic;

$R^4$ is selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, and optionally substituted $C_{1-6}$ aliphatic;

or $R^3$ and $R^4$, together with their intervening atoms, form an optionally substituted fused Ring A, wherein fused Ring A is selected from fused 5- to 7-membered monocyclic carbocycle and fused 5- to 7-membered heterocycle having 1-2 heteroatoms selected from oxygen, nitrogen, or sulfur;

each $R^5$ is selected from H and $C_{1-6}$ aliphatic;

$R^6$ is selected from H or an optionally substituted group selected from phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur; or $R^5$ and $R^6$, taken together with their intervening atoms, form an optionally substituted fused 5- to 7-membered monocyclic carbocycle or an optionally substituted fused 5- to 7-membered monocyclic heterocycle having 1-2 heteroatoms selected from oxygen, nitrogen, or sulfur;

each $R^7$ is independently selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or optionally substituted $C_{1-6}$ aliphatic; and each R is independently hydrogen or an optionally substituted group selected from $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur; or two R groups on the same nitrogen are taken together with their intervening atoms to form an optionally substituted ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

wherein the compound is other than:

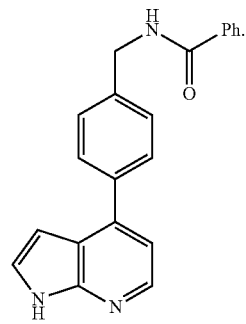 [SMILES: O=C(NCc1ccc(-c2ccnc3[nH]ccc23)cc1)c1ccccc1]

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "fused 5- to 7-membered monocyclic carbocycle" refers to a monocyclic hydrocarbon that shares two or three atoms with the core structure. By way of illustration, Compound 154 possesses a 5-membered fused monocyclic carbocycle, as indicated by the dotted lines below:

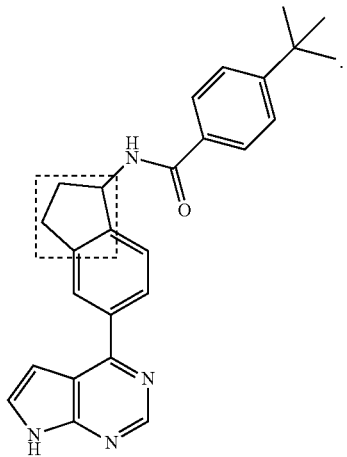

I-154

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "fused 5- to 7-membered monocyclic heterocycle" refers to a monocyclic heterocyclic moiety that shares two or three atoms with the core structure.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SRO$, $-(CH_2)_{0-4}OC(O)NR^\circ_2$; $-C(O)N(OR)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenylyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitobenzyl carbamate, p-chlorobenzyl carbamate, diphenylmethyl carbamate, 2-methylsulfonylethyl carbamate, 2-(p-toluenesulfonyl) ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl) benzyl carbamate, m-nitrophenyl carbamate, 3,5-dimethoxybenzyl carbamate, o-nitrobenzyl carbamate, phenyl(o-nitrophenyl)methyl carbamate, N'-p-toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trichloroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzylsulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol " ∼∼∼ ", except when used as a bond to depict unknown or mixed stereochemistry, denotes the point of attachment of a chemical moiety to the remainder of a molecule or chemical formula.

The articles "a" and "an" are used herein to refer to one or to more than one (i.e., to at least one) of the grammatical object of the article. By way of example, "an element" means one element or more than one element.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" sample or subject is one that is sufficiently similar to a particular sample or subject of interest to permit a relevant comparison. In some embodiments, information about a reference sample is obtained simultaneously with information about a particular sample. In some embodiments, information about a reference sample is historical. In some embodiments, information about a reference sample is stored, for example in a computer-readable medium. In some embodiments, comparison of a particular sample of interest with a reference sample establishes identity with, similarity to, or difference of the particular sample of interest relative to the reference.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood, e.g., whole blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from a subject. In some embodiments, obtained cells are or include cells from a subject from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood (e.g., whole blood), lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

In general, a "small molecule" is a molecule that is less than about 5 kilodaltons (kD) in size. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, small molecules are non-polymeric.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

I. Compounds

As described above, in certain embodiments provided compounds are of formula I:

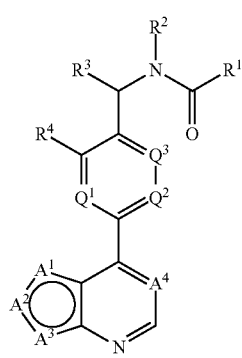

or a pharmaceutically acceptable salt thereof, wherein each of $R^1$, $R^2$, $R^3$, $R^4$, $Q^1$, $Q^2$, $Q^3$, $A^1$, $A^2$, $A^3$, and $A^4$ is as defined above and described in classes and subclasses herein, both singly and in combination.

As used herein, unless otherwise stated, references to formula I also include all subgenera of formula I defined and described herein (e.g., formulae I', II-a, II-b, II-c, II-d, III-a, III-b, III-c, III-d, IVa, IV-b, IV-c, IV-d, V-a, V-b, V-c, V-d, VI-a, VI-b, VI-c, VI-d, VII-a, VII-b, VII-c, VII-d, VII-e, and VII-f).

In some embodiments, one of $A^1$ and $A^3$ is N—$R^5$, O, or S, $A^2$ is N, O, or S, and the other of $A^1$ and $A^3$ is CH. In some embodiments, one of $A^1$ and $A^3$ is N—$R^5$, O, or S, $A^2$ is N, and the other of $A^1$ and $A^3$ is CH. In some embodiments, one of $A^1$ and $A^3$ is N—$R^5$, $A^2$ is N, and the other of $A^1$ and $A^3$ is CH.

In some embodiments, one of $A^1$ and $A^3$ is N—$R^5$, O, or S, $A^2$ is C—$R^6$, and the other of $A^1$ and $A^3$ is selected from C—$R^5$ and N. In some embodiments, one of $A^1$ and $A^3$ is N—$R^5$, $A^2$ is C—$R^6$, and the other of $A^1$ and $A^3$ is selected from C—$R^5$ and N.

In some embodiments, $A^4$ is C—H. In other embodiments, $A^4$ is N.

In some embodiments, $Q^1$, $Q^2$, and $Q^3$ are C—$R^7$. In some embodiments, $Q^1$ is N, and $Q^2$ and $Q^3$ are C—$R^7$. In some embodiments, $Q^2$ is N, and $Q^1$ and $Q^3$ are C—$R^7$. In some embodiments, $Q^3$ is N, and $Q^1$ and $Q^2$ are C—$R^7$.

In certain embodiments, $R^1$ is an optionally substituted group selected from 5- to 6-membered heteroaryl having 1-4 heteroatoms selected from oxygen, nitrogen, or sulfur, phenyl, or 3- to 7-membered saturated or partially unsaturated monocyclic heterocyclyl having 1-2 heteroatoms selected from oxygen, nitrogen, or sulfur.

In some embodiments, $R^1$ is optionally substituted phenyl. In some embodiments, $R^1$ is phenyl substituted with halogen, —$CF_3$, t-butyl, or a combination thereof.

In some embodiments, $R^1$ is optionally substituted 5-membered heteroaryl having 1-4 heteroatoms selected from oxygen, nitrogen, or sulfur. In some embodiments, $R^1$ is an optionally substituted group selected from thiazolyl, thiophenyl, thiadiazolyl, or imidazolyl. In some embodiments, $R^1$ is thiazolyl substituted with t-butyl, i-propyl, methyl, or —$CF_3$.

In some embodiments, $R^1$ is optionally substituted 6-membered heteroaryl having 1-4 heteroatoms selected from oxygen, nitrogen, or sulfur. In some embodiments, $R^1$ is optionally substituted pyridyl. In some embodiments, $R^1$ is pyridyl substituted with t-butyl or —$CF_3$.

In other embodiments, $R^1$ is optionally substituted 3- to 7-membered saturated or partially unsaturated monocyclic heterocyclyl having 1-2 heteroatoms selected from oxygen, nitrogen, or sulfur. In some embodiments, $R^1$ is an optionally substituted group selected from piperidinyl or azetidinyl. In some embodiments, $R^1$ is piperidinyl substituted with t-butyl or —$CF_3$. In some embodiments, $R^1$ is azetidinyl substituted with —$OC_{1-6}$ alkyl.

In some embodiments, $R^1$ is optionally substituted 7- to 10-membered saturated or partially unsaturated bicyclic heterocyclyl having 1-4 heteroatoms selected from oxygen, nitrogen, or sulfur. In some embodiments, $R^1$ is optionally substituted 7- to 10-membered bicyclic heteroaryl having 1-4 heteroatoms selected from oxygen, nitrogen, or sulfur. In some embodiments, $R^1$ is optionally substituted 3- to 7-membered saturated or partially unsaturated monocyclic carbocyclyl.

In some embodiments, $R^1$ is optionally substituted with one or more groups selected from halogen, $C_{3-7}$ carbocyclic, $C_{1-6}$ aliphatic optionally substituted with halogen, or —OR.

In some embodiments, $R^1$ is selected from the following:

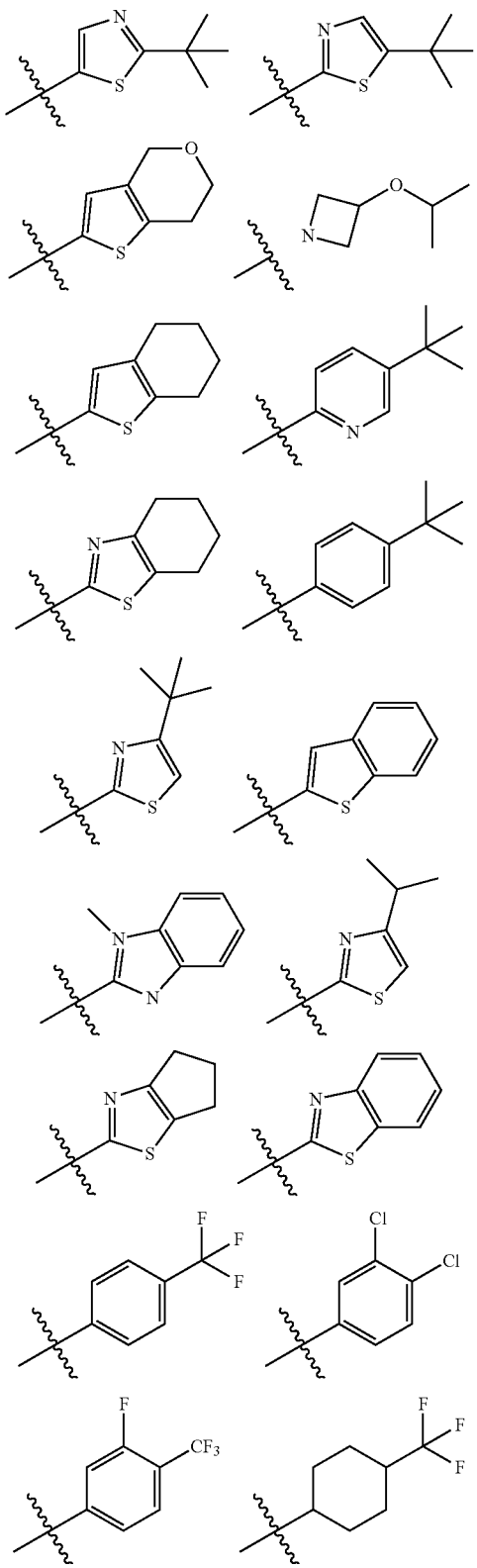

15

-continued

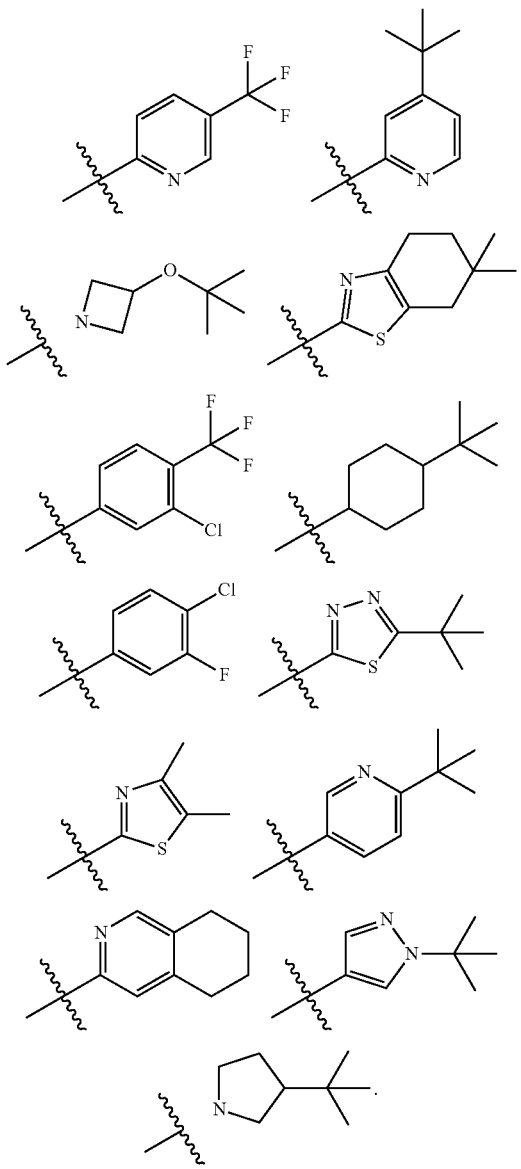

In some embodiments, R¹ is

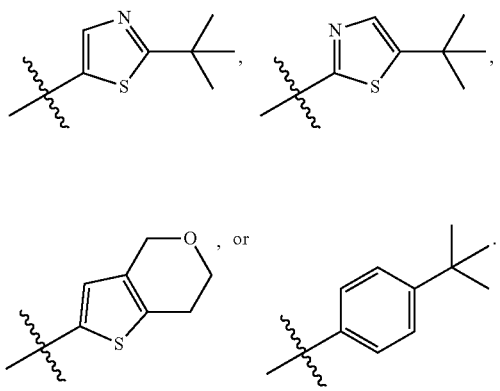

16

In certain embodiments, R¹ is

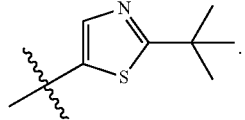

In some embodiments, R¹ is —N(R)₂. In some embodiments, R¹ is —N(R)₂ and R is an optionally substituted group selected from phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, and 5- to 6-membered heteroaryl having 1-4 heteroatoms selected from oxygen, nitrogen, or sulfur. In some embodiments, R¹ is —N(R)₂ and R is a 3- to 8-membered saturated or partially unsaturated carbocyclyl ring.

In some embodiments, R² is hydrogen. In some embodiments, R² is optionally substituted $C_{1-6}$ aliphatic. In some embodiments, R² is methyl.

In some embodiments, R¹ and R², together with their intervening atoms, form an optionally substituted ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, or sulfur.

In some embodiments, when R¹ and R² are taken together they form a 7- to 10-membered bicyclic heterocyclyl having 1-4 heteroatoms selected from oxygen, nitrogen, or sulfur, optionally substituted with $C_{1-6}$ aliphatic or halogen. In some embodiments, when R¹ and R² are taken together they form a 7- to 10-membered bicyclic heterocyclyl having 1-4 heteroatoms selected from oxygen, nitrogen, or sulfur, optionally substituted with halogen, t-butyl or cyclopropyl. In some embodiments, R¹ and R² are taken together to form a 7- to 10-membered bicyclic heterocyclyl:

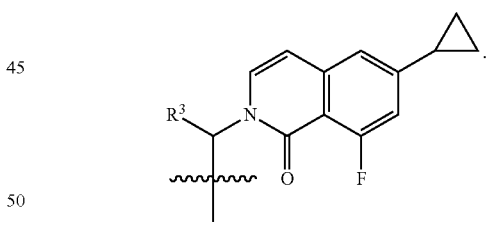

In some embodiments, R³ is hydrogen. In some embodiments, R³ is —C(O)N(R)₂. In some embodiments, R³ is —C(O)N(R)₂ and R is H. In certain embodiments, R³ is —C(O)OR. In some embodiments, R³ is optionally substituted $C_{1-6}$ aliphatic. In some embodiments, R³ is $C_{1-6}$ alkyl. In some embodiments, R³ is methyl. In some embodiments, R³ is hydroxymethyl.

In certain embodiments, R⁴ is halogen, —OR, —SR, —N(R)₂, —C(O)R, —C(O)OR, —S(O)R, —S(O)₂R, —C(O)N(R)₂, —SO₂N(R)₂, —OC(O)R, —N(R)C(O)R, —N(R)C(O)OR, —N(R)SO₂R, —OC(O)N(R)₂, or optionally substituted $C_{1-6}$ aliphatic. In some embodiments, R⁴ is —C(O)N(R)₂.

In some embodiments, R⁴ is optionally substituted $C_{1-6}$ aliphatic. In some embodiments, R⁴ is $C_{1-6}$ alkyl. In some embodiments, $R^4$ is methyl. In some embodiments, $R^4$ is ethyl. In some embodiments, $R^4$ is trifluoromethyl.

In some embodiments, $R^4$ is halogen.

In some embodiments, $R^4$ is hydrogen.

In certain embodiments, $R^3$ and $R^4$, together with their intervening atoms, form optionally substituted fused Ring A (indicated by the dotted lines in the structure below):

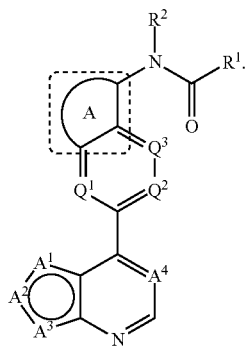

Fused Ring A is selected from fused 5- to 7-membered monocyclic carbocycle and 5- to 7-membered monocyclic heterocycle having 1-2 heteroatoms selected from oxygen, nitrogen, and sulfur.

In some embodiments, fused Ring A is fused 5- to 7-membered monocyclic carbocycle. It is to be understood that in the context of "fused Ring A," the carbon chain formed by $R^3$ and $R^4$ is a saturated carbon chain. For example, in compound I-154, fused Ring A (indicated by dotted lines in the structure below) is a five-membered ring in which $R^3$ and $R^4$ form a —$CH_2$—$CH_2$— chain:

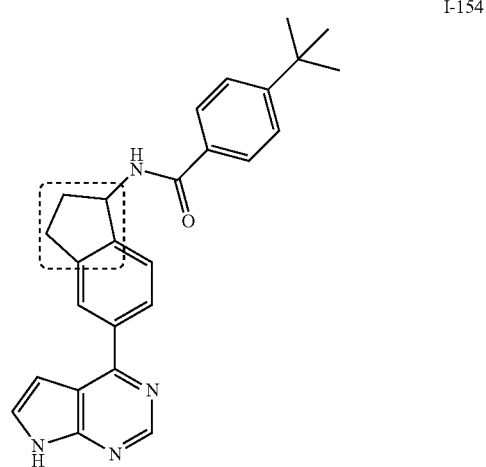 [SMILES: CC(C)(C)c1ccc(C(=O)NC2CCc3cc(-c4ncnc5[nH]ccc45)ccc32)cc1]

I-154

In some embodiments, fused Ring A is fused 5- to 7-membered monocyclic heterocycle having 1 heteroatom selected from oxygen or nitrogen. It is to be understood that in the context of "fused Ring A," the chain formed by $R^3$ and $R^4$ is a saturated chain.

In some embodiments, fused Ring A is fused 5-membered monocyclic heterocycle having 1 oxygen. In some embodiments, fused Ring A is fused 6-membered monocyclic heterocycle having 1 oxygen. In some embodiments, fused Ring A is fused 7-membered monocyclic heterocycle having 1 oxygen. In some embodiments, fused Ring A is fused 5-membered monocyclic heterocycle having 1 nitrogen. In some embodiments, fused Ring A is fused 6-membered monocyclic heterocycle having 1 nitrogen. In some embodiments, fused Ring A is fused 7-membered monocyclic heterocycle having 1 nitrogen.

In some embodiments, $R^5$ is H. In other embodiments, $R^5$ is $C_{1-6}$ aliphatic. In some embodiments, $R^5$ is methyl.

In some embodiments, $R^6$ is H.

In some embodiments, $R^6$ is optionally substituted phenyl.

In some embodiments, $R^6$ is optionally substituted 3- to 7-membered saturated or partially unsaturated monocyclic heterocyclyl having 1-2 heteroatoms selected from oxygen, nitrogen, or sulfur. In some embodiments, $R^6$ is an optionally substituted group selected from morpholinyl, piperidinyl, pyrrolidinyl, piperazinyl, and azetidinyl. In some embodiments, $R^6$ is morpholinyl optionally substituted with —C(O)OH. In some embodiments, $R^6$ is piperidinyl optionally substituted with methyl, dimethylamino, —C(O)NMe$_2$, or —C(O)OH. In some embodiments, $R^6$ is pyrrolidinyl optionally substituted with dimethylamino or —C(O)OH. In some embodiments, $R^6$ is piperazinyl optionally substituted with methyl. In some embodiments, $R^6$ is azetidinyl optionally substituted with dimethylamino.

In some embodiments, $R^6$ is a 5- to 6-membered cyclic saturated or partially unsaturated sulfone group.

In some embodiments, $R^6$ is an optionally substituted 7- to 10-membered bicyclic heterocyclyl having 1-4 heteroatoms selected from oxygen, nitrogen, or sulfur. In some embodiments, $R^6$ is an optionally substituted 9-membered bicyclic heterocyclyl having 2-4 heteroatoms selected from oxygen, nitrogen, or sulfur.

In certain embodiments, $R^6$ is optionally substituted 5- to 6-membered heteroaryl having 1-4 heteroatoms selected from oxygen, nitrogen, or sulfur. In some embodiments, $R^6$ is optionally substituted pyrazolyl. In some embodiments, $R^6$ is pyrazolyl optionally substituted with methyl or ethyl.

In some embodiments, $R^6$ is selected from the following:

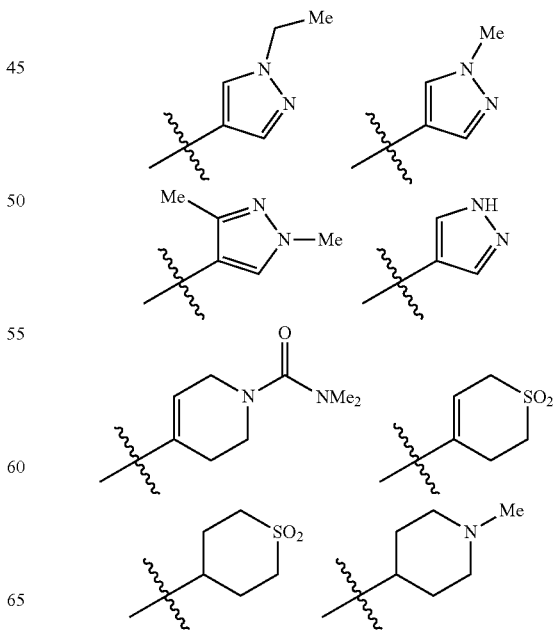

-continued

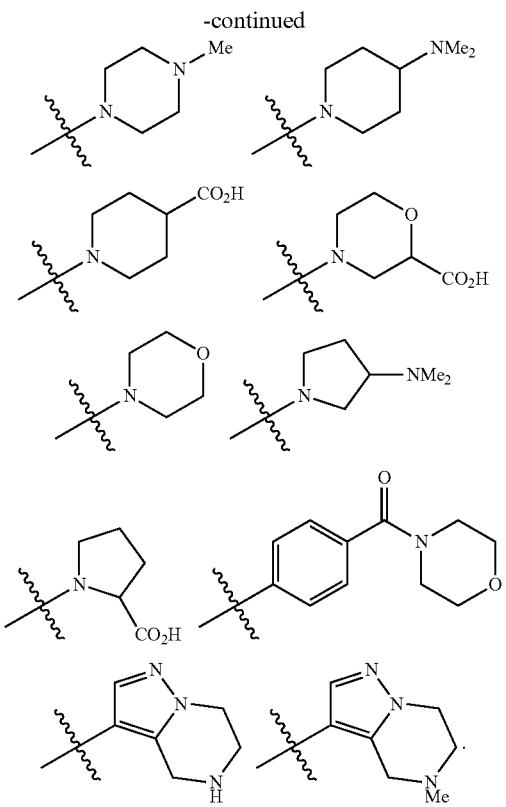

In some embodiments, $R^6$ is

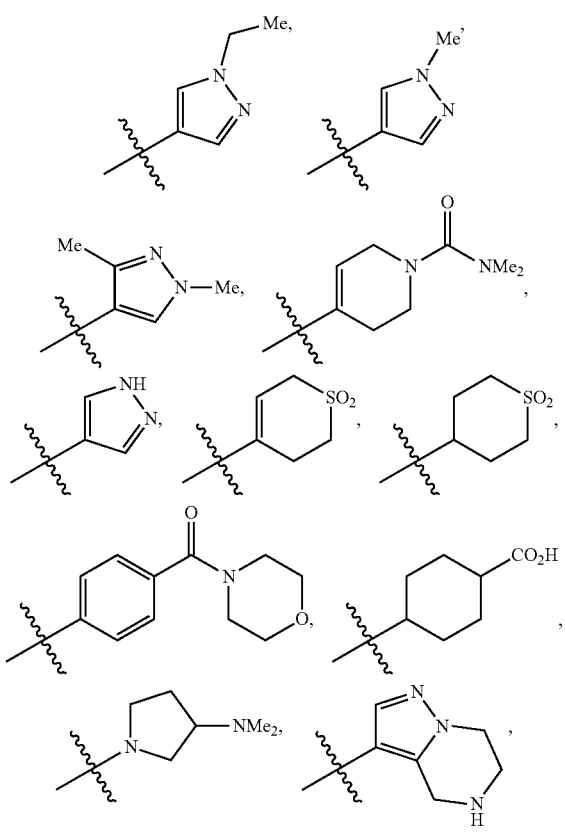

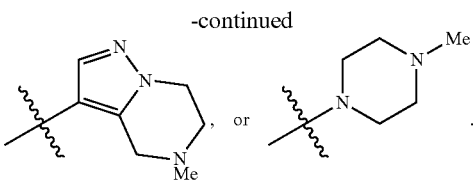

In some embodiments, $R^5$ and $R^6$, taken together with their intervening atoms, form an optionally substituted fused 5- to 7-membered monocyclic carbocycle or optionally substituted fused 5- to 7-membered monocyclic heterocycle having 1-2 heteroatoms selected from oxygen, nitrogen, or sulfur. For example, in compound I-141, the fused ring (indicated by dotted lines in the structure below) is a five-membered monocyclic carbocycle in which $R^5$ and $R^6$ form a —$CH_2$—$CH_2$—CH2-chain:

I-141

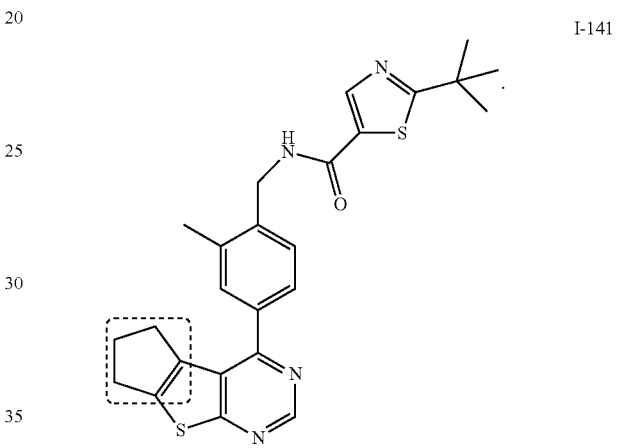

In certain embodiments, each $R^7$ is independently selected from hydrogen or halogen. In some embodiments, each $R^7$ is hydrogen. In some embodiments, when $R^4$ is halogen, one $R^7$ is halogen and other $R^7$ groups are hydrogen.

In some embodiments, provided compounds are of formula I':

I'

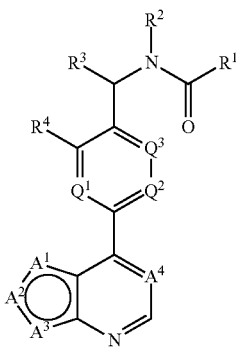

or a pharmaceutically acceptable salt thereof, wherein:
one of $A^1$ and $A^3$ is N—$R^5$, O, or S, and:
   i) $A^2$ is N, O, or S, and the other of $A^1$ and $A^3$ is CH; or
   ii) $A^2$ is C—$R^6$, and the other of $A^1$ and $A^3$ is selected from C—$R^5$ and N;
$A^4$ is selected from C—H and N;
$Q^1$ is selected from C—$R^7$ and N;

$Q^2$ is selected from C—$R^7$ and N;
$Q^3$ is selected from C—$R^7$ and N;
  wherein at most one of $Q^1$, $Q^2$, and $Q^3$ is N;
$R^1$ is selected from —$N(R)_2$, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and 8- to 10-membered bicyclic aryl, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and 8- to 10-membered bicyclic aryl are optionally substituted with one or more $R^{10}$;
$R^2$ is H or $C_{1-6}$ aliphatic,
  or $R^1$ and $R^2$, together with their intervening atoms, form a ring selected from 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, or 7- to 10-membered bicyclic heteroaryl having 1-4 heteroatoms selected from oxygen, nitrogen, wherein said ring is optionally substituted with one or more $R^{20}$;
$R^3$ is selected from H, halogen, —$C(O)N(R)_2$, —C(O)OR, —C(O)R, and $C_{1-6}$ aliphatic, wherein the $C_{1-6}$ aliphatic group is optionally substituted with hydroxyl;
$R^4$ is selected from H, halogen, —$NO_2$, —CN, —OR, —SR, —$N(R)_2$, —C(O)R, —C(O)OR, —S(O)R, —$S(O)_2R$, —$C(O)N(R)_2$, —$SO_2N(R)_2$, —OC(O)R, —N(R)C(O)R, —N(R)C(O)OR, —$N(R)SO_2R$, —$OC(O)N(R)_2$, and $C_{1-6}$ aliphatic, wherein said $C_{1-6}$ aliphatic is optionally substituted with one or more $R^{40}$;
  or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;
each $R^5$ is selected from H and $C_{1-6}$ aliphatic;
$R^6$ is selected from H, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur, are optionally substituted with one or more $R^{60}$;
  or
$R^5$ and $R^6$, taken together with their intervening atoms, form a fused 5- to 7-membered monocyclic carbocycle or fused 5- to 7-membered monocyclic heterocycle having 1-2 heteroatoms selected from oxygen, nitrogen, or sulfur; wherein said monocyclic carbocycle or heterocycle is optionally substituted with one or more $R^{60}$;
each $R^7$ is independently selected from H, halogen, —$NO_2$, —CN, —OR, —SR, —$N(R)_2$, —C(O)R, —C(O)OR, —S(O)R, —$S(O)_2R$, —$C(O)N(R)_2$, —$SO_2N(R)_2$, —OC(O)R, —N(R)C(O)R, —N(R)C(O)OR, —$N(R)SO_2R$, —$OC(O)N(R)_2$, or $C_{1-6}$ aliphatic; and
each R is independently hydrogen or $C_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said $C_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{60}$; or
  two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{60}$;
each $R^{10}$ is independently selected from halogen, —$OR^{10a}$, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;
each $R^{15}$ is independently selected from halogen and —$OR^{15a}$;
$R^{10a}$ is $C_{1-6}$alkyl;
$R^{15a}$ is $C_{1-6}$alkyl;
each $R^{20}$ is independently selected from halogen, $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said $C_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{40}$ is independently selected from halogen, 4- to 6-membered monocyclic heterocyclyl, $-N(R^{40a})_2$, $-N(R^{40a})C(O)(R^{40b})$, $-N(R^{40a})C(O)_2(R^{40a})$, $-OR^{40a}$, $-SR^{40a}$, and $-C(O)_2R^{40a}$;

each $R^{40a}$ is independently selected from H and $C_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from $C_{2-6}$alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is $C_{1-6}$alkyl;

each $R^{60}$ is independently selected from $C_{1-6}$alkyl, $-OR^{60a}$, $-N(R^{60a})_2$, $-C(O)N(R^{60a})_2$; $-C(O)_2R^{60a}$; $-C(O)R^{60b}$, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, wherein said 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{65}$;

$R^{60a}$ is selected from H and $C_{1-6}$alkyl; or two $R^{60a}$ groups are taken together with their intervening atoms to form a 3- to 6-membered heterocycyl having 1-2 heteroatoms selected from oxygen, nitrogen, or sulfur;

$R^{60b}$ is 5- or 6-membered monocyclic heterocycyl;

each $R^{65}$ is independently selected from $C_{1-6}$alkyl, $-OR^{65a}$, $-N(R^{65a})_2$, $-C(O)_2R^{65a}$, $-S(O)_2R^{65b}$, and $-S(O)_2(NR^{65a})_2$;

$R^{65a}$ is selected from H and $C_{1-6}$alkyl; and $R^{65b}$ is $C_{1-6}$alkyl;

wherein the compound is other than:

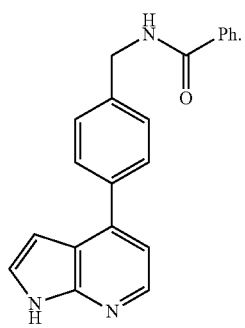 [SMILES: O=C(NCc1ccc(-c2ccnc3[nH]ccc23)cc1)c1ccccc1]

In some embodiments, provided compounds are of formula II-a, II-b, II-c, or II-d:

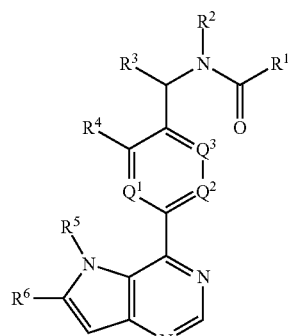

II-a

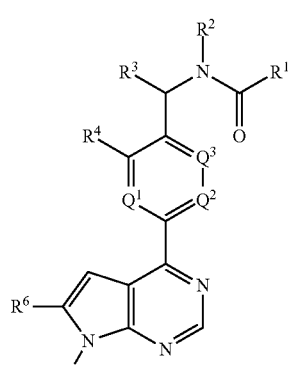

II-b

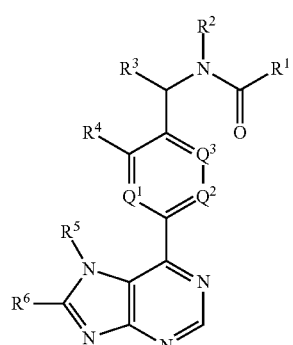

II-c

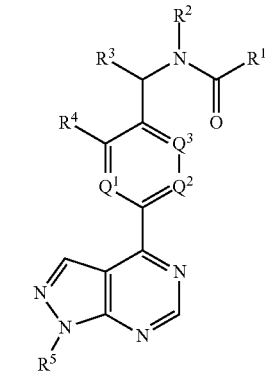

II-d or a pharmaceutically acceptable salt thereof, wherein each of $R^1$, $R^2$, $R^3$, $R^4$, $R^5$, $R^6$, $Q^1$, $Q^2$, and $Q^3$ is as defined above and described in classes and subclasses herein, both singly and in combination.

In some embodiments, provided compounds are of formula III-a, III-b, III-c, or III-d:

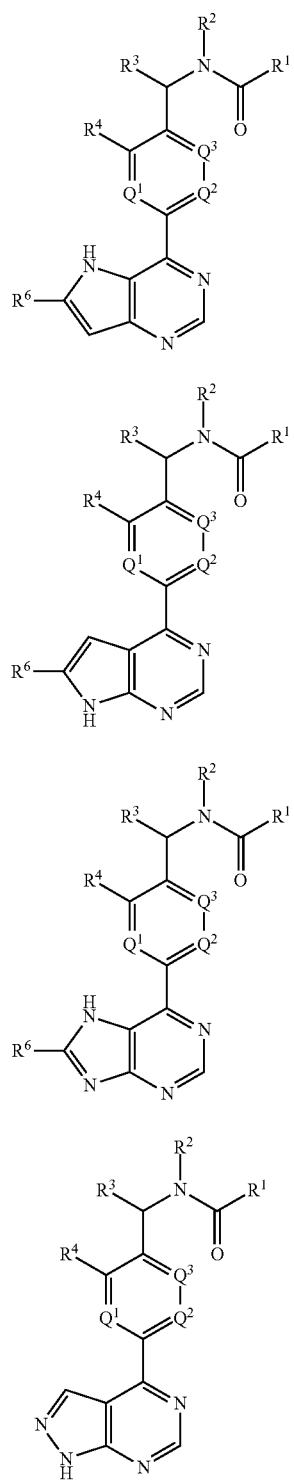

or a pharmaceutically acceptable salt thereof, wherein each of $R^1$, $R^2$, $R^3$, $R^4$, $R^6$, $Q^1$, $Q^2$, and $Q^3$ is as defined above and described in classes and subclasses herein, both singly and in combination.

In certain embodiments, $Q^1$, $Q^2$, and $Q^3$ are $CR^7$. In some embodiments, provided compounds are of formula IV-a, IV-b, IV-c, or IV-d:

or a pharmaceutically acceptable salt thereof, wherein each of $R^1$, $R^2$, $R^3$, $R^4$, $R^6$, $Q^1$, $Q^2$, and $Q^3$ is as defined above and described in classes and subclasses herein, both singly and in combination.

In some embodiments, provided compounds are of formula V-a, V-b, V-c, or V-d:

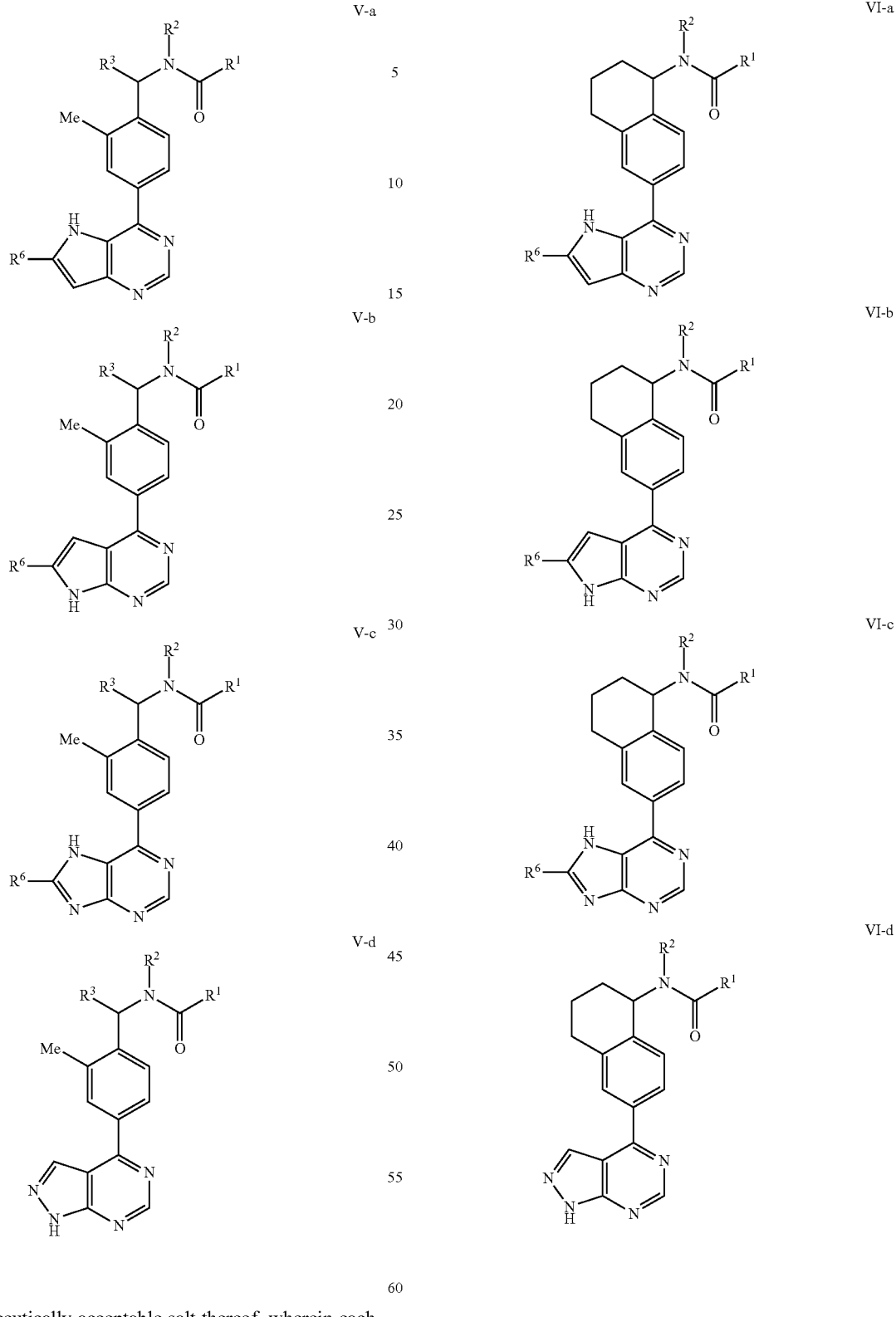

or a pharmaceutically acceptable salt thereof, wherein each of $R^1$, $R^2$, $R^3$, and $R^6$ is as defined above and described in classes and subclasses herein, both singly and in combination.

In certain embodiments, provided compounds are of formula VI-a, VI-b, VI-c, or VI-d:

or a pharmaceutically acceptable salt thereof, wherein each of $R^1$, $R^2$, and $R^6$ is as defined above and described in classes and subclasses herein, both singly and in combination.

In certain embodiments, provided compounds are of formula VII-a, VII-b, VII-c, VII-d, VII-e, or VII-f:

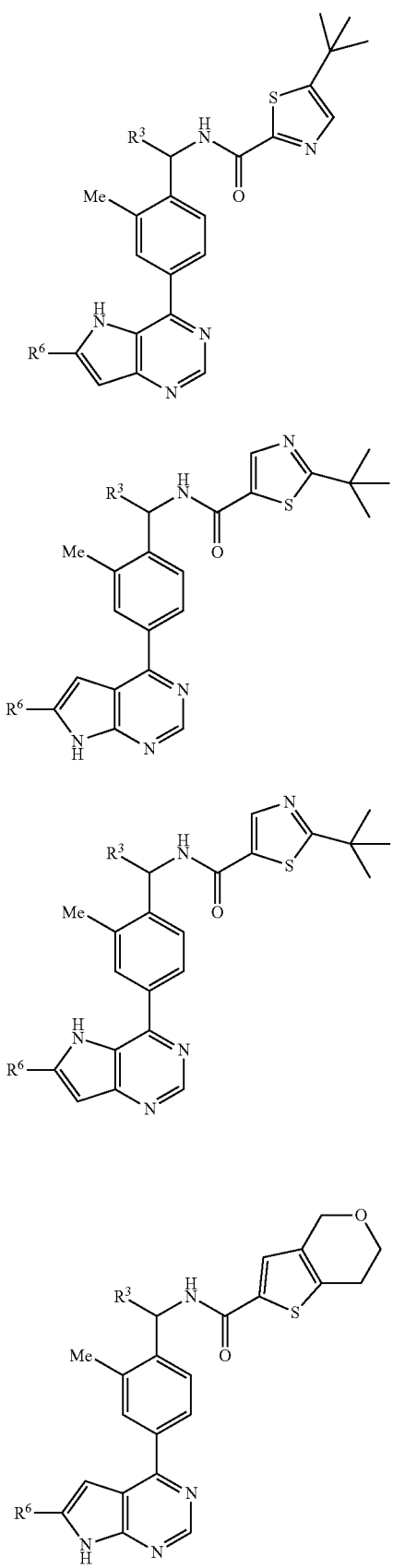
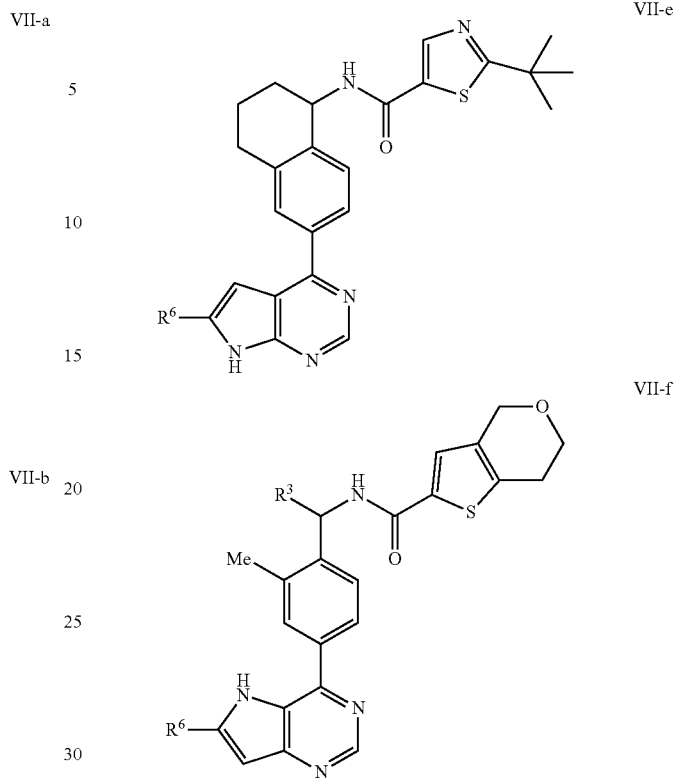

or a pharmaceutically acceptable salt thereof, wherein: $R^3$ is methyl, hydrogen, or —CH$_2$OH, and $R^6$ is as defined above and described in classes and subclasses herein.

In some embodiments, a provided compound is a compound selected from the following, or a pharmaceutically acceptable salt thereof: 5-(tert-butyl)-N-(2-methyl-4-(7H-pyrrolo[2,3-d]pyrimidin-4-yl)benzyl)picolinamide (I-1), 4-(tert-butyl)-N-(2-methyl-4-(7H-pyrrolo[2,3-d]pyrimidin-4-yl)benzyl)benzamide (I-2), N-(4-(7H-pyrrolo[2,3-d]pyrimidin-4-yl)-2-(trifluoromethyl)benzyl)-4-(tert-butyl)benzamide (I-3), N-(4-(7H-pyrrolo[2,3-d]pyrimidin-4-yl)-2-(trifluoromethyl)benzyl)-5-(tert-butyl)picolinamide (I-4), 5-(tert-butyl)-N-(2-chloro-4-(7H-pyrrolo[2,3-d]pyrimidin-4-yl)benzyl)picolinamide (I-5), 5-(tert-butyl)-N-(2-cyano-4-(7H-pyrrolo[2,3-d]pyrimidin-4-yl)benzyl)picolinamide (I-6), 5-(tert-butyl)-N-(2-carbamoyl-4-(7H-pyrrolo[2,3-d]pyrimidin-4-yl)benzyl)picolinamide (I-7), 4-(tert-butyl)-N-(2-cyano-4-(7H-pyrrolo[2,3-d]pyrimidin-4-yl)benzyl)benzamide (I-8), 4-(tert-butyl)-N-(2-carbamoyl-4-(7H-pyrrolo[2,3-d]pyrimidin-4-yl)benzyl)benzamide (I-9), 4-(tert-butyl)-N-(2-ethyl-4-(7H-pyrrolo[2,3-d]pyrimidin-4-yl)benzyl) benzamide (I-10), 5-(tert-butyl)-N-(2-ethyl-4-(7H-pyrrolo[2,3-d]pyrimidin-4-yl)benzyl)picolinamide (I-11), tert-butyl 2-methyl-4-(4,4,5,5-tetramethyl-1,3,2-dioxaborolan-2-yl) benzylcarbamate (I-12), 5-(tert-butyl)-N-(2-chloro-5-fluoro-4-(7H-pyrrolo[2,3-d]pyrimidin-4-yl)benzyl)picolinamide (I-13), N-(6-(7H-pyrrolo[2,3-d]pyrimidin-4-yl)-1,2,3,4-tetrahydronaphthalen-1-yl)-4-(tert-butyl)benzamide (I-14), N-(6-(7H-pyrrolo[2,3-d]pyrimidin-4-yl)-1,2,3,4-tetrahydronaphthalen-1-yl)-5-(tert-butyl)picolinamide (I-15), N-(6-(7H-pyrrolo[2,3-d]pyrimidin-4-yl)-1,2,3,4-tetrahydronaphthalen-1-yl)-4,5,6,7-tetrahydrobenzo[b]thiophene-2-carboxamide (I-16), N-(6-(7H-pyrrolo[2,3-d]pyrimidin-4-yl)-1,2,3,4-tetrahydronaphthalen-1-yl)-4,5,6,7- tetrahydrobenzo[d]thiazole-2-carboxamide (I-17), 5-(tert-butyl)-N-(4-(6-(1-(dimethylcarbamoyl)-1,2,3,6-tetrahydropyridin-4-yl)-5H-pyrrolo[3,2-d]pyrimidin-4-yl)-2-methylbenzyl)thiazole-2-carboxamide (I-18), 2-(tert-butyl)-N-(4-(6-(1-(dimethylcarbamoyl)-1,2,3,6-tetrahydropyridin-4-yl)-7H-pyrrolo[2,3-d]pyrimidin-4-yl)-2-methylbenzyl)thiazole-5-carboxamide (I-19), methyl 4-(4-(4-((2-(tert-butyl)thiazole-5-carboxamido)methyl)-3-methylphenyl)-7H-pyrrolo[2,3-d]pyrimidin-6-yl)benzoate (I-20), 2-(tert-butyl)-N-(4-(6-(1,1-dioxido-3,6-dihydro-2H-thiopyran-4-yl)-7H-pyrrolo[2,3-d]pyrimidin-4-yl)-2-methylbenzyl)thiazole-5-carboxamide (I-21), 2-(tert-butyl)-N-(4-(6-(1,1-dioxido-3,6-dihydro-2H-thiopyran-4-yl)-5H-pyrrolo[3,2-d]pyrimidin-4-yl)-2-methylbenzyl)thiazole-5-carboxamide (I-22), 2-(tert-butyl)-N-(4-(6-(1,1-dioxidotetrahydro-2H-thiopyran-4-yl)-5H-pyrrolo[3,2-d]pyrimidin-4-yl)-2-methylbenzyl)thiazole-5-carboxamide (I-23), 2-(tert-butyl)-N-(4-(6-(1,1-dioxidotetrahydro-2H-thiopyran-4-yl)-5-methyl-5H-pyrrolo[3,2-d]pyrimidin-4-yl)-2-methylbenzyl)thiazole-5-carboxamide (I-24), 2-(tert-butyl)-N-(2-methyl-4-(6-(1-methylpiperidin-4-yl)-5H-pyrrolo[3,2-d]pyrimidin-4-yl)benzyl)thiazole-5-carboxamide (I-25), 2-(tert-butyl)-N-(2-methyl-4-(6-(1-methyl-1H-pyrazol-4-yl)-7H-pyrrolo[2,3-d]pyrimidin-4-yl)benzyl)thiazole-5-carboxamide (I-26), 2-(tert-butyl)-N-(2-methyl-4-(7-methyl-6-(1-methyl-1H-pyrazol-4-yl)-7H-pyrrolo[2,3-d]pyrimidin-4-yl)benzyl)thiazole-5-carboxamide (I-27), 2-(tert-butyl)-N-(4-(6-(1,3-dimethyl-1H-pyrazol-4-yl)-7-methyl-7H-pyrrolo[2,3-d]pyrimidin-4-yl)-2-methylbenzyl)thiazole-5-carboxamide (I-28), 2-(tert-butyl)-N-(1-(4-(6-(1,1-dioxido-3,6-dihydro-2H-thiopyran-4-yl)-5H-pyrrolo[3,2-d]pyrimidin-4-yl)phenyl)-2-hydroxyethyl)thiazole-5-carboxamide (I-29), 2-(tert-butyl)-N-(1-(4-(6-(1,1-dioxido-3,6-dihydro-2H-thiopyran-4-yl)-7H-pyrrolo[2,3-d]pyrimidin-4-yl)phenyl)-2-hydroxyethyl)thiazole-5-carboxamide (I-30), 2-(tert-butyl)-N-(2-hydroxy-1-(2-methyl-4-(6-(1-methyl-1H-pyrazol-4-yl)-7H-pyrrolo[2,3-d]pyrimidin-4-yl)phenyl)ethyl)thiazole-5-carboxamide (I-31), N-(2-hydroxy-1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide (I-32), N-(2-methyl-4-(6-(1-methyl-1H-pyrazol-4-yl)-7H-pyrrolo[2,3-d]pyrimidin-4-yl)benzyl)-6,7-dihydro-4H-thieno[3,2-c]pyran-2-carboxamide (I-33), 2-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)thiazole-5-carboxamide (I-34), N-(6-(6-(1-methyl-1H-pyrazol-4-yl)-7H-pyrrolo[2,3-d]pyrimidin-4-yl)-1,2,3,4-tetrahydronaphthalen-1-yl)-6,7-dihydro-4H-thieno[3,2-c]pyran-2-carboxamide (I-35), 5-(tert-butyl)-N-(2-methyl-4-(6-(1-methyl-1H-pyrazol-4-yl)-5H-pyrrolo[3,2-d]pyrimidin-4-yl)benzyl)thiazole-2-carboxamide (I-36), 2-(tert-butyl)-N-(6-(6-(1-methyl-1H-pyrazol-4-yl)-5H-pyrrolo[3,2-d]pyrimidin-4-yl)-1,2,3,4-tetrahydronaphthalen-1-yl)thiazole-5-carboxamide (I-37), 2-(tert-butyl)-N-(2-methyl-4-(5-methyl-6-(1-methyl-1H-pyrazol-4-yl)-5H-pyrrolo[3,2-d]pyrimidin-4-yl)benzyl)thiazole-5-carboxamide (I-38), 2-(tert-butyl)-N-(4-(6-(1,3-dimethyl-1H-pyrazol-4-yl)-5H-pyrrolo[3,2-d]pyrimidin-4-yl)-2-methylbenzyl)thiazole-5-carboxamide (I-39), 5-(tert-butyl)-N-(4-(6-(1-ethyl-1H-pyrazol-4-yl)-5H-pyrrolo[3,2-d]pyrimidin-4-yl)-2-methylbenzyl)thiazole-2-carboxamide (I-40), N-(4-(6-(1H-pyrazol-4-yl)-5H-pyrrolo[3,2-d]pyrimidin-4-yl)-2-methylbenzyl)-5-(tert-butyl)thiazole-2-carboxamide (I-41), N-(2-methyl-4-(6-(1-methyl-5H-pyrazol-4-yl)-5H-pyrrolo[3,2-d]pyrimidin-4-yl)benzyl)-6,7-dihydro-4H-thieno[3,2-c]pyran-2-carboxamide (I-42), 3-isopropoxy-N-(2-methyl-4-(6-(1-methyl-1H-pyrazol-4-yl)-5H-pyrrolo[3,2-d]pyrimidin-4-yl)benzyl)azetidine-1-carboxamide (I-43), 2-(tert-butyl)-N-(2-hydroxy-1-(2-methyl-4-(6-(1-methyl-1H-pyrazol-4-yl)-5H-pyrrolo[3,2-d]pyrimidin-4-yl)phenyl)ethyl)thiazole-5-carboxamide (I-44), N-(2-hydroxy-1-(2-methyl-4-(6-(1-methyl-1H-pyrazol-4-yl)-5H-pyrrolo[32-d]pyrimidin-4-yl)phenyl)ethyl)-6,7-dihydro-4H-thieno[3,2-c]pyran-2-carboxamide (I-45), 2-(tert-butyl)-N-(1-(2-methyl-4-(6-(1-methyl-1H-pyrazol-4-yl)-5H-pyrrolo[3,2-d]pyrimidin-4-yl)phenyl)ethyl)thiazole-5-carboxamide (I-46), 2-(tert-butyl)-N-(2-methyl-4-(8-(4-methylpiperazin-1-yl)-7H-purin-6-yl)benzyl)thiazole-5-carboxamide (I-47), 2-(tert-butyl)-N-(2-methyl-4-(8-morpholino-7H-purin-6-yl)benzyl)thiazole-5-carboxamide (I-48), 2-(tert-butyl)-N-(4-(8-(4-(dimethylamino)piperidin-1-yl)-7H-purin-6-yl)-2-methylbenzyl)thiazole-5-carboxamide (I-49), 2-(tert-butyl)-N-(4-(8-(3-(dimethylamino)pyrrolidin-1-yl)-7H-purin-6-yl)-2-methylbenzyl)thiazole-5-carboxamide (I-50), 1-(6-(4-((2-(tert-butyl)thiazole-5-carboxamido)methyl)-3-methylphenyl)-7H-purin-8-yl)pyrrolidine-3-carboxylic acid (I-51), 1-(6-(4-((2-(tert-butyl)thiazole-5-carboxamido)methyl)-3-methylphenyl)-7H-purin-8-yl)piperidine-4-carboxylic acid (I-52), 2-(tert-butyl)-N-(4-(8-(3-(dimethylamino)azetidin-1-yl)-7H-purin-6-yl)-2-methylbenzyl)thiazole-5-carboxamide (I-53), 2-(tert-butyl)-N-(2-methyl-4-(8-(1-methylpiperidin-4-yl)-7H-purin-6-yl)benzyl)thiazole-5-carboxamide (I-54), 1-(6-(4-((2-(tert-butyl)thiazole-5-carboxamido)methyl)-3-methylphenyl)-7H-purin-8-yl)pyrrolidine-2-carboxylic acid (I-55), N-(4-(7H-pyrrolo[2,3-d]pyrimidin-4-yl)benzyl)-4-(tert-butyl)benzamide (I-56), N-(4-(7H-pyrrolo[2,3-d]pyrimidin-4-yl)benzyl)-5,6,7,8-tetrahydroisoquinoline-3-carboxamide (I-57), N-(4-(7H-pyrrolo[2,3-d]pyrimidin-4-yl)benzyl)-5,6,7,8-tetrahydroquinoline-2-carboxamide (I-58), N-(4-(7H-pyrrolo[2,3-d]pyrimidin-4-yl)benzyl)-6,7-dihydro-5H-pyrrolo[1,2-a]imidazole-2-carboxamide (I-59), N-(4-(7H-pyrrolo[2,3-d]pyrimidin-4-yl)benzyl)-2,3-dihydro-1H-indene-2-carboxamide (I-60), N-(4-(7H-pyrrolo[2,3-d]pyrimidin-4-yl)benzyl)benzo[b]thiophene-2-carboxamide (I-61), N-(4-(7H-pyrrolo[2,3-d]pyrimidin-4-yl)benzyl)-4,5,6,7-tetrahydrobenzo[d]thiazole-2-carboxamide (I-62), N-(4-(7H-pyrrolo[2,3-d]pyrimidin-4-yl)benzyl)-5-chloro-4-(trifluoromethyl)picolinamide (I-63), N-(4-(7H-pyrrolo[2,3-d]pyrimidin-4-yl)benzyl)-5,6,7,8-tetrahydroimidazo[1,2-a]pyridine-2-carboxamide (I-64), N-(4-(7H-pyrrolo[2,3-d]pyrimidin-4-yl)benzyl)-4,5,6,7-tetrahydrobenzo[b]thiophene-2-carboxamide (I-65), N-(4-(7H-pyrrolo[2,3-d]pyrimidin-4-yl)benzyl)-4-(trifluoromethyl)benzamide (I-66), N-(4-(7H-pyrrolo[2,3-d]pyrimidin-4-yl)benzyl)-6-(tert-butyl)nicotinamide (I-67), N-(4-(7H-pyrrolo[2,3-d]pyrimidin-4-yl)benzyl)-5-(tert-butyl)picolinamide (I-68), N-(4-(7H-pyrrolo[2,3-d]pyrimidin-4-yl)benzyl)isoindoline-2-carboxamide (I-69), N-((5-(7H-pyrrolo[2,3-d]pyrimidin-4-yl)pyridin-2-yl)methyl)-4-(tert-butyl)benzamide (I-70), N-((5-(7H-pyrrolo[2,3-d]pyrimidin-4-yl)pyridin-2-yl)methyl)-4,5,6,7-tetrahydrobenzo[b]thiophene-2-carboxamide (I-71), N-((6-(1H-pyrrolo[2,3-b]pyridin-4-yl)pyridin-3-yl)methyl)-5-(tert-butyl)picolinamide (I-72), N-((6-(1H-pyrrolo[2,3-b]pyridin-4-yl)pyridin-3-yl)methyl)-4,5,6,7-tetrahydrobenzo[b]thiophene-2-carboxamide (I-73), (R)—N-(1-(4-(7H-pyrrolo[2,3-d]pyrimidin-4-yl)phenyl)ethyl)-4,5,6,7-tetrahydrobenzo[d]thiazole-2-carboxamide (I-74), (S)—N-(1-(4-(7H-pyrrolo[2,3-d]pyrimidin-4-yl)phenyl)ethyl)-4,5,6,7-tetrahydrobenzo[d]thiazole-2-carboxamide (I-75), 2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide hydrochloride (I-76), N-(1-(2-methyl-4-(7H-pyrrolo[2,3-d]pyrimidin-4-yl)phenyl)ethyl)-4,5,6,7-tetrahydrobenzo[d]thiazole-2-carboxamide (I-77), N-(1-(2-methyl-4-(7H-pyrrolo[2,3-d]pyrimidin-4-yl)phenyl)ethyl)-4,5,6,7-tetrahydrobenzo[b]thiophene-2-carboxamide (I-78), N-(1-(4-(7H-pyrrolo[2,3-d]pyrimidin-4-yl)-2-(trifluoromethyl)phenyl)ethyl)-4,5,6,7-tetrahydrobenzo[d]thiazole-2-carboxamide (I-79), N-(1-(4-(7H-pyrrolo[2,3-d]pyrimidin-4-yl)-2-(trifluoromethyl)phenyl)ethyl)-4,5,6,7-tetrahydrobenzo[b]thiophene-2-carboxamide (I-80), (R)—N-(6-(7H-Pyrrolo[2,3-d]pyrimidin-4-yl)-1,2,3,4-tetrahydronaphthalen-1-yl)-4,5,6,7-tetrahydrobenzo[b]thiophene-2-carboxamide (I-81), N-(7-(7H-pyrrolo[2,3-d]pyrimidin-4-yl)isochroman-4-yl)-5-(tert-butyl)picolinamide (I-82), N-(7-(7H-pyrrolo[2,3-d]pyrimidin-4-yl)isochroman-4-yl)-4-(tert-butyl)benzamide (I-83), N-(4-(1H-pyrazolo[3,4-d]pyrimidin-4-yl)benzyl)-4-(tert-butyl)benzamide (I-84), N-(2-methyl-4-(1H-pyrazolo[3,4-d]pyrimidin-4-yl)benzyl)-4,5,6,7-tetrahydrobenzo[b]thiophene-2-carboxamide (I-85), (R)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide (I-86), (S)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide (I-87), N-(6-(1H-pyrazolo[3,4-d]pyrimidin-4-yl)-1,2,3,4-tetrahydronaphthalen-1-yl)-4-(tert-butyl)benzamide (I-88), (S)—N-(6-(7H-Pyrrolo[2,3-d]pyrimidin-4-yl)-1,2,3,4-tetrahydronaphthalen-1-yl)-4,5,6,7-tetrahydrobenzo[b]thiophene-2-carboxamide (I-89), N-(6-(1H-pyrazolo[3,4-d]pyrimidin-4-yl)-1,2,3,4-tetrahydronaphthalen-1-yl)-4-chloro-3-fluorobenzamide (I-90), N-(6-(1H-pyrazolo[3,4-d]pyrimidin-4-yl)-1,2,3,4-tetrahydronaphthalen-1-yl)-3-fluoro-4-(trifluoromethyl)benzamide (I-91), N-(6-(1H-pyrazolo[3,4-d]pyrimidin-4-yl)-1,2,3,4-tetrahydronaphthalen-1-yl)-3-chloro-4-(trifluoromethyl)benzamide (I-92), N-(6-(1H-pyrazolo[3,4-d]pyrimidin-4-yl)-1,2,3,4-tetrahydronaphthalen-1-yl)-3,4-dichlorobenzamide (I-93), N-(6-(1H-pyrazolo[3,4-d]pyrimidin-4-yl)-1,2,3,4-tetrahydronaphthalen-1-yl)-5,6-dihydro-4H-cyclopenta[b]thiophene-2-carboxamide (I-94), N-(6-(1H-pyrazolo[3,4-d]pyrimidin-4-yl)-1,2,3,4-tetrahydronaphthalen-1-yl)-4,5-dimethylthiazole-2-carboxamide (I-95), N-(6-(1H-pyrazolo[3,4-d]pyrimidin-4-yl)-1,2,3,4-tetrahydronaphthalen-1-yl)-4-isopropylthiazole-2-carboxamide (I-96), N-(6-(1H-pyrazolo[3,4-d]pyrimidin-4-yl)-1,2,3,4-tetrahydronaphthalen-1-yl)-4-(trifluoromethyl)benzamide (I-97), N-(6-(1H-pyrazolo[3,4-d]pyrimidin-4-yl)-1,2,3,4-tetrahydronaphthalen-1-yl)-4-(tert-butyl)thiazole-2-carboxamide (I-98), (R)—N-(6-(1H-pyrazolo[3,4-d]pyrimidin-4-yl)-1,2,3,4-tetrahydronaphthalen-1-yl)-4-(tert-butyl)thiazole-2-carboxamide (I-99), (R)—N-(6-(1H-pyrazolo[3,4-d]pyrimidin-4-yl)-1,2,3,4-tetrahydronaphthalen-1-yl)-4-(tert-butyl)thiazole-2-carboxamide (I-100), N-(6-(1H-pyrazolo[3,4-d]pyrimidin-4-yl)-1,2,3,4-tetrahydronaphthalen-1-yl)-1-methyl-1H-benzo[d]imidazole-2-carboxamide (I-101), 2-(tert-butyl)-N-(2-methyl-4-(6-(5-methyl-4,5,6,7-tetrahydropyrazolo[1,5-a]pyrazin-3-yl)-7H-pyrrolo[2,3-d]pyrimidin-4-yl)benzyl)thiazole-5-carboxamide (I-102), N-(6-(1H-pyrazolo[3,4-d]pyrimidin-4-yl)-1,2,3,4-tetrahydronaphthalen-1-yl)-5-(tert-butyl)-1,3,4-thiadiazole-2-carboxamide (I-103), N-(6-(1H-pyrazolo[3,4-d]pyrimidin-4-yl)-1,2,3,4-tetrahydronaphthalen-1-yl)-4-(tert-butyl)cyclohexanecarboxamide (I-104), trans-N—((R)-6-(1H-pyrazolo[3,4-d]pyrimidin-4-yl)-1,2,3,4-tetrahydronaphthalen-1-yl)-4-(trifluoromethyl)cyclohexanecarboxamide (I-105), N-(6-(1H-pyrazolo[3,4-d]pyrimidin-4-yl)-1,2,3,4-tetrahydronaphthalen-1-yl)benzo[d]thiazole-2-carboxamide (I-106), N-(6-(1H-pyrazolo[3,4-d]pyrimidin-4-yl)-1,2,3,4-tetrahydronaphthalen-1-yl)-4,5,6,7-tetrahydrobenzo[b]thiophene-2-carboxamide (I-107), N-(4-(1H-pyrazolo[3,4-d]pyrimidin-4-yl)-2-(trifluoromethyl)benzyl)-4,5,6,7-tetrahydrobenzo[d]thiazole-2-carboxamide (I-108), N-((3-fluoro-5-(1H-pyrazolo[3,4-d]pyrimidin-4-yl)pyridin-2-yl)methyl)-4,5,6,7-tetrahydrobenzo[b]thiophene-2-carboxamide (I-109), N-((3-fluoro-5-(1H-pyrazolo[3,4-b]pyridin-4-yl)pyridin-2-yl)methyl)-4,5,6,7-tetrahydrobenzo[b]thiophene-2-carboxamide (I-110), 4-(tert-butyl)-N-(4-(6-(4-(morpholine-4-carbonyl)phenyl)-7H-pyrrolo[2,3-d]pyrimidin-4-yl)benzyl)benzamide (I-111), 2-(tert-butyl)-N-(1-(2-methyl-4-(6-(1-methyl-1H-pyrazol-4-yl)-7H-pyrrolo[2,3-d]pyrimidin-4-yl)phenyl)ethyl)thiazole-5-carboxamide (I-112), N-(1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide (I-113), 2-(tert-butyl)-N-(1-(4.-(6-(1-methyl-1H-pyrazol-4-yl)-5H-pyrrolo[3,2-d]pyrimidin-4-yl)phenyl)ethyl)thiazole-5-carboxamide (I-114), 2-(tert-butyl)-N-(2-methyl-4-(5H-pyrrolo[3,2-d]pyrimidin-4-yl)benzyl)thiazole-5-carboxamide (I-115), N-(2-methyl-4-(5H-pyrrolo[3,2-d]pyrimidin-4-yl)benzyl)-4,5,6,7-tetrahydrobenzo[b]thiophene-2-carboxamide (I-116), N-((4-methyl-6-(1H-pyrazolo[3,4-b]pyridin-4-yl)pyridin-3-yl)methyl)-4,5,6,7-tetrahydrobenzo[b]thiophene-2-carboxamide (I-117), N-((2-methyl-6-(1H-pyrazolo[3,4-b]pyridin-4-yl)pyridin-3-yl)methyl)-4,5,6,7-tetrahydrobenzo[b]thiophene-2-carboxamide (I-118), 4,5,6,7-Tetrahydro-benzothiazole-2-carboxylic acid 2-methyl-4-(1H-pyrazolo[3,4-d]pyrimidin-4-yl)-benzylamide (I-119), N-(6-(1H-pyrazolo[3,4-d]pyrimidin-4-yl)-1,2,3,4-tetrahydronaphthalen-1-yl)benzo[b]thiophene-2-carboxamide (I-120), N-(1-(2-methyl-4-(1H-pyrazolo[3,4-d]pyrimidin-4-yl)phenyl)ethyl)-4,5,6,7-tetrahydrobenzo[b]thiophene-2-carboxamide (I-121), N-(4-(7H-pyrrolo[2,3-d]pyrimidin-4-yl)-2-(trifluoromethyl)benzyl)-4,5,6,7-tetrahydrobenzo[d]thiazole-2-carboxamide (I-122), N-(1-(2-methyl-4-(5H-pyrrolo[3,2-d]pyrimidin-4-yl)phenyl)ethyl)-4,5,6,7-tetrahydrobenzo[b]thiophene-2-carboxamide (I-123), 4-(6-(4-((2-(tert-butyl)thiazole-5-carboxamido)methyl)-3-methylphenyl)-7H-purin-8-yl)morpholine-2-carboxylic acid (I-124), N-((3-methyl-5-(1H-pyrazolo[3,4-d]pyrimidin-4-yl)pyridin-2-yl)methyl)-4,5,6,7-tetrahydrobenzo[b]thiophene-2-carboxamide (I-125), N-((3-methyl-5-(1H-pyrrolo[2,3-b]pyridin-4-yl)pyridin-2-yl)methyl)-4,5,6,7-tetrahydrobenzo[b]thiophene-2-carboxamide (I-126), N-(1-(2-methyl-4-(1H-pyrazolo[3,4-d]pyrimidin-4-yl)phenyl)ethyl)-4,5,6,7-tetrahydrobenzo[d]thiazole-2-carboxamide (I-127), 2-(tert-butyl)-N-(1-(2-methyl-4-(1H-pyrazolo[3,4-d]pyrimidin-4-yl)phenyl)ethyl)thiazole-5-carboxamide (I-128), N-(6-(5H-pyrrolo[3,2-d]pyrimidin-4-yl)-1,2,3,4-tetrahydronaphthalen-1-yl)-2-(tert-butyl)thiazole-5-carboxamide (I-129), N-(6-(1H-pyrazolo[3,4-d]pyrimidin-4-yl)-1,2,3,4-tetrahydronaphthalen-1-yl)-5,6-dihydro-4H-cyclopenta[d]thiazole-2-carboxamide (I-130), N-(6-(1H-pyrazolo[3,4-d]pyrimidin-4-yl)-1,2,3,4-tetrahydronaphthalen-1-yl)-5-(tert-butyl)picolinamide (I-131), N-(1-(4-(1H-pyrazolo[3,4-d]pyrimidin-4-yl)phenyl)-2-hydroxyethyl)-4,5,6,7-tetrahydrobenzo[b]thiophene-2-carboxamide (I-132), 2-(tert-butyl)-N-(2-methyl-4-(2-(4-methylpiperazin-1-yl)thiazolo[4,5-d]pyrimidin-7-yl)benzyl)thiazole-5-carboxamide (I-133), 2-(tert-butyl)-N-(1-(2-methyl-4-(5H-pyrrolo[3,2-d]pyrimidin-4-yl)phenyl)ethyl)thiazole-5-carboxamide (I-134), N-(1-(4-(1H-pyrazolo[3,4-d]pyrimidin-4-yl)-2-(trifluoromethyl)phenyl)ethyl)-4,5,6,7-tetrahydrobenzo[b]thiophene-2-carboxamide (I-135), N-(6-(1H-pyrazolo[3,4-d]pyrimidin-4-yl)-1,2,3,4- tetrahydronaphthalen-1-yl)-6,6-dimethyl-4,5,6,7-tetrahydrobenzo[d]thiazole-2-carboxamide (I-136), N-(6-(1H-pyrazolo[3,4-d]pyrimidin-4-yl)-1,2,3,4-tetrahydronaphthalen-1-yl)-4,5,6,7-tetrahydrobenzo[d]thiazole-2-carboxamide (I-137), 2-(6-(1H-pyrazolo[3,4-d]pyrimidin-4-yl)-1,2,3,4-tetrahydronaphthalen-1-yl)-6-cyclopropyl-8-fluoroisoquinolin-1(2H)-one (I-138), N-((3-methyl-5-(1H-pyrazolo[3,4-b]pyridin-4-yl)pyridin-2-yl)methyl)-4,5,6,7-tetrahydrobenzo[b]thiophene-2-carboxamide (I-139), N-((3-methyl-5-(5H-pyrrolo[3,2-d]pyrimidin-4-yl)pyridin-2-yl)methyl)-4,5,6,7-tetrahydrobenzo[b]thiophene-2-carboxamide (I-140), N-(6-(1H-pyrazolo[3,4-d]pyrimidin-4-yl)-1,2,3,4-tetrahydronaphthalen-1-yl)-6-(tert-butyl)nicotinamide (I-142), N-(1-(4-(1H-pyrazolo[3,4-d]pyrimidin-4-yl)phenyl)propyl)-4,5,6,7-tetrahydrobenzo[b]thiophene-2-carboxamide (I-143), (R)—N-(3-(1H-pyrazolo[3,4-b]pyridin-4-yl)-5,6,7,8-tetrahydroquinolin-8-yl)-2-(tert-butyl)thiazole-5-carboxamide (I-144), N-(1-(4-(1H-pyrazolo[3,4-d]pyrimidin-4-yl)-2-(trifluoromethyl)phenyl)ethyl)-4,5,6,7-tetrahydrobenzo[d]thiazole-2-carboxamide (I-145), N-(6-(1H-pyrazolo[3,4-d]pyrimidin-4-yl)-1,2,3,4-tetrahydronaphthalen-1-yl)-5-(trifluoromethyl)picolinamide (I-147), N-(1-(4-(1H-pyrazolo[3,4-d]pyrimidin-4-yl)phenyl)-2-methylpropyl)-4,5,6,7-tetrahydrobenzo[b]thiophene-2-carboxamide (I-149), N-(6-(1H-pyrazolo[3,4-d]pyrimidin-4-yl)-1,2,3,4-tetrahydronaphthalen-1-yl)-4-(tert-butyl)picolinamide (I-150), N-(1-(4-(1H-pyrazolo[3,4-d]pyrimidin-4-yl)phenyl)-2-amino-2-oxoethyl)-4,5,6,7-tetrahydrobenzo[b]thiophene-2-carboxamide (I-151), (S)—N-(3-(1H-pyrazolo[3,4-b]pyridin-4-yl)-5,6,7,8-tetrahydroquinolin-8-yl)-2-(tert-butyl)thiazole-5-carboxamide (I-152), N-((3-methyl-5-(7H-pyrrolo[2,3-d]pyrimidin-4-yl)pyridin-2-yl)methyl)-4,5,6,7-tetrahydrobenzo[b]thiophene-2-carboxamide (I-153), N-(5-(7H-pyrrolo[2,3-d]pyrimidin-4-yl)-2,3-dihydro-1H-inden-1-yl)-4-(tert-butyl)benzamide (I-154), 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide (I-156), 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide (I-157), 3-isopropoxy-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide (I-158), 3-(tert-butoxy)-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide (I-159), 1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide (I-160), 2-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)thiazole-5-carboxamide (I-161), 3-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)pyrrolidine-1-carboxamide (I-162), 3-isopropoxy-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide (I-163), and 3-(tert-butoxy)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide (I-164).

In some embodiments, a provided compound is a compound selected from the following, or a pharmaceutically acceptable salt thereof:

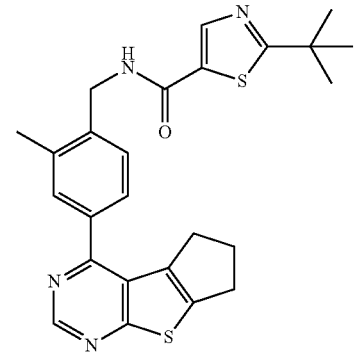
I-141

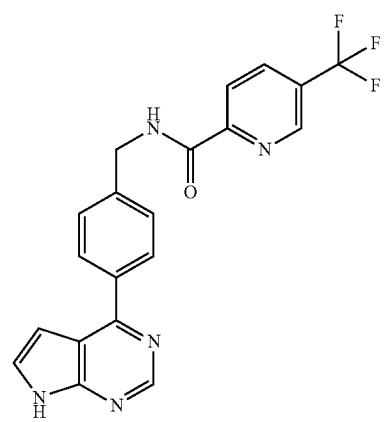
I-146

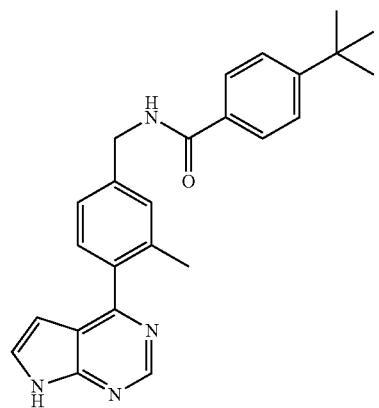
I-148 and

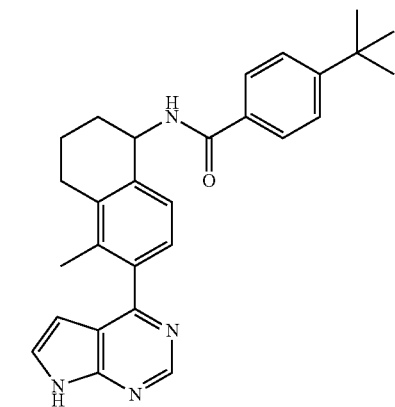
I-155 which may be made using procedures similar to those in the ensuing Examples.

General Methods of Providing the Present Compounds

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

In certain embodiments, the present compounds are generally prepared according to Scheme A set forth below:

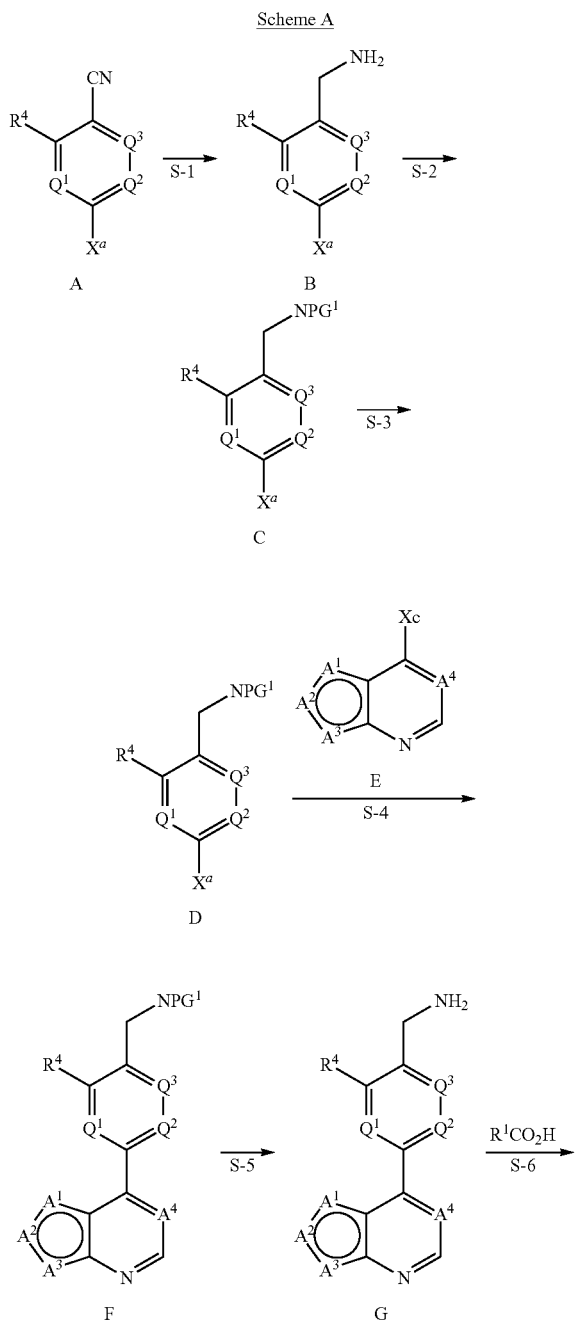

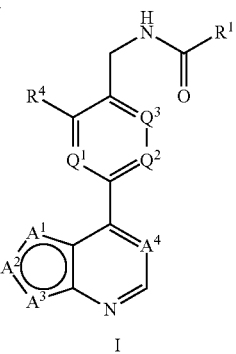

In one aspect, the present invention provides methods for preparing compounds of formula I, according to the steps depicted in Scheme A above wherein each variable is as defined and described herein and each $PG^1$ is a suitable protecting group. For compounds having an $X^a$ or $X^b$ group, $X^a$ and $X^b$ are defined as a moiety suitable for biaryl coupling with an aryl group of formula E, or a group capable of being converted to such a moiety. In some embodiments, $X^a$ and $X^b$ are the same. In some embodiments, $X^a$ is a group that is converted to $X^b$ in order to facilitate coupling with a compound of formula E. In some embodiments, $X^a$ is halogen. In some embodiments, $X^b$ is halogen, a boronic acid, or a boronic ester. In some embodiments, $X^c$ is halogen, a boronic acid, or a boronic ester. It will be appreciated that the reacting partners in a biaryl coupling will be complimentary, and therefore the identity of $X^b$ will depend upon the choice of $X^c$ in formula E. For example, in some embodiments, $X^b$ is a boronic acid or ester, and $X^c$ is halogen. In other embodiments, $X^c$ is a boronic acid or ester, and $X^b$ is halogen.

At step S-1, nitrile A is reduced under suitable conditions to form amine B. Suitable nitrile reduction conditions are well known in the art. In some embodiments, the conditions comprise borane.

At step S-2, amine B is protected using a suitable amino protecting group. Suitable amino protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable mono-protected amines include those defined herein. In some embodiments, $PG^1$ is a Boc protecting group.

At step S-3, protected amine C is optionally converted to protected amine D, depending upon the choice of biaryl couple chemistry as described above. In some embodiments, $X^a$ is halogen and is converted to a boronic ester in step S-3 in order to couple with a compound of formula E. Suitable conditions for the preparation of aryl boronic esters and acids are known in the art. In some embodiments, step S-3 comprises bis(pinacolato) diboron and catalytic palladium. In some embodiments, such as when formula E comprises a boronic ester, $X^a$ is halogen and step S-3 is omitted.

At step S-4, protected amine D is coupled with a compound of formula E to produce biaryl formula F. In some embodiments, step S-4 comprises a Suzuki coupling and $X^b$ and $X^c$ are selected accordingly. In some embodiments, $X^d$ is the same as X. Methods of carrying out Suzuki couplings are well known in the art and include those described by March (supra). Suitable conditions for the Suzuki reaction employ a palladium catalyst. In some embodiments, a palladium catalyst is PdCl₂dppf. Step S-4 typically employs a base. In some embodiments, the base is K₂CO₃.

At step S-5, the amine group of formula F is deprotected to provide amine G. Suitable conditions for the removal of an amino protecting group are known in the art and include those described by Greene (supra).

At step S-6, amine G is coupled with a carboxylic acid to provide a compound of formula I. Suitable peptide coupling conditions are known in the art. In some embodiments, step S-6 comprises a peptide coupling reagent selected from a carbodiimide or triazole activating reagent, in the presence of a base such as DIEA or other bases familiar to one skilled in the art.

In certain embodiments, each of the aforementioned synthetic steps may be performed sequentially with isolation of each intermediate performed after each step. Alternatively, each of steps S-1, S-2, S-3, S-4, S-5, and S-6 as depicted in Scheme A above, may be performed in a manner whereby no isolation of one or more intermediates B, C, D, F, or G is performed.

In certain embodiments, all the steps of the aforementioned synthesis may be performed to prepare the desired final product. In other embodiments, two, three, four, five, or more sequential steps may be performed to prepare an intermediate or the desired final product.

In other embodiments, the present compounds are generally prepared according to Scheme B set forth below.

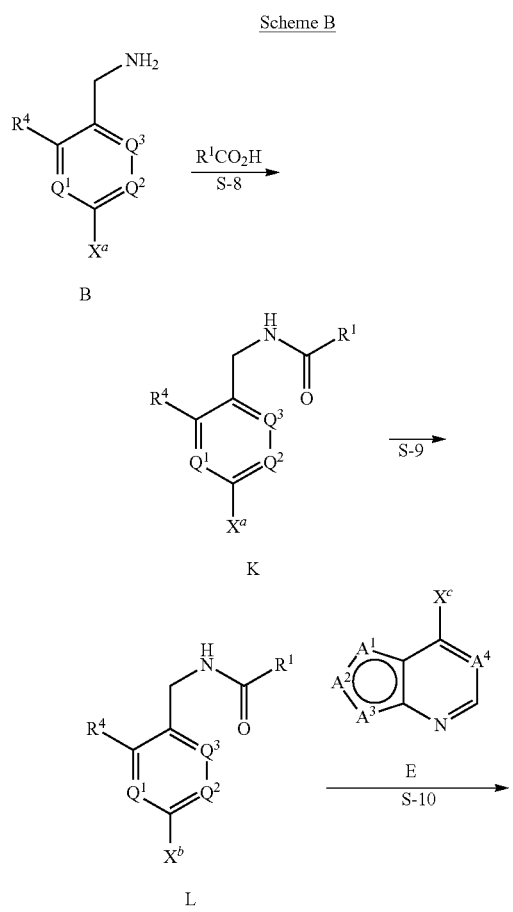

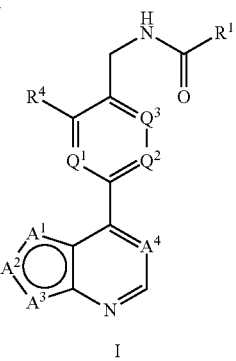

In one aspect, the present invention provides methods for preparing compounds of formula I, according to the steps depicted in Scheme B above wherein each variable is as defined and described herein.

At step S-8, amine B is coupled with a carboxylic acid to provide a compound of formula K. Suitable peptide coupling conditions are known in the art. In some embodiments, step S-8 comprises a peptide coupling reagent selected from a carbodiimide or triazole activating reagent, in the presence of a base such as DIPEA or other bases familiar to one skilled in the art.

At step S-9, formula K is optionally converted to formula L, depending upon the choice of biaryl couple chemistry to be performed in step S-10, as described above for Scheme A and step S-3.

At step S-10, formula L is coupled with amine E to provide formula M in a manner similar to that of step S-4 described above in Scheme A.

In certain embodiments, each of the aforementioned synthetic steps may be performed sequentially with isolation of each intermediate performed after each step. Alternatively, each of steps S-8, S-9, and S-10, as depicted in Scheme B above, may be performed in a manner whereby no isolation of one or more intermediates K, or L is performed.

In certain embodiments, all the steps of the aforementioned synthesis may be performed to prepare the desired final product. In other embodiments, two, three, or four sequential steps may be performed to prepare an intermediate or the desired final product.

Compounds of formula I may also be prepared according to Schemes 1-25 in the ensuing Examples.

II. Methods of Use

In certain embodiments, compounds of the present invention are for use in medicine. In some embodiments, compounds of the present invention are useful as kinase inhibitors. In certain embodiments, compounds of the present invention are selective inhibitors of Btk. In some embodiments, the present invention provides methods of decreasing Btk enzymatic activity. Such methods include contacting a Btk with an effective amount of a Btk inhibitor. Therefore, the present invention further provides methods of inhibiting Btk enzymatic activity by contacting a Btk with a Btk inhibitor of the present invention.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration ($IC_{50}$) of the Btk inhibitor against Btk is less than 1 µM. In some embodiments, the $IC_{50}$ of the Btk inhibitor against Btk is less than 500 nM. In some embodiments, the $IC_{50}$ of the Btk inhibitor against Btk is less than 100 nM. In some embodiments, the $IC_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 µM. In some embodiments, the $IC_{50}$ of the Btk inhibitor against Btk is from 0.1 nM to 1 µM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In some embodiments, Btk inhibitors are useful for the treatment of diseases and disorders that may be alleviated by inhibiting (i.e., decreasing) Btk enzymatic activity. By "diseases" is meant diseases or disease symptoms. Thus, the present invention provides methods of treating autoimmune disorders, inflammatory disorders, and cancers in a subject in need thereof. Such methods include administering to the subject a therapeutically effective amount of a Btk inhibitor.

The present disclosure includes methods of selecting a treatment regimen based on measured level of Tec kinase activity, e.g., Btk activity. For example, it is known in the art that certain diseases or disorders, e.g., diseases or disorders described herein, are mediated by, or are associated with, an increased level of Tec kinase activity, e.g., Btk activity, relative to activity in healthy, non-diseased subjects. The present disclosure provides methods of identifying and/or selecting subjects based on aberrant Tec kinase activity, e.g., Btk activity, for treatment for a particular disease or disorder.

In some embodiments, methods described herein are useful for evaluating treatment of a disease or disorder described herein, e.g., a Tec kinase related disease or disorder. Any agent, e.g., any provided compound or other test agent described herein, can be evaluated. The agent can have known pharmacological activities or can be previously unknown to have such activities.

Treatments can be evaluated for their efficacy in treating one or more diseases or disorders described herein by measuring the effect on one or more Tec kinase, e.g., Btk, e.g., Btk activity. In some embodiments, Tec kinase activity, e.g., Btk kinase activity, is measured in a biological sample, e.g., a whole blood sample, from a subject at one or more time points (e.g., prior to, concurrent with, and/or following treatment) to evaluate efficacy of treatment. In some embodiments, methods of the present disclosure are used to measure the level of Tec kinase activity, e.g., Btk activity, in whole blood after treatment to facilitate selection of a more informed treatment regimen.

In some embodiments, methods of evaluating efficacy of a provided compound, a test pharmaceutical agent, or biological agent in a subject includes determining level of Tec kinase activity (e.g., Btk activity) in a sample of whole blood from a subject. In some embodiments, the method includes obtaining a sample of whole blood from the subject. Some such methods can further include administering a provided compound or test agent to the subject and determining level of Tec kinase activity (e.g., Btk activity) in a second sample of whole blood from the subject, e.g., a second sample of whole blood obtained from the subject at a period of time following administration of the provided compound or test agent. In some embodiments, the second sample of whole blood is obtained at and/or after a period of time following administration of a provided compound or test agent sufficient to show a measurable and/or significant change in Tec kinase activity, e.g., in whole blood. The period of time may vary depending upon many factors including the expected efficacy of the provided compound or test agent, expected response time of Tec kinase activity, and/or other factors peculiar to other elements or indicia in the method. The period of time can vary, e.g., can range from about 1, 2, 3, 4, 5, 6, or 7 days to about one or two years, but could be any appropriate length of time given the provided compound or test agent and the test protocol. In some embodiments, Tec kinase levels of the two samples are compared. Tec kinase level in the second whole blood sample could increase or decrease compared to the Tec kinase level of the first whole blood sample. The efficacy of the provided compound, test pharmaceutical agent, or test biological agent to treat the condition is indicated if Tec kinase activity level is decreased in the second whole blood sample relative to the first whole blood sample.

In some embodiments, after the first level of Tec kinase activity is compared with the second level of Tec kinase activity to determine whether the provided compound or test agent is efficacious in treating a disease or disorder, a determination can also be made about the dosage or dosing regimen of the provided compound, test pharmaceutical agent, or test biological agent. For example, a determination can be made that the dosage should be increased or administered in a pattern over time, or reduced.

Additionally or alternatively, methods of the present disclosure can be performed in vitro. For example, a sample of whole blood can be contacted with a provided compound or test agent described herein, and level of Tec kinase activity can be determined. In some embodiments, level of Tec kinase activity is compared to a reference level (e.g., level of Tec kinase activity in a sample of whole blood not contacted with a provided compound or test agent), and the effect of the provided compound or test agent on Tec kinase activity is determined.

In some embodiments, methods described herein are used to determine pharmacokinetic and/or pharmacodynamic profiles of a provided compound or test agent described herein, e.g., a pharmaceutical or biological agent undergoing regulatory review. Pharmacokinetics and/or pharmacodynamics may be used to determine the administration of a provided compound or test agent to a subject. For example, in some embodiments, methods of the present disclosure facilitate analysis of efficacy of a provided compound or test agent to inhibit a Tek kinase activity, e.g., Btk activity, e.g., in the treatment of a disease or disorder described herein. In some embodiments, a sample of whole blood is from a subject being treated as part of a clinical trial, and determining Tec kinase activity is used to evaluate whether a provided compound or test agent is efficacious in humans.

In some embodiments, results are used to make a decision, e.g., selecting between a first course of action and a second course of action. In a preferred embodiment, the decision includes comparing the data to a reference and making the decision based on the relationship of the data to the reference. For example, the data can be a value or other term for the likelihood of response and if the value or other term has a preselected relationship to the reference, e.g., if the value or term in the data is greater than a reference, selecting a first course of action and if the data is less than a reference selecting a second course of action. A course of action can be, e.g., providing or not providing service or treatment, e.g., a Tec kinase inhibitor, or paying for or not paying for all or part of a service or treatment, a Tec kinase inhibitor.

In a some embodiments, the first course of action is suggesting or providing a first course of medical treatment, e.g., treatment with a Tec kinase inhibitor, and the second course of action is suggesting or deciding that the treatment not be given or not providing the treatment.

In some embodiments, the first course of action includes or results in the authorization or transfer of funds to pay for a service or treatment, e.g., treatment with a Tec kinase inhibitor, provided to a subject and the second course of action includes or results in the refusal to pay for a service or treatment provided to a subject. For example, an entity, e.g., a hospital, caregiver, government entity, or an insurance company or other entity, that pays for, or reimburses, medical expenses can use the outcome of a method described herein to determine whether a party, e.g., a party other than the subject, will pay for services or treatment provided to the subject. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, a physician, or other care-giver, for a service or treatment provided to a patient.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), hemolytic anemia, autoimmune hepatitis, bullous pemphigoid (BP), Coeliac disease, dermatomyositis, diabetes mellitus type 1, Goodpasture's syndrome, Graves' disease, Guillain-Barré syndrome (GBS), Hashimoto's disease, idiopathic thrombocytopenic purpura, lupus erythematosus, mixed connective tissue disease, multiple sclerosis, myasthenia gravis, pemphigus vulgaris, hemophilia with inhibitors, pernicious anaemia, polymyositis, primary biliary cirrhosis, Sjögren's syndrome, temporal arteritis, and Wegener's granulomatosis.

The term "inflammatory disorders" includes diseases or disorders involving acute or chronic inflammation such as, but not limited to, allergies, asthma (e.g., allergic asthma), atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection (including transplant patients with a positive cross-match) and vasculitis. In certain embodiments, the present disclosure provides methods of evaluating treatment of disease, disorders, or conditions that approved for treatment with rituximab (a monoclonal antibody against CD20), including non-Hodgkin's lymphoma (NHL), chronic lymphocytic leukemia (CLL), RA, Wegener's granulomatosis (WG), and microscopic polyangiitis (MPA). In some embodiments, the present disclosure provides methods of evaluating treatment of rheumatoid arthritis (RA), SLE, and/or atopic dermatitis using one or more Tec kinase inhibitor.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, B cell derived lymphoma (e.g., ABC-DLBCL, GC-DLBCL, Burkitt's, Follicular, CLL, and Mantle Zone), and colon cancer (e.g. microsatellite instability-high colorectal cancer). In some embodiments, the present invention provides a method of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

III. Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

In some embodiments, a test agent as described herein can be incorporated into a pharmaceutical composition for administration by methods known to those skilled in the art and described herein for provided compounds.

IV. Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

V. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any provided compound or test agent, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

VI. Assays

To develop useful Tec kinase family inhibitors, candidate inhibitors capable of decreasing Tec kinase family enzymatic activity may be identified in vitro. The activity of the inhibitor compounds can be assayed utilizing methods known in the art and/or those methods presented herein.

Compounds that decrease Tec kinase family members' enzymatic activity may be identified and tested using a biologically active Tec kinase family member, either recombinant or naturally occurring. Tec kinases can be found in native cells, isolated in vitro, or co-expressed or expressed in a cell. Measuring the reduction in the Tec kinase family member enzymatic activity in the presence of an inhibitor relative to the activity in the absence of the inhibitor may be performed using a variety of methods known in the art, such as the POLYGAT-LS assays described below in the Examples. Other methods for assaying the activity of Btk and other Tec kinases are known in the art. The selection of appropriate assay methods is well within the capabilities of those of skill in the art.

Once compounds are identified that are capable of reducing Tec kinase family members' enzymatic activity, the compounds may be further tested for their ability to selectively inhibit a Tec kinase family member relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to a Tec kinase family member activity. In addition to cell cultures, animal models may be used to test Tec kinase family member inhibitors for their ability to treat autoimmune disorders, inflammatory disorders, or cancer in an animal model.

The activation states of Tec kinases are determined by phosphorylation states at one or more amino acid residues (see, e.g., Joseph et al., J. Mol. Biol. 403:231-242 (2010); Joseph et al., J. Mol. Biol. 373:1281-1292 (2007); Wahl et al., Proc. Natl. Acad. Sci. USA 94:11526-33 (1997)). For example, Btk activity is mediated by trans-phosphorylation at Tyr551 and autophosphorylation at Tyr223. Accordingly, in some methods described herein, Tec kinase activity is determined by measuring or detecting level of phosphorylation at one or more of such amino acid residues.

In some embodiments, the disclosure provides methods of determining level of Tec kinase activity, e.g., Btk activity, and correlating the results obtained therein with a diagnosis or prognostic assessment of a disease or disorder described herein. In some embodiments, the disclosure provides methods of determining efficacy of a test agent to modulate level of Tec kinase activity, e.g., Btk activity, and correlating the results obtained therein with effectiveness of the test agent to treat a disease or disorder described herein.

Generally, such methods include a step of detecting activity of a Tec kinase, e.g., Btk, in a sample of whole blood. In certain embodiments it may prove advantageous to combine detection of Tec kinase activity, e.g., Btk activity, with detection of one or more diagnostic parameters for a particular disease or disorder described herein.

a. Tec Kinase Analysis

As is well known in the art, a polypeptide may be detected using any of a variety of techniques and binding agents. Any such technique and/or agent can be used in methods to determine Tec kinase activity according to the present disclosure. In certain embodiments, a binding agent is an antibody that binds specifically to a Tec kinase, e.g., Btk, e.g., a phosphorylated Btk. For example, the presence of a Tec kinase, e.g., Btk, can be detected by contacting a biological sample, e.g., a whole blood sample, with an antibody that specifically recognizes the Tec kinase polypeptide, e.g., using standard electrophoretic and liquid or solid immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassay; immunoelectrophoresis; and immunoprecipitation. In some embodiments, Tec kinase is detected in a biological sample using immunoprecipitation with an antibody that specifically recognizes a Tec kinase, followed by measuring phosphorylated Tec kinase using an anti-phosphotyrosine antibody.

The disclosure also encompasses the use of protein arrays, including antibody arrays, for detection of Tec kinase activity, e.g., Btk activity. The use of antibody arrays is described, for example, in Haab et al., Genome Biol. 2(2): RESEARCH0004 (2001). Other types of protein arrays are known in the art. In general, antibodies that bind specifically to a Tec kinase, e.g., phosphorylated Tec kinase, can be generated by methods well known in the art and described, for example, in Harlow, E, Lane, E, and Harlow, E, (eds.) Using Antibodies: A Laboratory Manual, Cold Spring Harbor Laboratory Press, Cold Spring Harbor, 1998. Details and references for the production of antibodies may also be found in U.S. Pat. No. 6,008,337. Antibodies may include, but are not limited to, polyclonal, monoclonal, chimeric (e.g., "humanized"), single chain antibodies, Fab fragments, antibodies generated using phage display technology, etc.

Antibodies that recognize Tec kinases, e.g., Btk, are known and commercially available (e.g., D3H5 and C82B8 from Cell Signaling Technology, Danvers, Mass.; E-9 from Santa Cruz Biotechnology, Dallas, Tex.; 7F12H4 from Novus Biologicals, Littleton, Colo.; and 53/BTK from BD Biosciences, San Jose, Calif.); anti-phosphotyrosine antibodies are known and commercially available (e.g., rabbit phospho-Btk (Tyr223) antibody 5082 from Cell Signaling Technology, Danvers, Mass.; rabbit anti-Btk (phospho Y223) (ab68217) available from Abcam, Cambridge, Mass.; Wahl et al., Proc. Natl. Acad. Sci. USA 94:11526-11533 (1997); Nisitani et al., Proc. Natl. Acad. Sci. USA 96:2221-6 (1999)).

Antibody detection methods are well known in the art including, but are not limited to, enzyme-linked immunosorbant assays (ELISAs) and Western blots. Some such methods are amenable to being performed in an array format.

In addition, in some embodiments, Tec kinases, e.g., Btk, are detected using other specific binding agents known in the art for the detection of polypeptides, such as aptamers (Aptamers, Molecular Diagnosis, Vol. 4, No. 4, 1999), reagents derived from combinatorial libraries for specific detection of proteins in complex mixtures, random peptide affinity reagents, etc. In general, any appropriate binding agent for detecting a polypeptide may be used in conjunction with methods described herein, although antibodies may represent a particularly appropriate modality.

In certain embodiments, a single binding agent (e.g., antibody) is used whereas in other embodiments, multiple binding agents, directed either against the same or against different Tec kinases can be used to increase the sensitivity or specificity of the detection technique or to provide more detailed information than that provided by a single binding agent. Thus the disclosure encompasses use of a battery of binding agents that bind to Tec kinases.

In general, Tec kinase activity, e.g., Btk activity, is detected in a sample of whole blood that has been obtained from a subject. Similar methods may be applied to other biological samples, e.g., ascites, urine, saliva, etc.

In certain embodiments, binding of a Tec kinase binding agent to a Tec kinase (e.g., binding of a Btk binding agent to Btk) can be detected by adding a detectable label to a binding agent. In some embodiments, binding can be detected by using a labeled secondary binding agent that associates specifically with a primary binding agent, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Indirectly detectable labels include chemiluminescent labels, e.g., enzymes that are capable of converting a substrate to a chromogenic product such as alkaline phosphatase, horseradish peroxidase and the like.

Once a labeled binding agent has bound a Tec kinase, the complex can be visualized or detected in a variety of ways, with the particular manner of detection being chosen based on the particular detectable label. Representative detection means include, e.g., scintillation counting, autoradiography, measurement of paramagnetism, fluorescence measurement, light absorption measurement, measurement of light scattering and the like. Depending upon the nature of the sample, appropriate detection techniques include, but are not limited to, immunohistochemistry (IHC), radioimmunoassay, ELISA, immunoblotting and fluorescence activated cell sorting (FACS). Additional exemplary detection methods include electrochemiluminescence immunoassays as described and available from, e.g., Meso Scale Discovery, Rockville, Md.

In certain embodiments, detection techniques of the methods described herein include a negative control, which can involve analysing Tec kinase activity in a reference sample (e.g., from a subject not administered a test agent) so that the signal obtained thereby can be compared with the signal obtained from a sample of whole blood being tested. In tests in which a secondary binding agent is used to detect a primary binding agent that binds to a Tec kinase, an appropriate negative control can involve performing the test on a portion of a sample with the omission of the primary binding agent.

In general, the results of the detection methods described herein can be presented in any of a variety of formats. The results can be presented in a qualitative fashion. For example, the test report may indicate only whether or not a Tec kinase activity was detected, perhaps also with an indication of the limits of detection. The results may be presented in a semi-quantitative fashion. For example, various ranges may be defined, and the ranges may be assigned a score (e.g., 0 to 3 where 0 means no activity detected and 3 means high level of activity detected) that provides a certain degree of quantitative information. Such a score may reflect various factors, e.g., the number of cells in which activity is detected, the intensity of the signal (which may indicate the level of activity), etc. The results may be presented in a quantitative fashion, e.g., as protein concentration, etc. As will be appreciated by one of ordinary skill in the art, the type of output provided by a test will vary depending upon the technical limitations of the test and the biological significance associated with detection of Tec kinase activity. In some embodiments, a purely qualitative output (e.g., whether or not activity is detected at a certain detection level) provides significant information. In other embodiments, a more quantitative output (e.g., a ratio of the level of activity in the sample being tested versus the normal level) is determined.

b. Detectable Moieties

In some embodiments, certain binding agents used in methods of the disclosure comprise one or more detectable entities or moieties, i.e., such molecules are "labeled" with such entities or moieties. Any of a wide variety of detectable entities or moieties can be used in the practice of methods of the present disclosure. Suitable detectable entities or moieties include, but are not limited to, various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

In some embodiments, a detectable moiety is a fluorescent dye. Numerous known fluorescent dyes of a wide variety of chemical structures and physical characteristics are suitable for use in the practice of methods of the present disclosure. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

A detectable moiety can include more than one chemical entity such as in fluorescent resonance energy transfer (FRET). Resonance transfer results an overall enhancement of the emission intensity. See, e.g., Ju et al., Proc. Natl. Acad. Sci. USA 92: 4347 (1995). To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526. Donor/acceptor pairs of dyes that can be used include, for example, fluorescein/tetramethylrohdamine, IAEDANS/fluroescein, EDANS/DABCYL, fluorescein/fluorescein, BODIPY FL/BODIPY FL, and Fluorescein/QSY 7 dye. See, e.g., U.S. Pat. No. 5,945,526. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

In some embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme can be conjugated to a molecule using a linker group such as a carbodiimide, a diisocyanate, a glutaraldehyde, and the like.

In some embodiments, a detectable moiety is a radioactive isotope. For example, a molecule can be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (e.g., $^3$H, $^{13}$C, $^{14}$C, $^{18}$F, $^{19}$F, $^{32}$P, $^{35}$S, $^{64}$Cu, $^{67}$Cu, $^{67}$Ga, $^{90}$Y, $^{99m}$Tc, $^{111}$In, $^{125}$I, $^{123}$I, $^{129}$I, $^{131}$I, $^{135}$I, $^{186}$Re, $^{187}$Re, $^{201}$Tl, $^{212}$Bi, $^{213}$Bi, $^{211}$At, $^{153}$Sm, $^{177}$Lu).

c. Whole Blood Assays

Among other things, the present disclosure includes the demonstration that Tec kinase activity, e.g., Btk activity, can be measured in whole blood without having to isolate particular cells or having to simulate or activate the Tec kinase, e.g., Btk, prior to the measurement. The ability to determine level (e.g., a decreased level) of Tec kinase activity, e.g., Btk activity, in whole blood without pre-stimulation can be utilized in a variety of methods that, among other things, are quicker, easier, and less complicated than standard methods. According to the present invention, level of Tec kinase activity, e.g., Btk activity, in whole blood can be used in diagnostic and therapeutic methods, such as methods to evaluate efficacy of treatment.

In some embodiments, level of one or more Tec kinase activity in whole blood, e.g., a sample of whole blood, is useful for diagnosis and prognosis of diseases and disorders described herein. In some embodiments, levels of Tec kinase activity in whole blood are useful for determining the likelihood of a subject developing a disease or disorder described herein.

In some embodiments, the disclosure includes methods comprises determining a level of a Tec kinase, e.g., Btk, in a sample of whole blood from a subject; comparing the determined Tec kinase activity level, e.g., Btk activity level, with that of a reference correlated with predetermined probability of having or at risk of developing a disease or disorder described herein; and based on the comparing, determining that the subject has an increased or decreased probability, relative to the reference, of having or at risk of developing a disease or disorder described herein. Moreover, the present disclosure offers the possibility of providing additional diagnostic, prognostic, or predictive information based on modification of existing protocols to include determination of Tec kinase activity, e.g., Btk activity, according to methods described herein.

In some embodiments, analysis of Tec kinase activity, e.g., Btk activity, comprises identifying whether Tec kinase activity, e.g., Btk activity, in a sample of whole blood is increased or decreased relative to a reference or baseline. The reference may be derived from average Tec kinase activity across a population of individuals or may be Tec kinase activity in at least one prior whole blood sample derived from the subject. The analyses of samples from single individuals or across a population (i.e., large group of individuals) provides a library of data sets for use as a reference or baseline. Different levels of Tec kinase activity, e.g., Btk activity, relative to the reference can then be determined, which provides a qualitative or quantitative comparative value that is informative about the diagnosis of a disease or disorder described herein, long-term prognosis, response to therapy, etc. Levels of Tec kinase activity can be cross-referenced with analysis of one or more markers or indicators of a disease or disorder to provide a synergistic diagnosis. Levels of Tec kinase activity relative to a reference can also be annotated with medical information about the subject.

Determining whether level of Tec kinase activity, e.g., Btk activity, in a sample of whole blood is increased or decreased, relative to a reference, can be performed using a statistical test to determine statistical significance of any difference observed and/or measured. In some embodiments, statistical significance is determined using a parametric statistical test. The parametric statistical test can comprise, for example, a fractional factorial design, analysis of variance (ANOVA), a t-test, least squares, a Pearson correlation, simple linear regression, nonlinear regression, multiple linear regression, or multiple nonlinear regression. Additionally or alternatively, the parametric statistical test can comprise a one-way analysis of variance, two-way analysis of variance, or repeated measures analysis of variance. In some embodiments, statistical significance is determined using a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test. In some embodiments, statistical significance is determined at a p-value of less than about 0.05, 0.01, 0.005, 0.001, 0.0005, or 0.0001.

In some embodiments, determining whether level of Tec kinase activity, e.g., Btk activity, in a sample of whole blood is increased or decreased, relative to a reference, can also be performed by analysing the degree of any differences in activity. For example, Tec kinase activity, e.g., Btk activity, can be considered to be increased in a sample of whole blood when the fold-change in level of activity is at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold compared to a reference.

d. Test Agents

In some embodiments, Tec kinase activity (e.g., Btk activity) is determined in whole blood (e.g., a sample of whole blood) after being contacted with a test agent. In some embodiments, Tec kinase activity (e.g., Btk activity) is determined in whole blood (e.g., a sample of whole blood) from a subject to whom a test agent has been administered. Any test agent can be employed in methods described herein, and methods of the disclosure are not limited to any particular test agent. In some embodiments, one or more test agents can be evaluated in combination. For example, a test agent can be evaluated in combination with a second agent, e.g., a second agent having a known effect on Tec kinase activity.

In some embodiments, a test agent is a known or putative Tec kinase inhibitor, e.g., Btk inhibitor. Exemplary Btk inhibitors include, but are not limited to, Ibrutinib (Pharmacyclics/Janssen), CC-292 (formerly AVL-292, Avila/Celgene), CGI-1746 (CGI Pharmaceuticals), GDC-0834 (Genentech), RN486 (Roche/Genenetech), and Dasatinib (formerly BMS-354825, BMS). In some embodiments, a test agent can be any clinically acceptable pharmaceutical or therapeutic agent for testing in humans or animals in an effort to treat a disease or disorder described herein. In some embodiments, a test agent is a compound disclosed herein. In some embodiments, a test agent is a compound disclosed in WO 2011/029043, or WO 2012/058645, the entire contents of each of which are hereby incorporated by reference.

A test agent can be, e.g., a small molecule or a biological agent. A biological agent may be any biologically active molecule, also having the potential to act as a drug in the body, but the activity of a biological agent is a biological activity such as, for example an ability to bind to another molecule that it contacts. Biological agents can be, for example, proteins, or parts of proteins, peptides, polypeptides, nucleic acids, lipids, fatty acids, or other molecules having an origin in molecules found within the body. In some embodiments, the test agent can be considered a candidate for the clinical study if it is believed that it can treat a disease or disorder described herein, or a symptom thereof.

Test agents that can be used in methods described herein include, e.g., crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these.

In one example, combinatorial chemical libraries can be produced or obtained that sample chemical compounds that are structurally or chemically related or unrelated. Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res. 37:487-493 (1991); and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Thus, the present invention provides, among other things, the following embodiments, both singly and in combination:

i. a method of detecting Bruton's tyrosine kinase (Btk) activity in whole blood, the method comprising contacting a sample of whole blood with a Btk binding agent; and detecting binding of the Btk binding agent to Btk, thereby detecting Btk activity, wherein the method does not include activating the Btk;

ii. the method of embodiment i, wherein the Btk binding agent detects phosphorylated Btk;

iii. the method of embodiment i or ii, wherein the Btk binding agent is an antibody;

iv. the method of any one of embodiments i-iii, wherein the sample of whole blood is a sample of human whole blood;

v. the method of any one of embodiments i-iv, wherein the sample of whole blood is from a subject having or at risk of developing an autoimmune disorder;

vi. the method of any one of embodiments i-v, wherein the sample of whole blood is from a subject treated with a Btk inhibitor;

vii. the method of any one of embodiments i-vi, further comprising comparing a level of detected Btk activity to a reference level;

viii. the method of embodiment vii, wherein the reference level is a level of Btk activity detected in a sample of whole blood from a subject not having or at risk of developing an autoimmune disorder;

ix. the method of embodiment vii, wherein the reference level is a level of Btk activity detected in a sample of whole blood from a subject not treated with a Btk inhibitor;

x. a method of detecting modulation of Btk activity in whole blood, the method comprising contacting a sample of whole blood with a test agent, wherein the whole blood sample comprises Btk; measuring Btk activity level in the whole blood sample after the contacting step; and comparing measured Btk activity level to a reference level, wherein a difference of the measured Btk activity level relative to the reference level indicates the test agent modulates Btk activity;

xi. the method of embodiment x, wherein the measuring step comprises contacting the whole blood sample with a Btk binding agent;

xii. the method of embodiment xi, wherein the Btk binding agent detects phosphorylated Btk;

xiii. the method of embodiment xi or xii, wherein the Btk binding agent is an antibody;

xiv. the method of any one of embodiments x-xiii, wherein the test agent is a small molecule or a biologic;

xv. the method of any one of embodiments x-xiv, wherein the test agent is a Btk inhibitor;

xvi. the method of any one of embodiments x-xv, wherein the whole blood sample is a human whole blood sample;

xvii. the method of any one of embodiments x-xvi, wherein a measured Btk activity level that is reduced relative to the reference level indicates the test agent inhibits Btk activity;

xviii. the method of any one of embodiments x-xvii, wherein the method does not comprise activating the Btk;

xix. the method of any one of embodiments x-xviii, wherein the reference level is Btk activity level in a whole blood sample not contacted with the test agent;

xx. the method of any one of embodiments x-xix, wherein the sample of whole blood is from a subject having or at risk of developing an autoimmune disorder;

xxi. a method of detecting modulation of Btk activity in whole blood, the method comprising administering a test agent to a subject; measuring Btk activity level in a sample of whole blood from the subject after the administering step; and comparing measured Btk activity level to a reference level, wherein a difference of the measured Btk activity level relative to the reference level indicates the test agent modulates Btk activity;

xxii. the method of embodiment xxi, wherein the measuring step comprises contacting the whole blood sample with a Btk binding agent;

xxiii. the method of embodiment xxii, wherein the Btk binding agent detects phosphorylated BTK;

xxiv. the method of embodiment xxii or xxiii, wherein the Btk binding agent is an antibody;

xxv. the method of any one of embodiments xxi-xxiv, wherein the test agent is a small molecule or a biologic;

xxvi. the method of any one of embodiments xxi-xxv, wherein the test agent is a Btk inhibitor;

xxvii. the method of any one of embodiments xxi-xxvi, wherein the subject is a human;

xxviii. the method of any one of embodiments xxi-xxvii, wherein a measured Btk activity level that is reduced relative to the reference level indicates the test agent inhibits Btk activity;

xxix. the method of any one of embodiments xxi-xxviii, wherein the method does not comprise activating the Btk;

xxx. the method of any one of embodiments xxi-xxix, wherein the reference level is Btk activity level in a whole blood sample from a subject not administered the test agent;

xxxi. the method of any one of embodiments xxi-xxx, wherein the subject has or is at risk of developing an autoimmune disorder;

xxxii. the method of any one of embodiments xxi-xxxi, further comprising repeating the measuring step on a second sample of whole blood from the subject;

xxxiii. a method of detecting Btk activity in whole blood, the method comprising measuring a first Btk activity level in a first sample of whole blood from a subject; administering a test agent to the subject; measuring a second Btk activity level in a second sample of whole blood from the subject; and comparing the first and second Btk activity levels;

xxxiv. the method of embodiment xxxiii, wherein the method does not comprise activating the Btk;

xxxv. a method of evaluating efficacy of a test agent to inhibit Btk activity, the method comprising providing a sample of whole blood from a subject treated with a test agent; measuring Btk activity level in the sample; and comparing the Btk activity level to a reference, thereby evaluating efficacy of the test agent;

xxxvi. the method of embodiment xxxv, wherein a measured Btk activity level that is decreased relative to the reference identifies the test agent as an inhibitor of Btk.

EXAMPLES

The examples below are meant to illustrate certain embodiments of the invention, and not to limit the scope of the invention. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

It will be appreciated that where an Example refers to another Example by referring to "Example I-XX", the reference is to the synthesis of the respective Compound I-XX, or the relevant portion of the synthesis.

Example 1

Scheme 1

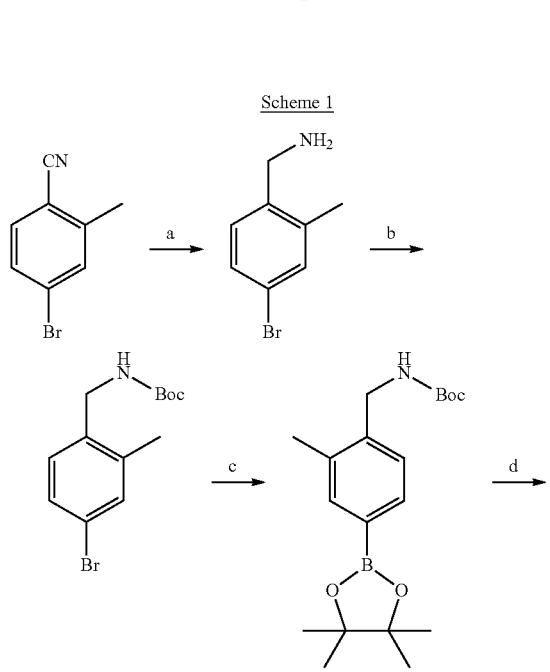

Reagent and condition: (a) BH₃, THF 0-80° C. (b) Boc anhydride, Et₃N, DCM. (c) 4,4,4',4',5,5,5',5'-octamethyl-2,2'-bi(1,3,2-dioxaborolane), PdCl₂(dppf), K₂CO₃, dioxane/water 90° C., 2h. (d) 4-Chloro-7-tosyl-7H-pyrrolo[2,3-d]pyrimidine, PdCl₂(dppf), K₂CO₃, dioxane/water 90° C., 2h. (e) N₂H₄, EtOH, rt. (e) TFA, DCM, rt, 30 min. (f) 5-(tert-butyl)picolinic acid, CDI, Et₃N, DMF, rt, 12h.

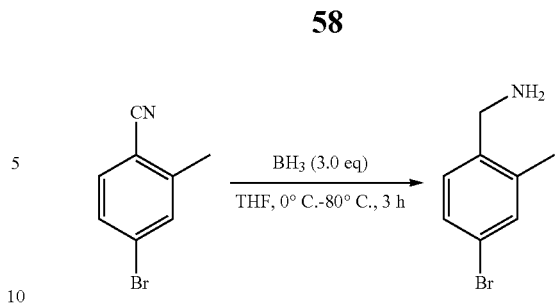

The Synthesis of (4-bromo-2-methylphenyl)methanamine

To a solution of 4-bromo-2-methylbenzonitrile (3 g, 15 mmol) in THF (20 mL) was added BH₃.THF (45 mL, 45 mmol) at 0° C. The solution was stirred for 1 h and heated to 80° C. for 2 h. The mixture was quenched with H₂O and extracted with EtOAc (50 mL×3). The organic layer was concentrated in vacuo to afford a residue which was suspended in saturated HCl/EtOAc and filtered. The filter cake was washed with diethyl ether (20 mL×3) and dried under vacuum to afford the desired product (2.1 g, yield 69%) as white solid. ESI-MS (M+H)⁺: 200.1.

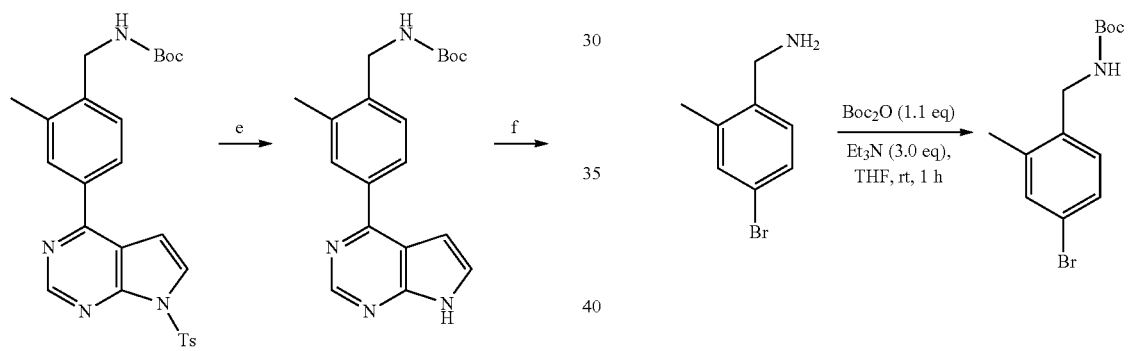

The Synthesis of tert-butyl 4-bromo-2-methylbenzylcarbamate

To a solution of amine (1.2 g, 6 mmol) in CH₂Cl₂ (30 mL) were added TEA (1.82 g, 18 mmol) and Boc₂O (1.43 g, 6.6 mmol). The mixture was stirred at rt for 1 h, diluted with water (50 mL) and extracted with CH₂Cl₂ (50 mL×2). The organic phase was washed with brine (50 mL), dried (Na₂SO₄), filtered and concentrated in vacuo to afford the title product (1.7 g, yield 95%) as a white solid, which was used directly in the next step without further purification. ESI-MS (M+H)⁺: 300.1.

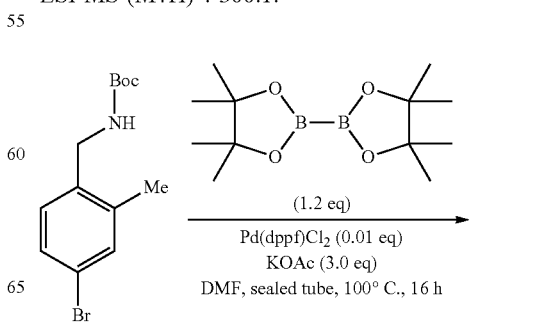

The Synthesis of tert-butyl 2-methyl-4-(4,4,5,5-tetramethyl-1,3,2-dioxaborolan-2-yl)benzylcarbamate

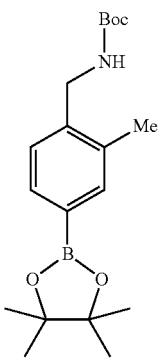

To a solution of aryl bromide (1.5 g, 5.0 mmol) in DMF (6 mL) were added 4,4,4',4',5,5,5',5'-octamethyl-2,2'-bi(1,3,2-dioxaborolane) (1.52 g, 6.0 mmol), KOAc (1.75 g, 18 mmol) and Pd(dppf)Cl$_2$DCM (407 mg, 0.5 mmol) under nitrogen. The mixture was stirred at 100° C. for 2 h, allowed to cool to rt, diluted with water (50 mL) and extracted with EtOAc (100 mL×3). The combined organic layer was washed with brine, dried, concentrated in vacuo and purified by silica gel column (petroleum ether/EtOAc, 10:1) to give the tittle compound (1.2 g, yield: 69%) as white solid. ESI-MS (M+H)$^+$: 348.2. $^1$H NMR (400 MHz, CDCl$_3$) δ: 7.61-7.59 (m, 2H), 7.26 (s, 1H), 4.68 (br, 1H), 4.33 (d, J=5.6 Hz, 2H), 2.32 (s, 3H), 1.45 (s, 9H), 1.34 (s, 12H).

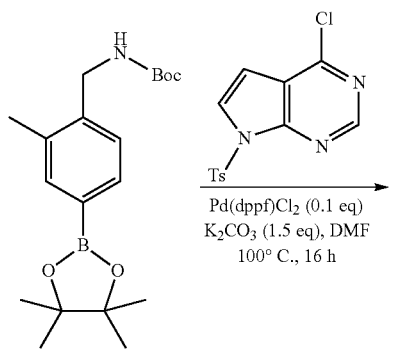

The Synthesis of tert-butyl 2-methyl-4-(7-tosyl-7H-pyrrolo[2,3-d]pyrimidin-4-yl)benzylcarbamate To a solution of boronate (1.7 g, 4.9 mmol) in dioxane/H$_2$O (4:1) (15 mL) was added 4-chloro-7-tosyl-7H-pyrrolo[2,3-d]pyrimidine (1.5 g, 4.9 mmol) followed by Pd(dppf)Cl$_2$DCM (457 mg, 0.5 mmol) and K$_2$CO$_3$ (2.0 g, 14.7 mmol) under nitrogen. The mixture was stirred at 90° C. for 6 h. After cooling to rt, the mixture was diluted with water and extracted with EtOAc (100 mL×2). The organic layer was washed with brine (80 mL), dried (Na$_2$SO$_4$), filtered and concentrated. The residue was purified by column chromatography (petroleum ether/EtOAc, 3:1) to give the title compound (1.8 g, yield: 75%) as an orange oil. ESI-MS (M+H)$^+$: 493.2

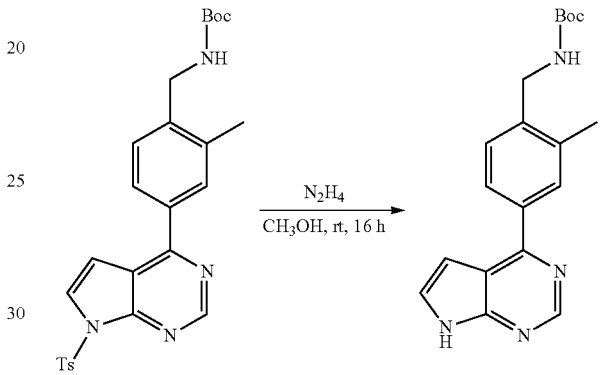

The Synthesis of tert-butyl 2-methyl-4-(7H-pyrrolo[2,3-d]pyrimidin-4-yl)benzylcarbamate To a suspension of tert-butyl 2-methyl-4-(7-tosyl-7H-pyrrolo[2,3-d]pyrimidin-4-yl)benzylcarbamate (1.1 g, 2.2 mmol) in CH$_3$OH (10.0 mL) was added N$_2$H$_4$·H$_2$O (5 mL). The reaction mixture was stirred at rt for 16 h. Then the solvent was concentrated via rotary evaporator and the residue was purified by column chromatography (petroleum ether/EtOAc, 1:1) to afford the title compound (567 mg, yield 77%) as a yellow solid. ESI-MS (M+H)$^+$: 339.2. $^1$H NMR (400 MHz, CDCl$_3$) δ: 10.48 (br, 1H), 8.93 (s, 1H), 7.96 (s, 1H), 7.46-7.36 (m, 3H), 6.85 (s, 1H), 4.88 (br, 1H), 4.41 (d, J=5.6 Hz, 2H), 2.45 (s, 3H), 1.49 (s, 9H).

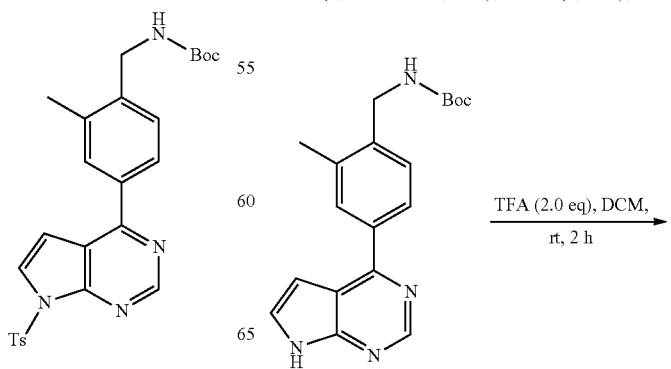

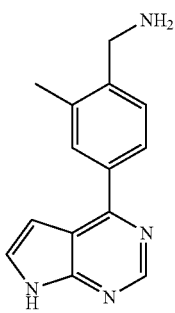

The Synthesis of (2-methyl-4-(7H-pyrrolo[2,3-d]pyrimidin-4-yl)phenyl)methanamine A solution of tert-butyl 2-methyl-4-(7H-pyrrolo[2,3-d]pyrimidin-4-yl)benzylcarbamate (567 mg, 1.7 mmol) in CH$_2$Cl$_2$ (5 mL)/TFA (5 mL) was stirred at rt for 2 h. The mixture was concentrated in vacuo to afford the title compound (305 mg, yield 76%) as an orange oil which was used in next step without further purification, ESI-MS (M+H)$^+$: 239.2

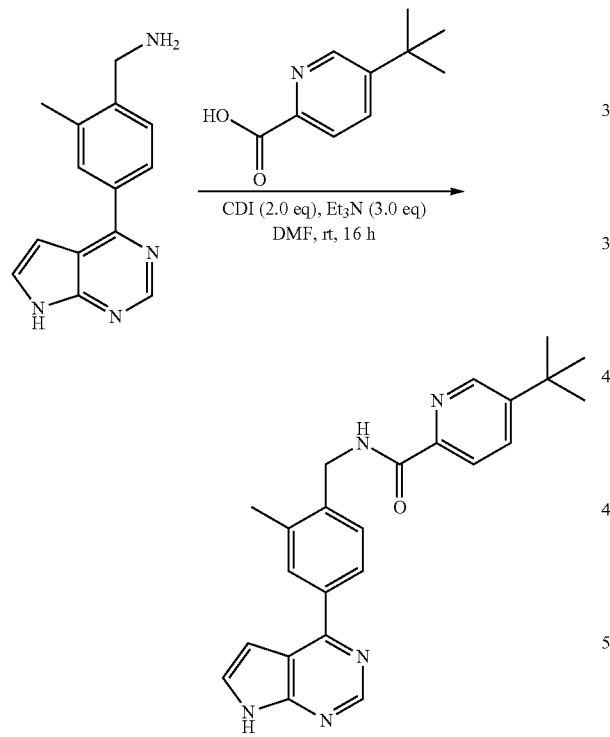

I-1

The Synthesis of 5-(tert-butyl)-N-(2-methyl-4-(7H-pyrrolo[2,3-d]pyrimidin-4-yl)benzyl)picolinamide (I-1)

A solution of carboxylic acid (80 mg, 0.45 mmol) and CDI (145 mg, 0.90 mmol) in DMF (4 mL) was stirred at rt for 0.5 h, followed by the addition of the amine (110 mg, 0.45 mmol) and Et$_3$N (137 mg, 1.35 mmol) and the mixture was stirred at rt for 16 h. After diluted with water (5 mL), the mixture was extracted with EtOAc (5 mL×2). The combined organics were concentrated in vacuo and the residue was purified by reverse phase chromatography (MeOH/H$_2$O with 0.05% NH$_3$.H$_2$O as mobile phase) to afford the title compound (26 mg, yield 15%) as a yellow solid. ESI-MS (M+H)$^+$: 400.2. $^1$H NMR (400 MHz, CD$_3$OD) δ: 8.77-8.74 (m, 2H), 8.06-8.03 (m, 2H), 7.92-7.95 (m, 2H), 7.54-7.51 (m, 2H), 6.86 (d, J=4.0 Hz, 1H), 4.74 (s, 2H), 2.53 (s, 3H), 1.42 (s, 9H).

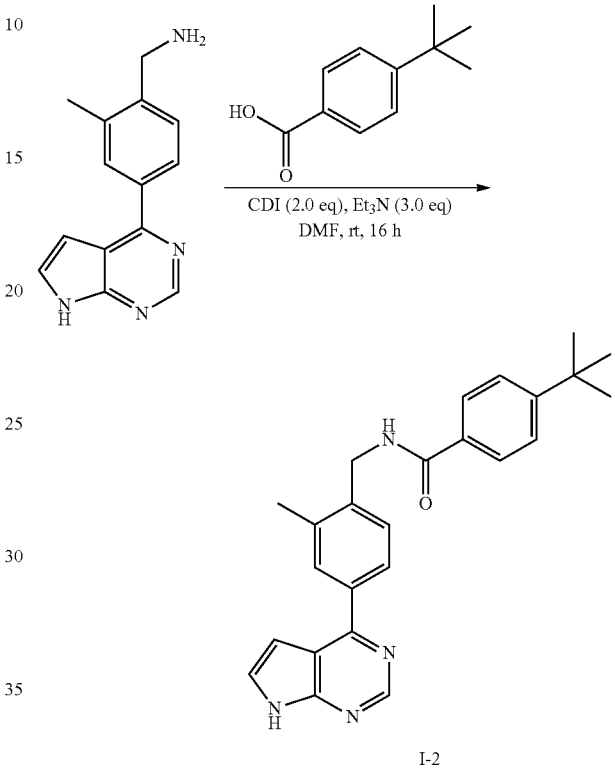

I-2

The Synthesis of 4-(tert-butyl)-N-(2-methyl-4-(7H-pyrrolo[2,3-d]pyrimidin-4-yl)benzyl)benzamide (I-2)

Compound I-2 was prepared in a similar manner as described above for compound I-1 except 4-(tert-butyl)benzoic acid was substituted for 5-(tert-butyl)picolinic acid. ESI-MS (M+H)$^+$: 399.2. $^1$H NMR (400 MHz, CDCl$_3$) δ: 9.43 (br, 1H), 8.98 (s, 1H), 8.02 (s, 1H), 7.93 (d, J=8.0 Hz, 1H), 7.76 (d, J=8.4 Hz, 2H), 7.48-7.40 (m, 3H), 7.39 (d, J=3.2 Hz, 1H), 6.87 (d, J=3.2 Hz, 1H), 6.29 (br, 1H), 4.75 (d, J=5.2 Hz, 2H), 2.50 (s, 3H), 1.34 (s, 9H).

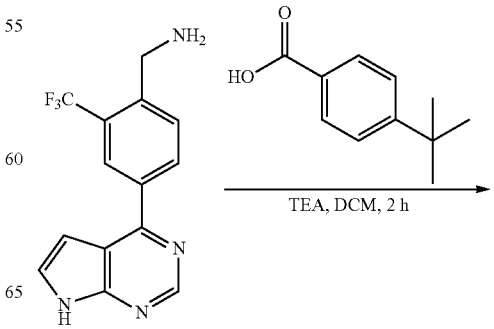

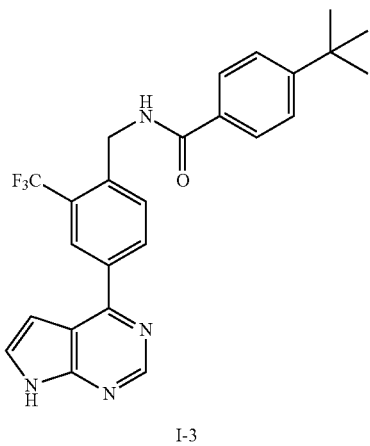

I-3

The Synthesis of N-(4-(7H-pyrrolo[2,3-d]pyrimidin-4-yl)-2-(trifluoromethyl)benzyl)-4-(tert-butyl)benzamide (I-3)

Compound I-3 was prepared in a similar manner as described above for compound I-1 except 4-bromo-2-(trifluoromethyl)benzonitrile was substituted for 4-bromo-2-methylbenzonitrile. ESI-MS (M+H)+: 453.1. $^1$H NMR (400 MHz, CD$_3$OD) δ: 8.83 (s, 1H), 8.47 (d, J=1.2 Hz, 1H), 8.36 (d, J=8.4 Hz, 1H), 7.89 (d, J=6.8 Hz, 2H), 7.78 (d, J=4.0 Hz, 1H), 7.60-7.55 (m, 3H), 6.88 (d, J=3.6 Hz, 1H), 4.90 (s, 2H), 1.37 (s, 9H).

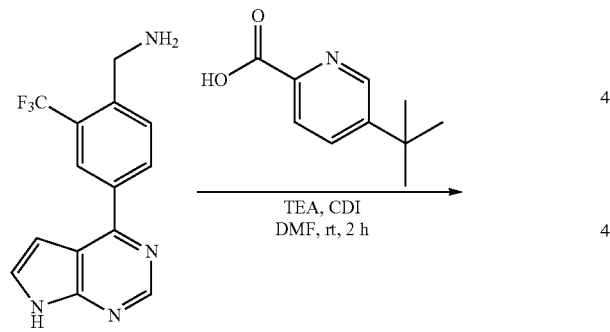

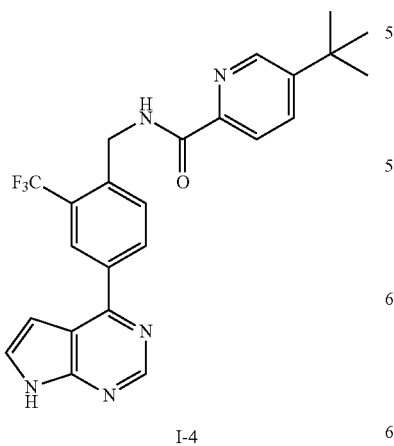

I-4

The Synthesis of N-(4-(7H-pyrrolo[2,3-d]pyrimidin-4-yl)-2-(trifluoromethyl)benzyl)-5-(tert-butyl)picolinamide (I-4)

Compound I-4 was prepared in a similar manner as described above for compound I-1 except 4-bromo-2-(trifluoromethyl)benzonitrile was substituted for 4-bromo-2-methylbenzonitrile. ESI-MS (M+H)+: 454.2. $^1$H NMR (400 MHz, CD$_3$OD) δ: 8.83 (s, 1H), 8.77 (d, J=1.6 Hz, 1H), 8.48 (s, 1H), 8.35 (d, J=8.0 Hz, 1H), 8.09-8.04 (m, 2H), 7.79 (d, J=8.0 Hz, 1H), 7.58 (d, J=4.0 Hz, 1H), 6.87 (d, J=3.6 Hz, 1H), 4.95 (s, 2H), 1.42 (s, 9H).

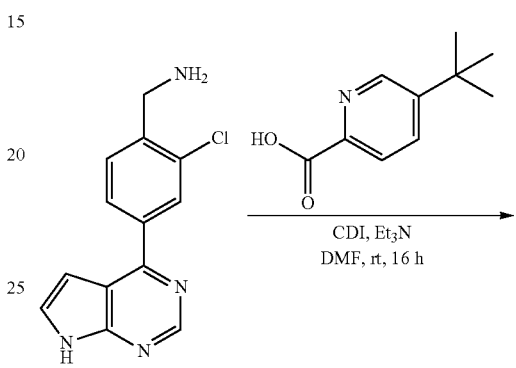

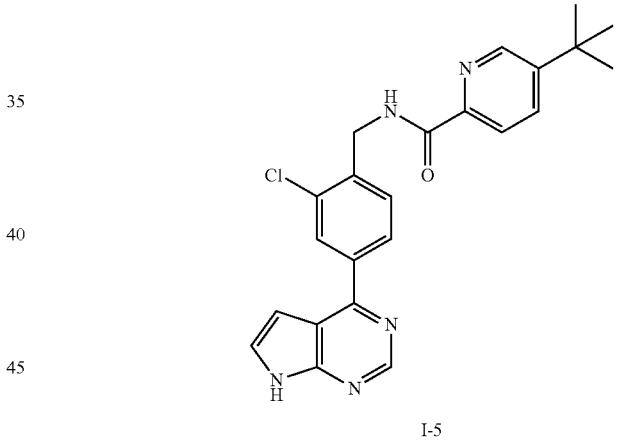

I-5

The Synthesis of 5-(tert-butyl)-N-(2-chloro-4-(7H-pyrrolo[2,3-d]pyrimidin-4-yl)benzyl)picolinamide (I-5)

Compound I-5 was prepared in a similar manner as described above for compound I-1 except (4-bromo-2-chlorophenyl)methanamine (Haddenham, D. et. Al. JOC 2009, 74, 1964-1970) was substituted for (4-bromo-2-methylphenyl)methanamine. ESI-MS (M+H)+: 420.2. $^1$H NMR (400 MHz, CD$_3$OD) δ: 8.80 (s, 1H), 8.76 (d, J=2.0 Hz, 1H), 8.16 (d, J=2.0 Hz, 1H), 8.06-8.03 (m, 3H), 7.62 (d, J=8.0 Hz, 1H), 7.56 (d, J=4.0 Hz, 1H), 6.87 (d, J=4.0 Hz, 1H), 4.83 (s, 2H), 1.42 (s, 9H)

Scheme 2

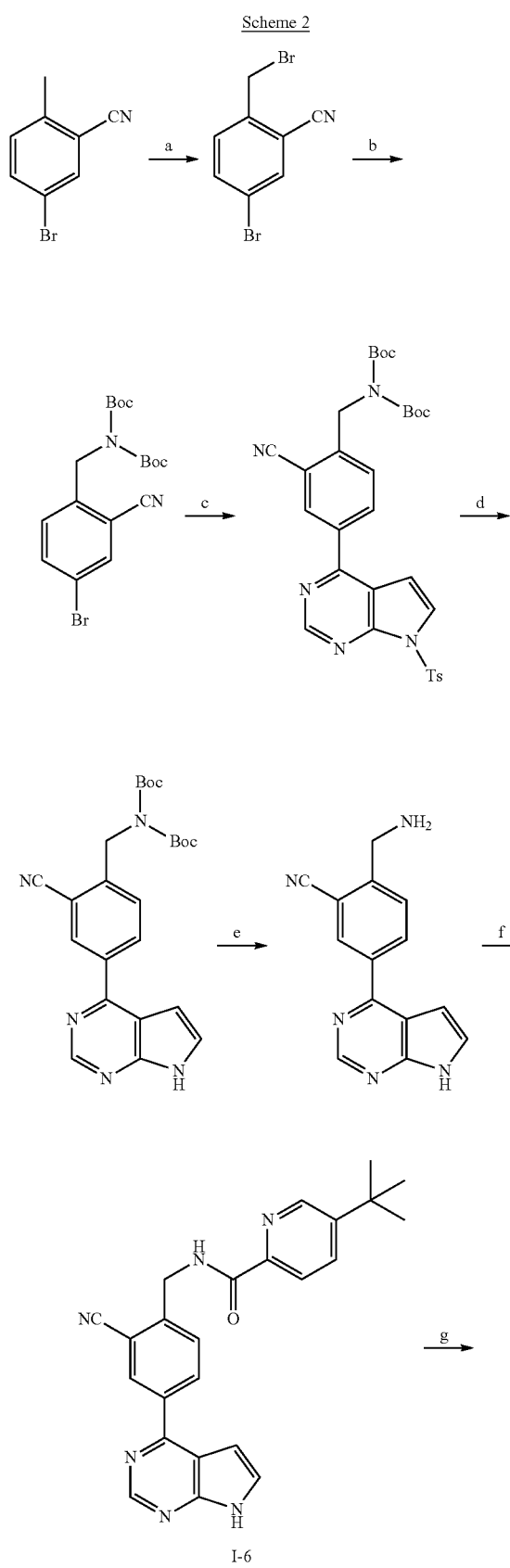

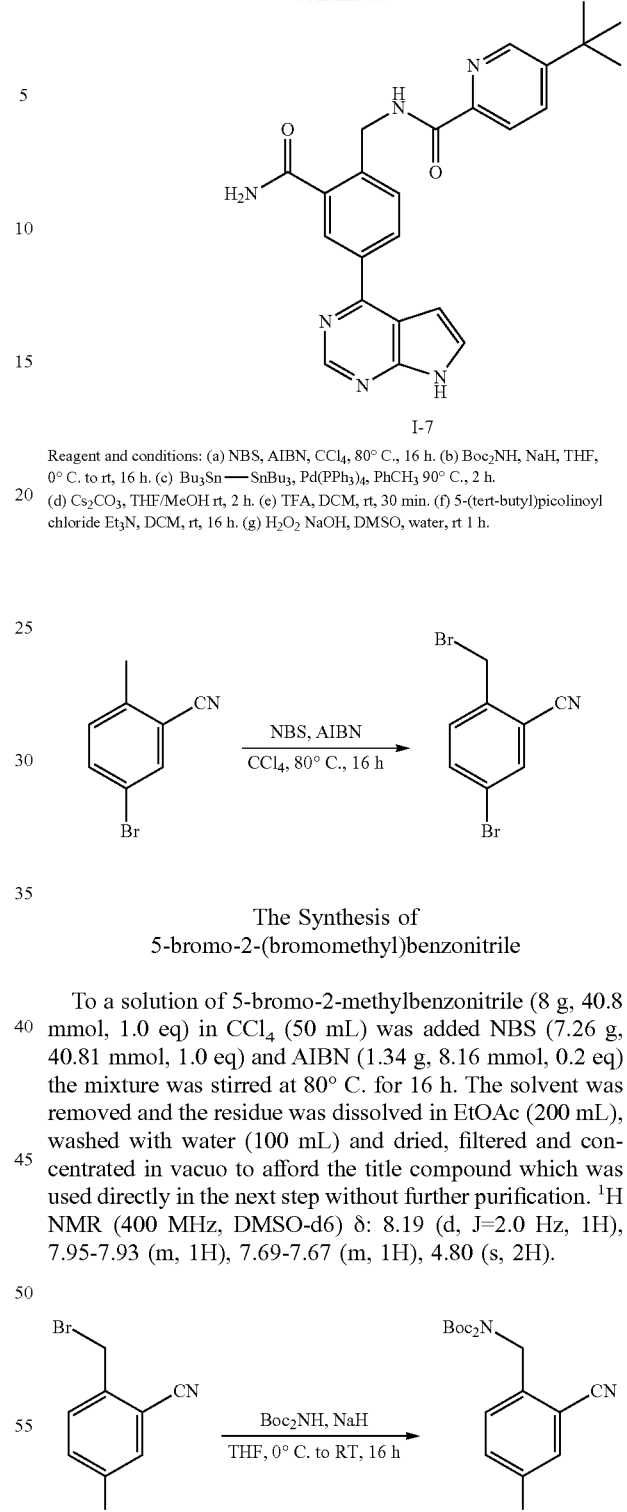

Reagent and conditions: (a) NBS, AIBN, CCl₄, 80° C., 16 h. (b) Boc₂NH, NaH, THF, 0° C. to rt, 16 h. (c) Bu₃Sn—SnBu₃, Pd(PPh₃)₄, PhCH₃ 90° C., 2 h. (d) Cs₂CO₃, THF/MeOH rt, 2 h. (e) TFA, DCM, rt, 30 min. (f) 5-(tert-butyl)picolinoyl chloride Et₃N, DCM, rt, 16 h. (g) H₂O₂ NaOH, DMSO, water, rt 1 h.

The Synthesis of 5-bromo-2-(bromomethyl)benzonitrile

To a solution of 5-bromo-2-methylbenzonitrile (8 g, 40.8 mmol, 1.0 eq) in CCl₄ (50 mL) was added NBS (7.26 g, 40.81 mmol, 1.0 eq) and AIBN (1.34 g, 8.16 mmol, 0.2 eq) the mixture was stirred at 80° C. for 16 h. The solvent was removed and the residue was dissolved in EtOAc (200 mL), washed with water (100 mL) and dried, filtered and concentrated in vacuo to afford the title compound which was used directly in the next step without further purification. ¹H NMR (400 MHz, DMSO-d6) δ: 8.19 (d, J=2.0 Hz, 1H), 7.95-7.93 (m, 1H), 7.69-7.67 (m, 1H), 4.80 (s, 2H).

The Synthesis of di-tert-butyl 4-bromo-2-cyanobenzylcarbamate

To a solution of Boc₂NH (13 g, 58 mmol, 1.2 eq) in THF (150 mL) was added NaH (2.9 g, 73 mmol, 1.5 eq) at 0° C. and the mixture was stirred at rt for 2 h. To the mixture was added 5-bromo-2-(bromomethyl)benzonitrile and the reaction was stirred at rt for 16 h, quenched upon the addition of water (250 mL), and extracted with EtOAc (250 mL*3). The combined organics were washed with brine, dried, concentrated in vacuo to afford a solid which was purified by chromatography (petroleum ether EtOAc 10:1) to give the title compound (6.2 g, yield 37%) as a colorless oil. ESI-MS (M+H)$^+$: 411.0

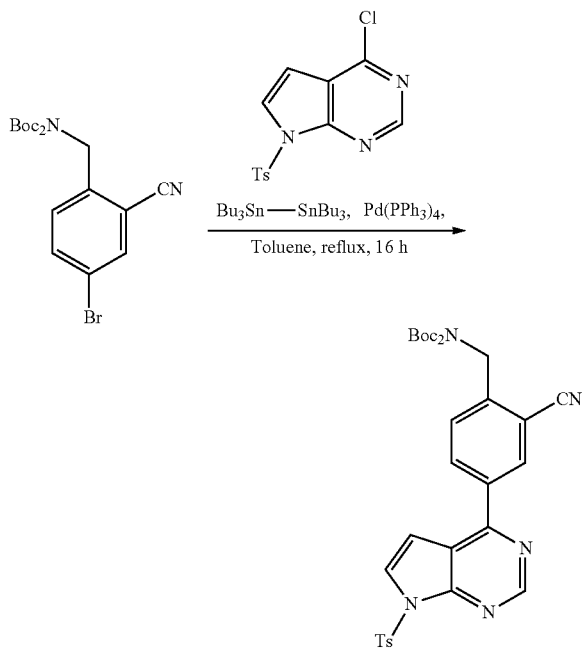

The Synthesis of di-tert-butyl 2-cyano-4-(7-tosyl-7H-pyrrolo[2,3-d]pyrimidin-4-yl)benzylcarbamate To a solution of di-tert-butyl 4-bromo-2-cyanobenzylcarbamate (2.0 g, 4.9 mmol, 1.0 eq), 4-chloro-7-tosyl-7H-pyrrolo[2,3-d]pyrimidine (1.5 g, 4.9 mmol, 1.0 eq) in toluene (15 mL), Bu$_3$Sn—SnBu$_3$ (5.7 g, 9.8 mmol, 2.0 eq) and Pd(PPh$_3$)$_4$ (400 mg, 0.2 eq) were added. The mixture was refluxed for 16 h. The mixture was diluted with EtOAc (200 mL) and washed with brine (100 mL×2). The organic phase was dried, filtered and concentrated. The residue was purified by chromatography (petroleum ether: EtOAc 4:1) to afford the desired compound (1.8 g, yield 14%) as a yellow solid. ESI-MS (M+H)$^+$: 604.2. $^1$H NMR (400 MHz, CDCl$_3$) δ: 9.09 (s, 1H), 8.33 (d, J=2.0 Hz, 1H), 8.23 (dd, J=8.0, 2.0 Hz, 1H), 8.14 (d, J=8.0 Hz, 2H), 7.87 (d, J=4.0 Hz, 1H), 7.51 (d, J=8.0 Hz, 1H), 7.32 (d, J=8.0 Hz, 2H), 6.89 (d, J=4.0 Hz, 1H), 5.12 (s, 2H), 2.42 (s, 3H), 1.48 (s, 18H).

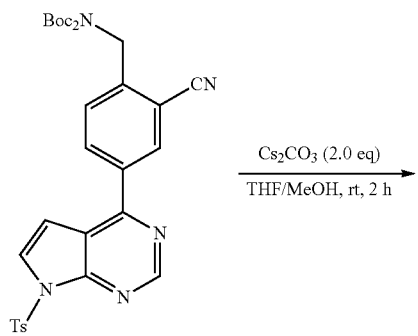

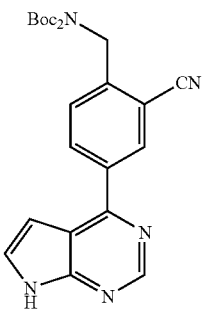

The Synthesis of di-tert-butyl 2-cyano-4-(7H-pyrrolo[2,3-d]pyrimidin-4-yl)benzylcarbamate A mixture of di-tert-butyl 2-cyano-4-(7-tosyl-7H-pyrrolo[2,3-d]pyrimidin-4-yl)benzylcarbamate (300 mg, 0.5 mmol) and Cs$_2$CO$_3$ (325 mg, 1.0 mmol) in THF/MeOH (1:1, 5 mL) was stirred at rt for 2 h. After diluted with water (12 mL), the mixture was extracted with ethyl acetate (10 mL×2). The combined organics were washed with brine, dried, concentrated in vacuo and purified by chromatography (petroleum ether/EtOAc 3:1) to afford the title compound (100 mg, yield 51%) as a white solid. ESI-MS (M+H)$^+$: 450.2. $^1$H NMR (400 MHz, CD$_3$OD): δ: 8.84 (s, 1H), 8.47 (d, J=2.0 Hz, 1H), 8.43 (dd, J=8.0, 2.0 Hz, 1H), 7.62-7.60 (m, 2H), 6.91 (d, J=3.6 Hz, 1H), 5.13 (s, 2H), 1.49 (s, 18H).

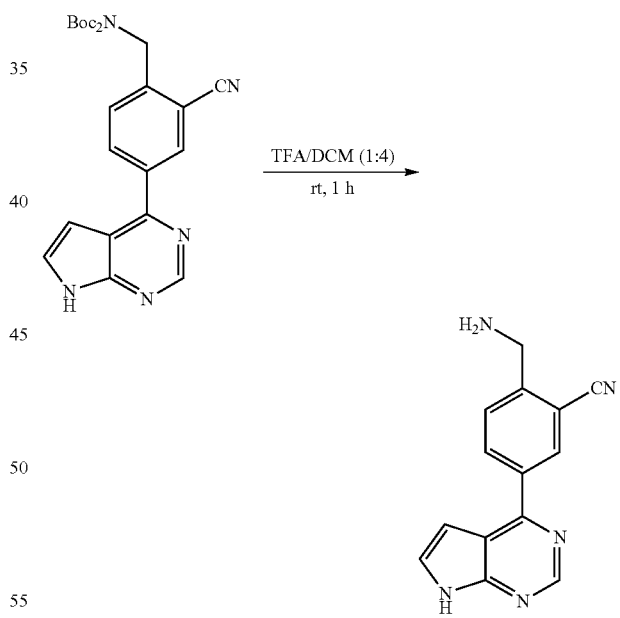

The Synthesis of 2-(aminomethyl)-5-(7H-pyrrolo[2,3-d]pyrimidin-4-yl)benzonitrile A solution of di-tert-butyl 2-cyano-4-(7H-pyrrolo[2,3-d]pyrimidin-4-yl)benzylcarbamate (100 mg, 0.22 mmol, 1.0 eq) in TFA/DCM (1:2, 3 mL) was stirred at rt for 1 h. The solvent was reduced in vacuo to afford a residue (55 mg, brown solid, yield: 100%) which was used in the next step without further purification. ESI-MS (M+H)$^+$:250.1

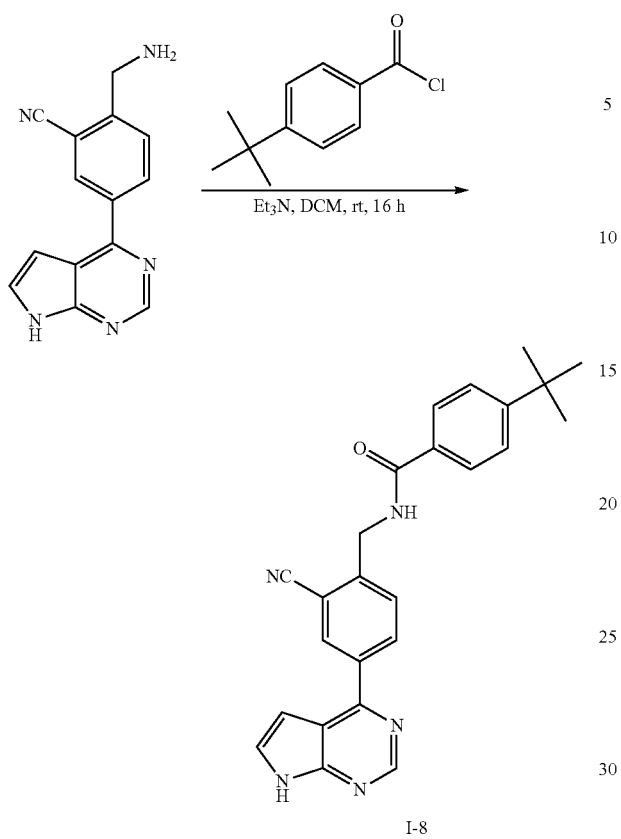

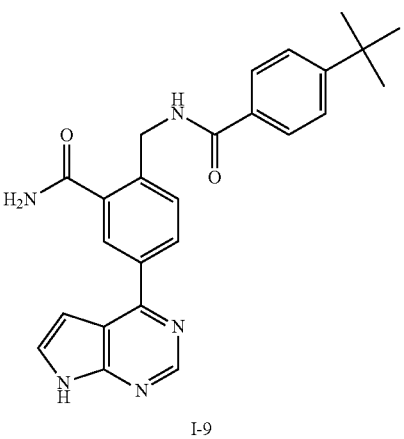

I-9

The Synthesis of 4-(tert-butyl)-N-(2-carbamoyl-4-(7H-pyrrolo[2,3-d]pyrimidin-4-yl)benzyl)benzamide (I-9)

To a solution of 4-(tert-butyl)-N-(2-cyano-4-(7H-pyrrolo[2,3-d]pyrimidin-4-yl)benzyl)benzamide (40 mg, 0.10 mmol. 1.0 eq) in DMSO (3 mL) and water (0.5 mL) was added H$_2$O$_2$ (17 mg, 0.50 mmol, 5.0 eq) and NaOH (8 mg, 0.2 mmol, 2.0 eq) and stirred at rt for 1 h. The mixture was diluted with EtOAc (5 mL) and the organic phase was washed with water (5 mL), brine (5 mL), dried (Na$_2$SO$_4$), filtered and concentrated in vacuo to afford a residue which was purified by reverse phase chromatography (MeOH/H$_2$O with 0.05% NH$_3$.H$_2$O as mobile phase) to give the title compound I-9 (28 mg, yield: 67%) as a yellow solid. ESI-MS (M+H)$^+$: 428.2. $^1$H NMR (400 MHz, DMSO-d6) δ: 12.27 (s, 1H), 9.01 (t, J=6.0 Hz, 1H), 8.84 (s, 1H), 8.24-8.19 (m, 3H), 7.87 (d, J=8.8 Hz, 2H), 7.67-7.51 (m, 5H), 6.96 (d, J=3.6 Hz, 1H), 4.72 (s, 2H), 1.31 (s, 9H).

The Synthesis of 4-(tert-butyl)-N-(2-cyano-4-(7H-pyrrolo[2,3-d]pyrimidin-4-yl)benzyl)benzamide (I-8)

To a suspension of 2-(aminomethyl)-5-(7H-pyrrolo[2,3-d]pyrimidin-4-yl)benzonitrile (150 mg, 0.6 mmol) in CH$_2$Cl$_2$ (10 mL) were added Et$_3$N (0.4 mL, 1.8 mmol) and 4-tert-butyl benzoyl chloride (118 mg, 0.6 mmol). The reaction mixture was stirred at rt for 2 h, diluted with water (2 mL) and extracted with CH$_2$Cl$_2$ (3 mL×2). The organic layer was concentrated and the residue was purified by reverse phase chromatography (CH$_3$CN/H$_2$O with 0.05% NH$_3$.H$_2$O as mobile phase) to afford the title compound (40 mg, yield: 44%) as a yellow solid. ESI-MS (M+H)$^+$: 410.2

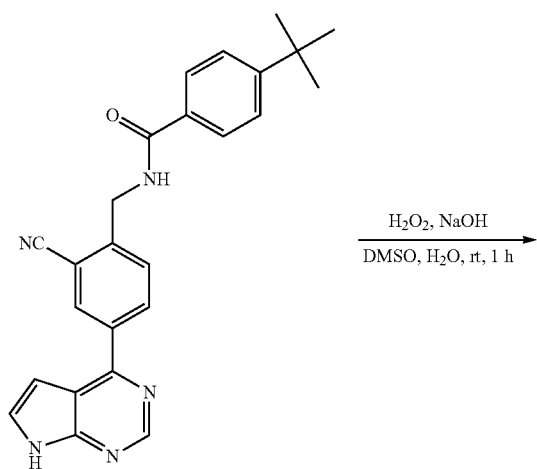

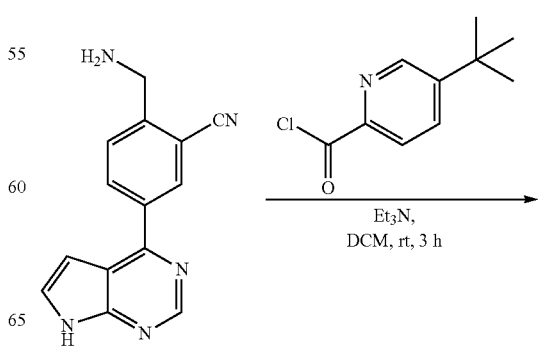

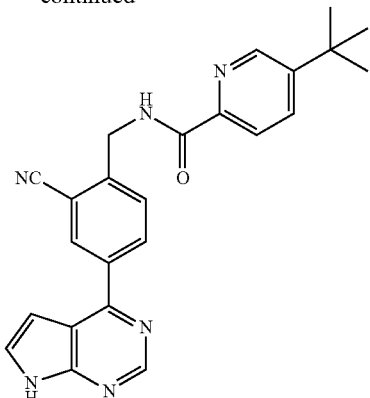

I-6

The Synthesis of 5-(tert-butyl)-N-(2-cyano-4-(7H-pyrrolo[2,3-d]pyrimidin-4-yl)benzyl)picolinamide (I-6)

Compound I-6 was prepared in a similar manner as described in Example I-8 5-(tert-butyl)picolinoyl chloride was substituted for 4-(tert-butyl)benzoyl chloride. ESI-MS (M+H)+: 411.2. HPLC: (214 nm: 100%, 254 nm: 100%). $^1$H NMR (400 MHz, CD$_3$OD): δ: 8.70 (s, 1H), 8.64 (d, J=2.0 Hz, 1H), 8.33 (d, J=1.6 Hz, 1H), 8.25-8.23 (m, 1H), 7.96-7.90 (m, 2H), 7.63 (d, J=8.4 Hz, 1H), 7.47 (d, J=4.0 Hz, 1H), 6.77 (d, J=4.0 Hz, 1H), 4.81 (s, 2H), 1.30 (s, 9H).

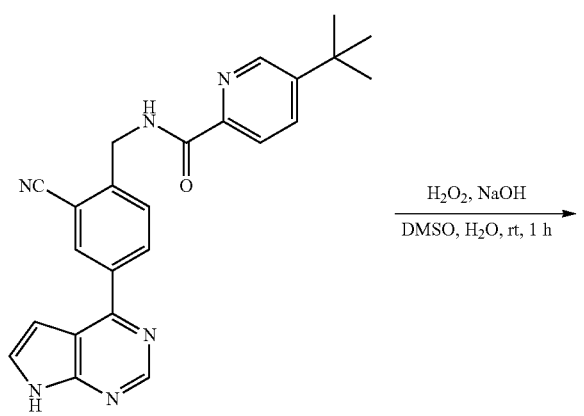

I-7

The Synthesis of 5-(tert-butyl)-N-(2-carbamoyl-4-(7H-pyrrolo[2,3-d]pyrimidin-4-yl)benzyl)picolinamide (I-7)

Compound I-7 was prepared in a similar manner as described above for compound I-9 except 5-(tert-butyl)-N-(2-cyano-4-(7H-pyrrolo[2,3-d]pyrimidin-4-yl)benzyl)picolinamide was substituted for 4-(tert-butyl)-N-(2-cyano-4-(7H-pyrrolo[2,3-d]pyrimidin-4-yl)benzyl)benzamide. ESI-MS (M+H)+: 429.2. $^1$H NMR (400 MHz, CD$_3$OD&DMSO-d6): δ: 7.94 (s, 1H), 7.82 (s, 1H), 7.44 (s, 1H), 7.33-7.31 (m, 1H), 7.16-7.08 (m, 2H), 6.81 (d, J=8.0 Hz, 1H), 6.69 (d, J=3.2 Hz, 1H), 6.06 (d, J=3.2 Hz, 1H), 3.94 (s, 2H), 0.49 (s, 9H).

Scheme 3

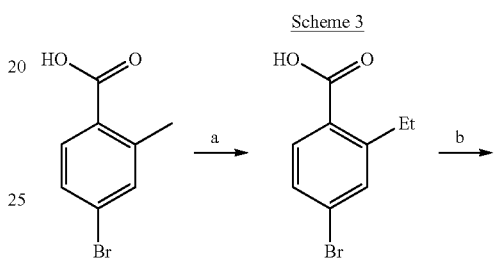

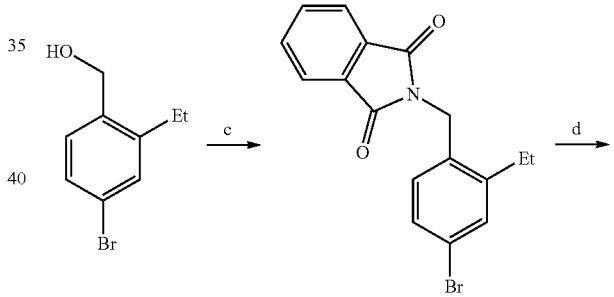

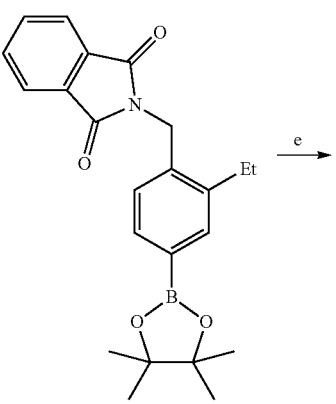

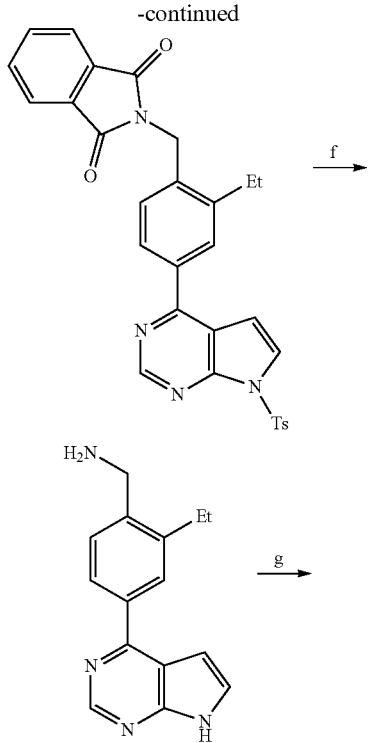

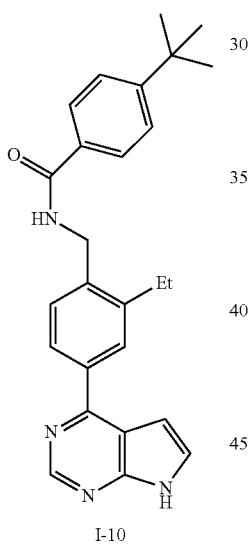

I-10

Reagents and conditions: (a) C₉H₁₈LiN, CH₃I, THF, 0° C., rt, 16 h. (b) BH₃, THF rt, 16 h. (c) Isoindoline-1,3-dione, DIAD, PPh₃, THF, rt, 16 h. (d) 4,4,4',4',5,5,5',5'-octamethyl-2,2'-bi(1,3,2-dioxaborolane), Pd(dppf)Cl₂ KOAc, DMF, 100° C., 1.5 h. (e) 4-chloro-7-tosyl-7H-pyrrolo[2,3-d]pyrimidine, Pd(dppf)Cl₂, K₂CO₃, Dioxane/H₂O (4:1), MW, 130° C., 2 h. (f) i. NH₂NH₂•H₂O, EtOH, rt 1 h. ii. Cs₂CO₃, MeOH/water. (g) 4-tert-butyl benzoyl chloride, Et₃N, CH₂Cl₂, rt.

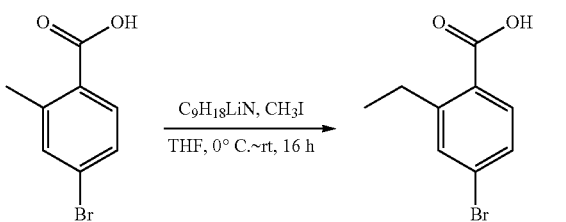

The Synthesis of 4-bromo-2-ethylbenzoic acid

To a solution of lithium 2,2,6,6-tetramethylpiperidin-1-ide (3.23 g, 22.0 mmol) in THF (40 mL) at −78° C. under an atmosphere of N₂ was added dropwise a solution of 4-bromo-2-methylbenzoic acid (2.13 g, 10.0 mmol) in THF (20 mL) and stirred for 1 h at −78° C., followed by the addition of CH₃I (4.41 g, 30.0 mmol) in THF (10 mL). The solution was allowed to warm up to rt, and stirred for an additional 16 h. The reaction was quenched upon the addition of 2 N HCl (final pH=3-4 for the solution), and extracted with EtOAc (150 mL×2). The combined organic layers were dried over Na₂SO₄ and concentrated in vacuo to afford the desired product (2.3 g, yield 60%) as a yellow solid, which was used in subsequent step without additional purification. ESI-MS (M+H)⁺: 230.0.

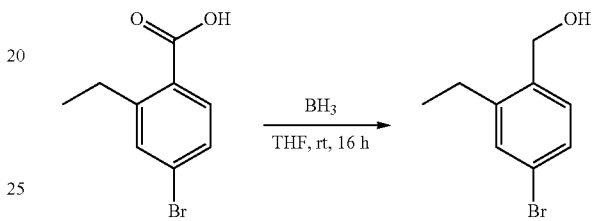

The Synthesis of (4-bromo-2-ethylphenyl)methanol

To a solution of acid (2.10 g, 9.2 mmol) in THF (20 mL) was added 1N BH3 in THF (9.20 mL, 18.4 mmol) at −78° C. The resulting mixture was stirred at room temperature for 16 h. After diluting with water (100 mL), the mixture was extracted with EtOAc (100 mL×2). The combined organic layers were dried over Na₂SO₄ and concentrated in vacuo to afford a residue which was purified by column chromatography (petroleum ether/EtOAC 4:1) to give the title product (1.3 g, yield: 61% for two steps) as a yellow solid. ESI-MS (M+H−18)⁺: 198.1. ¹H NMR (400 MHz, CDCl₃) δ: 7.35-7.31 (m, 2H), 7.25-7.23 (m, 1H), 4.66 (s, 2H), 2.65 (q, J=7.6 Hz, 2H), 1.22 (t, J=7.6 Hz, 3H).

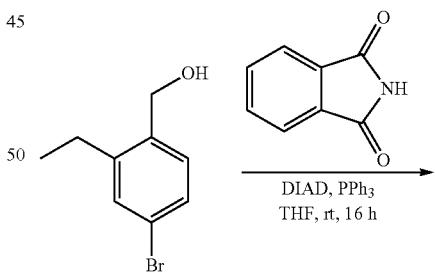

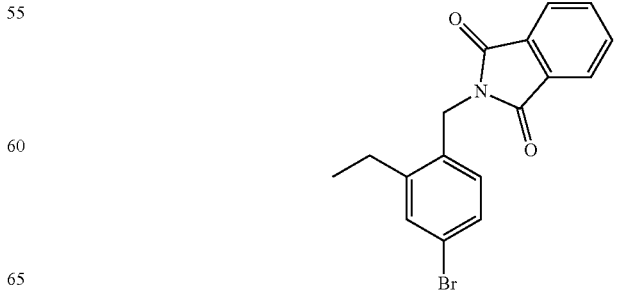

The Synthesis of 2-(4-bromo-2-ethylbenzyl)isoindoline-1,3-dione

To a solution of benzyl alcohol (1.3 g, 6.1 mmol) and phthalic amide (0.9 g, 6.1 mmol) in THF (100 mL) was added PPh$_3$ (2.34 g, 9.2 mmol) under nitrogen. After cooling to 0° C., DIAD (1.86 g, 9.2 mmol) was added in one portion. The resulting mixture was stirred at rt for 16 h. The reaction mixture was diluted with water (100 mL) and extracted with EtOAc (100 mL×2), separated, dried (Na$_2$SO$_4$) and concentrated in vacuo to afford a residue which was purified by column chromatography (petroleum ether/EtOAc=8:1) to give the title compound (1.7 g, yield: 81%) as a white solid. ESI-MS (M+H)$^+$: 344.1. $^1$H NMR (400 MHz, CDCl$_3$) δ: 7.86-7.84 (m, 2H), 7.74-7.72 (m, 2H), 7.34 (d, J=2.4 Hz, 1H), 7.24 (dd, J=8.4, 2.4 Hz, 1H), 7.14 (d, J=8.4 Hz, 1H), 4.83 (s, 2H), 2.85 (q, J=7.6 Hz, 2H), 1.26 (t, J=7.6 Hz, 3H).

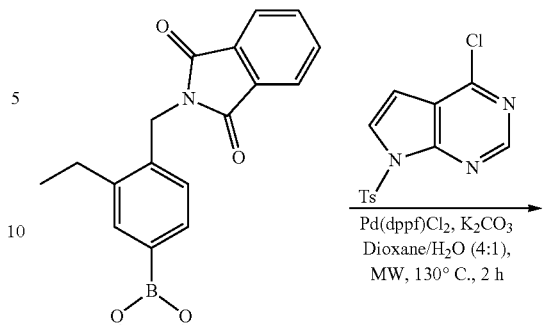

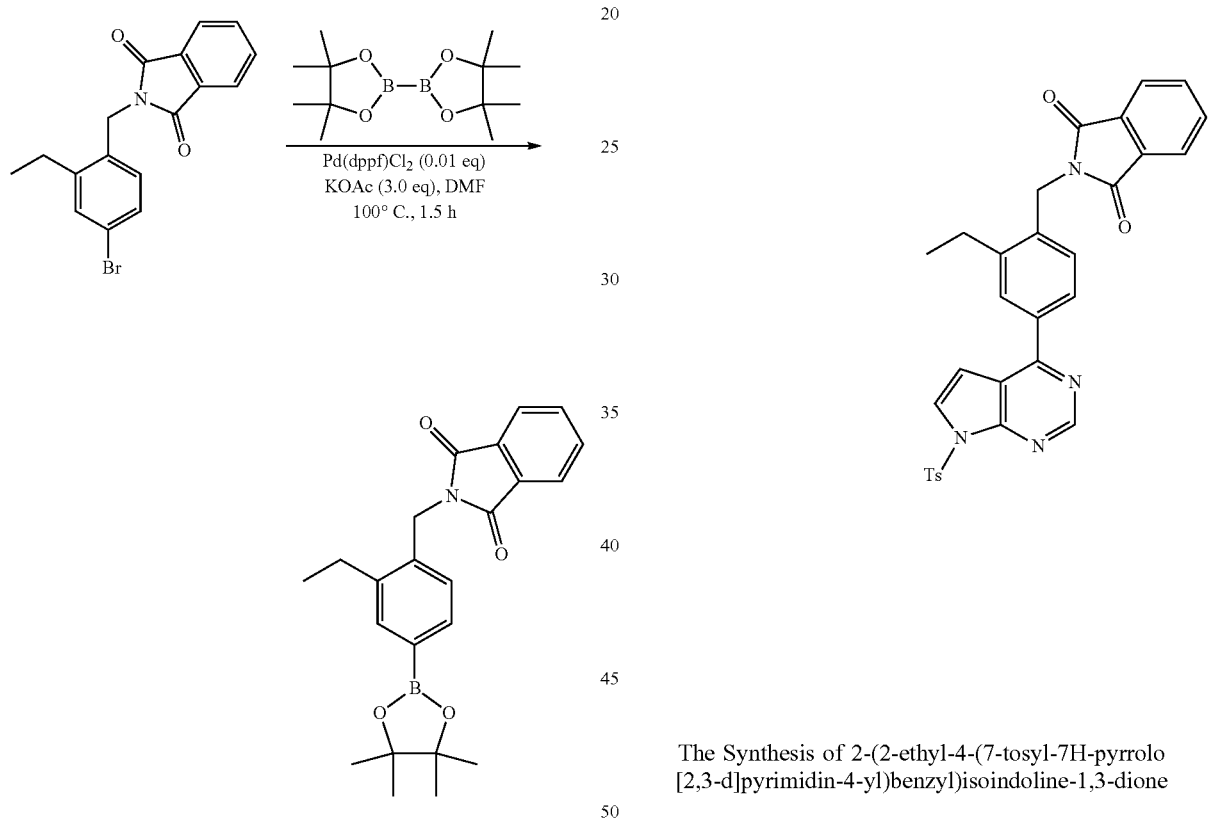

The Synthesis of 2-(2-ethyl-4-(4,4,5,5-tetramethyl-1,3,2-dioxaborolan-2-yl)benzyl)isoindoline-1,3-dione To a solution of aryl bromide (1.5 g, 5.0 mmol) in DMF (6 mL) were added 4,4,4',4',5,5,5',5'-octamethyl-2,2'-bi(1,3,2-dioxaborolane) (1.52 g, 6.0 mmol), KOAc (1.75 g, 18 mmol) and Pd(dppf)Cl$_2$DCM (407 mg, 0.5 mmol) under nitrogen. The mixture was stirred at 100° C. for 2 h, allowed to cool to rt, diluted with water (50 mL) and extracted with EtOAc (100 mL×3). The combined organic layer was washed with brine, dried, concentrated in vacuo and purified by silica gel column (petroleum ether/EtOAc, 10:1) to give the tittle compound (1.5 g, yield: 90%) as a white solid. ESI-MS (M+H)$^+$: 392.0.

The Synthesis of 2-(2-ethyl-4-(7-tosyl-7H-pyrrolo[2,3-d]pyrimidin-4-yl)benzyl)isoindoline-1,3-dione To a solution of the boronate ester (1.7 g, 4.9 mmol) in dioxane/H$_2$O (4:1) (15 mL) was added 4-chloro-7-tosyl-7H-pyrrolo[2,3-d]pyrimidine (1.5 g, 4.9 mmol) followed by Pd(dppf)Cl$_2$DCM (457 mg, 0.5 mmol) and K$_2$CO$_3$ (2.0 g, 14.7 mmol) under nitrogen. The mixture was stirred at 90° C. for 6 h. After cooling to rt, the mixture was diluted with water and extracted with EtOAc (100 mL×2). The organic layer was washed with brine (80 mL), dried (Na$_2$SO$_4$), filtered and concentrated. The residue was purified by column chromatography (petroleum ether/EtOAc, 3:1) to give the title compound (650 mg, yield 28%) as a white solid. ESI-MS (M+H)$^+$: 537.0. $^1$H NMR (400 MHz, CDCl$_3$) δ: 9.03 (s, 1H), 8.11 (d, J=8.8 Hz, 2H), 7.89-7.85 (m, 3H), 7.76-7.71 (m, 3H), 7.40 (d, J=8.0 Hz, 2H), 7.32 (d, J=8.0 Hz, 2H), 6.85 (d, J=8.0 Hz, 1H), 4.97 (s, 2H), 2.96 (q, J=7.6 Hz, 2H), 2.42 (s, 3H), 1.29 (t, J=7.6 Hz, 3H).

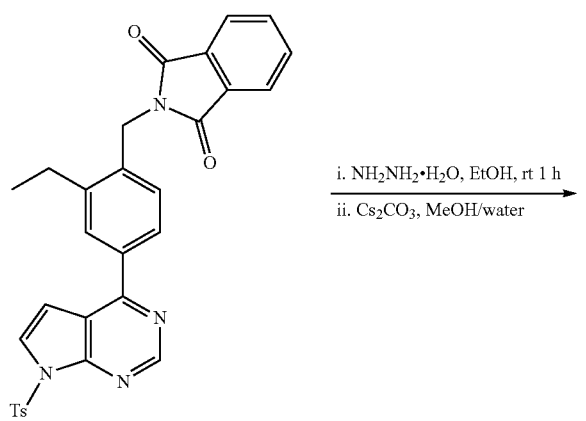

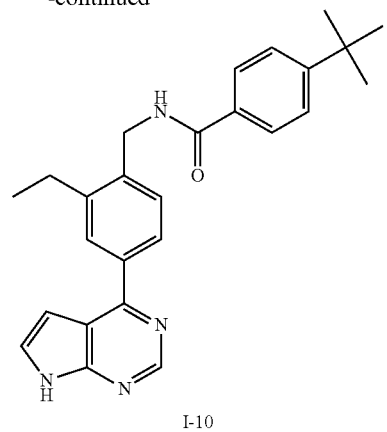

I-10

The Synthesis of 4-(tert-butyl)-N-(2-ethyl-4-(7H-pyrrolo[2,3-d]pyrimidin-4-yl)benzyl)benzamide (I-10)

To a suspension of amine (150 mg, 0.6 mmol) in $CH_2C_2$ (10.0 mL) was added $Et_3N$ (0.4 mL, 1.8 mmol) and 4-tert-butyl benzoyl chloride (118 mg, 0.6 mmol). The reaction mixture was stirred at rt for 2 h. Then the mixture was quenched with water (20 mL) and extracted with $CH_2Cl_2$ (30 mL×2). The organic layer was concentrated and the residue was purified by reverse phase chromatography ($CH_3CN/H_2O$ with 0.05% $NH_3.H_2O$ as mobile phase) to give the title compound I-10 (77 mg, yield 31%) as a grey solid. ESI-MS $(M+H)^+$: 413.2. $^1H$ NMR (400 MHz, $CD_3OD$) δ: 8.81 (s, 1H), 8.00 (s, 1H), 7.95 (dd, J=8.0, 1.2 Hz, 1H), 7.87 (d, J=8.4 Hz, 2H), 7.59-7.51 (m, 4H), 6.88 (d, J=3.2 Hz, 1H), 4.67 (s, 2H), 2.87 (q, J=7.6 Hz, 2H), 1.35-1.25 (m, 12H).

The Synthesis of (2-ethyl-4-(7H-pyrrolo[2,3-d]pyrimidin-4-yl)phenyl)methanamine To a suspension of N-substituted phthalimide (0.5 mmol) in EtOH (40 mL) was added hydrazine hydrate (0.5 mL). The reaction mixture was refluxed for 5 h, cooled rt and concentrated in vacuo to afford the crude amine. The amine (300 mg, 0.5 mmol) and $Cs_2CO_3$ (325 mg, 1.0 mmol) in THF/MeOH (1:1, 5 mL) was stirred at rt for 2 h, diluted with water (12 mL) and extracted with EtOAc (10 mL×2). The combined organics were washed with brine, dried, concentrated in vacuo and purified by reverse phase chromatography to afford the title compound (140 mg, yield 73%) as yellow solid was used in the next step without further purification. ESI-MS $(M+H)^+$: 253.1

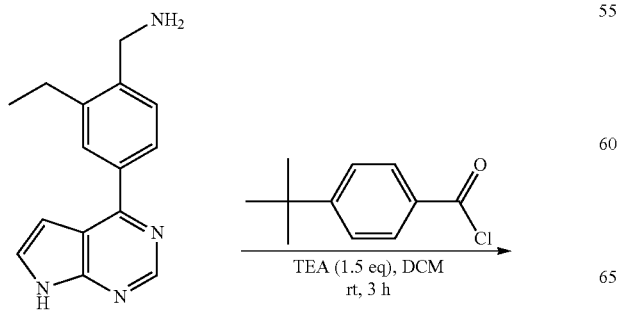

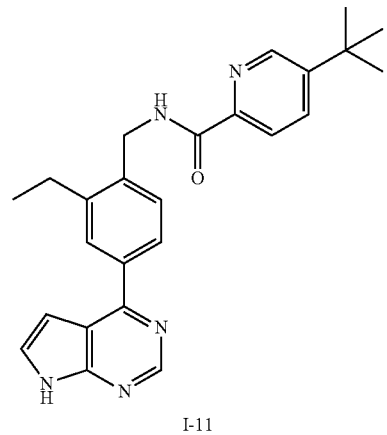

I-11

The Synthesis of 5-(tert-butyl)-N-(2-ethyl-4-(7H-pyrrolo[2,3-d]pyrimidin-4-yl)benzyl)picolinamide (I-11)

Compound I-11 was prepared in a similar manner as described in Example 6 except 5-(tert-butyl)picolinoyl chloride was substituted for 4-(tert-butyl)benzoyl chloride (28 mg, yield: 28%) as a yellow solid. ESI-MS (M+H)+: 414.2. ¹H NMR (400 MHz, DMSO-d6) δ: 12.28 (s, 1H), 9.27 (t, J=7.2 Hz, 1H), 8.81 (s, 1H), 8.72 (s, 1H), 8.04-7.99 (m, 3H), 7.96-7.93 (m, 1H), 7.64 (d, J=3.2 Hz, 1H), 7.43 (d, J=4.0 Hz, 1H), 6.86 (d, J=3.6 Hz, 1H), 4.62 (d, J=6.4 Hz, 2H), 2.83 (q, J=7.6 Hz, 2H), 1.36 (s, 9H), 1.26 (t, J=7.6 Hz, 3H).

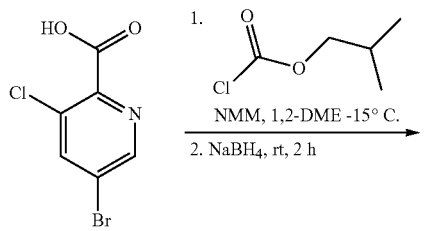

The Synthesis of (5-bromo-3-chloropyridin-2-yl)methanol

To a solution of 5-bromo-3-chloropicolinic acid (2.3 g, 10.0 mmol) in DME (10 mL) were added isobutyl carbonochloridate and NMM (1.5 g, 10.0 mmol) at −10° C. The resulting mixture was stirred at room temperature for 30 min, filtered and the resulting filtration was treated with NaBH₄ (740 mg, 20 mmol) and the mixture was stirred at rt for 1 h. The reaction was diluted with water (80 mL), the mixture was extracted with EtOAc (80 mL×2), separated, dried (Na₂SO₄), filtered and concentrated in vacuo to afford a residue that was purified by column chromatography (petroleum-EtOAc=4:1) to afford the title product (1.4 g, yield 72%) as a white solid. ESI-MS (M+H)+: 221.9.

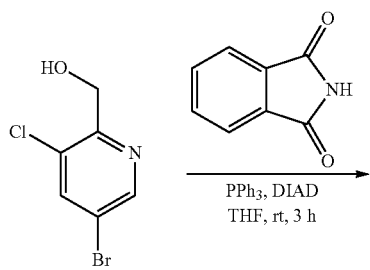

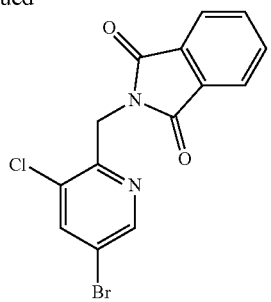

The Synthesis of 2-((5-bromo-3-chloropyridin-2-yl)methyl)isoindoline-1,3-dione This compound was prepared in a similar manner as described above for compound I-10 except (5-bromo-3-chloropyridin-2-yl)methanol was substituted for (4-bromo-2-ethylphenyl)methanol to afford the title compound (1.1 g, yield 50%) was obtained as a yellow solid. ESI-MS (M+H)+: 350.9. ¹H NMR (400 MHz, CDCl₃) δ: 8.54 (d, J=2.0 Hz, 1H), 8.40 (d, J=1.6 Hz, 1H), 7.95-7.88 (m, 4H), 4.97 (s, 2H).

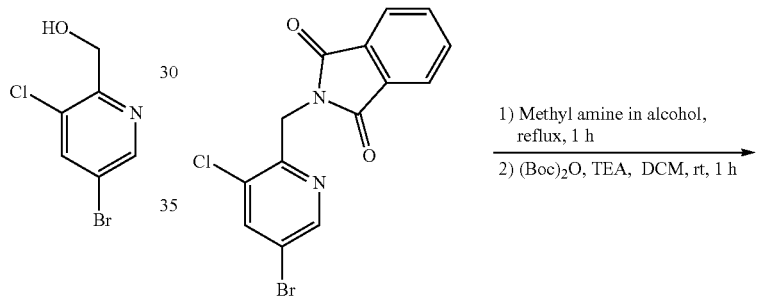

The Synthesis of tert-butyl ((5-bromo-3-chloropyridin-2-yl)methyl)carbamate

To a solution of phthalic amide (1.2 g, 3.3 mmol) in EtOH (15 mL) were added 2N methylamine in methanol (10 mL). The resulting mixture was stirred at 60° C. for 16 h, cooled to rt and the solvent was removed in vacuo to give the benzyl amine (1.2 g). The benzyl amine (0.76 g, 3.3 mmol) was dissolved in CH₂Cl₂ (30 mL) were added TEA (1.82 g, 18 mmol) and Boc₂O (1.43 g, 6.6 mmol). The mixture was stirred at rt for 1 h, diluted with water (50 mL) and extracted with CH₂Cl₂ (50 mL×2). The organic phase was washed with brine (50 mL), dried (Na₂SO₄), filtered and concentrated in vacuo to afford the title compound (740 mg, yield 70%) as a white solid. ESI-MS (M+H)+: 320.94. ¹H NMR (400 MHz, CDCl₃) δ: 8.64 (d, J=1.6 Hz, 1H), 8.29 (d, J=2.0 Hz, 1H), 7.19 (t, J=5.6 Hz, 1H), 4.29 (d, J=6.0 Hz, 2H), 1.38 (s,

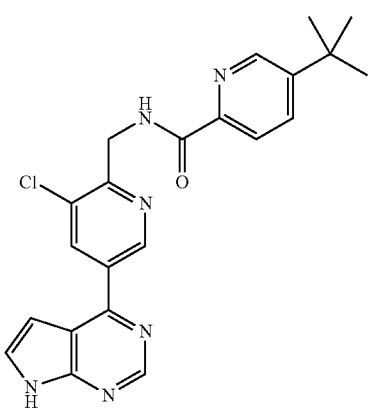

tert-butyl 2-methyl-4-(4,4,5,5-tetramethyl-1,3,2-dioxaborolan-2-yl)benzylcarbamate (I-12)

Compound I-12 was prepared in a similar manner as described in Example 1 except tert-butyl ((5-bromo-3-chloropyridin-2-yl)methyl)carbamate was substituted for tert-butyl 4-bromo-2-methylbenzylcarbamate to afford the title compound (28 mg, yield 40%) as a white solid. ESI-MS (M+H)+: 421.15. ¹H NMR (400 MHz, DMSO-d6) δ: 12.43 (s, 1H), 9.31-9.27 (m, 2H), 8.90 (s, 1H), 8.77 (t, J=6.8 Hz, 1H), 8.60 (d, J=2.0 Hz, 1H), 8.03 (d, J=1.6 Hz, 2H), 7.73 (d, J=3.6 Hz, 1H), 7.00 (d, J=4.0 Hz, 1H), 4.85 (d, J=5.2 Hz, 2H), 1.38 (s, 9H).

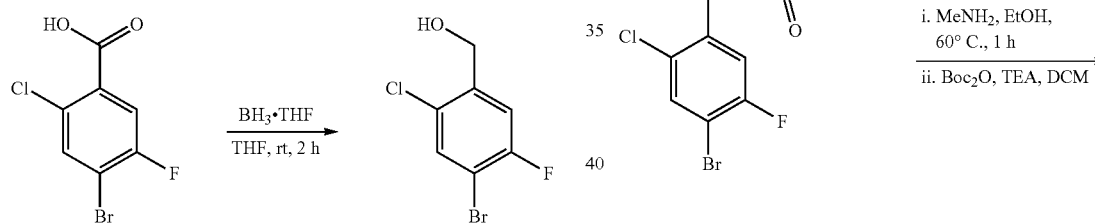

The Synthesis of (4-bromo-2-chloro-5-fluorophenyl)methanol

This compound was prepared in a similar manner as described as described above for compound I-10 except 4-bromo-2-chloro-5-fluorobenzoic acid was substituted for 4-bromo-2-ethylbenzoic acid to afford the title compound (1.1 g, yield 85%) as a white solid. ¹H NMR (400 MHz, DMSO-d6) δ: 7.84 (d, J=6.4 Hz, 1H), 7.45 (d, J=9.2 Hz, 1H), 5.66 (br, 1H), 2.26 (s, 2H).

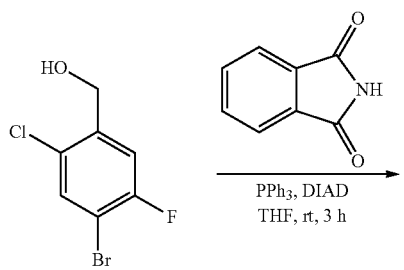

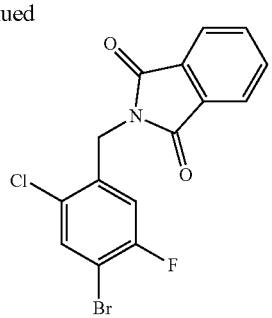

The Synthesis of 2-(4-bromo-2-chloro-5-fluorobenzyl)isoindoline-1,3-dione

This compound was prepared in a similar manner as described above for compound I-12 except (4-bromo-2-chloro-5-fluorophenyl)methanol was substituted for (5-bromo-3-chloropyridin-2-yl)methanol to afford the title compound (1.2 g, yield 81%) as a white solid. ESI-MS (M+H)+: 369.1. ¹H NMR (400 MHz, CDCl₃) δ: 7.91-7.89 (m, 2H), 7.79-7.77 (m, 2H), 7.59 (d, J=6.0 Hz, 1H), 6.99 (d, J=8.8 Hz 1H), 4.91 (s, 2H).

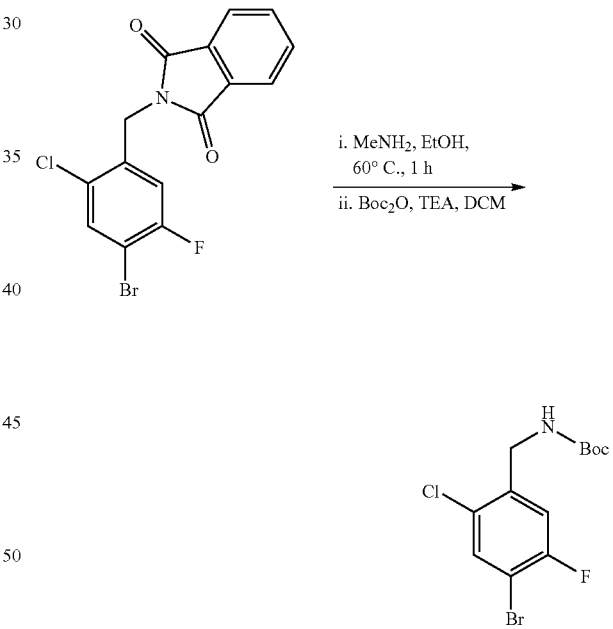

The Synthesis of tert-butyl 4-bromo-2-chloro-5-fluorobenzylcarbamate

This was prepared as described above for compound I-12 except 2-(4-bromo-2-chloro-5-fluorobenzyl)isoindoline-1,3-dione was substituted for (2-((5-bromo-3-chloropyridin-2-yl)methyl)isoindoline-1,3-dione to afford the title compound (1.1 g, yield: 92%) as a white solid. ESI-MS (M+H)+: 338.0. ¹H NMR (400 MHz, CDCl₃) δ: 7.58 (d, J=6.0 Hz, 1H), 7.19 (d, J=8.8 Hz, 1H), 4.32 (d, J=6.4 Hz, 2H), 1.42 (s, 9H).

I-13

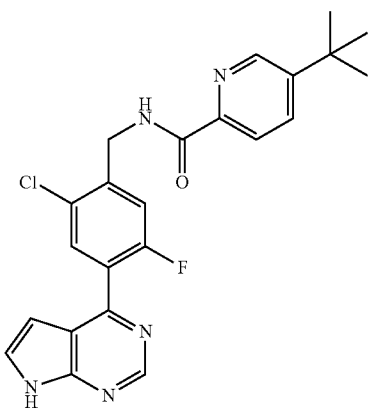

The Synthesis of 5-(tert-butyl)-N-(2-chloro-5-fluoro-4-(7H-pyrrolo[2,3-d]pyrimidin-4-yl)benzyl)picolinamide (I-13)

Compound I-13 was prepared in a similar manner as described in Example 1 except tert-butyl 4-bromo-2-chloro-5-fluorobenzylcarbamate was substituted for tert-butyl 4-bromo-2-methylbenzylcarbamate to afford the title compound (42 mg, yield: 67%) as a white solid. ESI-MS (M+H)+: 438.14. ¹H NMR (400 MHz, CD₃OD) δ: 8.83 (s, 1H), 8.78 (d, J=1.2 Hz, 1H), 8.09-8.04 (m, 2H), 7.86 (d, J=6.4 Hz, 1H), 7.54 (d, J=3.2 Hz, 1H), 7.35 (d, J=10.8 Hz, 1H), 6.58 (t, J=3.6 Hz, 1H), 4.80 (s, 2H), 1.43 (s, 9H).

I-74

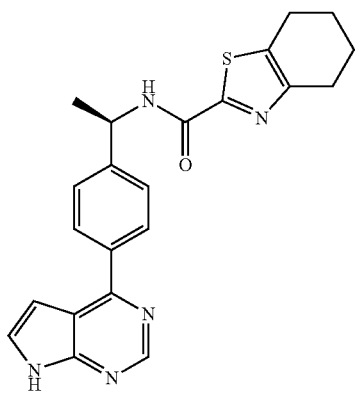

The Synthesis of (R)—N-(1-(4-(7H-pyrrolo[2,3-d]pyrimidin-4-yl)phenyl)ethyl)-4,5,6,7-tetrahydrobenzo[d]thiazole-2-carboxamide (I-74)

Compound I-74 was prepared in a similar manner as described in Example 6 except (R)-1-(4-bromophenyl)ethanamine was substituted for (4-bromophenyl)methanamine to afford the title compound I-74 (34 mg, yield 32%) as a solid. ESI-MS (M+H)+: 404.1. ¹H NMR (400 MHz, CDCl₃) δ: 12.0 (br, 1H), 9.08 (s, 1H), 8.09 (d, J=8.4 Hz, 2H), 7.63 (d, J=8.0 Hz, 2H), 7.57-7.52 (m, 2H), 6.96 (s, 1H), 5.40-5.32 (m, 1H), 2.86-2.80 (m, 4H), 1.90-1.88 (m, 4H), 1.67 (d, J=7.2 Hz, 3H).

I-75

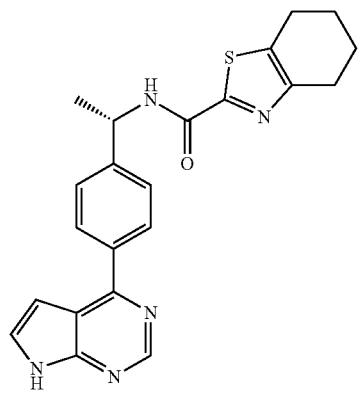

The Synthesis of (S)—N-(1-(4-(7H-pyrrolo[2,3-d]pyrimidin-4-yl)phenyl)ethyl)-4,5,6,7-tetrahydrobenzo[d]thiazole-2-carboxamide (I-75)

Compound I-75 was prepared in a similar manner as described in Example 6 except (S)-1-(4-bromophenyl)ethanamine was substituted for (4-bromophenyl)methanamine to afford the title compound (62 mg, yield 40%) as a solid. ESI-MS (M+H)+: 404.1. ¹H NMR (400 MHz, CD₃OD) δ: 8.78 (s, 1H), 8.07 (d, J=8.4 Hz, 2H), 7.64 (d, J=8.0 Hz, 2H), 7.53 (d, J=3.6 Hz, 1H), 6.87 (d, J=3.6 Hz, 1H), 5.33-5.27 (m, 1H), 2.89-2.83 (m, 4H), 1.92-1.90 (m, 4H), 1.66 (d, J=7.2 Hz, 3H).

Example 2

Scheme 4

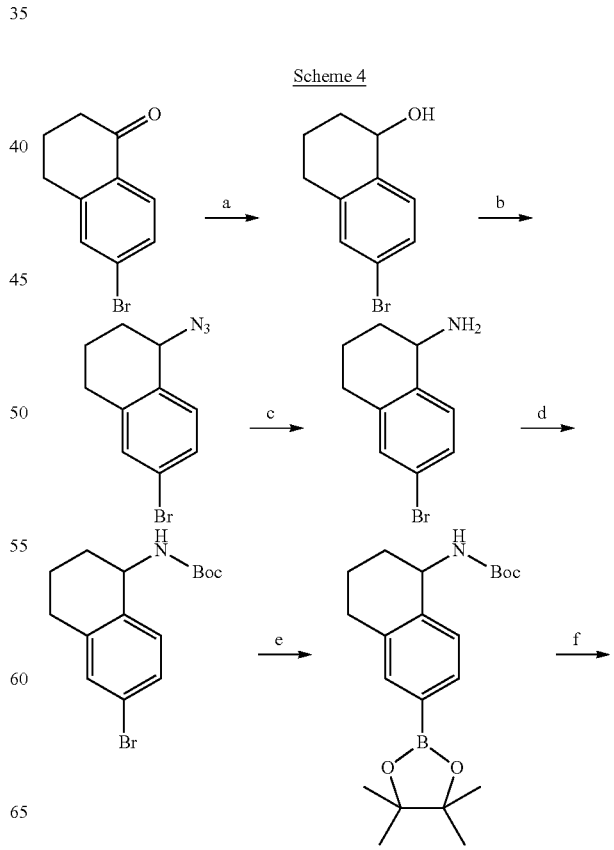

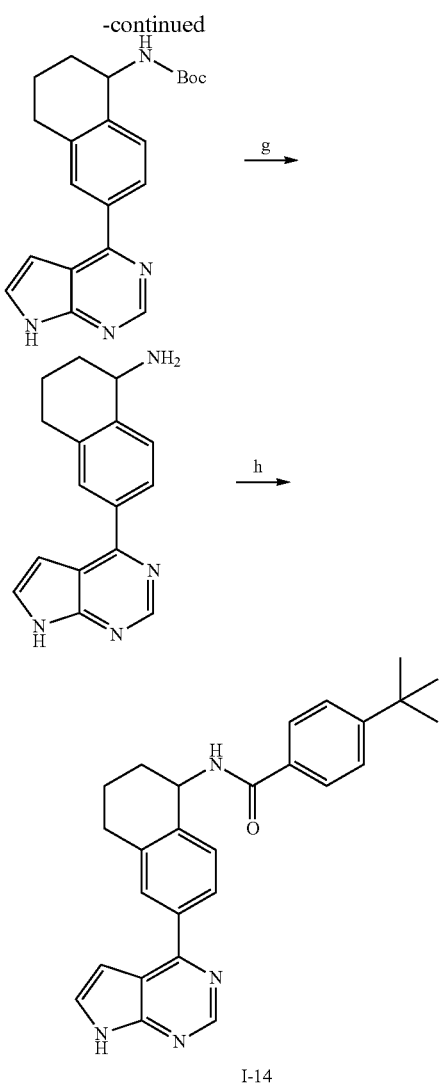

I-14

Reagents and conditions: (a) NaBH₄, MeOH, rt, 30 min. (b) DPPA, DBU, PhCH₃, rt, 16 h. (c) SnCl₂·H₂O MeOH, rt, 16 h. (d) Boc₂O, Et₃N, DCM, rt, 16 h. (e) 4,4,4',4',5,5,5',5'-octamethyl-2,2'-bi(1,3,2-dioxaborolane), PdCl₂(dppf), KOAc, DMF, MW 100° C., 2 h. (f) 4-chloro-7H-pyrrolo[2,3-d]pyrimidine, PdCl₂(dppf), K₂CO₃, dioxane/water MW 130° C., 2 h. (g) TFA, DCM, rt 1 h. (h) 4-(tert-butyl)benzoyl chloride, Et₃N, THF, rt 2 h.

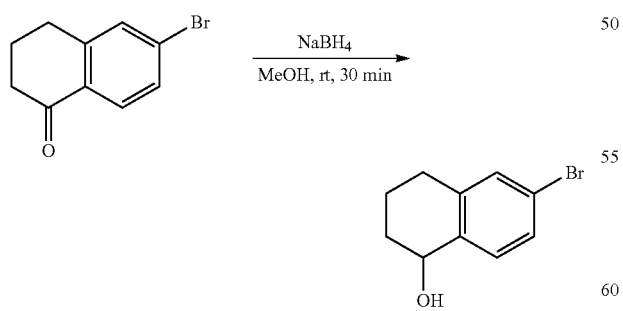

The Synthesis of 6-bromo-1,2,3,4-tetrahydronaphthalen-1-ol

To a solution of 6-bromo-3,4-dihydronaphthalen-1(2H)-one (1.5 g, 6.7 mmol) in MeOH (30 mL) was added NaBH₄ (540 mg, 14.22 mmol) and stirred at rt for 30 min. The solvent was removed in vacuo and the residue was purified by silica gel chromatography (EtOAc/hexane=1:2) to afford the alcohol (1.5 g, yield 100%) as a white solid. ESI-MS: 209.0, 211.1 (M+H−H₂O). ¹H NMR (400 MHz, CDCl₃) δ: 7.32 (s, 2H), 7.26 (s, 1H), 4.73 (t, J=4.8 Hz, 1H), 2.82-2.67 (m, 2H), 2.02-1.85 (m, 3H), 1.81-1.75 (m, 1H), 1.62 (br, 1H).

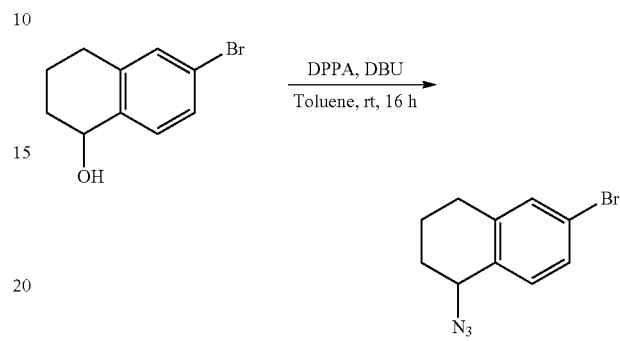

The Synthesis of 1-azido-6-bromo-1,2,3,4-tetrahydronaphthalene

To a cooled solution of alcohol (1.4 g, 6.7 mmol) in PhCH₃ (30 mL) was added DPPA (2.17 g, 7.88 mmol) and DBU (1.2 g, 7.88 mmol) dropwise while maintaining the temperature below 5° C. The reaction temperature was kept at 0° C. for 1 h and then warmed to rt for 16 h, diluted with EtOAc (50 mL), washed with 2N HCl (2*30 mL), brine and the organic layer was dried (Na₂SO₄), filtered and concentrated in vacuo to afford a residue which was purified by silica chromatography (petroleum ether) to afford the azide (1.1 g, yield 72%) as a colorless oil. ESI-MS (M+H)⁺: 252.0 ¹H NMR (400 MHz, CDCl₃) δ: 7.35-7.30 (m, 2H), 7.18-7.16 (m, 1H), 4.52 (t, J=4.8 Hz, 1H), 2.86-2.68 (m, 2H), 2.02-1.90 (m, 3H), 1.85-1.56 (m, 1H).

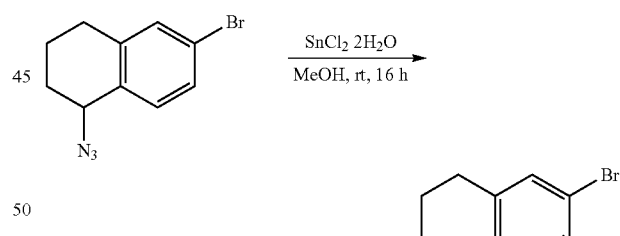

The Synthesis of 6-bromo-1,2,3,4-tetrahydronaphthalen-1-amine

A solution of azide (1.34 g, 5.3 mmol) in MeOH (30 mL) was treated with SnCl₂·H₂O (2.53 g, 11.26 mmol). The mixture was stirred at rt for 16 h, concentrated in vacuo to afford a residue which was treated with 2N NaOH (100 mL), extracted with EtOAc (4×30 mL). The combined organic extracts were filtered through Celite, washed with 1 N HCl (30 mL×4), followed by water (30 mL). The aqueous layers were cooled to 0° C. and adjusted to pH 11 with sat. NaOH solution. The solution was extracted with EtOAc (3×30 mL), separated, dried (Na₂SO₄), filtered and concentrated in vacuo to afford the title compound (0.65 g, yield 59%) as a yellow oil, which was used in the next step without further purification. ESI-MS (M-NH₂)⁺: 210.0. ¹H NMR (400 MHz, CDCl₃) δ: 7.29-7.28 (m, 2H), 7.23 (s, 1H), 3.92 (t, J=4.8 Hz, 1H), 2.78-2.71 (m, 2H), 2.04-1.98 (m, 1H), 1.96-1.87 (m, 1H), 1.80-1.71 (m, 1H), 1.70-1.62 (m, 1H).

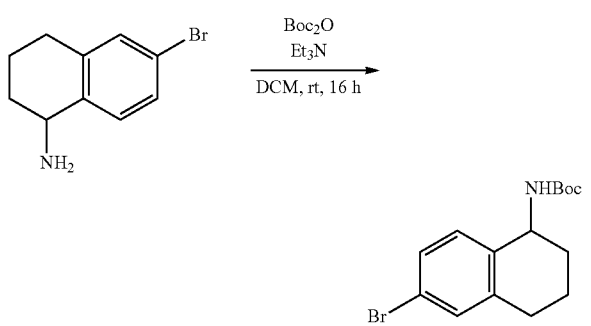

The Synthesis of tert-butyl (6-bromo-1,2,3,4-tetrahydronaphthalen-1-yl)carbamate To a solution of amine (1.02 g, 4.5 mmol) in CH₂Cl₂ (30 mL) was added Et₃N (0.73 g, 7.22 mmol) and Boc₂O (1.15 g, 5.29 mmol). The reaction solution was stirred at rt for 16 h and the mixture was concentrated in vacuo to afford a residue which was purified by silica gel chromatography (1.24 mg, yield 84%) to give a white solid. ESI-MS (M−56+H)⁺: 270.0. ¹H NMR (400 MHz, CDCl₃) δ: 7.29-7.27 (m, 1H), 7.22-7.20 (m, 2H), 4.80-4.71 (m, 2H), 2.76-2.70 (m, 2H), 2.03-2.01 (m, 1H), 1.84-1.74 (m, 3H), 1.48 (s, 9H).

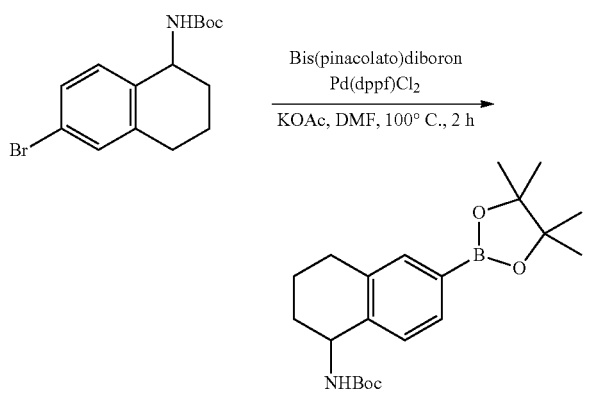

The Synthesis of tert-butyl (6-(4,4,5,5-tetramethyl-1,3,2-dioxaborolan-2-yl)-1,2,3,4-tetrahydronaphthalen-1-yl)carbamate This compound was prepared in a similar manner as described in Example 1 except tert-butyl (6-bromo-1,2,3,4-tetrahydronaphthalen-1-yl)carbamate was substituted for tert-butyl 4-bromo-2-methylbenzylcarbamate. ¹H NMR (400 MHz, CDCl₃) δ: 7.60 (d, J=7.6 Hz, 1H), 7.54 (s, 1H), 7.50 (d, J=7.6 Hz, 1H), 4.86-4.74 (m, 2H), 2.80-2.71 (m, 2H), 2.05-2.01 (m, 1H), 1.84-1.74 (m, 3H), 1.48 (s, 9H), 1.34 (s, 12H).

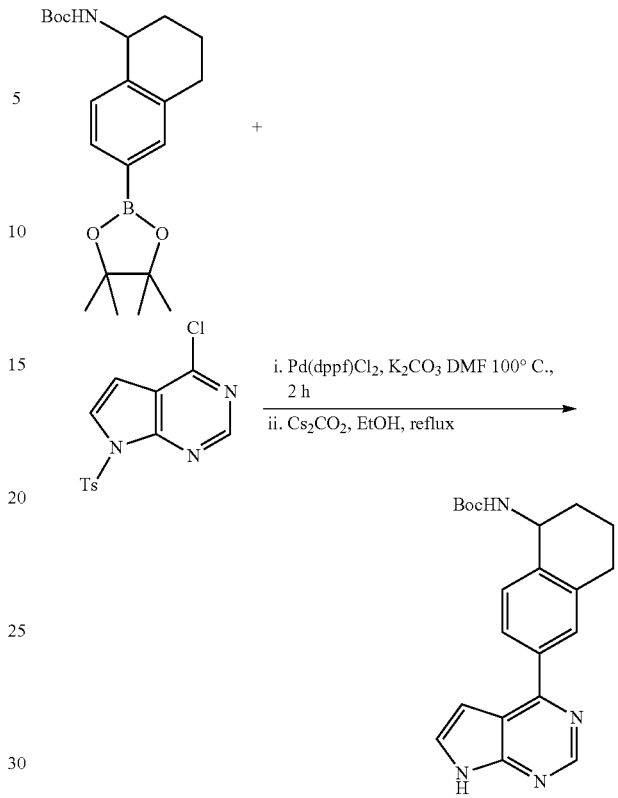

The Synthesis of tert-butyl (6-(7H-pyrrolo[2,3-d]pyrimidin-4-yl)-1,2,3,4-tetrahydronaphthalen-1-yl)carbamate This compound was prepared in a similar manner as described in Example I-1 except tert-butyl (6-(4,4,5,5-tetramethyl-1,3,2-dioxaborolan-2-yl)-1,2,3,4-tetrahydronaphthalen-1-yl)carbamate was substituted for tert-butyl 4-(4,4,5,5-tetramethyl-1,3,2-dioxaborolan-2-yl)benzylcarbamate to afford the title compound (130 mg, yield 38%) as a white solid. ESI-MS (M+H)⁺: 365.1. ¹H NMR (400 MHz, CDCl₃) δ: 9.99 (br, 1H), 9.03 (s, 1H), 7.92-7.88 (m, 2H), 7.57-7.52 (m, 1H), 7.43 (s, 1H), 6.91 (s, 1H), 4.96-4.82 (m, 2H), 2.93-2.88 (m, 2H), 2.13-2.08 (m, 2H), 1.92-1.82 (m, 2H), 1.31 (s, 9H).

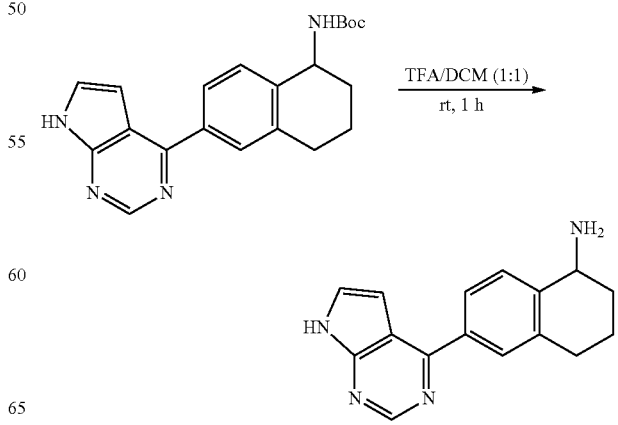

The Synthesis of 6-(7H-pyrrolo[2,3-d]pyrimidin-4-yl)-1,2,3,4-tetrahydronaphthalen-1-amine This compound was prepared in a similar manner as described in Example 1 except tert-butyl (6-(7H-pyrrolo[2,3-d]pyrimidin-4-yl)-1,2,3,4-tetrahydronaphthalen-1-yl)carbamate was substituted for di-tert-butyl 2-cyano-4-(7H-pyrrolo[2,3-d]pyrimidin-4-yl)benzylcarbamate to afford the title compound (94 mg, yield 100%) which was used in the next step without further purification. ESI-MS (M+H)+: 265.1

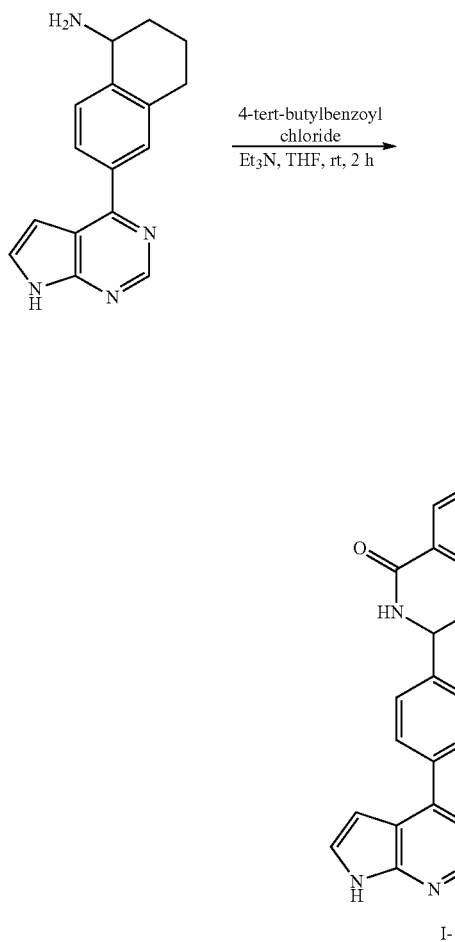

I-14

The Synthesis of N-(6-(7H-pyrrolo[2,3-d]pyrimidin-4-yl)-1,2,3,4-tetrahydronaphthalen-1-yl)-4-(tert-butyl)benzamide (I-14)

Compound I-14 was prepared in a similar manner as described in Example 1 except 6-(7H-pyrrolo[2,3-d]pyrimidin-4-yl)-1,2,3,4-tetrahydronaphthalen-1-amine was substituted for 2-(aminomethyl)-5-(7H-pyrrolo[2,3-d]pyrimidin-4-yl)benzonitrile to afford the title compound I-14 (20 mg, yield: 13%). ESI-MS (M+H)+: 425.2 $^1$H NMR (400 MHz, DMSO-d$_6$) δ: 12.22 (br, 1H), 8.81 (s, 1H), 8.78 (d, J=8.4 Hz, 1H), 7.96-7.94 (m, 2H), 7.89 (d, J=8.4 Hz, 2H), 7.64-7.62 (m, 1H), 7.50 (d, J=8.8 Hz, 2H), 7.38 (d, J=8.4 Hz, 1H), 6.88-6.87 (m, 1H), 5.35-5.31 (m, 1H), 2.95-2.93 (m, 2H), 2.08-2.03 (m, 2H), 1.92-1.82 (m, 2H), 1.31 (s, 9H).

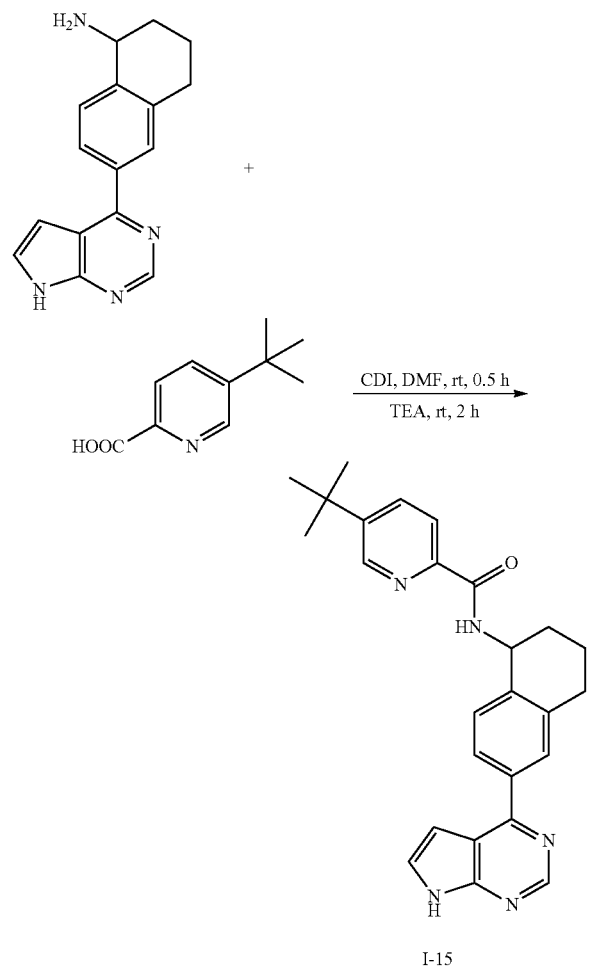

I-15

The Synthesis of N-(6-(7H-pyrrolo[2,3-d]pyrimidin-4-yl)-1,2,3,4-tetrahydronaphthalen-1-yl)-5-(tert-butyl)picolinamide (I-15)

Compound I-15 was prepared in a similar manner as described in Example 1 except 6-(7H-pyrrolo[2,3-d]pyrimidin-4-yl)-1,2,3,4-tetrahydronaphthalen-1-amine was substituted for 2-(aminomethyl)-5-(7H-pyrrolo[2,3-d]pyrimidin-4-yl)benzonitrile to afford the title compound I-15 (52 mg, yield: 36%) as a white solid. ESI-MS (M+H)+: 426.22. $^1$H NMR (400 MHz, CD$_3$OD) δ: 8.77 (s, 1H), 8.70 (d, J=2.0 Hz, 1H), 8.12-8.02 (m, 2H), 7.87-7.85 (m, 2H), 7.53 (d, J=3.6 Hz, 1H), 7.47 (d, J=8.8 Hz, 1H), 6.86 (d, J=3.6 Hz, 1H), 5.42-5.40 (m, 1H), 3.04-3.00 (m, 2H), 2.06-1.98 (m, 4H), 1.41 (s, 9H).

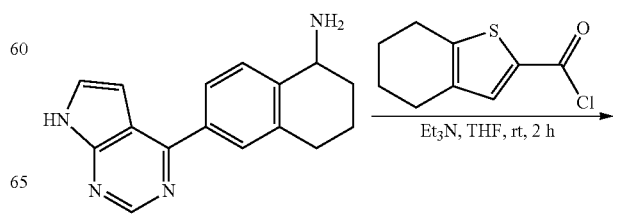

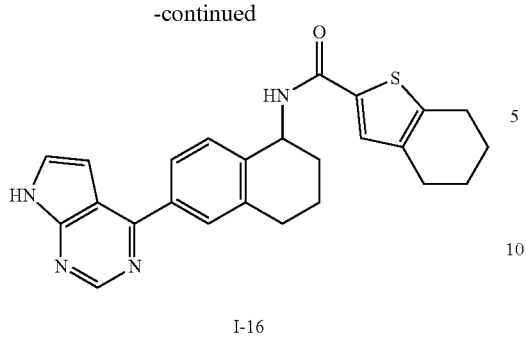

I-16

The Synthesis of N-(6-(7H-pyrrolo[2,3-d]pyrimidin-4-yl)-1,2,3,4-tetrahydronaphthalen-1-yl)-4,5,6,7-tetrahydrobenzo[b]thiophene-2-carboxamide (I-16)

Compound I-16 was prepared in a similar manner as described in Example 2 except 4,5,6,7-tetrahydrobenzo[b]thiophene-2-carbonyl chloride (Mitschke, U. *European JOC* 2000, 3, 425.) was substituted for 4-(tert-butyl)benzoyl chloride to afford the title compound (41 mg, Y: 32%). ESI-MS (M+H)+: 429.2. $^1$H NMR (400 MHz, CD$_3$OD) δ: 9.03 (s, 1H), 7.94-7.93 (m, 1H), 7.87-7.84 (m, 2H), 7.61 (d, J=8.0 Hz, 1H), 7.41 (s, 1H), 7.16 (d, J=4.0 Hz, 1H), 5.40-5.38 (m, 1H), 3.04-3.00 (m, 2H), 2.81 (t, J=6.0 Hz, 2H), 2.62 (t, J=6.0 Hz, 2H), 2.23-2.17 (m, 1H), 2.16-2.10 (m, 1H), 1.99-1.95 (m, 2H), 1.88-1.81 (m, 4H).

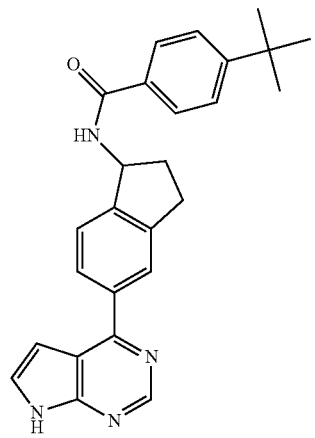

I-154

The Synthesis of N-(5-(7H-pyrrolo[2,3-d]pyrimidin-4-yl)-2,3-dihydro-1H-inden-1-yl)-4-(tert-butyl)benzamide (I-154)

Compound I-154 was prepared in a similar manner as described for I-14 except 5-bromo-2,3-dihydro-1H-inden-1-one was substituted for 6-bromo-3,4-dihydronaphthalen-1(2H)-one to afford the title compound (140 mg, yield 61%). ESI-MS (M+H)+: 411.2. $^1$H NMR (400 MHz, DMSO-d$_6$) δ: 12.26 (br, 1H), 8.81-8.79 (m, 2H), 8.06 (s, 1H), 8.02 (d, J=8.0 Hz, 1H), 7.90-7.87 (m, 2H), 7.64 (d, J=3.6 Hz, 1H), 7.51-7.48 (m, 2H), 7.40 (d, J=7.6 Hz, 1H), 6.87 (d, J=3.2 Hz, 1H), 5.66 (q, J=8.0 Hz, 1H), 3.16-3.10 (m, 1H), 3.02-2.96 (m, 1H), 2.56-2.53 (m, 1H), 2.11-2.06 (m, 1H), 1.31 (s, 9H).

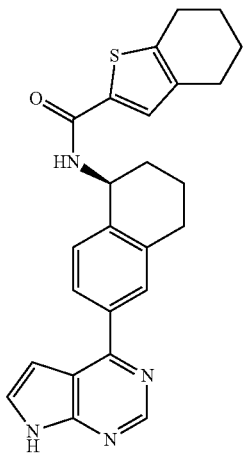

I-89

(S)—N-(6-(7H-Pyrrolo[2,3-d]pyrimidin-4-yl)-1,2,3,4-tetrahydronaphthalen-1-yl)-4,5,6,7-tetrahydrobenzo[b]thiophene-2-carboxamide (I-89)

I-89 was purified from I-16 by SFC chromatography HPLC (10-90% ACN w/0.1% TFA, 2 min, 3 ml/min, xterra 4.6×20 mm 2.5 um): 1.23 min (95% purity). ES (+) MS m/e=429.0 (M+1). 1H NMR (400 MHz, CHLOROFORM-d) δ: 9.25 (br. s., 1H), 8.98 (br. s., 1H), 7.85-7.98 (m, 2H), 7.53 (d, J=8.28 Hz, 1H), 7.39 (br. s., 1H), 7.21 (s, 1H), 6.86 (br. s., 1H), 6.09 (d, J=8.53 Hz, 1H), 5.38-5.54 (m, 1H), 2.97 (d, J=8.53 Hz, 2H), 2.79 (t, J=5.77 Hz, 2H), 2.61 (t, J=5.90 Hz, 2H), 2.13-2.29 (m, 1H), 1.95 (br. s., 3H), 1.74-1.90 (m, 4H).

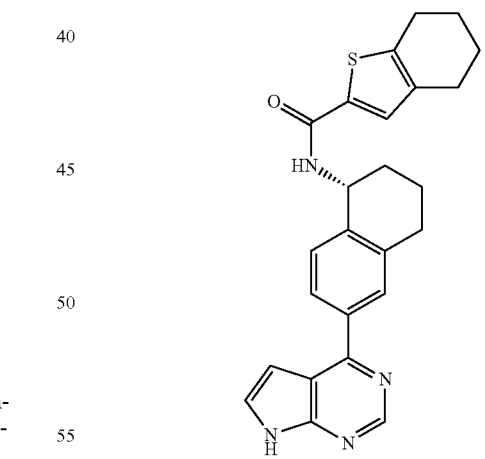

I-81

(R)—N-(6-(7H-Pyrrolo[2,3-d]pyrimidin-4-yl)-1,2,3,4-tetrahydronaphthalen-1-yl)-4,5,6,7-tetrahydrobenzo[b]thiophene-2-carboxamide (I-81)

I-81 was purified from I-16 by SFC chromatography HPLC (10-90% ACN w/0.1% TFA, 2 min, 3 ml/min, xterra 4.6×20 mm 2.5 um): 1.24 min (95% purity). ES (+) MS m/e=429.0 (M+1). $^1$H NMR (400 MHz, CHLOROFORM-d) δ: 9.25 (br. s., 1H), 8.98 (br. s., 1H), 7.85-7.98 (m, 2H), 7.53

(d, J=8.28 Hz, 1H), 7.39 (br. s., 1H), 7.21 (s, 1H), 6.86 (br. s., 1H), 6.09 (d, J=8.53 Hz, 1H), 5.38-5.54 (m, 1H), 2.97 (d, J=8.53 Hz, 2H), 2.79 (t, J=5.77 Hz, 2H), 2.61 (t, J=5.90 Hz, 2H), 2.13-2.29 (m, 1H), 1.95 (br. s., 3H), 1.74-1.90 (m, 4H).

Example 3

Scheme 5

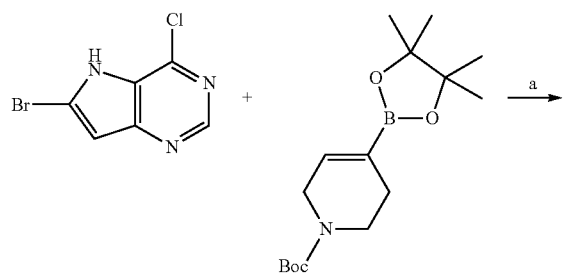
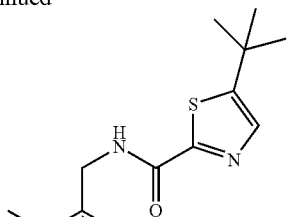

I-18

Reagents and conditions: (a) Pd(dppf)Cl2, K2CO3, 1,4-dioxane/H2O (10/1), 110° C., 4 h. (b) Pd(dppf)Cl2, K2CO3, 1,4-dioxane/H2O (10/1), 110° C., 4 h. (c) i. TFA, DCM rt, 2 h. ii. Me2NCOCl, TEA, THF, rt, 2 h.

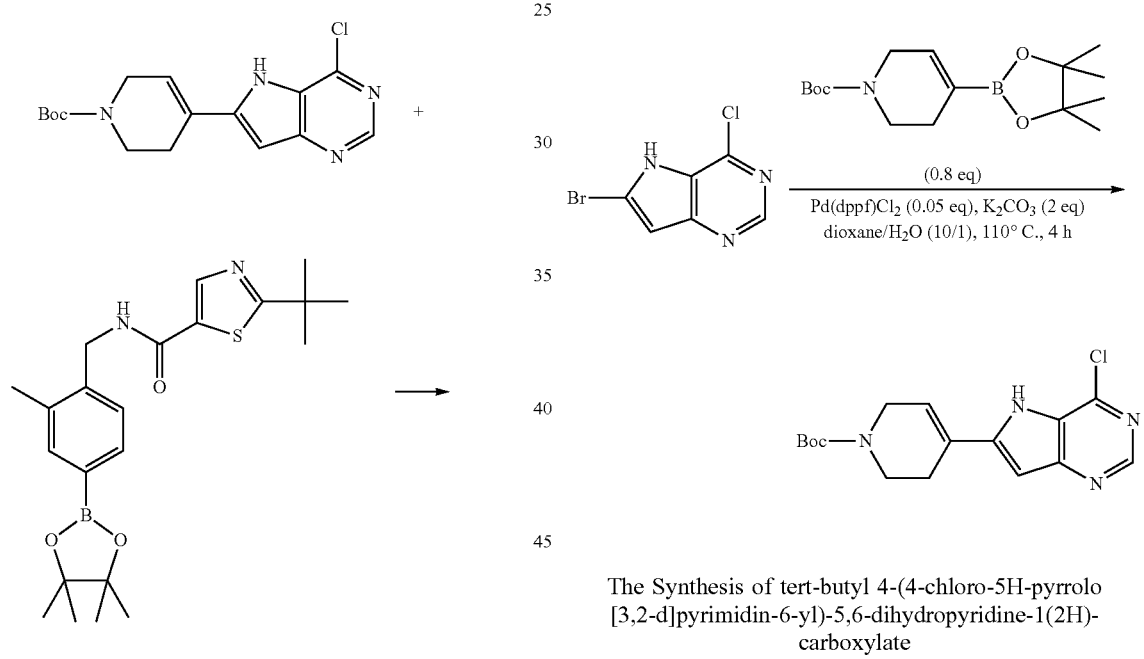

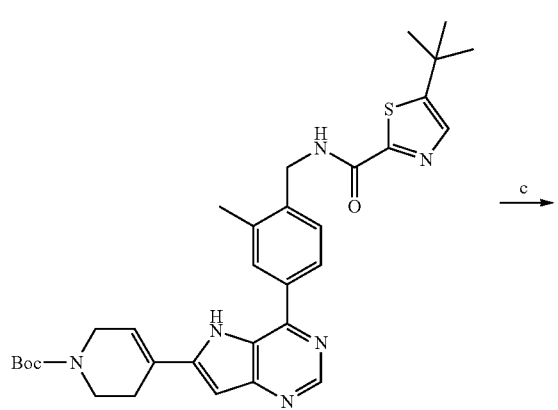

The Synthesis of tert-butyl 4-(4-chloro-5H-pyrrolo[3,2-d]pyrimidin-6-yl)-5,6-dihydropyridine-1(2H)-carboxylate To a solution of aryl bromide (233 mg, 1.0 mmol) in 1,4-dioxane (8 mL) and H$_2$O (2 mL) was added tert-butyl 4-(4,4,5,5-tetramethyl-1,3,2-dioxaborolan-2-yl)-5,6-dihyropyridine-1(2H)-carboxylate (Eunkyuing, K. et al Bioorganic & Medicinal Chemistry Letters 2008, 18, 4993-4996) (245 mg, 0.8 mmol), Pd(dppf)Cl$_2$.DCM (41 mg, 0.05 mmol) and K$_2$CO$_3$ (276 mg, 2.0 mmol) under N$_2$. The mixture was stirred at 110° C. for 4 h, cooled to rt, diluted with H$_2$O (80 mL) and extracted with EtOAc (60 mL×3). The organic layers separated, dried (Na$_2$SO$_4$) concentrated in vacuo to afford a residue which was purified by column chromatography (petroleum ether/EtOAc=5:1 to 2:1) to give the title compound (77 mg, yield 23%) as yellow solid ESI-MS (M+H)$^+$: 335.2. $^1$H NMR (400 MHz, CDCl$_3$) δ: 10.82 (br, 1H), 8.71 (s, 1H), 6.73 (s, 1H), 6.68-6.56 (m, 1H), 4.16-4.13 (m, 2H), 3.70-3.65 (m, 2H), 2.62-2.60 (m, 2H), 1.46 (s, 9H).

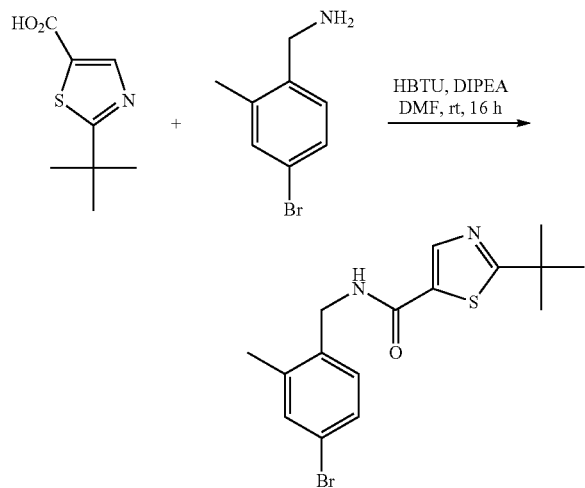

The Synthesis of N-(4-bromo-2-methylbenzyl)-2-(tert-butyl)thiazole-5-carboxamide To a solution of acid (185 mg, 1.0 mmol) in DMF (5 mL) was added HBTU (455 mg, 1.2 mmol) and DIPEA (387 mg, 3.0 mmol) and stirred at rt for 15 min, followed by the addition of 4-bromo-2-methylphenyl)methanamine (300 mg, 1.5 mmol), and the solution was stirred at rt for 16 h. Diluted with water (40 mL), the mixture was extracted with EtOAc (80 mL×2). The organic phase was concentrated in vacuo to afford a residue which was purified by silica gel column chromatography (petroleum ether/EtOAc=10:1-4:1) to give the title compound (220 mg, yield: 60%) as a yellow solid. ESI-MS (M+H)+: 367.1. $^1$H NMR (400 MHz, CDCl$_3$) δ: 8.20 (s, 1H), 7.35 (d, J=1.6 Hz, 1H), 7.32 (dd, J=8.0, 1.6 Hz, 1H), 7.17 (d, J=8.4 Hz, 1H), 4.55 (d, J=5.6 Hz, 2H), 2.34 (s, 3H), 1.47 (s, 9H).

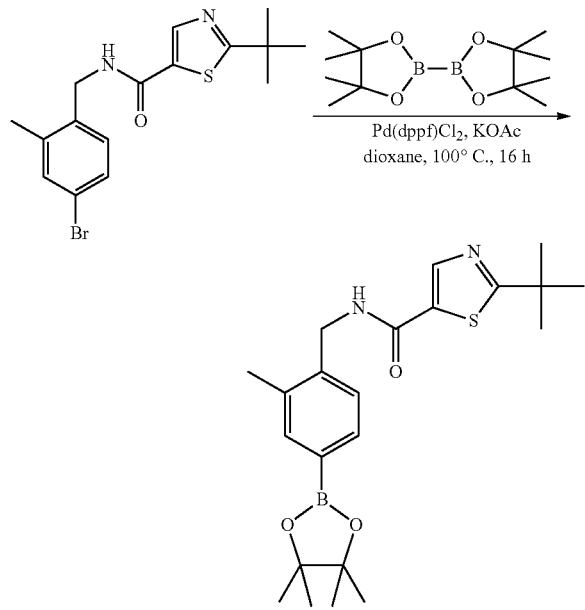

The Synthesis of 2-(tert-butyl)-N-(2-methyl-4-(4,4,5,5-tetramethyl-1,3,2-dioxaborolan-2-yl)benzyl)thiazole-5-carboxamide A mixture of aryl bromide (220 mg, 0.6 mmol), KOAc (176 mg, 1.8 mmol) and Pd(dppf)Cl$_2$DCM (130 mg, 0.06 mmol), bis(pinacolato)diboron (168 mg, 0.66 mmol) in dry 1,4-dioxane (6 mL) was stirred at 100° C. for 16 h under nitrogen. After cooling down to rt, the mixture was diluted with water (20 mL) and extracted with EtOAc (50 mL×2). The combined organic layer was washed with brine, dried (Na$_2$SO$_4$), concentrated in vacuo to afford a residue which was purified by silica gel chromatography (petroleum ether:EtOAc 4:1) to give the title compound (188 mg, yield: 75%) as a white solid. ESI-MS (M+H)+: 415.0. $^1$H NMR (400 MHz, CDCl$_3$) δ: 8.02 (s, 1H), 7.66 (s, 1H), 7.64 (d, J=8.0 Hz, 1H), 7.29 (d, J=8.0, 1H), 6.00 (br, 1H), 4.62 (d, J=5.6 Hz, 2H), 2.36 (s, 3H), 1.44 (s, 9H), 1.35 (s, 12H).

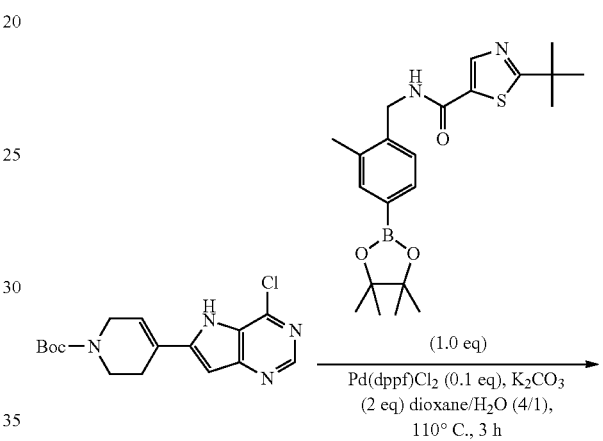

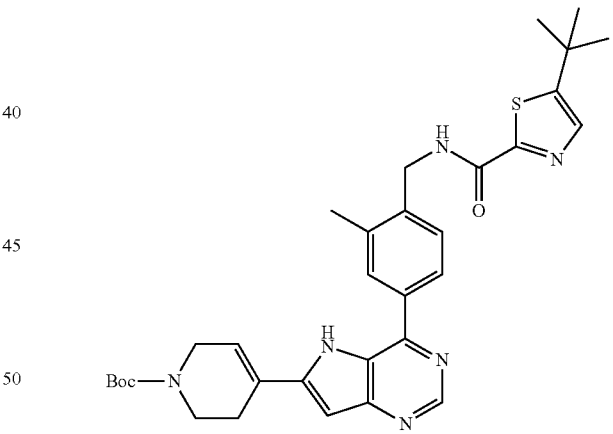

The Synthesis of tert-butyl 4-(4-(4-((5-(tert-butyl)thiazole-2-carboxamido)methyl)-3-methylphenyl)-5H-pyrrolo[3,2-d]pyrimidin-6-yl)-5,6-dihydropyridine-1(2H)-carboxylate To a solution of tert-butyl 4-(4-chloro-5H-pyrrolo[3,2-d]pyrimidin-6-yl)-5,6-dihydropyridine-1(2H)-carboxylate (67 mg, 0.2 mmol) in 1,4-dioxane (4 mL) and H$_2$O (1 mL), was added 2-(tert-butyl)-N-(2-methyl-4-(4,4,5,5-tetramethyl-1,3,2-dioxaborolan-2-yl)benzyl)thiazole-5-carboxamide (83 mg, 0.2 mmol), Pd(dppf)Cl$_2$.DCM (17 mg, 0.02 mmol) and K$_2$CO$_3$ (55 mg, 0.4 mmol) under an atmosphere of N$_2$. The mixture was stirred at 110° C. for 3 h, cooled to rt, diluted with H₂O (20 mL) and extracted with EtOAc (60 mL×2). The organic layers were collected, concentrated in vacuo to afford a residue which was purified by column chromatography (petroleum ether/EtOAc=1:1 to 1:2) to give the title compound (70 mg, yield: 60%) as yellow solid ESI-MS (M+H)⁺: 587.1. ¹H NMR (400 MHz, CD₃OD) δ: 8.60 (br, 1H), 8.12 (s, 1H), 7.60-7.58 (m, 2H), 7.32-7.30 (m, 1H), 6.49 (s, 1H), 6.43-6.40 (m, 1H), 4.45 (s, 2H), 3.99-3.96 (m, 2H), 3.50-3.48 (m, 2H), 2.44-2.40 (m, 2H), 2.29 (s, 3H), 1.35 (s, 9H), 1.30 (s, 9H).

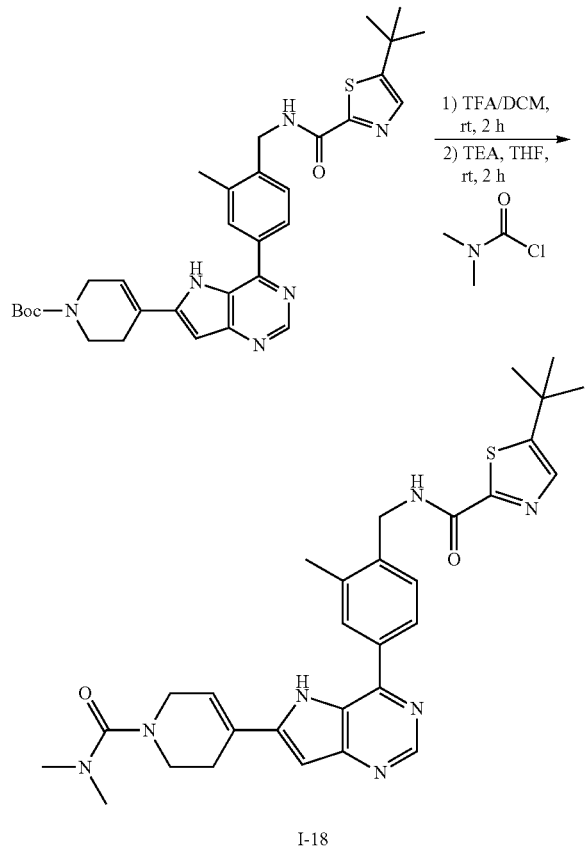

I-18

The Synthesis of 5-(tert-butyl)-N-(4-(6-(1-(dimethylcarbamoyl)-1,2,3,6-tetrahydropyridin-4-yl)-5H-pyrrolo[3,2-d]pyrimidin-4-yl)-2-methylbenzyl)thiazole-2-carboxamide (I-18)

A solution of Boc amine (70 mg, 0.12 mmol) in DCM/TFA (4 mL, 1:1) was stirred at rt for 2 h. The mixture was concentrated in vacuo and the residue was dissolved in THF (4 mL) and treated with Et₃N (60 mg, 0.6 mmol) and dimethylcarbamic chloride (16 mg, 0.15 mmol). The mixture was stirred at rt for 2 h, diluted with EtOAc (80 mL), and washed with water (60 mL). The organic layer was collected, concentrated in vacuo to afford a residue which was purified by reverse phase chromatography (CH₃CN/H₂O with 0.05% NH₃.H₂O as mobile phase) to give the title compound I-18 (50 mg, yield: 75%) as yellow solid ESI-MS (M+H)⁺: 558.2. ¹H NMR (400 MHz, CD₃OD) δ: 8.74 (s, 1H), 8.25 (s, 1H), 7.75-7.72 (m, 2H), 7.45 (d, J=8.0 Hz, 1H), 6.63 (s, 1H), 6.59-6.57 (m, 1H), 4.59 (s, 2H), 3.95-3.92 (m, 2H), 3.44-3.40 (m, 2H), 2.85 (s, 6H), 2.64-2.60 (m, 2H), 2.44 (s, 3H), 1.44 (s, 9H).

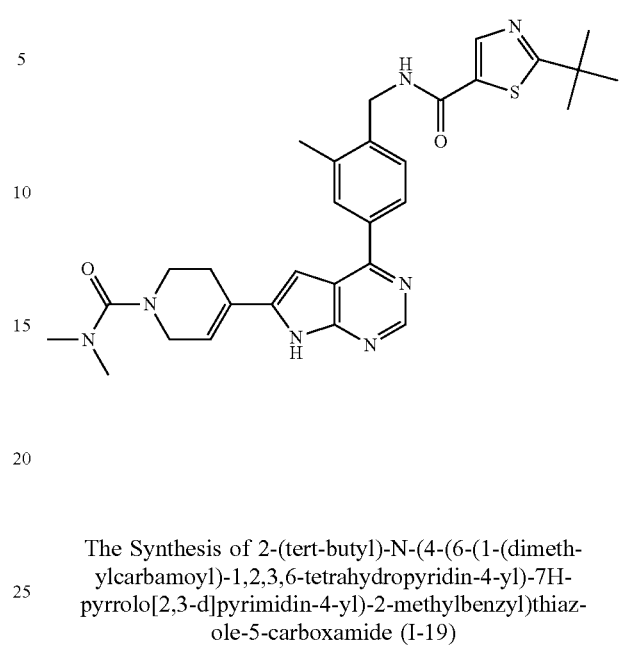

I-19

The Synthesis of 2-(tert-butyl)-N-(4-(6-(1-(dimethylcarbamoyl)-1,2,3,6-tetrahydropyridin-4-yl)-7H-pyrrolo[2,3-d]pyrimidin-4-yl)-2-methylbenzyl)thiazole-5-carboxamide (I-19)

Compound I-19 was prepared in a similar manner as described for I-18 except 6-bromo-4-chloro-7H-pyrrolo[2,3-d]pyrimidine was substituted for 6-bromo-4-chloro-5H-pyrrolo[3,2-d]pyrimidine to afford the title compound (55 mg, yield 55%) as a brown solid. ESI-MS (M+H)⁺: 558.3. ¹H NMR (400 MHz, DMSO-d₆) δ: 12.36 (s, 1H), 9.14 (t, J=5.6 Hz, 1H), 8.77 (s, 1H), 8.35 (s, 1H), 8.01-7.99 (m, 2H), 7.42 (d, J=8.4 Hz, 1H), 6.88 (s, 1H), 6.58-6.56 (m, 1H), 4.52 (d, J=5.6 Hz, 2H), 3.90-3.89 (m, 2H), 3.35 (t, J=6.0 Hz, 2H), 2.77 (s, 6H), 2.61-2.59 (m, 2H), 2.44 (s, 3H), 1.40 (s, 9H).

Scheme 6

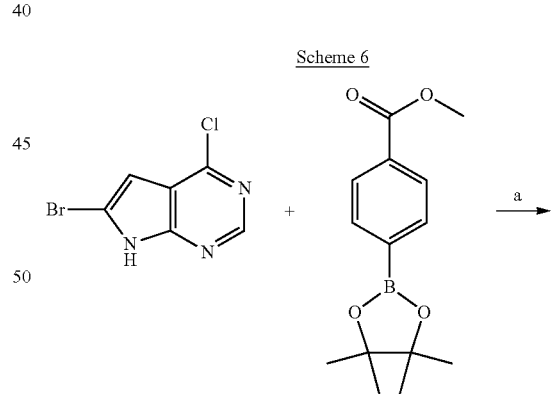

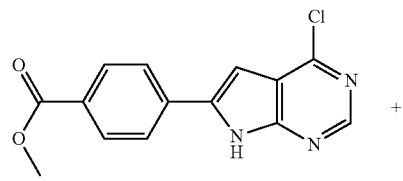

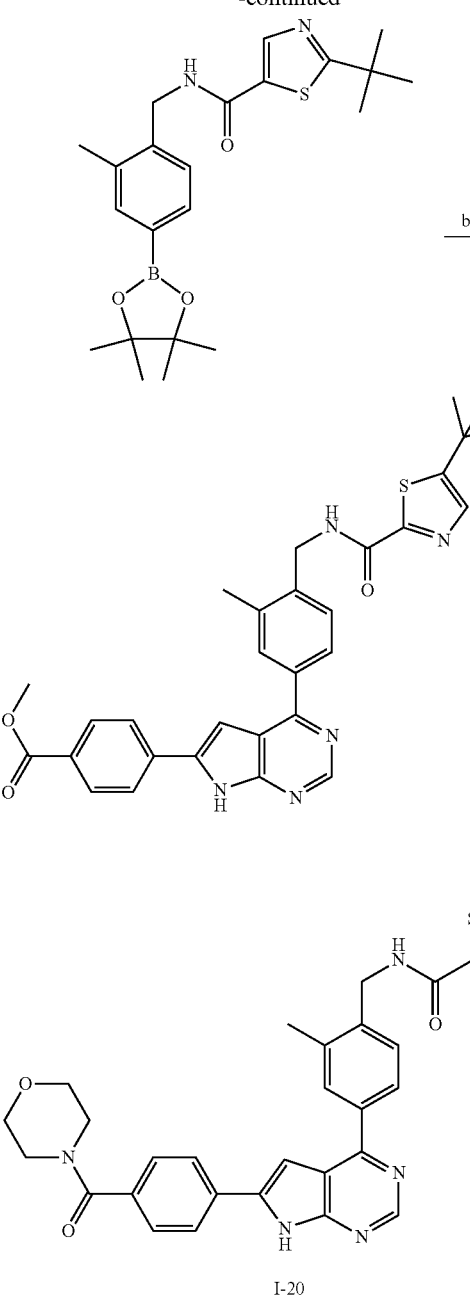

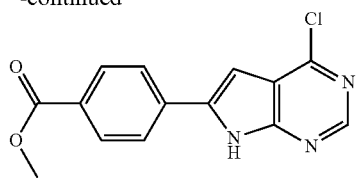

The Synthesis of methyl 4-(4-chloro-7H-pyrrolo[2,3-d]pyrimidin-6-yl)benzoate

This compound was prepared in a similar manner as described for I-18 except 6-bromo-4-chloro-7H-pyrrolo[2,3-d]pyrimidine and methyl 4-(4,4,5,5-tetramethyl-1,3,2-dioxaborolan-2-yl)benzoate were substituted for tert-butyl 4-(4,4,5,5-tetramethyl-1,3,2-dioxaborolan-2-yl)-5,6-dihydropyridine-1(2H)-carboxylate and 6-bromo-4-chloro-5H-pyrrolo[3,2-d]pyrimidine to afford the title compound (140 mg, yield 48%) as a yellow solid. ESI-MS (M+H)$^+$: 287.8. $^1$H NMR (400 MHz, CD$_3$OD) δ: 8.13 (s, 1H), 7.66 (d, J=8.4 Hz, 2H), 7.57 (d, J=8.8 Hz, 2H), 6.55 (s, 1H), 3.49 (s, 3H).

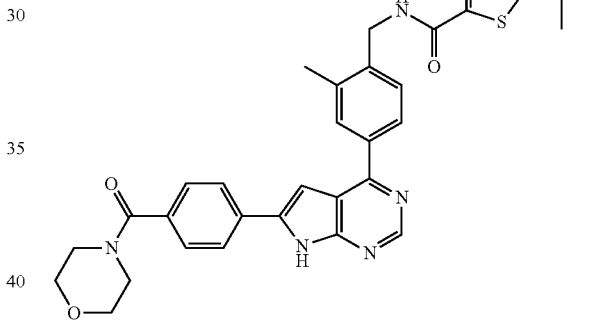

I-20

The Synthesis of methyl 4-(4-(4-(((2-(tert-butyl)thiazole-5-carboxamido)methyl)-3-methylphenyl)-7H-pyrrolo[2,3-d]pyrimidin-6-yl)benzoate (I-20)

Compound I-21 was prepared in a similar manner as described in Example 6 except 2-(tert-butyl)-N-(2-methyl-4-(4,4,5,5-tetramethyl-1,3,2-dioxaborolan-2-yl)benzyl)thiazole-5-carboxamide was substituted for tert-butyl 4-(4,4,5,5-tetramethyl-1,3,2-dioxaborolan-2-yl)benzylcarbamate to afford the title compound (40 mg, yield 46%) ESI-MS (M+H)$^+$: 595.3. $^1$H NMR (400 MHz, CD$_3$OD) δ: 8.77 (s, 1H), 8.27 (s, 1H), 8.01 (d, J=8.4 Hz, 2H), 7.97 (s, 1H), 7.96 (d, J=6.4 Hz, 1H), 7.55 (d, J=8.4 Hz, 2H), 7.51 (d, J=8.4 Hz, 1H), 7.30 (s, 1H), 4.64 (s, 2H), 3.80-3.46 (m, 8H), 2.51 (s, 3H), 1.44 (s, 9H).

Reagent and conditions: (a) Pd(dppf)Cl$_2$, 1,4-dioxane/water, K$_2$CO$_3$, DMF, 110° C., 4 h. (b) Pd(dppf)Cl$_2$•DCM, 1,4-dioxane/water, K$_2$CO$_3$, DMF, 110° C., 4 h. (c) i. NaOH, EtOH, rt, 2 h. ii. Morpholine, HATU, DMF, Et$_3$N, rt, 2 h..

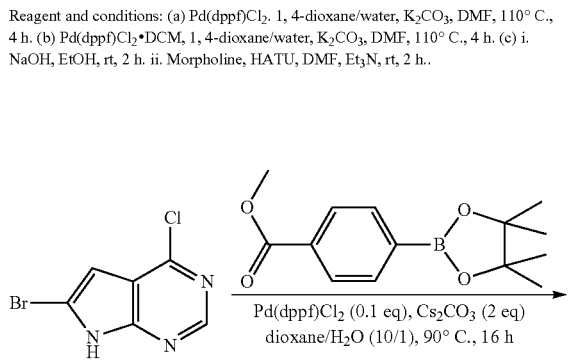

Scheme 7

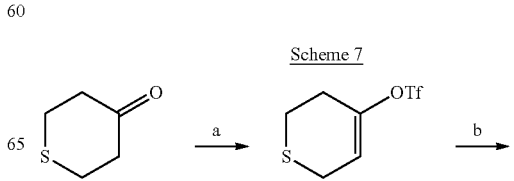

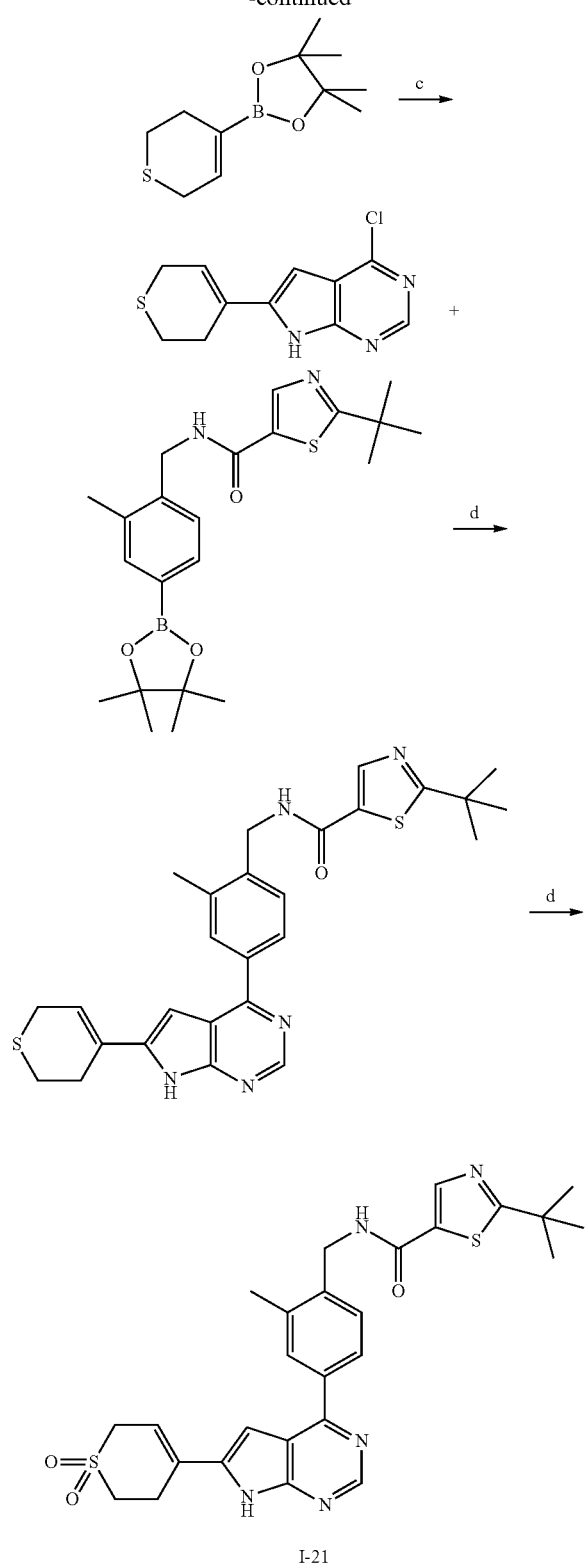

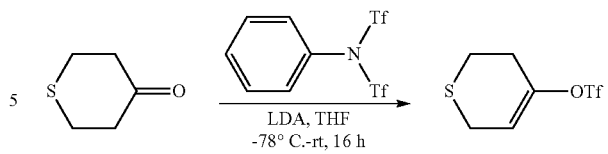

The Synthesis of 3,6-dihydro-2H-thiopyran-4-yl trifluoromethanesulfonate

To a solution of LDA (6.5 mL, 13 mmol, 1.5 eq, 2M in THF) in THF (10 mL) at −78° C. under N₂ was added dihydro-2H-thiopyran-4(3H)-one (1 g, 8.62 mmol) in THF (10 mL) dropwise over 20 minutes and stirred at −78° C. for 20 minutes. To the solution was added N-phenylbis(trifluoromethanesulfonimide) (3.39 g, 9.5 mmol, 1.1 eq) and allowed to warm to rt and stirred for 16 h. The reaction was diluted with diethyl ether (80 mL), washed with NaOH (1M, 20 mL), water (30 mL), and brine (30 mL), dried (Na₂SO₄) and concentrated in vacuo. The crude was purified by column chromatography (EtOAc/Petroleum ether, 1/20) to give the title compound (1.4 g, yield 65%). ¹H NMR (400 MHz, CDCl₃) δ: 6.01-5.98 (m, 1H), 3.30-3.28 (m, 2H), 2.86 (t, J=5.6 Hz, 2H), 2.64-2.59 (m, 2H).

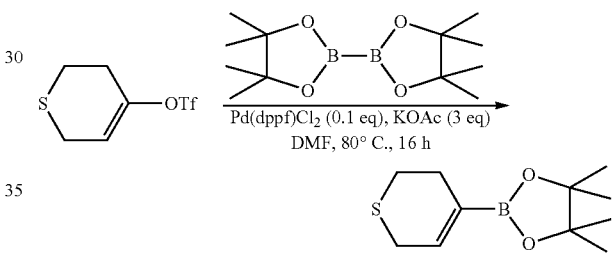

The Synthesis of 3,6-dihydro-2H-thiopyran-4-yl trifluoromethanesulfonate

Performed as shown above to yield the title compound (1.06 g, yield 80%) as a yellow solid. ESI-MS (M+H)⁺: 227.2.

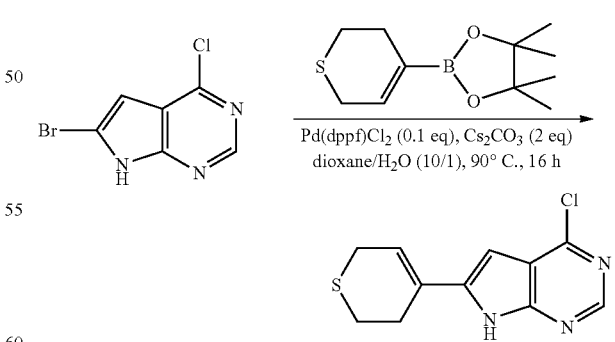

The Synthesis of 4-chloro-6-(3,6-dihydro-2H-thiopyran-4-yl)-7H-pyrrolo[2,3-d]pyrimidine This compound was prepared in a similar manner as described in Example 3 except 2-(3,6-dihydro-2H-thiopy-

I-21

Reagent and conditions: (a) 1,1,1-trifluoro-N-phenyl-N-((trifluoromethyl)sulfonyl)methane sulfonamide, LDA, THF, -78° C., rt, 16 h. (b) Pd(dppf)Cl₂. DCM, KOAc, DMF, 80° C., 16 h, yield 80%. (c) Pd(dppf)Cl₂. 1,4-dioxane/water, Cs₂CO₃, DMF, 90° C., 16 h, yield 33%. (d) Pd(dppf)Cl₂. 1,4-dioxane/water, Cs₂CO₃, DMF, 100° C., 16 h, yield 65%. (e) oxone, THF/water, rt to 60° C., 1 h.

ran-4-yl)-4,4,5,5-tetramethyl-1,3,2-dioxaborolane was substituted for tert-butyl 4-(4,4,5,5-tetramethyl-1,3,2-dioxaborolan-2-yl)-5,6-dihyropyridine-1(2H)-carboxylate to afford the title compound (55 mg, yield 33%) as a yellow solid. ESI-MS (M+H)+: 252.1. $^1$H NMR (400 MHz, DMSO-$d_6$) δ: 12.41 (s, 1H), 8.49 (s, 1H), 6.78 (s, 1H), 6.47-6.46 (m, 1H), 3.39-3.37 (m, 2H), 2.89 (t, J=5.6 Hz, 2H), 2.75-2.73 (m, 2H).

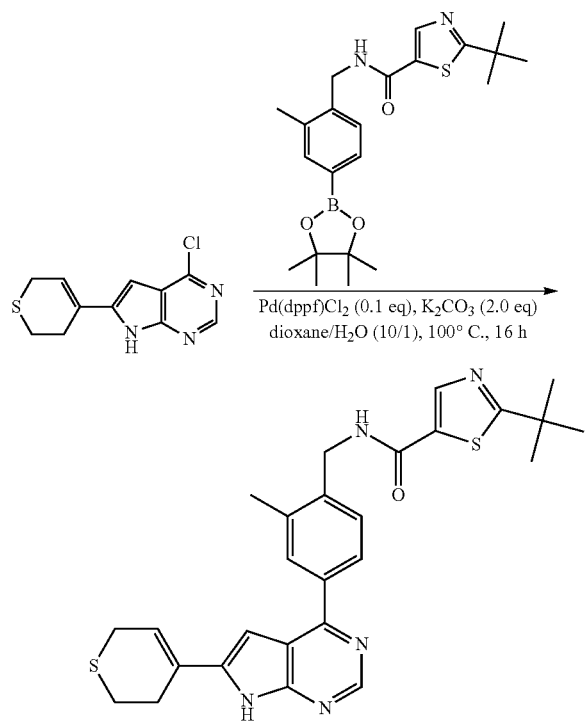

The Synthesis of 2-(tert-butyl)-N-(4-(6-(3,6-dihydro-2H-thiopyran-4-yl)-7H-pyrrolo[2,3-d]pyrimidin-4-yl)-2-methylbenzyl)thiazole-5-carboxamide This compound was prepared in a similar manner as described in Example I-18 except 4-chloro-6-(3,6-dihydro-2H-thiopyran-4-yl)-7H-pyrrolo[2,3-d]pyrimidine was substituted for tert-butyl 4-(4-chloro-5H-pyrrolo[3,2-d]pyrimidin-6-yl)-5,6-dihydropyridine-1(2H)-carboxylate to afford the title compound (60 mg, yield: 65%) as a yellow solid. ESI-MS (M+H)+: 504.1.

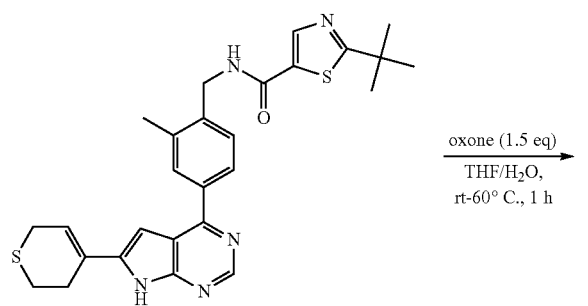

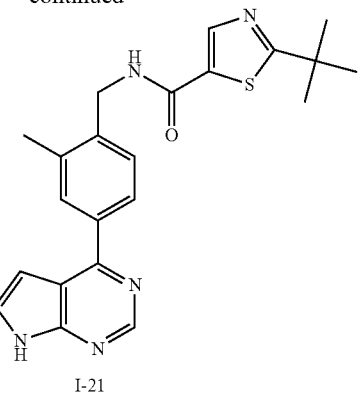

I-21

The Synthesis of 2-(tert-butyl)-N-(4-(6-(1,1-dioxido-3,6-dihydro-2H-thiopyran-4-yl)-7H-pyrrolo[2,3-d]pyrimidin-4-yl)-2-methylbenzyl)thiazole-5-carboxamide (I-21)

To a solution of 2-(tert-butyl)-N-(4-(6-(3,6-dihydro-2H-thiopyran-4-yl)-7H-pyrrolo[2,3-d]pyrimidin-4-yl)-2-methylbenzyl)thiazole-5-carboxamide (50 mg, 0.1 mmol) in THF and water (8 mL, 3:1) was added oxone (92 mg, 0.15 mmol). The mixture was stirred at rt for 60° C. for 1 h. allowed to cool to rt, diluted with water (20 mL) and extracted with EtOAc (50 mL×2). The organic layer was dried (Na$_2$SO$_4$), concentrated in vacuo and purified by column chromatography (MeOH/DCM=1/15) to give the title compound (13 mg, yield: 24%) as a yellow solid. ESI-MS (M+H)+: 536.1. $^1$H NMR (400 MHz, CD$_3$OD) δ: 8.85 (s, 1H), 8.36 (s, 1H), 8.04-8.02 (m, 2H), 7.57 (d, J=8.0 Hz, 1H), 7.02 (s, 1H), 6.53 (t, J=4.0 Hz, 1H), 4.68 (s, 2H), 4.04-4.03 (m, 2H), 3.45 (t, J=6.0 Hz, 2H), 3.30-3.25 (m, 2H), 2.56 (s, 3H), 1.51 (s, 9H).

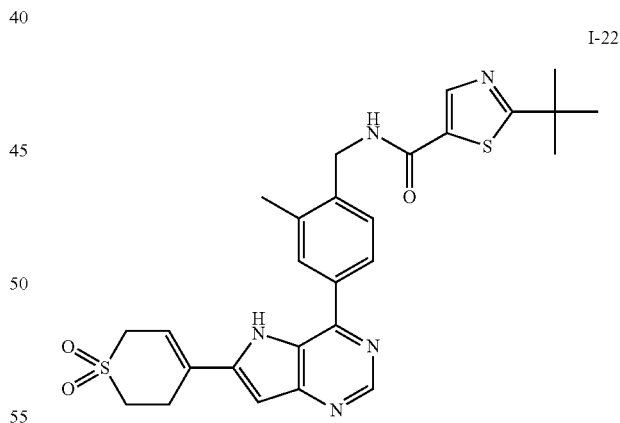

I-22

The Synthesis of 2-(tert-butyl)-N-(4-(6-(1,1-dioxido-3,6-dihydro-2H-thiopyran-4-yl)-5H-pyrrolo[3,2-d]pyrimidin-4-yl)-2-methylbenzyl)thiazole-5-carboxamide (I-22)

Compound I-22 was prepared in a similar manner as described in Example 3 except 6-bromo-4-chloro-5H-pyrrolo[3,2-d]pyrimidine was substituted for 6-bromo-4-chloro-7H-pyrrolo[2,3-d]pyrimidine to afford the title compound (43 mg, yield: 46%) as a white solid. ESI-MS (M+H)+: 536.2. ¹H NMR (400 MHz, CD₃OD) δ: 8.70 (s, 1H), 8.14 (s, 1H), 7.72 (s, 1H), 7.70 (d, J=8.0 Hz, 1H), 7.42 (d, J=8.0 Hz, 1H), 6.69 (s, 1H), 6.41 (t, J=4.4 Hz, 1H), 4.55 (s, 2H), 3.84-3.83 (m, 2H), 3.29 (t, J=6.4 Hz, 2H), 3.16 (t, J=5.6 Hz, 2H), 2.41 (s, 3H), 1.36 (s, 9H).

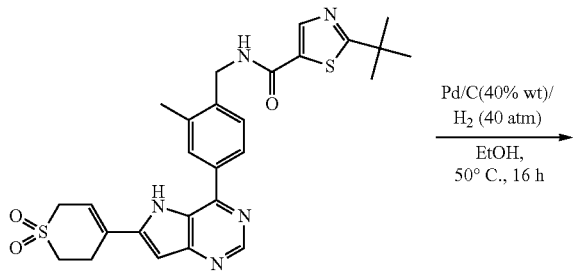

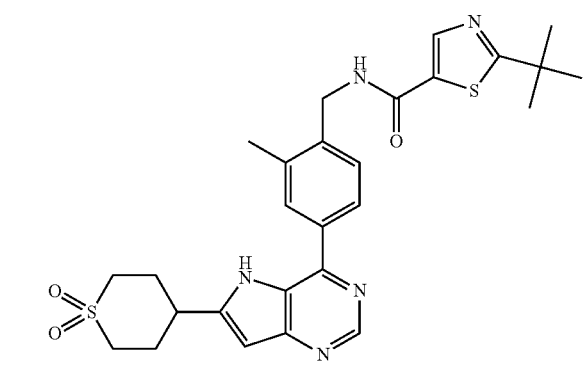

I-23

The Synthesis of 2-(tert-butyl)-N-(4-(6-(1,1-dioxidotetrahydro-2H-thiopyran-4-yl)-5H-pyrrolo[3,2-d]pyrimidin-4-yl)-2-methylbenzyl)thiazole-5-carboxamide (I-23)

A solution of 2-(tert-butyl)-N-(4-(6-(1,1-dioxido-3,6-dihydro-2H-thiopyran-4-yl)-5H-pyrrolo[3,2-d]pyrimidin-4-yl)-2-methylbenzyl)thiazole-5-carboxamide (54 mg, 0.1 mmol) in 20 mL EtOH was treated with Pd/C (22 mg, 40% wt) at 50° C. for 16 h under hydrogen atmosphere (40 atm). The solid was filtered off and the filtrate was concentrated in vacuo to afford a residue which was purified by column chromatography (MeOH/DCM=1/15) to give the title compound (4 mg, yield 9%) as a white solid. ESI-MS (M+H)+: 538.2. ¹H NMR (400 MHz, CD₃OD) δ: 8.68 (s, 1H), 8.14 (s, 1H), 7.71-7.67 (m, 2H), 7.43 (d, J=8.0 Hz, 1H), 6.47 (s, 1H), 4.55 (s, 2H), 3.32-3.25 (m, 3H), 3.10-3.09 (m, 2H), 2.42 (s, 3H), 2.36-2.31 (m, 4H), 1.36 (s, 9H).

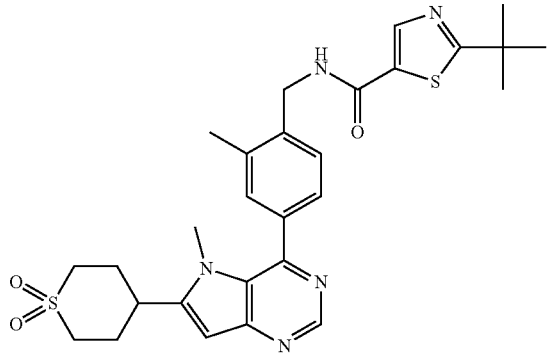

I-24

The Synthesis of 2-(tert-butyl)-N-(4-(6-(1,1-dioxidotetrahydro-2H-thiopyran-4-yl)-5-methyl-5H-pyrrolo[3,2-d]pyrimidin-4-yl)-2-methylbenzyl)thiazole-5-carboxamide (I-24)

Compound I-24 was prepared in a similar manner as described in Example 3 except 6-bromo-4-chloro-5-methyl-5H-pyrrolo[3,2-d]pyrimidine was substituted for 6-bromo-4-chloro-7H-pyrrolo[2,3-d]pyrimidine to afford the title compound (20 mg, yield 55%) as a yellow solid. ESI-MS (M+H)+: 552.2. ¹H NMR (400 MHz, CD₃OD) δ: 8.63 (s, 1H), 8.14 (s, 1H), 7.39 (d, J=8.4 Hz, 1H), 7.36 (s, 1H), 7.31 (dd, J=7.6, 1.6 Hz, 1H), 6.54 (s, 1H), 4.55 (s, 2H), 3.36 (s, 3H), 3.32-3.24 (m, 3H), 3.08-3.04 (m, 2H), 2.38 (s, 3H), 2.32-2.18 (m, 4H), 1.35 (s, 9H).

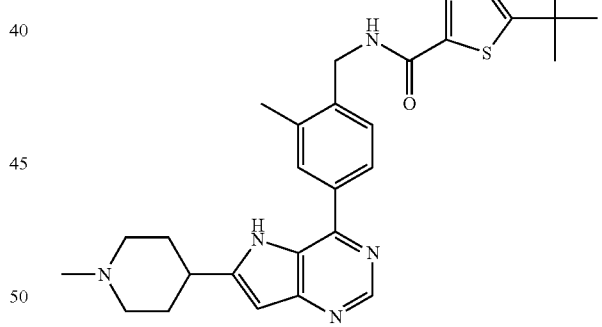

I-25

The Synthesis of 2-(tert-butyl)-N-(2-methyl-4-(6-(1-methylpiperidin-4-yl)-5H-pyrrolo[3,2-d]pyrimidin-4-yl)benzyl)thiazole-5-carboxamide (I-25)

Compound I-25 was prepared in a similar manner as described for compound I-23 except 1-methylpiperidin-4-one was substituted for dihydro-2H-thiopyran-4(3H)-one to afford the title compound (13 mg, yield: 33%) as a yellow solid. ESI-MS (M+H)+: 502.2. ¹H NMR (400 MHz, CD₃OD) δ: 8.66 (s, 1H), 8.14 (s, 1H), 7.69 (s, 1H), 7.66 (d, J=8.0 Hz, 1H), 7.41 (d, J=8.0 Hz, 1H), 6.41 (s, 1H), 4.54 (s, 2H), 3.20-3.14 (m, 2H), 2.95-2.93 (m, 1H), 2.51-2.46 (m, 5H), 2.40 (s, 3H), 2.11-2.08 (m, 2H), 1.87-1.84 (m, 2H), 1.36 (s, 9H).

Scheme 8

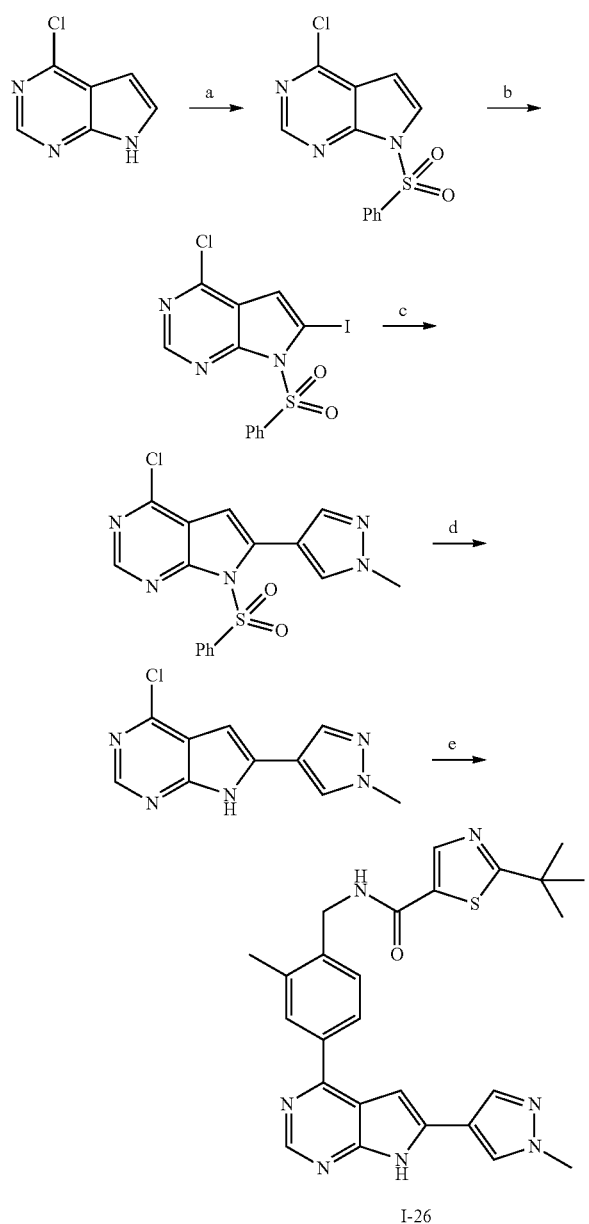

I-26

Reagents and conditions: (a) PhSO₂Cl, NaH, THF, 0° C., rt 16 h. (b) LDA, I2, THF, -78° C., 0.5 h, rt, 2 h. (c) Cs₂CO₃, THF—MeO, 0° C. to rt. (d) 1-methyl-4-(4,4,5,5-tetramethyl-1,3,2-dioxaborolan-2-yl)-1H-pyrazole, Pd(dppf)Cl2, K₂CO₃, 1,4-dioxane/H₂O, 110° C. 4h. (e) 2-(tert-butyl)-N-(2-methyl-4-(4,4,5,5-tetramethyl-1,3,2-dioxaborolan-2-yl)benzyl)thiazole-5-carboxamide, Pd(dppf)Cl2, K₂CO₃, 1,4-dioxane/water, 100° C. 2h.

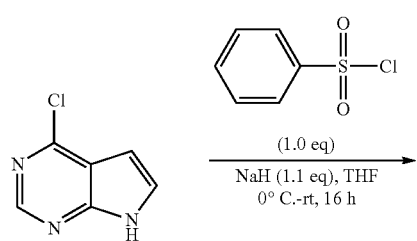

(1.0 eq)

NaH (1.1 eq), THF
0° C.-rt, 16 h

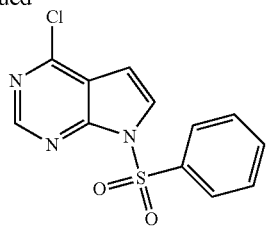

The Synthesis of 4-chloro-7-(phenylsulfonyl)-7H-pyrrolo[2,3-d]pyrimidine

To a solution of 4-chloro-7H-pyrrolo[2,3-d]pyrimidine (5.0 g, 33 mmol) in THF (50 mL) was added NaH (870 mg, 36 mmol) at 0° C. The solution was stirred at rt for 30 m followed by the addition of benzenesulfonyl chloride (5.8 g, 33 mmol) and the reaction was stirred at rt for 16 h. The reaction was diluted with water (50 mL) and extracted with EtOAc (80 mL×2). The organic layer was washed with water (50 mL), brine (50 mL), dried (Na₂SO₄), filtered and concentrated in vacuo to afford a residue which was purified by column chromatograph (EtOAc/Petroleum ether=1:2) to give afford the title compound (7.5 g, yield 79%). ESI-MS (M+H)⁺: 293.9. ¹H NMR (400 MHz, CD₃OD) δ: 8.71 (s, 1H), 8.24-8.22 (m, 2H), 8.02 (d, J=4.0 Hz, 1H), 7.73 (t, J=7.2 Hz, 1H), 7.63-7.61 (m, 2H), 6.88 (d, J=4.0 Hz, 1H).

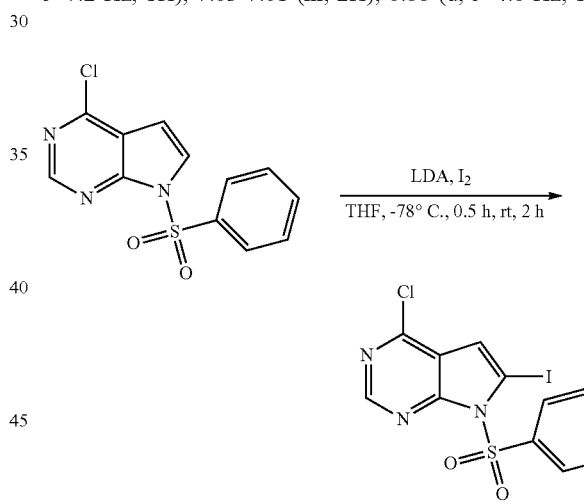

The Synthesis of 4-chloro-6-iodo-7-(phenylsulfonyl)-7H-pyrrolo[2,3-d]pyrimidine To a solution of 4-chloro-7-(phenylsulfonyl)-7H-pyrrolo[2,3-d]pyrimidine (5.0 g, 17 mmol) in THF (100 mL) was added LDA (10.2 mL, 20 mmol) at -78° C. The mixture was stirred at -78° C. for 0.5 h followed by addition of I₂ (8.6 g, 34 mmol) and allowed to warmed to rt while stirring for another 2 h. It was then diluted with water (80 mL) and extracted with EtOAc (100 mL×2). The organic layer was washed with water (60 mL), brine (60 mL), dried (Na₂SO₄), filtered and concentrated in vacuo to afford a residue was purified by column chromatography (EtOAc/Petroleum ether=1:1) to give the title compound (4.2 g, yield 59%). ESI-MS (M+H)⁺: 419.9. ¹H NMR (400 MHz, DMSO-d₆) δ: 8.78 (s, 1H), 8.12-8.10 (m, 2H), 7.80 (t, J=7.6 Hz, 1H), 7.71-7.68 (m, 2H), 7.39 (s, 1H).

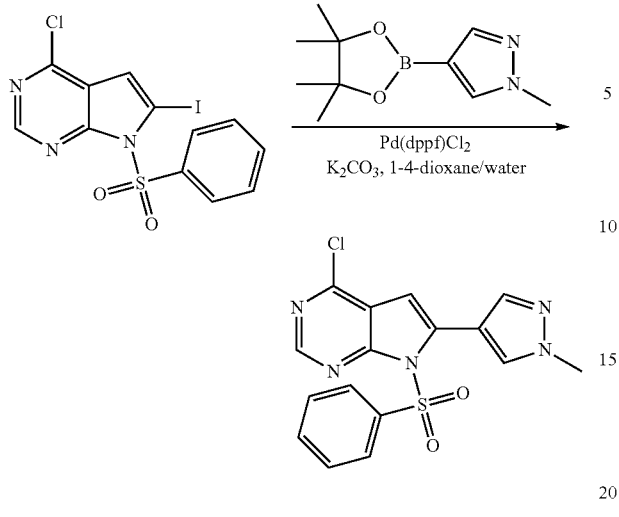

The Synthesis of 4-chloro-6-(1-methyl-1H-pyrazol-4-yl)-7-(phenylsulfonyl)-7H-pyrrolo[2,3-d]pyrimidine This compound was prepared in a similar manner as described Example I-18 except 1-methyl-4-(4,4,5,5-tetramethyl-1,3,2-dioxaborolan-2-yl)-1H-pyrazole was substituted for tert-butyl 4-(4,4,5,5-tetramethyl-1,3,2-dioxaborolan-2-yl)-5,6-dihyropyridine-1(2H)-carboxylate to afford the title compound (2.12 g, yield 54%). ESI-MS (M+H)$^+$: 373.7. $^1$H NMR (400 MHz, CDCl$_3$) δ: 8.80 (s, 1H), 7.88 (d, J=7.6 Hz, 2H), 7.77 (s, 1H), 7.65 (s, 1H), 7.57 (t, J=8.0 Hz, 1H), 7.44 (t, J=8.0 Hz, 2H), 6.57 (s, 1H), 4.03 (s, 3H).

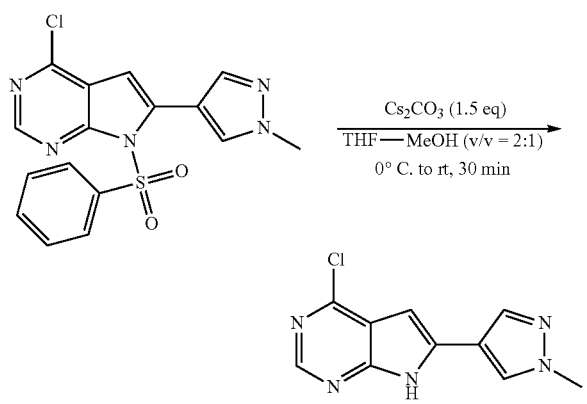

The Synthesis of 4-chloro-6-(1-methyl-1H-pyrazol-4-yl)-7H-pyrrolo[2,3-d]pyrimidine To a solution of 4-chloro-6-(1-methyl-1H-pyrazol-4-yl)-7-(phenylsulfonyl)-7H-pyrrolo[2,3-d]pyrimidine (1.0 g, 2.7 mmol) in THF-MeOH (24 mL, 2:1) was added Cs$_2$CO$_3$ (1.32 g, 4.1 mmol) at 0° C. The mixture was stirred at rt for 0.5 h, diluted with water (20 mL) and extracted with EtOAc (80 mL×2). The organic layer was washed with water (50 mL), brine (40 mL), dried (Na$_2$SO$_4$), filtered and concentrated in vacuo to afford a residue was purified by silica gel column chromatography (EtOAc/Petroleum ether=1:2) to afford the title compound (485 mg, yield 71%). ESI-MS (M+H)$^+$: 233.9. $^1$H NMR (400 MHz, CDCl$_3$) δ: 10.59 (s, 1H), 8.61 (s, 1H), 7.86 (s, 1H), 7.77 (s, 1H), 6.61 (s, 1H), 4.02 (s, 3H).

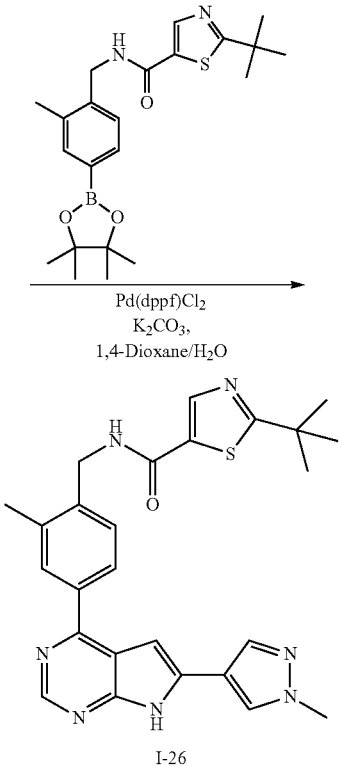

The Synthesis of 2-(tert-butyl)-N-(2-methyl-4-(6-(1-methyl-1H-pyrazol-4-yl)-7H-pyrrolo[2,3-d]pyrimidin-4-yl)benzyl)thiazole-5-carboxamide (I-26)

Compound I-26 was prepared in a similar manner as described in Example 3 except 4-chloro-6-(1-methyl-1H-pyrazol-4-yl)-7H-pyrrolo[2,3-d]pyrimidine was substituted for 4-(4-chloro-5H-pyrrolo[3,2-d]pyrimidin-6-yl)-5,6-dihydropyridine-1(2H)-carboxylate to afford the title compound (40 mg, yield 20%). ESI-MS (M+H)$^+$: 485.8. $^1$H NMR (400 MHz, CD$_3$OD) δ: 8.70 (s, 1H), 8.26 (s, 1H), 8.14 (s, 1H), 8.00 (s, 1H), 7.92-7.90 (m, 2H), 7.57 (d, J=8.0 Hz, 1H), 6.96 (s, 1H), 4.67 (s, 2H), 3.97 (s, 3H), 2.53 (s, 3H), 1.48 (s, 9H).

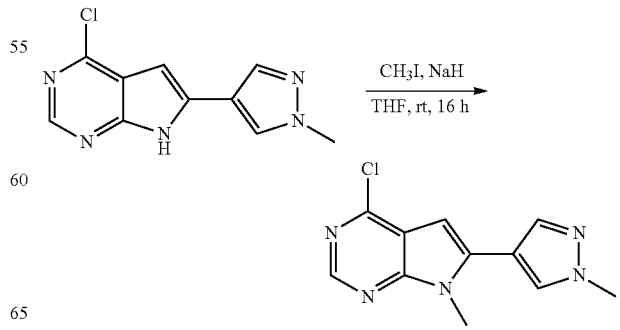

The Synthesis of 4-chloro-6-(1-methyl-1H-pyrazol-4-yl)-7H-pyrrolo[2,3-d]pyrimidine To a solution of 4-chloro-6-(1-methyl-1H-pyrazol-4-yl)-7H-pyrrolo[2,3-d]pyrimidine (120 mg, 0.52 mmol) in THF (10 mL) were added NaH (14 mg, 0.57 mmol) and CH$_3$I (220 mg, 1.53 mmol) at 0° C. The mixture was stirred at rt for 16 h, diluted with water (20 mL) and extracted with EtOAc (60 mL×2). The organic layer was washed with water (50 mL), dried (Na$_2$SO$_4$), filtered and concentrated in vacuo to give a residue which was purified by column chromatography (EtOAc/Petroleum ether=1:2) to give the title compound (156 mg, yield 92%). ESI-MS (M+H)$^+$: 247.9. $^1$H NMR (400 MHz, CD$_3$OD) δ: 8.43 (s, 1H), 8.06 (s, 1H), 7.84 (s, 1H), 6.63 (s, 1H), 3.91 (s, 3H), 3.86 (s, 3H).

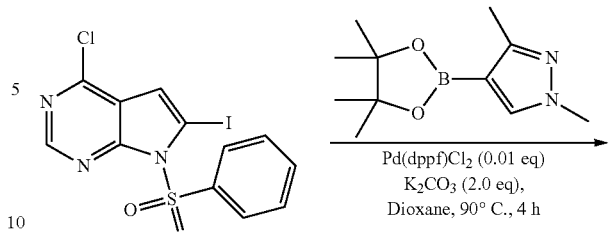

The Synthesis of 2-(tert-butyl)-N-(2-methyl-4-(7-methyl-6-(1-methyl-1H-pyrazol-4-yl)-7H-pyrrolo[2,3-d]pyrimidin-4-yl)benzyl)thiazole-5-carboxamide (I-27)

Compound I-27 was prepared in a similar manner as described for compound I-26 except 4-chloro-6-(1-methyl-1H-pyrazol-4-yl)-7H-pyrrolo[2,3-d]pyrimidine was substituted for 4-chloro-6-(1-methyl-1H-pyrazol-4-yl)-7H-pyrrolo[2,3-d]pyrimidine to afford the title compound (40 mg, yield 33%). ESI-MS (M+H)$^+$: 500.1. HPLC: (214 nm: 96%, 254 nm: 100%). $^1$H NMR (400 MHz, CD$_3$OD) δ: 8.64 (s, 1H), 8.15 (s, 1H), 8.03 (s, 1H), 7.82-7.77 (m, 3H), 7.40 (d, J=7.6 Hz, 1H), 6.81-6.79 (m, 1H), 4.54 (s, 2H), 3.88 (s, 3H), 3.85 (s, 3H), 2.40 (s, 3H), 1.36 (s, 9H).

The Synthesis of 4-chloro-6-(1,3-dimethyl-1H-pyrazol-4-yl)-7H-pyrrolo[2,3-d]pyrimidine This compound was prepared in a similar manner as described for compound I-26 in Example 3 except 1,3-dimethyl-4-(4,4,5,5-tetramethyl-1,3,2-dioxaborolan-2-yl)-1H-pyrazole was substituted for 1-methyl-4-(4,4,5,5-tetramethyl-1,3,2-dioxaborolan-2-yl)-1H-pyrazole to afford the title compound (120 mg, yield 20%). ESI-MS (M+H)$^+$: 248.0. $^1$H NMR (400 MHz, CDCl$_3$) δ: 10.09 (s, 1H), 8.59 (s, 1H), 7.67 (s, 1H), 6.56 (s, 1H), 3.94 (s, 3H), 2.52 (s, 3H).

The Synthesis of 4-chloro-6-(1,3-dimethyl-1H-pyrazol-4-yl)-7-methyl-7H-pyrrolo[2,3-d]pyrimidine This compound was prepared in a similar manner as described for compound I-26 in Example 3 except 4-chloro-6-(1,3-dimethyl-1H-pyrazol-4-yl)-7H-pyrrolo[2,3-d]pyrimidine was substituted for 4-chloro-6-(1-methyl-1H-pyrazol-4-yl)-7H-pyrrolo[2,3-d]pyrimidine afford the title compound (156 mg, yield 92%). ESI-MS (M+H)$^+$: 261.9

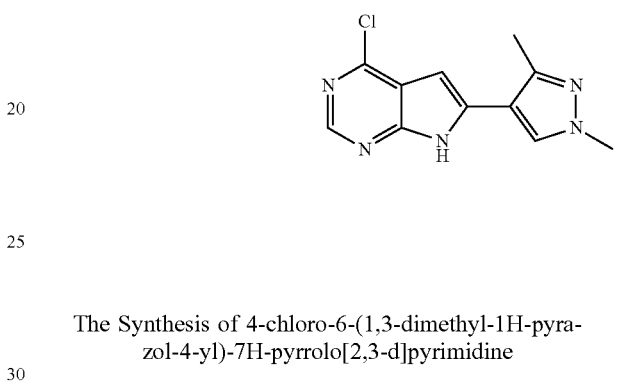

113
-continued

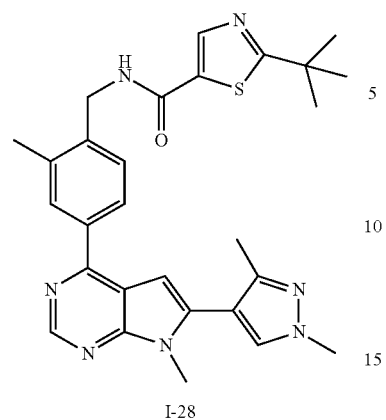

I-28

The Synthesis of 2-(tert-butyl)-N-(4-(6-(1,3-dimethyl-1H-pyrazol-4-yl)-7-methyl-7H-pyrrolo[2,3-d]pyrimidin-4-yl)-2-methylbenzyl)thiazole-5-carboxamide (I-28)

Compound I-28 was prepared in a similar manner as described for I-26 except 4-chloro-6-(1,3-dimethyl-1H-pyrazol-4-yl)-7-methyl-7H-pyrrolo[2,3-d]pyrimidine was substituted for 4-chloro-6-(1-methyl-1H-pyrazol-4-yl)-7H-pyrrolo[2,3-d]pyrimidine afford the title (31 mg, yield 32%). ESI-MS (M+H)⁺: 514.2. ¹H NMR (400 MHz, CD₃OD) δ: 8.68 (s, 1H), 8.14 (s, 1H), 7.81-7.60 (m, 3H), 7.40 (d, J=8.0 Hz, 1H), 6.68 (s, 1H), 4.54 (s, 2H), 3.82 (s, 3H), 3.71 (s, 3H), 2.39 (s, 3H), 2.20 (s, 3H), 1.35 (s, 9H).

114
-continued

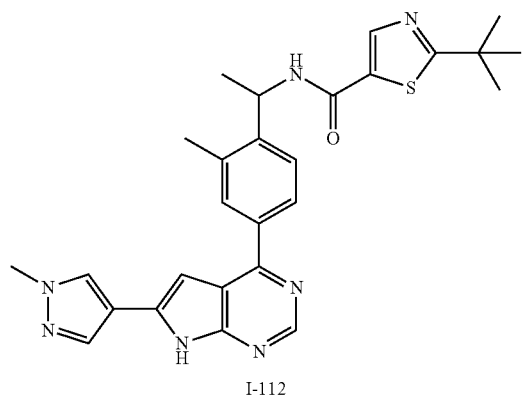

I-112

The Synthesis of 2-(tert-butyl)-N-(1-(2-methyl-4-(6-(1-methyl-1H-pyrazol-4-yl)-7H-pyrrolo[2,3-d]pyrimidin-4-yl)phenyl)ethyl)thiazole-5-carboxamide (I-112)

Compound I-112 was prepared in a similar manner as described in Example I-15 except 4-chloro-6-(1,3-dimethyl-1H-pyrazol-4-yl)-7H-pyrrolo[2,3-d]pyrimidine and 2-(tert-butyl)thiazole-5-carboxylic acid were s substituted for 4-chloro-7H-pyrrolo[2,3-d]pyrimidine and 5-(tert-butyl)picolinic acid afford the titled compound (32 mg, yield 32%) as a solid. ESI-MS (M+H)⁺: 500.2. ¹H NMR (400 MHz, CD₃OD) δ: 8.59 (s, 1H), 8.20 (s, 1H), 8.02 (s, 1H), 7.89 (s, 1H), 7.82-7.78 (m, 2H), 7.52-7.50 (m, 1H), 6.85 (s, 1H), 5.35 (q, J=7.2 Hz, 1H), 3.86 (s, 3H), 2.47 (s, 3H), 1.50 (d, J=6.8 Hz, 3H), 1.35 (s, 9H).

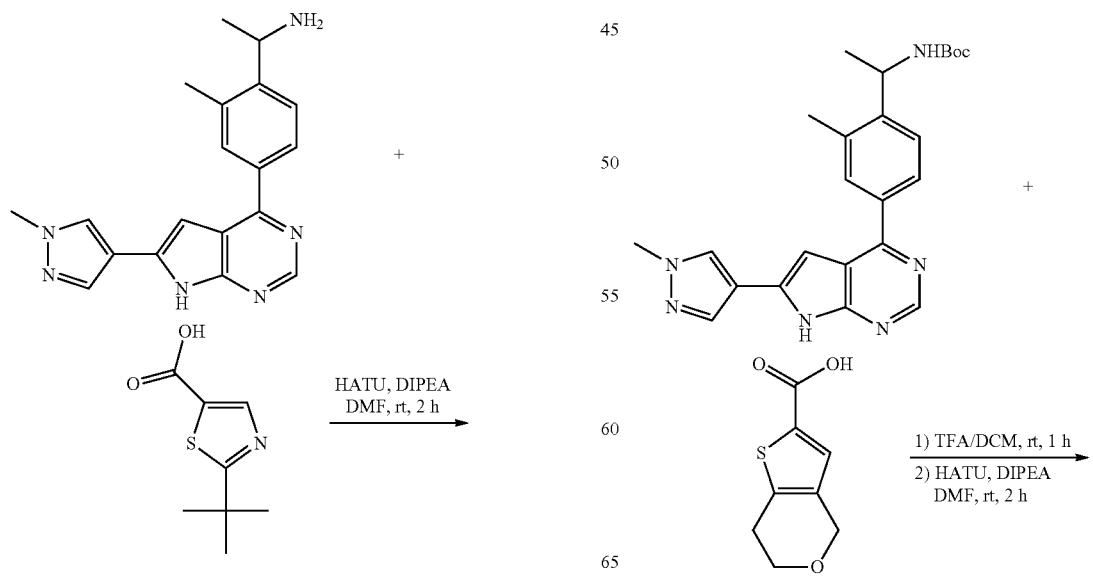

115

-continued

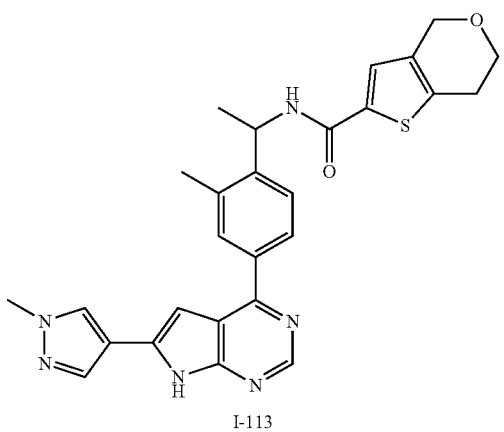

I-113

The Synthesis of N-(1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide (I-113)

Compound I-113 was prepared in a similar manner as described for compound I-112 except 6,7-dihydro-4H-thieno[3,2-c]pyran-2-carboxylic acid was substituted for 2-(tert-butyl)thiazole-5-carboxylic acid afford the titled compound (62 mg, yield 65%) as a solid. ESI-MS (M+H)$^+$: 499.1. $^1$H NMR (400 MHz, CD$_3$OD) δ: 8.69 (s, 1H), 8.13 (s, 1H), 7.80 (s, 1H), 7.92-7.89 (m, 2H), 7.63-7.61 (m, 1H), 7.47 (s, 1H), 6.94 (s, 1H), 5.45 (q, J=7.2 Hz, 1H), 4.69 (s, 2H), 3.97 (t, J=5.6 Hz, 2H), 3.97 (s, 3H), 2.89 (t, J=5.6 Hz, 2H), 2.57 (s, 3H), 1.58 (d, J=7.2 Hz, 3H).

Example 4

Scheme 9

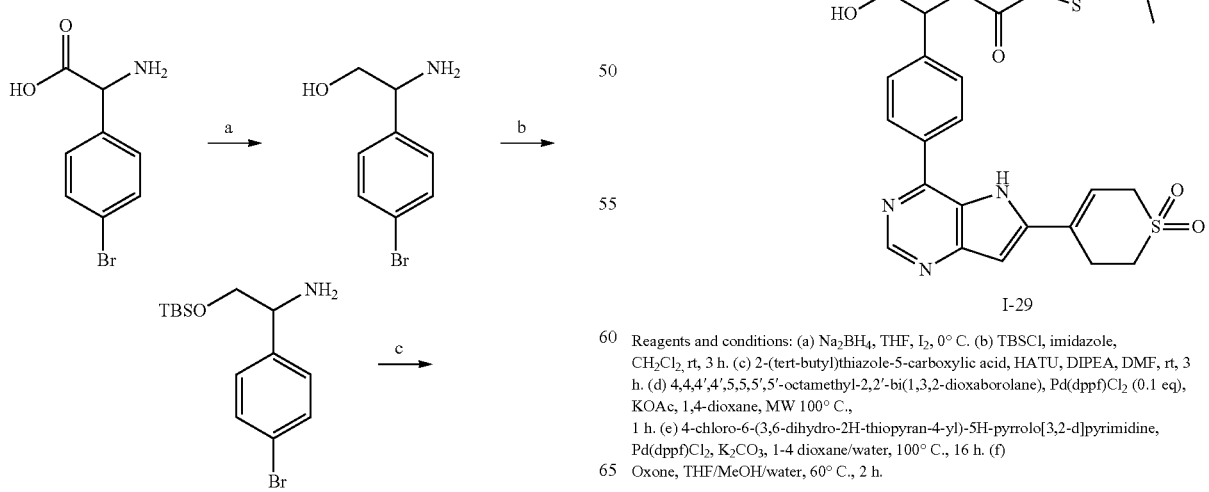

116

-continued

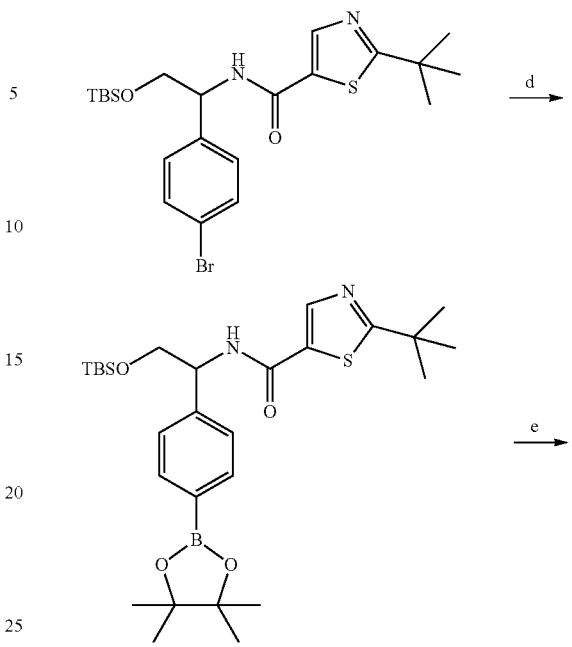

I-29

Reagents and conditions: (a) Na$_2$BH$_4$, THF, I$_2$, 0° C. (b) TBSCl, imidazole, CH$_2$Cl$_2$, rt, 3 h. (c) 2-(tert-butyl)thiazole-5-carboxylic acid, HATU, DIPEA, DMF, rt, 3 h. (d) 4,4,4',4',5,5,5',5'-octamethyl-2,2'-bi(1,3,2-dioxaborolane), Pd(dppf)Cl$_2$ (0.1 eq), KOAc, 1,4-dioxane, MW 100° C., 1 h. (e) 4-chloro-6-(3,6-dihydro-2H-thiopyran-4-yl)-5H-pyrrolo[3,2-d]pyrimidine, Pd(dppf)Cl$_2$, K$_2$CO$_3$, 1-4 dioxane/water, 100° C., 16 h. (f) Oxone, THF/MeOH/water, 60° C., 2 h.

117

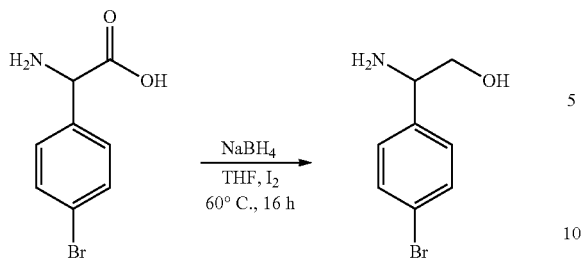

The Synthesis of 2-amino-2-(4-bromophenyl)ethanol

To a solution of 2-amino-2-(4-bromophenyl)acetic acid (0.9 g, 3.93 mmol) in THF (30 mL) were added NaBH$_4$ (291 mg, 7.86 mmol) and I$_2$ (994 mg, 3.93 mmol). The mixture was stirred at 60° C. for 16 h, the solution was concentrated in vacuo to afford a residue which was dissolved in EtOAc (200 mL), washed with water (100 mL) and brine (100 mL), separated, dried (Na$_2$SO$_4$), filtered and concentrated in vacuo to afford the title compound (650 mg, yield 77%) as colorless oil which was used to next step without further purification. ESI-MS (M+H)$^+$: 215.0. $^1$H NMR (400 MHz, CD$_3$OD) δ: 7.50-7.44 (m, 2H), 7.35-7.29 (m, 2H), 4.01-3.98 (m, 1H), 3.72-3.67 (m, 1H), 3.60-3.55 (m, 1H).

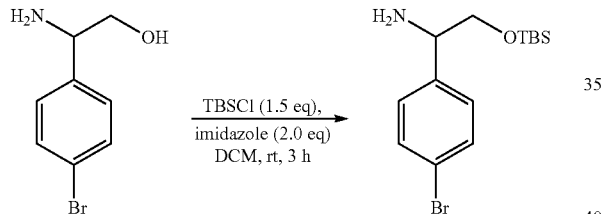

The Synthesis of 1-(4-bromophenyl)-2-((tert-butyldimethylsilyl)oxy)ethanamine To a solution of 2-amino-2-(4-bromophenyl)ethanol (650 mg, 3.02 mmol) in CH$_2$Cl$_2$ (30 mL) were added TBSCl (768 mg, 4.53 mmol) and imidazole (561 mg, 6.04 mmol). The mixture was stirred at rt for 2 h, diluted with CH$_2$Cl$_2$ (200 mL), washed with water (80 mL) and brine (100 mL). The organic phase was dried (Na$_2$SO$_4$), filtered and concentrated in vacuo to give the title compound (780 mg, yield 78%) as yellow solid, which was used to next step without further purification. ESI-MS (M+H)$^+$: 330.1.

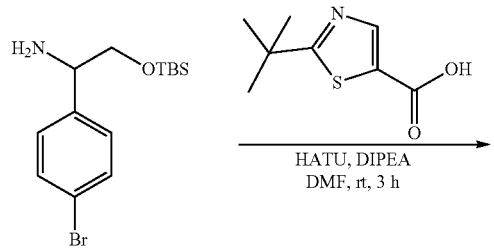

118

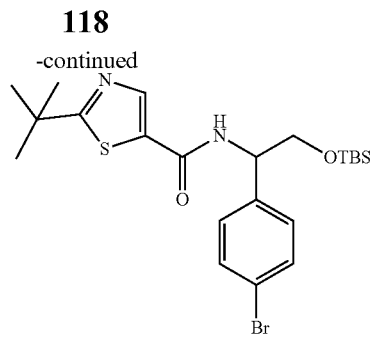

The Synthesis of N-(1-(4-bromophenyl)-2-((tert-butyldimethylsilyl)oxy)ethyl)-2-(tert-butyl)thiazole-5-carboxamide This compound was prepared in a similar manner as described in 1-20 except 1-(4-bromophenyl)-2-((tert-butyldimethylsilyl)oxy)ethanamine was substituted for (4-bromo-2-methylphenyl)methanamineto afford the title compound (220 mg, yield 49%). ESI-MS (M+H)$^+$: 497.2.

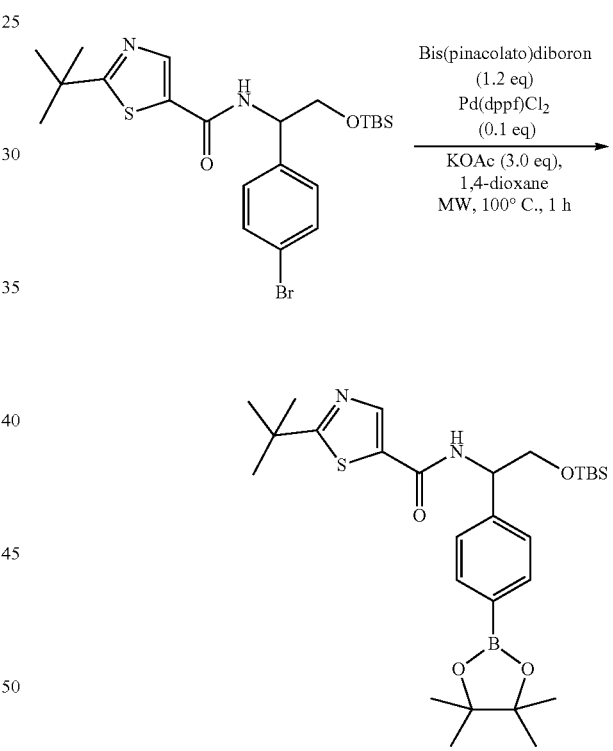

The Synthesis of 2-(tert-butyl)-N-(2-((tert-butyldimethylsilyl)oxy)-1-(4-(4,4,5,5-tetramethyl-1,3,2-dioxaborolan-2-yl)phenyl)ethyl)thiazole-5-carboxamide This compound was prepared in a similar manner as described in Example I-23 except N-(1-(4-bromophenyl)-2-((tert-butyldimethylsilyl)oxy)ethyl)-2-(tert-butyl)thiazole-5-carboxamide was substituted for N-(4-bromo-2-methylbenzyl)-2-(tert-butyl)thiazole-5-carboxamide to afford the title compound (160 mg, yield 66%). ESI-MS (M+H)$^+$: 545.3.

119

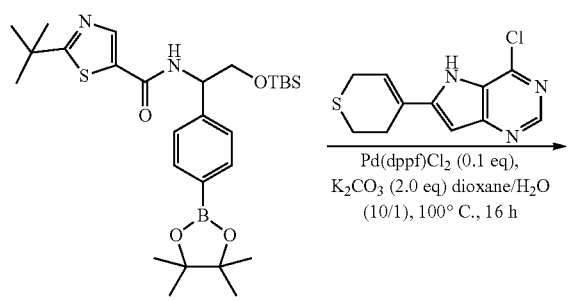

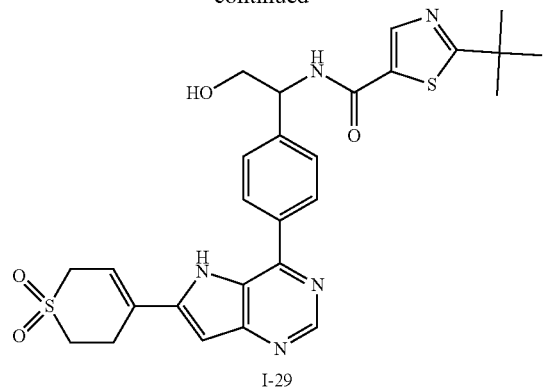

I-29

The Synthesis of 2-(tert-butyl)-N-(1-(4-(6-(1,1-dioxido-3,6-dihydro-2H-thiopyran-4-yl)-5H-pyrrolo[3,2-d]pyrimidin-4-yl)phenyl)-2-hydroxyethyl)thiazole-5-carboxamide (I-29)

Compound I-29 was prepared in a similar manner as described in Example I-21 except 2-(tert-butyl)-N-(1-(4-(6-(3,6-dihydro-2H-thiopyran-4-yl)-5H-pyrrolo[3,2-d]pyrimidin-4-yl)phenyl)-2-hydroxyethyl)thiazole-5-carboxamide was substituted for 2-(tert-butyl)-N-(4-(6-(1,1-dioxido-3,6-dihydro-2H-thiopyran-4-yl)-7H-pyrrolo[2,3-d]pyrimidin-4-yl)-2-methylbenzyl)thiazole-5-carboxamide to afford the title compound (9 mg, yield: 20%) as a white solid. ESI-MS (M+H)+: 552.2. 1H NMR (400 MHz, CD3OD) δ: 9.01 (s, 1H), 8.35 (s, 1H), 8.06 (d, J=8.4 Hz, 2H), 7.74 (d, J=8.0 Hz, 2H), 7.08 (s, 1H), 6.72-6.71 (m, 1H), 5.27-5.26 (m, 1H), 4.90 (s, 2H), 4.00-3.95 (m, 4H), 3.44-3.41 (m, 2H), 1.46 (s, 9H).

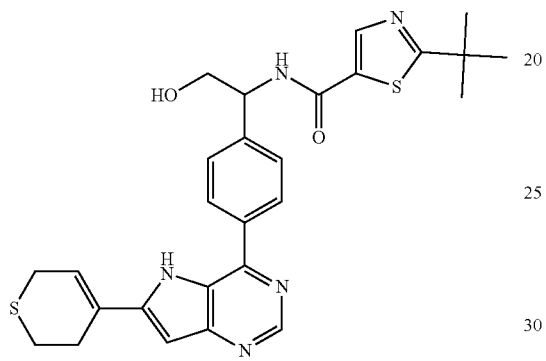

The Synthesis of 2-(tert-butyl)-N-(1-(4-(6-(3,6-dihydro-2H-thiopyran-4-yl)-5H-pyrrolo[3,2-d]pyrimidin-4-yl)phenyl)-2-hydroxyethyl)thiazole-5-carboxamide This compound was prepared in a similar manner as described in Example I-21 except 2-(tert-butyl)-N-(2-((tert-butyldimethylsilyl)oxy)-1-(4-(4,4,5,5-tetramethyl-1,3,2-dioxaborolan-2-yl)phenyl)ethyl)thiazole-5-carboxamide was substituted for 2-(tert-butyl)-N-(2-methyl-4-(4,4,5,5-tetramethyl-1,3,2-dioxaborolan-2-yl)benzyl)thiazole-5-carboxamide to afford the title compound (160 mg, yield: 47%). ESI-MS (M+H)+: 520.2

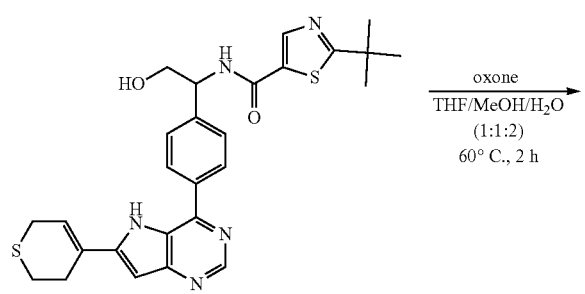

I-30

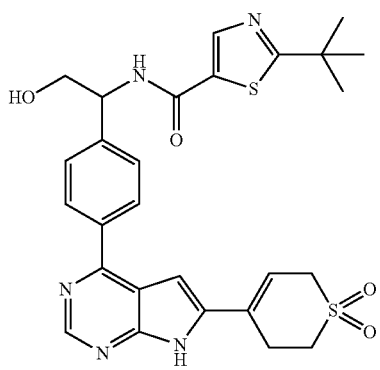

The Synthesis of 2-(tert-butyl)-N-(1-(4-(6-(1,1-dioxido-3,6-dihydro-2H-thiopyran-4-yl)-7H-pyrrolo[2,3-d]pyrimidin-4-yl)phenyl)-2-hydroxyethyl)thiazole-5-carboxamide (I-30)

Compound I-30 was prepared in a similar manner as described in Example I-29 except 4-chloro-6-(3,6-dihydro-2H-thiopyran-4-yl)-7H-pyrrolo[2,3-d]pyrimidine was substituted for the 4-chloro-6-(3,6-dihydro-2H-thiopyran-4-yl)-5H-pyrrolo[3,2-d]pyrimidine to afford the title compound (45 mg, yield 43%). ESI-MS (M+H)+: 552.2. 1H NMR (400 MHz, CD3OD) δ: 9.00 (s, 1H), 8.36 (s, 1H), 8.05 (d, J=8.4

Hz, 2H), 7.77 (d, J=8.0 Hz, 2H), 7.18 (s, 1H), 6.54-6.53 (m, 1H), 5.27-5.26 (m, 1H), 4.00-3.95 (m, 4H), 3.44-3.26 (m, 4H), 1.46 (s, 9H).

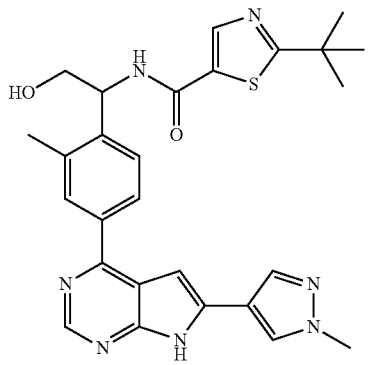

The Synthesis of 2-(tert-butyl)-N-(2-hydroxy-1-(2-methyl-4-(6-(1-methyl-1H-pyrazol-4-yl)-7H-pyrrolo[2,3-d]pyrimidin-4-yl)phenyl)ethyl)thiazole-5-carboxamide (I-31)

Compound I-31 was prepared in a similar manner as described in Example I-112 except tert-butyl (1-(4-bromo-2-methylphenyl)-2-((tert-butyldimethylsilyl)oxy)ethyl)carbamate was substituted for the tert-butyl (1-(4-bromo-2-methylphenyl)ethyl)carbamate to afford the title compound (52 mg, yield 91%). ESI-MS (M+H)+: 516.0. 1H NMR (400 MHz, CD3OD) δ: 8.70 (s, 1H), 8.35 (s, 1H), 8.13 (s, 1H), 8.00 (d, J=0.4 Hz, 1H), 7.92-7.91 (m, 2H), 7.62-7.59 (m, 1H), 6.95 (s, 1H), 5.50 (t, J=7.2 Hz, 1H), 3.97 (s, 3H), 3.90-3.87 (m, 2H), 2.63 (s, 3H), 1.47 (s, 9H).

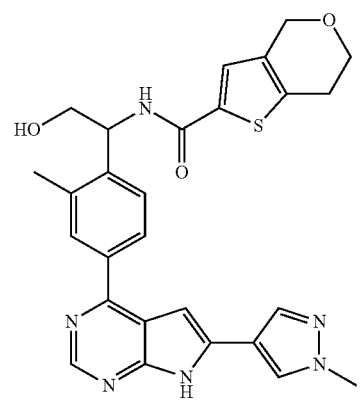

The Synthesis of N-(2-hydroxy-1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide (I-32)

Compound I-32 was prepared in a similar manner as described in Example I-31 except 6,7-dihydro-4H-thieno[3,2-c]pyran-2-carboxylic acid was substituted for the 2-(tert-butyl)thiazole-5-carboxylic acid to afford the title compound (56 mg, yield 86%). ESI-MS (M+H)+: 515.0. 1H NMR (400 MHz, CD3OD) δ: 8.70 (s, 1H), 8.13 (s, 1H), 8.00 (d, J=0.8 Hz, 1H), 7.92-7.90 (m, 2H), 7.60 (d, J=8.4 Hz, 1H), 7.92 (s, 1H), 6.95 (s, 1H), 5.48 (t, J=6.8 Hz, 1H), 4.71 (s, 2H), 3.98 (t, J=5.6 Hz, 2H), 3.97 (s, 3H), 3.88 (d, J=6.8 Hz, 2H), 2.90 (t, J=5.6 Hz, 2H), 2.63 (s, 3H).

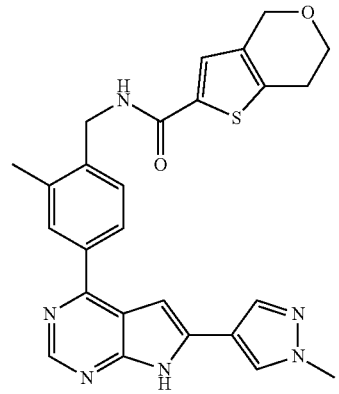

The Synthesis of N-(2-methyl-4-(6-(1-methyl-1H-pyrazol-4-yl)-7H-pyrrolo[2,3-d]pyrimidin-4-yl)benzyl)-6,7-dihydro-4H-thieno[3,2-c]pyran-2-carboxamide (I-33)

Compound I-33 was prepared in a similar manner as described in Example I-26 except 6,7-dihydro-4H-thieno[3,2-c]pyran-2-carboxylic acid was substituted for the 2-(tert-butyl)thiazole-5-carboxylic acid to afford the title compound (28 mg, yield 52%). 1H NMR (400 MHz, CD3OD) δ: 8.79 (s, 1H), 8.11 (s, 1H), 7.96 (s, 1H), 7.79-7.78 (m, 2H), 7.52 (d, J=8.8 Hz, 1H), 7.32 (s, 1H), 7.09 (s, 1H), 4.58 (s, 2H), 4.56 (s, 2H), 3.88-3.86 (m, 5H), 2.80 (t, J=5.2 Hz, 2H), 2.46 (s, 3H).

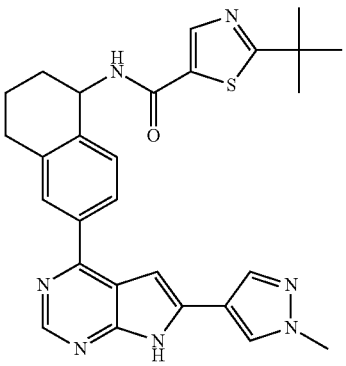

The Synthesis of 2-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)thiazole-5-carboxamide (I-34)

Compound I-34 was prepared in a similar manner as described in Example I-26 except 6-bromo-1,2,3,4-tetrahydronaphthalen-1-amine were substituted for the (4-bromo-2-methylphenyl)methanamine to afford the title compound (128 mg, yield: 81%). ESI-MS (M+H)⁺: 512.2. ¹H NMR (400 MHz, DMSO-d₆) δ: 12.40 (s, 1H), 8.96 (s, 1H), 8.70 (s, 1H), 8.32 (s, 1H), 8.22-8.21 (m, 1H), 8.03-8.02 (m, 1H), 7.98-7.95 (m, 2H), 7.39 (d, J=8.0 Hz, 1H), 6.96-6.95 (m, 1H), 5.28-5.27 (m, 1H), 3.90 (s, 3H), 2.94-2.92 (m, 2H), 2.04-2.03 (m, 2H), 1.86-1.84 (m, 2H), 1.40 (s, 9H).

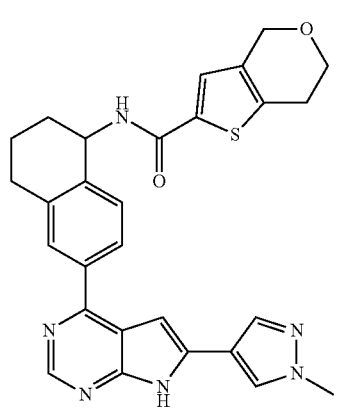

I-35

The Synthesis of N-(6-(6-(1-methyl-1H-pyrazol-4-yl)-7H-pyrrolo[2,3-d]pyrimidin-4-yl)-1,2,3,4-tetrahydronaphthalen-1-yl)-6,7-dihydro-4H-thieno[3,2-c]pyran-2-carboxamide (I-35)

Compound I-35 was prepared in a similar manner as described for Example _1-34 except 6,7-dihydro-4H-thieno[3,2-c]pyran-2-carboxylic acid were substituted for the 5-(tert-butyl)thiazole-2-carboxylic acid to afford the title compound (110 mg, yield: 70%). ESI-MS (M+H)⁺: 511.1. ¹H NMR (400 MHz, DMSO-d₆) δ: 12.5 (s, 1H), 8.80 (d, J=8.8 Hz, 1H), 8.74 (s, 1H), 8.28 (s, 1H), 8.08 (s, 1H), 7.99 (d, J=8.0 Hz, 1H), 7.97 (s, 1H), 7.56 (s, 1H), 7.37 (d, J=8.0 Hz, 1H), 7.05 (s, 1H), 5.26-5.25 (m, 1H), 4.59 (s, 2H), 3.91 (s, 3H), 3.88 (t, J=5.6 Hz, 2H), 2.95-2.93 (m, 2H), 2.85 (t, J=5.6 Hz, 2H), 2.04-2.02 (m, 2H), 1.86-1.84 (m, 2H).

Scheme 10

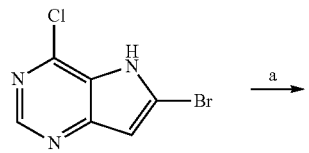

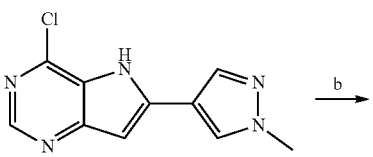

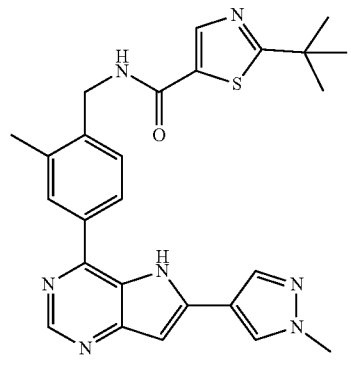

I-36

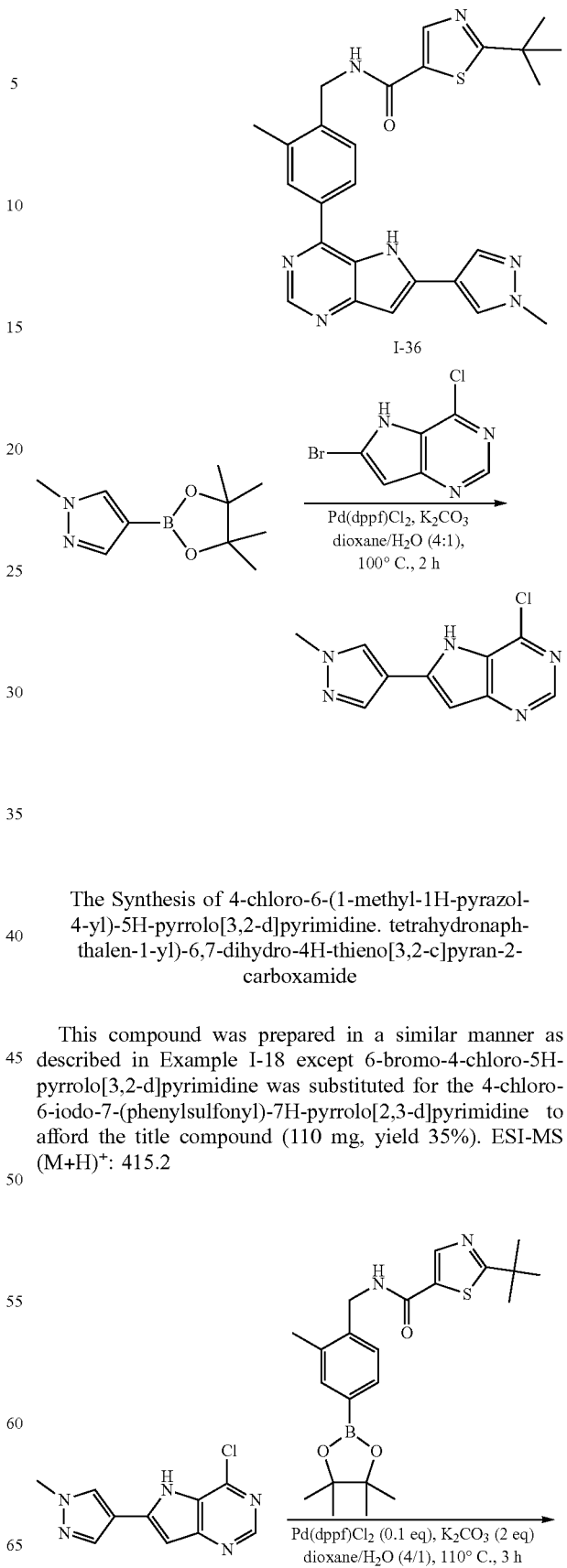

The Synthesis of 4-chloro-6-(1-methyl-1H-pyrazol-4-yl)-5H-pyrrolo[3,2-d]pyrimidine. tetrahydronaphthalen-1-yl)-6,7-dihydro-4H-thieno[3,2-c]pyran-2-carboxamide This compound was prepared in a similar manner as described in Example I-18 except 6-bromo-4-chloro-5H-pyrrolo[3,2-d]pyrimidine was substituted for the 4-chloro-6-iodo-7-(phenylsulfonyl)-7H-pyrrolo[2,3-d]pyrimidine to afford the title compound (110 mg, yield 35%). ESI-MS (M+H)⁺: 415.2

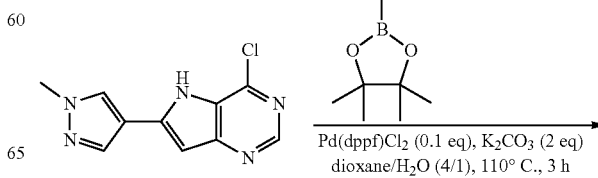

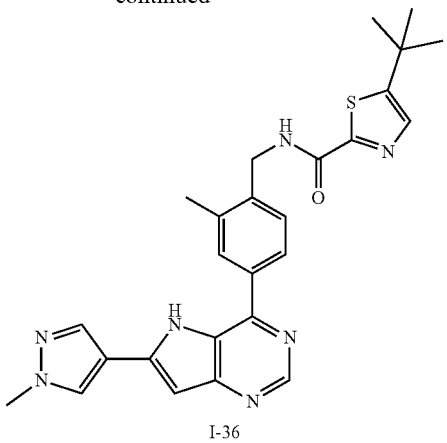

I-36

The Synthesis of 5-(tert-butyl)-N-(2-methyl-4-(6-(1-methyl-H-pyrazol-4-yl)-5H-pyrrolo[3,2-d]pyrimidin-4-yl)phenyl)ethyl)thiazole-5-carboxamide (I-36)

Compound I-36 was prepared in a similar manner as described in Example I-18 4-chloro-6-(1-methyl-1H-pyrazol-4-yl)-5H-pyrrolo[3,2-d]pyrimidine was substituted for the tert-butyl 4-(4-chloro-H-pyrrol)ethanamine[3,2-d]pyrimidin-6-yl)-5,6-dihydropyridine-1(2H)-carboxylate to afford the title compound (90 mg, yield 70%) as a yellow solid. ESI-MS (M+H)⁺: 486.2. ¹H NMR (400 MHz, CD₃OD) δ: 8.64 (s, 1H), 8.15-8.13 (m, 2H), 7.96 (s, 1H), 7.70-7.68 (m, 2H), 7.43 (d, J=8.0 Hz, 1H), 6.70 (s, 1H), 4.55 (s, 2H), 3.86 (s, 3H), 2.42 (s, 3H), 1.36 (s, 9H).

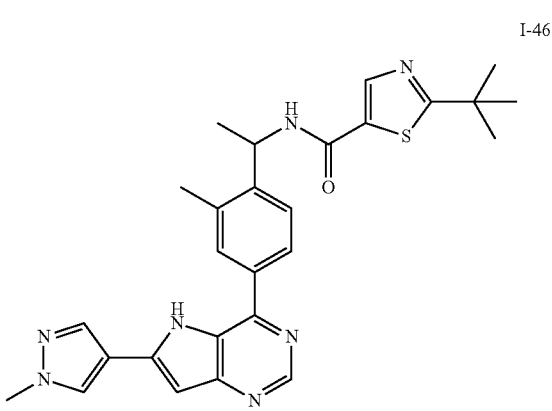 [SMILES: Cc1cc(-c2ncnc3cc(-c4cnn(C)c4)[nH]c23)ccc1C(C)NC(=O)c1cnc(C(C)(C)C)s1]

I-46

The synthesis of 2-(tert-butyl)-N-(1-(2-methyl-4-(6-(1-methyl-1H-pyrazol-4-yl)-5H-pyrrolo[3,2-d]pyrimidin-4-yl)phenyl)ethyl)thiazole-5-carboxamide (I-46)

Compound I-46 was prepared in a similar manner as described for I-36 except (4-bromo-2-methylphenyl)methanamine was substituted for the 1-(4-bromo-2-methylphenyl)ethanamine to afford the title compound (83 mg, yield 83%) as a solid. ESI-MS (M+H)⁺: 500.1. ¹H NMR (400 MHz, CD₃OD) δ: 8.64 (s, 1H), 8.21 (s, 1H), 8.13 (s, 1H), 7.96 (s, 1H), 7.69 (d, J=7.6 Hz, 1H), 7.68 (s, 1H), 7.53 (d, J=7.6 Hz, 1H), 6.71 (s, 1H), 5.36 (q, J=7.2 Hz, 1H), 3.86 (s, 3H), 2.49 (s, 3H), 1.49 (d, J=7.2 Hz, 3H), 1.35 (s, 9H).

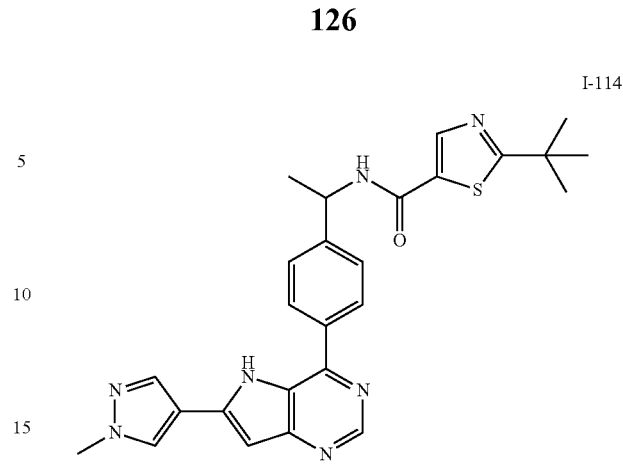

I-114

The Synthesis of 2-(tert-butyl)-N-(1-(4.-(6-(1-methyl-1H-pyrazol-4-yl)-5H-pyrrolo[3,2-d]pyrimidin-4-yl)phenyl)ethyl)thiazole-5-carboxamide (I-114)

Compound I-114 was prepared in a similar manner as described for I-36 except 1-(4-bromophenyl)ethanamine was substituted for 1-(4-bromo-2-methylphenyl)ethanamine to afford the title compound (65 mg, yield 42%) as a solid. ESI-MS (M+H)⁺: 486.2. ¹H NMR (400 MHz, CD₃OD) δ: 8.73 (s, 1H), 8.31 (s, 1H), 8.22 (s, 1H), 8.06 (s, 1H), 7.93 (d, J=8.4 Hz, 2H), 7.62 (d, J=8.0 Hz, 2H), 6.79 (s, 1H), 5.28-5.26 (m, 1H), 3.95 (s, 3H), 1.63 (d, J=7.2 Hz, 3H), 1.44 (s, 9H).

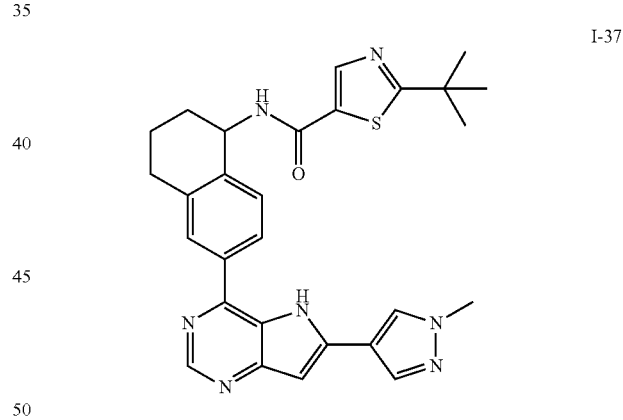

I-37

The Synthesis of 2-(tert-butyl)-N-(6-(6-(1-methyl-1H-pyrazol-4-yl)-5H-pyrrolo[3,2-d]pyrimidin-4-yl)-1,2,3,4-tetrahydronaphthalen-1-yl)thiazole-5-carboxamide (I-37)

Compound I-37 was prepared in a similar manner as described in Example I-36 except (4-bromo-2-methylphenyl)methanamine was substituted for the 6-bromo-1,2,3,4-tetrahydronaphthalen-1-amine (48 mg, yield: 42%) as a yellow solid. ESI-MS (M+1)⁺: 512.2 ¹H NMR (400 MHz, CDCl₃) δ: 9.99 (s, 1H), 8.76 (s, 1H), 8.40 (s, 1H), 7.91 (s, 1H), 7.87 (s, 1H), 7.46 (d, J=7.6 Hz, 1H), 7.40 (s, 1H), 7.28 (d, J=8.4 Hz, 1H), 7.20 (d, J=8.0 Hz, 1H), 6.63 (s, 1H), 5.27-5.22 (m, 1H), 3.94 (s, 3H), 2.67-2.55 (m, 2H), 2.08-1.83 (m, 4H), 1.44 (s, 9H).

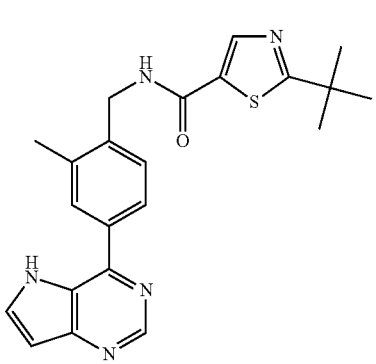

I-115

The Synthesis of 2-(tert-butyl)-N-(2-methyl-4-(5H-pyrrolo[3,2-d]pyrimidin-4-yl)benzyl)thiazole-5-carboxamide (I-115)

Compound I-115 was prepared in a similar manner as described for compound I-1 except 4-chloro-5H-pyrrolo[3,2-d]pyrimidine was substituted for 4-chloro-7H-pyrrolo[2,3-d]pyrimidine and 2-(tert-butyl)thiazole-5-carboxylic acid was substituted for 5-(tert-butyl)picolinic acid to afford the title compound (70 mg, yield 41%) as grey solid. ESI-MS (M+H)+: 405.9. $^1$H NMR (400 MHz, CD$_3$OD) δ: 8.74 (s, 1H), 8.15 (s 1H), 7.77-7.72 (m, 3H), 7.44 (d, J=8.0 Hz, 1H), 6.63 (d, J=3.2 Hz, 1H), 4.56 (s, 2H), 2.42 (s, 3H), 1.35 (s, 9H).

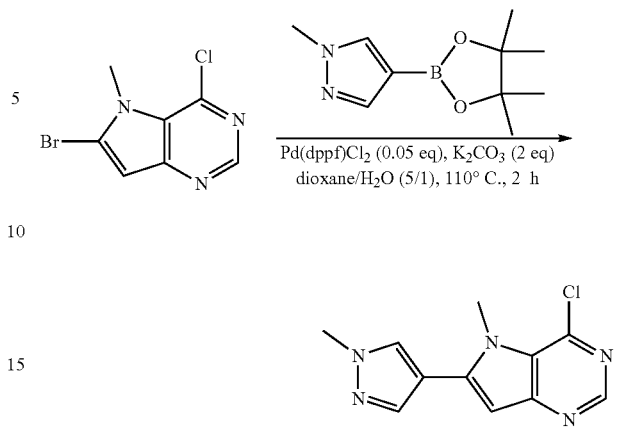

The Synthesis of 4-chloro-5-methyl-6-(1-methyl-1H-pyrazol-4-yl)-5H-pyrrolo[3,2-d]pyrimidine This compound was prepared in a similar manner as described for compound I-22 in Example I-36 except 6-bromo-4-chloro-5-methyl-5H-pyrrolo[3,2-d]pyrimidine was substituted for the 6-bromo-4-chloro-5H-pyrrolo[3,2-d]pyrimidine to afford the title compound (130 mg, yield 43%). ESI-MS (M+H)+: 248.1. $^1$H NMR (400 MHz, CDCl$_3$) δ: 8.65 (s, 1H), 7.74 (s, 1H), 7.68 (s, 1H), 6.68 (s, 1H), 4.14 (s, 3H), 4.03 (s, 3H).

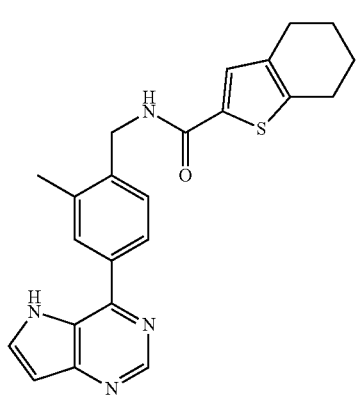

I-116

The Synthesis of N-(2-methyl-4-(5H-pyrrolo[3,2-d]pyrimidin-4-yl)benzyl)-4,5,6,7-tetrahydrobenzo[b]thiophene-2-carboxamide (I-116)

Compound I-116 was prepared in a similar manner as described for I-115 except 2-(tert-butyl)thiazole-5-carboxylic acid was substituted with 4,5,6,7-tetrahydrobenzo[b]thiophene-2-carboxylic acid to afford the title compound (122 mg, yield 68%) as a white solid. ESI-MS (M+H)+: 403.1. $^1$H NMR (400 MHz, DMSO-d$_6$) δ: 11.93 (s, 1H), 8.89-8.87 (m, 2H), 7.90-7.88 (m, 3H), 7.54 (s, 1H), 7.42 (d, J=8.0 Hz, 1H), 6.70-6.69 (m, 1H), 4.49 (d, J=6.0 Hz, 2H), 2.73 (t, J=4.8 Hz, 2H), 2.57 (t, J=5.2 Hz, 2H), 2.45 (s, 3H), 1.79-1.73 (m, 4H).

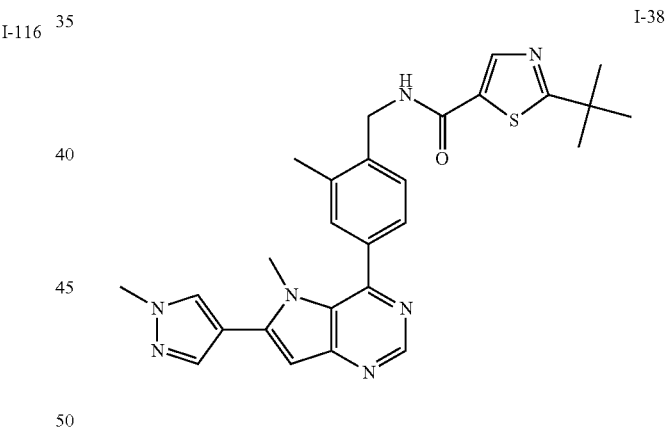

I-38

The Synthesis of 2-(tert-butyl)-N-(2-methyl-4-(5-methyl-6-(1-methyl-1H-pyrazol-4-yl)-5H-pyrrolo[3,2-d]pyrimidin-4-yl)benzyl)thiazole-5-carboxamide (I-38)

Compound I-38 was prepared in a similar manner as described in Example I-36 except 4-chloro-5-methyl-6-(1-methyl-1H-pyrazol-4-yl)-5H-pyrrolo[3,2-d]pyrimidine was substituted for the 4-chloro-6-(1-methyl-1H-pyrazol-4-yl)-5H-pyrrolo[3,2-d]pyrimidine to give the title compound (65 mg, yield 65%) as a light brown solid. ESI-MS (M+H)+: 500.2. $^1$H NMR (400 MHz, CD$_3$OD) δ: 8.65 (s, 1H), 8.15 (s, 1H), 8.04 (s, 1H), 7.82 (s, 1H), 7.43-7.41 (m, 3H), 6.71 (s, 1H), 4.57 (s, 2H), 3.89 (s, 3H), 3.42 (s, 3H), 2.40 (s, 3H), 1.36 (s, 9H).

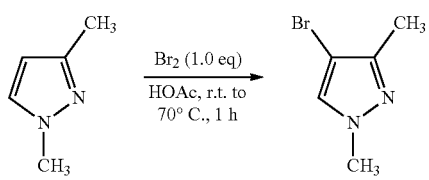

The Synthesis of 4-bromo-1,3-dimethyl-1H-pyrazole

To a solution of 1,3-dimethyl-1H-pyrazole (3.92 g, 40.80 mmol) in acetic acid (10 mL) was added bromine (2.0 mL, 40.80 mmol) dropwise at rt. The reaction mixture was heated at 70° C. for 1 h, cooled and concentrated in vacuo to afford a residue which was adjusted to pH=7-8 with saturated sodium carbonate solution. The mixture was extracted with EtOAc (50 mL×3) and the combined organic phase was dried (Na$_2$SO$_4$), filtered and concentrated in vacuo to afford a residue which was purified by column chromatography (EtOAc/Petroleum ether=1/6 to 1/4) to afford the title compound 1 (3.30 g, yield: 46%) as an oil. ESI-MS (M+H)$^+$: 175.1. $^1$H NMR (400 MHz, CDCl$_3$) δ: 7.30 (s, 1H), 3.83 (s, 3H), 2.23 (s, 3H).

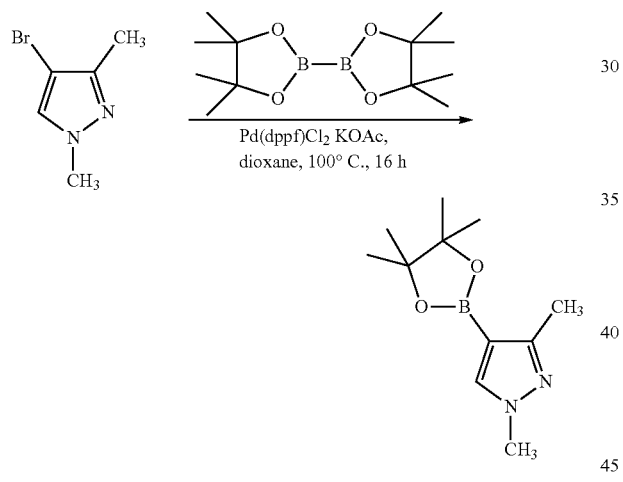

The Synthesis of 1,3-dimethyl-4-(4,4,5,5-tetramethyl-1,3,2-dioxaborolan-2-yl)-1H-pyrazole This compound was prepared in a similar manner as described by Sturino, Claudio et al PCT Int. Appl., WO/2013091096 to afford the title compound (2.52 g, yield 85%). ESI-MS (M+H)$^+$: 223.2.

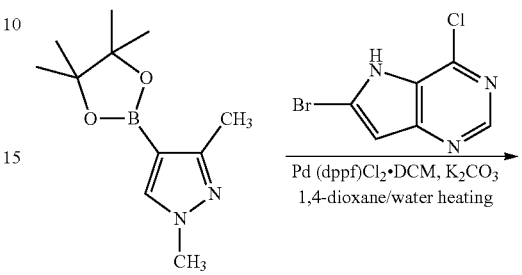

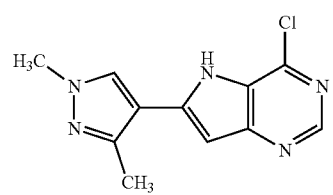

The Synthesis of 4-chloro-6-(1,3-dimethyl-1H-pyrazol-4-yl)-5H-pyrrolo[3,2-d]pyrimidine This compound was prepared in a similar manner as described in Example I-36 except 1,3-dimethyl-4-(4,4,5,5-tetramethyl-1,3,2-dioxaborolan-2-yl)-1H-pyrazole was substituted for the 1-methyl-4-(4,4,5,5-tetramethyl-1,3,2-dioxaborolan-2-yl)-1H-pyrazole to afford the title compound (24 mg, yield 17%). ESI-MS (M+H)$^+$: 248.0.

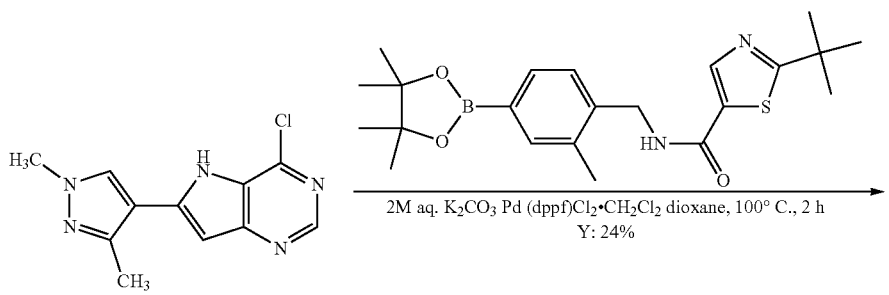

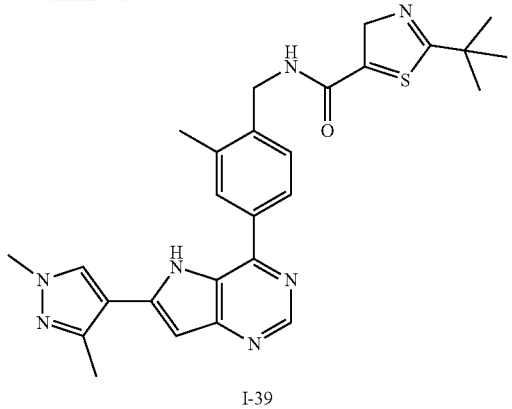

I-39

The Synthesis of 2-(tert-butyl)-N-(4-(6-(1,3-dimethyl-1H-pyrazol-4-yl)-5H-pyrrolo[3,2-d]pyrimidin-4-yl)-2-methylbenzyl)thiazole-5-carboxamide (I-39)

Compound I-39 was prepared in a similar manner as described in Example I-36 except 4-chloro-6-(1,3-dimethyl-1H-pyrazol-4-yl)-5H-pyrrolo[3,2-d]pyrimidine was substituted for the 4-chloro-6-(1-methyl-1H-pyrazol-4-yl)-5H-pyrrolo[3,2-d]pyrimidine to afford the title compound (12 mg, yield 24%). ESI-MS (M+H)$^+$: 500.2. $^1$H NMR (400 MHz, CD$_3$OD) δ: 8.77 (s, 1H), 8.26 (s, 1H), 8.09 (s, 1H), 7.84-7.82 (m, 2H), 7.54 (d, J=8.0 Hz, 1H), 6.73 (s, 1H), 4.66 (s, 2H), 3.89 (s, 3H), 2.53 (s, 3H), 2.49 (s, 3H), 1.45 (s, 9H).

The Synthesis of 5-(tert-butyl)-N-(4-(6-(1-ethyl-1H-pyrazol-4-yl)-5H-pyrrolo[3,2-d]pyrimidin-4-yl)-2-methylbenzyl)thiazole-2-carboxamide (I-40)

Compound I-40 was prepared in a similar manner as described in Example I-36 except 4-chloro-6-(1-ethyl-1H-pyrazol-4-yl)-5H-pyrrolo[3,2-d]pyrimidine was substituted for the 4-chloro-6-(1-ethyl-1H-pyrazol-4-yl)-5H-pyrrolo[3,2-d]pyrimidine to afford the title compound (13 mg, yield: 33%). ESI-MS (M+H)$^+$: 500.2. $^1$H NMR (400 MHz, CD$_3$OD) δ: 8.74 (s, 1H), 8.30 (s, 1H), 8.26 (s, 1H), 8.09 (s, 1H), 7.80-7.77 (m, 2H), 7.75 (d, J=7.6 Hz, 1H), 6.81 (s, 1H), 4.65 (s, 2H), 4.25 (q, J=7.2 Hz, 2H), 2.51 (s, 3H), 1.53-1.46 (m, 12H).

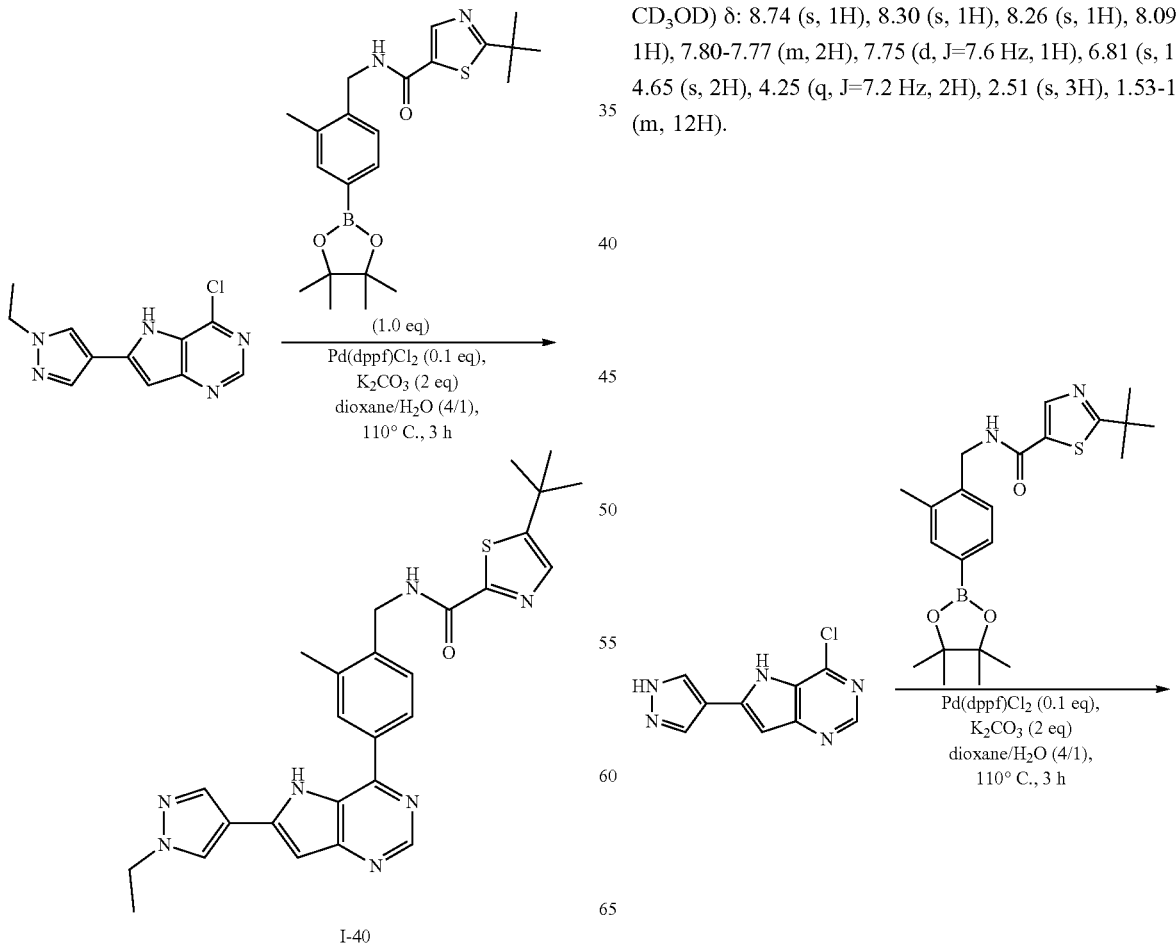

I-40

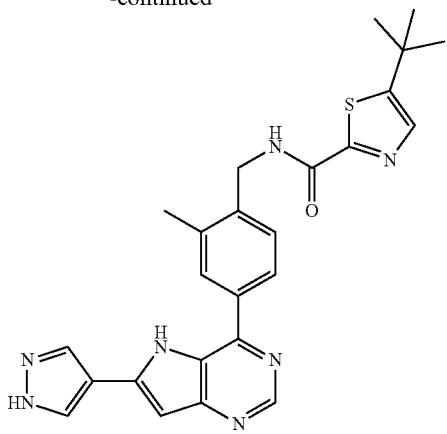

I-41

The Synthesis of N-(4-(6-(1H-pyrazol-4-yl)-5H-pyrrolo[3,2-d]pyrimidin-4-yl)-2-methylbenzyl)-5-(tert-butyl)thiazole-2-carboxamide (I-41)

Compound I-41 was prepared in a similar manner as described in Example I-36 except 4-chloro-6-(1H-pyrazol-4-yl)-5H-pyrrolo[3,2-d]pyrimidine was substituted for the 4-chloro-6-(1-methyl-1H-pyrazol-4-yl)-5H-pyrrolo[3,2-d]pyrimidine to afford the title compound (13 mg, yield: 23%). ESI-MS (M+H)+: 472.2. ¹H NMR (400 MHz, CD₃OD) δ: 8.75 (s, 1H), 8.26-8.24 (m, 3H), 7.82-7.80 (m, 2H), 7.54 (d, J=8.0 Hz, 1H), 6.86 (s, 1H), 4.66 (s, 2H), 2.53 (s, 3H), 1.47 (s, 9H).

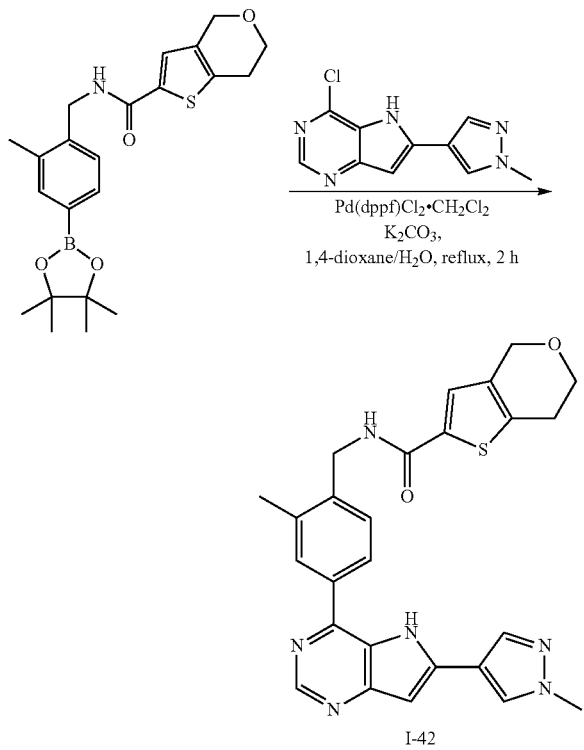

I-42

The Synthesis of N-(2-methyl-4-(6-(1-methyl-1H-pyrazol-4-yl)-5H-pyrrolo[3,2-d]pyrimidin-4-yl)benzyl)-6,7-dihydro-4H-thieno[3,2-c]pyran-2-carboxamide (I-42)

Compound I-42 was prepared in a similar manner as described in Example I-33 except 4-chloro-6-(1-methyl-1H-pyrazol-4-yl)-5H-pyrrolo[3,2-d]pyrimidine was substituted for the 4-chloro-6-(1-methyl-1H-pyrazol-4-yl)-7H-pyrrolo[2,3-d]pyrimidineto afford the title compound (85 mg, yield 87%). ESI-MS (M+H)+: 485.0. ¹H NMR (400 MHz, CD₃OD) δ: 8.74 (s, 1H), 8.24 (s, 1H), 8.08 (s, 1H), 7.80 (s, 1H), 7.78 (d, J=8.0 Hz, 1H), 7.52 (d, J=8.0 Hz, 1H), 7.42 (s, 1H), 6.81 (s, 1H), 4.68 (s, 2H), 4.64 (s, 2H), 3.99 (t, J=5.2 Hz, 2H), 3.97 (s, 3H), 2.90 (t, J=5.2 Hz, 2H), 2.52 (s, 3H).

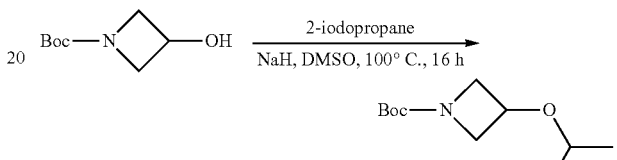

The Synthesis of tert-butyl 3-isopropoxyazetidine-1-carboxylate

To a solution of 3-hydroxy-1-Boc-azetidine (3.46 g, 20 mmol) in DMSO (60 mL) was added NaH (960 mg, 24 mmol, 1.2 eq) at 0° C. followed by the addition of 2-iodopropane (6 g, 35 mmol, 1.75 eq). The mixture was heated to 100° C. for 16 h. The mixture was cooled to rt, diluted with EtOAc (200 mL), washed with water (60 mL), brine (60 mL×2) and concentrated in vacuo to afford a residue which was purified by silica gel column chromatography (EtOAc/Petroleum ether=1/20) to give the title compound as yellow oil (345 mg, yield 7%). ESI-MS (M+H−56)+: 160.1. ¹H NMR (400 MHz, CDCl₃) δ: 4.30-4.24 (m, 1H), 4.09-4.05 (m, 2H), 3.83-3.79 (m, 2H), 3.62-3.53 (m, 1H), 1.43 (s, 9H), 1.14 (d, J=6.0 Hz, 6H).

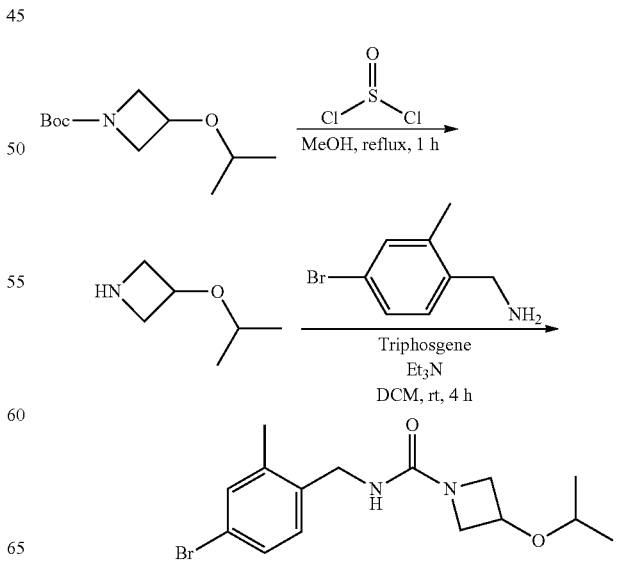

The Synthesis of N-(4-bromo-2-methylbenzyl)-3-isopropoxyazetidine-1-carboxamide To a solution of tert-butyl 3-isopropoxyazetidine-1-carboxylate (345 mg, 1.6 mmol) in MeOH (30 mL) was dropwise added SOCl₂ (1.88 g, 16 mmol, 10 eq). The mixture was stirred at 65° C. for 1 h and the solvent was evaporated to afford a residue which was dissolved in DCM (6 mL) and treated with triphosgene (189 mg, 0.64 mmol) and TEA (800 mg, 8.0 mmol). After the mixture was stirred at rt for 0.5 h 4-bromo-2-methylbenzyl amine (312 mg, 1.57 mmol, 1 eq) was added and the mixture was stirred for another 3 h. The solvent was concentrated in vacuo to afford a residue which was purified by prep-HPLC (CH₃CN/H₂O with 0.05% TFA as mobile phase) to give the title compound (150 mg, 27%) as a yellow solid. ESI-MS (M+H)⁺: 341.0.

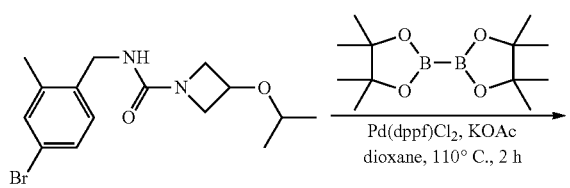

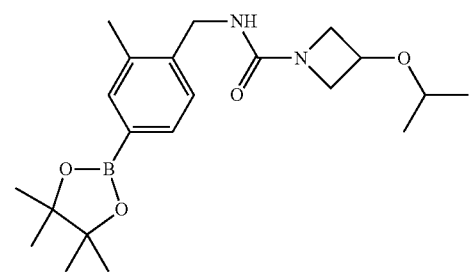

The Synthesis of 3-isopropoxy-N-(2-methyl-4-(4,4,5,5-tetramethyl-1,3,2-dioxaborolan-2-yl)benzyl)azetidine-1-carboxamide To a solution of aryl bromide (1.5 g, 5.0 mmol) in DMF (6 mL) were added 4,4,4',4',5,5,5',5'-octamethyl-2,2'-bi(1,3,2-dioxaborolane) (1.52 g, 6.0 mmol), KOAc (1.75 g, 18 mmol) and Pd(dppf)Cl₂DCM (407 mg, 0.5 mmol) under nitrogen. The mixture was stirred at 100° C. for 2 h, allowed to cool to rt, diluted with water (50 mL) and extracted with EtOAc (100 mL×3). The combined organic layer was washed with brine, dried, concentrated in vacuo and purified by silica gel column chromatography (EtOAc/Petroleum ether=1/1) to give the title compound (40 mg, yield 50%) as a white solid. ESI-MS (M+H)⁺: 389.2.

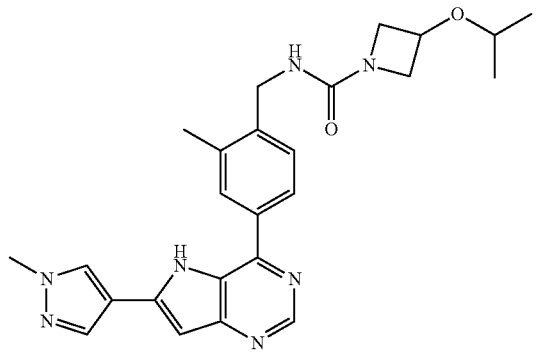

I-43

The Synthesis of 3-isopropoxy-N-(2-methyl-4-(6-(1-methyl-1H-pyrazol-4-yl)-5H-pyrrolo[3,2-d]pyrimidin-4-yl)benzyl)azetidine-1-carboxamide (I-43)

Compound I-43 was prepared in a similar manner as described in Example I-36 except 3-isopropoxy-N-(2-methyl-4-(4,4,5,5-tetramethyl-1,3,2-dioxaborolan-2-yl)benzyl)azetidine-1-carboxamide was substituted for the 2-(tert-butyl)-N-(2-methyl-4-(4,4,5,5-tetramethyl-1,3,2-dioxaborolan-2-yl)benzyl)thiazole-5-carboxamide to afford the title compound (25 mg, yield 40%). ESI-MS (M+H)⁺: 460.1. ¹H NMR (400 MHz, CD₃OD) δ: 8.63 (s, 1H), 8.14 (s, 1H), 7.97 (s, 1H), 7.68-7.66 (m, 2H), 7.39 (d, J=7.6 Hz, 1H), 6.70 (s, 1H), 4.34-4.31 (m, 3H), 4.10-4.06 (m, 2H), 3.86 (s, 3H), 3.72-3.69 (m, 2H), 3.57-3.54 (m, 1H), 2.36 (s, 3H), 1.06 (d, J=6.0 Hz, 6H).

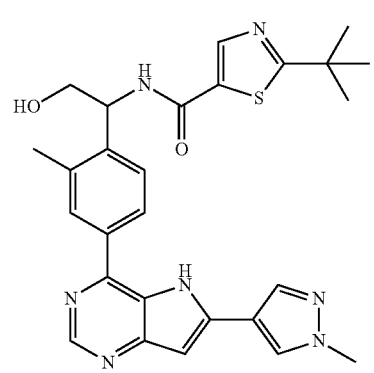

I-44

The Synthesis of 2-(tert-butyl)-N-(2-hydroxy-1-(2-methyl-4-(6-(1-methyl-1H-pyrazol-4-yl)-5H-pyrrolo[3,2-d]pyrimidin-4-yl)phenyl)ethyl)thiazole-5-carboxamide (I-44)

Compound I-44 was prepared in a similar manner as described for I-31 except 4-chloro-6-(1-methyl-1H-pyrazol-4-yl)-5H-pyrrolo[3,2-d]pyrimidine was substituted for the 4-chloro-6-(1-methyl-1H-pyrazol-4-yl)-7H-pyrrolo[2,3-d]pyrimidine to afford the title compound (45 mg, yield 75%). ESI-MS (M+H)⁺: 516.0. ¹H NMR (400 MHz, CD₃OD) δ: 8.74 (s, 1H), 8.34 (s, 1H), 8.21 (s, 1H), 8.05 (s, 1H), 7.79 (s, 1H), 7.78 (d, J=7.6 Hz, 1H), 7.61 (d, J=7.6 Hz, 1H), 6.80 (s, 1H), 5.51-5.47 (m, 1H), 3.96 (s, 3H), 3.90-3.86 (m, 2H), 2.63 (s, 3H), 1.46 (s, 9H).

I-45

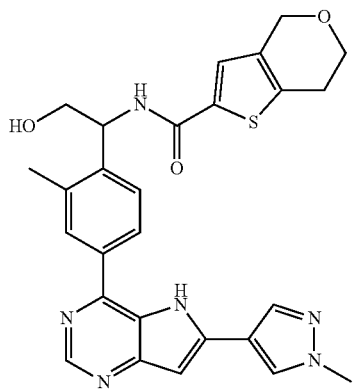

The Synthesis of N-(2-hydroxy-1-(2-methyl-4-(6-(1-methyl-1H-pyrazol-4-yl)-5H-pyrrolo[3,2-d]pyrimidin-4-yl)phenyl)ethyl)-6,7-dihydro-4H-thieno[3,2-c]pyran-2-carboxamide (I-45)

Compound I-45 was prepared in a similar manner as described for compound I-44 except 6,7-dihydro-4H-thieno[3,2-c]pyran-2-carboxylic acid was substituted for the 2-(tert-butyl)thiazole-5-carboxylic acid to afford the title compound (52 mg, yield 74%). ESI-MS (M+H)$^+$: 515.0. $^1$H NMR (400 MHz, DMSO-d6) δ: 11.70 (s, 1H), 8.83 (d, J=7.6 Hz, 1H), 8.76 (s, 1H), 8.41 (s, 1H), 8.13 (s, 1H), 7.81 (d, J=8.8 Hz, 1H), 7.79 (s, 1H), 7.67 (s, 1H), 7.61 (d, J=8.8 Hz, 1H), 6.84 (s, 1H), 5.32-5.29 (m, 1H), 5.05 (t, J=5.6 Hz, 1H), 4.65 (s, 2H), 3.90 (s, 3H), 3.88 (t, J=5.2 Hz, 2H), 3.75-3.64 (m, 2H), 2.82 (t, J=5.2 Hz, 2H), 2.55 (s, 3H).

Example 5

Scheme 11

Method A

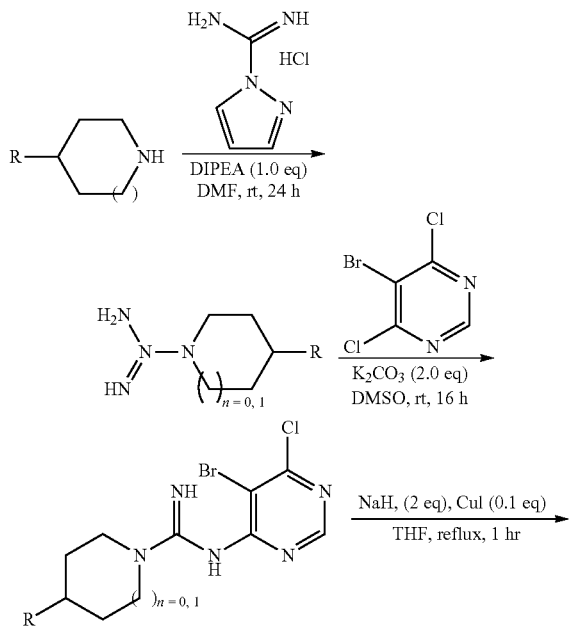

Method B

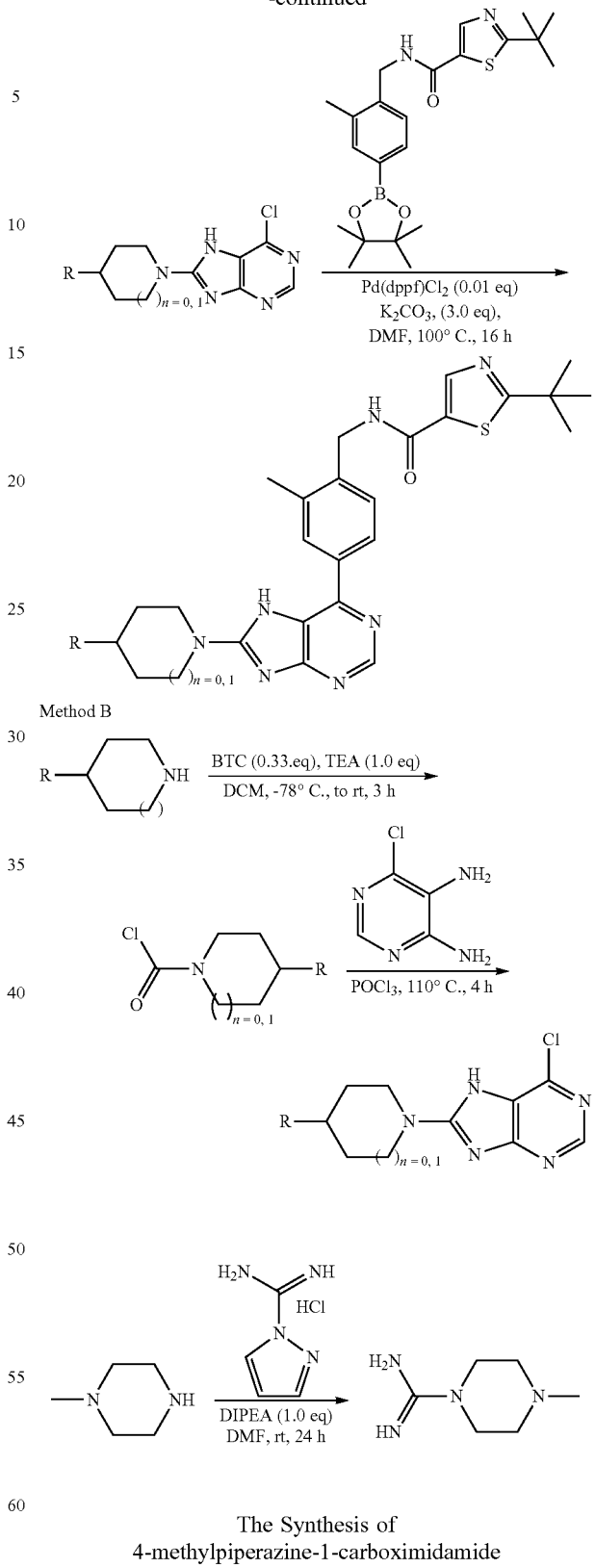

The Synthesis of 4-methylpiperazine-1-carboximidamide

To a solution of 1-methylpiperazine (2 g, 20.0 mmol) and 1H-pyrazole-1-carboximidamide (2.92 g, 20.0 mmol) in DMF (5 mL) was added DIPEA (2.58 g, 2.0 mmol). The mixture was stirred at rt for 24 h, diluted with diethyl ether (80 mL) and stirred at rt 2 h. The resulting precipitate was collected and washed with diethyl ether (20 mL) and dried to give title product (2.2 g, yield 78%) as a white solid, which was used to next step without further purification.

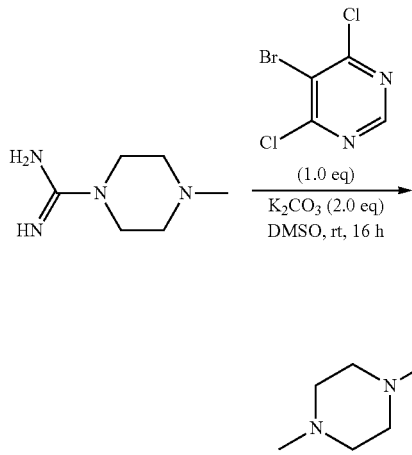

The Synthesis of N-(5-bromo-6-chloropyrimidin-4-yl)-4-methylpiperazine-1-carboximidamide To a solution of 4-methylpiperazine-1-carboximidamide (284 mg, 2.0 mmol) and 5-bromo-4,6-dichloropyrimidine (454 mg, 2.0 mmol) in DMSO (5 mL) was added K$_2$CO$_3$ (552 mg, 4.0 mmol). The mixture was stirred at rt for 16 h, diluted with water (50 mL) and extracted with EtOAc (60 mL×2). The organic phase was washed with water (80 mL), concentrated in vacuo and the crude product was purified by reverse phase chromatography CH$_3$CN/H$_2$O with 0.05% NH$_3$.H$_2$O as mobile phase) to give the title compound (133 mg, yield 20%) as a white solid. ESI-MS (M+H)$^+$: 333.1. $^1$H NMR (400 MHz, DMSO-d$_6$) δ: 8.52 (br, 2H), 8.27 (s, 1H), 3.67-3.65 (m, 4H), 2.36-2.33 (m, 4H), 2.20 (s, 3H).

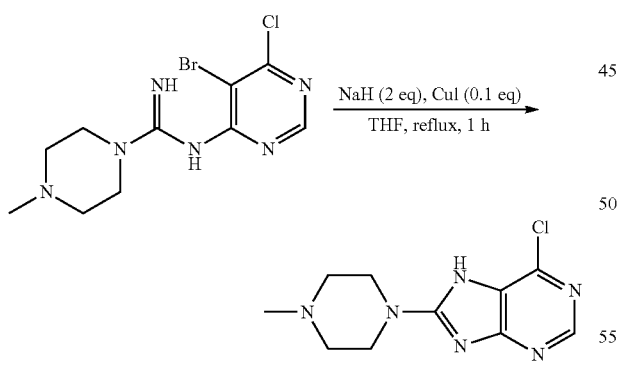

The Synthesis of 6-chloro-8-(4-methylpiperazin-1-yl)-7H-purine

To a solution of N-(5-bromo-6-chloropyrimidin-4-yl)-4-methylpiperazine-1-carboximidamide (333 mg, 1.0 mmol) and NaH (80 mg, 2.0 mmol) in THF (8 mL) was added CuI (19 mg, 0.10 mmol). The mixture was stirred at reflux for 3 h under N$_2$, quenched with water and concentrated in vacuo and purified by reverse phase chromatography (CH$_3$CN/ H$_2$O with 0.05% NH$_3$.H$_2$O as mobile phase) to give the title compound (286 mg, yield 75%) as a white solid. ESI-MS (M+H)$^+$: 253.2. $^1$H NMR (400 MHz, DMSO-d$_6$) δ: 8.30 (s, 1H), 3.64 (t, J=4.8 Hz, 4H), 2.42 (t, J=4.8 Hz, 4H), 2.23 (s, 3H).

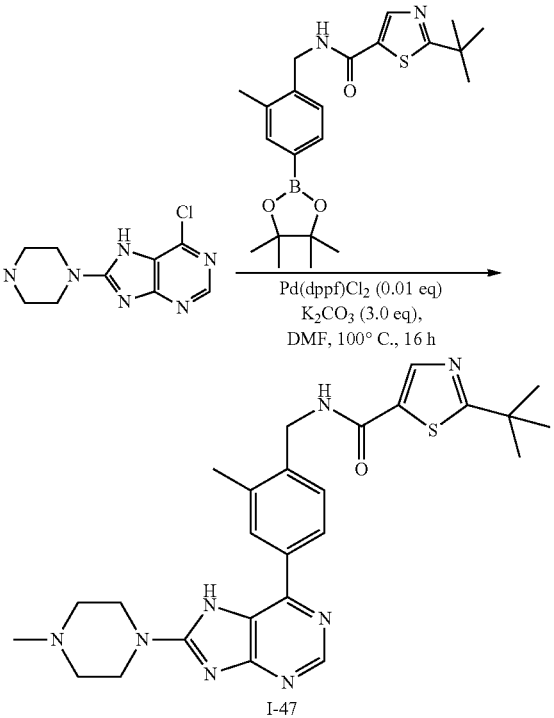

The Synthesis of 2-(tert-butyl)-N-(2-methyl-4-(8-(4-methylpiperazin-1-yl)-7H-purin-6-yl)benzyl)thiazole-5-carboxamide (I-47)

Compound I-47 was prepared in a similar manner as described in Example I-36 except 6-chloro-8-(4-methylpiperazin-1-yl)-7H-purine was substituted for the 4-chloro-6-(1-methyl-1H-pyrazol-4-yl)-7H-pyrrolo[2,3-d]pyrimidine to afford the title compound (55 mg, yield 10%). ESI-MS (M+H)$^+$: 505.2. $^1$H NMR (400 MHz, DMSO-d$_6$) δ: 9.07 (t, J=5.6 Hz, 1H), 8.62 (d, J=7.2 Hz, 1H), 8.51 (s, 1H), 8.40 (s, 1H), 8.34 (s, 1H), 7.62 (d, J=7.6 Hz, 1H), 4.50 (d, J=5.6 Hz, 2H), 3.66-3.65 (m, 4H), 2.42-2.22 (m, 7H), 2.22 (s, 3H), 1.39 (s, 9H).

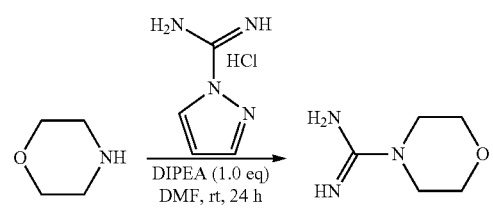 [SMILES: C1COCCN1 ; N=C(N)n1cccn1 ; Cl ; N=C(N)N1CCOCC1]

The Synthesis of morpholine-4-carboximidamide

This compound was prepared in a similar manner as described above for 4-methylpiperazine-1-carboximidamide except morpholine was substituted for the 1-methylpiperazine to afford the title compound. ESI-MS (M+H)+: 130.0.

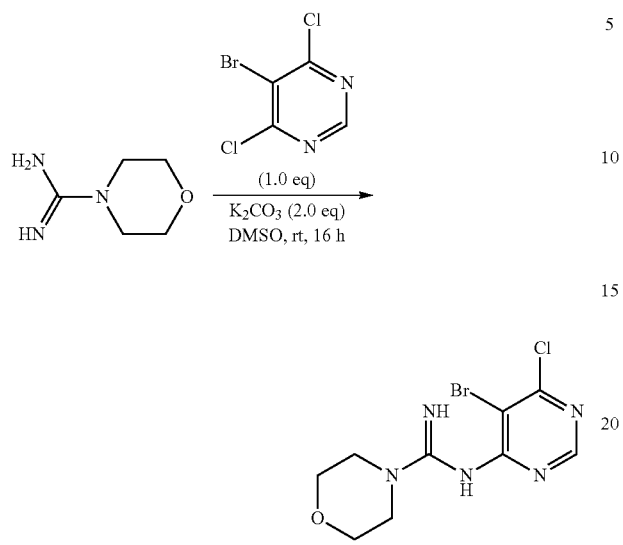

The Synthesis of N-(5-bromo-6-chloropyrimidin-4-yl)morpholine-4-carboximidamide This compound was prepared in a similar manner as described above for N-(5-bromo-6-chloropyrimidin-4-yl)-4-methylpiperazine-1-carboximidamide except morpholine-4-carboximidamide was substituted for the 4-methylpiperazine-1-carboximidamide to afford the title compound (120 mg, yield 17%). ESI-MS (M+H)+: 319.8.

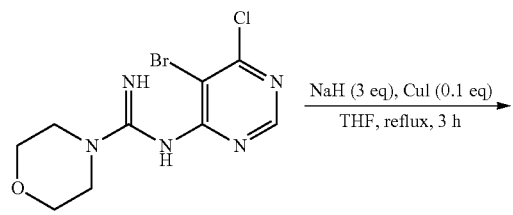

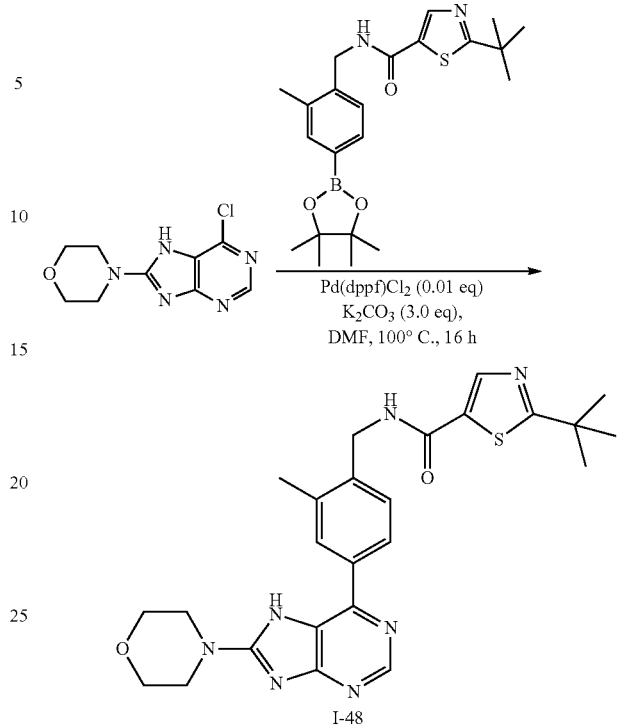

The Synthesis of 2-(tert-butyl)-N-(2-methyl-4-(8-morpholino-7H-purin-6-yl)benzyl)thiazole-5-carboxamide (I-48)

Compound I-48 was prepared in a similar manner as described in Example I-47 except 4-(6-chloro-7H-purin-8-yl)morpholine was substituted for the 4-chloro-6-(1-methyl-1H-pyrazol-4-yl)-7H-pyrrolo[2,3-d]pyrimidine to afford the title compound (55 mg, yield 36%). $^1$H NMR (400 MHz, DMSO-$d_6$) δ: 9.14 (t, J=5.6 Hz, 1H), 8.70 (s, 1H), 8.37-8.34 (m, 3H), 7.42 (d, J=8.4 Hz, 1H), 4.51 (d, J=5.2 Hz, 2H), 3.75-3.70 (m, 8H), 2.43 (s, 3H), 1.39 (s, 9H).

The Synthesis of 4-(6-chloro-7H-purin-8-yl)morpholine

This compound was prepared in a similar manner as described above except N-(5-bromo-6-chloropyrimidin-4-yl)morpholine-4-carboximidamide was substituted for the N-(5-bromo-6-chloropyrimidin-4-yl)-4-methylpiperazine-1-carboximidamide to afford the title compound (78 mg, yield 86%). ESI-MS (M+H)+: 240.1.

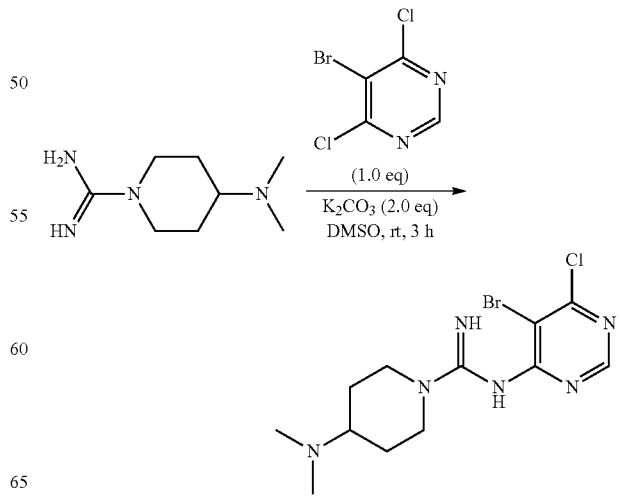

The Synthesis of N-(5-bromo-6-chloropyrimidin-4-yl)-4-(dimethylamino)piperidine-1-carboximidamide This compound was prepared in a similar manner as described above for N-(5-bromo-6-chloropyrimidin-4-yl)-4-methylpiperazine-1-carboximidamide except 4-(dimethylamino)piperidine-1-carboximidamide was substituted for the 4-methylpiperazine-1-carboximidamide to afford the title compound (198 mg, yield 28%). ESI-MS (M+H)⁺: 361.1.

$^1$H NMR (400 MHz, CD$_3$OD) δ: 8.71 (s, 1H), 8.14 (s, 1H), 7.90-7.87 (m, 2H), 7.47 (d, J=8.4 Hz, 1H), 4.55-4.51 (m, 4H), 3.56-3.44 (m, 1H), 3.27-3.21 (m, 2H), 2.81 (s, 6H), 2.43 (s, 3H), 2.18-2.15 (m, 2H), 1.78-1.74 (m, 2H), 1.36 (s, 9H).

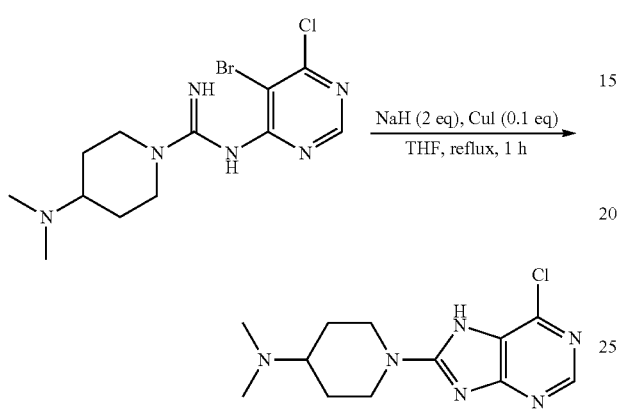

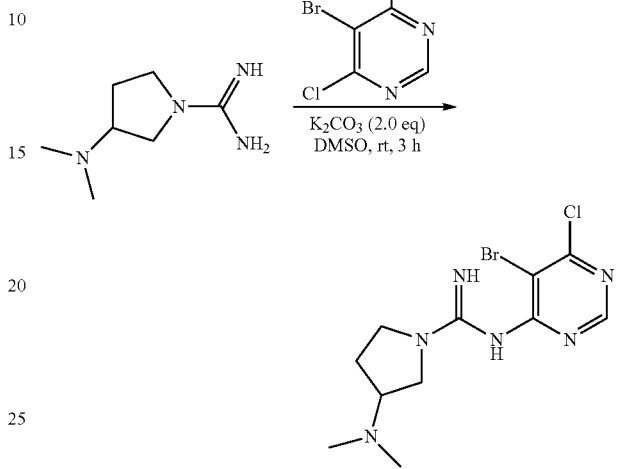

The Synthesis of 1-(6-chloro-7H-purin-8-yl)-N,N-dimethylpiperidin-4-amine

This compound was prepared in a similar manner as described above in this Example except N-(5-bromo-6-chloropyrimidin-4-yl)-4-(dimethylamino)piperidine-1-carboximidamide was substituted for the N-(5-bromo-6-chloropyrimidin-4-yl)-4-methylpiperazine-1-carboximidamide to afford the title compound (131 mg, yield 85%). ESI-MS (M+H)⁺: 280.9.

The Synthesis of N-(5-bromo-6-chloropyrimidin-4-yl)-3-(dimethylamino)pyrrolidine-1-carboximidamide This compound was prepared in a similar manner as described above in this Example except 3-(dimethylamino)pyrrolidine-1-carboximidamide was substituted for the 4-methylpiperazine-1-carboximidamide to afford the title compound (282 mg, yield 27%). ESI-MS (M+H)⁺: 346.8.

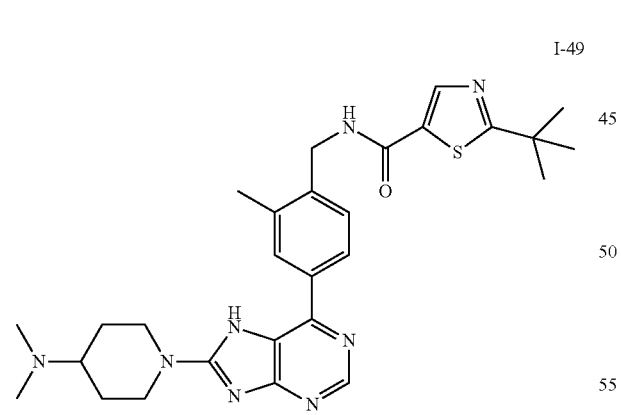

I-49

The Synthesis of 2-(tert-butyl)-N-(4-(8-(4-(dimethylamino)piperidin-1-yl)-7H-purin-6-yl)-2-methylbenzyl)thiazole-5-carboxamide (I-49)

Compound I-49 was prepared in a similar manner as described in Example I-47 except 4-(6-chloro-7H-purin-8-yl)morpholine was substituted for the 4-chloro-6-(1-methyl-1H-pyrazol-4-yl)-7H-pyrrolo[2,3-d]pyrimidine to afford the title compound (16 mg, yield 16%). ESI-MS (M+H)⁺: 532.9.

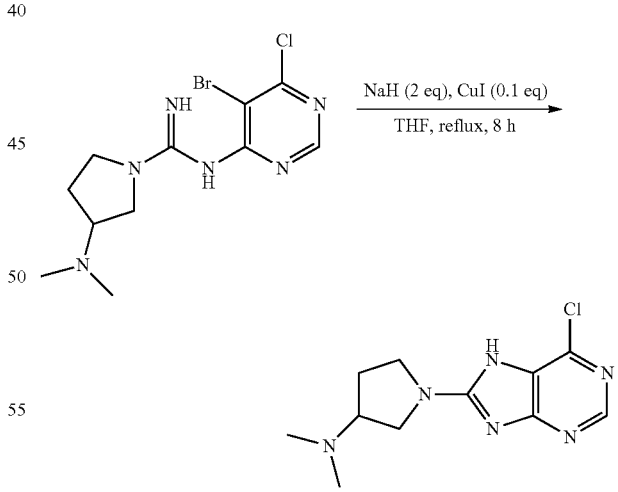

The Synthesis of 1-(6-chloro-7H-purin-8-yl)-N,N-dimethylpyrrolidin-3-amine

This compound was prepared in a similar manner as described above in this Example except N-(5-bromo-6-chloropyrimidin-4-yl)-3-(dimethylamino)pyrrolidine-1-carboximidamide was substituted for the N-(5-bromo-6-chloropyrimidin-4-yl)-4-methylpiperazine-1-carboximidamide to afford the title compound (152 mg, yield 85%). ESI-MS (M+H)$^+$: 267.1. $^1$H NMR (400 MHz, CD$_3$OD) δ: 8.04 (s, 1H), 3.99-3.95 (m, 1H), 3.89-3.83 (m, 1H), 3.62-3.56 (m, 1H), 3.44-3.39 (m, 1H), 2.97-2.89 (m, 1H), 2.36 (s, 6H), 2.32-2.26 (m, 1H), 1.97-1.86 (m, 1H).

I-50

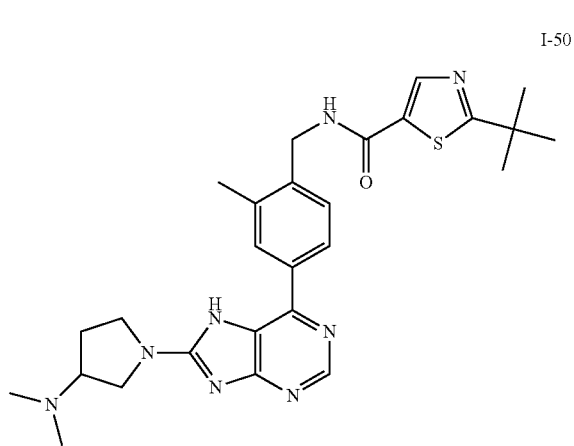 [SMILES: Cc1cc(-c2ncnc3nc(N4CCC(N(C)C)C4)[nH]c23)ccc1CNC(=O)c1cnc(C(C)(C)C)s1]

The Synthesis of 2-(tert-butyl)-N-(4-(8-(3-(dimethylamino)pyrrolidin-1-yl)-7H-purin-6-yl)-2-methylbenzyl)thiazole-5-carboxamide (I-50)

Compound I-50 was prepared in a similar manner as described in Example 3 except 1-(6-chloro-7H-purin-8-yl)-N,N-dimethylpyrrolidin-3-amine was substituted for the 4-chloro-6-(1-methyl-1H-pyrazol-4-yl)-7H-pyrrolo[2,3-d]pyrimidine to afford the title compound (16 mg, yield 16%). $^1$H NMR (400 MHz, CD$_3$OD) δ: 8.44 (s, 1H), 8.14 (s, 1H), 7.88-7.87 (m, 2H), 7.36-7.34 (m, 1H), 4.52 (s, 2H), 3.86-3.75 (m, 2H), 3.56-3.52 (m, 1H), 3.36-3.32 (m, 1H), 2.89-2.88 (m, 1H), 2.38 (s, 3H), 2.25 (s, 6H), 2.24-2.23 (m, 1H), 1.89-1.85 (m, 1H), 1.36 (s, 9H).

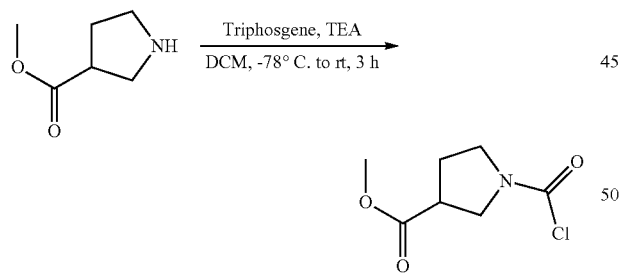

The Synthesis of methyl 1-(chlorocarbonyl)pyrrolidine-3-carboxylate

To a solution of triphosgene (bis(trichloromethyl) carbonate (376 mg, 1.28 mmol) in DCM (20 ml) was added methyl pyrrolidine-3-carboxylate (500 mg, 3.88 mmol) and TEA (392 mg, 3.88 mmol) at −78° C. The mixture was stirred at rt for 3 h, diluted with water (50 mL) and extracted with CH$_2$Cl$_2$ (50 mL×3). The organic layer was washed with water (50 mL), dried (Na$_2$SO$_4$), filtered and concentrated in vacuo to afford the crude product (350 mg, yield 47%) which was used without further purification.

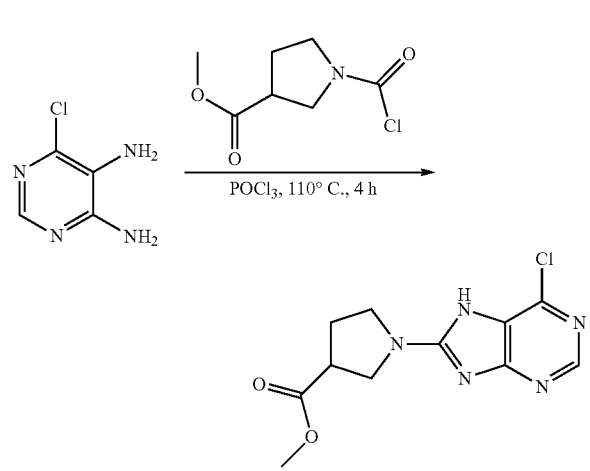

The Synthesis of methyl 1-(6-chloro-7H-purin-8-yl)pyrrolidine-3-carboxylate

To a solution of 6-chloropyrimidine-4,5-diamine (220 mg, 1.53 mmol) in POCl$_3$ (4 ml) was added methyl 1-(chlorocarbonyl)pyrrolidine-3-carboxylate (350 mg, 1.83 mmol). The mixture was stirred at 110° C. for 4 h, cooled to rt, and poured into ice water slowly, neutralized with sat. Na$_2$CO$_3$ to pH 7-8. The mixture was concentrated and purified by reverse phase chromatography (CH$_3$CN/H$_2$O with 0.05% NH$_3$.H$_2$O as mobile phase) to afford the title compound (180 mg, yield 42%). ESI-MS (M+H)$^+$: 282.0.

I-51

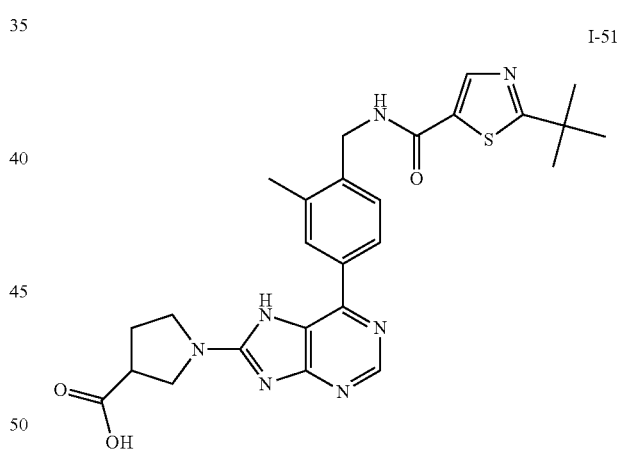

The Synthesis of 1-(6-(4-((2-(tert-butyl)thiazole-5-carboxamido)methyl)-3-methylphenyl)-7H-purin-8-yl)pyrrolidine-3-carboxylic acid (I-51)

Compound I-51 was prepared in a similar manner as described in Example I-47 except methyl 1-(6-chloro-7H-purin-8-yl)pyrrolidine-3-carboxylate was substituted for the 4-chloro-6-(1-methyl-1H-pyrazol-4-yl)-7H-pyrrolo[2,3-d]pyrimidine to afford the title compound (15 mg, yield 6%). ESI-MS (M+H)$^+$: 520.0. $^1$H NMR (400 MHz, DMSO-d$_6$) δ: 9.08 (t, J=5.2 Hz, 1H), 8.59-8.52 (m, 3H), 8.33 (s, 1H), 7.39 (d, J=8.4 Hz, 1H), 4.51 (d, J=5.6 Hz, 2H), 3.78-3.76 (m, 2H), 3.66-3.59 (m, 2H), 3.23-3.18 (m, 1H), 2.41 (s, 3H), 2.23-2.18 (m, 2H), 1.39 (s, 9H).

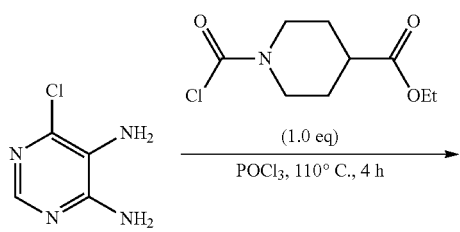
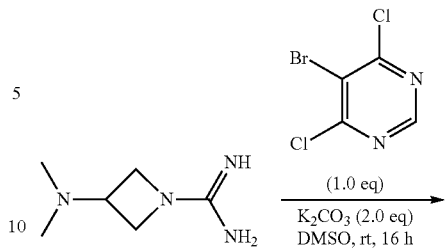

The Synthesis of ethyl 1-(6-chloro-7H-purin-8-yl)piperidine-4-carboxylate

This compound was prepared in a similar manner as described above in this Example except ethyl piperidine-4-carboxylate was substituted for the methyl pyrrolidine-3-carboxylate to afford the title compound (50 mg, yield 23%). ESI-MS (M+H)$^+$: 310.1.

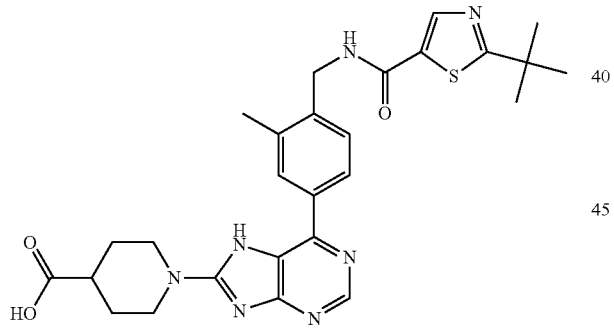

I-52

The Synthesis of 1-(6-(4-((2-(tert-butyl)thiazole-5-carboxamido)methyl)-3-methylphenyl)-7H-purin-8-yl)piperidine-4-carboxylic acid (I-52)

Compound I-52 was prepared in a similar manner as described in Example I-47 except ethyl 1-(6-chloro-7H-purin-8-yl)piperidine-4-carboxylate was substituted for the 4-chloro-6-(1-methyl-1H-pyrazol-4-yl)-7H-pyrrolo[2,3-d]pyrimidine to afford the title compound (30 mg, yield 81%). ESI-MS (M+H)$^+$: 534.2. $^1$H NMR (400 MHz, DMSO-d$_6$) δ: 9.08 (t, J=5.2 Hz, 1H), 8.58-8.41 (m, 3H), 8.34 (s, 1H), 7.35 (d, J=8.0 Hz, 1H), 4.49 (d, J=5.2 Hz, 2H), 4.28-4.25 (m, 2H), 3.09-3.07 (m, 2H), 2.39 (s, 3H), 2.31-2.30 (m, 1H), 1.88-1.86 (m, 2H), 1.61-1.52 (m, 2H), 1.39 (s, 9H).

The Synthesis of N-(5-bromo-6-chloropyrimidin-4-yl)-3-(dimethylamino)azetidine-1-carboximidamide This compound was prepared in a similar manner as described above in this Example except N,N-dimethylazetidin-3-amine was substituted for the 1-methylpiperazine to afford the title compound (80 mg, yield 6.9%). ESI-MS (M+H)$^+$: 332.9.

The Synthesis of N-(5-bromo-6-chloropyrimidin-4-yl)-3-(dimethylamino)azetidine-1-carboximidamide This compound was prepared in a similar manner as described above in this Example except N-(5-bromo-6-chloropyrimidin-4-yl)-3-(dimethylamino)azetidine-1-carboximidamide was substituted for the N-(5-bromo-6-chloropyrimidin-4-yl)-4-methylpiperazine-1-carboximidamide to afford the title compound (80 mg, yield 83%). ESI-MS (M+H)$^+$: 252.9.

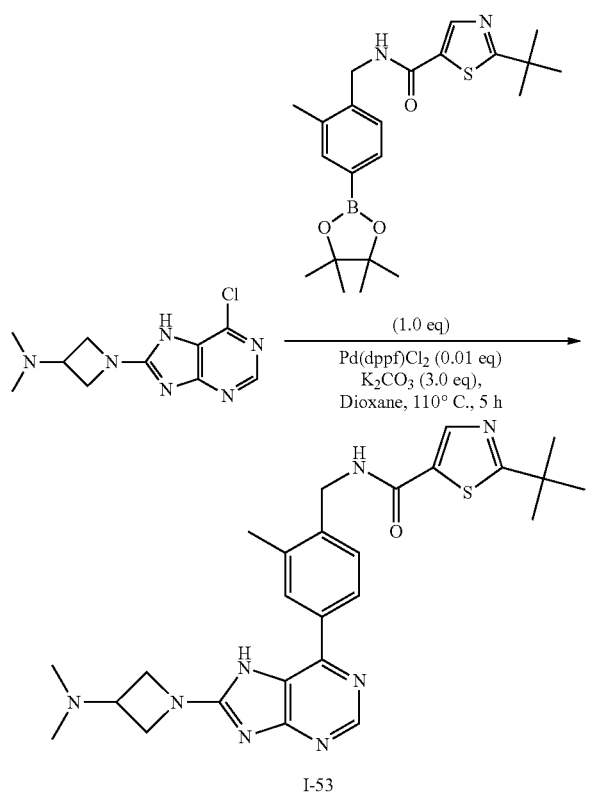

The Synthesis of 2-(tert-butyl)-N-(4-(8-(3-(dimethylamino)azetidin-1-yl)-7H-purin-6-yl)-2-methylbenzyl)thiazole-5-carboxamide (I-53)

Compound I-53 was prepared in a similar manner as described in Example I-47 except ethyl 1-(6-chloro-7H-purin-8-yl)piperidine-4-carboxylate was substituted for the 4-chloro-6-(1-methyl-1H-pyrazol-4-yl)-7H-pyrrolo[2,3-d]pyrimidine to afford the title compound (18 mg, yield: 12%). ESI-MS (M+H)$^+$: 505.2. $^1$H NMR (400 MHz, CD$_3$OD) δ: 8.32 (s, 1H), 8.15 (s, 1H), 7.92-7.91 (m, 2H), 7.32 (d, J=7.6 Hz, 1H), 4.51 (s, 2H), 4.19-4.18 (m, 2H), 3.99-3.95 (m, 2H), 3.24-3.21 (m, 1H), 2.36 (s, 3H), 2.13 (s, 6H), 1.36 (s, 9H).

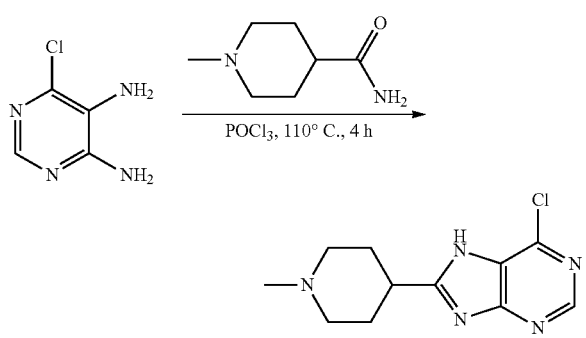

The Synthesis of 6-chloro-8-(1-methylpiperidin-4-yl)-7H-purine

This compound was prepared in a similar manner as described above in this Example except ethyl piperidine-4-carboxylate was substituted for the methyl pyrrolidine-3-carboxylate to afford the title compound (112 mg, yield 43%).

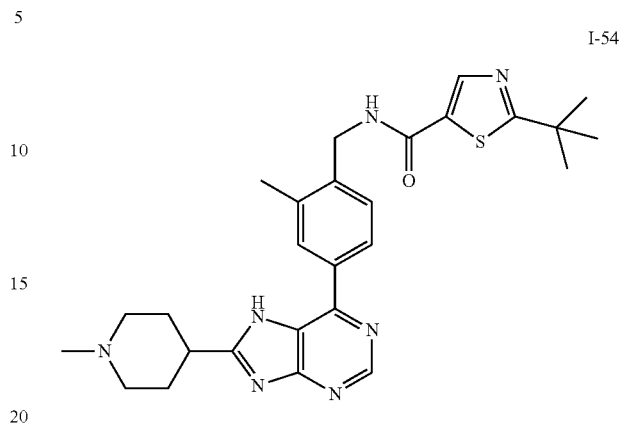

The Synthesis of 2-(tert-butyl)-N-(2-methyl-4-(8-(1-methylpiperidin-4-yl)-7H-purin-6-yl)benzyl)thiazole-5-carboxamide (I-54)

Compound I-54 was prepared in a similar manner as described in Example I-47 except 6-chloro-8-(1-methylpiperidin-4-yl)-7H-purine was substituted for the 4-chloro-6-(1-methyl-1H-pyrazol-4-yl)-7H-pyrrolo[2,3-d]pyrimidine to afford the title compound (31 mg, yield 19%). ESI-MS (M+H)$^+$: 504.2. $^1$H NMR (400 MHz, CD$_3$OD) δ: 8.89 (s, 1H), 8.38-8.36 (m, 2H), 8.23 (s, 1H), 7.49 (d, J=8.4 Hz, 1H), 4.65 (s, 2H), 3.70-3.68 (m, 2H), 3.28-3.20 (m, 2H), 2.93 (s, 3H), 2.88-2.87 (m, 1H), 2.49 (s, 3H), 2.47-2.43 (m, 2H), 2.26-2.13 (m, 2H), 1.46 (s, 9H).

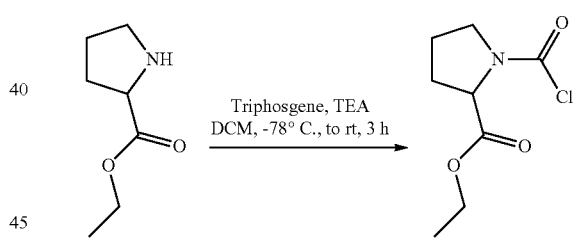

The Synthesis of ethyl 1-(chlorocarbonyl)pyrrolidine-2-carboxylate

This compound was prepared in a similar manner as described above in this Example except ethyl pyrrolidine-2-carboxylate was substituted for the methyl pyrrolidine-3-carboxylate to afford the title compound (720 mg, yield 69%) was used in the next step without further purification.

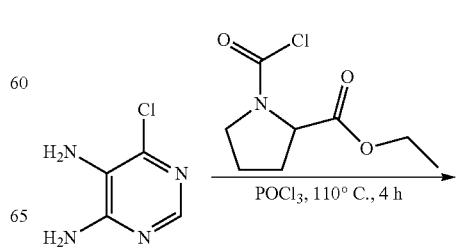

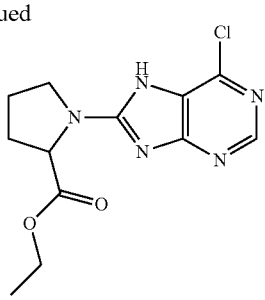

The Synthesis of ethyl 1-(6-chloro-7H-purin-8-yl) pyrrolidine-2-carboxylate

This compound was prepared in a similar manner as described above in this Example except ethyl piperidine-4-carboxylate was substituted for the methyl pyrrolidine-3-carboxylate to afford the title compound (58 mg, yield 20%). ESI-MS (M+H)$^+$: 296.0.

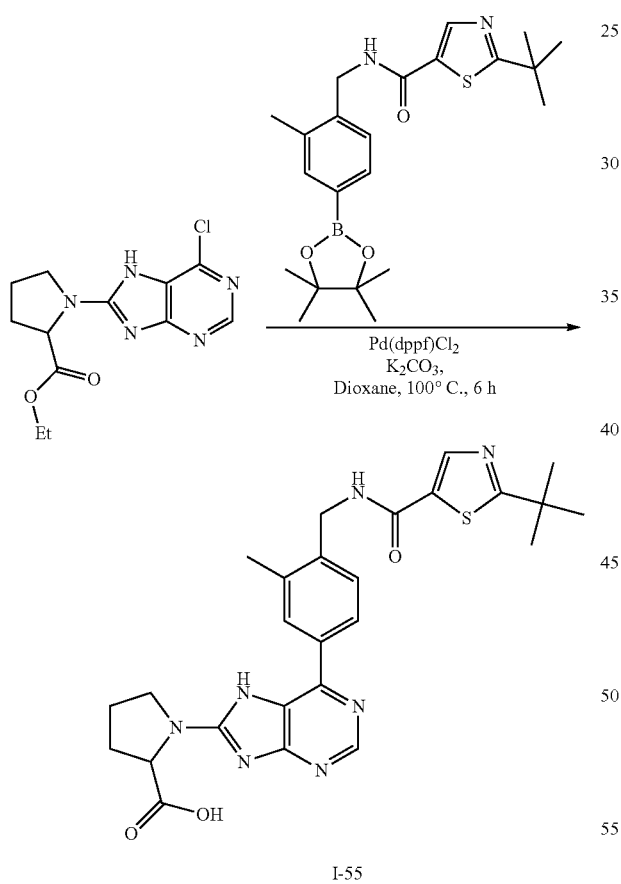

I-55

The Synthesis of 1-(6-(4-((2-(tert-butyl)thiazole-5-carboxamido)methyl)-3-methylphenyl)-7H-purin-8-yl)pyrrolidine-2-carboxylic acid (I-55)

Compound I-55 was prepared in a similar manner as described in Example I-52 except ethyl 1-(6-chloro-7H-purin-8-yl)piperidine-4-carboxylate was substituted for the 4-chloro-6-(1-methyl-1H-pyrazol-4-yl)-7H-pyrrolo[2,3-d]pyrimidine to afford the title compound (58 mg, yield: 20%). ESI-MS (M+H)$^+$: 520.2. $^1$H NMR (400 MHz, DMSO-d$_6$) δ: 9.11 (s, 1H), 8.65 (s, 1H), 8.51-8.19 (m, 3H), 7.41 (d, J=7.6 Hz, 1H), 4.61 (d, J=7.6 Hz, 1H), 4.51 (t, J=5.6 Hz, 2H), 3.78-3.64 (m, 2H), 2.42 (s, 3H), 2.38-2.28 (m, 1H), 2.14-1.97 (m, 3H), 1.39 (s, 9H).

Example 6

Scheme 12

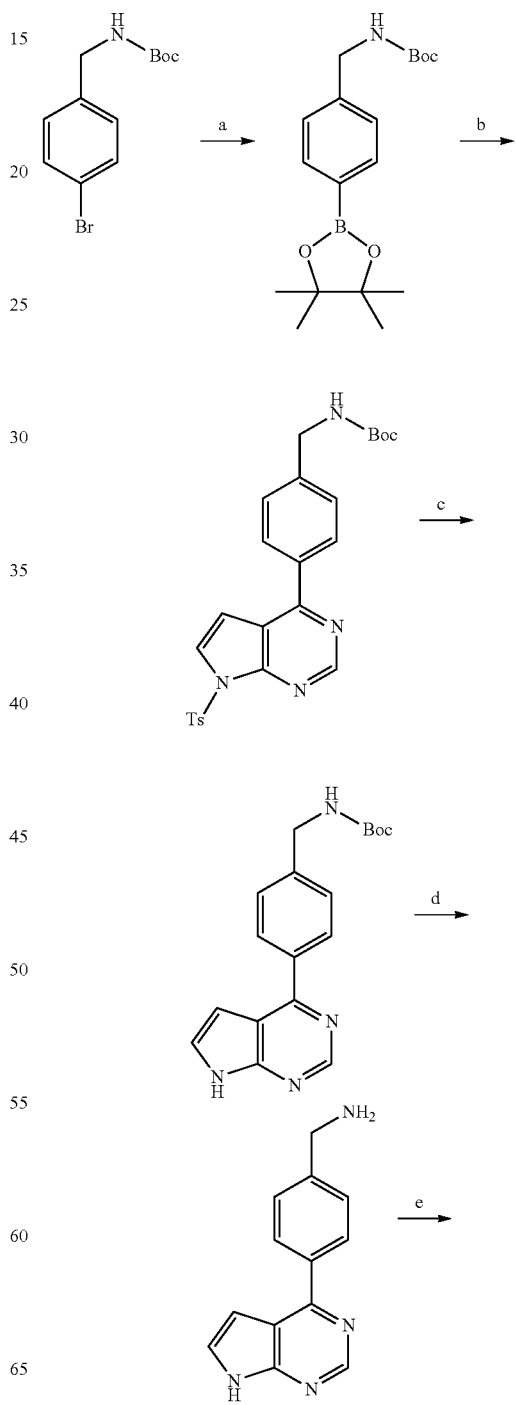

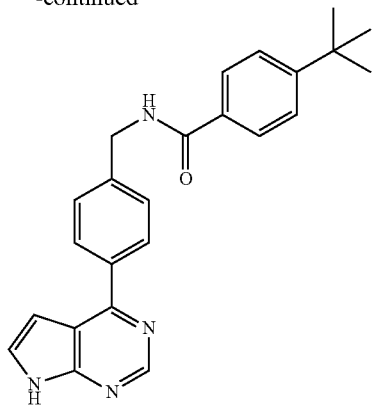

I-56

Reagents and conditions: (a) i. Boc anhydride, THF, 1 h, rt. ii. PdCl₂(dppf), KOAc, bis(pinanacolato)diboron, DMSO, 85° C. 12 h. (b) 4-Chloro-7-tosyl-7H-pyrrolo[2,3-d]pyrimidine, PdCl₂(dppf), K₂CO₃, dioxane/water 90° C., 2 h. (c) Cs₂CO₃, THF/MeOH rt, 2 h. (d) TFA, DCM, rt, 30 min. (e) 4-(Tert-butyl)benzoic acid, CDI, Et₃N, DMF, rt, 12 h.

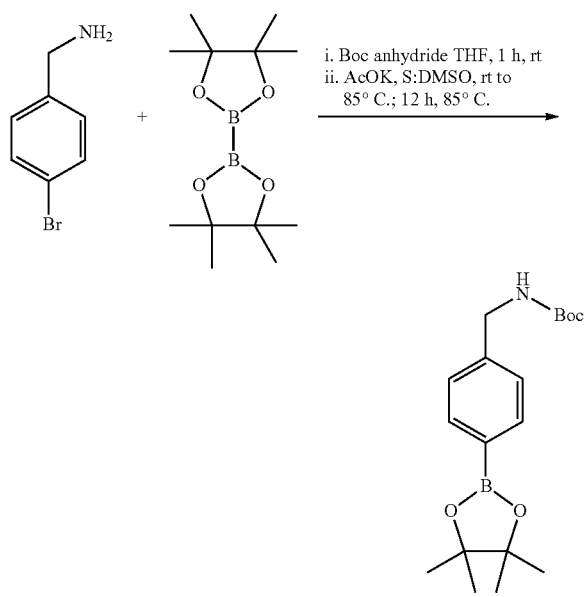

Synthesis of tert-butyl 4-(4,4,5,5-tetramethyl-1,3,2-dioxaborolan-2-yl)benzylcarbamate A solution of 4-bromobenzylamine (40.0 g, 217.0 mmol) in THF (150 mL) was treated with di-tert-butyl dicarbonate (46.0 g, 217 mmol) and stirred at rt for 1 h. The reaction mixture was concentrated in vacuo to afford a solid which was purified by chromatography (80:20 Hexanes: EtOAc) afforded the Boc protected amine (63.0 g, 95%) as a white solid. A solution of the aryl bromide (30.0 g, 98.0 mmol) in DMSO (100 mL) was treated with bis(pinacolato)diboron (30.0 g, 118 mmol), KOAc (30.0 g, 306 mmol), and PdCl₂(dppf) (0.2 mmol) and warmed to 85° C. for 12 h. The reaction mixture was diluted with EtOAc (250 mL) and washed with water (2×150 mL) and brine (100 mL). The organic layer was dried (Na₂SO₄) and concentrated in vacuo to afford a solid which was purification by chromatography (80:20 hexanes: EtOAc) afforded the desired cmpd (31.0 g, yield 97%) as a white solid. ESI-MS (M+H)⁺: 334.

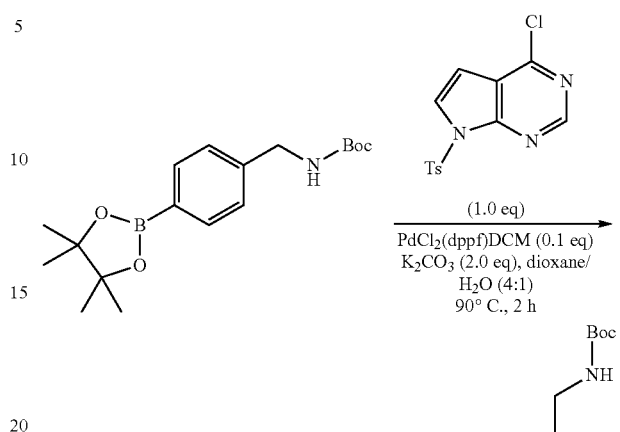

Synthesis of tert-butyl 4-(7-tosyl-7H-pyrrolo[2,3-d]pyrimidin-4-yl)benzylcarbamate To a solution of tert-butyl 4-(4,4,5,5-tetramethyl-1,3,2-dioxaborolan-2-yl)benzylcarbamate (320 mg, 0.96 mmol, 1.0 eq) in DMF (3 mL) were added K₂CO₃ (187 mg, 1.4 mmol, 1.5 eq), Pd(dppf)Cl₂ (81 mg, 0.1 mmol, 0.01 eq) and 4-chloro-7-tosyl-7H-pyrrolo[2,3-d]pyrimidine (340 mg, 1.1 mmol, 1.2 eq). The mixture was stirred at 100° C. in a sealed tube N₂ for 16 h. After cooling down to rt, the residue was purified by column chromatography (silica, petroleum ether/EtOAc=5:1) to afford tert-butyl 4-(7-tosyl-7H-pyrrolo[2,3-d]pyrimidin-4-yl)benzylcarbamate (370 mg, yield: 80%) as a yellow solid. ESI-MS (M+H)⁺: 479.17. ¹H NMR (400 MHz, CDCl₃) δ: 9.06 (s, 1H), 8.13 (d, J=8.4 Hz, 2H), 7.96 (d, J=8.0 Hz, 2H), 7.79 (d, J=3.6 Hz, 1H), 7.45 (d, J=8.4 Hz, 2H), 7.33 (d, J=8.0 Hz, 2H), 6.90 (d, J=4.0 Hz, 1H), 4.41 (d, J=5.6 Hz, 2H), 2.40 (s, 3H), 1.47 (s, 9H).

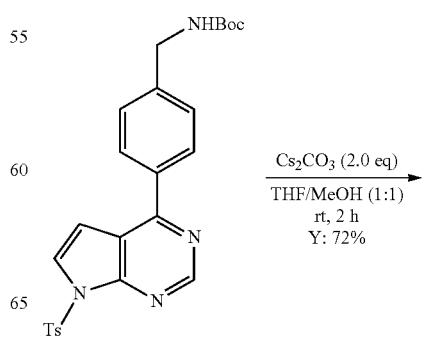

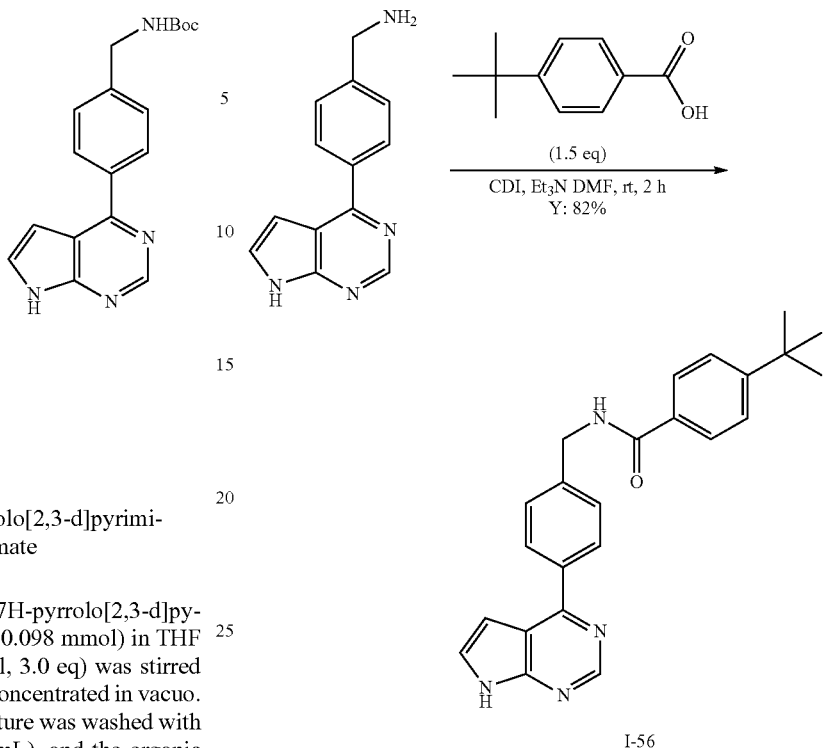

Synthesis of tert-butyl 4-(7H-pyrrolo[2,3-d]pyrimidin-4-yl)benzylcarbamate

A mixture of tert-butyl 4-(7-tosyl-7H-pyrrolo[2,3-d]pyrimidin-4-yl)benzylcarbamate (47 mg, 0.098 mmol) in THF (2 mL) and Cs$_2$CO$_3$ (80 mg, 0.2 mmol, 3.0 eq) was stirred at room temperature for 16 h and then concentrated in vacuo. EtOAc (10 mL) was added and the mixture was washed with sat. NaHCO$_3$ (5 mL×2) and brine (5 mL), and the organic phase was dried (Na$_2$SO$_4$), filtered and concentrated in vacuo to afford a solid, which was purified by prep-HPLC (MeOH/H$_2$O with 0.05% NH$_3$.H$_2$O as mobile phase) to afford tert-butyl 4-(7H-pyrrolo[2,3-d]pyrimidin-4-yl)benzylcarbamate (23 mg, yield: 72%). ESI-MS (M+H)$^+$: 325.16. $^1$H NMR (400 MHz, DMSO-d6) δ: 12.24 (s, 1H), 8.89-8.81 (m, 1H), 8.15 (d, J=8.4 Hz, 2H), 7.72-7.62 (m, 1H), 7.56-7.47 (m, 1H), 7.45 (d, J=8.0 Hz, 2H), 6.96-6.88 (m, 1H), 4.24 (d, J=6.0 Hz, 2H), 1.42 (s, 9H).

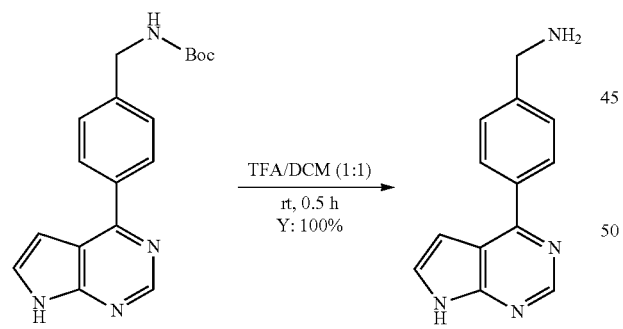

Synthesis of (4-(7H-pyrrolo[2,3-d]pyrimidin-4-yl)phenyl)methanamine

A mixture of tert-butyl 4-(7H-pyrrolo[2,3-d]pyrimidin-4-yl)benzylcarbamate (120 mg, 0.36 mmol) in TFA (2 mL) and DCM (2 mL) was stirred for 30 minutes at room temperature and then concentrated in vacuo, diluted with EtOAc (10 mL) and washed with sat. NaHCO$_3$ (5 mL×2) and brine (5 mL). The crude (83 mg, yield: 100%) was used directly in the next step without further purification. ESI-MS (M+H)$^+$: 225.11.

Synthesis of N-(4-(7H-pyrrolo[2,3-d]pyrimidin-4-yl)benzyl)-4-(tert-butyl)benzamide (I-56)

To a solution of 4-(tert-butyl)benzoic acid (78 mg, 0.44 mmol) in DMF (10 mL) and CDI (142 mg, 0.88 mmol) was added Et$_3$N (101 mg, 1.0 mmol) and the solution was stirred at rt for 30 min. The (4-(7H-pyrrolo[2,3-d]pyrimidin-4-yl)phenyl)methanamine TFA salt (66 mg, 0.29 mmol) was added and the solution was stirred at rt for 12 h. The mixture was purified by prep-HPLC (MeCN/H$_2$O with 0.05% NH$_3$.H$_2$O as mobile phase) to afford N-(4-(7H-pyrrolo[2,3-d]pyrimidin-4-yl)benzyl)-4-(tert-butyl)benzamide (I-56) (278 mg, yield: 82%). ESI-MS (M+H)$^+$: 385.

Example 7

Scheme 13

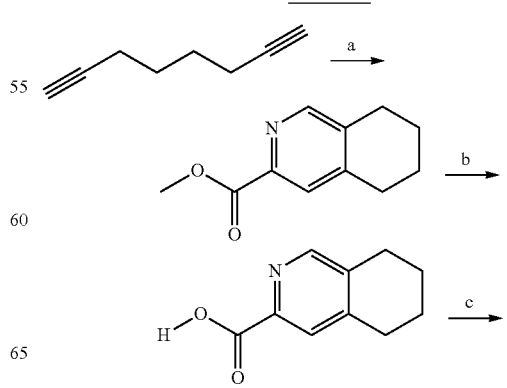

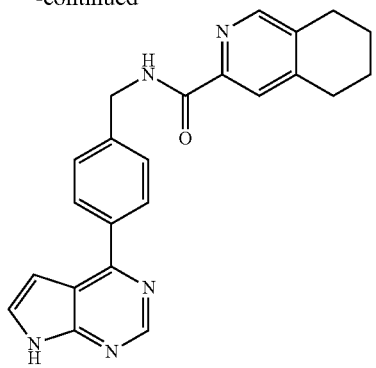

I-57

Reagent and conditions: a) C₄H₅NO₂, cyclopentadienyl-Cobalt(I)-dicarbonyl, 1,4-dioxane, reflux, 18 h. b) NaOH, THF/water 2 h reflux. c) (4-(7H-pyrrolo[2,3-d]pyrimidin-4-yl)phenyl)methanamine TFA salt, CDI, Et₃N, 100° C., 2 h.

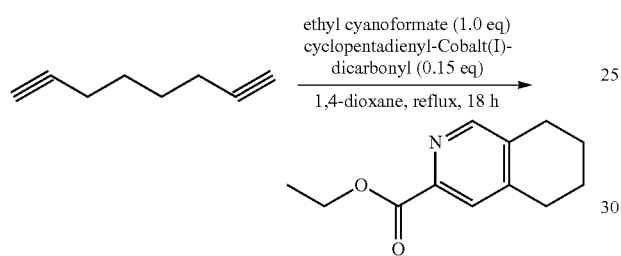

Synthesis of ethyl 5,6,7,8-tetrahydroisoquinoline-3-carboxylate

A solution of 1,7-octadiyne (4.00 ml, 30.1 mmol) and ethyl cyanoformate (2.95 ml, 30.1 mmol) in dry degassed 1,4-dioxane (500 ml) under nitrogen at rt was treated with cyclopentadienyl-cobalt(I)-dicarbonyl (0.814 g, 4.52 mmol) and heated at reflux for 18 h. The mixture was then concentrated in vacuo, treated with PhCH₃ (100 ml), concentrated in vacuo, dissolved in CH₂Cl₂ (100 ml), filtered through a short pad of Celite, eluted with CH₂Cl₂, concentrated in vacuo to afford a residue which was purified by silica gel column chromatography (Petroleum ether/EtOAc=4:1) to give the product as a brown oil (90 mg, yield: 3%). ESI-MS (M+H⁺): 206.1. ¹H NMR (400 MHz, CDCl₃) δ: 8.42 (s, 1H), 7.84 (s, 1H), 4.60 (q, J=7.2 Hz, 2H), 2.81-2.74 (m, 4H), 1.85-1.84 (m, 4H), 1.44 (t, J=7.2 Hz, 3H).

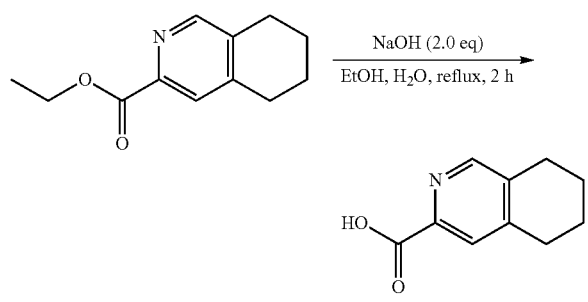

Synthesis of 5,6,7,8-tetrahydroisoquinoline-3-carboxylic acid

To a solution of ethyl 5,6,7,8-tetrahydroisoquinoline-3-carboxylate (90 mg, 0.44 mmol) in EtOH/H₂O (4:1, 20 mL) was added NaOH (35 mg, 0.88 mmol) and the mixture was refluxed for 2 h. After cooling to rt the solution was acidified with 1 M HCl to pH=4 and volume was reduced to afford a residue which was dissolved in MeOH, filtered, and the solvent was concentrated in vacuo to give afford the acid (78 mg. yield: 100%) as a yellow solid, which was used in the next step without further purification. ESI-MS (M+H⁺): 178.1.

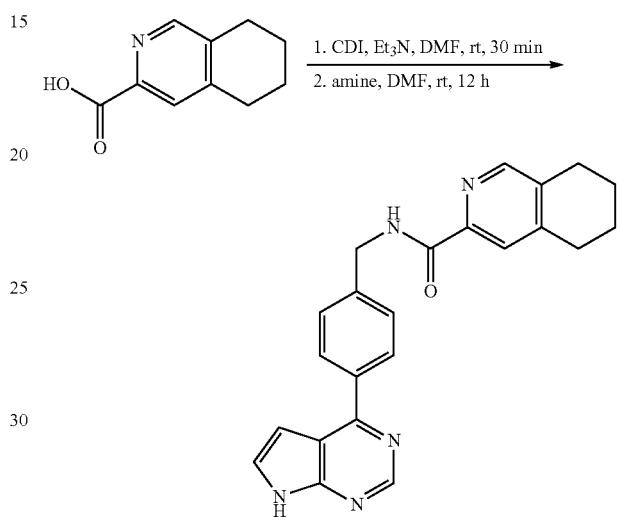

I-57

Synthesis of N-(4-(7H-pyrrolo[2,3-d]pyrimidin-4-yl)benzyl)-5,6,7,8-tetrahydroisoquinoline-3-carboxamide (I-57)

Compound I-57 was prepared in a similar manner as described in Example I-56 except 5,6,7,8-tetrahydroisoquinoline-3-carboxylic acid was substituted for 4-(tert-butyl)benzoic acid. ESI-MS (M+H⁺): 384.2. ¹H NMR (400 MHz, CD₃OD) δ: 8.67 (s, 1H), 8.22 (s, 1H), 7.85 (d, J=8.4 Hz, 2H), 7.71 (s, 1H), 7.48 (d, J=8.4 Hz, 2H), 7.42 (d, J=3.2 Hz, 1H), 6.75 (d, J=3.2 Hz, 1H), 4.61 (s, 2H), 2.76-2.73 (m, 4H), 1.77-1.75 (m, 4H).

Example 8

Scheme 14

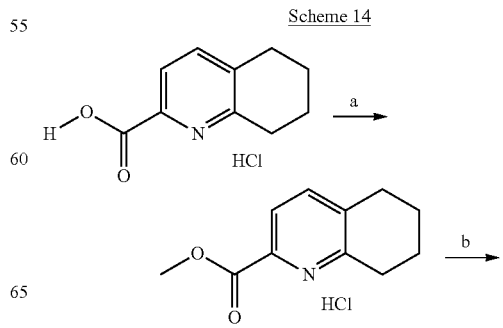

-continued

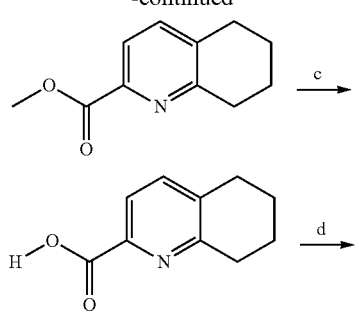

I-58

Reagent and conditions: a) SOCl₂, MeOH, reflux, 3 h. b) PtO₂, H₂, TFA, rt. c) NaOH, EtOH, reflux, 1 h. d) amine, CDI, Et₃N, DMF, rt.

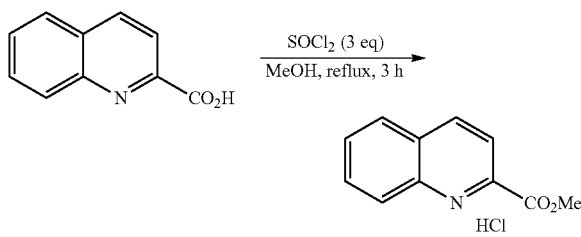

The Synthesis of methyl quinoline-2-carboxylate hydrochloride

To a solution of quinoline-2-carboxylic acid (3.46 g, 20 mmol) in MeOH (40 mL) was added SOCl₂ (7.08 g, 60 mmol, 3 eq). The mixture was heated to reflux for 3 h and concentrated in vacuo to afford the crude product (6.5 g, yield 95%), which was used in the next step without further purification. ESI-MS: 188.1 (M+H)⁺.

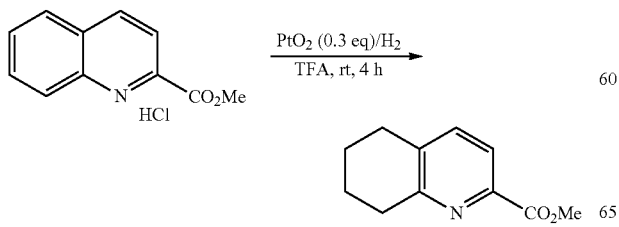

The Synthesis of methyl 5,6,7,8-tetrahydroquinoline-2-carboxylate

To a solution of methyl quinoline-2-carboxylate (446 mg, 2 mmol) in TFA (6 mL) was added PtO₂ (136 mg, 0.6 mmol, 0.3 eq) under N₂. The mixture was stirred at rt for 4 h under H₂ atmosphere, filtered through a pad of Celite, washed with methanol (5 mL×3), and the filtrate was concentrated in vacuo to afford the title compound (205 mg, yield 54%) as a pale-white solid. ESI-MS: 192.1 (M+H)⁺. ¹H NMR (400 MHz, CDCl₃) δ: 7.88 (d, J=8.0 Hz, 1H), 7.49 (d, J=7.6 Hz, 1H), 3.98 (s, 3H), 3.03 (t, J=6.4 Hz, 2H), 2.84 (t, J=6.4 Hz, 2H), 1.94-1.89 (m, 2H), 1.86-1.82 (m, 2H).

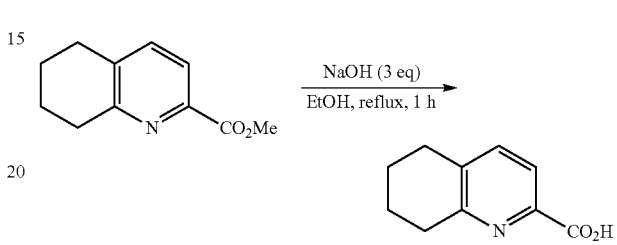

The Synthesis of 5,6,7,8-tetrahydroquinoline-2-carboxylic acid

To a solution of ester (205 mg, 1.07 mmol) in EtOH (5 mL) was added NaOH (1N, 3.22 mmol, 3.0 eq) The mixture was stirred at reflux for 1 h and cooled to rt, adjusted to pH=3 with HCl (1N). The resulting precipitate was filtered and washed with water (1 mL). to afford the acid (140 mg, yield 70%) as a white solid. ESI-MS: 178.1 (M+H)+. ¹H NMR (400 MHz, DMSO-d₆) δ: 7.73 (d, J=7.6 Hz, 1H), 7.49 (d, J=8.0 Hz, 1H), 2.86 (t, J=6.4 Hz, 2H), 2.75 (t, J=6.4 Hz, 2H), 1.83-1.72 (m, 4H).

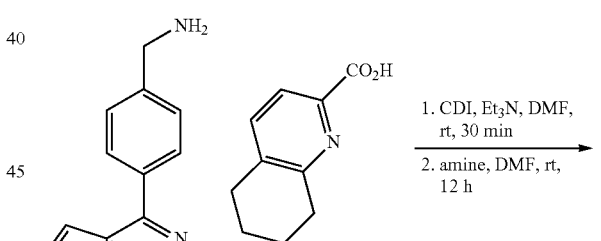

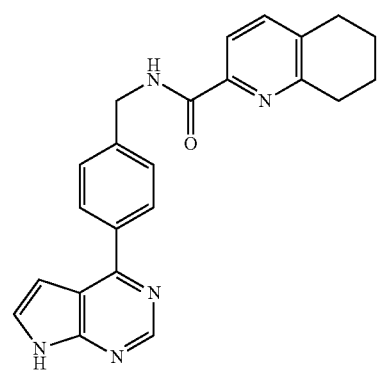

I-58

The Synthesis of N-(4-(7H-pyrrolo[2,3-d]pyrimidin-4-yl)benzyl)-5,6,7,8-tetrahydroquinoline-2-carboxamide (I-58)

Compound I-58 was prepared in a similar manner as described in Example I-56 except 5,6,7,8-tetrahydroquinoline-2-carboxylic acid was substituted for 4-(tert-butyl)benzoic acid. ESI-MS: 384.0 (M+H)+. HPLC: (214 nm: 100%, 254 nm: 100%). $^1$H NMR (400 MHz, CD$_3$OD) δ: 9.04 (s, 1H), 8.05 (d, J=8.4 Hz, 2H), 7.93 (d, J=3.6 Hz, 1H), 7.87 (d, J=8.0 Hz, 1H), 7.75 (d, J=8.0 Hz, 2H), 7.68 (d, J=8.0 Hz, 1H), 7.17 (d, J=4.0 Hz, 1H), 4.78 (s, 2H), 2.99 (t, J=6.0 Hz, 2H), 2.89 (t, J=6.0 Hz, 2H), 1.96-1.87 (m, 4H).

Example 9

Scheme 15

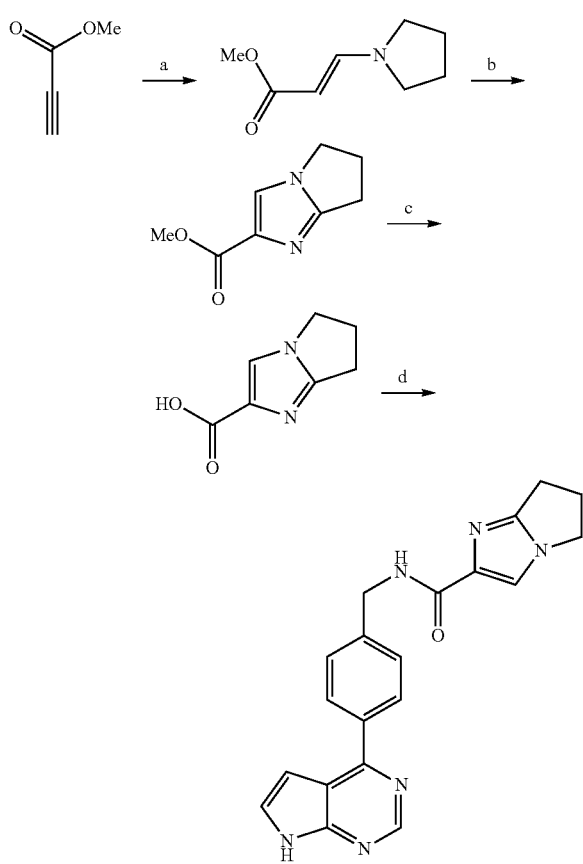

I-59
Reagent and conditions: a) Pyrrolidine, acetonitrile, rt, 1 h. b) PhN$_2$BF$_4$ acetonitrile, rt, 1 h, Et$_3$N. c) NaOH, EtOH/water, reflux 16 h. d) amine, CDI, Et$_3$N, DMF, rt.

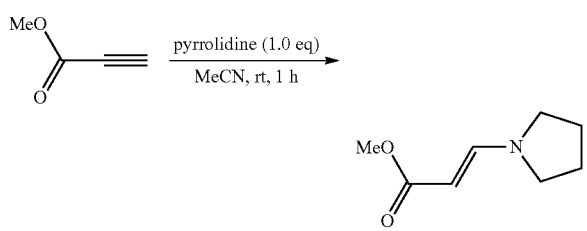

The Synthesis of (E)-methyl 3-(pyrrolidin-1-yl)acrylate

To a solution of methyl propiolate (4.2 g, 0.05 mol) in acetonitrile (100 mL) was added pyrrolidine (3.55 g, 0.05 mol) dropwise at rt. After stirring at rt for 1 h, the mixture was concentrated in vacuo to afford the ester (7.6 g, yield 98%) as yellow solid, which was used in the next step without further purification. ESI-MS (M+H$^+$): 156.1. $^1$H NMR (400 MHz, CDCl$_3$) δ: 7.66 (d, J=13.2 Hz, 1H), 4.48 (d, J=13.2 Hz, 1H), 3.66 (s, 3H), 3.48-3.12 (m, 4H), 2.01-1.93 (m, 4H).

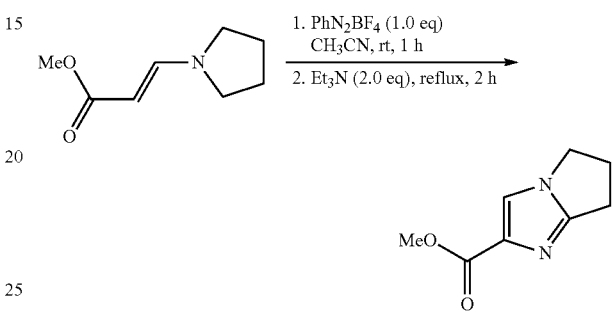

The Synthesis of methyl 6,7-dihydro-5H-pyrrolo[1,2-a]imidazole-2-carboxylate To a solution (E)-methyl 3-(pyrrolidin-1-yl)acrylate of (3.1 g, 0.02 mol) in dry MeCN (50 mL), benzenediazonium tetrafluoroborate (3.84 g, 0.02 mol) was added and the mixture was stirred for 1 h at rt. To the mixture was added Et$_3$N (4.04 g, 0.04 mol) and the solution was refluxed for 2 h. The solvent was concentrated and the resulting residue was purified on a silica gel column (petroleum ether and EtOAc, 1:1) to afford the ester (650 mg. yield 20%) as a yellow solid. ESI-MS (M+H$^+$): 167.1. $^1$H NMR (400 MHz, DMSO-d6) δ: 7.80 (s, 1H), 3.98 (t, J=7.2 Hz, 2H), 3.71 (s, 3H), 2.73 (t, J=7.6 Hz, 2H), 2.54-2.49 (m, 2H).

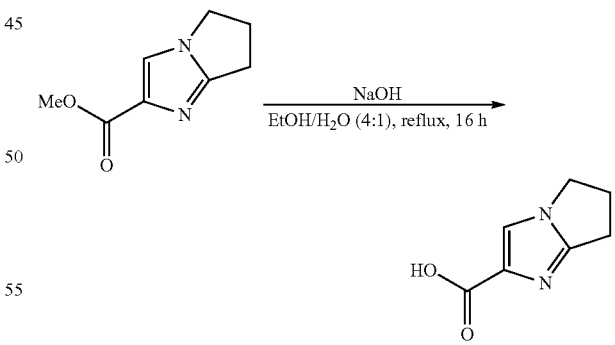

Synthesis of 6,7-dihydro-5H-pyrrolo[1,2-a]imidazole-2-carboxylic acid

To a solution of ester (205 mg, 1.07 mmol) in EtOH (5 mL) was added NaOH (1N, 3.22 mmol, 3.0 eq). The mixture was stirred at reflux for 1 h and cooled to rt, adjusted to pH=3 with HCl (1N). The resulting precipitate was filtered and washed with water (1 mL) to afford the crude acid (170 mg. yield 93%) as a yellow solid which was used in the next step without further purification. ESI-MS (M+H⁻): 153.1. ¹H NMR (400 MHz, DMSO-d6) δ: 7.69 (s, 1H), 3.97 (t, J=7.2 Hz, 2H), 2.73 (t, J=7.6 Hz, 2H), 2.54-2.49 (m, 2H).

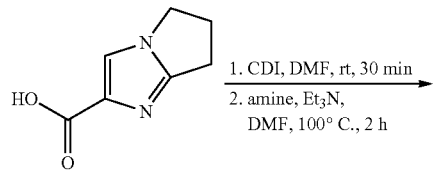

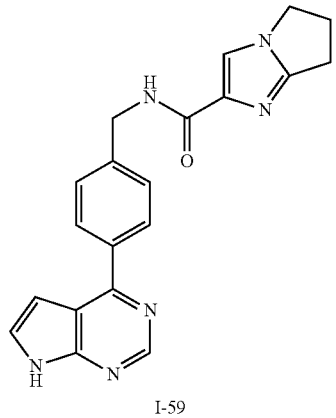

I-59

Synthesis of N-(4-(7H-pyrrolo[2,3-d]pyrimidin-4-yl)benzyl)-6,7-dihydro-5H-pyrrolo[1,2-a]imidazole-2-carboxamide (I-59)

Compound I-59 was prepared in a similar manner as described in Example I-5 6 except 6,7-dihydro-5H-pyrrolo[1,2-a]imidazole-2-carboxylic acid was substituted for 4-(tert-butyl)benzoic acid. ESI-MS (M+H)⁺: 359.2. HPLC: (214 nm: 97.4%, 254 nm: 99.3%). ¹H NMR (400 MHz, CD₃OD) δ: 8.78 (s, 1H), 8.07 (d, J=8.0 Hz, 2H), 7.64 (s, 1H), 7.59 (d, J=7.6 Hz, 2H), 7.54 (d, J=3.2 Hz, 1H), 6.87 (d, J=3.6 Hz, 1H), 4.68 (s, 2H), 4.09 (t, J=7.2 Hz, 2H), 2.86 (t, J=7.6 Hz, 2H), 2.68-2.60 (m, 2H).

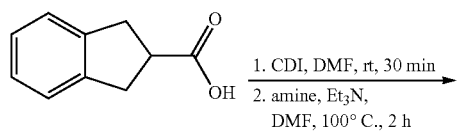

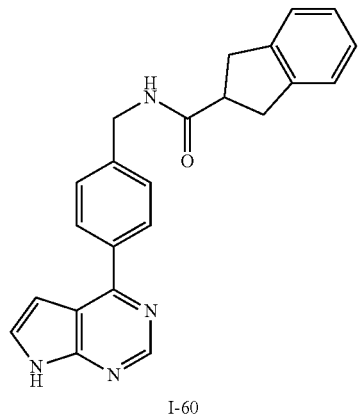

I-60

The Synthesis of N-(4-(7H-pyrrolo[2,3-d]pyrimidin-4-yl)benzyl)-2,3-dihydro-1H-indene-2-carboxamide (I-60)

Compound I-60 was prepared in a similar manner as described in Example I-56 except 6,7-dihydro-5H-pyrrolo[1,2-a]imidazole-2-carboxylic acid was substituted for 4-(tert-butyl)benzoic acid. ESI-MS: 369.0 (M+H)+. HPLC: (214 nm: 100%, 254 nm: 100%). ¹H NMR (400 MHz, DMSO-d₆) δ: 12.26 (br, 1H), 8.82 (s, 1H), 8.61 (t, J=6.0 Hz, 1H), 8.16 (d, J=8.4 Hz, 2H), 7.66-7.65 (m, 1H), 7.48 (d, J=8.0 Hz, 2H), 7.22-7.19 (m, 2H), 7.15-7.12 (m, 2H), 6.91-6.90 (m, 1H), 4.42 (d, J=6.0 Hz, 2H), 3.29-3.25 (m, 1H), 3.13-3.11 (m, 4H).

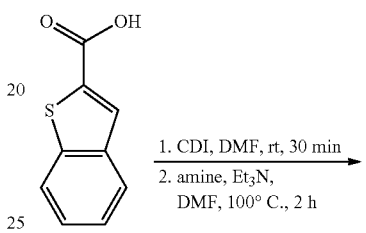

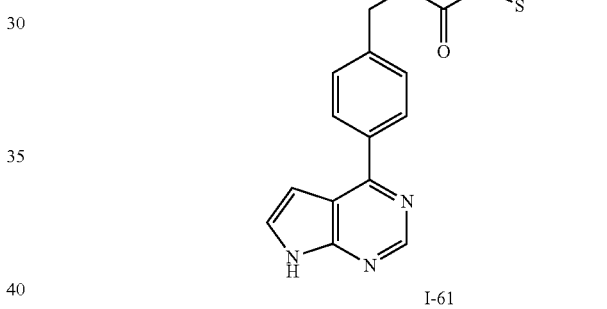

I-61

The Synthesis of N-(4-(7H-pyrrolo[2,3-d]pyrimidin-4-yl)benzyl)benzo[b]thiophene-2-carboxamide (I-61)

Compound I-61 was prepared in a similar manner as described in Example I-56 except benzo[b]thiophene-2-carboxylic acid was substituted for 4-(tert-butyl)benzoic acid. ESI-MS: 384.0 (M+H)+. ¹H NMR (400 MHz, DMSO-d₆) δ: 12.27 (br, 1H), 9.45 (t, J=5.6 Hz, 1H), 8.83 (s, 1H), 8.19-8.17 (m, 3H), 8.04 (d, J=7.6 Hz, 1H), 7.96 (d, J=6.8 Hz, 1H), 7.65 (d, J=3.2 Hz, 1H), 7.56 (d, J=8.0 Hz, 2H), 7.49-7.43 (m, 2H), 6.89 (d, J=3.2 Hz, 1H), 4.61 (d, J=5.6 Hz, 2H).

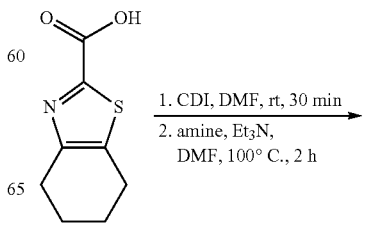

165

-continued

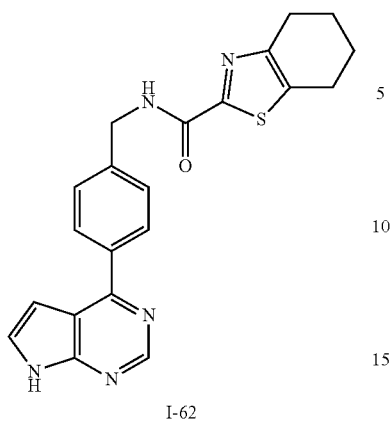

I-62

The Synthesis of N-(4-(7H-pyrrolo[2,3-d]pyrimidin-4-yl)benzyl)-4,5,6,7-tetrahydrobenzo[d]thiazole-2-carboxamide (I-62)

Compound I-62 was prepared in a similar manner as described in Example I-56 except 4,5,6,7-tetrahydrobenzo[d]thiazole-2-carboxylic acid was substituted for 4-(tert-butyl)benzoic acid. ESI-MS: 389.0 (M+H)+. HPLC: (214 nm: 100%, 254 nm: 100%). $^1$H NMR (400 MHz, CDCl$_3$) δ: 9.26 (br, 1H), 8.98 (s, 1H), 8.12 (d, J=8.0 Hz, 2H), 7.61-7.58 (m, 1H), 7.55 (d, J=8.0 Hz, 2H), 7.41-7.39 (m, 1H), 6.87-6.85 (m, 1H), 4.73 (d, J=6.4 Hz, 2H), 2.86 (t, J=4.0 Hz, 2H), 2.78 (d, J=4.0 Hz, 2H), 1.89-1.87 (m, 4H).

Example 10

Scheme 16

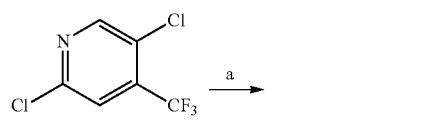

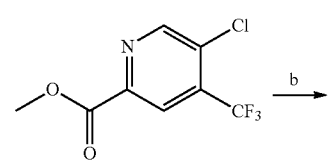

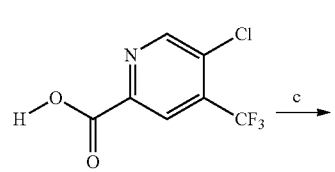

166

-continued

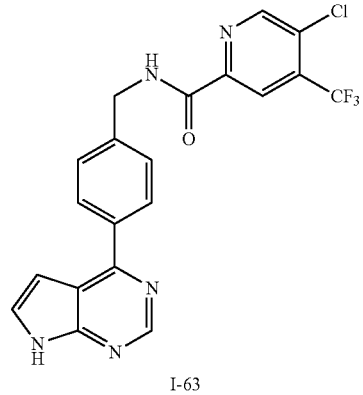

I-63

Reagent and conditions:
a) BINAP, Pd(dppf)Cl$_2$, DIEA, CO, EtOH 60° C., 20 atm 16 h.
b) LiOH, THF/MeOH/water, rt, 2 h.
c) Amine, CDI, Et$_3$N, DMF, rt.

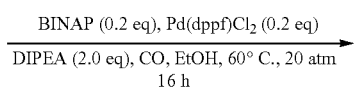

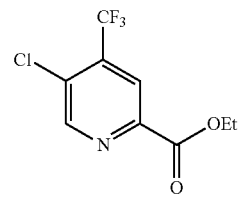

The Synthesis of ethyl 5-chloro-4-(trifluoromethyl)picolinate

To a solution of 2,5-dichloro-4-(trifluoromethyl)pyridine (150 mg, 0.69 mmol, 1.0 eq) in EtOH (40 mL), BINAP (87 mg, 0.14 mmol, 0.2 eq), Pd(dppf)Cl$_2$ (102 mg, 0.14 mmol, 0.2 eq) and DIPEA (178 mg, 1.38 mmol, 2.0 eq) were added and the mixture was stirred at 60° C. under CO atmosphere (20 atm) for 16 h. The solvent was removed and the residue was purified by column chromatography (silica, petroleum ether/EtOAc=10:1) to afford the desired ester (100 mg, yield: 57%) as a slight yellow solid. ESI-MS (M+H)$^+$: 254.01. $^1$H NMR (400 MHz, CDCl$_3$) δ:8.88 (s, 1H), 8.39 (s, 1H), 4.52 (q, J=7.2 Hz, 2H), 1.46 (t, J=7.2 Hz, 3H).

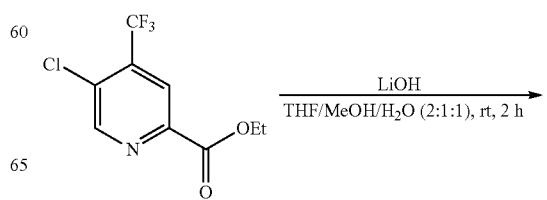

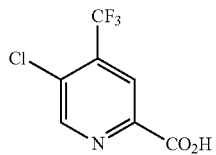

The Synthesis of 5-chloro-4-(trifluoromethyl)picolinic acid

To a solution of ester (96 mg, 0.38 mmol) in EtOH (3 mL) was added NaOH (1N, 1.1 mmol, 3.0 eq) The mixture was stirred at reflux for 1 h and cooled to rt, adjusted to pH=3 with HCl (1N). The resulting precipitate was filtered and washed with water (1 mL) to afford the crude acid (64 mg. yield 73%) as a white solid which was used in the next step without further purification. ESI-MS (M+H)$^+$: 225.98.

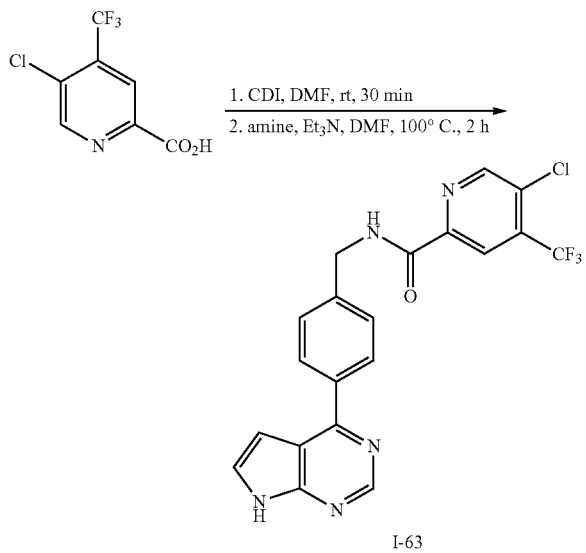

I-63

The Synthesis of N-(4-(7H-pyrrolo[2,3-d]pyrimidin-4-yl)benzyl)-5-chloro-4-(trifluoromethyl)picolinamide (I-63)

Compound I-63 was prepared in a similar manner as described Example I-56 except 4,5,6,7-tetrahydrobenzo[d]thiazole-2-carboxylic acid was substituted for 4-(tert-butyl)benzoic acid. ESI-MS (M+H)$^+$: 432.08. $^1$H NMR (400 MHz, CD$_3$OD) δ: 8.92 (s, 1H), 8.78 (s, 1H), 8.41 (s, 1H), 8.08 (d, J=8.4 Hz, 2H), 7.59 (d, J=8.4 Hz, 2H), 7.54 (d, J=3.6 Hz, 1H), 6.85 (d, J=3.6 Hz, 1H), 4.73 (s, 2H).

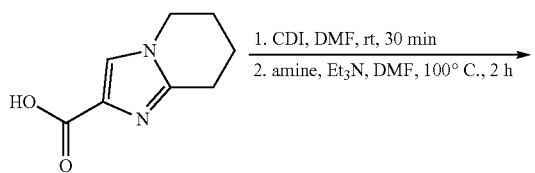

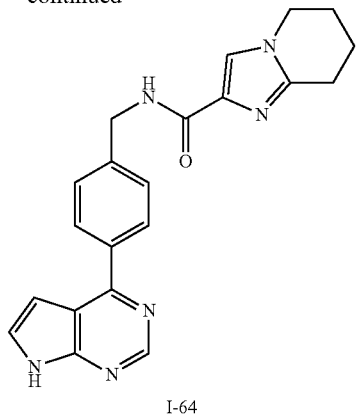

I-64

The Synthesis of N-(4-(7H-pyrrolo[2,3-d]pyrimidin-4-yl)benzyl)-5,6,7,8-tetrahydroimidazo[1,2-a]pyridine-2-carboxamide (I-64)

Compound I-64 was prepared in a similar manner as described in Example I-56 except 4,5,6,7-tetrahydrobenzo[d]thiazole-2-carboxylic acid was substituted for 4-(tert-butyl)benzoic acid. ESI-MS (M+H)$^+$: 372.2. $^1$H NMR (400 MHz, CD$_3$OD) δ: 8.78 (s, 1H), 8.06 (d, J=8.0 Hz, 2H), 7.59-7.54 (m, 4H), 6.87 (d, J=3.6 Hz, 1H), 4.67 (s, 2H), 4.07 (t, J=6.0 Hz, 2H), 2.84 (t, J=6.4 Hz, 2H), 2.03-1.95 (m, 4H).

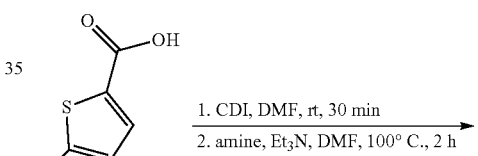

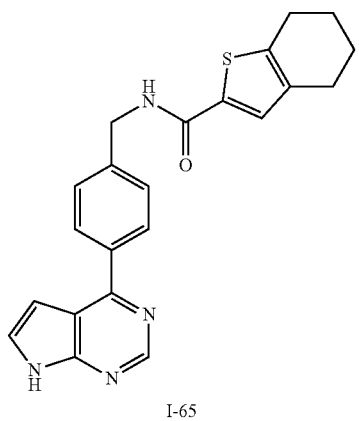

I-65

The Synthesis of N-(4-(7H-pyrrolo[2,3-d]pyrimidin-4-yl)benzyl)-4,5,6,7-tetrahydrobenzo[b]thiophene-2-carboxamide (I-65)

Compound I-65 was prepared in a similar manner as described in Example I-56 except 4,5,6,7-tetrahydrobenzo[b]thiophene-2-carboxylic acid was substituted for 4-(tert-butyl)benzoic acid. ESI-MS (M+H)$^+$: 389.14. $^1$H NMR (400

MHz, DMSO-d6) δ: 12.22 (s, 1H), 8.95 (t, J=6.0 Hz, 1H), 8.81 (s, 1H), 8.15 (d, J=8.4 Hz, 2H), 7.63 (s, 1H), 7.53-7.46 (m, 3H), 6.88 (d, J=3.6 Hz, 1H), 4.52 (d, J=6.0 Hz, 2H), 2.77-2.70 (m, 2H), 2.60-2.54 (m, 2H), 1.83-1.69 (m, 4H).

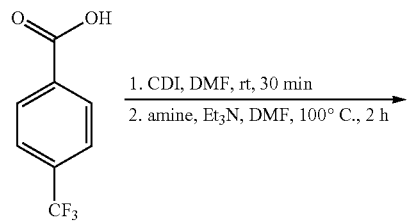

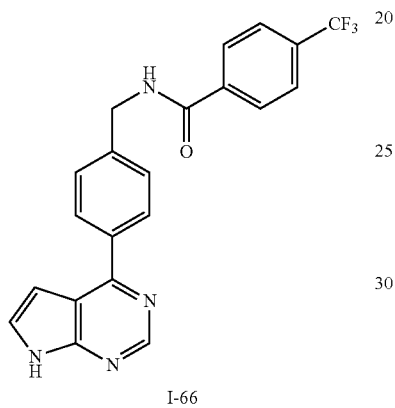

I-66

The Synthesis of N-(4-(7H-pyrrolo[2,3-d]pyrimidin-4-yl)benzyl)-4-(trifluoromethyl)benzamide (I-66)

Compound I-66 was prepared in a similar manner as described in Example I-56 except 4-(trifluoromethyl)benzoic acid was substituted for 4-(tert-butyl)benzoic acid. ESI-MS (M+H)⁺: 397.12. ¹H NMR (400 MHz, DMSO-d6) δ: 12.24 (s, 1H), 9.39 (t, J=6.0 Hz, 1H), 8.82 (s, 1H), 8.20-8.08 (m, 4H), 7.89 (d, J=8.0 Hz, 2H), 7.67-7.62 (m, 1H), 7.54 (d, J=8.4 Hz, 2H), 6.89 (d, J=3.6 Hz, 1H), 4.60 (d, J=4.2 Hz, 2H).

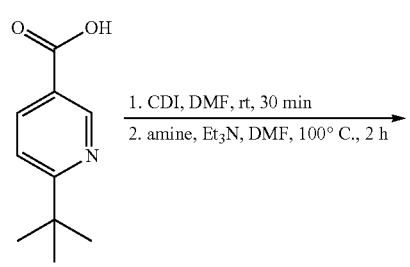

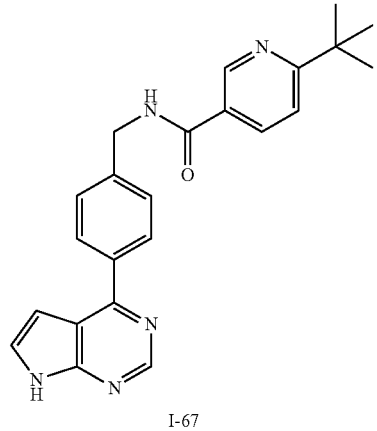

I-67

The Synthesis of N-(4-(7H-pyrrolo[2,3-d]pyrimidin-4-yl)benzyl)-6-(tert-butyl)nicotinamide (I-67)

Compound I-67 was prepared in a similar manner as described in Example I-56 except 6-(tert-butyl)nicotinic acid was substituted for 4-(tert-butyl)benzoic acid. ESI-MS (M+H)⁺: 386.19. ¹H NMR (400 MHz, DMSO-d6) δ: 9.26 (t, J=6.0 Hz, 1H), 9.03 (t, J=2.0 Hz, 1H), 8.83 (s, 1H), 8.21 (dd, J=8.4, 2.4 Hz, 1H), 8.17 (d, J=8.4 Hz, 2H), 7.65-7.64 (d, J=3.6 Hz, 1H), 7.60-7.50 (m, 3H), 6.89 (d, J=4.0 Hz, 1H), 4.62 (d, J=6.0 Hz, 2H), 1.34 (s, 9H).

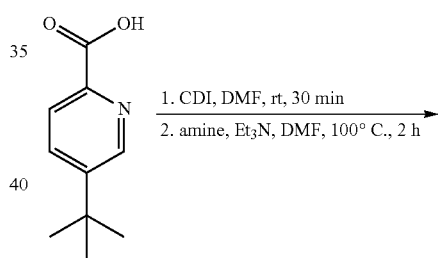

I-68

The Synthesis of N-(4-(7H-pyrrolo[2,3-d]pyrimidin-4-yl)benzyl)-5-(tert-butyl)picolinamide (I-68)

Compound I-68 was prepared in a similar manner as described in Example I-56 except 5-(tert-butyl)picolinic acid was substituted for 4-(tert-butyl)benzoic acid. ESI-MS (M+H)+: 386.19. 1H NMR (400 MHz, DMSO-d6) δ: 12.24 (s, 1H), 9.38 (t, J=6.4 Hz, 1H), 8.82 (s, 1H), 8.71 (d, J=1.2 Hz, 1H), 8.14 (d, J=8.4 Hz, 2H), 8.01 (s, 2H), 7.64 (dd, J=6.4, 2.4 Hz, 1H), 7.52 (d, J=8.0 Hz, 2H), 6.89 (d, J=2.0 Hz, 1H), 4.62 (d, J=6.4 Hz, 2H), 1.35 (s, 9H).

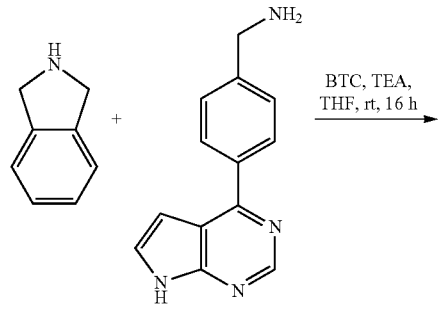

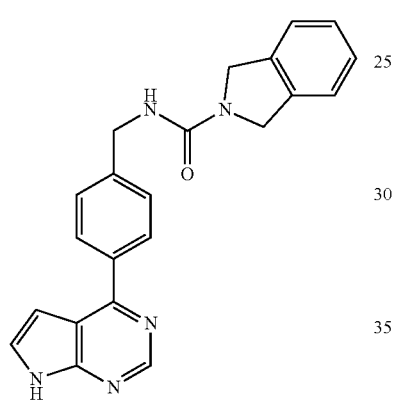

I-69

The Synthesis of N-(4-(7H-pyrrolo[2,3-d]pyrimidin-4-yl)benzyl)isoindoline-2-carboxamide (I-69)

To a solution of amine (50 mg, 0.22 mmol) in anhydrous THF (3 mL) at 0° C. under nitrogen was added bis(trichloromethyl)carbonate BTC (39 mg, 0.13 mmol) and Et₃N (50 mg, 0.5 mmol). After stirring for 1 h, isoindoline (31 mg, 0.26 mmol) was added and the resulting solution was allowed to warm up to rt and stirred for 2 h. The solution was diluted with water (3 mL), the mixture was extracted with EtOAc (5 mL×2). The combined organic layers were dried over Na₂SO₄ and concentrated in vacuo to afford a residue which was purified by prep-HPLC to afford the desired product I-69 (8 mg, yield 9%). ESI-MS (M+H)+: 370.0. 1H NMR (400 MHz, DMSO-d6) δ: 12.26 (s, 1H), 8.26 (s, 1H), 8.14 (d, J=8.0 Hz, 2H), 7.65 (d, J=2.4 Hz, 1H), 7.53 (d, J=8.0 Hz, 2H), 7.36-7.28 (m, 4H), 7.11 (t, J=6.0 Hz, 1H), 6.89 (d, J=3.6 Hz, 1H), 4.76 (s, 4H), 4.42 (d, J=6.0 Hz, 2H).

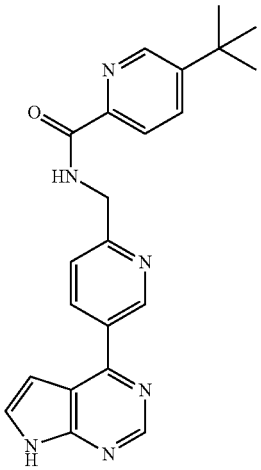

I-70

The Synthesis of N-((5-(7H-pyrrolo[2,3-d]pyrimidin-4-yl)pyridin-2-yl)methyl)-4-(tert-butyl)benzamide (I-70)

Compound I-70 was prepared in a similar manner as described in Example I-56 except (5-bromopyridin-2-yl)methanamine was substituted for (4-bromophenyl)methanamine to afford the title compound (20 mg, yield: 20%). ESI-MS (M+H)+: 387.1. 1H NMR (400 MHz, CD₃OD) δ: 9.13 (s, 1H), 8.82 (s, 1H), 8.65 (s, 1H), 8.45 (dd, J=6.4, 2.0 Hz, 1H), 7.96-7.93 (m, 2H), 7.64-7.61 (m, 2H), 6.87 (d, J=4.0 Hz, 1H), 4.80 (s, 2H), 1.30 (s, 9H).

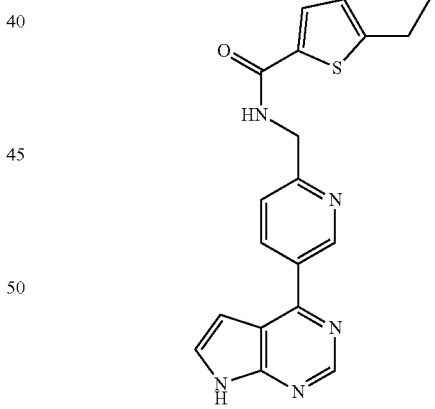

I-71

The Synthesis of N-((5-(7H-pyrrolo[2,3-d]pyrimidin-4-yl)pyridin-2-yl)methyl)-4,5,6,7-tetrahydrobenzo[b]thiophene-2-carboxamide (I-71)

Compound I-71 was prepared in a similar manner as described for compound I-70 except 4,5,6,7-tetrahydrobenzo[b]thiophene-2-carboxylic acid was substituted for 5-(tert-butyl)picolinic acid to afford (48 mg, yield: 56%). ESI-MS (M+H)+: 390.1. 1H NMR (400 MHz, CD₃OD) δ: 9.18 (d, J=1.6 Hz, 1H), 8.88 (s, 1H), 8.53 (dd, J=5.6, 1.6 Hz, 1H), 7.68-7.66 (m, 2H), 7.39 (s, 1H), 6.94 (d, J=4.0 Hz, 1H), 4.73 (s, 2H), 2.76 (t, J=5.6 Hz, 2H), 2.61 (t, J=5.6 Hz, 2H), 1.85-1.78 (m, 4H).

robenzo[b]thiophene-2-carboxylic acid was substituted for 5-(tert-butyl)picolinic acid to afford (38 mg, yield: 36%) as a solid. ESI-MS (M+H)+: 389.1. $^1$H NMR (400 MHz, DMSO-$d_6$) δ: 11.79 (s, 1H), 8.98 (t, J=5.6 Hz, 1H), 8.72 (d, J=2.0 Hz, 1H), 8.31 (d, J=4.8 Hz, 1H), 8.05 (d, J=8.0 Hz, 1H), 7.86 (dd, J=8.0, 2.4 Hz, 1H), 7.57-7.56 (m, 2H), 7.49 (s, 1H), 6.97-6.96 (m, 1H), 4.51 (d, J=6.0 Hz, 2H), 2.73 (t, J=5.6 Hz, 2H), 2.57 (t, J=5.6 Hz, 2H), 1.78-1.72 (m, 4H).

Example 11

I-72

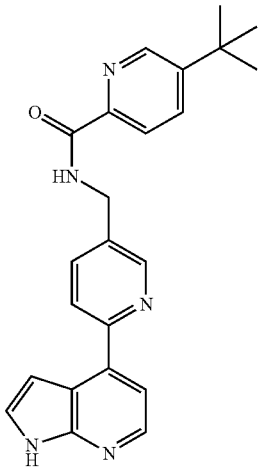

The Synthesis of N-((6-(1H-pyrrolo[2,3-b]pyridin-4-yl)pyridin-3-yl)methyl)-5-(tert-butyl)picolinamide (I-72)

Compound I-72 was prepared in a similar manner as described in Example I-1 except (6-bromopyridin-3-yl)methanamine and 4-chloro-1H-pyrrolo[2,3-b]pyridine were substituted for (4-bromo-2-methylphenyl)methanamine and 4-chloro-7H-pyrrolo[2,3-d]pyrimidine to afford the title compound (30 mg, yield: 25%) as a solid. ESI-MS (M+H)+: 386.19. $^1$H NMR (400 MHz, CD$_3$OD) δ: 8.77 (s, 1H), 8.74 (d, J=2.4 Hz, 1H), 8.30 (d, J=4.8 Hz, 1H), 8.07-8.00 (m, 4H), 7.52-7.49 (m, 2H), 6.89 (t, J=3.6 Hz, 1H), 4.75 (s, 2H), 1.41 (s, 9H).

I-73

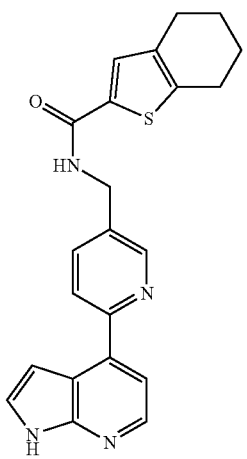

The Synthesis of N-((6-(1H-pyrrolo[2,3-b]pyridin-4-yl)pyridin-3-yl)methyl)-4,5,6,7-tetrahydrobenzo[b]thiophene-2-carboxamide (I-73)

Compound I-73 was prepared in a similar manner as described for compound I-72 except 4,5,6,7-tetrahyd- Scheme 17

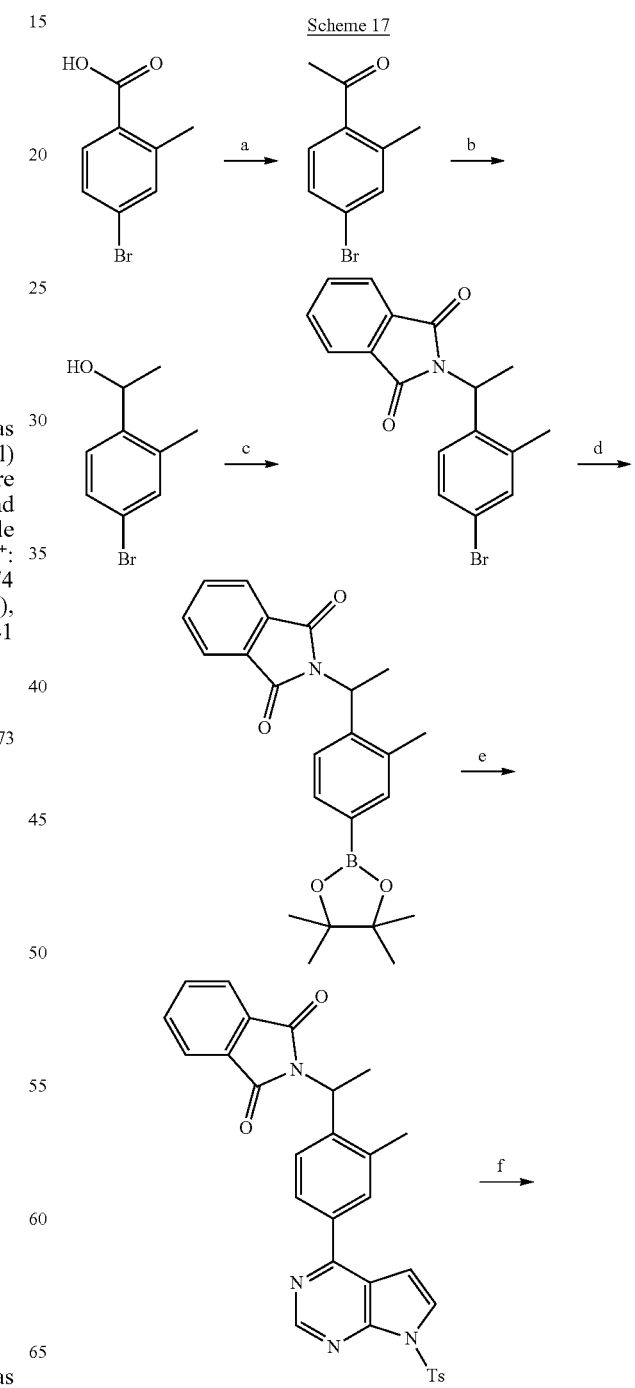

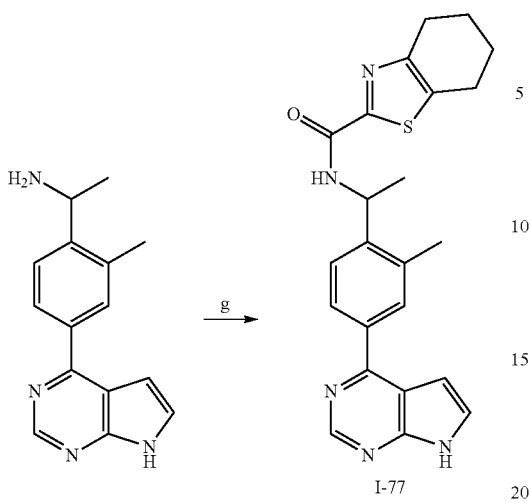

Reagents and conditions: (a) i. N,O-Dimethylhydroxylamine hydrochloride, HBTU, DIPEA, DMF, 16 h. ii. MeMgCl, THF, -78° C.~rt, 7 h. (b) NaBH₄, CH₃OH, 0° C.~rt, 1 h. (c) Isoindoline-1,3-dione, DIAD, PPh₃, THF, rt, 16 h.
(d) 4,4,4',4',5,5,5',5'-octamethyl-2,2'-bi(1,3,2-dioxaborolane), Pd(dppf)Cl₂ KOAc, DMF, 100° C., 1.5 h. (e) 4-chloro-7-tosyl-7H-pyrrolo[2,3-d]pyrimidine, Pd(dppf)Cl₂, K₂CO₃, Dioxane/H₂O (4:1), MW, 130° C., 2 h.
(f) i. NH₂NH₂•H₂O, EtOH, rt 1 h. ii. Cs₂CO₃, MeOH/water. (g) 4-tert-butyl benzoyl chloride, Et₃N, CH₂Cl₂, rt.

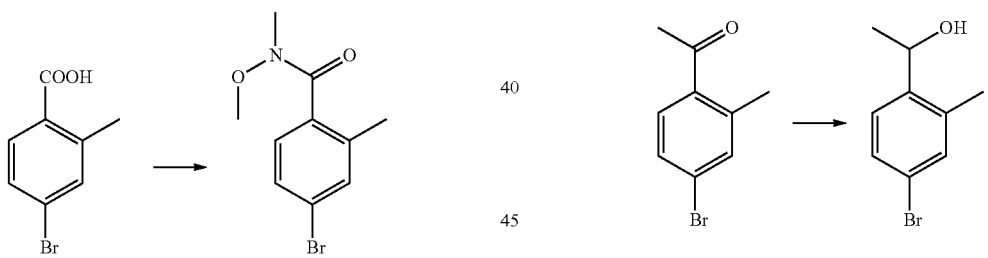

The Synthesis of 4-bromo-N-methoxy-N,2-dimethylbenzamide

To a solution of 4-bromo-2-methylbenzoic acid (5.3 g, 24.8 mmol) in DMF (50 mL) were added HBTU (11.3 g, 30.0 mmol), DIPEA (9.6 g, 74.4 mmol) and N, O-dimethylhydroxylamine hydrochloride (2.9 g, 30 mmol). The reaction mixture was stirred at rt for 16 h, diluted with water (50 mL), and extracted with EtOAc (100 mL×3). The organic layer was washed with brine (100 mL×3), dried (Na₂SO₄) and concentrated in vacuo to afford a residue which was purified by column chromatography (silica, petroleum ether/EtOAc=8:1 to 6:1) to give the title compound (5.1 g, yield 79%) as a colorless oil. ESI-MS (M+H)⁺: 258.0. ¹H NMR (400 MHz, CDCl₃) δ: 7.38 (s, 1H), 7.34 (d, J=8.0 Hz, 1H), 7.15 (d, J=8.0 Hz, 1H), 3.31 (s, 3H), 2.80 (s, 3H), 2.31 (s, 3H).

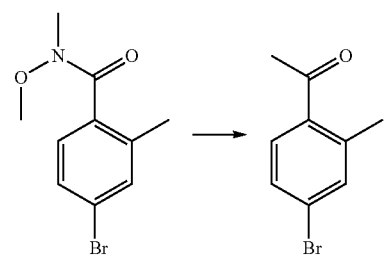

The Synthesis of 1-(4-bromo-2-methylphenyl)ethanone

To a solution of 4-bromo-N-methoxy-N,2-dimethylbenzamide (5.1 g, 20.0 mmol) in THF (80 mL) was added dropwise MeMgCl (20 mL, 60.0 mmol, 3 M in THF) -78° C. under nitrogen. The solution was allowed to stir at -78° C. for 1 h and then warmed to rt and stirred for 6 h. The mixture was quenched with water (100 mL) and extracted with EtOAc (100 mL×2). The combined organic layers was separated, dried (Na₂SO₄) and concentrated in vacuo to afford a residue which was purified by column chromatography (silica, petroleum ether/EtOAc=10:1) to give the title compound as slightly yellow oil (2.4 g, yield: 57%). ESI-MS (M+H)⁺: 312.9. ¹H NMR (400 MHz, CDCl₃) δ: 7.60 (d, J=8.4 Hz, 1H), 7.42-7.39 (m, 2H), 2.55 (s, 3H), 2.50 (s, 3H).

The Synthesis of 1-(4-bromo-2-methylphenyl)ethanol

To a solution of 1-(4-bromo-2-methylphenyl)ethanone (2.4 g, 11.3 mmol) in MeOH (20 mL) was added NaBH₄ (836 mg, 22.6 mmol) at 0° C. The reaction solution was stirred at rt for 1 h and the solvent was concentrated to afford a residue which then dissolved in water (80 mL), The aqueous phase was extracted with EtOAc (100 mL×2), combined and washed with brine (100 mL), dried (Na₂SO₄), filtered and concentrated in vacuo to afford the title compound (2.2 g, yield 90%), which was used directly in the next step without further purification. ESI-MS (M+H)⁺: 215.0.

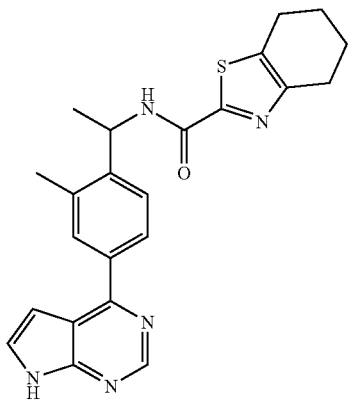

I-77

The Synthesis of N-(1-(2-methyl-4-(7H-pyrrolo[2,3-d]pyrimidin-4-yl)phenyl)ethyl)-4,5,6,7-tetrahydrobenzo[d]thiazole-2-carboxamide (I-77)

Compound I-77 was prepared in a similar manner as described in Example 1 for compound I-62 except 1-(4-bromo-2-methylphenyl)ethanamine were substituted for (4-bromophenyl)methanamine to afford the title compound (36 mg, yield 16%) as a solid. ESI-MS (M+H)$^+$: 418.2. $^1$H NMR (400 MHz, CD$_3$OD) δ: 8.78 (s, 1H), 7.93-7.90 (m, 2H), 7.66 (d, J=8.0 Hz, 1H), 7.53 (d, J=3.2 Hz, 1H), 6.87 (d, J=4.0 Hz, 1H), 5.48 (q, J=6.8 Hz, 1H), 2.89-2.83 (m, 4H), 2.58 (s, 3H), 1.93-1.91 (m, 4H), 1.62 (d, J=7.2 Hz, 3H).

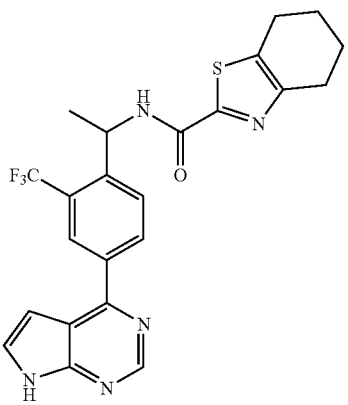

I-79

The Synthesis of N-(1-(4-(7H-pyrrolo[2,3-d]pyrimidin-4-yl)-2-(trifluoromethyl)phenyl)ethyl)-4,5,6,7-tetrahydrobenzo[d]thiazole-2-carboxamide (I-79)

Compound I-79 was prepared in a similar manner as described in Example I-77 except 4-Bromo-2-trifluoromethyl)benzoic acid was substituted for 4-bromo-2-methylbenzoic acid to afford the title compound (188 mg, yield 42%) as a solid. ESI-MS (M+H)$^+$: 472.0. $^1$H NMR (400 MHz, CD$_3$OD) δ: 8.88 (s, 1H), 8.41 (s, 1H), 8.34 (d, J=8.0 Hz, 1H), 8.04 (d, J=8.0 Hz, 1H), 7.67 (d, J=3.6 Hz, 1H), 6.92 (d, J=3.6 Hz, 1H), 5.61 (q, J=6.8 Hz, 1H), 2.92-2.80 (m, 4H), 1.94-1.88 (m, 4H), 1.65 (d, J=7.2 Hz, 3H).

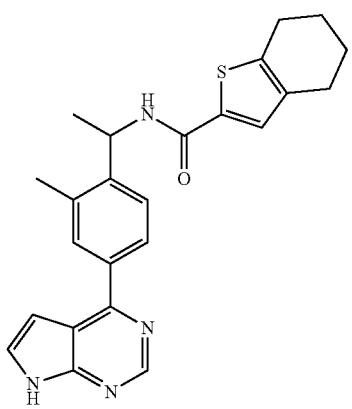

I-78

The Synthesis of N-(1-(2-methyl-4-(7H-pyrrolo[2,3-d]pyrimidin-4-yl)phenyl)ethyl)-4,5,6,7-tetrahydrobenzo[b]thiophene-2-carboxamide (I-78)

Compound I-78 was prepared in a similar manner as described in Example I-77 except 4,5,6,7-tetrahydrobenzo[b]thiophene-2-carboxylic acid was substituted for 4,5,6,7-tetrahydrobenzo[d]thiazole-2-carboxylic acid to afford the title compound (120 mg, yield 62%). ESI-MS (M+H)$^+$: 417.2. $^1$H NMR (400 MHz, DMSO-d6) δ: 12.21 (s, 1H), 8.80 (s, 1H), 8.75 (d, J=8.0 Hz, 1H), 7.98 (d, J=8.0 Hz, 1H), 7.95 (s, 1H), 7.63-7.61 (m, 2H), 7.59 (s, 1H), 6.89 (d, J=3.2 Hz, 1H), 5.31-5.27 (m, 1H), 2.70 (d, J=5.6 Hz, 2H), 2.59 (d, J=5.6 Hz, 2H), 2.48 (s, 3H), 1.77-1.72 (m, 4H), 1.47 (d, J=7.2 Hz, 3H).

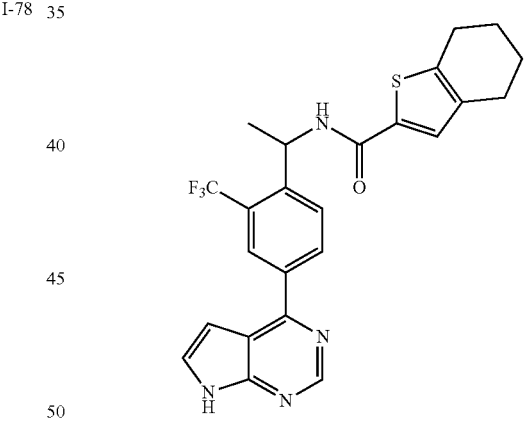

I-80

The Synthesis of N-(1-(4-(7H-pyrrolo[2,3-d]pyrimidin-4-yl)-2-(trifluoromethyl)phenyl)ethyl)-4,5,6,7-tetrahydrobenzo[b]thiophene-2-carboxamide (I-80)

Compound I-80 was prepared in a similar manner as described in Example I-79 except 4,5,6,7-tetrahydrobenzo[b]thiophene-2-carboxylic acid was substituted for 4,5,6,7-tetrahydrobenzo[d]thiazole-2-carboxylic acid to afford the title compound I-80 (63 mg, yield 33%) as yellow solid. ESI-MS (M+H)$^+$: 471.1. $^1$H NMR (400 MHz, CD$_3$OD) δ: 8.83 (s, 1H), 8.42 (s, 1H), 8.35 (d, J=8.0 Hz, 1H), 7.94 (d, J=8.4 Hz, 1H), 7.59 (d, J=4.0 Hz, 1H), 7.50 (s, 1H), 6.87 (d, J=3.6 Hz, 1H), 5.58 (q, J=6.8 Hz, 1H), 2.77 (t, J=5.2 Hz, 2H), 2.65 (t, J=5.2 Hz, 2H), 1.87-1.80 (m, 4H), 1.61 (d, J=6.8 Hz, 3H).

Example 12

Scheme 18

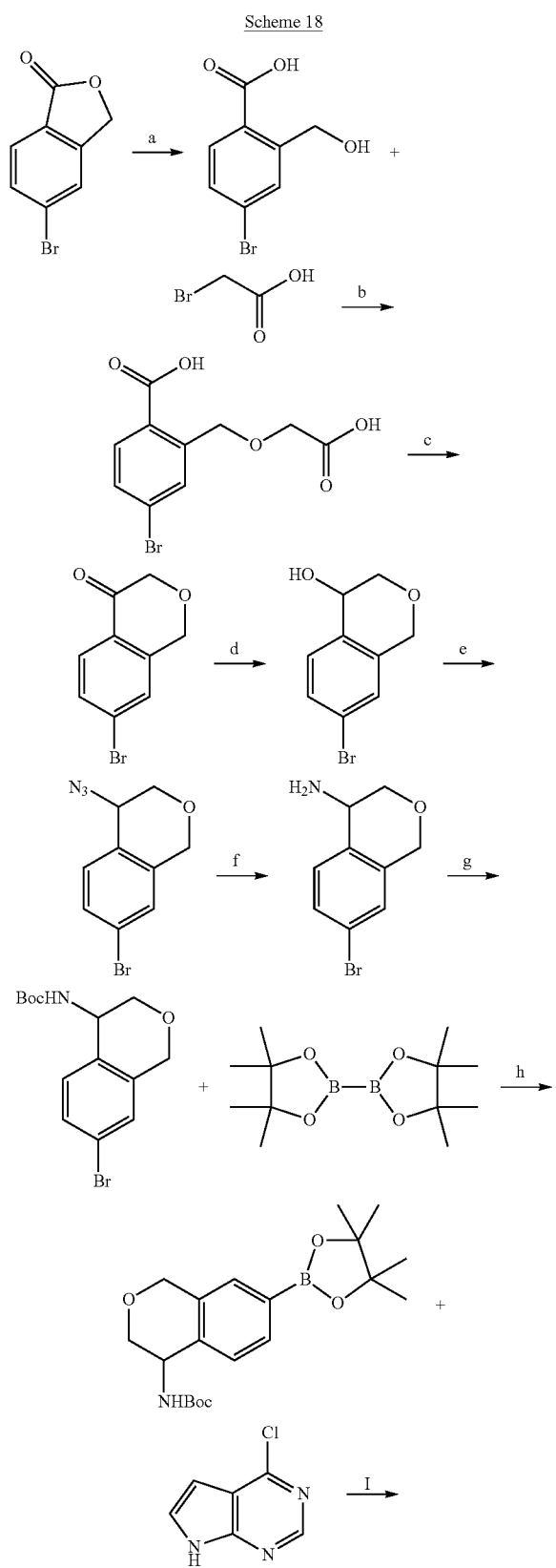

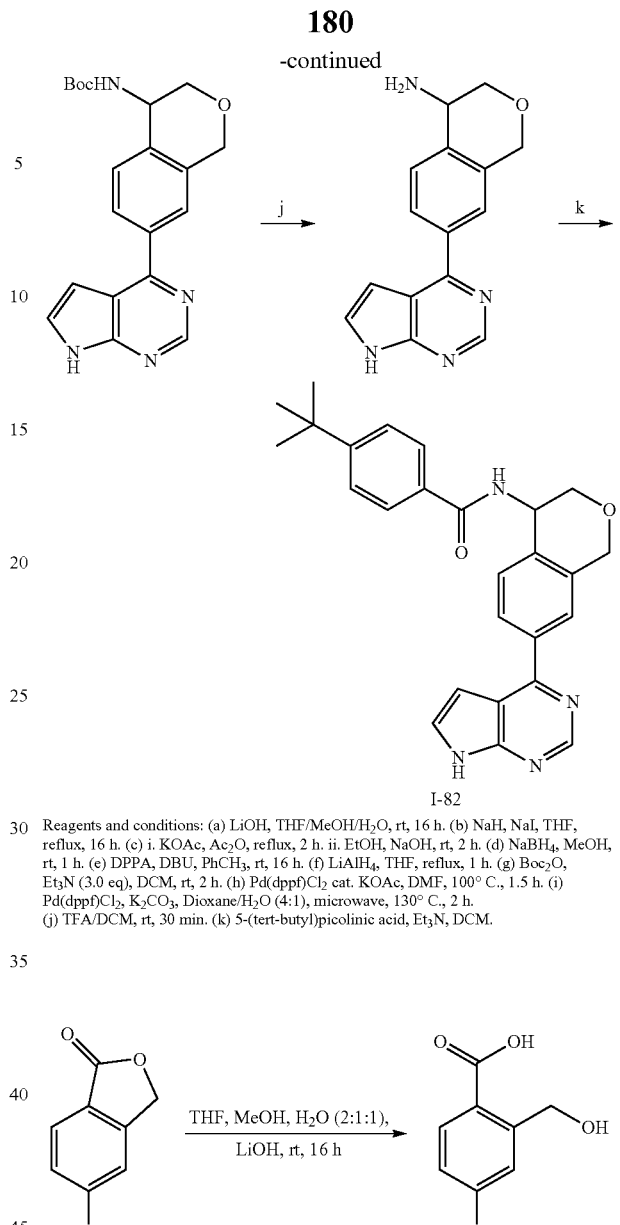

Reagents and conditions: (a) LiOH, THF/MeOH/H₂O, rt, 16 h. (b) NaH, NaI, THF, reflux, 16 h. (c) i. KOAc, Ac₂O, reflux, 2 h. ii. EtOH, NaOH, rt, 2 h. (d) NaBH₄, MeOH, rt, 1 h. (e) DPPA, DBU, PhCH₃, rt, 16 h. (f) LiAlH₄, THF, reflux, 1 h. (g) Boc₂O, Et₃N (3.0 eq), DCM, rt, 2 h. (h) Pd(dppf)Cl₂ cat. KOAc, DMF, 100° C., 1.5 h. (i) Pd(dppf)Cl₂, K₂CO₃, Dioxane/H₂O (4:1), microwave, 130° C., 2 h. (j) TFA/DCM, rt, 30 min. (k) 5-(tert-butyl)picolinic acid, Et₃N, DCM.

The Synthesis of 4-bromo-2-(hydroxymethyl)benzoic acid

Lithium hydroxide (3.45 g, 70.42 mmol, 3.0 eq) was added to a solution of 5-bromophthalide (5.0 g, 23.47 mmol, 1.0 eq) in THF/MeOH/H₂O (2:1:1, 80 mL) and stirred at rt for 16 h, then the solvent was concentrated to afford a residue which was diluted with water (100 mL), adjusted to pH=3 with HCl (2 N) and extracted with EtOAc (100 mL×3). The organic layers were collected, dried (Na₂SO₄), filtered, and concentrated in vacuo to give title product (3.47 g, yield: 94%) as a white solid, which was used in the next step without further purification. ESI-MS (M+H)⁺: 231.1 ¹H NMR (400 MHz, CD₃OD) δ: 7.88-7.86 (m, 2H), 7.45 (dd, J=8.4, 2.0 Hz, 1H), 4.90 (s, 2H)

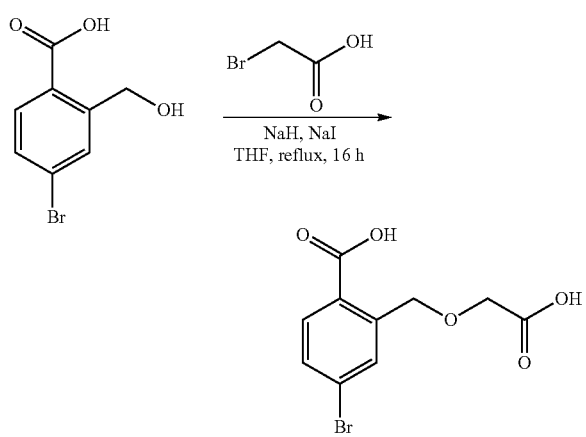

The Synthesis of 4-bromo-2-((carboxymethoxy)methyl)benzoic acid

Sodium hydride (3.46 g, 86.56 mmol, 4.0 eq) was added in small portions over the course of 0.5 h at rt to a mixture of 4-bromo-2-(hydroxymethyl)benzoic acid (5.0 g, 21.64 mmol, 1.0 eq) and bromoacetic acid (2.99 g, 21.64 mmol) in THF (60 mL), followed by the addition of sodium iodide (324.6 mg, 2.164 mmol, 0.1 mmol). The reaction mixture was heated at reflux for 16 h, cooled to rt, diluted with water (150 mL) and extracted with diethyl ether (100 mL×3). The aqueous phase was acidified with 10% hydrochloric acid to pH=3-4 and extracted with EtOAc (200 mL×3). The combined organic phases were washed with water (150 mL) and brine, dried (Na$_2$SO$_4$), filtered, and concentrated to give the title compound as a white solid (4.37 g, yield 70%), which was used for next step without further purification. $^1$H NMR (400 MHz, CD$_3$OD) δ: 7.93-7.87 (m, 2H), 7.55-7.52 (m, 1H), 4.98 (s, 2H), 4.23 (s, 2H).

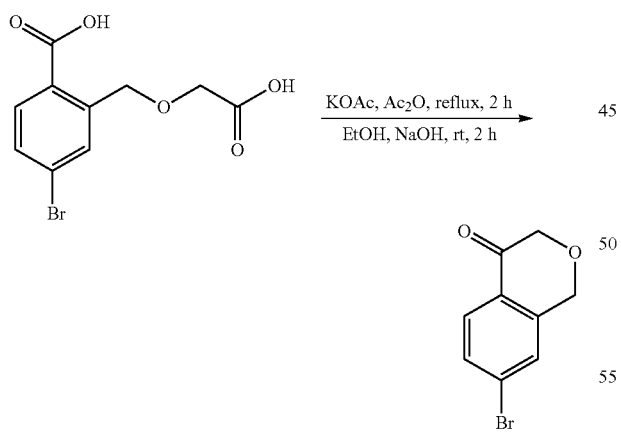

The Synthesis of 7-bromoisochroman-4-one

A solution of 4-bromo-2-((carboxymethoxy)methyl)benzoic acid (5.2 g, 18.06 mmol, 1.0 eq) in acetic anhydride (100 mL) containing KOAc (7.61 g, 77.64 mmol, 4.3 eq) was heated at reflux for 2 h. The reaction mixture was cooled to rt, concentrated under reduced pressure, and the residue partitioned between EtOAc (200 mL) and water (100 mL). Then the aqueous phase was separated and extracted with EtOAc (100 mL×3). The combined EtOAc phases were then washed with brine, dried (Na$_2$SO$_4$), filtered and concentrated in vacuo to afford a residue which was dissolved in EtOH (50 mL) and treated with NaOH (2.89 g, 72.24 mmol, 4.0 eq). The reaction mixture was stirred at rt for 2 h, concentrated and the residue was portioned between EtOAc (200 mL) and water (100 mL). The organic phase was separated, washed with saturated brine, dried (Na$_2$SO$_4$), filtered and concentrated in vacuo to give a residue which was purified by column chromatography (silica, petroleum ether/EtOAc=1:1) to afford the title compound (725 mg, yield: 18%) as a slight yellow solid. ESI-MS (M+H)$^+$: 227.0. $^1$H NMR (400 MHz, CDCl$_3$) δ: 7.90 (d, J=8.4 Hz, 1H), 7.56 (dd, J=8.4, 2.0 Hz, 1H), 7.42 (s, 1H), 4.86 (s, 2H), 4.36 (s, 2H).

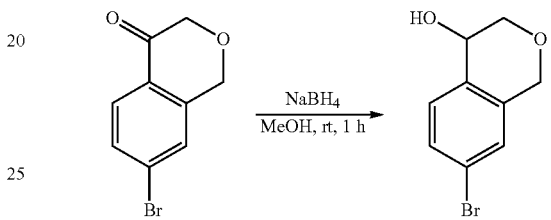

The Synthesis of 7-bromoisochroman-4-ol

To a solution of 7-bromoisochroman-4-one (1.5 g, 6.7 mmol) in MeOH (30 mL) was added NaBH$_4$ (540 mg, 14.22 mmol) and stirred at rt for 30 min. The solvent was removed in vacuo and the residue was purified by silica gel chromatography (EtOAc/hexane=1:2) to afford the alcohol (1.5 g, yield 100%) as a white solid ESI-MS (M+H)$^+$: 229.0 $^1$H NMR (400 MHz, CDCl$_3$) δ: 7.42-7.40 (m, 1H), 7.34-7.32 (m, 1H), 7.17 (s, 1H), 4.66 (ABq, J=20.4, 15.2 Hz, 2H), 4.51-4.50 (m, 1H), 4.12-4.10 (m, 1H), 3.84-3.80 (m, 1H).

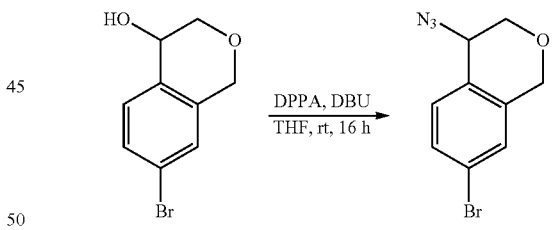

The Synthesis of 4-azido-7-bromoisochroman

To a cooled solution of alcohol (1.4 g, 6.7 mmol) in PhCH$_3$ (30 mL) was added DPPA (2.17 g, 7.88 mmol) and DBU (1.2 g, 7.88 mmol) dropwise while maintaining the temperature below 5° C. The reaction temperature was kept at 0° C. for 1 h and then was warmed to room temperature for 16 h, diluted with EtOAc (50 mL), washed with 2N HCl (2*30 mL), brine, and the organic layer was dried (Na$_2$SO$_4$), filtered and concentrated in vacuo to afford a residue which was purified by silica chromatography (silica, petroleum ether/EtOAc=50:1) to afford the azide (0.59 g, yield 39%) as a solid. ESI-MS (M+H−28)$^+$: 226.0. $^1$H NMR (400 MHz, CDCl$_3$) δ: 7.47-7.44 (m, 1H), 7.28-7.24 (m, 2H), 4.77 (q, J=20.4, 15.6 Hz, 2H), 4.22-4.16 (m, 2H), 3.96-3.92 (m, 1H).

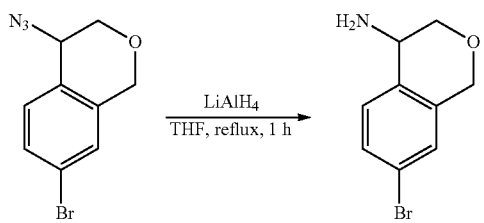 [SMILES: [N-]=[N+]=NC1COCc2cc(Br)ccc21 ; "LiAlH4" ; "THF, reflux, 1 h" ; NC1COCc2cc(Br)ccc21]

The Synthesis of 7-bromoisochroman-4-amine

To a solution of 4-azido-7-bromoisochroman (207 mg, 0.82 mmol, 1.0 eq) in THF (5 mL), 1N LiAlH₄ (0.82 mL, 0.82 mmol, 1.0 eq) was added at 0° C. Then the mixture was refluxed for 1 h. After cooling down to rt, Na₂SO₄ 0.10 H₂O was added and the mixture was stirred for another 0.5 h. The solid was filtered off and the filtrate was concentrated to give title product (153 mg, yield: 82%), which was used directly for next step without further purification. ESI-MS (M+H)⁺: 228.0.

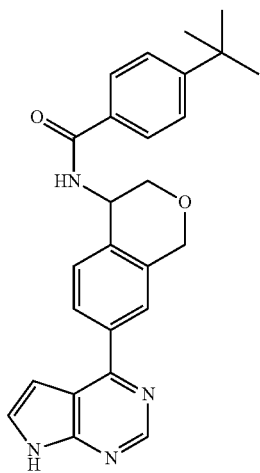

I-83

The Synthesis of N-(7-(7H-pyrrolo[2,3-d]pyrimidin-4-yl)isochroman-4-yl)-4-(tert-butyl)benzamide (I-83)

Compound I-83 was prepared in a similar manner as described in Example I-14 except 7-bromoisochroman-4-amine was substituted for 6-bromo-1,2,3,4-tetrahydronaphthalen-1-amine to afford the title compound I-83 (45 mg, yield: 45%) as a white solid. ESI-MS (M+H)⁺: 427.2. ¹H NMR (400 MHz, DMSO-d6) δ: 8.85-8.82 (m, 2H), 8.06 (dd, J=8.4, 1.6 Hz, 1H), 7.94 (s, 1H), 7.89 (d, J=8.4 Hz, 2H), 7.66 (d, J=3.6 Hz, 1H), 7.50-7.47 (m, 3H), 6.92 (d, J=4.0 Hz, 1H), 5.37-5.36 (m, 1H), 4.92 (s, 2H), 4.09-4.05 (m, 1H), 3.84-3.80 (m, 1H), 1.30 (s, 9H).

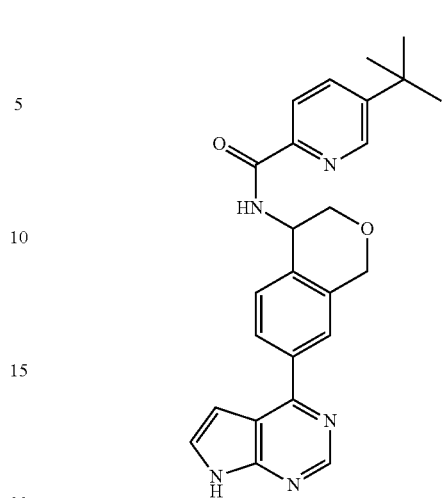

I-82

The Synthesis of N-(7-(7H-pyrrolo[2,3-d]pyrimidin-4-yl)isochroman-4-yl)-5-(tert-butyl)picolinamide (I-82)

Compound I-82 was prepared in a similar manner as described in Example I-15 except 6-(7H-pyrrolo[2,3-d]pyrimidin-4-yl)-1,2,3,4-tetrahydronaphthalen-1-amine was substituted with 7-(7H-pyrrolo[2,3-d]pyrimidin-4-yl)isochroman-4-amine to afford the title compound I-82 (42 mg, yield: 24%) as a white solid. ESI-MS (M+H)⁺: 428.2. ¹H NMR (400 MHz, DMSO-d6) δ: 12.26 (s, 1H), 8.83-8.80 (m, 2H), 8.68-8.67 (m, 1H), 8.07-8.02 (m, 3H), 7.94 (s, 1H), 7.66 (d, J=3.2 Hz, 1H), 7.49 (d, J=8.4 Hz, 1H), 6.93 (d, J=3.6 Hz, 1H), 5.33-5.29 (m, 1H), 4.93 (ABq, J=29.2, 11.6 Hz, 2H), 4.07-3.98 (m, 2H), 1.34 (s, 9H).

Example 13

Scheme 19

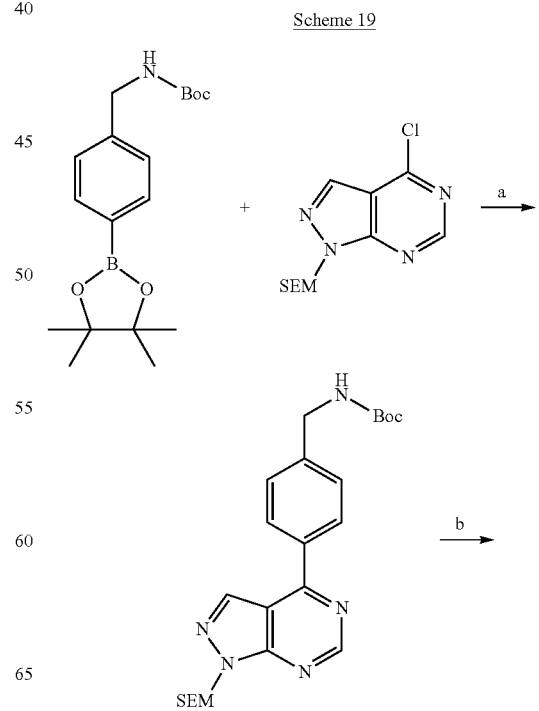

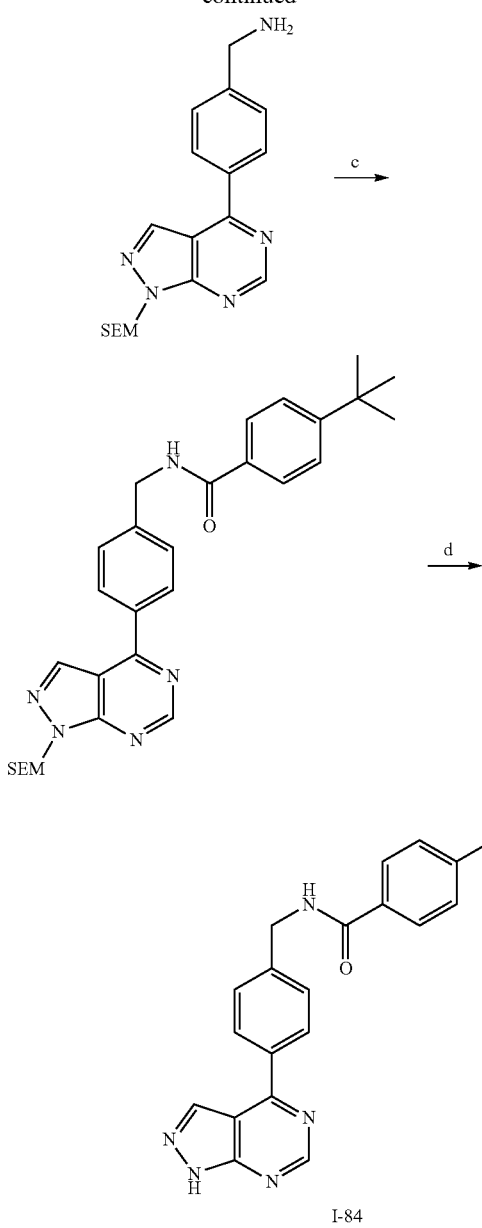

I-84

Reagent and conditions: a) 4-chloro-1-((2-(trimethylsilyl)ethoxy)methyl)-1H-pyrazolo[3,4-d]pyrimidine, PdCl₂(dppf), K₂CO₃, dioxane/water 90° C., 2 h. c) Cs₂CO₃, THF/MeOH rt, 2 h. TFA, DCM, rt, 30 min. e) 4-Tert-butyl)benzoic acid, CDI, Et₃N, DMF, rt, 12 h.

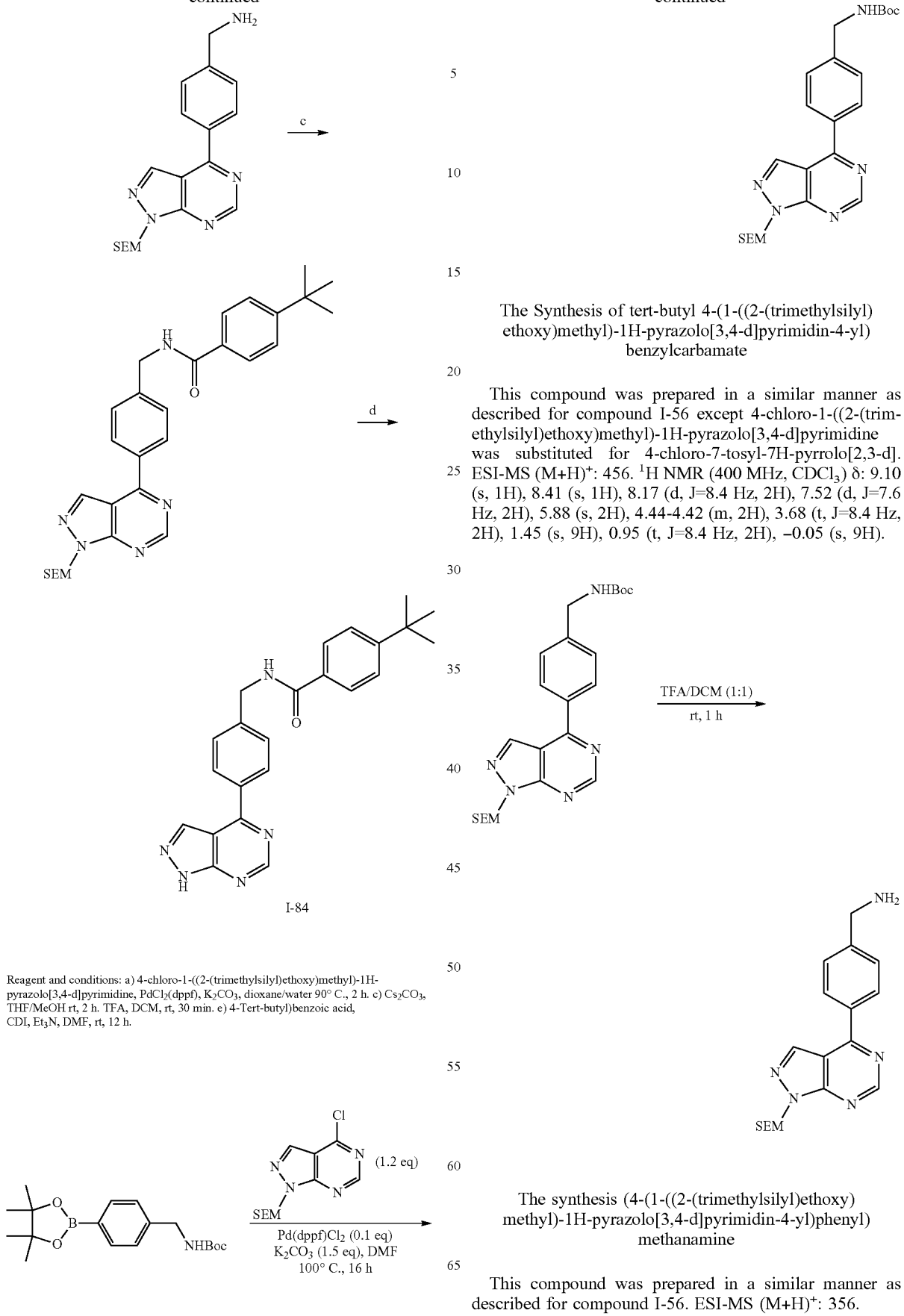

The Synthesis of tert-butyl 4-(1-((2-(trimethylsilyl)ethoxy)methyl)-1H-pyrazolo[3,4-d]pyrimidin-4-yl)benzylcarbamate This compound was prepared in a similar manner as described for compound I-56 except 4-chloro-1-((2-(trimethylsilyl)ethoxy)methyl)-1H-pyrazolo[3,4-d]pyrimidine was substituted for 4-chloro-7-tosyl-7H-pyrrolo[2,3-d]. ESI-MS (M+H)⁺: 456. ¹H NMR (400 MHz, CDCl₃) δ: 9.10 (s, 1H), 8.41 (s, 1H), 8.17 (d, J=8.4 Hz, 2H), 7.52 (d, J=7.6 Hz, 2H), 5.88 (s, 2H), 4.44-4.42 (m, 2H), 3.68 (t, J=8.4 Hz, 2H), 1.45 (s, 9H), 0.95 (t, J=8.4 Hz, 2H), −0.05 (s, 9H).

The synthesis (4-(1-((2-(trimethylsilyl)ethoxy)methyl)-1H-pyrazolo[3,4-d]pyrimidin-4-yl)phenyl)methanamine This compound was prepared in a similar manner as described for compound I-56. ESI-MS (M+H)⁺: 356.

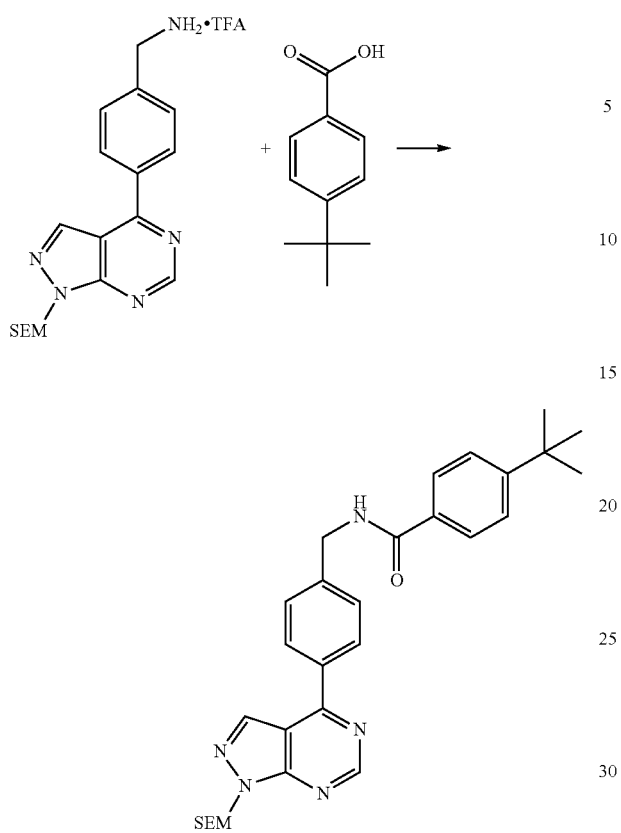

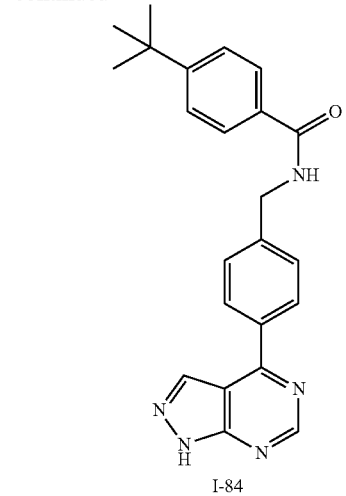

The Synthesis of 4-(tert-butyl)-N-(4-(1-((2-(trimethylsilyl)ethoxy)methyl)-1H-pyrazolo[3,4-d]pyrimidin-4-yl)benzyl)benzamide This compound was prepared in a similar manner as described for compound I-56 except (4-(1-((2-(trimethylsilyl)ethoxy)methyl)-1H-pyrazolo[3,4-d]pyrimidin-4-yl)phenyl)methanamine TFA salt was substituted for (4-(7-tosyl-7H-pyrrolo[2,3-d]pyrimidin-4-yl)phenyl)methanamine. ESI-MS (M+H)+: 386, 516.

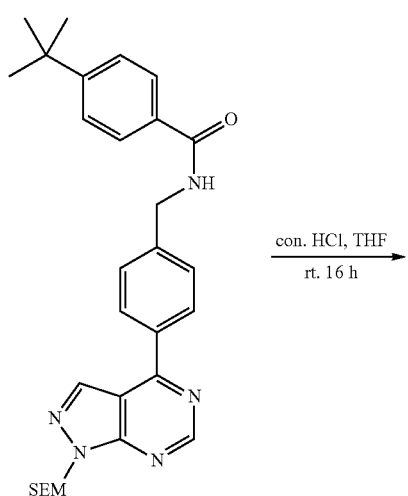

Synthesis of N-(4-(1H-pyrazolo[3,4-d]pyrimidin-4-yl)benzyl)-4-(tert-butyl)benzamide (I-84)

To a solution of 4-(tert-butyl)-N-(4-(1-((2-(trimethylsilyl)ethoxy)methyl)-1H-pyrazolo[3,4-d]pyrimidin-4-yl)benzyl)benzamide (80 mg, 1.0 eq) in THF (2 mL) was added con. HCl (2 mL) and stirred for 16 h at rt. The solution was concentrated in vacuo to afford a residue which was dissolved in EtOAc (10 mL) and washed with sat.NaHCO₃ (10 mL×2) and brine (10 mL). The organic layer was concentrated in vacuo to give a solid which was purified by prep-HPLC to afford the desired product I-84 (39 mg, yield: 66%) as a yellow solid. ESI-MS (M+H)+: 386. ¹H NMR (400 MHz, DMSO) δ: 14.18 (s, 1H), 9.11 (t, J=6.0 Hz, 1H), 9.02 (s, 1H), 8.71 (s, 1H), 8.30 (d, J=8.4 Hz, 2H), 7.87 (d, J=8.8 Hz, 2H), 7.56 (d, J=8.4 Hz, 2H), 7.51 (d, J=8.8 Hz, 2H), 4.60 (d, J=4.8 Hz, 2H), 1.31 (s, 9H).

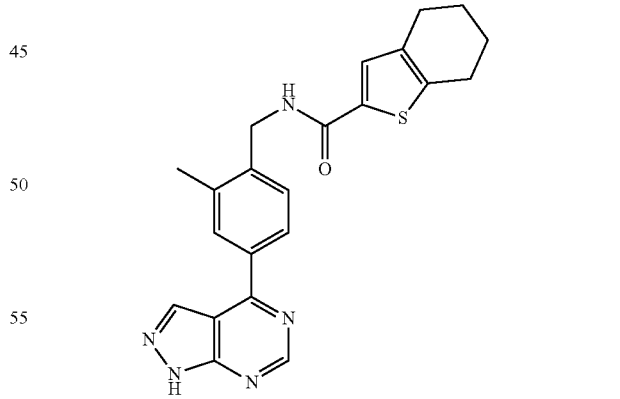

The Synthesis of N-(2-methyl-4-(1H-pyrazolo[3,4-d]pyrimidin-4-yl)benzyl)-4,5,6,7-tetrahydrobenzo[b]thiophene-2-carboxamide (I-85)

Compound I-85 was prepared in a similar manner as described in Example I-84 except (4-bromo-2-methylphenyl)methanamine and 4,5,6,7-tetrahydrobenzo[b]thiophene- 2-carboxylic acid was substituted for (4-bromophenyl)methanamine and 4-(tert-butyl)benzoic acid. ES (+) MS m/e=404.0 (M+1). ¹H NMR (400 MHz, DMSO-d6) δ: 14.17 (br. s., 1H), 9.01 (s, 1H), 8.88 (t, J=5.65 Hz, 1H), 8.72 (s, 1H), 8.06-8.20 (m, 2H), 7.55 (s, 1H), 7.46 (d, J=8.53 Hz, 1H), 4.51 (d, J=5.52 Hz, 2H), 2.74 (t, J=5.27 Hz, 2H), 2.58 (t, J=5.27 Hz, 2H), 2.47 (s, 3H), 1.63-1.90 (m, 4H).

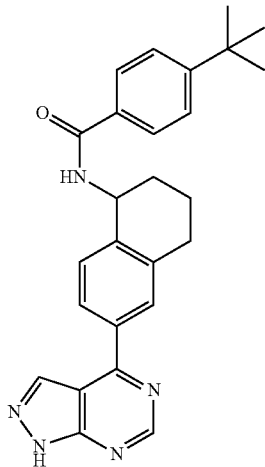

I-88

The Synthesis of N-(6-(1H-pyrazolo[3,4-d]pyrimidin-4-yl)-1,2,3,4-tetrahydronaphthalen-1-yl)-4-(tert-butyl)benzamide (I-88)

Compound I-88 was prepared in a similar manner as described in Example I-84 except 6-bromo-1,2,3,4-tetrahydronaphthalen-1-amine was substituted for (4-bromophenyl)methanamine to afford the title compound (26 mg, yield: 50%) as a yellow solid. ESI-MS (M+H)⁺: 425.2. ¹H NMR (400 MHz, DMSO-d6) δ: 14.18 (br, 1H), 9.01 (s, 1H), 8.81 (d, J=8.4 Hz, 1H), 8.71 (s, 1H), 8.11-8.08 (m, 2H), 7.89 (d, J=8.4 Hz, 2H), 7.49 (d, J=8.4 Hz, 2H), 7.42 (d, J=8.0 Hz, 1H), 5.36-5.32 (m, 1H), 2.96-2.94 (m, 2H), 2.06-1.99 (m, 2H), 1.63-1.88 (m, 2H), 1.30 (s, 9H).

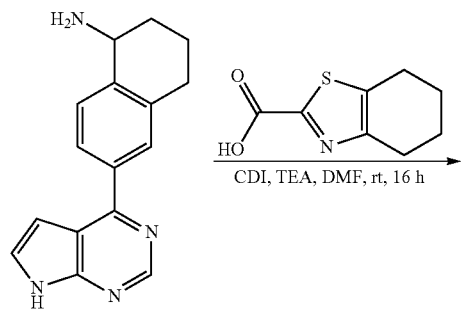

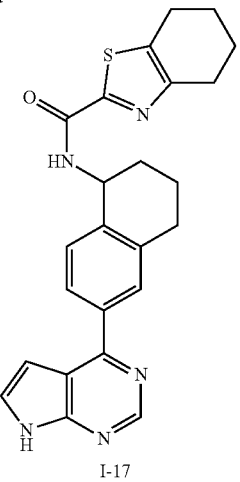

I-17

The Synthesis of N-(6-(7H-pyrrolo[2,3-d]pyrimidin-4-yl)-1,2,3,4-tetrahydronaphthalen-1-yl)-4,5,6,7-tetrahydrobenzo[d]thiazole-2-carboxamide (I-17)

Compound I-17 was prepared in a similar manner as described for compound I-88 except 4,5,6,7-tetrahydrobenzo[d]thiazole-2-carboxylic acid was substituted for 4-(tert-butyl)benzoic acid to afford the title compound (39 mg, yield: 30%). ESI-MS (M+H)⁺: 430.16. ¹H NMR (400 MHz, CD₃OD) δ: 8.76 (s, 1H), 7.85-7.83 (m, 2H), 7.52 (d, J=3.6 Hz, 1H), 7.46 (d, J=8.0 Hz, 1H), 6.84 (d, J=3.2 Hz, 1H), 5.36-5.34 (m, 1H), 3.03-2.96 (m, 2H), 2.88-2.85 (m, 2H), 2.77-2.74 (m, 2H), 2.16-2.05 (m, 1H), 2.02-1.88 (m, 7H).

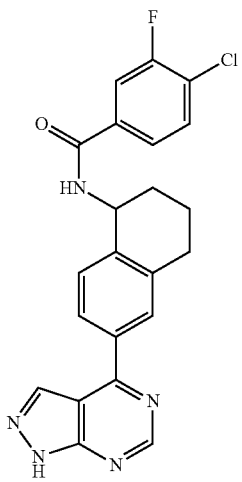

I-90

The Synthesis of N-(6-(1H-pyrazolo[3,4-d]pyrimidin-4-yl)-1,2,3,4-tetrahydronaphthalen-1-yl)-4-chloro-3-fluorobenzamide (I-90)

Compound I-90 was prepared in a similar manner as described for compound I-88 except 3-fluoro-4-chlorobenzoic acid was substituted for 4-(tert-butyl)benzoic acid to afford the title compound (34 mg, yield 25%) ¹H NMR (400

MHz, DMSO-d6) δ: 14.20 (s, 1H), 9.06 (d, J=8.0 Hz, 1H), 9.01 (s, 1H), 8.70 (s, 1H), 8.11-8.08 (m, 2H), 7.95 (d, J=8.4 Hz, 1H), 7.83 (d, J=8.0 Hz, 1H), 7.74-7.72 (m, 1H), 7.43 (d, J=8.0 Hz, 1H), 5.35-5.32 (m, 1H), 2.96-2.94 (m, 2H), 2.04-1.98 (m, 2H), 1.98-1.90 (m, 2H).

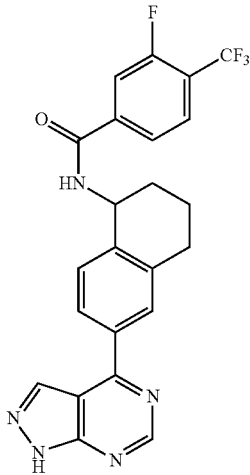

I-91

The Synthesis of N-(6-(1H-pyrazolo[3,4-d]pyrimidin-4-yl)-1,2,3,4-tetrahydronaphthalen-1-yl)-3-fluoro-4-(trifluoromethyl)benzamide (I-91)

Compound I-91 was prepared in a similar manner as described for compound I-88 except 3-fluoro-4-(trifluoromethyl)benzoic acid was substituted for 4-(tert-butyl)benzoic acid to afford the title compound (36 mg, yield: 18%) ESI-MS (M+H)⁺: 456.1. ¹H NMR (400 MHz, DMSO-d₆) δ: 14.20 (s, 1H), 9.22 (d, J=8.0 Hz, 1H), 9.02 (s, 1H), 8.71 (s, 1H), 8.12-8.09 (m, 2H), 8.02-7.93 (m, 3H), 7.45 (d, J=8.0 Hz, 1H), 5.37-5.32 (m, 1H), 2.98-2.96 (m, 2H), 2.07-2.00 (m, 2H), 1.94-1.87 (m, 2H).

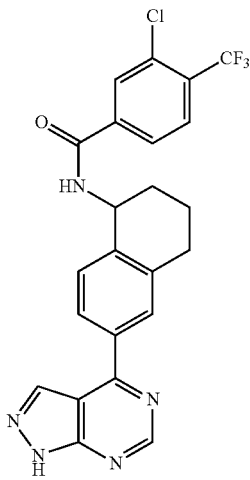

I-92

The Synthesis of N-(6-(1H-pyrazolo[3,4-d]pyrimidin-4-yl)-1,2,3,4-tetrahydronaphthalen-1-yl)-3-chloro-4-(trifluoromethyl)benzamide (I-92)

Compound I-92 was prepared in a similar manner as described for compound I-88 except 3-chloro-4-(trifluoromethyl)benzoic acid was substituted for 4-(tert-butyl)benzoic acid to afford the title compound (20 mg, yield: 35%) ESI-MS (M+H)⁺: 472.1. ¹H NMR (400 MHz, DMSO-d6) δ: 14.15 (br, 1H), 9.25 (d, J=8.4 Hz, 1H), 9.00 (s, 1H), 8.70 (s, 1H), 8.24 (s, 1H), 8.12-8.08 (m, 3H), 8.02-8.00 (m, 1H), 7.45 (d, J=8.0 Hz, 1H), 5.35-5.33 (m, 1H), 2.97-2.95 (m, 2H), 2.08-1.84 (m, 4H).

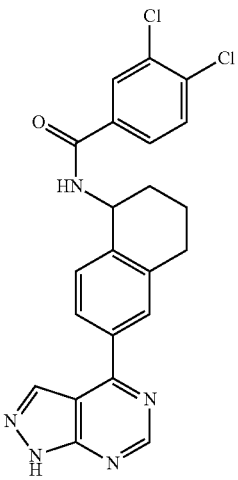

I-93

The Synthesis of N-(6-(1H-pyrazolo[3,4-d]pyrimidin-4-yl)-1,2,3,4-tetrahydronaphthalen-1-yl)-3,4-dichlorobenzamide (I-93)

Compound I-93 was prepared in a similar manner as described for compound I-88 except 3,4-di-chlorobenzoic acid was substituted for 4-(tert-butyl)benzoic acid to afford the title compound (11 mg, yield 18%). ESI-MS (M+H)⁺: 438.1. ¹H NMR (400 MHz, DMSO-d6) δ: 14.15 (s, 1H), 9.07 (d, J=8.4 Hz, 1H), 8.99 (s, 1H), 8.84 (s, 1H), 8.25 (d, J=1.6 Hz, 1H), 8.09-8.07 (m, 2H), 7.94 (dd, J=8.4, 2.0 Hz, 1H), 7.72 (d, J=8.4 Hz, 1H), 7.44 (d, J=8.0 Hz, 1H), 5.36-5.32 (m, 1H), 2.97-2.95 (m, 2H), 2.06-2.03 (m, 2H), 1.92-1.84 (m, 2H).

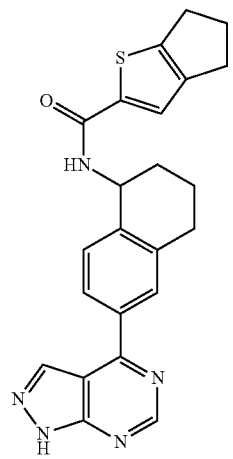

I-94

The Synthesis of N-(6-(1H-pyrazolo[3,4-d]pyrimidin-4-yl)-1,2,3,4-tetrahydronaphthalen-1-yl)-5,6-dihydro-4H-cyclopenta[b]thiophene-2-carboxamide (I-94)

Compound I-94 was prepared in a similar manner as described for compound I-88 except 5,6-dihydro-4H-cyclopenta[b]thiophene-2-carboxylic acid was substituted for 4-(tert-butyl)benzoic acid to afford the title compound (15 mg, yield: 10%) as a yellow solid. ESI-MS (M+H)$^+$: 417.2. $^1$H NMR (400 MHz, DMSO-d6) δ: 14.34 (s, 1H), 9.09 (d, J=7.2 Hz, 1H), 9.01 (s, 1H), 8.70 (s, 1H), 8.08 (d, J=6.8 Hz, 1H), 8.05 (s, 1H), 7.40 (d, J=6.4 Hz, 1H), 5.27-5.26 (m, 1H), 2.98-2.83 (m, 4H), 2.80-2.74 (m, 2H), 2.52-2.48 (m, 2H), 2.04-1.98 (m, 3H), 1.98-1.94 (m, 1H).

The Synthesis of N-(6-(1H-pyrazolo[3,4-d]pyrimidin-4-yl)-1,2,3,4-tetrahydronaphthalen-1-yl)-4-isopropylthiazole-2-carboxamide (I-96)

Compound I-96 was prepared in a similar manner as described for compound I-88 except 4-isopropylthiazole-2-carboxylic acid was substituted for 4-(tert-butyl)benzoic acid to afford the title compound (40 mg, yield 40%) as a white solid, ESI-MS (M+H)$^+$: 418.9. $^1$H NMR (400 MHz, DMSO-d$_6$) δ: 14.19 (s, 1H), 9.12 (d, J=9.2 Hz, 1H), 9.02 (s, 1H), 8.72 (s, 1H), 8.11 (d, J=8.0 Hz, 1H), 8.08 (s, 1H), 7.64 (s, 1H), 7.41 (d, J=8.0 Hz, 1H), 5.32-5.27 (m, 1H), 3.12-3.05 (m, 1H), 2.95-2.93 (m, 2H), 2.06-2.02 (m, 3H), 1.86-1.79 (m, 1H), 1.29-1.27 (d, J=6.8 Hz, 6H)

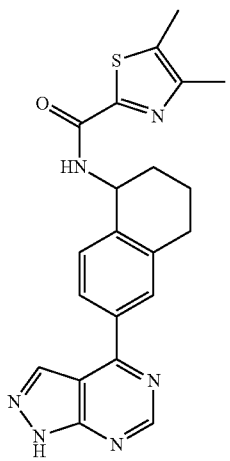

I-95

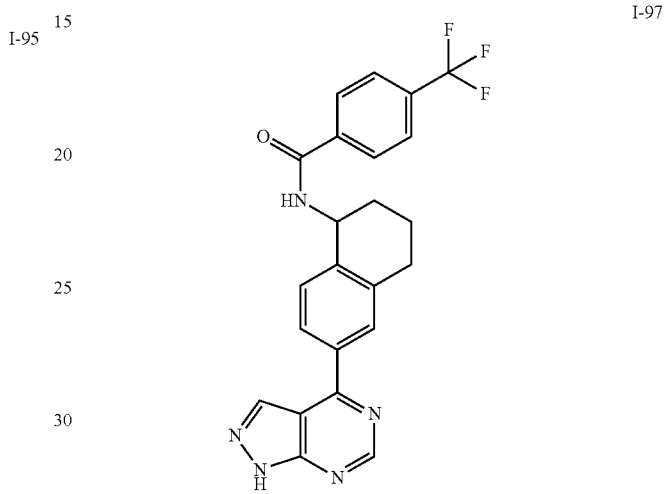

I-97

The Synthesis of N-(6-(1H-pyrazolo[3,4-d]pyrimidin-4-yl)-1,2,3,4-tetrahydronaphthalen-1-yl)-4,5-dimethylthiazole-2-carboxamide (I-95)

Compound I-95 was prepared in a similar manner as described for compound I-88 except 4,5-dimethylthiazole-2-carboxylic acid was substituted for 4-(tert-butyl)benzoic acid to afford the title compound (33 mg, yield 26%) as a solid. ESI-MS (M+H)$^+$: 405.1. $^1$H NMR (400 MHz, CD$_3$OD) δ: 8.78 (s, 1H), 8.34 (s, 1H), 7.80-7.77 (m, 2H), 7.31 (d, J=8.0 Hz, 1H), 5.20-5.17 (m, 1H), 2.84-2.75 (m, 2H), 2.30 (s, 3H), 2.23 (s, 3H), 1.93-1.89 (m, 1H), 1.87-1.78 (m, 3H).

The Synthesis of N-(6-(1H-pyrazolo[3,4-d]pyrimidin-4-yl)-1,2,3,4-tetrahydronaphthalen-1-yl)-4-(trifluoromethyl)benzamide (I-97)

Compound I-97 was prepared in a similar manner as described for compound I-88 except 4-trifluoromethylbenzoic acid was substituted for 4-(tert-butyl)benzoic acid to afford the title compound (50 mg, yield: 55%) as a yellow solid. ESI-MS (M+H)$^+$: 437.2. $^1$H NMR (400 MHz, DMSO-d6) δ: 14.19 (br, 1H), 9.18 (d, J=8.8 Hz, 1H), 9.02 (s, 1H), 8.71 (s, 1H), 8.16-8.09 (m, 4H), 7.87 (d, J=8.8 Hz, 2H), 7.45 (d, J=8.8 Hz, 1H), 5.37-5.33 (m, 1H), 2.99-2.97 (m, 2H), 2.07-2.03 (m, 2H), 1.92-1.85 (m, 2H).

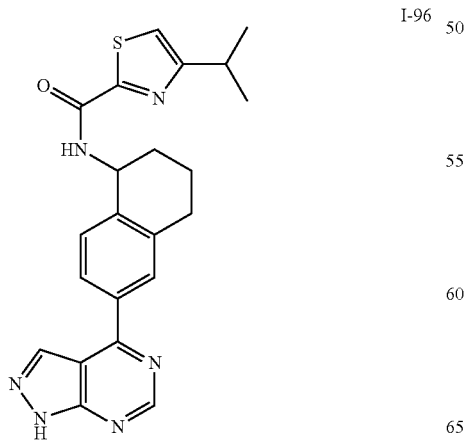

I-96

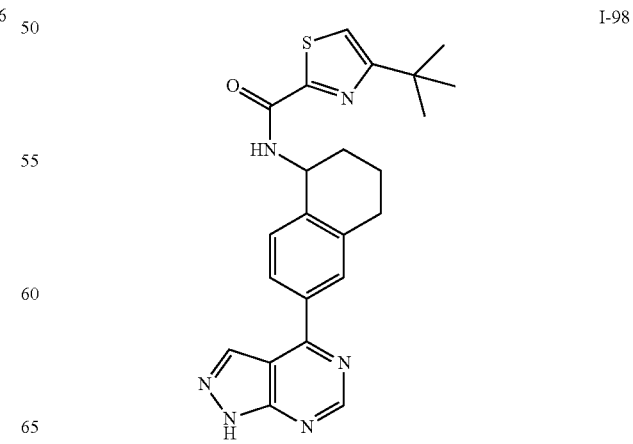

I-98

The Synthesis of N-(6-(1H-pyrazolo[3,4-d]pyrimidin-4-yl)-1,2,3,4-tetrahydro naphthalen-1-yl)-4-(tert-butyl) thiazole-2-carboxamide (I-98)

Compound I-98 was prepared in a similar manner as described for compound I-88 except 5-(tert-butyl)thiazole-2-carboxylic acid was substituted for 4-(tert-butyl)benzoic acid to afford the title compound (40 mg, yield: 27%) as a solid. ESI-MS (M+H)$^+$: 433.2. $^1$H NMR (400 MHz, DMSO-d6) δ: 14.17 (br, 1H), 9.05-9.02 (m, 2H), 8.71 (s, 1H), 8.13-8.09 (m, 2H), 7.63 (s, 1H), 7.43 (d, J=8.4 Hz, 1H), 5.32-5.30 (m, 1H), 2.97-2.96 (m, 2H), 2.06-1.82 (m, 4H), 1.46 (s, 9H).

I-99

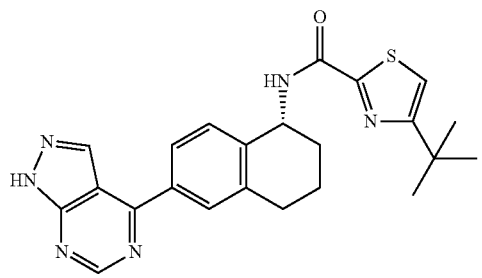

(R)—N-(6-(1H-pyrazolo[3,4-d]pyrimidin-4-yl)-1,2,3,4-tetrahydronaphthalen-1-yl)-4-(tert-butyl)thiazole-2-carboxamide (I-99)

Chiral separation of 1-98 using SFC separation (IA (2×25 cm), 30% isopropanol, 10% DCM (0.1% DEA)/CO2, 100 bar, 70 mL/min, 220 nm. inj vol.: 3 mL, 3.5 mg/mL 1:1 DCM:ethanol) gave I-99 (22 mg, chemical purity >99%, ee >99%). LC/MS (214 nm): RT=1.71 min, m/z=433.00. $^1$H NMR (400 MHz, METHANOL-d$_4$) δ 8.96 (s, 1H), 8.53 (s, 1H), 7.91-8.09 (m, 2H), 7.52 (d, J=7.78 Hz, 1H), 7.49 (s, 1H), 5.40 (t, J=6.78 Hz, 1H), 2.86-3.16 (m, 2H), 1.84-2.37 (m, 4H).

I-100

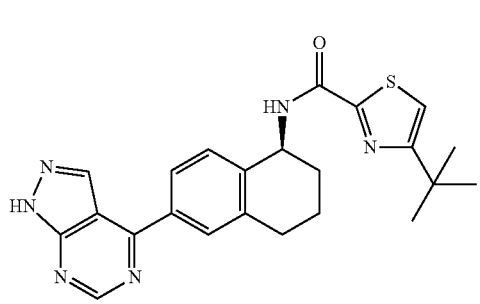

(R)—N-(6-(1H-pyrazolo[3,4-d]pyrimidin-4-yl)-1,2,3,4-tetrahydronaphthalen-1-yl)-4-(tert-butyl)thiazole-2-carboxamide (I-100)

Chiral separation of I-98 using SFC separation (IA (2×25 cm), 30% isopropanol, 10% DCM (0.1% DEA)/CO2, 100 bar, 70 mL/min, 220 nm. inj vol.: 3 mL, 3.5 mg/mL 1:1 DCM:ethanol) gave I-100 (23 mg, chemical purity >99%, ee>99%). LC/MS (214 nm): RT=1.71 min, m/z=433.00. $^1$H NMR (400 MHz, METHANOL-d$_4$) δ 8.98 (s, 1H), 8.56 (s, 1H), 7.94-8.13 (m, 2H), 7.55 (d, J=8.53 Hz, 1H), 7.50 (s, 1H), 5.42 (t, J=6.90 Hz, 1H), 2.84-3.19 (m, 2H), 1.85-2.47 (m, 4H), 1.38 (s, 9H).

I-101

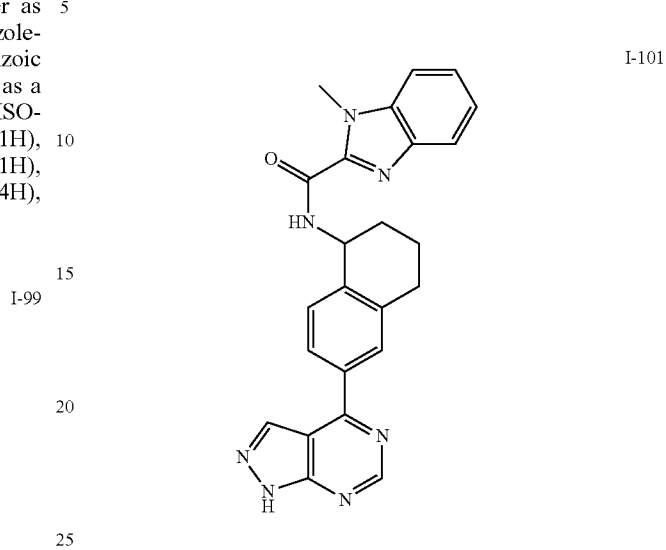

The Synthesis of N-(6-(1H-pyrazolo[3,4-d]pyrimidin-4-yl)-1,2,3,4-tetrahydronaphthalen-1-yl)-1-methyl-1H-benzo[d]imidazole-2-carboxamide (I-101)

Compound I-101 was prepared in a similar manner as described for compound I-88 except 1-methyl-1H-benzo[d]imidazole-2-carboxylic acid was substituted for 4-(tert-butyl)benzoic acid chloride to afford the title compound (5 mg, yield: 2%) as a solid. ESI-MS (M+H)$^+$: 424.2. $^1$H NMR (400 MHz, DMSO-d6) δ: 14.21 (br, 1H), 9.27 (d, J=9.2 Hz, 1H), 9.02 (s, 1H), 8.72 (s, 1H), 8.12-8.08 (m, 2H), 7.74-7.71 (m, 2H), 7.48-7.43 (m, 3H), 5.34-5.32 (m, 1H), 4.20 (s, 3H), 2.96-2.95 (m, 2H), 2.07-1.86 (m, 4H).

I-103

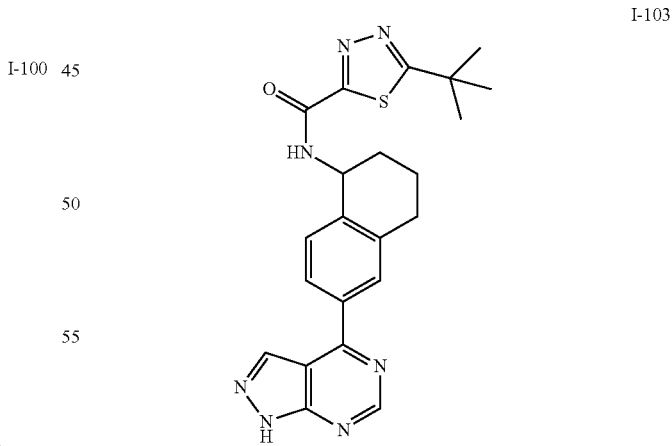

The Synthesis of N-(6-(1H-pyrazolo[3,4-d]pyrimidin-4-yl)-1,2,3,4-tetrahydronaphthalen-1-yl)-5-(tert-butyl)-1,3,4-thiadiazole-2-carboxamide (I-103)

Compound I-103 was prepared in a similar manner as described for compound I-88 except 5-(tert-butyl)-1,3,4- thiadiazole-2-carboxylic acid was substituted for 4-(tert-butyl)benzoic acid to afford the title compound (18 mg, yield 16%) as solid. ESI-MS (M+H)$^+$: 434.2. $^1$H NMR (400 MHz, DMSO-d6) δ: 9.02 (s, 1H), 8.69 (s, 1H), 8.11-8.08 (m, 2H), 7.46 (d, J=8.4 Hz, 1H), 5.32-5.29 (m, 1H), 3.52-3.50 (m, 1H), 3.14-2.96 (m, 2H), 2.07-1.83 (m, 4H), 1.48 (s, 9H).

I-104

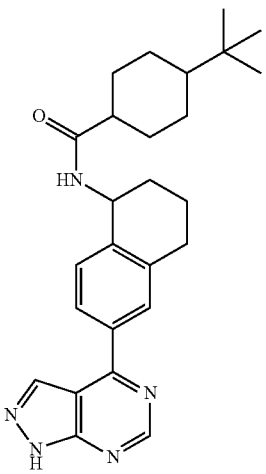

The Synthesis of N-(6-(1H-pyrazolo[3,4-d]pyrimidin-4-yl)-1,2,3,4-tetrahydronaphthalen-1-yl)-4-(tert-butyl)cyclohexanecarboxamide (I-104)

Compound I-104 was prepared in a similar manner as described for compound I-88 except 4-(tert-butyl)cyclohexanecarboxylic acid was substituted for 4-(tert-butyl)benzoic acid to afford the title compound (26 mg, yield: 18%) as a solid. ESI-MS (M+H)$^+$: 432.2. $^1$H NMR (400 MHz, DMSO-d6) δ: 14.17 (s, 1H), 9.01 (s, 1H), 8.71 (s, 1H), 8.16 (d, J=6.8 Hz, 1H), 8.09 (d, J=6.8 Hz, 1H), 8.04 (s, 1H), 7.35 (d, J=6.4 Hz, 1H), 5.02-5.07 (m, 1H), 2.90-2.89 (m, 2H), 2.12-2.07 (m, 1H), 1.95-1.67 (m, 8H), 1.48-1.36 (m, 2H), 1.02-0.92 (m, 3H), 0.84 (s, 9H).

trans-N—((R)-6-(1H-pyrazolo[3,4-d]pyrimidin-4-yl)-1,2,3,4-tetrahydronaphthalen-1-yl)-4-(trifluoromethyl)cyclohexanecarboxamide (I-105)

Compound I-105 was prepared in a similar manner as described for compound I-88 except trans-4-(trifluoromethyl)cyclohexanecarboxylic acid was substituted for 4-(tert-butyl)benzoic acid to afford the title compound. ESI-MS (M+H)$^+$:444.10. $^1$H NMR (400 MHz, METHANOL-d4): δ=8.99 (s, 1H), 8.56 (s, 1H), 8.46-8.31 (m, 1H), 8.01 (s, 2H), 7.46 (d, J=8.0 Hz, 1H), 5.26-5.09 (m, 1H), 3.05-2.90 (m, 2H), 2.40-0.99 (m, 14H).

I-106

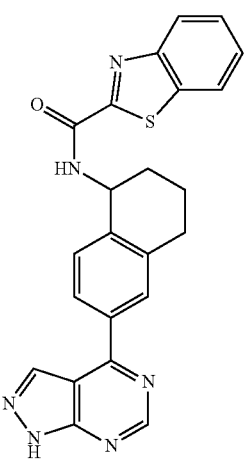

The Synthesis of N-(6-(1H-pyrazolo[3,4-d]pyrimidin-4-yl)-1,2,3,4-tetrahydronaphthalen-1-yl)benzo[d]thiazole-2-carboxamide (I-106)

Compound I-106 was prepared in a similar manner as described in Example I-88 except benzo[d]thiazole-2-carboxylic acid was substituted for 4-(tert-butyl)benzoic acid to afford the title compound as a solid (19 mg, yield 36%). ESI-MS (M+H)$^+$: 427.1. $^1$H NMR (400 MHz, DMSO-d6) δ: 14.11 (s, 1H), 9.57 (d, J=9.2 Hz, 1H), 9.01 (s, 1H), 8.70 (s, 1H), 8.26 (d, J=7.2 Hz, 1H), 8.14-8.08 (m, 3H), 7.64-7.60 (m, 2H), 7.45 (d, J=8.0 Hz, 1H), 5.34-5.32 (m, 1H), 2.98-2.96 (m, 2H), 2.09-1.74 (m, 4H).

I-105

I-107

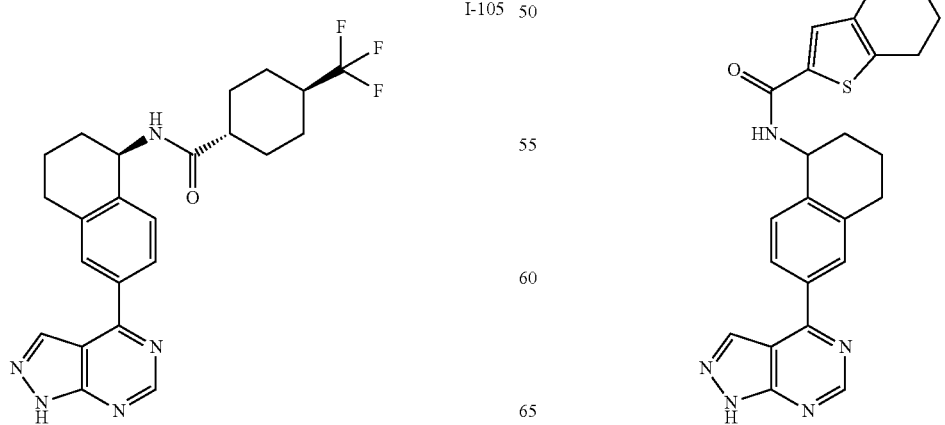

The Synthesis of N-(6-(1H-pyrazolo[3,4-d]pyrimidin-4-yl)-1,2,3,4-tetrahydronaphthalen-1-yl)-4,5,6,7-tetrahydrobenzo[b]thiophene-2-carboxamide (I-107)

Compound I-107 was prepared in a similar manner as described for compound I-88 except 4,5,6,7-tetrahydrobenzo[b]thiophene-2-carboxylic acid was substituted for 4-(tert-butyl)benzoic acid to afford the title compound (19 mg, yield 15%) as a yellow solid. ESI-MS (M+H)+: 430.2. $^1$H NMR (400 MHz, DMSO-d6) δ: 14.18 (br, 1H), 9.01 (s, 1H), 8.74-8.71 (m, 2H), 8.11-8.07 (m, 2H), 7.55 (s, 1H), 7.40 (d, J=8.4 Hz, 1H), 5.25-5.24 (m, 1H), 2.94-2.92 (m, 2H), 2.74-2.73 (m, 2H), 2.56-2.54 (m, 2H), 2.03-2.01 (m, 2H), 1.84-1.71 (m, 6H).

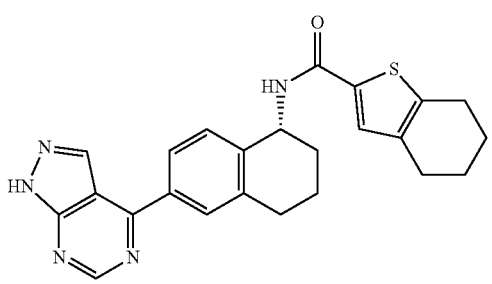

I-86

(R)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide (I-86)

The SFC separation of 1-107 using (OJ-H(2×25 cm), 40% ethanol (0.1% DEA)/CO2, 100 bar, 50 mL/min, 220 nm. inj vol.: 3 mL, 0.76 mg/mL 2:3 DCM:ethanol) yielded 1-86 (94 mg, chemical purity >99%, ee>99%). LC/MS (214 nm): RT=1.60 min, m/z=430.00. $^1$H NMR (400 MHz, METHANOL-d$_4$) δ 8.98 (s, 1H), 8.56 (s, 1H), 7.96-8.14 (m, 2H), 7.52 (s, 1H), 7.42 (s, 1H), 5.26-5.49 (m, 1H), 2.50-3.12 (m, 6H), 1.71-2.36 (m, 8H).

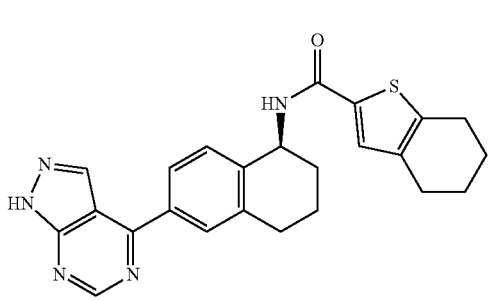

I-87

(S)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide (I-87)

The SFC separation of 1-107 (OJ-H(2×25 cm), 40% ethanol (0.1% DEA)/CO2, 100 bar, 50 mL/min, 220 nm. inj vol.: 3 mL, 0.76 mg/mL 2:3 DCM:ethanol) to yield 1-87 (106 mg, chemical purity >99%, ee>99%). LC/MS (214 nm): RT=1.60 min, m/z=430.00. $^1$H NMR (400 MHz, METHANOL-d$_4$) δ 8.98 (s, 1H), 8.56 (s, 1H), 7.92-8.15 (m, 2H), 7.53 (d, J=8.03 Hz, 1H), 7.42 (s, 1H), 5.27-5.46 (m, 1H), 2.54-3.10 (m, 6H), 1.74-2.31 (m, 8H).

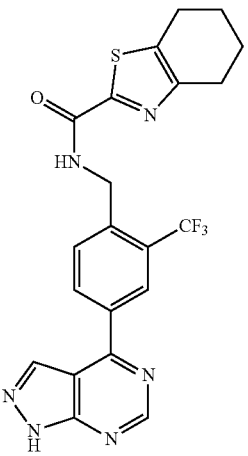

I-108

The Synthesis of N-(4-(1H-pyrazolo[3,4-d]pyrimidin-4-yl)-2-(trifluoromethyl)benzyl)-4,5,6,7-tetrahydrobenzo[d]thiazole-2-carboxamide (I-108)

Compound I-108 was prepared in a similar manner as described in Example I-17 except (4-bromo-2-(trifluoromethyl)phenyl)methanamine was substituted for 6-bromo-1,2,3,4-tetrahydronaphthalen-1-amine to afford the title compound (30 mg, yield: 18%) as a white solid. ESI-MS (M+H)+: 459.11. $^1$H NMR (400 MHz, DMSO-d6) δ: 9.58 (t, J=3.6 Hz, 1H), 9.04 (s, 1H), 8.72 (s, 1H), 8.62-8.61 (m, 2H), 7.74 (d, J=8.8 Hz, 1H), 4.75 (d, J=5.6 Hz, 2H), 2.87-2.81 (m, 4H), 1.87-1.84 (m, 4H).

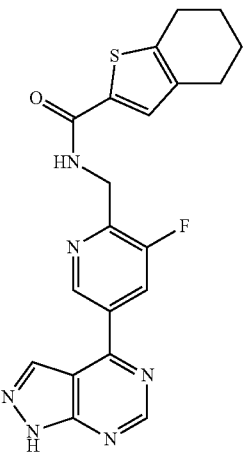

I-109

The Synthesis of N-((3-fluoro-5-(1H-pyrazolo[3,4-d]pyrimidin-4-yl)pyridin-2-yl)methyl)-4,5,6,7-tetrahydrobenzo[b]thiophene-2-carboxamide (I-109)

Compound I-109 was prepared in a similar manner as described in Example I-107 except (5-bromo-3-fluoropyridin-2-yl)methanamine was substituted for 6-bromo-1,2,3,4- tetrahydronaphthalen-1-amine to afford the title compound (12 mg, yield: 26%) as a solid. ESI-MS (M+H)+: 409.1. ¹H NMR (400 MHz, DMSO-d₆) δ: 14.34 (s, 1H), 9.29 (s, 1H), 9.11 (s, 1H), 8.97 (t, J=5.2 Hz, 1H), 8.85 (s, 1H), 8.50-8.48 (m, 1H), 7.52 (s, 1H), 4.70 (d, J=5.2 Hz, 2H), 2.71 (t, J=5.6 Hz, 2H), 2.57 (t, J=5.6 Hz, 2H), 1.76-1.72 (m, 4H).

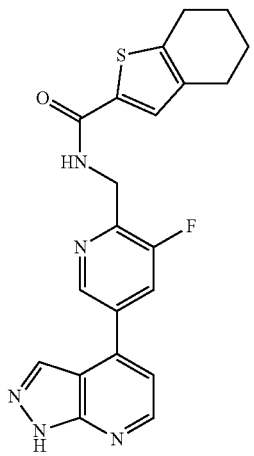

I-110

The Synthesis of N-((3-fluoro-5-(1H-pyrazolo[3,4-b]pyridin-4-yl)pyridin-2-yl)methyl)-4,5,6,7-tetrahydrobenzo[b]thiophene-2-carboxamide (I-110)

Compound I-110 was prepared in a similar manner as described in Example I-109 except 4-chloro-1-((2-(trimethylsilyl)ethoxy)methyl)-1H-pyrazolo[3,4-b]pyridine was substituted for 4-chloro-1-((2-(trimethylsilyl)ethoxy)methyl)-1H-pyrazolo[3,4-d]pyrimidine to afford the title compound. ESI-MS (M+H)+: 408.1. ¹H NMR (400 MHz, CD₃OD) δ: 13.92 (s, 1H), 8.95-8.90 (m, 2H), 8.63 (d, J=4.4 Hz, 1H), 8.42 (s, 1H), 8.24 (dd, J=10.8, 1.6 Hz, 1H), 7.52-7.49 (m, 2H), 4.67 (s, 2H), 2.71 (t, J=5.6 Hz, 2H), 2.55 (t, J=5.6 Hz, 2H), 1.76-1.72 (m, 4H)

Example 14

Scheme 20

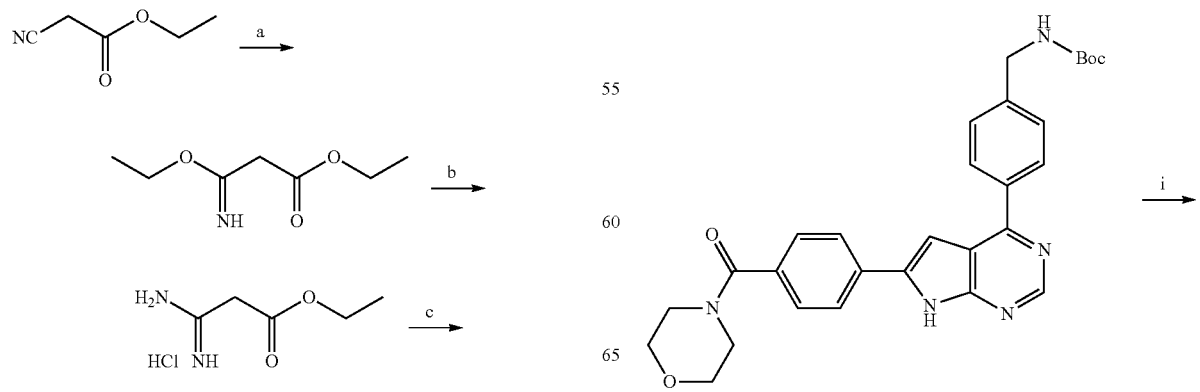

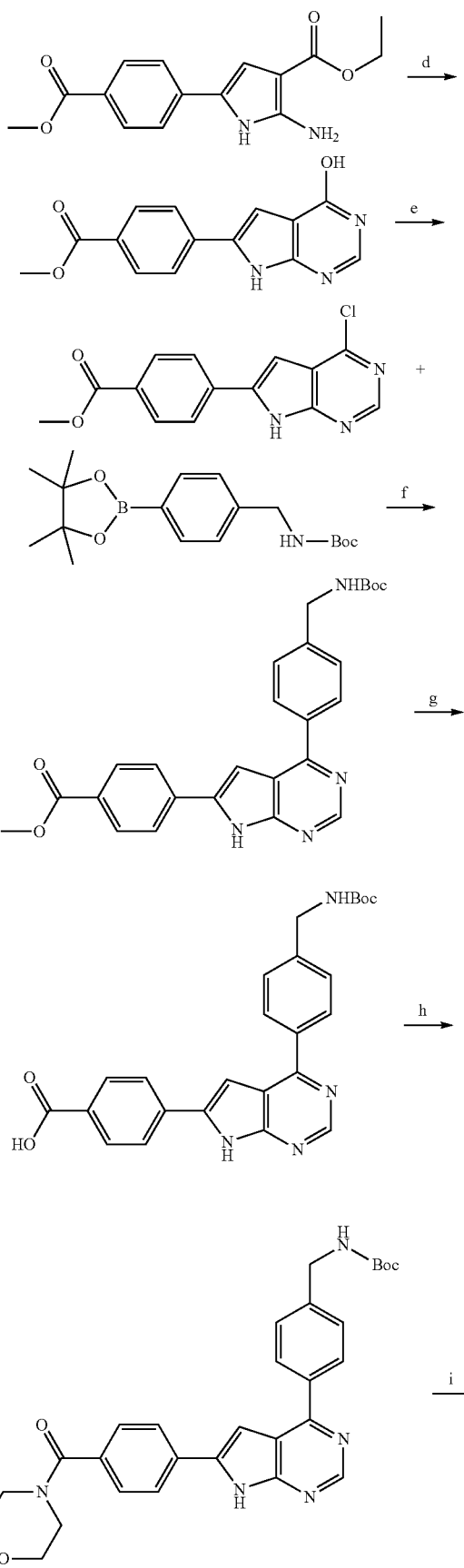

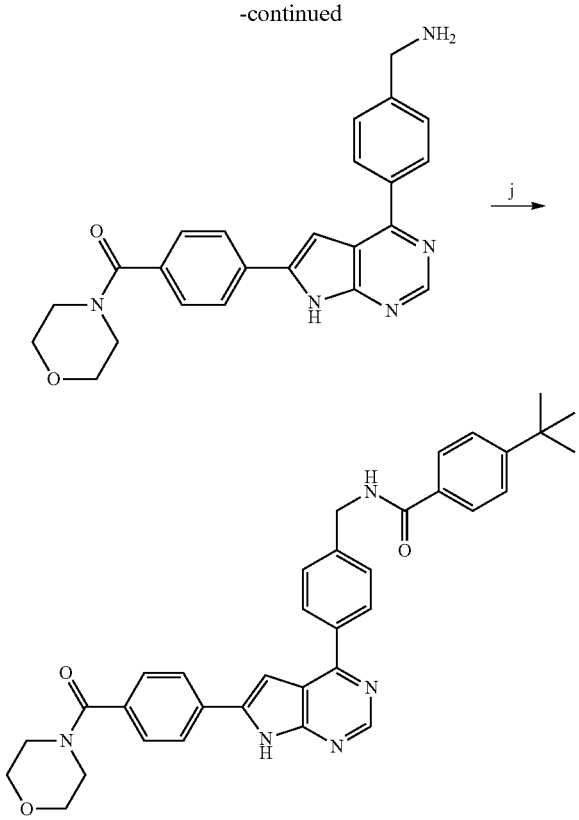

I-111

Reagents and conditions: (a) i. EtOH/HCl, rt, 16 h. ii. K₂CO₃, Et2O/H₂O, rt, 1 h, yield 88%. (b) NH₄Cl, EtOH, 80° C., 16 h, yield 84%. (c) Methyl 4-(2-bromoacetyl) benzoate, EtONa, EtOH, rt, 16 h, yield 80%. (d) H₂NCHO:HCOOH (4:1), DMF, 120° C., 36 h, yield 63%. (e) POCl₃, 110° C., 3 h, yield 93%. (e) Pd(dppf)Cl₂. DCM, K₂CO₃, DMF, 100° C., 3 h, yield 60%. (g) NaOH, EtOH, reflux. (h) Morpholine, HBTU, DIPEA, DMF, rt, 16 h, yield 76%. (i) CF₃COOH: CH₂Cl₂, rt, 2 h, yield 86%. (j) 4-(tert-Butyl)benzoyl chloride, NEt₃, CH₂Cl₂, rt, 8 h, yield 78%.

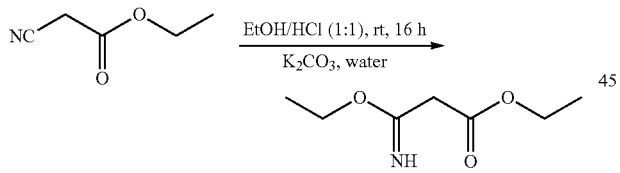

The Synthesis of ethyl 3-ethoxy-3-iminopropanoate

Ethyl 2-cyanoacetate (10.0 g, 88.5 mmol, 1.0 eq) was added to a solution of HCl/EtOH (1:1, 7.3 g, 1.0 eq), the mixture was cooled to <5° C. and stirred for 1 h. The reaction was warmed to rt for 16 h to give a suspension which was added to a mixture of diethyl ether and a solution of K₂CO₃ (10.6 g, 76.9 mmol, 1.5 eq) in water (20 mL). The diethyl ether layer was separated, dried (Na₂SO₄), filtered and in vacuo to give the title (7.2 g, yield 88%) as a colorless oil.

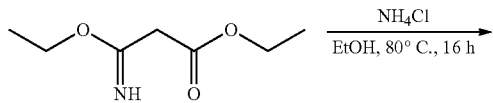

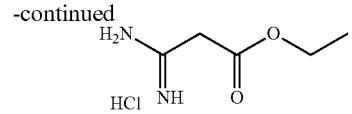

The Synthesis of ethyl 3-amino-3-iminopropanoate hydrochloride

A mixture of compound ethyl 3-ethoxy-3-iminopropanoate (3.0 g, 18.9 mmol, 1.0 eq) and NH₄Cl (1.5 g, 28.3 mmol, 1.5 eq) in EtOH (50 mmol) was heated to reflux for 16 h. The reaction was filtered and the filtrate was concentrated in vacuo to afford a residue which was washed with diethyl ether and acetone to give ethyl 3-amino-3-iminopropanoate (2.6 g, yield: 84%) as a white solid. ESI-MS (M+H)⁺: 131.0. ¹H NMR (400 MHz, DMSO-d₆) δ: 9.38 (s, 2H), 9.07 (s, 2H), 4.14 (q, J=7.2 Hz, 2H), 3.70 (s, 2H), 1.21 (t, J=7.2 Hz, 3H).

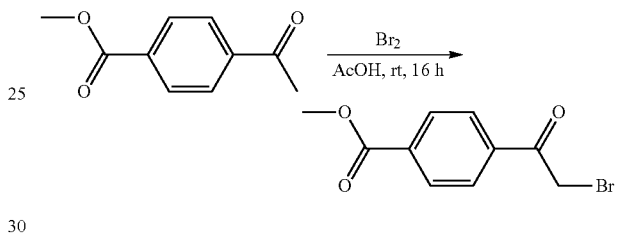

The Synthesis of methyl 4-(2-bromoacetyl)benzoate

Methyl 4-acetylbenzoate (8.0 g, 45.0 mmol, 1.0 eq) was suspended in AcOH (80 mL) and stirred until all solid dissolved. Bromine (8.5 g, 54.0 mmol, 1.2 eq) was added dropwise to the mixture and stirred at rt until all the bromine was consumed. The solution was cooled to 0° C. upon which a precipitate formed which the solid was collected and washed with 50% aqueous MeOH, dried to give the title compound (8.5 g, yield 74%) as a white solid. ESI-MS (M+H)⁺: 258.1. ¹H NMR (400 MHz, CD₃Cl) δ: 8.16 (d, J=7.6 Hz, 2H), 7.60 (d, J=8.4 Hz, 2H), 4.48 (s, 2H), 3.97 (s, 3H).

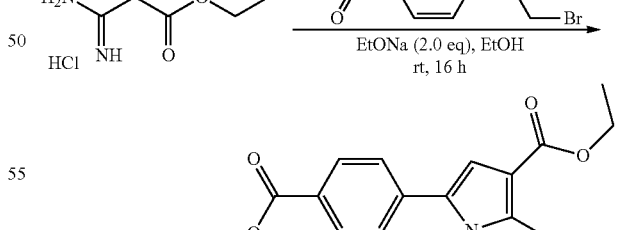

The Synthesis of ethyl 2-amino-5-(4-(methoxycarbonyl)phenyl)-1H-pyrrole-3-carboxylate Sodium metal (0.5 g, 21.6 mmol, 2.0 eq) was dissolved in dry EtOH (50 mL), the solution was cooled to 0° C. To this, ethyl 3-amino-3-iminopropanoate hydrochloride (1.8 g, 10.8 mmol, 1.0 eq) was added and stirred for 0.5 h, followed by the addition of methyl 4-(2-bromoacetyl)benzoate (5.5 g, 21.6 mmol, 2.0 eq). The mixture was stirred at rt for 16 h and concentrated in vacuo to afford a residue which was dissolved with EtOAc (50 mL), filtered and the filtrate was washed with H₂O (20 mL), separated and the aqueous phase was re-extracted with EtOAc (20 mL×3). The combined organic layers were washed with brine (20 mL), dried (Na₂SO₄) and filtered and concentrated in vacuo to give residue was purified by column chromatography (petroleum ether/EtOAc=1:1) to give the title compound (2.5 g, yield: 80%) as a light yellow solid. ESI-MS (M+H)⁺: 289.0. ¹H NMR (400 MHz, DMSO-d₆) δ: 10.95 (s, 1H), 7.86 (d, J=8.0 Hz, 2H), 7.60 (d, J=8.4 Hz, 2H), 6.72 (s, 1H), 6.83 (s, 2H), 4.16 (q, J=7.2 Hz, 2H), 3.82 (s, 3H), 1.26 (t, J=7.2 Hz, 3H).

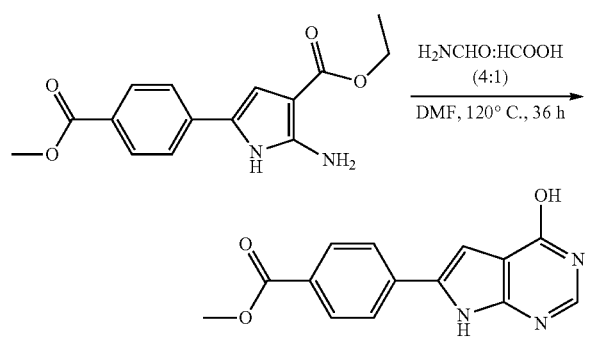

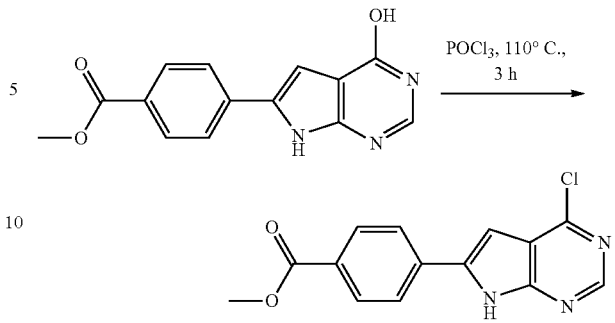

The Synthesis of methyl 4-(4-chloro-7H-pyrrolo[2,3-d]pyrimidin-6-yl)benzoate

A mixture of compound methyl 4-(4-hydroxy-7H-pyrrolo[2,3-d]pyrimidin-6-yl)benzoate (1.3 g, 4.5 mmol, 1.0 eq) and POCl₃ (10 mL) was heated at reflux for 3 h. The excessive POCl₃ was removed under reduced pressure and the residue was dissolved in EtOAc, washed with aqueous NaHCO₃ solution, brine, dried (Na₂SO₄), filtered and concentrated in vacuo to afford the title compound (1.0 g, yield: 93%) as a light yellow solid. ESI-MS (M+H)⁺: 288.0. ¹H NMR (400 MHz, CD₃OD) δ: 14.01 (s, 1H), 9.46 (s, 1H), 8.99 (d, J=8.8 Hz, 2H), 8.87 (d, J=8.4 Hz, 2H), 8.10 (s, 1H), 3.87 (s, 3H).

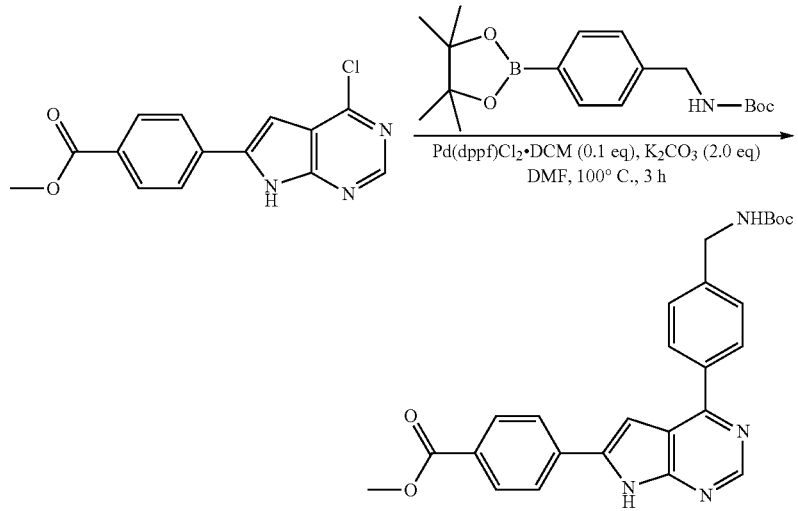

The Synthesis of methyl 4-(4-hydroxy-7H-pyrrolo[2,3-d]pyrimidin-6-yl)benzoate

A mixture of ethyl 2-amino-5-(4-(methoxycarbonyl)phenyl)-1H-pyrrole-3-carboxylate (3.0 g, 18.9 mmol, 1.0 eq), formic acid (5.0 mL) and formamide (20 mL) in DMF (20 mL) was heated at 120° C. for 36 h. The reaction mixture was cooled and diluted with isopropanol and the precipitate was isolated, washed with isopropanol and hexane to give the title compound (1.3 g, yield 63%) as a light yellow solid. ESI-MS (M+H)⁺: 170.0. ¹H NMR (400 MHz, DMSO-d₆) δ: 12.55 (s, 1H), 11.97 (s, 1H), 8.01 (s, 1H), 7.99-7.94 (m, 4H), 7.15 (s, 1H), 3.87 (s, 3H).

The Synthesis of methyl 4-(4-(4-(((tert-butoxycarbonyl)amino)methyl)phenyl)-7H-pyrrolo[2,3-d]pyrimidin-6-yl)benzoate To a solution of methyl 4-(4-chloro-7H-pyrrolo[2,3-d]pyrimidin-6-yl)benzoate (0.95 g, 3.3 mmol, 1.0 eq) in DMF (10 mL), was added tert-butyl 4-(4,4,5,5-tetramethyl-1,3,2-dioxaborolan-2-yl)benzylcarbamate (1.3 g, 3.9 mmol, 1.2 eq), Pd(dppf)Cl₂.DCM (0.2 g, 0.33 mmol, 0.1 eq) and K₂CO₃ (0.9 g, 6.6 mmol, 2.0 eq). The reaction solution was stirred at 100° C. for 3 h, cooled to rt and diluted with water (20 mL) and EtOAc (50 mL). The organic layer was separated and the aqueous was extracted with EtOAc (50 mL×2). The combined organic layers were concentrated in vacuo to afford a residue which was purified by column chromatography (petroleum ether/EtOAc=1:1) to afford the title compound (0.9 g, yield: 60%). ESI-MS (M+H−56)$^+$: 459.1. $^1$H NMR (400 MHz, DMSO-d$_6$) δ: 12.89 (s, 1H), 8.86 (s, 1H), 8.26-8.22 (m, 4H) 8.05 (d, J=8.8 Hz, 2H), 7.64 (s, 1H), 7.55-7.52 (m, 1H), 7.48-7.46 (m, 2H), 4.25 (d, J=6.0 Hz, 2H), 3.89 (s, 3H), 1.40 (s, 9H).

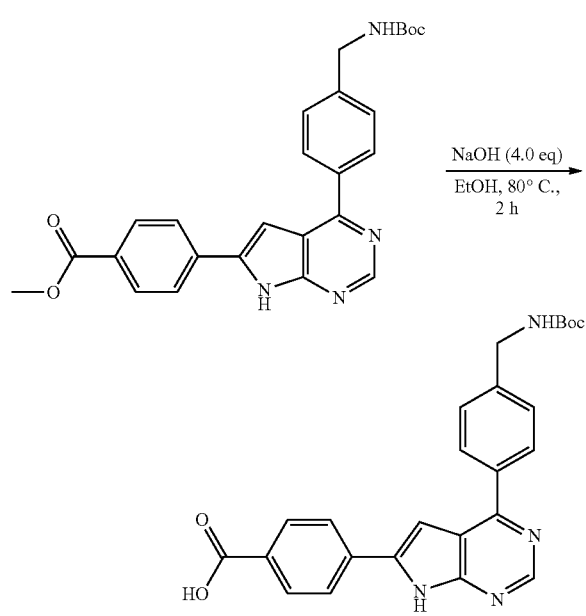

The Synthesis of 4-(4-(4-(((tert-butoxycarbonyl)amino)methyl)phenyl)-7H-pyrrolo[2,3-d]pyrimidin-6-yl)benzoic acid To a solution of ester (0.9 g, 2.0 mmol, 1.0 eq) in EtOH (20 mL) was added NaOH (0.32 g, 8.0 mmol, 4.0 eq) and the solution was stirred at 80° C. for 1 h. The solvent was removed in vacuo and the residue was dissolved with H$_2$O (20 mL) and adjusted to pH=6 with HCl (4 N). The precipitate was separated and filtered to afford the title compound (0.8 g, yield 87%) as yellow solid which was used in the next step without further purification. ESI-MS (M+H)$^+$: 445.1. $^1$H NMR (400 MHz, DMSO-d$_6$) δ: 12.85 (s, 1H), 8.83 (s, 1H), 8.26 (d, J=7.6 Hz, 2H), 8.05-8.02 (m, 4H), 7.57-7.46 (m, 5H), 4.25 (d, J=5.2 Hz, 2H), 1.42 (s, 9H).

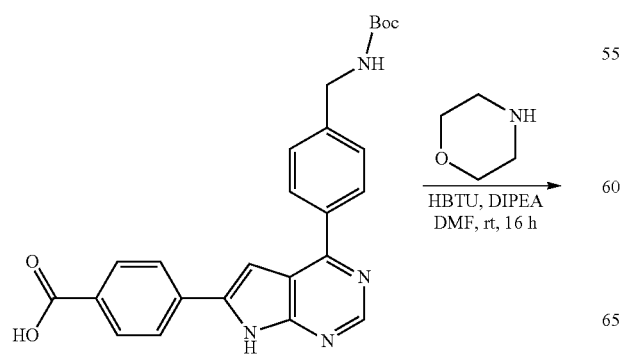

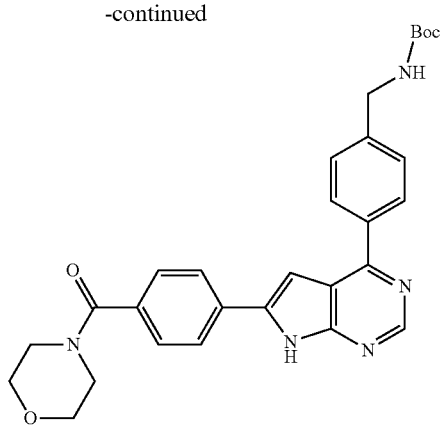

The Synthesis of tert-butyl 4-(6-(4-(morpholine-4-carbonyl)phenyl)-7H-pyrrolo[2,3-d]pyrimidin-4-yl)benzylcarbamate To the solution of acid (0.795 g, 1.8 mmol, 1.0 eq) in DMF (5 mL) was added morpholine (0.47 g, 5.4 mmol, 3.0 eq), HBTU (1.4 g, 3.6 mmol, 2.0 eq) and DIPEA (0.7 g, 5.4 mmol, 3.0 eq). The solution was stirred at rt for 16 h, diluted with EtOAc (20 mL) and washed with H$_2$O (20 mL), brine (20 mL). The organic phase was separated, dried (Na$_2$SO$_4$) and concentrated in vacuo to afford a residue which was purified by column chromatography (petroleum ether/EtOAc=1:1) to give the title compound (0.7 g, yield: 76%) as a light yellow solid. ESI-MS (M+H$^+$): 514.3. $^1$H NMR (400 MHz, DMSO-d$_6$) δ: 12.82 (s, 1H), 8.85 (s, 1H), 8.25 (d, J=7.6 Hz, 2H), 8.14 (d, J=7.6 Hz, 2H), 7.55-7.46 (m, 6H), 4.25 (d, J=6.0 Hz, 2H) 3.72-3.42 (s, 8H), 1.43 (s, 9H).

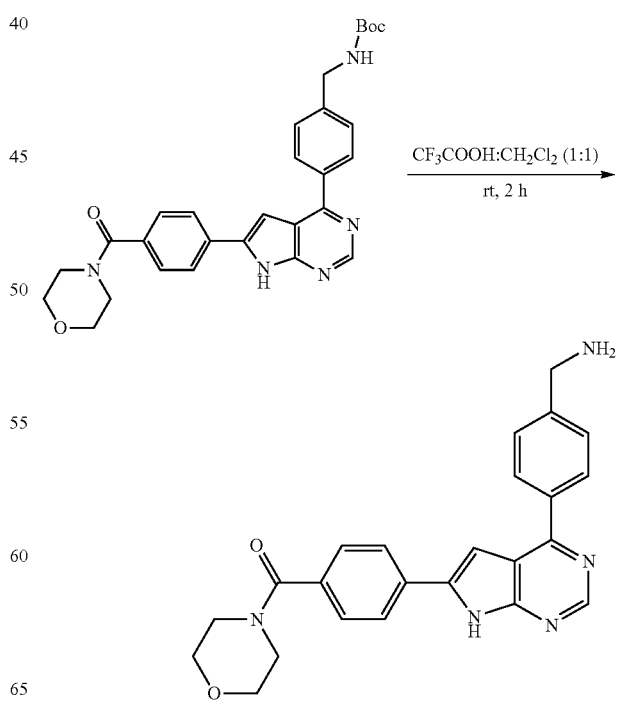

The Synthesis of (4-(4-(4-(aminomethyl)phenyl)-7H-pyrrolo[2,3-d]pyrimidin-6-yl)phenyl)(morpholino)methanone To the solution of the carbamate (650 mg, 1.3 mmol, 1.0 eq) in CH₂Cl₂ (2.0 mL) was added CF₃COOH (2.0 mL) at rt. The reaction solution was stirred at rt for 2 h, concentrated in vacuo to afford the title compound (450 mg, yield 86%) which was used without further purification. ESI-MS (M+H)⁺: 414.2.

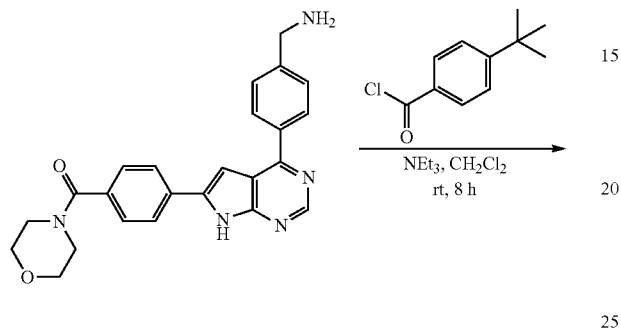

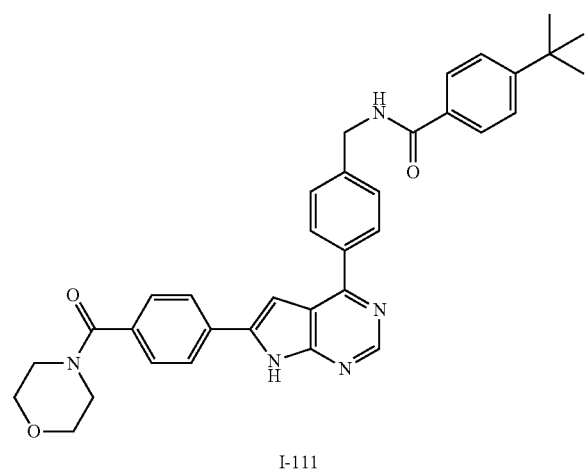

I-111

The Synthesis of 4-(tert-butyl)-N-(4-(6-(4-(morpholine-4-carbonyl)phenyl)-7H-pyrrolo[2,3-d]pyrimidin-4-yl)benzyl)benzamide (I-111)

To the solution of amine (0.44 g, 1.1 mmol, 1.0 eq) in CH₂Cl₂ (5 mL) was added 4-tert-butylbenzoyl chloride (0.26 g, 1.3 mmol, 1.2 eq) and NEt₃ (0.22 g, 2.2 mmol, 2.0 eq). The reaction was stirred at rt for 8 h, diluted with EtOAc (20 mL) and washed sequentially with H₂O (20 mL), brine (20 mL) and concentrated in vacuo to a solid which was purified by column chromatography (silica, CH₂Cl₂/MeOH=10:1) to give the title compound (0.48 g, yield: 78%) as a light yellow solid. ESI-MS (M+H)⁺: 537.27. ¹H NMR (400 MHz, DMSO-d₆) δ: 12.82 (s, 1H), 9.11 (t, J=6.0 Hz, 1H), 8.84 (s, 1H), 8.25 (d, J=8.0 Hz, 2H), 8.13 (d, J=8.0 Hz, 2H), 7.88 (d, J=8.0 Hz, 2H), 7.55-7.50 (m, 7H), 4.61 (d, J=5.6 Hz, 2H) 3.70-3.50 (m, 8H), 1.31 (s, 9H).

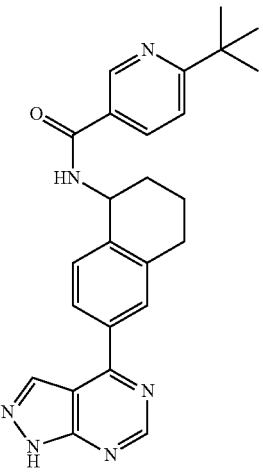

I-142

The Synthesis of N-(6-(1H-pyrazolo[3,4-d]pyrimidin-4-yl)-1,2,3,4-tetrahydronaphthalen-1-yl)-6-(tert-butyl)nicotinamide (I-142)

Compound I-142 was prepared in a similar manner as described I-88 except 6-(tert-butyl)nicotinic acid was substituted for 4-(tert-butyl)benzoic acid to afford the title compound (30 mg, yield: 23%) as a white solid. ESI-MS (M+H)⁺: 427.0. ¹H NMR (400 MHz, CD₃OD) δ: 9.10 (d, J=1.6 Hz, 1H), 8.95 (s, 1H), 8.59 (s, 1H), 8.39 (dd, J=8.4, 2.0 Hz, 1H), 8.05-8.03 (m, 2H), 7.65 (d, J=8.8 Hz, 1H), 7.45 (d, J=8.0 Hz, 1H), 5.35-5.32 (m, 1H), 2.95-2.92 (m, 2H), 2.08-2.00 (m, 2H), 2.00-1.84 (m, 2H).

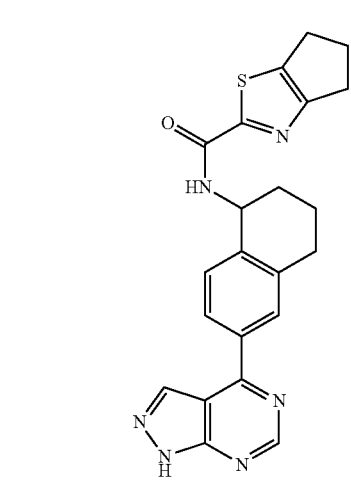

I-130

The Synthesis of N-(6-(1H-pyrazolo[3,4-d]pyrimidin-4-yl)-1,2,3,4-tetrahydronaphthalen-1-yl)-5,6-dihydro-4H-cyclopenta[d]thiazole-2-carboxamide (I-130)

Compound I-130 was prepared in a similar manner as described for compound I-88 except 5,6-dihydro-4H-cyclopenta[d]thiazole-2-carboxylic acid was substituted for 4-(tert-butyl)benzoic acid to afford the title compound (15 mg, yield: 10%) as a yellow solid. ESI-MS (M+H)⁺: 417.2.

¹H NMR (400 MHz, DMSO-d6) δ: 14.34 (s, 1H), 9.09 (d, J=7.2 Hz, 1H), 9.01 (s, 1H), 8.70 (s, 1H), 8.08 (d, J=6.8 Hz, 1H), 8.05 (s, 1H), 7.40 (d, J=6.4 Hz, 1H), 5.27-5.26 (m, 1H), 2.98-2.83 (m, 4H), 2.80-2.74 (m, 2H), 2.52-2.48 (m, 2H), 2.04-1.98 (m, 3H), 1.98-1.94 (m, 1H).

stituted for 4-(tert-butyl)benzoic acid to afford the title compound (38 mg, yield 28%). ESI-MS (M+H)⁺: 427.2. ¹H NMR (400 MHz, DMSO-d6) δ: 14.15 (br, 1H), 9.01-8.98 (m, 2H), 8.70 (s, 1H), 8.55 (d, J=5.2 Hz, 1H), 8.13 (s, 1H), 8.09-8.07 (m, 2H), 7.64 (dd, J=5.2, 1.6 Hz, 1H), 7.41 (d, J=8.0 Hz, 1H), 5.35-5.29 (m, 1H), 296-2.95 (m, 2H), 2.05-2.00 (m, 3H), 1.88-1.85 (m, 1H), 1.34 (s, 9H).

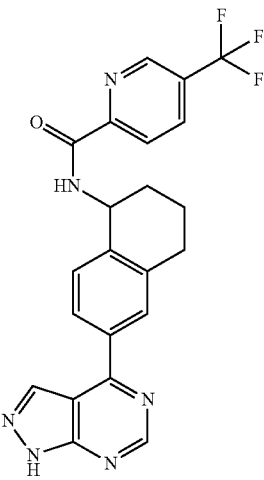

I-147

The Synthesis of N-(6-(1H-pyrazolo[3,4-d]pyrimidin-4-yl)-1,2,3,4-tetrahydronaphthalen-1-yl)-5-(trifluoromethyl)picolinamide (I-147)

Compound I-147 was prepared in a similar manner as compound I-88 except 5-(trifluoromethyl)picolinic acid was substituted for 4-(tert-butyl)benzoic acid to afford the title compound as a yellow solid (7 mg, yield 10%), ESI-MS (M+H)⁺: 439.1 ¹H NMR (400 MHz, DMSO-d6) δ: 9.28 (d, J=9.2 Hz, 1H), 8.96 (d, J=4.8 Hz, 1H), 8.93 (s, 1H), 8.64 (s, 1H), 8.34 (s, 1H), 8.08-8.05 (m, 3H), 7.41 (d, J=9.2 Hz, 1H), 5.36-5.34 (m, 1H), 2.96-2.94 (m, 2H), 2.07-1.99 (m, 4H).

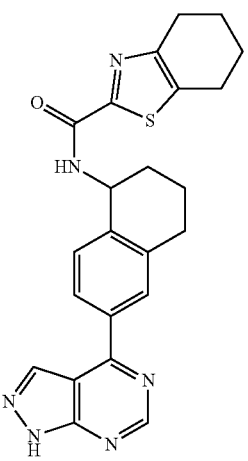

I-137

The Synthesis of N-(6-(1H-pyrazolo[3,4-d]pyrimidin-4-yl)-1,2,3,4-tetrahydronaphthalen-1-yl)-4,5,6,7-tetrahydrobenzo[d]thiazole-2-carboxamide (I-137)

Compound I-137 was prepared in a similar manner as described I-88 except 4,5,6,7-tetrahydrobenzo[d]thiazole-2-carboxylic acid was substituted for 4-(tert-butyl)benzoic acid to afford the title compound (42 mg, yield: 26%) as a white solid. ESI-MS (M)⁺: 430.1. ¹H NMR (400 MHz, CD₃OD) δ: 8.97 (s, 1H), 8.55 (s, 1H), 8.03-8.02 (m, 2H), 7.51 (d, J=8.4 Hz, 1H), 5.38-5.35 (m, 1H), 3.31-2.99 (m, 2H), 2.90-2.80 (m, 4H), 2.22-2.16 (m, 2H), 2.06-1.95 (m, 2H), 1.92-1.90 (m, 4H).

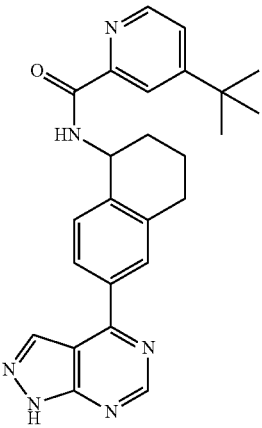

I-150

The Synthesis of N-(6-(1H-pyrazolo[3,4-d]pyrimidin-4-yl)-1,2,3,4-tetrahydronaphthalen-1-yl)-4-(tert-butyl)picolinamide (I-150)

Compound I-150 was prepared in a similar manner as compound I-88 except 4-(tert-butyl)picolinic acid was sub-

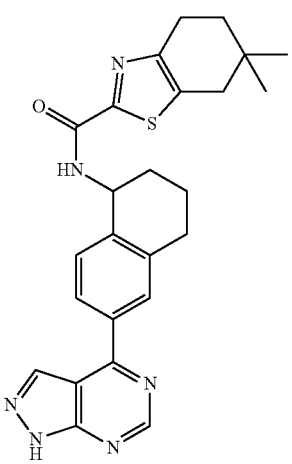

I-136

The Synthesis of N-(6-(1H-pyrazolo[3,4-d]pyrimidin-4-yl)-1,2,3,4-tetrahydronaphthalen-1-yl)-6,6-dimethyl-4,5,6,7-tetrahydrobenzo[d]thiazole-2-carboxamide (I-136)

Compound I-136 was prepared in a similar manner as described for compound I-88 except 6,6-dimethyl-4,5,6,7-tetrahydrobenzo[d]thiazole-2-carboxylic acid was substituted for 4-(tert-butyl)benzoic acid to afford the title compound (33 mg, yield 17%) as a pale white solid. ESI-MS (M+H)$^+$: 459.1. $^1$H NMR (400 MHz, DMSO-d$_6$) δ: 14.18 (s, 1H), 9.08 (d, J=8.8 Hz, 1H), 9.02 (s, 1H), 8.71 (s, 1H), 8.09 (d, J=8.0 Hz, 1H), 8.06 (s, 1H), 7.39 (d, J=8.0 Hz, 1H), 5.28-5.22 (m, 1H), 2.94-2.92 (m, 2H), 2.75 (t, J=5.6 Hz, 2H), 2.65 (s, 2H), 2.03-2.01 (m, 3H), 1.85-1.79 (m, 1H), 1.62 (t, J=6.0 Hz, 2H), 1.00 (s, 6H).

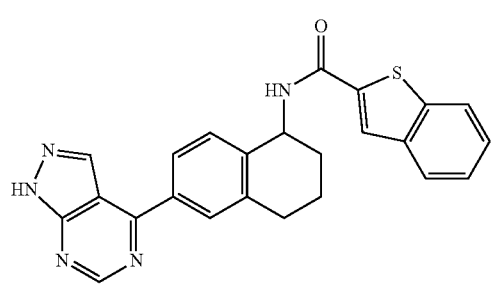

I-120

The Synthesis of N-(6-(1H-pyrazolo[3,4-d]pyrimidin-4-yl)-1,2,3,4-tetrahydronaphthalen-1-yl)benzo[b]thiophene-2-carboxamide (I-120)

Compound I-120 was prepared in a similar manner as described for compound I-88 except benzo[b]thiophene-2-carboxylic acid was substituted for 4-(tert-butyl)benzoic acid to afford the title compound (20 mg, yield 18%) as a yellow solid. ESI-MS (M+H)$^+$: 426.2. $^1$H NMR (400 MHz, DMSO-d6) δ: 14.18 (br, 1H), 9.20 (d, J=8.0 Hz, 1H), 9.02 (s, 1H), 8.71 (s, 1H), 8.21 (s, 1H), 8.13-8.10 (m, 2H), 8.04 (d, J=8.0 Hz, 1H), 7.92 (d, J=7.2 Hz, 1H), 7.49-7.43 (m, 3H), 5.33-5.32 (m, 1H), 2.97-2.96 (m, 2H), 2.08-1.89 (m, 4H).

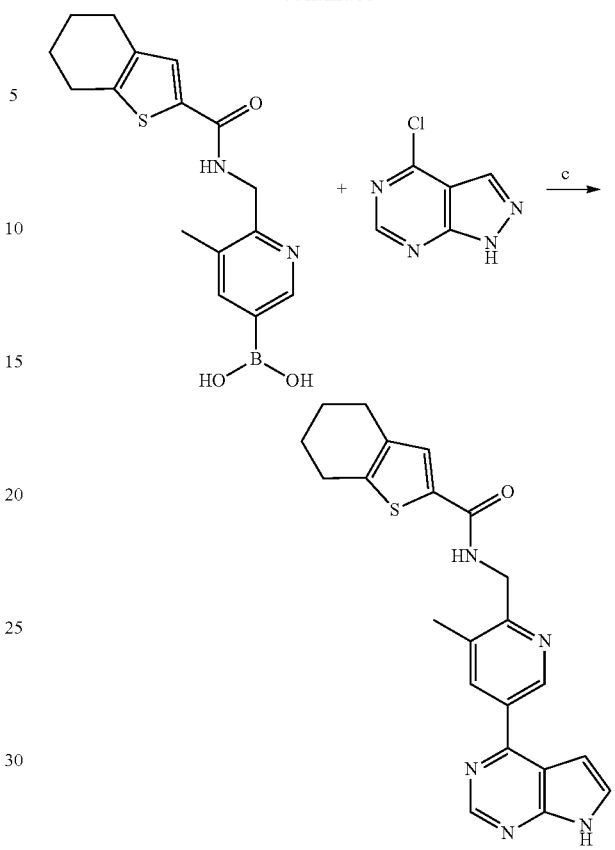

Reagent and conditions: (a) DIPEA, HBTU, DMF, rt, 16 h. (b) Bis(pinacolato)diborane, Pd(dppf)Cl$_2$, KOAc, microwave, 1,4-dioxane, 100° C., 1.5 h. (c) Pd(dppf)Cl$_2$, K$_2$CO$_3$, 1,4-Dioxane/water, 130° C., 2 h.

Scheme 21

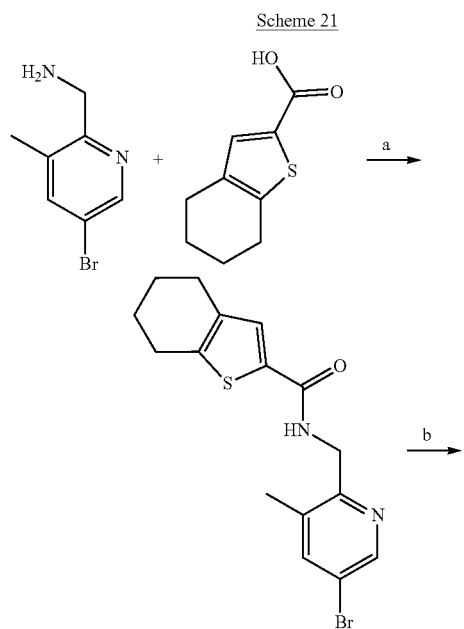

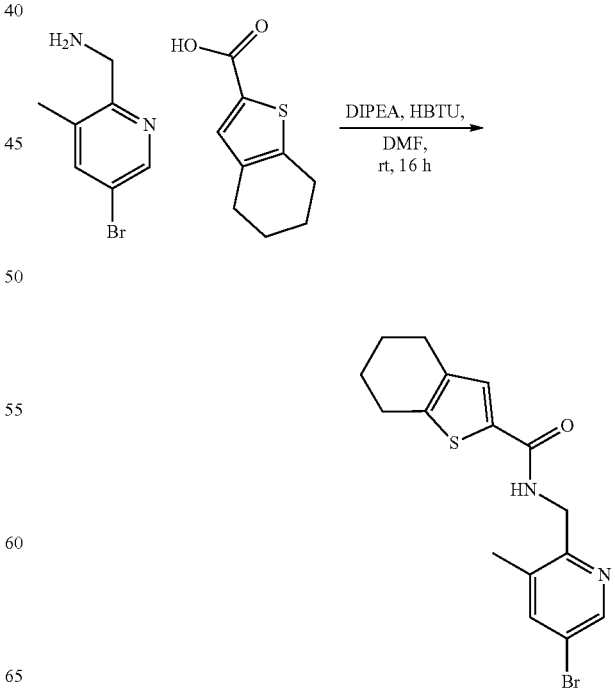

The Synthesis of N-((5-bromo-3-methylpyridin-2-yl)methyl)-4,5,6,7-tetrahydrobenzo[b]thiophene-2-carboxamide To a solution of (5-bromo-3-methylpyridin-2-yl)methanamine (802 mg, 4.0 mmol) in DMF (5.0 mL) were added HBTU (2.27 g, 6.0 mmol), DIPEA (1.37 mL, 8.0 mmol) and 4,5,6,7-tetrahydrobenzo[b]thiophene-2-carboxylic acid (728 mg, 4.0 mmol). The reaction mixture was stirred at rt for 16 h, diluted with water (50 mL) and extracted with EtOAc (80 mL×2). The organic phase was separated were dried ($Na_2SO_4$), filtered and concentrated in vacuo to afford a residue which was purified by silica gel column chromatography (Petroleum ether/EtOAc=1:1) to give the title product as a yellow solid (800 mg, yield 55%). ESI-MS (M+H)$^+$: 365.0.

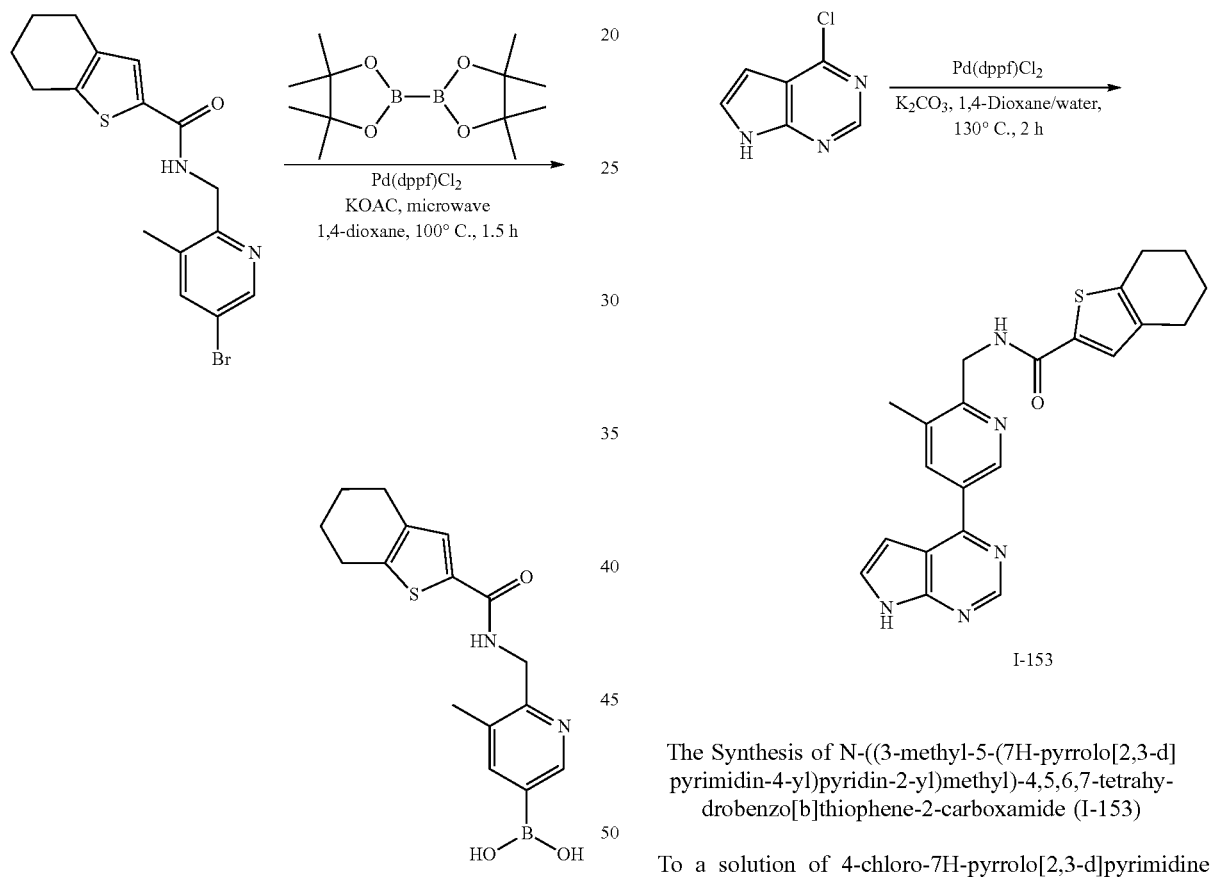

The Synthesis of (5-methyl-6-((4,5,6,7-tetrahydrobenzo[b]thiophene-2-carboxamido)methyl)pyridin-3-yl)boronic acid To a solution of aryl bromide (800 mg, 2.19 mmol) in 1,4-dioxane (20 mL) under $N_2$ were added bis(pinacolato) diboron (667 mg, 2.63 mmol), KOAc (448 mg, 4.68 mmol) and Pd(dppf)Cl$_2$DCM (38 mg, 0.02 mmol) and the mixture was heated in a microwave at 100° C. for 1.5 h. The solid was removed by filtration and the filtrate was purified by reverse column chromatography (MeOH/H$_2$O with 0.05% TFA as mobile phase) to give the title compound (660 mg, yield 80%) as a white solid. ESI-MS (M+H)$^+$: 331.1

The Synthesis of N-((3-methyl-5-(7H-pyrrolo[2,3-d]pyrimidin-4-yl)pyridin-2-yl)methyl)-4,5,6,7-tetrahydrobenzo[b]thiophene-2-carboxamide (I-153)

To a solution of 4-chloro-7H-pyrrolo[2,3-d]pyrimidine (214 mg, 1.0 mmol) in 1,4-dioxane (8 mL) and H$_2$O (2 mL), was added boronic acid (373 mg, 1.0 mmol), Pd(dppf)Cl$_2$ (7.5 mg, 0.01 mmol) and K$_2$CO$_3$ (414 mg, 3.0 mmol) under N$_2$. The mixture was stirred at 100° C. for 6 h, diluted with water (80 mL) and extracted with EtOAc (60 mL×3). The organic layers were collected, concentrated in vacuo to afford a residue which was purified by column chromatography (silica gel, Petroleum ether/EtOAc=1:1) to give the title compound (30 mg, yield 21%) as a yellow solid. ESI-MS (M+H)$^+$: 404.2. $^1$H NMR (400 MHz, DMSO-d6) δ: 12.34 (br, 1H), 9.12 (d, J=1.2 Hz, 1H), 8.86 (s, 1H), 8.77 (t, J=5.6 Hz, 1H), 8.32 (s, 1H), 7.70 (d, J=3.2 Hz, 1H), 7.54 (s, 1H), 6.96 (d, J=2.4 Hz, 1H), 4.63 (d, J=5.6 Hz, 2H), 2.72 (t, J=4.4 Hz, 2H), 2.56 (t J=4.0 Hz, 2H), 2.47 (s, 3H), 1.78-1.74 (m, 4H).

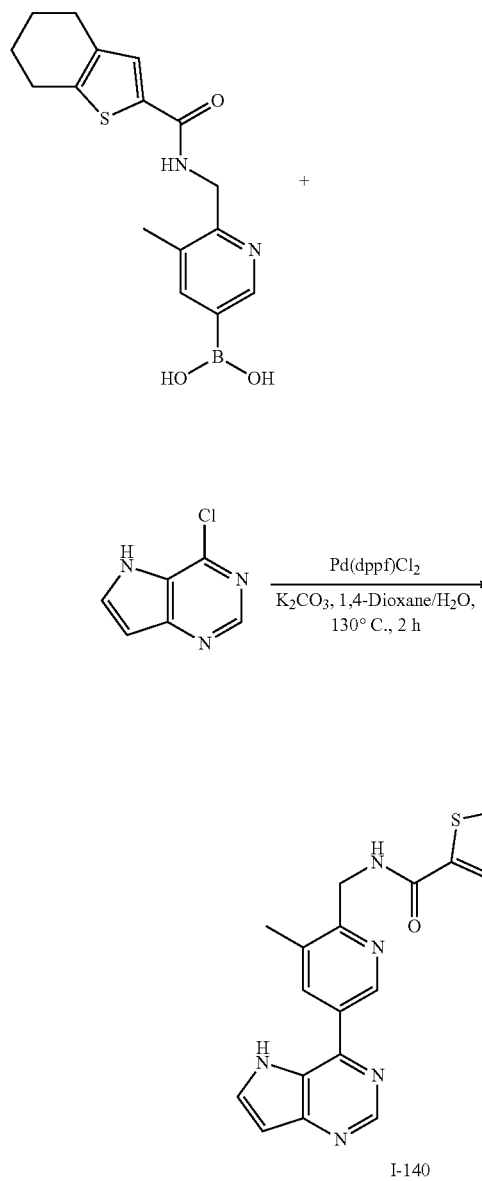

The Synthesis of N-((3-methyl-5-(5H-pyrrolo[3,2-d]pyrimidin-4-yl)pyridin-2-yl)methyl)-4,5,6,7-tetrahydrobenzo[b]thiophene-2-carboxamide (I-140)

Compound I-140 was prepared in a similar manner as described for compound I-153 except 4-chloro-5H-pyrrolo[3,2-d]pyrimidine was substituted for 4-chloro-7H-pyrrolo[2,3-d]pyrimidine to afford the title compound (32 mg, yield 21%) as a yellow solid. ESI-MS (M+H)$^+$: 404.2. $^1$H NMR (400 MHz, DMSO-d6) δ: 12.15 (br, 1H), 9.04 (d, J=2.0 Hz, 1H), 8.92 (s, 1H), 8.80 (t, J=4.8 Hz, 1H), 8.26 (d, J=1.2 Hz, 1H), 7.96-7.94 (m, 1H), 7.54 (s, 1H), 6.73 (d, J=2.4 Hz, 1H), 4.64 (d, J=5.2 Hz, 2H), 2.72 (t, J=6.4 Hz, 2H), 2.57 (t, J=6.4 Hz, 2H), 2.47 (s, 3H), 1.78-1.74 (m, 4H).

The Synthesis of N-((3-methyl-5-(1-(tetrahydro-2H-pyran-2-yl)-1H-pyrazolo[3,4-d]pyrimidin-4-yl)pyridin-2-yl)methyl)-4,5,6,7-tetrahydrobenzo[b]thiophene-2-carboxamide To a solution of 4-chloro-1-(tetrahydro-2H-pyran-2-yl)-1H-pyrazolo[3,4-d]pyrimidine (238 mg, 1.0 mmol) in 1,4-dioxane (10 mL) and water (2.5 mL), was added boronic acid (373 mg, 1.0 mmol), Pd(dppf)Cl$_2$ (7.5 mg, 0.01 mmol) and K$_2$CO$_3$ (414 mg, 3.0 mmol) under N$_2$. The mixture was stirred at 100° C. for 6 h, diluted with water (80 mL) and extracted with EtOAc (60 mL×3) and the organic layers were concentrated in vacuo to afford a residue which was purified by column chromatography (Petroleum ether/EtOAc=4:1) to give the title compound (65 mg, yield 44%) as a white solid. ESI-MS (M+H)$^+$: 489.2.

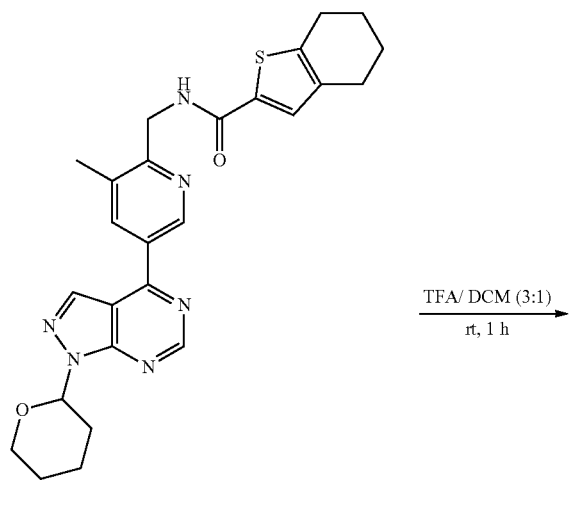

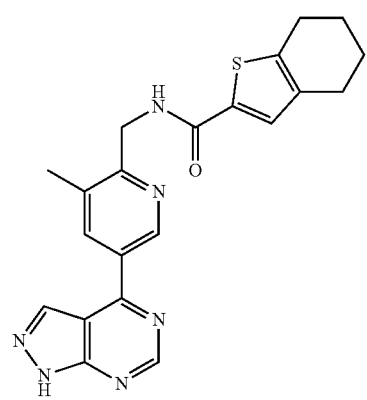

I-125

The Synthesis of N-((3-methyl-5-(1H-pyrazolo[3,4-d]pyrimidin-4-yl)pyridin-2-yl)methyl)-4,5,6,7-tetrahydrobenzo[b]thiophene-2-carboxamide (I-125)

A mixture of N-((3-methyl-5-(1-(tetrahydro-2H-pyran-2-yl)-1H-pyrazolo[3,4-d]pyrimidin-4-yl)pyridin-2-yl)methyl)-4,5,6,7-tetrahydrobenzo[b]thiophene-2-carboxamide (65 mg, 0.13 mmol) in TFA/DCM (3:1, 4 mL) was stirred at rt for 1 h, the solvent was reduced and the residue was purified by pre-HPLC (MeOH/H$_2$O with 0.05% NH$_3$.H$_2$O as mobile phase) to give the title compound (30 mg, yield: 57%) as a yellow solid. ESI-MS (M+H)$^+$: 405.1. $^1$H NMR (400 MHz, DMSO-d6) δ: 14.23 (br, 1H), 9.25 (d, J=2.4 Hz, 1H), 9.07 (s, 1H), 8.81-8.79 (m, 2H), 8.45 (d, J=1.2 Hz, 1H), 7.54 (s, 1H), 4.64 (d, J=5.6 Hz, 2H), 3.30 (s, 3H), 2.73 (t, J=5.2 Hz, 2H), 2.57 (t, J=5.2 Hz, 2H), 1.78-1.72 (m, 4H).

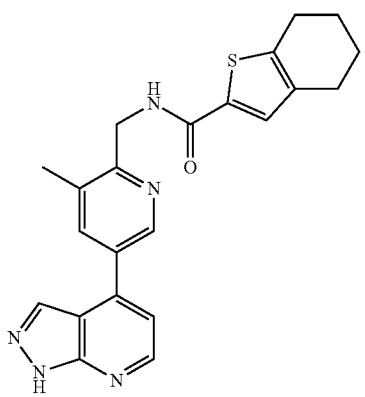

The Synthesis of N-((3-methyl-5-(1H-pyrazolo[3,4-b]pyridin-4-yl)pyridin-2-yl)methyl)-4,5,6,7-tetrahydrobenzo[b]thiophene-2-carboxamide (I-139)

Compound I-139 was prepared in a similar manner as described for compound I-125 except 4-chloro-1-(tetrahydro-2H-pyran-2-yl)-1H-pyrazolo[3,4-b]pyridine was substituted for 4-chloro-1-(tetrahydro-2H-pyran-2-yl)-1H-pyrazolo[3,4-d]pyrimidine to afford the title compound (30 mg, yield 51%) as a yellow solid. ESI-MS (M+H)$^+$: 404.2. $^1$H NMR (400 MHz, DMSO-d6) δ: 13.89 (br, 1H), 8.88 (d, J=2.0 Hz, 1H), 8.82 (t, J=4.8 Hz, 1H), 8.62 (d, J=4.8 Hz, 1H), 8.40 (s, 1H), 8.19 (s, 1H), 7.54 (s, 1H), 7.45 (d, J=4.8 Hz, 1H), 4.64 (d, J=5.2 Hz, 2H), 2.72 (t, J=6.4 Hz, 2H), 2.57 (t, J=6.4 Hz, 2H), 2.47 (s, 3H), 1.78-1.74 (m, 4H).

I-117

N-((4-methyl-6-(1H-pyrazolo[3,4-b]pyridin-4-yl)pyridin-3-yl)methyl)-4,5,6,7-tetrahydrobenzo[b]thiophene-2-carboxamide (I-117)

(55 mg, yield 68%). ESI-MS (M+H)$^+$: 404.1. $^1$H NMR (400 MHz, CD$_3$OD) δ: 8.60 (s, 1H), 8.57 (d, J=4.8 Hz, 1H), 8.53 (s, 1H), 7.96 (s, 1H), 7.61 (d, J=4.8 Hz, 1H), 7.29 (s, 1H), 4.58 (s, 2H), 2.70 (t, J=5.6 Hz, 2H), 2.54 (t, J=6.0 Hz, 2H), 2.50 (s, 3H), 1.77-1.71 (m, 4H).

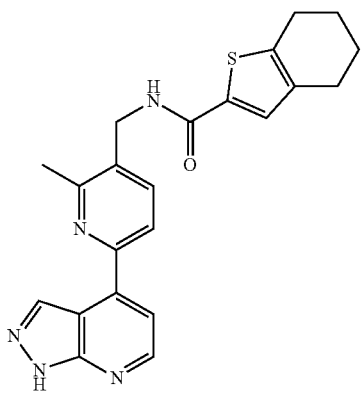

I-118

The Synthesis of N-((2-methyl-6-(1H-pyrazolo[3,4-b]pyridin-4-yl)pyridin-3-yl)methyl)-4,5,6,7-tetrahydrobenzo[b]thiophene-2-carboxamide (I-118)

(70 mg, yield 59%). ESI-MS (M+H)+: 404.1. ¹H NMR (400 MHz, CD₃OD) δ: 8.62 (s, 1H), 8.53 (d, J=5.2 Hz, 1H), 7.92 (d, J=8.0 Hz, 1H), 7.80 (d, J=8.0 Hz, 1H), 7.63 (d, J=5.6 Hz, 1H), 7.31 (s, 1H), 4.54 (s, 2H), 2.70 (t, J=5.6 Hz, 2H), 2.66 (s, 3H), 2.54 (t, J=5.2 Hz, 2H), 1.76-1.73 (m, 4H).

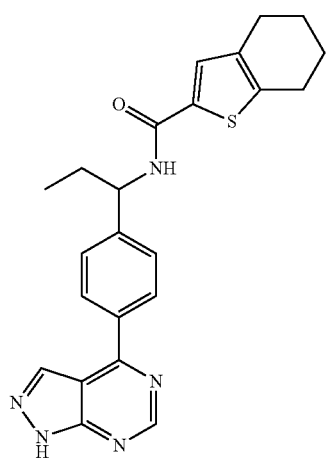

I-143

The Synthesis of N-(1-(4-(1H-pyrazolo[3,4-d]pyrimidin-4-yl)phenyl)propyl)-4,5,6,7-tetrahydrobenzo[b]thiophene-2-carboxamide (I-143)

Compound I-143 was prepared in a similar manner as described for compound I-85 except 1-(4-bromophenyl)propan-1-amine was substituted for (4-bromo-2-methylphenyl)methanamine to afford the title compound (70 mg, yield 40%) as a white solid. ESI-MS (M+H)+: 418.1. ¹H NMR (400 MHz, CDCl₃) δ: 9.10 (s, 1H), 8.43 (s, 1H), 8.17 (d, J=8.4 Hz, 2H), 7.57 (d, J=8.4 Hz, 2H), 7.24 (s, 1H), 6.12 (d, J=8.0 Hz, 1H), 5.16-5.11 (m, 1H), 2.78 (t, J=6.0 Hz, 2H), 2.61 (t, J=6.0 Hz, 2H), 2.01-1.94 (m, 2H), 1.88-1.78 (m, 4H), 1.01 (t, J=7.2 Hz, 3H).

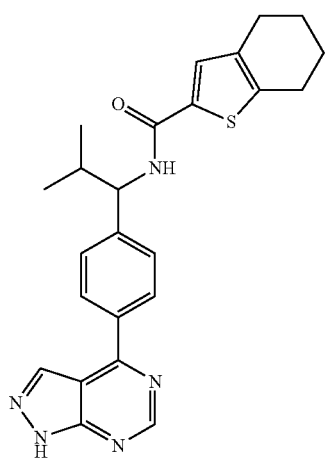

I-149

The Synthesis of N-(1-(4-(1H-pyrazolo[3,4-d]pyrimidin-4-yl)phenyl)-2-methylpropyl)-4,5,6,7-tetrahydrobenzo[b]thiophene-2-carboxamide (I-149)

Compound I-149 was prepared in a similar manner as described for compound I-85 except 1-(4-bromophenyl)-2-methylpropylamine was substituted for (4-bromo-2-methylphenyl)methanamine to afford the title compound (95 mg, yield 33%) as a white solid. ESI-MS (M+H)+: 432.1. ¹H NMR (400 MHz, DMSO-d₆) δ: 14.18 (s, 1H), 9.02 (s, 1H), 8.73 (s, 1H), 8.65 (d, J=8.8 Hz, 1H), 8.29 (d, J=8.4 Hz, 2H), 7.63 (s, 1H), 7.62 (d, J=8.4 Hz, 2H), 4.68 (t, J=9.2 Hz, 1H), 2.71-2.70 (m, 2H), 2.59-2.58 (m, 2H), 2.22-2.14 (m, 1H), 1.75-1.73 (m, 4H), 1.04 (d, J=6.4 Hz, 3H), 0.77 (d, J=6.4 Hz, 3H).

Scheme 22

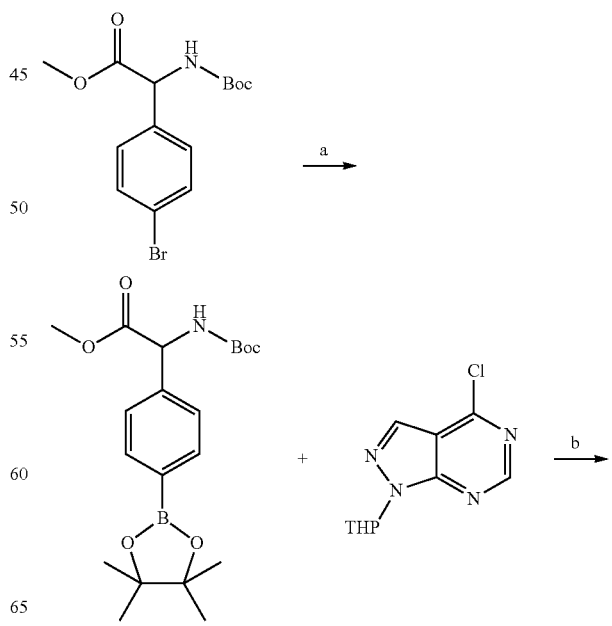

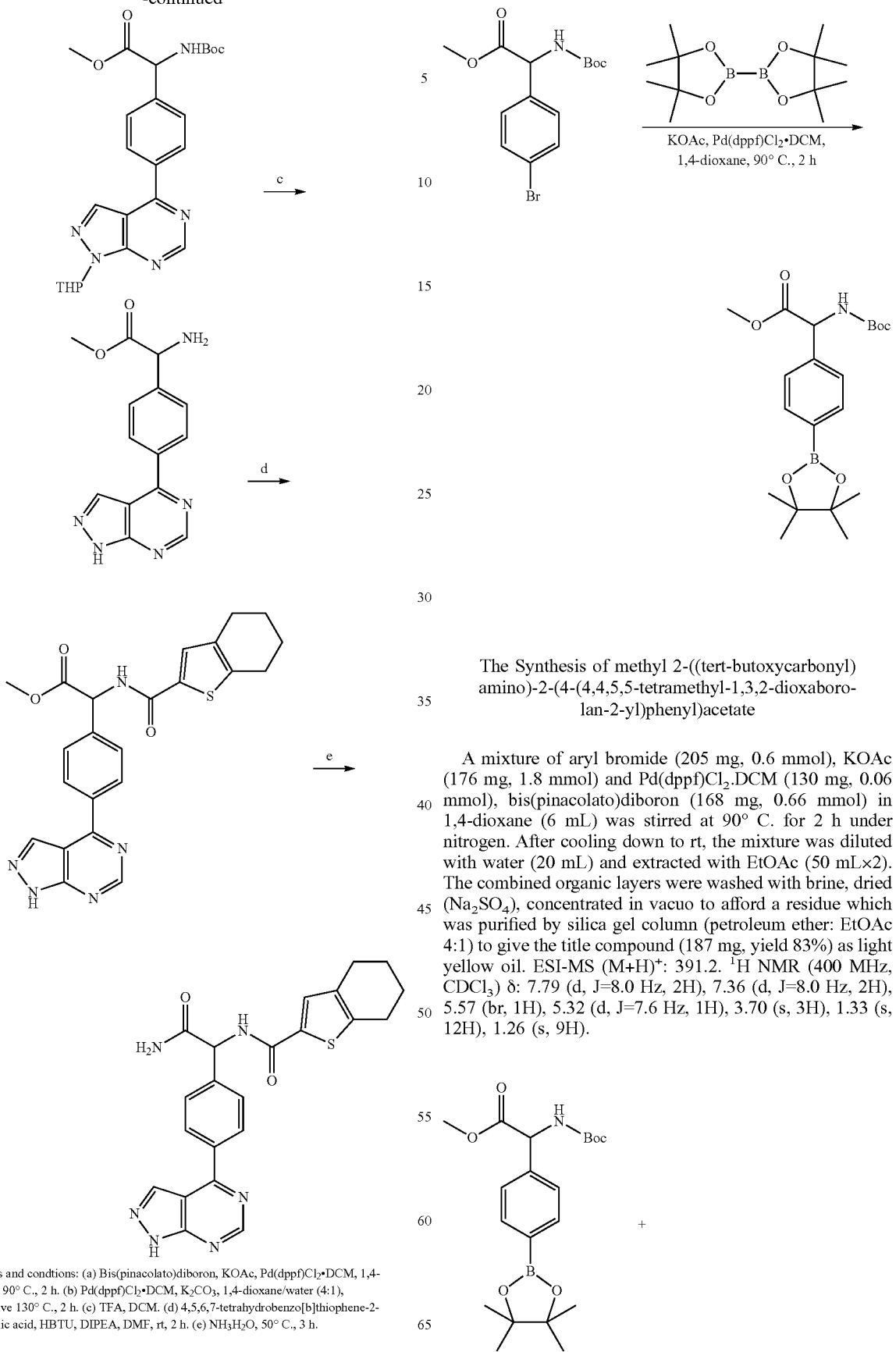

The Synthesis of methyl 2-((tert-butoxycarbonyl)amino)-2-(4-(4,4,5,5-tetramethyl-1,3,2-dioxaborolan-2-yl)phenyl)acetate A mixture of aryl bromide (205 mg, 0.6 mmol), KOAc (176 mg, 1.8 mmol) and Pd(dppf)Cl$_2$·DCM (130 mg, 0.06 mmol), bis(pinacolato)diboron (168 mg, 0.66 mmol) in 1,4-dioxane (6 mL) was stirred at 90° C. for 2 h under nitrogen. After cooling down to rt, the mixture was diluted with water (20 mL) and extracted with EtOAc (50 mL×2). The combined organic layers were washed with brine, dried (Na$_2$SO$_4$), concentrated in vacuo to afford a residue which was purified by silica gel column (petroleum ether: EtOAc 4:1) to give the title compound (187 mg, yield 83%) as light yellow oil. ESI-MS (M+H)$^+$: 391.2. $^1$H NMR (400 MHz, CDCl$_3$) δ: 7.79 (d, J=8.0 Hz, 2H), 7.36 (d, J=8.0 Hz, 2H), 5.57 (br, 1H), 5.32 (d, J=7.6 Hz, 1H), 3.70 (s, 3H), 1.33 (s, 12H), 1.26 (s, 9H).

Reagents and condtions: (a) Bis(pinacolato)diboron, KOAc, Pd(dppf)Cl$_2$·DCM, 1,4-dioxane, 90° C., 2 h. (b) Pd(dppf)Cl$_2$·DCM, K$_2$CO$_3$, 1,4-dioxane/water (4:1), microwave 130° C., 2 h. (c) TFA, DCM. (d) 4,5,6,7-tetrahydrobenzo[b]thiophene-2-carboxylic acid, HBTU, DIPEA, DMF, rt, 2 h. (e) NH$_3$H$_2$O, 50° C., 3 h.

-continued

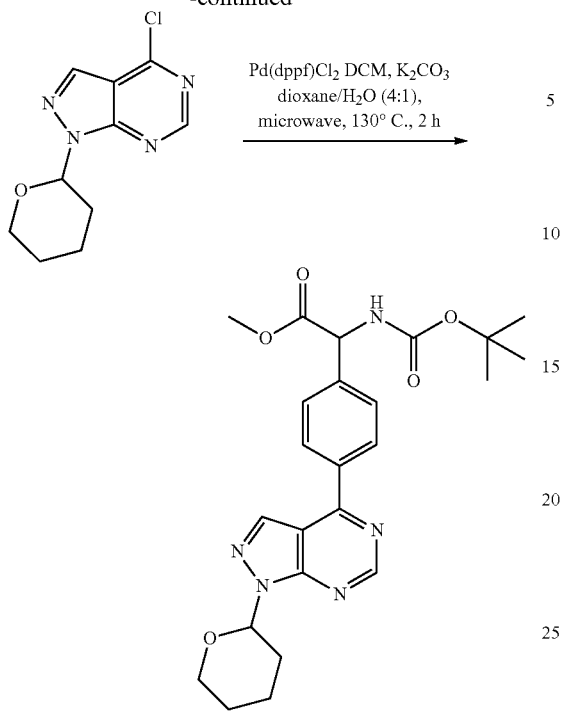

The Synthesis of methyl 2-((tert-butoxycarbonyl)amino)-2-(4-(1-(tetrahydro-2H-pyran-2-yl)-1H-pyrazolo[3,4-d]pyrimidin-4-yl)phenyl)acetate To a solution of boronate (1.7 g, 4.9 mmol) in dioxane/H$_2$O (4:1) (15 mL) was added 4-chloro-1-(tetrahydro-2H-pyran-2-yl)-1H-pyrazolo[3,4-d]pyrimidine (2.3 g, 4.9 mmol) followed by Pd(dppf)Cl$_2$.DCM (457 mg, 0.5 mmol) and K$_2$CO$_3$ (2.0 g, 14.7 mmol) under nitrogen. The mixture was stirred at 130° C. for 2 h. After cooling to rt, the mixture was diluted with water and extracted with EtOAc (100 mL×2). The organic layer was washed with brine (80 mL), dried (Na$_2$SO$_4$), filtered and concentrated. The residue was purified by column chromatography (silica, petroleum ether/EtOAc=5:1) to give compound the title compound (1.15 g, yield 82%) as yellow oil. ESI-MS (M+H)$^+$: 468.2. $^1$H NMR (400 MHz, CDCl$_3$) δ: 9.11 (s, 1H), 8.42 (s, 1H), 8.19 (d, J=8.0 Hz, 2H), 7.62 (d, J=8.0 Hz, 2H), 6.16-6.13 (m, 1H), 5.71 (br, 1H), 5.44 (s, 1H), 4.16-4.11 (m, 2H), 3.76 (s, 3H), 1.85-1.81 (m, 3H), 1.66-1.62 (m, 3H), 1.45 (s, 9H).

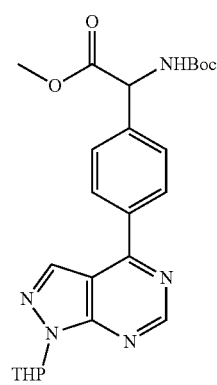

The Synthesis of methyl 2-(4-(1H-pyrazolo[3,4-d]pyrimidin-4-yl)phenyl)-2-aminoacetate A mixture of methyl 2-((tert-butoxycarbonyl)amino)-2-(4-(1-(tetrahydro-2H-pyran-2-yl)-1H-pyrazolo[3,4-d]pyrimidin-4-yl)phenyl)acetate (1.1 g, 2.4 mmol) in TFA/DCM (3:1, 40 mL) was stirred at rt for 1 h, the solvent was reduced to afford a residue (662 mg, yield 95%) which was used directly in the next step without further purification. ESI-MS (M+H)$^+$: 284.2.

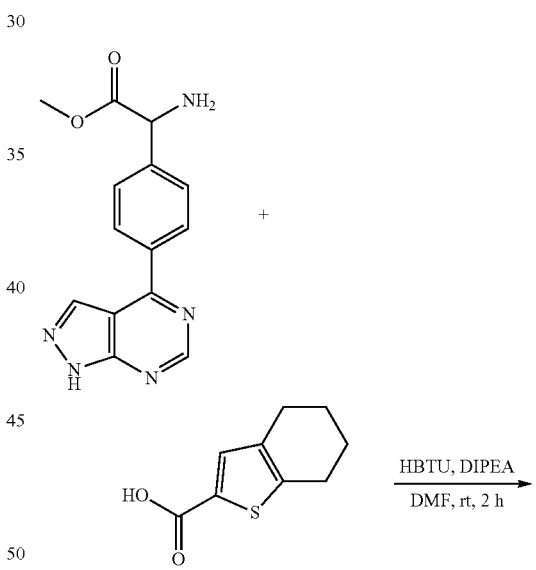

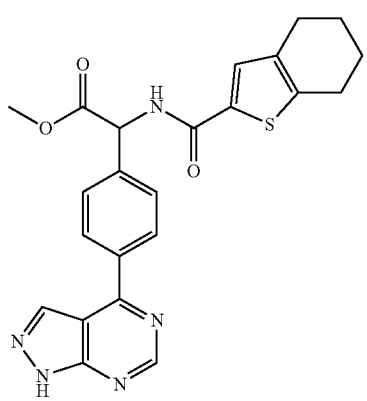

The Synthesis of methyl 2-(4-(1H-pyrazolo[3,4-d]pyrimidin-4-yl)phenyl)-2-(4,5,6,7-tetrahydrobenzo[b]thiophene-2-carboxamido)acetate This compound was prepared in a similar manner as described for compound I-1 except methyl 2-(4-(1H-pyrazolo[3,4-d]pyrimidin-4-yl)phenyl)-2-aminoacetate was substituted for (2-methyl-4-(7H-pyrrolo[2,3-d]pyrimidin-4-yl)phenyl)methanamine (940 mg, yield 90%) as yellow oil. ESI-MS (M+H)$^+$: 448.1. $^1$H NMR (400 MHz, CD$_3$OD) δ: 9.01 (s, 1H), 8.29 (d, J=8.4 Hz, 2H), 8.00 (s, 1H), 7.75 (d, J=8.4 Hz, 2H), 7.53 (s, 1H), 5.85 (s, 1H), 3.81 (s, 3H), 2.81 (t, J=5.6 Hz, 2H), 2.64 (t, J=5.6 Hz, 2H), 1.87-1.83 (m, 4H).

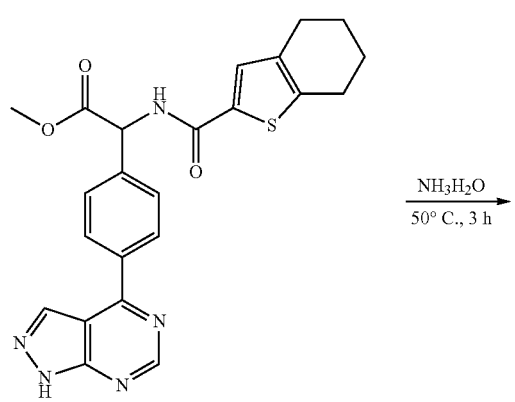

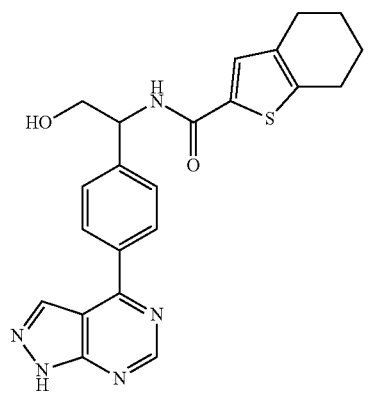

I-132

The Synthesis of N-(1-(4-(1H-pyrazolo[3,4-d]pyrimidin-4-yl)phenyl)-2-hydroxyethyl)-4,5,6,7-tetrahydrobenzo[b]thiophene-2-carboxamide (I-132)

Compound I-132 was prepared in a similar manner as described for compound I-107 except 2-amino-2-(4-bromophenyl)ethanol was substituted for 2-amino-2-(4-bromophenyl)ethanol to afford the title compound (30 mg, yield 10%) as yellow solid. ESI-MS (M+H)$^+$: 419.8. $^1$H NMR (400 MHz, CD$_3$OD) δ: 9.00 (s, 1H), 8.56 (s, 1H), 8.25 (d, J=8.4 Hz, 2H), 7.67 (d, J=8.4 Hz, 2H), 7.52 (s, 1H), 5.25 (t, J=6.4 Hz, 1H), 3.93 (d, J=6.4 Hz, 2H), 2.80 (t, J=6.0 Hz, 2H), 2.65 (t, J=6.0 Hz, 2H), 1.87-1.83 (m, 4H).

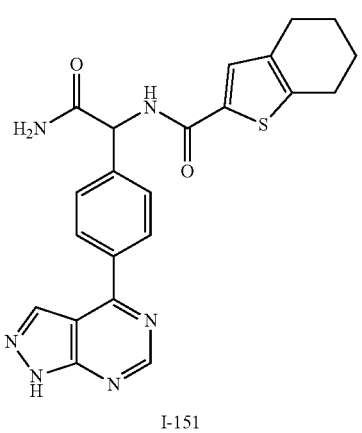

I-151

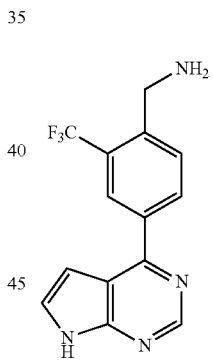

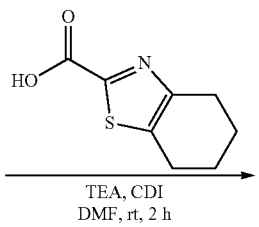

TEA, CDI
DMF, rt, 2 h

The Synthesis of N-(1-(4-(1H-pyrazolo[3,4-d]pyrimidin-4-yl)phenyl)-2-amino-2-oxoethyl)-4,5,6,7-tetrahydrobenzo[b]thiophene-2-carboxamide (I-151)

A mixture of ester (50 mg, 0.11 mmol) in ammonia (3 mL) and MeOH (2 mL) was stirred at 50° C. for 3 h. The mixture was purified by prep-HPLC (CH$_3$CN/H$_2$O with 0.05% NH$_3$.H$_2$O as mobile phase) to give the title compound (4.4 mg, yield 4%) as a yellow solid. ESI-MS (M+Na)$^+$: 455.0. $^1$H NMR (400 MHz, DMSO-d6) δ: 14.21 (br, 1H), 9.04 (s, 1H), 8.73 (d, J=6.4 Hz, 2H), 8.32 (d, J=8.4 Hz, 2H), 7.82 (s, 1H), 7.75-7.72 (m, 3H), 7.35 (s, 1H), 5.70 (d, J=8.0 Hz, 1H), 2.72 (t, J=6.0 Hz, 2H), 2.55 (t, J=6.0 Hz, 2H), 1.78-1.72 (m, 4H).

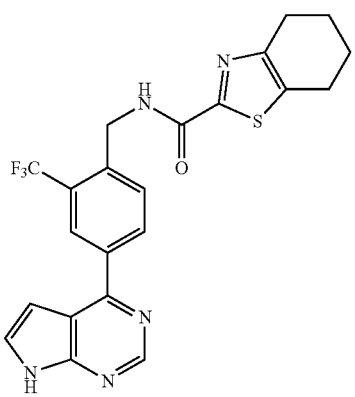

I-122

The Synthesis of N-(4-(7H-pyrrolo[2,3-d]pyrimidin-4-yl)-2-(trifluoromethyl)benzyl)-4,5,6,7-tetrahydrobenzo[d]thiazole-2-carboxamide (I-122)

Compound I-122 was prepared in a similar manner as described for compound I-3 except 4,5,6,7-tetrahydrobenzo[d]thiazole-2-carboxylic acid was substituted for 4-(tert-butyl)benzoic acid to afford the title compound (40 mg, yield: 21%) as a yellow solid. ESI-MS (M+H)$^+$: 458.2. $^1$H NMR (400 MHz, CD$_3$OD) δ: 8.83 (s, 1H), 8.47 (s, 1H), 8.36 (d, J=8.4 Hz, 1H), 7.79 (d, J=8.4 Hz, 1H), 7.59 (d, J=4.0 Hz, 1H), 6.88 (d, J=3.6 Hz, 1H), 4.90 (s, 2H), 2.90-2.84 (m, 4H), 1.94-1.92 (m, 4H).

The Synthesis of N-(1-(2-methyl-4-(1H-pyrazolo[3,4-d]pyrimidin-4-yl)phenyl)ethyl)-4,5,6,7-tetrahydrobenzo[d]thiazole-2-carboxamide (I-127)

Compound I-127 was prepared in a similar manner as described for compound I-128 except 4,5,6,7-tetrahydrobenzo[d]thiazole-2-carboxylic acid was substituted for 2-(tert-butyl)thiazole-5-carboxylic acid to afford the title compound (46 mg, yield 32%). ESI-MS (M+H)$^+$: 419.2. $^1$H NMR (400 MHz, CD$_3$OD) δ: 8.98 (s, 1H), 8.56 (s, 1H), 8.08-8.07 (m, 2H), 7.71 (d, J=6.4 Hz, 1H), 5.49 (q, J=5.6 Hz, 1H), 2.89-2.84 (m, 4H), 2.61 (s, 3H), 1.93-1.92 (m, 4H), 1.63 (d, J=5.6 Hz, 3H).

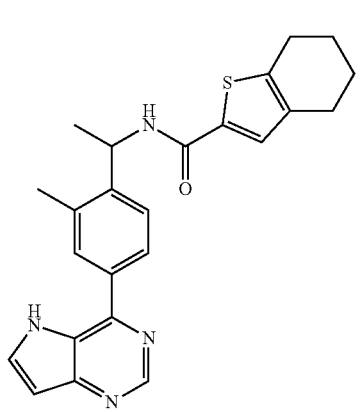

I-123

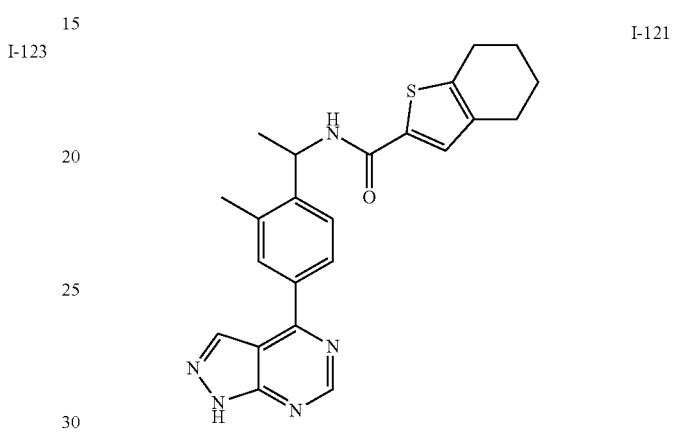

I-121

The Synthesis of N-(1-(2-methyl-4-(5H-pyrrolo[3,2-d]pyrimidin-4-yl)phenyl)ethyl)-4,5,6,7-tetrahydrobenzo[b]thiophene-2-carboxamide (I-123)

Compound I-123 was prepared in a similar manner as described for compound I-78 except 4-chloro-5H-pyrrolo[3,2-d]pyrimidine was substituted for 4-chloro-7-tosyl-7H-pyrrolo[2,3-d]pyrimidine to afford the title compound (32 mg, yield 20%) as a yellow solid. ESI-MS (M+H)$^+$: 417.2. $^1$H NMR (400 MHz, CD$_3$OD) δ: 8.71 (s, 1H), 7.72-7.68 (m, 3H), 7.52 (d, J=8.0 Hz, 1H), 7.34 (s, 1H), 6.59 (d, J=3.2 Hz, 1H), 5.33-5.30 (m, 1H), 2.66-2.63 (m, 2H), 2.52-2.49 (m, 2H), 2.44 (s, 3H), 1.73-1.67 (m, 4H), 1.45 (d, J=6.8 Hz, 3H).

The Synthesis of N-(1-(2-methyl-4-(1H-pyrazolo[3,4-d]pyrimidin-4-yl)phenyl)ethyl)-4,5,6,7-tetrahydrobenzo[b]thiophene-2-carboxamide (I-121)

Compound I-121 was prepared in a similar manner as described for compound I-128 except 4,5,6,7-tetrahydrobenzo[b]thiophene-2-carboxylic acid was substituted for 2-(tert-butyl)thiazole-5-carboxylic acid to afford the title compound (57 mg, yield 36%). ESI-MS (M+H)$^+$: 418.1. $^1$H NMR (400 MHz, DMSO-d6) δ: 14.17 (s, 1H), 9.00 (s, 1H), 8.79 (d, J=8.0 Hz, 1H), 8.72 (s, 1H), 8.13 (d, J=8.0 Hz, 1H), 8.09 (s, 1H), 7.64 (d, J=7.2 Hz, 2H), 5.31-5.27 (m, 1H), 2.71 (s, 3H), 2.59 (s, 3H), 1.74 (d, J=5.2 Hz, 4H), 1.47 (d, J=6.8 Hz, 3H).

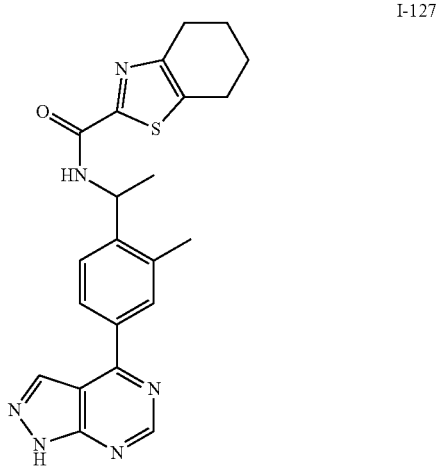 [SMILES: Cc1cc(-c2ncnc3[nH]ncc23)ccc1C(C)NC(=O)c1nc2c(s1)CCCC2]

I-127

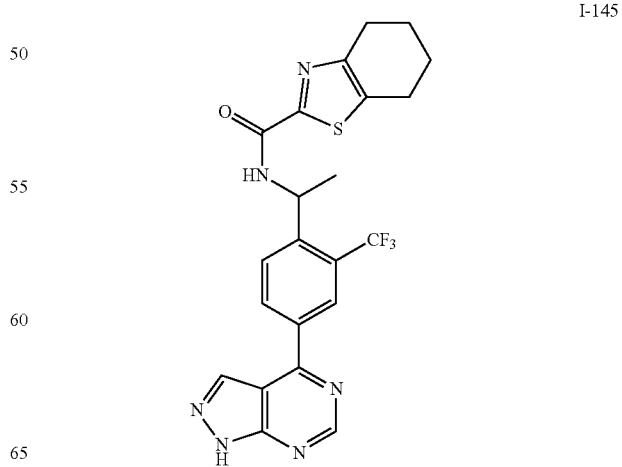

I-145

The Synthesis of N-(1-(4-(1H-pyrazolo[3,4-d]pyrimidin-4-yl)-2-(trifluoromethyl)phenyl)ethyl)-4,5,6,7-tetrahydrobenzo[d]thiazole-2-carboxamide (I-145)

Compound I-145 was prepared in a similar manner as described for compound I-108 except 1-(4-bromo-2-(trifluoromethyl)phenyl)ethanamine was substituted for (4-bromo-2-(trifluoromethyl)phenyl)methanamine to afford the title compound ESI-MS (M+H)$^+$: 473.2. $^1$H NMR (400 MHz, DMSO-d$_6$) δ: 14.32 (br, 1H), 9.61 (d, J=7.6 Hz, 1H), 9.08 (s, 1H), 8.77 (s, 1H), 8.62-8.56 (m, 2H), 8.16 (d, J=8.0 Hz, 1H), 5.50-5.45 (m, 1H), 2.86-2.80 (m, 4H), 1.84-1.80 (m, 4H), 1.57 (d, J=6.8 Hz, 3H).

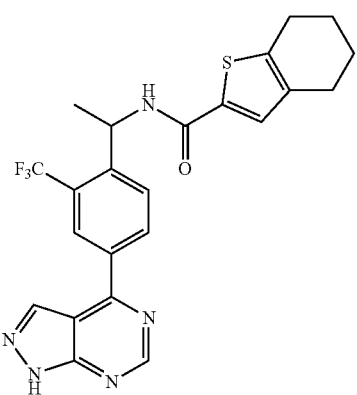

I-135

The Synthesis of N-(1-(4-(1H-pyrazolo[3,4-d]pyrimidin-4-yl)-2-(trifluoromethyl)phenyl)ethyl)-4,5,6,7-tetrahydrobenzo[b]thiophene-2-carboxamide (I-135)

Compound I-135 was prepared in a similar manner as described for compound I-145 except 4,5,6,7-tetrahydrobenzo[b]thiophene-2-carboxylic acid was substituted for 2-(tert-butyl)thiazole-5-carboxylic acid to afford the title compound (44 mg, yield 20%). ESI-MS (M+H)$^+$: 472.2. $^1$H NMR (400 MHz, CD$_3$OD) δ: 9.02 (s, 1H), 8.57-8.55 (m, 2H), 8.49 (d, J=8.4 Hz, 1H), 7.96 (d, J=8.4 Hz, 1H), 7.49 (s, 1H), 5.54 (q, J=6.8 Hz, 1H), 2.77 (t, J=5.2 Hz, 2H), 2.65 (t, J=5.2 Hz, 2H), 1.87-1.80 (m, 4H), 1.59 (d, J=6.8 Hz, 3H).

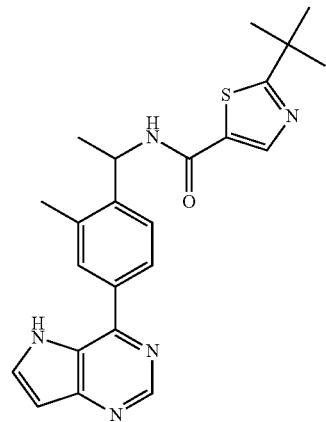

I-134

The Synthesis of 2-(tert-butyl)-N-(1-(2-methyl-4-(5H-pyrrolo[3,2-d]pyrimidin-4-yl)phenyl)ethyl)thiazole-5-carboxamide (I-134)

Compound I-134 was prepared in a similar manner as described for compound I-46 except 4-chloro-5H-pyrrolo[3,2-d]pyrimidine was substituted for 4-chloro-6-(1-methyl-1H-pyrazol-4-yl)-5H-pyrrolo[3,2-d]pyrimidine to afford the title compound (26 mg, yield 22%) as grey solid. ESI-MS (M+H)$^+$: 420.2. $^1$H NMR (400 MHz, DMSO-d$_6$) δ: 11.95 (s, 1H), 9.10 (d, J=7.6 Hz, 1H), 8.87 (s, 1H), 8.39 (s, 1H), 7.92-7.87 (m, 3H), 7.63 (d, J=7.6 Hz, 1H), 6.98 (br, 1H), 5.33 (q, J=7.2 Hz, 1H), 1.50 (d, J=6.8 Hz, 3H), 1.38 (s, 3H), 1.35 (s, 9H).

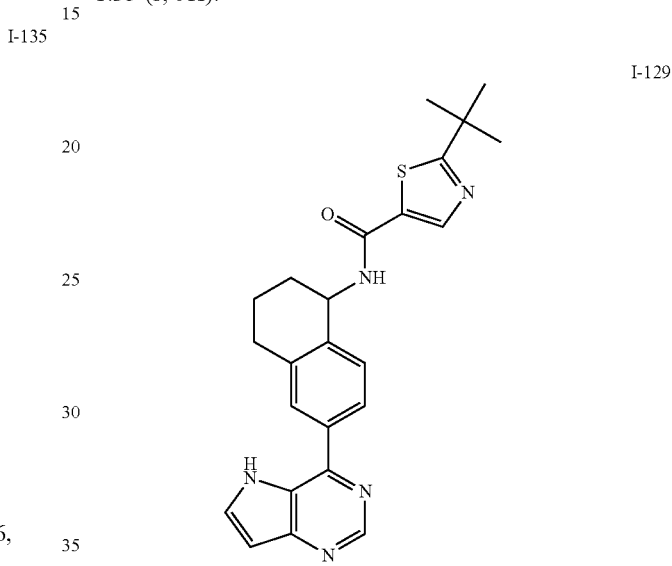

I-129

The Synthesis of N-(6-(5H-pyrrolo[3,2-d]pyrimidin-4-yl)-1,2,3,4-tetrahydronaphthalen-1-yl)-2-(tert-butyl)thiazole-5-carboxamide (I-129)

Compound I-129 was prepared in a similar manner as described for compound I-37 except 4-chloro-5H-pyrrolo[3,2-d]pyrimidine was substituted for 4-chloro-6-(1-methyl-1H-pyrazol-4-yl)-5H-pyrrolo[3,2-d]pyrimidine to afford the title compound (70 mg, yield 45%). ESI-MS (M+H)$^+$: 432.2. $^1$H NMR (400 MHz, DMSO-d$_6$) δ: 11.93 (s, 1H), 9.04 (d, J=8.4 Hz, 1H), 8.87 (s, 1H), 8.34 (s, 1H), 7.93-7.88 (m, 3H), 7.41 (d, J=8.0 Hz, 1H), 6.70 (d, J=2.8 Hz, 1H), 5.27-5.26 (m, 1H), 2.95-2.94 (m, 2H), 2.06-2.03 (m, 2H), 1.91-1.84 (m, 2H), 1.39 (s, 9H).

Example 15

Scheme 23

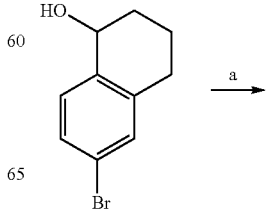

233
-continued

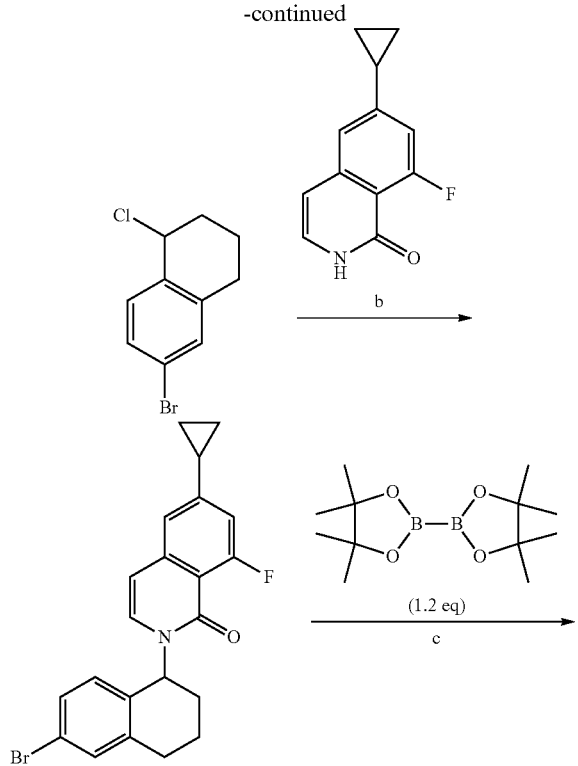

234
-continued

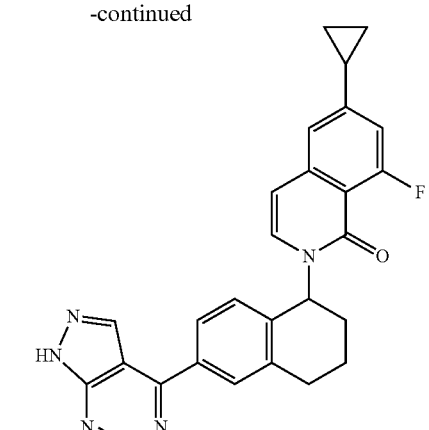

Reagent and condition: (a) SOCl₂ (3.0 eq), toluene, 60° C., 5 h. (b). NaH (2.0 eq), DMF (dry), NaI (cat), 80° C., 3 h. (c) Pd(dppf)Cl₂ (0.01 eq), KOAc (3.0 eq), 1,4-dioxane, 100° C., 2 h. (d) Pd(dppf)Cl₂ (0.01 eq), K₂CO₃ (2.0 eq), dioxane/H₂O (4:1), sealed tube, 130° C., 16 h. (e) TFA/DCM (3:1), rt, 2 h 2-(6-(1H-pyrazolo[3,4-d]pyrimidin-4-yl)-1,2,3,4-tetrahydronaphthalen-1-yl)-6-cyclopropyl-8-fluor-oisoquinolin-1(2H)-one

I-138

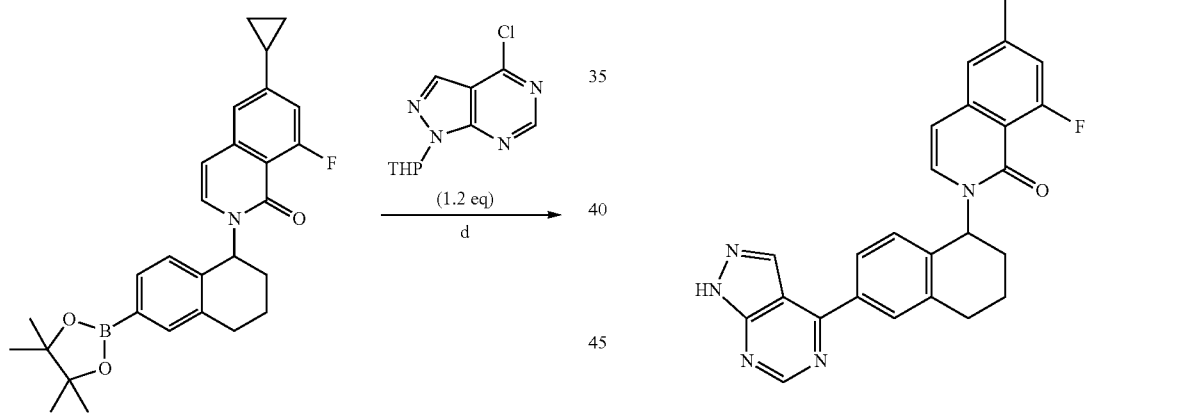

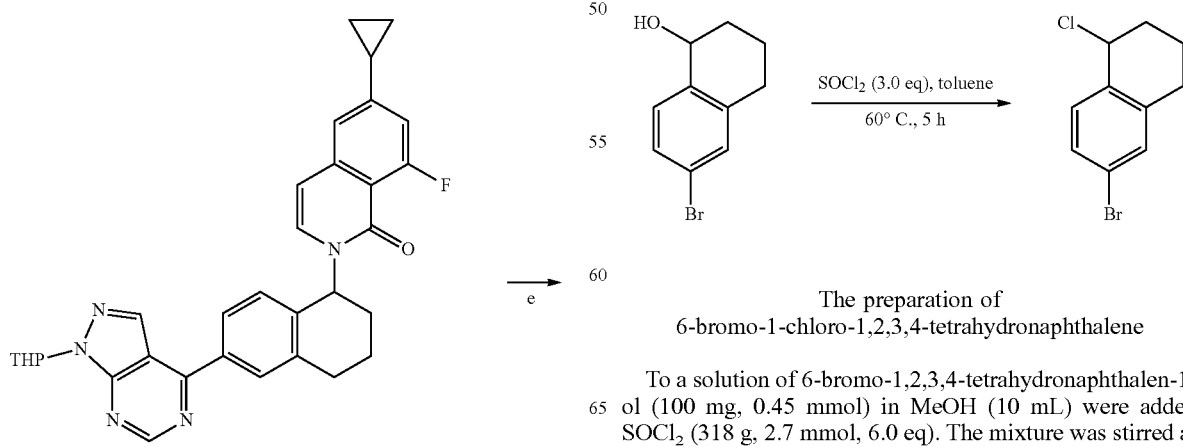

The preparation of 6-bromo-1-chloro-1,2,3,4-tetrahydronaphthalene

To a solution of 6-bromo-1,2,3,4-tetrahydronaphthalen-1-ol (100 mg, 0.45 mmol) in MeOH (10 mL) were added SOCl₂ (318 g, 2.7 mmol, 6.0 eq). The mixture was stirred at 70° C. for 1.5 h. The mixture was concentrated to give 6-bromo-1-chloro-1,2,3,4-tetrahydronaphthalene as a yellow solid (60 mg, yield 56%). ESI-MS (M+H)+: 245.0.

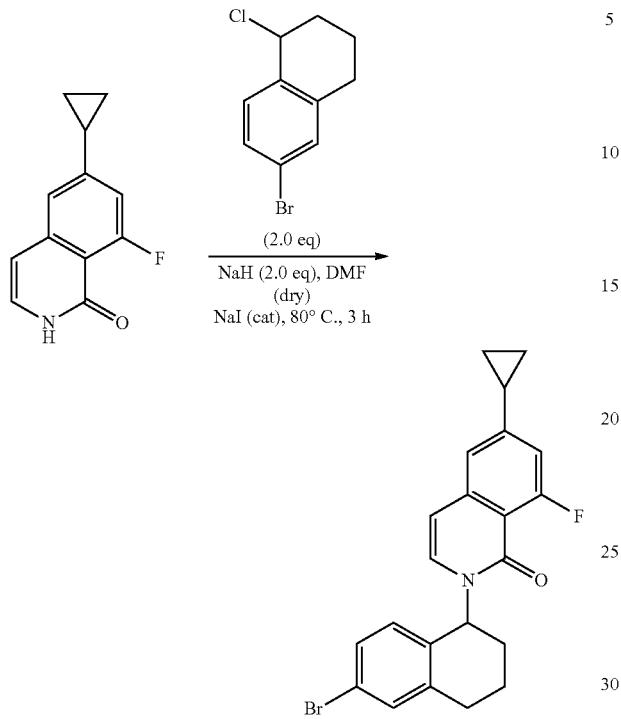

The preparation of 2-(6-bromo-1,2,3,4-tetrahydronaphthalen-1-yl)-6-cyclopropyl-8-fluoroisoquinolin-1(2H)-one To a solution of 6-cyclopropyl-8-fluoroisoquinolin-1(2H)-one (205 mg, 0.5 mmol) in DMF (dry, 10 mL) were added NaH (40 mg, 2 mmol, 2 eq) and stirred at rt 1 h, then 6-bromo-1-chloro-1,2,3,4-tetrahydronaphthalene (244 mg, 2.0 eq) and NaI (cat) was added. The mixture was stirred at 80° C. for 2 h under N₂. Then the mixture was cooled to rt, diluted with water (30 mL) and extracted with EA (50 mL×3). The organic layer was washed with H₂O (50 mL) and brine (50 mL), dried (Na₂SO₄), filtered and concentrated. The residue was purified by silica gel column (EA/PE=1:5) to give 2-(6-bromo-1,2,3,4-tetrahydronaphthalen-1-yl)-6-cyclopropyl-8-fluoroisoquinolin-1(2H)-one as yellow solid (200 mg, yield 49%). ESI-MS (M+H)+: 412.1.

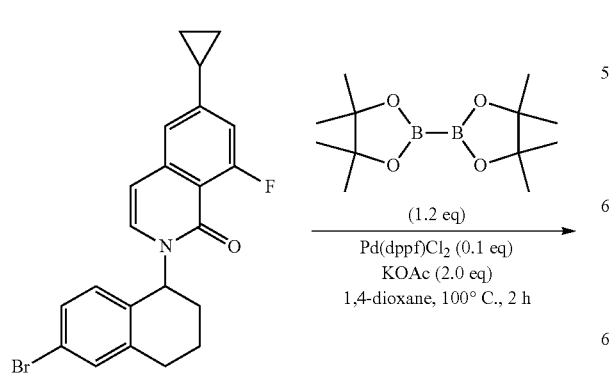

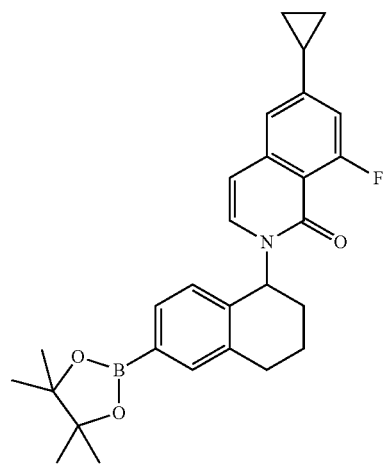

The preparation of 6-cyclopropyl-8-fluoro-2-(6-(4,4,5,5-tetramethyl-1,3,2-dioxaborolan-2-yl)-1,2,3,4-tetrahydronaphthalen-1-yl)isoquinolin-1(2H)-one To a solution of 2-(6-bromo-1,2,3,4-tetrahydronaphthalen-1-yl)-6-cyclopropyl-8-fluoroisoquinolin-1(2H)-one (205 mg, 0.5 mmol) in 1,4-dioxane (5 mL) were added 4,4,4',4',5,5,5',5'-octamethyl-2,2'-bi(1,3,2-dioxaborolane) (152 mg, 0.6 mmol), KOAc (98 mg, 1.0 mmol) and Pd(dppf)Cl₂DCM (41 mg, 0.05 mmol) under nitrogen. The mixture was stirred at 100° C. for 2 h. After cooling down to rt, the mixture was diluted with water (50 mL) and extracted with ethyl acetate (100 mL). The combined organic layer was washed with brine, dried, concentrated and purified by silica gel column (PE:EA=4:1) to give 6-cyclopropyl-8-fluoro-2-(6-(4,4,5,5-tetramethyl-1,3,2-dioxaborolan-2-yl)-1,2,3,4-tetrahydronaphthalen-1-yl)isoquinolin-1(2H)-one as yellow solid (200 mg, yield 89%). ESI-MS (M+H)+: 460.1.

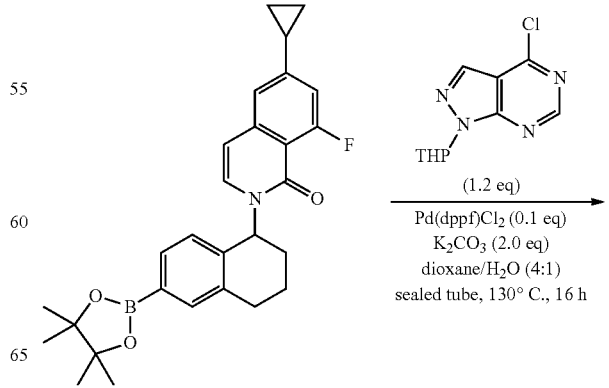

237

-continued

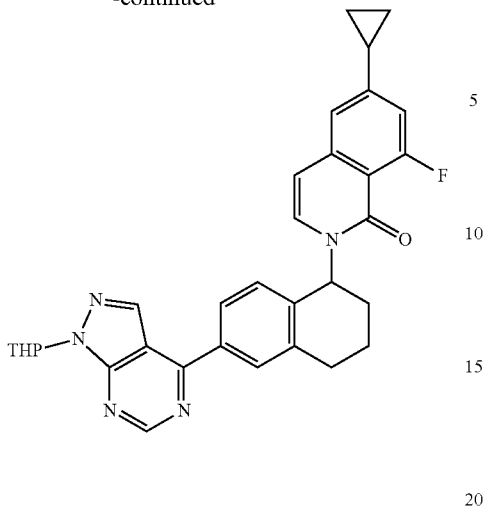

The preparation of 6-cyclopropyl-8-fluoro-2-(6-(1-(tetrahydro-2H-pyran-2-yl)-1H-pyrazolo[3,4-d]pyrimidin-4-yl)-1,2,3,4-tetrahydronaphthalen-1-yl)isoquinolin-1(2H)-one To a solution of 6-cyclopropyl-8-fluoro-2-(6-(4,4,5,5-tetramethyl-1,3,2-dioxaborolan-2-yl)-1,2,3,4-tetrahydronaphthalen-1-yl)isoquinolin-1(2H)-one (200 mg, 0.43 mmol) in 1,4-dioxane/water (5 mL, 4:1) were added 4-chloro-1-(tetrahydro-2H-pyran-2-yl)-1H-pyrazolo[3,4-d]pyrimidine (123 mg, 0.52 mmol), K$_2$CO$_3$ (123 mg, 0.9 mmol) and Pd(dppf)Cl$_2$DCM (41 mg, 0.05 mmol) under nitrogen. The mixture was stirred at 130° C. for 16 h. After cooling down to rt, the mixture was diluted with water (50 mL) and extracted with ethyl acetate (100 mL). The combined organic layer was washed with brine, dried, concentrated and purified by silica gel column (PE:EA=3:1) to give 6-cyclopropyl-8-fluoro-2-(6-(1-(tetrahydro-2H-pyran-2-yl)-1H-pyrazolo[3,4-d]pyrimidin-4-yl)-1,2,3,4-tetrahydronaphthalen-1-yl)isoquinolin-1(2H)-one as yellow solid (40 mg, yield 49%). ESI-MS (M+H)$^+$: 536.1.

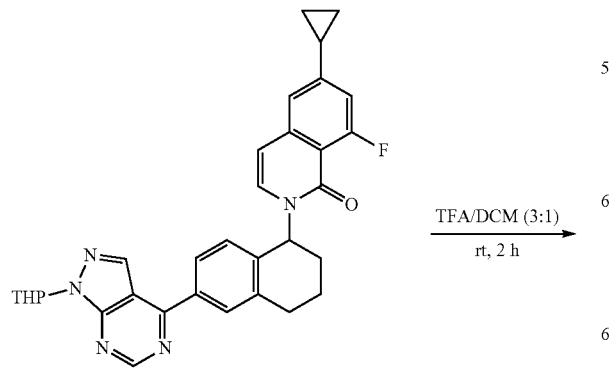

TFA/DCM (3:1)
rt, 2 h

238

-continued

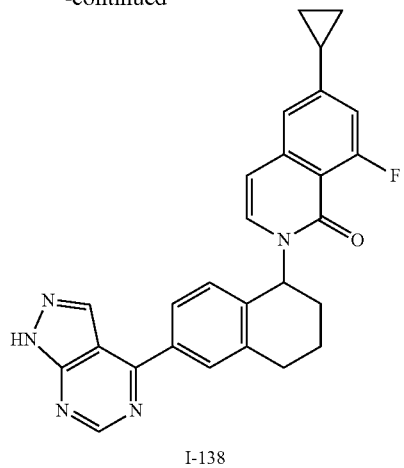

I-138

The preparation of 2-(6-(1H-pyrazolo[3,4-d]pyrimidin-4-yl)-1,2,3,4-tetrahydronaphthalen-1-yl)-6-cyclopropyl-8-fluoroisoquinolin-1(2H)-one (I-138)

To a solution of 6-cyclopropyl-8-fluoro-2-(6-(1-(tetrahydro-2H-pyran-2-yl)-1H-pyrazolo[3,4-d]pyrimidin-4-yl)-1,2,3,4-tetrahydronaphthalen-1-yl)isoquinolin-1(2H)-one (55 mg, 0.10 mmol) in DCM (1 mL) was added TFA (3 mL). The mixture was stirred at rt for 1 h. After concentrated, the residue was purified by pre-HPLC (MeCN/H$_2$O with 0.05% NH$_3$.H$_2$O as mobile phase) to give 2-(6-(1H-pyrazolo[3,4-d]pyrimidin-4-yl)-1,2,3,4-tetrahydronaphthalen-1-yl)-6-cyclopropyl-8-fluoroisoquinolin-1(2H)-one as yellow solid (20 mg, yield 43%). ESI-MS (M+H)$^+$: 452.2. $^1$H NMR (400 MHz, CD$_3$OD) δ: 8.85 (s, 1H), 8.43 (s, 1H), 7.98 (s, 1H), 7.87 (d, J=8.0 Hz, 1H), 7.01 (s, 1H), 6.97 (d, J=8.0 Hz, 1H), 6.92 (d, J=8.0 Hz, 1H), 6.80 (d, J=18.4 Hz, 1H), 6.45 (d, J=8.0 Hz, 1H), 6.27 (s, 1H), 3.21-2.95 (m, 2H), 2.20-1.87 (m, 5H), 1.20-1.01 (m, 2H), 0.78-0.67 (m, 2H).

Example 16

Scheme 24

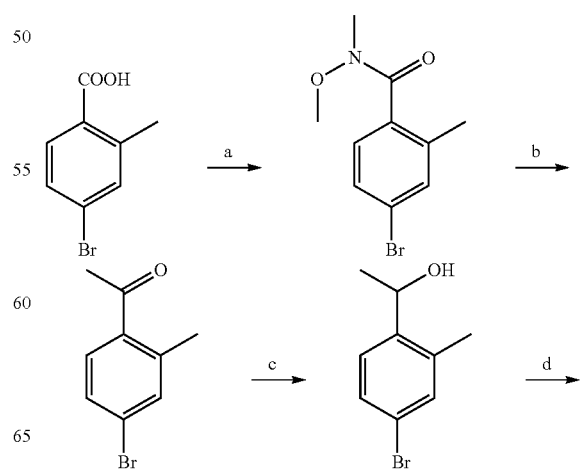

239
-continued

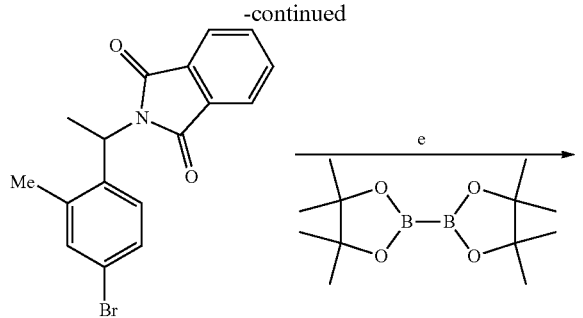

240
-continued

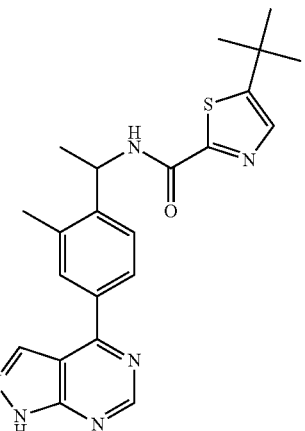

Reagent and condition: (a) N,O-dimethylhydroxylamine hydrochloride, HBTU (1.2 eq), DIPEA (3.0 eq), DMF, 16 h. yield 79%. (b) MeMgCl (3.0 eq), THF, -78° C.~rt, 7 h. yield 57%. (c) Ph₃P (1.5 eq), DIAD (1.5 eq), THF, rt, 3 h, yield 31%. (d) isoindoline-1,3-dionem Ph₃P (1.5 eq), DIAD (1.5 eq), THF, rt, 3 h, yield 31%. (e) Pd(dppf)Cl₂ (0.01 eq), KOAc (3.0 eq), dry 1,4-dioxane, MW, 100° C., 16 h, yield 45%. (f) Pd(dppf)Cl₂ (0.01 eq) K₂CO₃ (2.0 eq), dioxane/H₂O (4:1), sealed tube, 120° C., 16 h. yield 31%. (g) 1) N₂H₄•H₂O (10.0 eq), EtOH, rt, 3 h, 2) TFA/DCM, rt, 1 h. (h) HBTU (1.5 eq), DIPEA, (4.0 eq), DMF, rt, 16 h, yield 25%.

2-(tert-butyl)-N-(1-(2-methyl-4-(1H-pyrazolo[3,4-d]pyrimidin-4-yl)phenyl)ethyl)thiazole-5-carboxamide

I-128

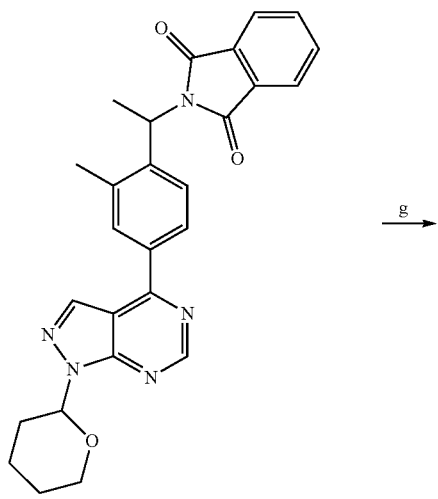

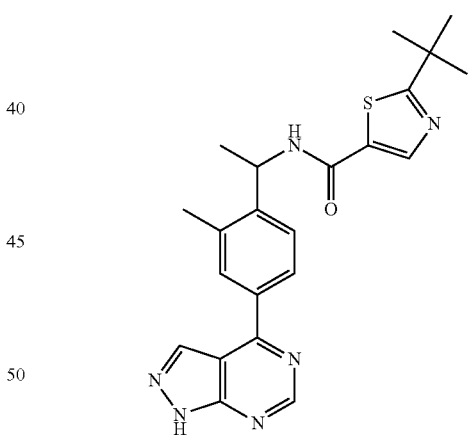

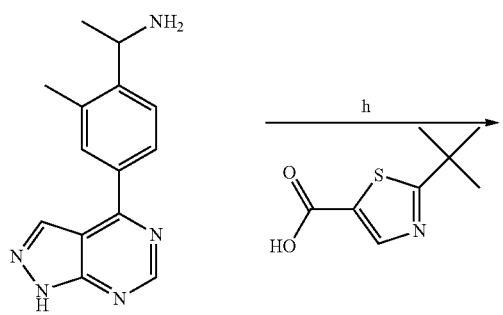

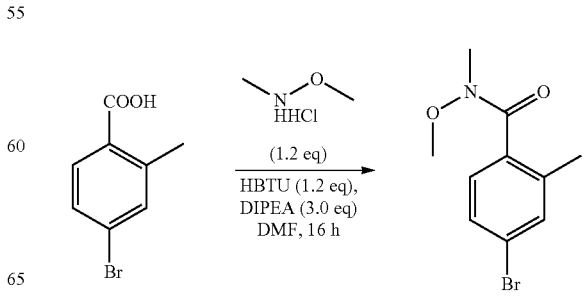

The preparation of 4-bromo-N-methoxy-N,2-dimethylbenzamide

To a solution of 4-bromo-2-methylbenzoic acid (5.3 g, 24.8 mmol) in DMF (50 mL) were added HBTU (11.3 g, 30.0 mmol), DIPEA (9.6 g, 74.4 mmol) and N,O-dimethylhydroxylamine hydrochloride (2.9 g, 30 mmol). The reaction mixture was stirred at rt for 16 h. Then, the mixture was quenched with H$_2$O (50 mL), and extracted with EA (100 mL×3). The organic layer was washed with brine (100 mL×3), dried and concentrated. The residue was purified by column chromatography (silica, petroleum ether/EtOAc=8:1 to 6:1) to give 4-bromo-N-methoxy-N,2-dimethylbenzamide (5.1 g, yield 79%) as a colorless oil. ESI-MS (M+H)$^+$: 258.0. $^1$H NMR (400 MHz, CDCl$_3$) δ: 7.38 (s, 1H), 7.34 (d, J=8.0 Hz, 1H), 7.15 (d, J=8.0 Hz, 1H), 3.31 (s, 3H), 2.80 (s, 3H), 2.31 (s, 3H).

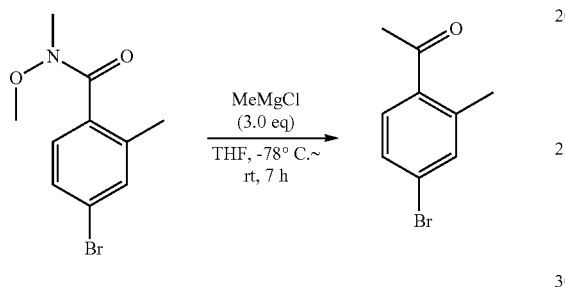

The preparation of 1-(4-bromo-2-methylphenyl)ethanone

In a separate flame-dried Schlenk flask, 4-bromo-N-methoxy-N,2-dimethylbenzamide (5.1 g, 20.0 mmol) was dissolved in dry THF (80 mL) and MeMgCl (20 mL, 60.0 mmol) was added via syringe at −78° C. under nitrogen. After stirring at this temperature for 1 h, the mixture was allowed to warm up to rt and stirred for another 6 h. Then, the mixture was quenched with H$_2$O (100 mL) and extracted with EA (100 mL×2). The combined organic layers were dried with Na$_2$SO$_4$ and concentrated under reduced pressure. The residue was purified by column chromatography (silica, petroleum ether/EtOAc=10:1) to give 1-(4-bromo-2-methylphenyl)ethanone as slight yellow oil (2.4 g, yield: 57%). ESI-MS (M+H)$^+$: 312.9. $^1$H NMR (400 MHz, CDCl$_3$) δ: 7.60 (d, J=8.4 Hz, 1H), 7.42-7.39 (m, 2H), 2.55 (s, 3H), 2.50 (s, 3H).

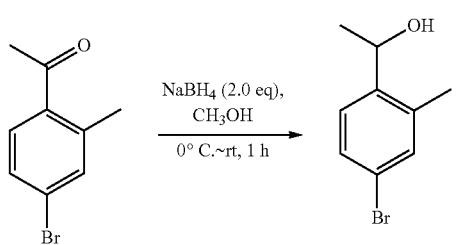

The preparation of 1-(4-bromo-2-methylphenyl)ethanol

To a solution of 1-(4-bromo-2-methylphenyl)ethanone (2.4 g, 11.3 mmol) in CH$_3$OH (20 mL) at 0° C., NaBH$_4$ (836 mg, 22.6 mmol) was added carefully. The reaction solution was stirred at rt for 1 h. Then the solvent was concentrated via rotary evaporator and the residue was quenched with H$_2$O (80 mL) and extracted with ethyl acetate (100 mL×2). The combined organics were washed with brine (100 mL), dried (Na$_2$SO$_4$), filtered and concentrated via rotary evaporator. The crude product (2.2 g, yield 90%) was used directly in the next step without further purification. ESI-MS (M+H)$^+$: 215.0.

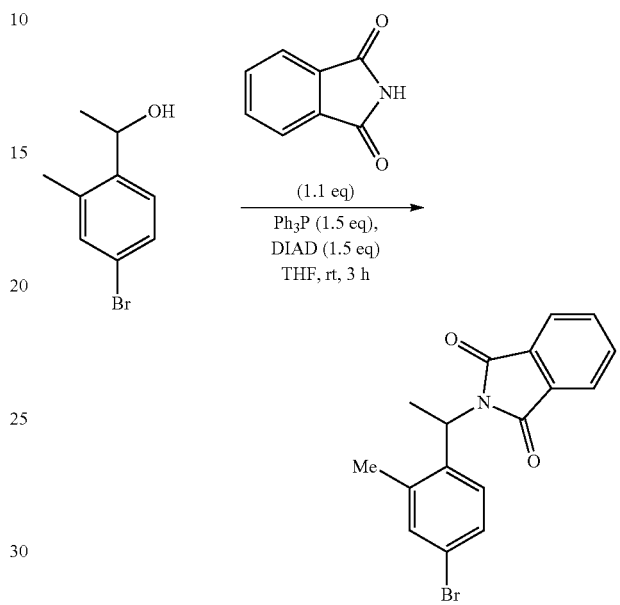

The preparation of 2-(1-(4-bromo-2-methylphenyl)ethyl)isoindoline-1,3-dione

To a solution of 1-(4-bromo-2-methylphenyl)ethanol (1.3 g, 6.1 mmol) and phthalic amide (0.9 g, 6.1 mmol) in THF (100 mL) was added PPh$_3$ (2.34 g, 9.2 mmol) under nitrogen. After cooling to 0° C. by ice-water, DIAD (1.86 g, 9.2 mmol) was added in one portion. The resulting mixture was stirred at room temperature for 16 h. The reaction mixture was diluted with water (100 mL) and extracted with EtOAc (100 mL×2). The combined organic layers were dried over Na$_2$SO$_4$ and concentrated under reduced pressure. The residue was purified by column chromatography (silica gel, Petroleum ether/EtOAc=8:1) to give the title product 2-(1-(4-bromo-2-methylphenyl)ethyl) isoindoline-1,3-dione (0.64 g, yield 31%) as a white solid. $^1$H NMR (400 MHz, CDCl$_3$) δ: 7.80-7.78 (m, 2H), 7.70-7.68 (m, 2H), 7.66 (d, J=7.2 Hz, 1H), 7.35 (dd, J=6.8, 1.6 Hz, 1H), 7.28 (s, 1H), 5.64 (q, J=5.6 Hz, 1H), 2.34 (s, 3H), 1.85 (d, J=6.0 Hz, 3H).

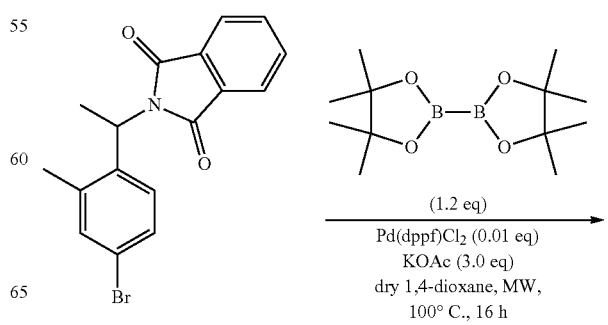

243
-continued

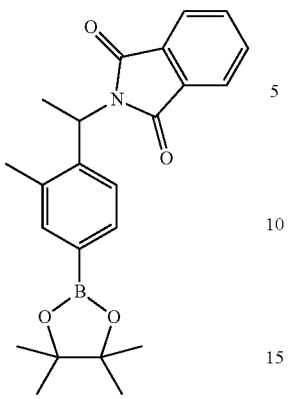

The preparation of 2-(1-(2-methyl-4-(4,4,5,5-tetramethyl-1,3,2-dioxaborolan-2-yl)phenyl)ethyl)isoindoline-1,3-dione To a solution of 2-(1-(4-bromo-2-methylphenyl)ethyl)isoindoline-1,3-dione (1.72 g, 5.0 mmol) in 1,4-dioxane (15 mL) were added 4,4,4',4',5,5,5',5'-octamethyl-2,2'-bi(1,3,2-dioxaborolane) (1.52 g, 6.0 mmol), KOAc (1.75 g, 18 mmol) and Pd(dppf)Cl$_2$DCM (407 mg, 0.5 mmol) under nitrogen. The mixture was stirred at 100° C. for 2 h. After cooling down to rt, the mixture was diluted with water (50 mL) and extracted with EtOAc (100 mL×3). The combined organic layer was washed with brine, dried, concentrated and purified by silica gel column (petroleum ether/EtOAc=4:1) to give 2-(1-(2-methyl-4-(4,4,5,5-tetramethyl-1,3,2-dioxaborolan-2-yl)phenyl)ethyl)isoindoline-1,3-dione (0.88 g, yield 45%) as white solid. ESI-MS (M+H)$^+$: 392.2. $^1$H NMR (400 MHz, CDCl$_3$) δ: 7.79-7.77 (m, 3H), 7.69-7.66 (m, 3H), 7.59 (s, 1H), 5.70 (q, J=7.2 Hz, 1H), 2.36 (s, 3H), 1.87 (d, J=7.2 Hz, 3H), 1.32-1.24 (m, 12H).

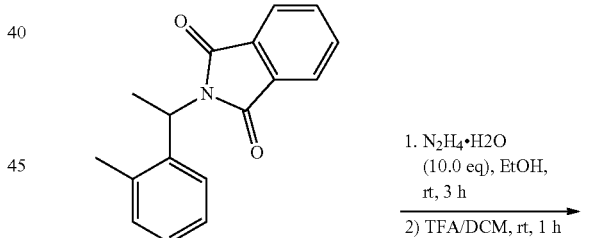

Pd(dppf)Cl$_2$
(0.05 eq),
K$_2$CO$_3$ (2.0 eq)
───────────────
Dioxane/H$_2$O (4:1),
120° C., 2 h

244
-continued

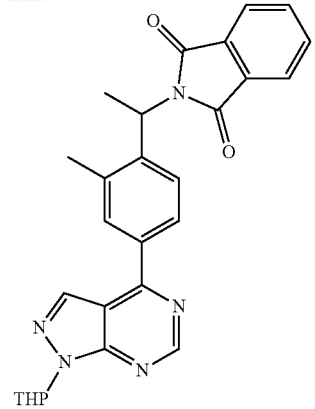

The preparation of 2-(1-(2-methyl-4-(1-(tetrahydro-2H-pyran-2-yl)-1H-pyrazolo[3,4-d]pyrimidin-4-yl)phenyl)ethyl)isoindoline-1,3-dione To a solution of 2-(1-(2-methyl-4-(4,4,5,5-tetramethyl-1,3,2-dioxaborolan-2-yl)phenyl)ethyl)isoindoline-1,3-dione (391 mg, 1.5 mmol) in 1,4-dioxane/water (5 mL, 4:1) were added 4-chloro-1-(tetrahydro-2H-pyran-2-yl)-1H-pyrazolo[3,4-d]pyrimidine (428 mg, 1.8 mmol), K$_2$CO$_3$ (414 mg, 3.0 mmol) and Pd(dppf)Cl$_2$DCM (61 mg, 0.075 mmol) under nitrogen. The mixture was stirred at 120° C. for 2 h. After cooling down to rt, the mixture was diluted with water (50 mL) and extracted with EtOAc (100 mL×2). The combined organic layer was washed with brine, dried, concentrated and purified by silica gel column (Petroleum ether/EtOAc=3:1) to give 2-(1-(2-methyl-4-(1-(tetrahydro-2H-pyran-2-yl)-1H-pyrazolo[3,4-d]pyrimidin-4-yl)phenyl)ethyl)isoindoline-1,3-dione as an orange oil (217 mg, yield 31%). ESI-MS (M+H)$^+$: 468.2.

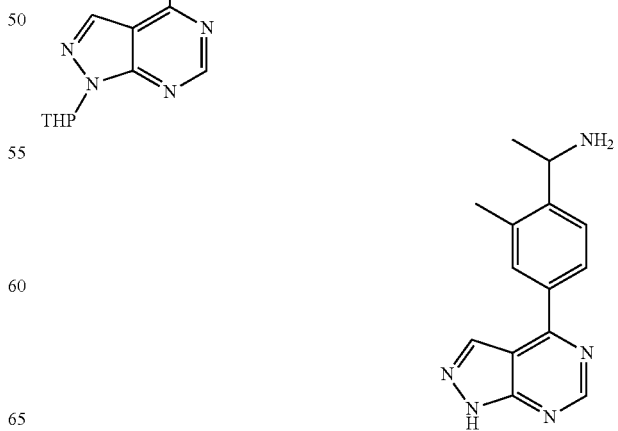

1. N$_2$H$_4$·H$_2$O
(10.0 eq), EtOH,
rt, 3 h
───────────────
2) TFA/DCM, rt, 1 h

245

The preparation of 1-(2-methyl-4-(1H-pyrazolo[3,4-d]pyrimidin-4-yl)phenyl)ethanamine A mixture of 2-(1-(2-methyl-4-(1-(tetrahydro-2H-pyran-2-yl)-1H-pyrazolo[3,4-d]pyrimidin-4-yl)phenyl)ethyl)isoindoline-1,3-dione (200 mg, 0.43 mmol) and $N_2H_4.H_2O$ (206 mg, 4.3 mmol) in ethanol (10 mL) was stirred at rt for 3 h. The white precipitate was filtered off and the filtrate was concentrated. The residue was dissolved in TFA/DCM (6 mL, 1:1) and stirred at rt for 1 h. After concentrated, crude 1-(2-methyl-4-(1H-pyrazolo[3,4-d]pyrimidin-4-yl)phenyl)ethanamine (97 mg, yield 80%) as an orange oil was used in next step without further purification, ESI-MS $(M+H)^+$: 254.1

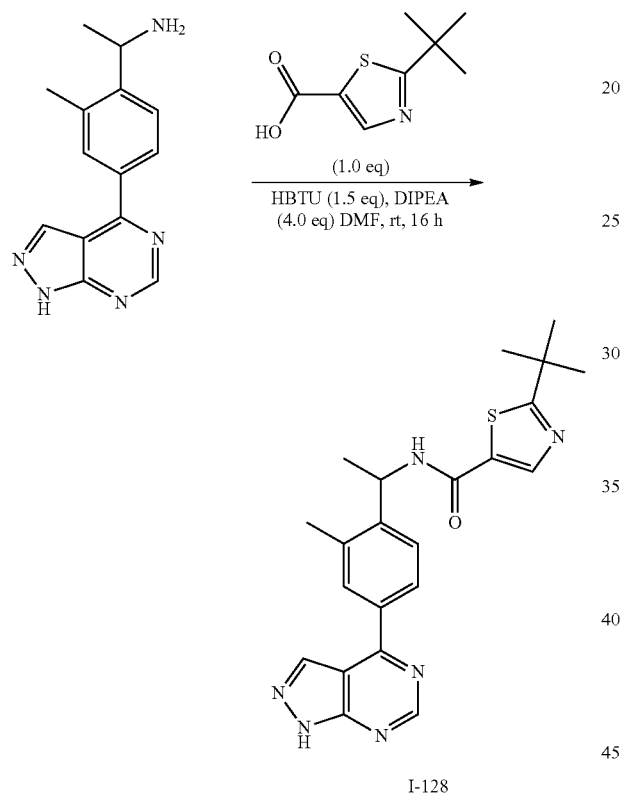

I-128

The preparation of 2-(tert-butyl)-N-(1-(2-methyl-4-(1H-pyrazolo[3,4-d]pyrimidin-4-yl)phenyl)ethyl)thiazole-5-carboxamide (I-128)

A mixture of 1-(2-methyl-4-(1H-pyrazolo[3,4-d]pyrimidin-4-yl)phenyl) ethanamine (114 mg, 0.45 mmol), 2-(tert-butyl)thiazole-5-carboxylic acid (83 mg, 0.45 mmol), HBTU (255 mg, 0.67 mmol) and DIPEA (232 mg, 1.8 mmol) in DMF (4 mL) was stirred at rt for 16 h. After diluted with water (20 mL), the mixture was extracted with EtOAc (50 mL×2). The combined organics were washed with water (50 mL), concentrated and the residue was purified by pre-HPLC (MeCN/$H_2O$ with 0.05% $NH_3.H_2O$ as mobile phase) to give the title product (47 mg, yield 25%) as a yellow solid. ESI-MS $(M+H)^+$: 421.2. $^1$H NMR (400 MHz, $CD_3OD$) δ: 8.84 (s, 1H), 8.41 (s, 1H), 8.20 (s, 1H), 7.94-7.92 (m, 2H), 7.53 (d, J=8.0 Hz, 1H), 5.35-5.33 (m, 1H), 2.46 (s, 3H), 1.48 (d, J=8.0 Hz, 3H), 1.26 (s, 9H).

246

Example 17

Scheme 25

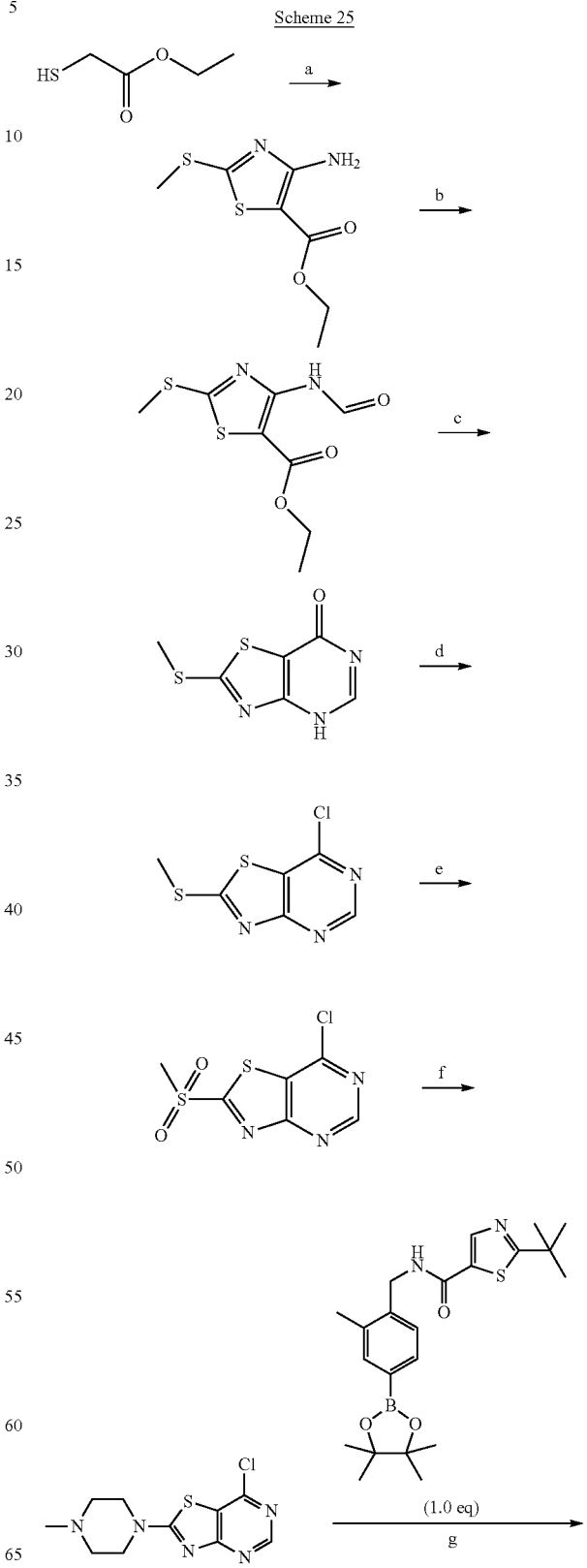

247
-continued

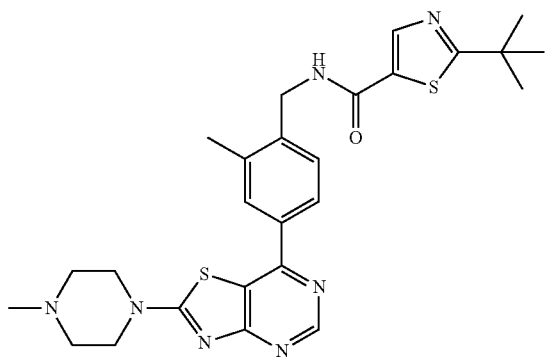

Reagent and condition: (a) dimethyl cyanocarbonimidodithioate, DIPEA (3.0 eq), DMF, 100° C., 24 h, Yield: 89%. (b) Ammoniumacetate (1.3 eq), formic acid, reflux, 46 h. (c) Ammonium formate (3.0 eq), formamide, 140° C., 2 h. (d) POCl$_3$, 140° C., 4 h, Yield: 30%. (e) m-CPBA (3.0 eq), DCM, rt, 16 h, Yield: 70%. (f) 1-Methylpiperazine, K$_2$CO$_3$ (3.0 eq), DMF, rt, 2 h, Yield: 46%. (g) Pd(dppf)Cl$_2$ (0.01 eq), K$_2$CO$_3$ (3.0 eq), Dioxane/H$_2$O, 100° C., 16 h. Yield: 44%.

2-(tert-butyl)-N-(2-methyl-4-(2-(4-methylpiperazin-1-yl)thiazolo[4,5-d]pyrimidin-7-yl)benzyl)thiazole-5-carboxamide

I-133

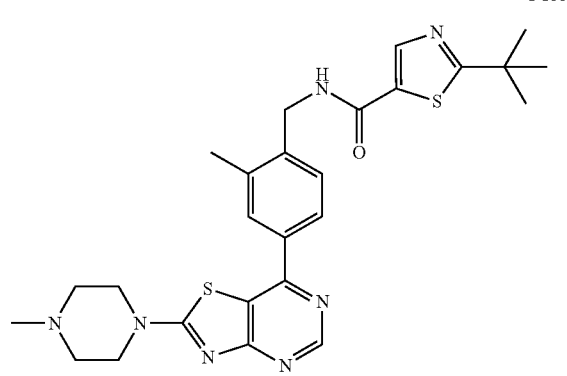

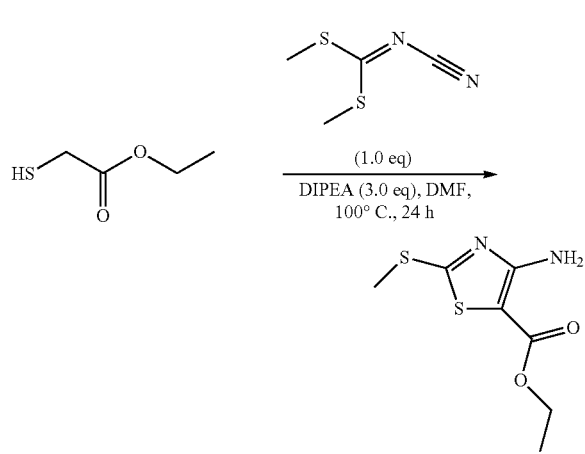

248

The preparation of ethyl 4-amino-2-(methylthio)thiazole-5-carboxylate

Ethyl 2-mercaptoacetate (5 g, 42 mmol, 1.0 eq) was dissolved in DMF (50 mL) and added with N-thienodithioimino carbonate (6.1 g, 42 mmol, 1.0 eq) and DIPEA (16.3 g, 126 mmol, 3.0 eq). After heating at 100° C. for 5 h, the mixture was diluted with saturated aqueous ammonium chloride (100 mL) and extracted with EtOAc (100 mL×2). The combined organic layer was washed with brine, dried, concentrated. The solid was washed with n-hexane and dried under vacuum to give the title compound (8 g, yield: 89%) as a yellow solid. ESI-MS (M+H)$^+$: 219.0.

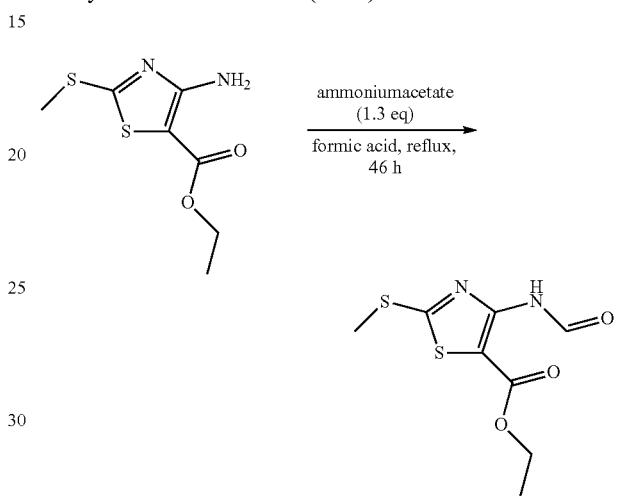

The preparation of ethyl 4-formamido-2-(methylthio)thiazole-5-carboxylate

Ethyl 4-amino-2-(methylthio)thiazole-5-carboxylate (1.7 g, 7.8 mmol) and ammonium acetate (780 mg, 10.1 mmol, 1.3 eq) were mixed with formic acid (20 mL) and the mixture was refluxed for 46 h. After concentrated, the mixture was concentrated under vacuum to remove the formic acid and extracted with EtOAc (100 mL×2). The combined organic layer was washed with NaHCO$_3$ (sat), dried and concentrated. Crude title compound (1.6 g) was obtained as yellow solid, which was used to next step without further purification. ESI-MS (M+H)$^+$: 247.0.

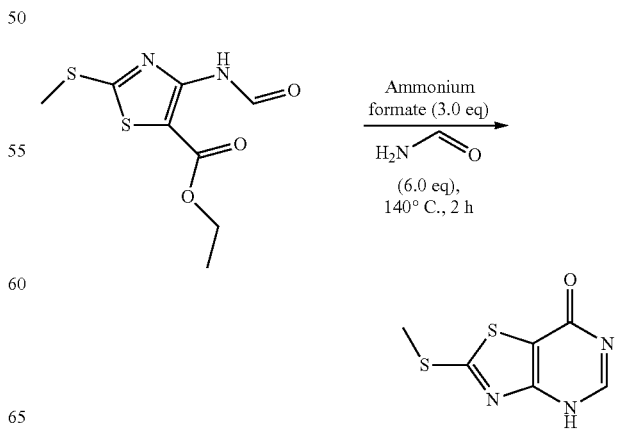

The preparation of 2-(methylthio)thiazolo[4,5-d]pyrimidin-7(4H)-one

Ethyl 4-formamido-2-(methylthio)thiazole-5-carboxylate (1.6 g, 6.5 mmol), ammonium formate (1.2 g, 19.5 mmol, 3.0 eq) and formamide (1.8 g, 39 mmol, 6.0 eq) were mixed and the mixture was heated at 140° C. for 2 h. After addition of H$_2$O (100 mL) and diethylether (200 mL), the mixture was stirred at rt for another 0.5 h. The organic phase was separated and concentrated. The solid was washed with n-hexane and dried under vacuum to give 2-(methylthio)thiazolo[4,5-d]pyrimidin-7(4H)-one (650 mg, yield: 43%) as yellow solid. ESI-MS (M+H)$^+$: 200.0.

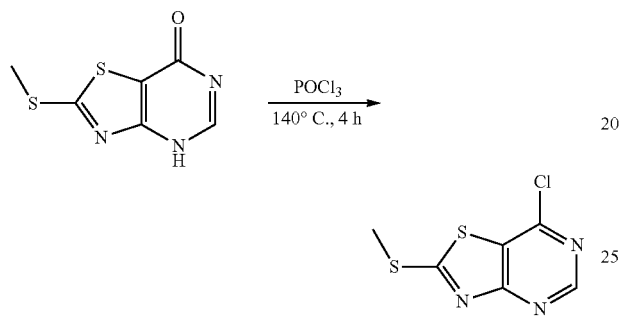

The preparation of 7-chloro-2-(methylthio)thiazolo[4,5-d]pyrimidine 2-(methylthio)thiazolo[4,5-d]pyrimidin-7(4H)-one (650 mg, 3.3 mmol) in phosphoryl chloride (10 mL) were heated at 130° C. for 4 h. After removing phosphoryl chloride by concentration under vacuum, ice-cold water (100 mL) was added and the mixture was stirred for 0.5 h. The solid was collected by filtration and washed with water and n-hexane to give 7-chloro-2-(methylthio)thiazolo[4,5-d]pyrimidine (210 mg, yield: 30%) as yellow solid. ESI-MS (M+H)$^+$: 218.0.

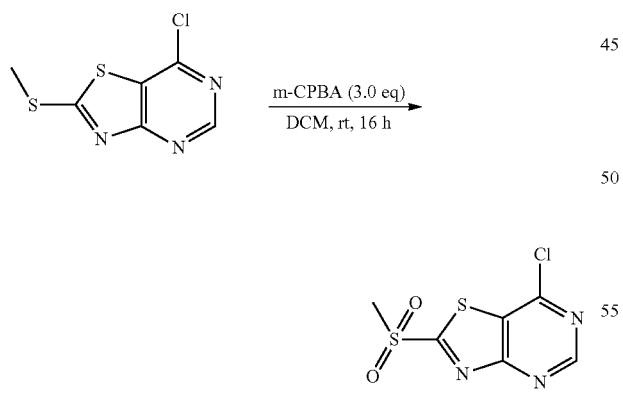

The preparation of 7-chloro-2-(methylsulfonyl)thiazolo[4,5-d]pyrimidine

To a mixture of 7-chloro-2-(methylthio)thiazolo[4,5-d]pyrimidine (130 mg, 0.6 mmol) in DCM (10 mL) were added m-CPBA (310 mg, 1.8 mmol, 3.0 eq). The mixture was stirred at rt for 16 h. After diluted with water (30 mL), the mixture was extracted with DCM (80 mL×2). The organic layer was washed with H$_2$O (30 mL×2) and brine (50 mL), dried (Na$_2$SO$_4$), filtered and concentrated. The residue was purified by silica gel chromatography (EtOAC/Petroleum ether=1:6) to give 7-chloro-2-(methylsulfonyl)thiazolo[4,5-d]pyrimidine as yellow solid (145 mg, yield: 70%). ESI-MS (M+H)$^+$: 250.0.

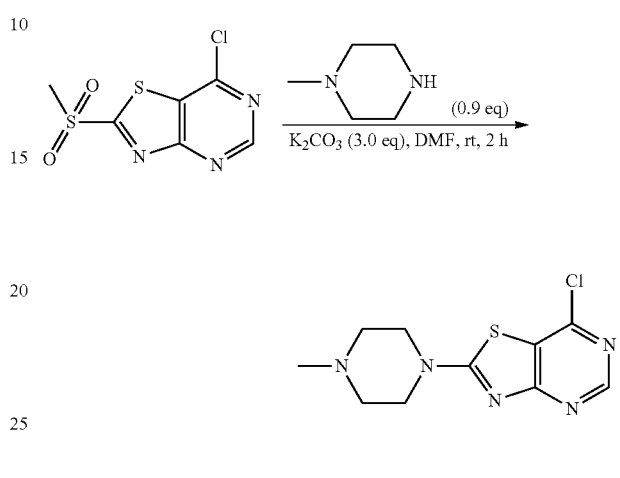

The preparation of 7-chloro-2-(4-methylpiperazin-1-yl) thiazolo[4,5-d]pyrimidine To a solution of 7-chloro-2-(methylsulfonyl)thiazolo[4,5-d]pyrimidine (140 mg, 0.56 mmol) in DMF (6 mL) were added 1-methylpiperazine (50 mg, 0.50 mmol, 0.9 eq) and K$_2$CO$_3$ (232 mg, 1.68 mmol, 3.0 eq). The mixture was stirred at rt for 2 h. After diluted with water (50 mL), the mixture was extracted with EtOAc (100 mL×2). The organic layer was washed with H$_2$O (60 mL) and brine (50 mL), dried (Na$_2$SO$_4$), filtered and concentrated. The residue was purified by silica gel chromatography (EA/PE=1:2) to give 7-chloro-2-(4-methylpiperazin-1-yl)thiazolo[4,5-d]pyrimidine as yellow solid (70 mg, yield: 46%). ESI-MS (M+H)$^+$: 270.0.

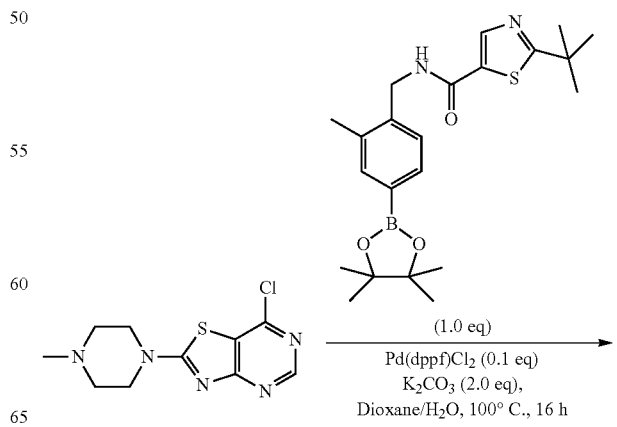

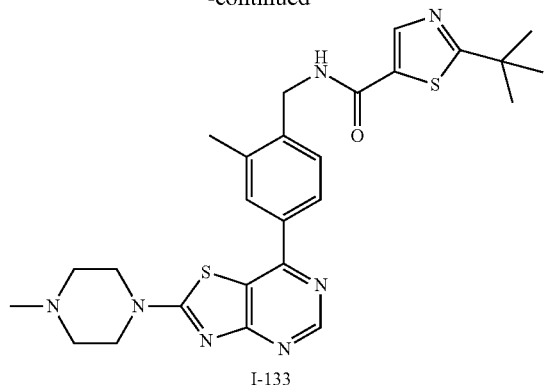

I-133

The preparation of 2-(tert-butyl)-N-(2-methyl-4-(2-(4-methylpiperazin-1-yl)thiazolo[4,5-d]pyrimidin-7-yl)benzyl)thiazole-5-carboxamide (I-133)

To a solution of 7-chloro-2-(4-methylpiperazin-1-yl)thiazolo[4,5-d]pyrimidine (70 mg, 0.25 mmol) in 1,4-dioxane/water (5 mL, 4:1) were added 2-(tert-butyl)-N-(2-methyl-4-(4,4,5,5-tetramethyl-1,3,2-dioxaborolan-2-yl)benzyl)thiazole-5-carboxamide (104 mg, 0.25 mmol), $K_2CO_3$ (70 mg, 0.5 mmol) and Pd(dppf)Cl$_2$DCM (20 mg, 0.025 mmol) under nitrogen. The mixture was stirred at 100° C. for 16 h. After cooling down to rt, the mixture was diluted with water (50 mL) and extracted with ethyl acetate (100 mL). The combined organic layer was washed with brine, dried, concentrated and purified by prep-HPLC (CH$_3$CN/H$_2$O with 0.05% NH$_3$.H$_2$O as mobile phase) to give compound 2-(tert-butyl)-N-(2-methyl-4-(2-(4-methylpiperazin-1-yl)thiazolo[4,5-d]pyrimidin-7-yl)benzyl)thiazole-5-carboxamide (60 mg, yield: 44%) as yellow solid. ESI-MS (M+H)$^+$: 522.2. $^1$H NMR (400 MHz, CD$_3$OD) δ: 8.77 (s, 1H), 8.17 (s, 1H), 7.79-7.75 (m, 2H), 7.42 (d, J=7.6 Hz, 1H), 4.56 (s, 2H), 3.76 (br, 4H), 2.53 (br, 4H), 2.41 (s, 3H), 2.30 (s, 3H), 1.39 (s, 9H).

4-(6-(4-((2-(tert-butyl) thiazole-5-carboxamido)methyl)-3-methylphenyl)-7H-purin-8-yl)morpholine-2-carboxylic acid

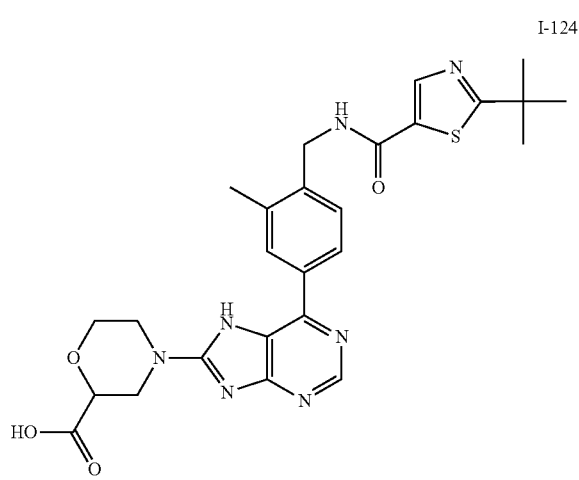 [SMILES: Cc1cc(-c2ncnc3nc(N4CCOC(C(=O)O)C4)[nH]c23)ccc1CNC(=O)c1cnc(C(C)(C)C)s1]

I-124

Synthesis of ethyl 4-(chlorocarbonyl)morpholine-2-carboxylate

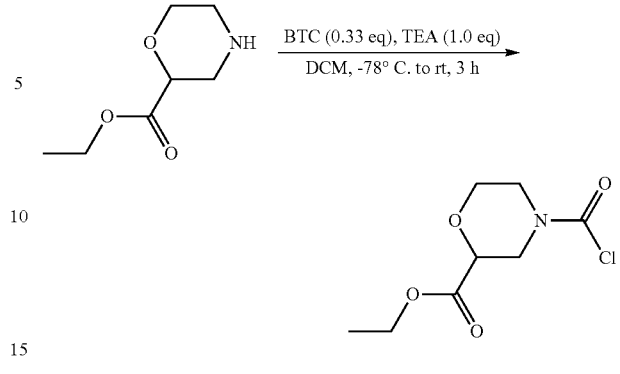

To a solution of triphosgene (376 mg, 1.28 mmol) in DCM (20 mL) were added ethyl morpholine-2-carboxylate (618 mg, 3.88 mmol) and TEA (392 mg, 3.88 mmol) at −78° C. The mixture was stirred at rt for 3 h. After diluted with water (50 mL), the mixture was extracted with DCM (50 mL×3). The organic layer was washed with H$_2$O (50 mL), dried (Na$_2$SO$_4$), filtered and concentrated. The crude product (220 mg, yield: 25%) was used in nest step without further purification.

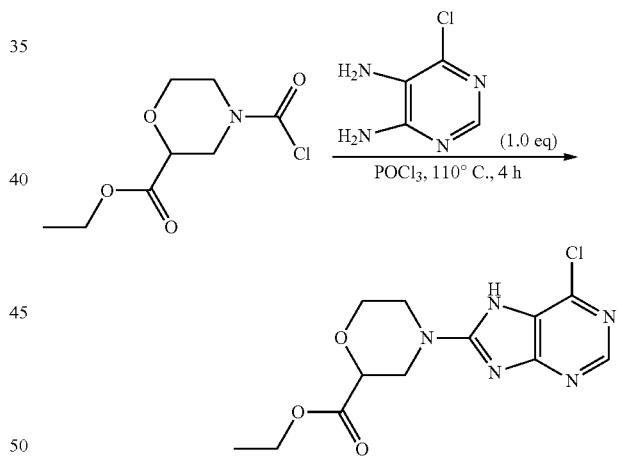

Synthesis of ethyl 4-(6-chloro-7H-purin-8-yl)morpholine-2-carboxylate

To a solution of ethyl 4-(chlorocarbonyl)morpholine-2-carboxylate (220 mg, 1.0 mmol) in POCl$_3$ (4 mL) was added 6-chloropyrimidine-4,5-diamine (144 mg, 1.0 mmol). The mixture was stirred at 110° C. for 4 h. After cooled to room temperature, the mixture was poured into ice water slowly, neutralized with sat. Na$_2$CO$_3$ to basic (pH 7-8). The mixture was concentrated and purified by prep-HPLC (CH$_3$CN/H$_2$O with 0.05% NH$_3$.H$_2$O as mobile phase) to give ethyl 4-(6-chloro-7H-purin-8-yl)morpholine-2-carboxylate as a white solid (80 mg, yield: 26%). ESI-MS (M+H)$^+$: 312.0.

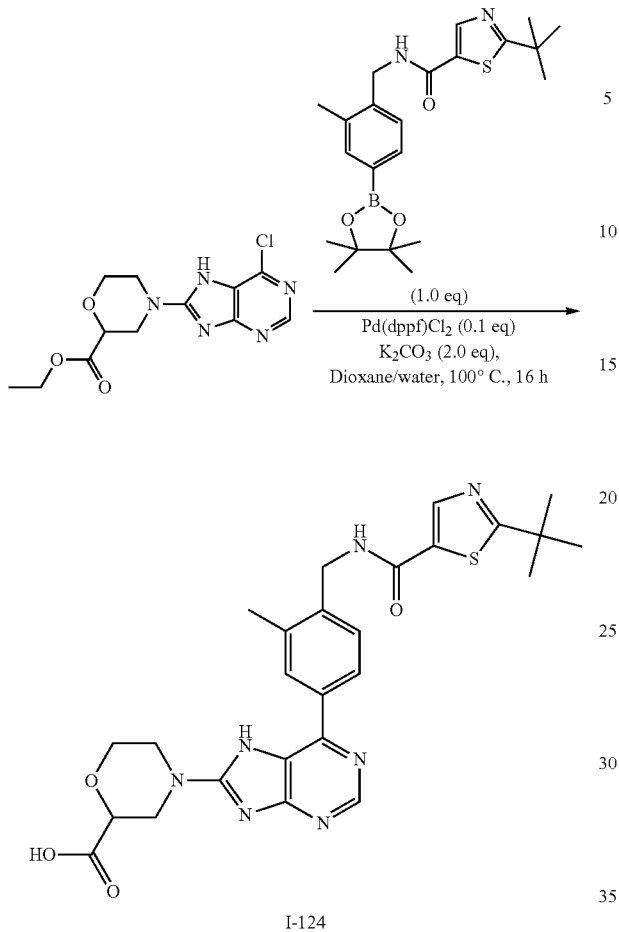

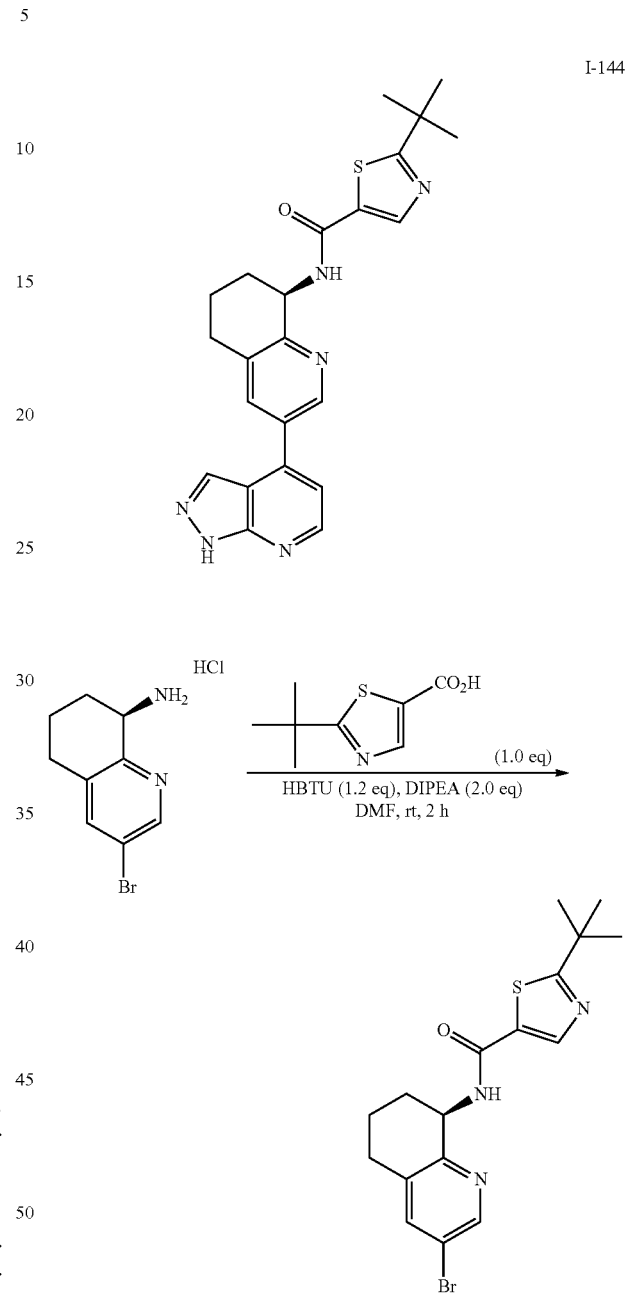

254

(R)—N-(3-(1H-pyrazolo[3,4-b]pyridin-4-yl)-5,6,7,8-tetrahydroquinolin-8-yl)-2-(tert-butyl)thiazole-5-carboxamide

I-144

Synthesis of 4-(6-(4-((2-(tert-butyl)thiazole-5-carboxamido)methyl)-3-methylphenyl)-7H-purin-8-yl)morpholine-2-carboxylic acid (I-124)

To a solution of ethyl 4-(6-chloro-7H-purin-8-yl)morpholine-2-carboxylate (80 mg, 0.25 mmol) in 1,4-dioxane/water (5 mL, 4:1) were added 2-(tert-butyl)-N-(2-methyl-4-(4,4,5,5-tetramethyl-1,3,2-dioxaborolan-2-yl)benzyl)thiazole-5-carboxamide (104 mg, 0.25 mmol), $K_2CO_3$ (70 mg, 0.5 mmol) and Pd(dppf)$Cl_2$DCM (20 mg, 0.025 mmol) under nitrogen. The mixture was stirred at 100° C. for 16 h. After cooling down to rt, the mixture was diluted with water (50 mL) and extracted with DCM (100 mL). The combined organic layer was washed with brine, dried, concentrated and purified by prep-HPLC ($CH_3CN/H_2O$ with 0.05% $NH_3.H_2O$ as mobile phase) to give 4-(6-(4-((2-(tert-butyl)thiazole-5-carboxamido)methyl)-3-methylphenyl)-7H-purin-8-yl)morpholine-2-carboxylic acid as a white solid (3 mg, yield: 2%). ESI-MS (M+H)$^+$: 536.1. HPLC: (214 nm: 100%, 254 nm: 100%). $^1$H NMR (400 MHz, DMSO-$d_6$) δ: 9.10 (t, J=5.6 Hz, 1H), 8.60 (s, 1H), 8.57-8.39 (m, 2H), 8.34 (s, 1H), 7.40 (d, J=8.4 Hz, 1H), 4.51 (d, J=5.6 Hz, 2H), 4.33-4.30 (m, 1H), 4.22-4.19 (m, 1H), 4.05-4.02 (m, 1H), 3.92-3.89 (m, 1H), 3.72-3.66 (m, 2H), 3.53-3.48 (m, 1H), 2.42 (s, 3H), 1.39 (s, 9H).

Synthesis of (R)—N-(3-bromo-5,6,7,8-tetrahydroquinolin-8-yl)-2-(tert-butyl)thiazole-5-carboxamide To a solution of (R)-3-bromo-5,6,7,8-tetrahydroquinolin-8-amine hydrochloride (158 mg, 0.70 mmol) in 5 mL DMF were added 2-(tert-butyl)thiazole-5-carboxylic acid (130 mg, 0.70 mmol), HATU (319 mg, 0.84 mmol) and DIPEA (271 mg, 2.10 mmol). The mixture was stirred at rt for 2 h. After diluted with water (20 mL), the mixture was extracted with EtOAc (60 mL×2). The combined organic layer was washed with $H_2O$ (40 mL×2), dried ($Na_2SO_4$), filtered and concentrated and purified by silica gel chromatograph column (petroleum ether/EtOAc=4:1) to give (R)—N-(3-bromo-5,6,7,8-tetrahydroquinolin-8-yl)-2-(tert-butyl)thiazole-5-carboxamide as a white solid (220 mg, yield: 84%). ESI-MS (M+H)$^+$: 394.1. $^1$H NMR (400 MHz, CDCl$_3$) δ: 8.48 (d, J=2.0 Hz, 1H), 8.06 (s, 1H), 7.64-7.63 (m, 1H), 7.00-6.98 (m, 1H), 4.50-4.96 (m, 1H), 2.87-2.80 (m, 2H), 2.70-2.66 (m, 1H), 1.99-1.85 (m, 2H), 1.76-1.67 (m, 1H), 1.47 (s, 9H).

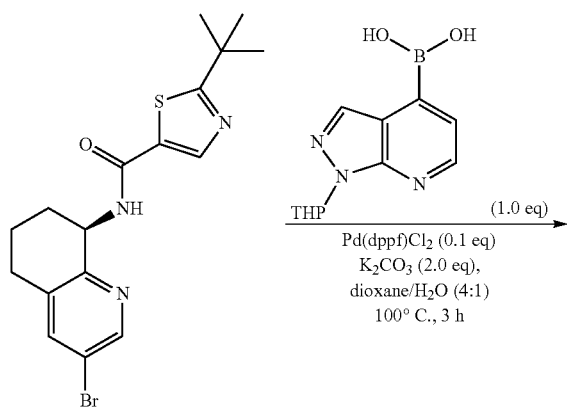

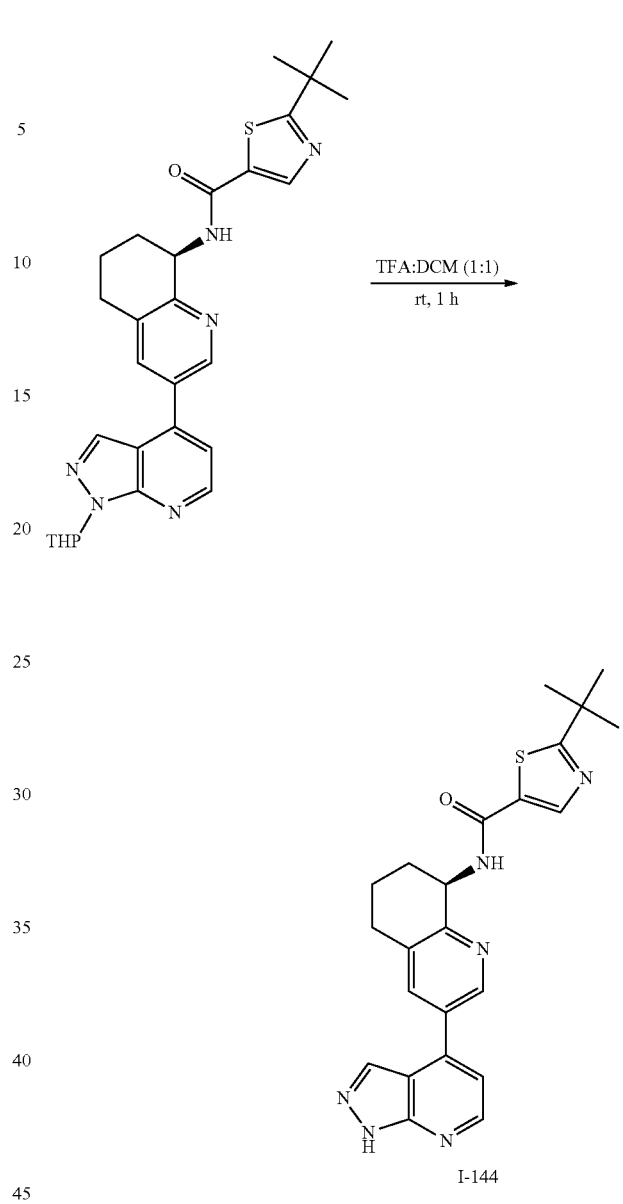

Synthesis of 2-(tert-butyl)-N-((8R)-3-(1-(tetrahydro-2H-pyran-2-yl)-1H-pyrazolo[3,4-b]pyridin-4-yl)-5,6,7,8-tetrahydroquinolin-8-yl)thiazole-5-carboxamide To a solution of (R)—N-(3-bromo-5,6,7,8-tetrahydroquinolin-8-yl)-2-(tert-butyl)thiazole-5-carboxamide (120 mg, 0.3 mmol) in 1,4-dioxane/water (5 mL, 4:1) were added (1-(tetrahydro-2H-pyran-2-yl)-1H-pyrazolo[3,4-b]pyridin-4-yl)boronic acid (74 mg, 0.3 mmol), K$_2$CO$_3$ (83 mg, 0.6 mmol) and Pd(dppf)Cl$_2$DCM (24 mg, 0.03 mmol) under nitrogen. The mixture was stirred at 120° C. for 2 h. After cooling down to rt, the mixture was diluted with water (50 mL) and extracted with ethyl acetate (100 mL×2). The combined organic layer was washed with brine, dried, concentrated and purified silica gel chromatograph column (petroleum ether/EtOAc=2:1) to give 2-(tert-butyl)-N-((8R)-3-(1-(tetrahydro-2H-pyran-2-yl)-1H-pyrazolo[3,4-b]pyridin-4-yl)-5,6,7,8-tetrahydroquinolin-8-yl)thiazole-5-carboxamide as a white solid (82 mg, yield: 53%). ESI-MS (M+H)$^+$: 516.9.

Synthesis of (R)—N-(3-(1H-pyrazolo[3,4-b]pyridin-4-yl)-5,6,7,8-tetrahydroquinolin-8-yl)-2-(tert-butyl)thiazole-5-carboxamide (I-144)

A mixture of 2-(tert-butyl)-N-((8R)-3-(1-(tetrahydro-2H-pyran-2-yl)-1H-pyrazolo[3,4-b]pyridin-4-yl)-5,6,7,8-tetrahydroquinolin-8-yl)thiazole-5-carboxamide (82 mg, 0.16 mmol) in TFA/DCM (6 mL, 1:1) was stirred at rt for 1 h. After concentrated, crude product was purified by prep-HPLC (CH$_3$CN/H$_2$O with 0.05% NH$_3$.H$_2$O as mobile phase) to give (R)—N-(3-(1H-pyrazolo[3,4-b]pyridin-4-yl)-5,6,7,8-tetrahydroquinolin-8-yl)-2-(tert-butyl)thiazole-5-carboxamide as a white solid (28 mg, yield: 38%). ESI-MS (M+H)$^+$: 432.9. HPLC: (214 nm: 100%, 254 nm: 99%). $^1$H NMR (400 MHz, CD$_3$OD) δ: 8.72 (d, J=2.4 Hz, 1H), 8.51 (d, J=4.8 Hz, 1H), 8.21 (s, 1H), 8.12 (s, 1H), 7.98 (d, J=2.0 Hz, 1H), 7.31 (d, J=4.8 Hz, 1H), 5.21 (t, J=6.4 Hz, 1H), 2.96-2.91 (m, 2H), 2.19-2.15 (m, 1H), 2.02-1.94 (m, 2H), 1.93-1.84 (m, 1H), 1.36 (s, 9H).

(S)—N-(3-(1H-pyrazolo[3,4-b]pyridin-4-yl)-5,6,7,8-tetrahydroquinolin-8-yl)-2-(tert-butyl)thiazole-5-carboxamide

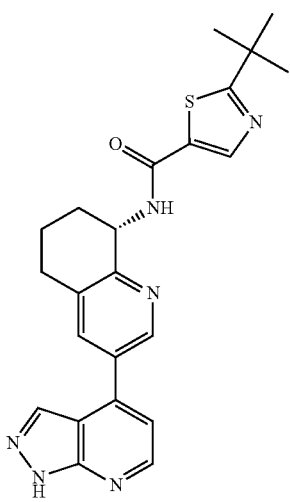

I-152

Synthesis of (S)—N-(3-(1H-pyrazolo[3,4-b]pyridin-4-yl)-5,6,7,8-tetrahydroquinolin-8-yl)-2-(tert-butyl)thiazole-5-carboxamide (I-152) was similar to that of compound I-144 except (S)-3-bromo-5,6,7,8-tetrahydroquinolin-8-amine hydrochloride was substituted for (R)-3-bromo-5,6,7,8-tetrahydroquinolin-8-amine hydrochloride. White solid (36 mg, yield: 42%). ESI-MS (M+H)+: 432.9. 1H NMR (400 MHz, CD3OD) δ: 8.73 (d, J=2.4 Hz, 1H), 8.50 (d, J=4.8 Hz, 1H), 8.21 (s, 1H), 8.12 (s, 1H), 7.99 (s, 1H), 7.31 (d, J=5.2 Hz, 1H), 5.21 (t, J=6.4 Hz, 1H), 2.97-2.91 (m, 2H), 2.19-2.17 (m, 1H), 2.05-1.94 (m, 2H), 1.90-1.86 (m, 1H), 1.36 (s, 9H).

I-119

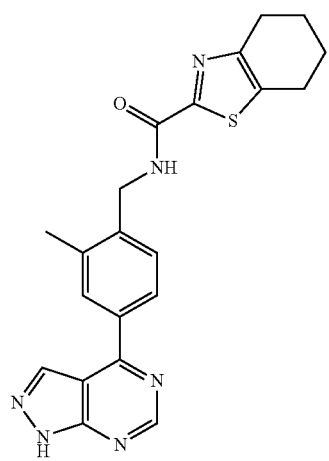

4,5,6,7-Tetrahydro-benzothiazole-2-carboxylic acid 2-methyl-4-(1H-pyrazolo[3,4-d]pyrimidin-4-yl)-benzylamide (I-119)

Compound I-119 was prepared in a similar manner as described for compound I-85 except 4,5,6,7-tetrahyd-robenzo[d]thiazole-2-carboxylic acid was substituted for 4,5,6,7-tetrahydrobenzo[b]thiophene-2-carboxylic acid to afford the title compound (12 mg, yield: 13%) as a white solid. ESI-MS (M+H)+: 405.0. 1H NMR (400 MHz, CHLOROFORM-d) Shift 13.14 (br. s., 1H), 8.97 (s, 1H), 8.30 (s, 1H), 7.98 (s, 1H), 7.93 (d, J=7.78 Hz, 1H), 7.53 (t, J=5.40 Hz, 1H), 7.47 (d, J=7.78 Hz, 1H), 4.65 (d, J=6.02 Hz, 2H), 2.76-2.91 (m, 2H), 2.65-2.76 (m, 2H), 2.45 (s, 3H), 1.74-1.91 (m, 4H).

I-126

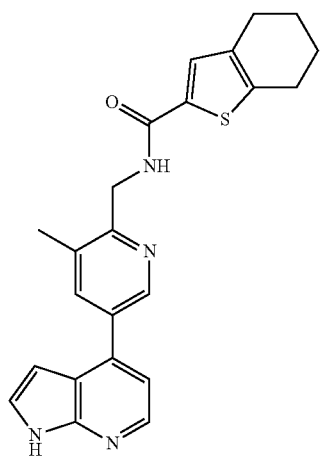

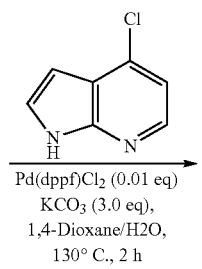

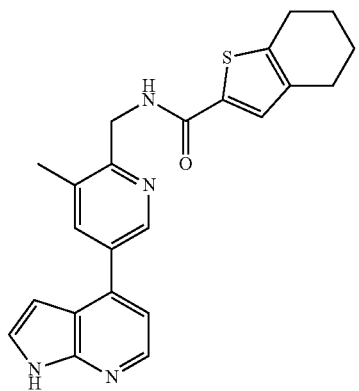

N-((3-methyl-5-(1H-pyrrolo[2,3-b]pyridin-4-yl)pyridin-2-yl)methyl)-4,5,6,7-tetrahydrobenzo[b]thiophene-2-carboxamide (I-126)

Synthesis of compound I-126 was similar to that of compound I-153 except 4-chloro-1H-pyrrolo[2,3-b]pyridine was substituted for 4-chloro-7H-pyrrolo[2,3-d]pyrimidine to give the titled compound (35 mg, yield: 23%) as a yellow solid. ESI-MS (M+H)$^+$: 403.2. $^1$H NMR (400 MHz, CD$_3$OD) δ: 8.66 (d, J=1.6 Hz, 1H), 8.18 (d, J=5.2 Hz, 1H), 7.91 (d, J=1.2 Hz, 1H), 7.39 (d, J=3.6 Hz, 1H), 7.32 (s, 1H), 7.15 (d, J=4.8 Hz, 1H), 6.57 (d, J=3.6 Hz, 1H), 4.63 (s, 2H), 2.72 (t, J=6.4 Hz, 2H), 2.57 (t, J=6.4 Hz, 2H), 2.41 (s, 3H), 1.76-1.72 (m, 4H).

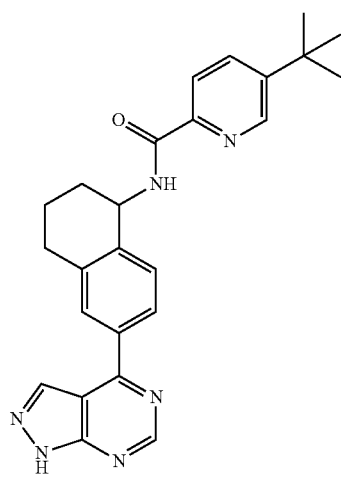

I-131

N-(6-(1H-pyrazolo[3,4-d]pyrimidin-4-yl)-1,2,3,4-tetrahydronaphthalen-1-yl)-5-(tert-butyl)picolinamide (I-131)

Compound I-131 was prepared in a similar manner as described for compound I-88 except 5-(tert-butyl)picolinic acid was substituted for 4-(tert-butyl)benzoic acid to give the title compound (18 mg, yield: 18%) as a yellow solid. ESI-MS (M+H)$^+$: 427.2. $^1$H NMR (400 MHz, CD$_3$OD) δ: 8.85 (s, 1H), 8.58 (s, 1H), 8.43 (s, 1H), 8.01-7.99 (m, 1H), 7.93-7.88 (m, 3H), 7.39 (d, J=7.6 Hz, 1H), 5.32-5.29 (m, 1H), 2.94-2.90 (m, 2H), 1.93-1.88 (m, 4H), 1.29 (s, 9H).

Example 18
2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide

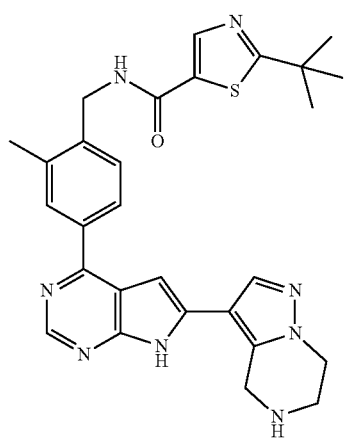

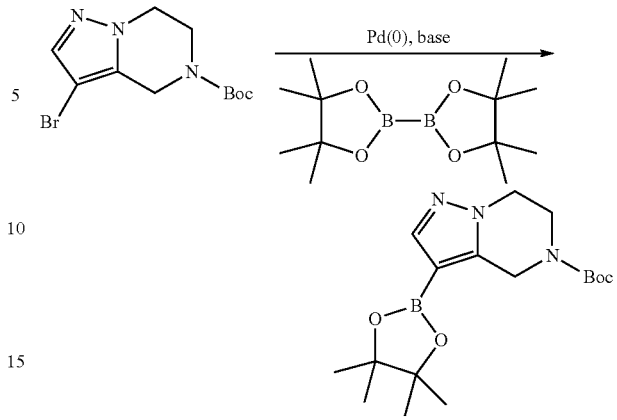

Synthesis of tert-butyl 3-(4,4,5,5-tetramethyl-1,3,2-dioxaborolan-2-yl)-6,7-dihydropyrazolo[1,5-a]pyrazine-5(4H)-carboxylate (I-76)

To a mixture of tert-butyl 3-bromo-6,7-dihydropyrazolo[1,5-a]pyrazine-5(4H)-carboxylate (5.0 g, 16 mmol), bis(pinacolato)diboron (4.6 g, 18 mmol) and [1,1'-Bis(diphenylphosphino)ferrocene]dichloropalladium(II), complex with dichloromethane (1:1) (1.4 g, 1.6 mmol) in 1,4-dioxane (20 mL, 200 mmol) was added potassium acetate (4.9 g, 50 mmol). The mixture was degassed for 15 min and stirred under N$_2$ for 12 hours at 100° C. The reaction was cooled to room temperature and quenched with saturated NaHCO$_3$ aqueous solution, and then extracted with ethyl acetate. The organic phase was separated and combined, washed with brine, and dried over anhydrous Na$_2$SO$_4$. The dried organic solution was concentrated and the residue was chromatographed on silica gel with ethyl acetate/heptane (0 to 70%) to give tert-butyl 3-(4,4,5,5-tetramethyl-1,3,2-dioxaborolan-2-yl)-6,7-dihydropyrazolo[1,5-a]pyrazine-5(4H)-carboxylate (2.7 g; Yield: 42%). $^1$H NMR (400 MHz, CHLOROFORM-d) d 7.75 (s, 1H), 4.75-4.87 (m, 2H), 4.12-4.22 (m, 2H), 3.82-3.95 (m, 2H), 1.50 (s, 9H), 1.22-1.31 (m, 16H); LC/MS: RT−1.71 min, MS: (M+H)$^+$: 350.2.

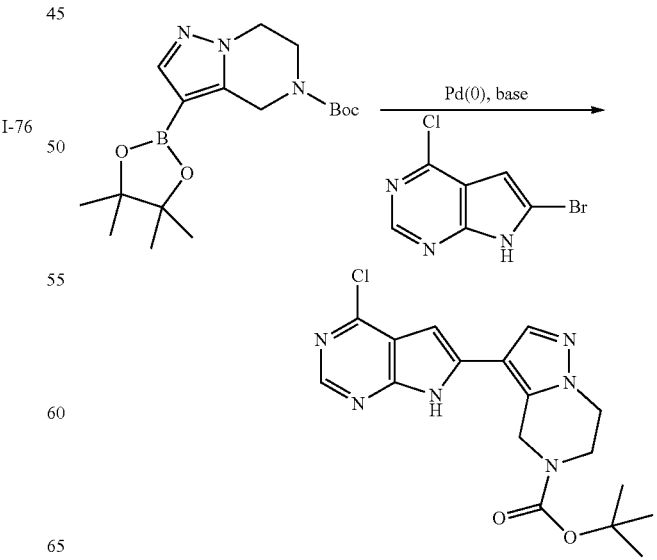

261

Synthesis of tert-butyl 3-(4-chloro-7H-pyrrolo[2,3-d]pyrimidin-6-yl)-6,7-dihydropyrazolo[1,5-a]pyrazine-5(4H)-carboxylate To a mixture of tert-butyl 3-(4,4,5,5-tetramethyl-1,3,2-dioxaborolan-2-yl)-6,7-dihydropyrazolo[1,5-a]pyrazine-5(4H)-carboxylate (1,100 mg, 3.1 mmol), 6-Bromo-4-chloro-7H-pyrrolo[2,3-d]pyrimidine (880 mg, 3.8 mmol) and [1,1'-Bis(diphenylphosphino)ferrocene]dichloropalladium(II), complex with dichloromethane (1:1) (260 mg, 0.31 mmol) in 1,4-Dioxane (5 mL, 60 mmol) was added potassium carbonate (1.3 g, 9.4 mmol) and water (1 mL, 60 mmol). The mixture was degassed for 15 min and stirred under $N_2$ for 12 hours at 90° C. The reaction was cooled to room temperature and quenched with saturated $NaHCO_3$ aqueous solution, and then extracted with ethyl acetate. The organic phase was separated and combined, washed with brine, and dried over anhydrous $Na_2SO_4$. The dried organic solution was concentrated and the residue was chromatographed on silica gel with ethyl acetate/heptane (0 to 100%) to give tert-butyl 3-(4-chloro-7H-pyrrolo[2,3-d]pyrimidin-6-yl)-6,7-dihydropyrazolo[1,5-a]pyrazine-5(4H)-carboxylate (0.41 g; Yield=31%) as a white solid. $^1$H NMR (400 MHz, CHLOROFORM-d) d 11.72-11.89 (m, 1H), 8.60 (s, 1H), 7.94 (s, 1H), 6.30-6.41 (m, 1H), 4.92 (br. s., 2H), 4.31 (br. s., 2H), 4.00 (br. s., 2H), 1.40-1.61 (m, 12H); LC/MS: RT–1.45 min, MS: $(M+H)^+$: 375.5.

262

Synthesis of tert-butyl 3-(4-(4-((2-(tert-butyl)thiazole-5-carboxamido)methyl)-3-methylphenyl)-7H-pyrrolo[2,3-d]pyrimidin-6-yl)-6,7-dihydropyrazolo[1,5-a]pyrazine-5(4H)-carboxylate To a mixture of 2-(tert-butyl)-N-(2-methyl-4-(4,4,5,5-tetramethyl-1,3,2-dioxaborolan-2-yl)benzyl)thiazole-5-carboxamide (40 mg, 0.10 mmol), tert-butyl 3-(4-chloro-7H-pyrrolo[2,3-d]pyrimidin-6-yl)-6,7-dihydropyrazolo[1,5-a]pyrazine-5(4H)-carboxylate (33 mg, 0.09 mmol) and [1,1'-Bis(diphenylphosphino)ferrocene]dichloropalladium(II), complex with dichloromethane (1:1) (7.2 mg, 0.009 mmol) in 1,4-dioxane (2 mL, 20 mmol) and water (0.13 mL, 7.2 mmol) was added potassium carbonate (36 mg, 0.26 mmol). The mixture was degassed and stirred under $N_2$. The reaction was microwaved at 120° C. for 60 minutes. The reaction was cooled to room temperature and quenched with saturated $NaHCO_3$ aqueous solution, and then extracted with ethyl acetate. The organic phase was separated and combined, washed with brine, and dried over anhydrous $Na_2SO_4$. The dried organic solution was concentrated and the residue was chromatographed on silica gel with ethyl acetate/heptane (0 to 100%) to give tert-butyl 3-(4-(4-((2-(tert-butyl)thiazole-5-carboxamido)methyl)-3-methylphenyl)-7H-pyrrolo[2,3-d]pyrimidin-6-yl)-6,7-dihydropyrazolo[1,5-a]pyrazine-5(4H)-carboxylate (34 mg; yield: 62%) as a white solid. $^1$H NMR (400 MHz, CHLOROFORM-d) d 8.70-8.85 (m, 1H), 8.14-8.24 (m, 1H), 7.69-7.97 (m, 3H), 7.29-7.38 (m, 1H), 6.36-6.51 (m, 1H), 5.30 (s, 1H), 4.80 (br. s., 2H), 4.60-4.73 (m, 2H), 4.20-4.31 (m, 2H), 3.89-4.00 (m, 2H), 2.44 (s, 3H), 1.36-1.55 (m, 18H); LC/MS: RT–1.37 min, MS: MS: $(M+H)^+$: 627.3.

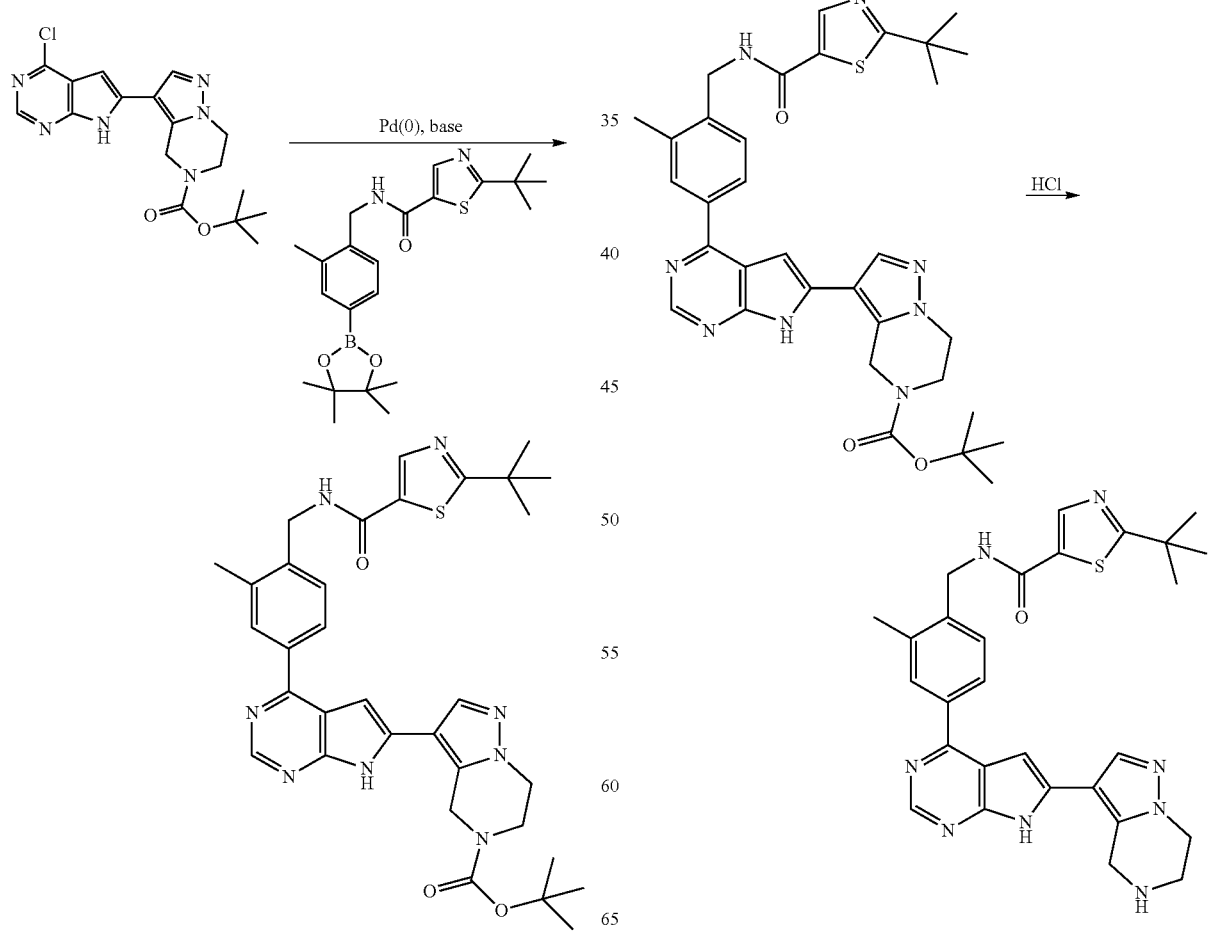

I-76

Synthesis of 2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide hydrochloride (I-76)

To a mixture of tert-butyl 3-(4-(4-((2-(tert-butyl)thiazole-5-carboxamido)methyl)-3-methylphenyl)-7H-pyrrolo[2,3-d]pyrimidin-6-yl)-6,7-dihydropyrazolo[1,5-a]pyrazine-5(4H)-carboxylate (32 mg, 0.05 mmol) in methylene chloride (2 mL, 30 mmol) was added 4 M of hydrogen chloride in 1,4-dioxane (0.038 mL, 0.15 mmol). The mixture was stirred at room temperature for 2 hours and the reaction was complete indicated by LC/MS. After the solution was concentrated and the residue was treated with ether, and then was filtered to give 2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide hydrochloride (21 mg; yield: 69%) as a yellow solid. $^1$H NMR (400 MHz, METHANOL-d4) δ 9.04 (s, 1H), 8.31 (s, 1H), 8.16 (s, 1H), 7.87-8.01 (m, 2H), 7.63-7.76 (m, 1H), 6.93-7.11 (m, 1H), 4.71 (s, 2H), 4.59 (br. s., 2H), 3.84-3.96 (m, 2H), 3.72-3.79 (m, 1H), 3.68 (d, J=5.27 Hz, 2H), 3.57-3.62 (m, 1H), 2.61 (s, 3H), 1.49 (s, 9H); LC/MS: RT–0.96 min, MS: (M+H)$^+$: 527.3.

Synthesis of 2-(tert-butyl)-N-(2-methyl-4-(6-(5-methyl-4,5,6,7-tetrahydropyrazolo[1,5-a]pyrazin-3-yl)-7H-pyrrolo[2,3-d]pyrimidin-4-yl)benzyl)thiazole-5-carboxamide (I-102)

To a solution of 2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide hydrochloride (200 mg, 0.40 mmol) in methylene chloride (3 mL, 50 mmol), methanol (2 mL, 50 mmol) was added triethylamine (0.050 mL, 0.40 mmol), acetic acid (0.020 mL, 0.40 mmol), formaldehyde (0.53 mL, 7.1 mmol). The mixture was stirred for 15 min and then sodium triacetoxyborohydride (220 mg, 1.1 mmol) was added. The mixture was stirred at room temperature for 2 hours and there is still a lot of starting material. The reaction was microwaved at 100° C. for 10 minutes and the residue was concentrated. The crude residue was chromatographed on silica gel with methanol/dichloromethane (0 to 10%) twice to afford 2-(tert-butyl)-N-(2-methyl-4-(6-(5-methyl-4,5,6,7-tetrahydropyrazolo[1,5-a]pyrazin-3-yl)-7H-pyrrolo[2,3-d]pyrimidin-4-yl)benzyl)thiazole-5-carboxamide (50 mg, yield: 20%) as white powder. $^1$H NMR (400 MHz, CHLOROFORM-d) δ 11.39-11.54 (m, 1H), 8.70-8.91 (m, 1H), 8.08-8.39 (m, 1H), 7.54-7.96 (m, 3H), 7.16-7.46 (m, 1H), 6.38 (s, 1H), 5.67 (s, 1H), 4.51-4.74 (m, 6H), 4.28 (br. s., 2H), 3.56-3.91 (m, 2H), 2.96 (br. s., 2H), 2.24-2.62 (m, 6H), 1.46 (d, J=2.01 Hz, 9H); $^1$H NMR (400 MHz, DMSO-d$_6$) d 12.34-12.51 (m, 1H), 9.07-9.20 (m, 1H), 8.69-8.91 (m, 1H), 8.35 (d, J=2.01 Hz, 1H), 7.95-8.09 (m, 3H), 7.33-7.50 (m, 1H), 6.78 (s, 1H), 6.51-6.69 (m, 1H), 5.56-5.76 (m, 1H), 4.53 (d, J=5.27 Hz, 2H), 4.11-4.27 (m, 2H), 3.66-3.98 (m, 1H), 2.64-2.96 (m, 1H), 2.45 (s, 5H), 1.39 (s, 9H); LC/MS: Rt–0.97 min, MS: (M+H)$^+$: 541.3.

Example 19

1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide

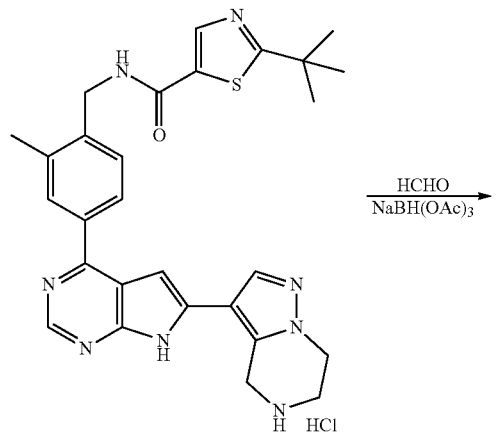

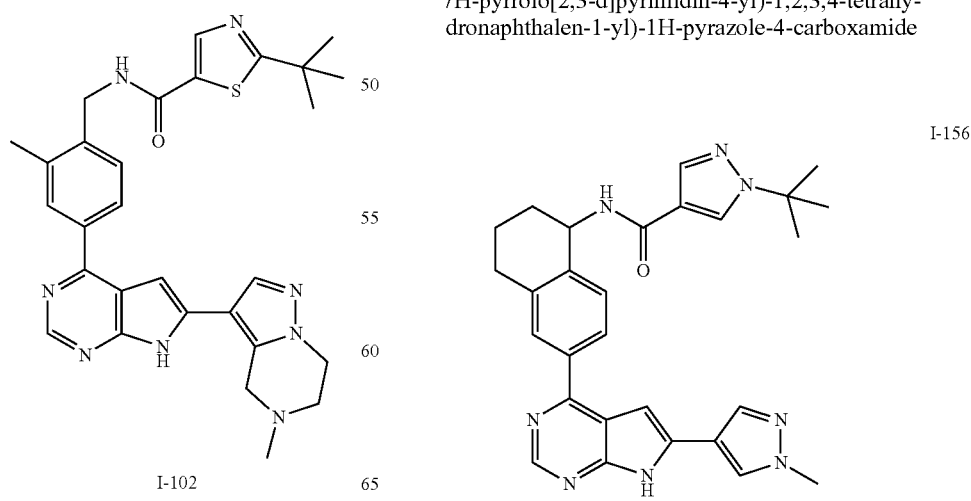

1. Synthesis of tert-butyl (6-(6-(1-methyl-1H-pyrazol-4-yl)-7H-pyrrolo[2,3-d]pyrimidin-4-yl)-1,2,3,4-tetrahydronaphthalen-1-yl)carbamate

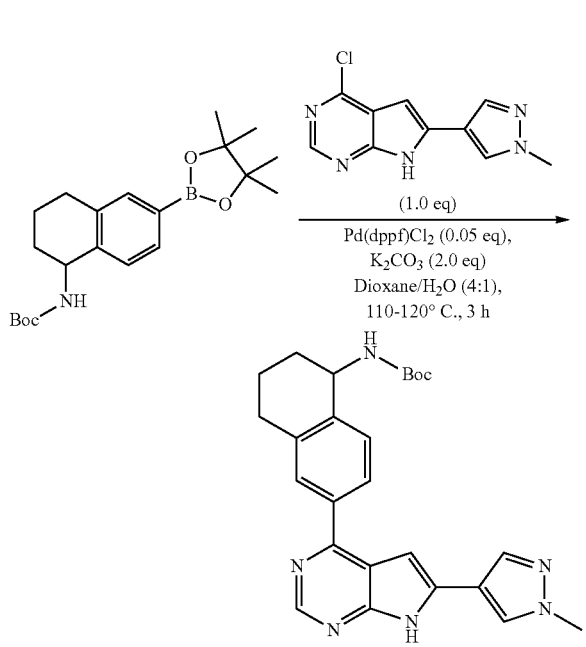

Synthesis of tert-butyl (6-(6-(1-methyl-1H-pyrazol-4-yl)-7H-pyrrolo[2,3-d]pyrimidin-4-yl)-1,2,3,4-tetrahydronaphthalen-1-yl)carbamate was similar to that of compound I-26 except tert-butyl (6-(4,4,5,5-tetramethyl-1,3,2-dioxaborolan-2-yl)-1,2,3,4-tetrahydronaphthalen-1-yl)carbamate was substituted for 2-(tert-butyl)-N-(2-methyl-4-(4,4,5,5-tetramethyl-1,3,2-dioxaborolan-2-yl)benzyl)thiazole-5-carboxamide. After concentration, the residue was purified by column chromatography (DCM/MeOH, 60:1 to 25:1) to give compound tert-butyl (6-(6-(1-methyl-1H-pyrazol-4-yl)-7H-pyrrolo[2,3-d]pyrimidin-4-yl)-1,2,3,4-tetrahydronaphthalen-1-yl)carbamate (241 mg, yield: 88%) as a light yellow solid. ESI-MS (M+H)$^+$: 445.1. $^1$H NMR (400 MHz, CD$_3$OD) δ: 8.68 (s, 1H), 8.07 (s, 1H), 7.95 (s, 1H), 7.84 (d, J=8.0 Hz, 1H), 7.77 (s, 1H), 7.48 (d, J=8.0 Hz, 1H), 6.86 (s, 1H), 5.24-5.23 (m, 1H), 3.96 (s, 3H), 2.91-2.89 (m, 2H), 2.08-2.06 (m, 1H), 1.99-1.98 (m, 1H), 1.85-1.84 (m, 2H), 1.50 (s, 9H).

2. Synthesis of 6-(6-(1-methyl-1H-pyrazol-4-yl)-7H-pyrrolo[2,3-d]pyrimidin-4-yl)-1,2,3,4-tetrahydronaphthalen-1-amine

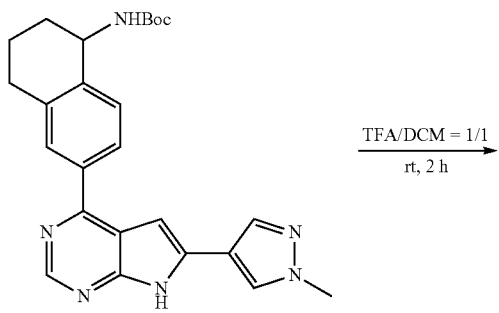

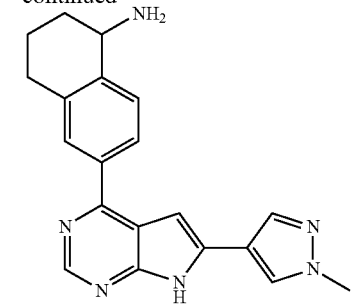

To a solution of tert-butyl (6-(6-(1-methyl-1H-pyrazol-4-yl)-7H-pyrrolo[2,3-d]pyrimidin-4-yl)-1,2,3,4-tetrahydronaphthalen-1-yl)carbamate (1.5 g, 3.38 mmol) in DCM (20 mL) was added TFA (20 mL). The mixture was stirred at rt for 2 h. Then the solvent was concentrated and the residue was dissolved in EA (100 mL). The organic layer was washed with aq. NaHCO$_3$ (20 mL), dried over Na$_2$SO$_4$, filtered and concentrated to afford the crude product 6-(6-(1-methyl-1H-pyrazol-4-yl)-7H-pyrrolo[2,3-d]pyrimidin-4-yl)-1,2,3,4-tetrahydronaphthalen-1-amine (985 mg, yield: 85%), which was used in the next step without further purification. ESI-MS (M+H)$^+$: 345.2.

3. Synthesis of 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide

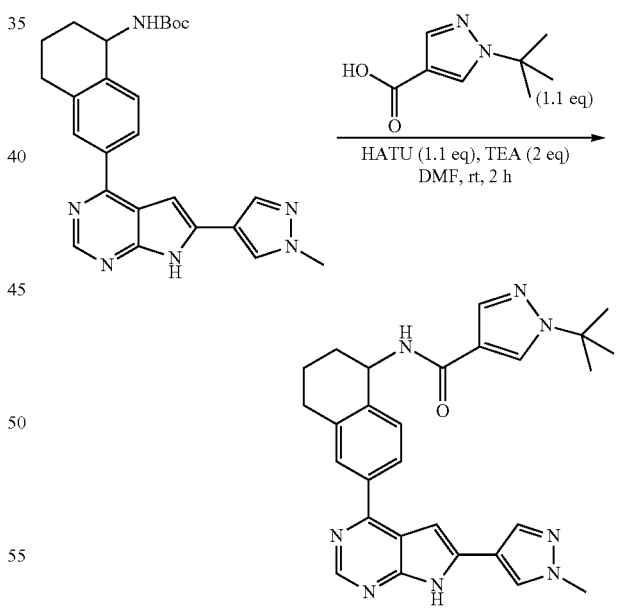

A mixture of 6-(6-(1-methyl-1H-pyrazol-4-yl)-7H-pyrrolo[2,3-d]pyrimidin-4-yl)-1,2,3,4-tetrahydronaphthalen-1-amine (200 mg, 0.58 mmol), 1-tert-butyl-1H-pyrazole-4-carboxylic acid (108 mg, 0.64 mmol), HATU (243 mg, 0.64 mmol) and TEA (131 mg, 1.28 mmol) in DMF (5 mL) was stirred at rt for 2 h. Then the reaction was diluted with water (20 mL) and extracted with EA (30 mL×2). The combined organic phases were washed with brine, dried over Na$_2$SO$_4$, filtered, and concentrated. The residue was purified by prep-HPLC (MeCN/H₂O with 0.05% NH₄OH as mobile phase) to give 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide (53 mg, yield: 18%) as a pale yellow solid. ESI-MS (M+H)⁺: 495.3. ¹H NMR (400 MHz, CDCl₃) δ: 10.08 (s, 1H), 8.89 (s, 1H), 8.07 (s, 1H), 7.95-7.89 (m, 2H), 7.86 (s, 1H), 7.77 (d, J=6.4 Hz, 2H), 7.53 (d, J=8.4 Hz, 1H), 6.80 (s, 1H), 6.02 (d, J=8.4 Hz, 1H), 5.56-5.43 (m, 1H), 4.00 (s, 3H), 3.08-2.84 (m, 2H), 2.25-2.15 (m, 1H), 2.01-1.91 (m, 3H), 1.61 (s, 9H).

Example 20

Synthesis of 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide

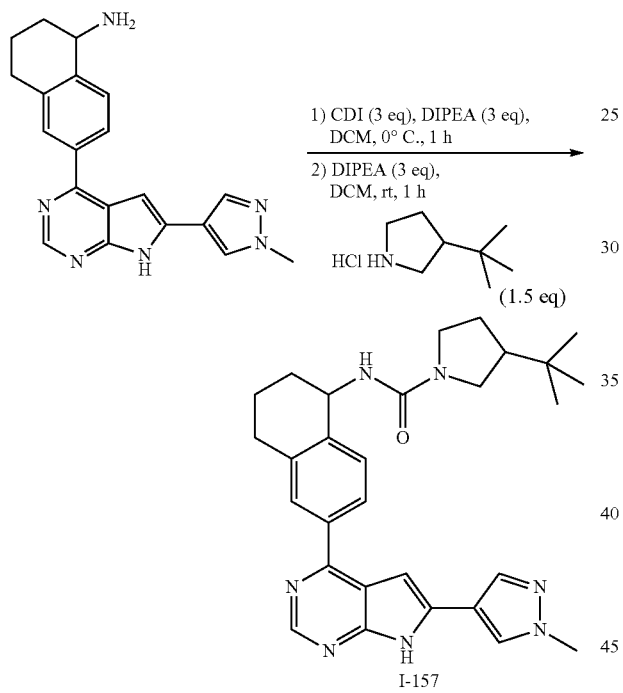

I-157

To a solution of CDI (424 mg, 2.62 mmol) and DIPEA (338 mg, 2.62 mmol) in DCM (20 mL) at 0° C. was added 6-(6-(1-methyl-1H-pyrazol-4-yl)-7H-pyrrolo[2,3-d]pyrimidin-4-yl)-1,2,3,4-tetrahydronaphthalen-1-amine (300 mg, 0.87 mmol) and the mixture was stirred at 0° C. for 1 h. Then the reaction was diluted with water (20 mL) and extracted with DCM (40 mL×2). The combined organic layers were washed with brine, dried over Na₂SO₄, filtered, and concentrated. The residue was dissolved in DCM (20 mL), then the solution of 3-(tert-butyl)pyrrolidine hydrochloride (214 mg, 1.31 mmol) and DIPEA (338 mg, 2.62 mmol) in DCM (10 mL) was added thereto. The mixture was stirred at rt for 2 h and concentrated. The residue was purified by prep-HPLC (MeOH/H₂O with 0.05% NH₄OH as mobile phase) to give 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide (129 mg, yield: 30%) as a pale yellow solid. ESI-MS (M+H)⁺: 498.3. ¹H NMR (400 MHz, CD₃OD) δ: 8.70 (s, 1H), 8.14 (s, 1H), 8.01 (s, 1H), 7.89 (d, J=8.4 Hz, 1H), 7.82 (s, 1H), 7.53 (d, J=8.0 Hz, 1H), 6.95 (s, 1H), 6.46-6.36 (m, 1H), 5.11 (s, 1H), 3.99 (s, 3H), 3.64-3.52 (m, 1H), 3.51-3.42 (m, 1H), 3.32-3.23 (m, 1H), 3.20-3.04 (m, 1H), 3.03-2.83 (m, 2H), 2.22-2.00 (m, 3H), 1.99-1.82 (m, 3H), 1.80-1.67 (m, 1H), 0.98 (s, 9H).

Example 21

3-isopropoxy-N-(6-(6-(1-methyl-7H-pyrazol-4-yl)-7H-pyrrolo[2,3-d]pyrimidin-4-yl)-1,2,3,4-tetrahydronaphthalen-1-yl)azetidine-1-carboxamide

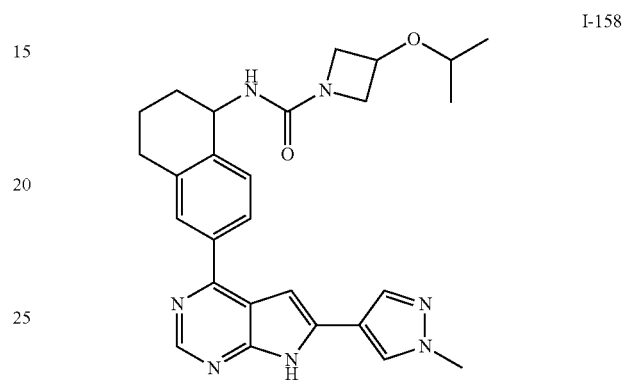

I-158

Synthesis of 3-isopropoxy-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide was similar to that of Example 20. The crude product was purified by prep-HPLC (MeCN/H₂O with 0.05% NH₄HCO₃ as mobile phrase) to give 3-isopropoxy-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide (200 mg, yield: 47%) as a yellow solid. ESI-MS (M+H)⁺: 486.2. ¹H NMR (400 MHz, CD₃OD) δ: 8.69 (s, 1H), 8.13 (s, 1H), 8.00 (s, 1H), 7.87 (d, J=8.0 Hz, 1H), 7.80 (s, 1H), 7.49 (d, J=8.4 Hz, 1H), 6.93-6.21 (m, 1H), 5.02 (t, J=7.2 Hz, 1H), 4.46-4.40 (m, 1H), 4.21-4.16 (m, 2H), 3.98 (s, 3H), 3.84-3.80 (m, 2H), 3.70-3.64 (m, 1H), 3.01-2.89 (m, 2H), 2.11-1.82 (m, 4H), 1.17 (d, J=6.0 Hz, 6H).

Example 22

3-(tert-butoxy)-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide

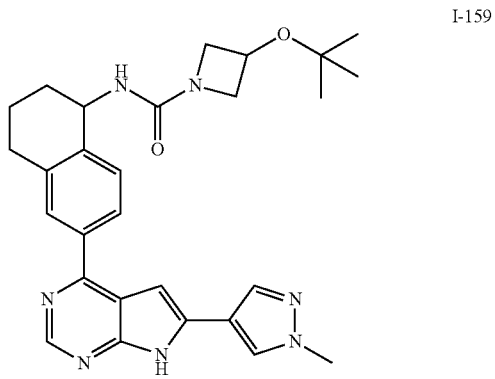 [SMILES: Cn1cc(-c2cc3c(-c4ccc5c(c4)CCCC5NC(=O)N4CC(OC(C)(C)C)C4)ncnc3[nH]2)cn1]

I-159

Synthesis of 3-(tert-butoxy)-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide was similar to that of 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide. The crude product was purified by prep-HPLC (MeCN/H₂O with 0.05% NH₄HCO₃ as mobile phase) to give 3-(tert-butoxy)-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide as a yellow solid (61 mg, yield: 14%). ESI-MS (M+H)⁺: 500.3. ¹H NMR (400 MHz, CD₃OD) δ: 8.68 (s, 1H), 8.11 (s, 1H), 7.99 (s, 1H), 7.86 (d, J=8.0 Hz, 1H), 7.79 (s, 1H), 7.48 (d, J=8.4 Hz, 1H), 6.90 (s, 1H), 5.02 (d, J=4.8 Hz, 1H), 4.61-4.56 (m, 1H), 4.20-4.16 (m, 2H), 3.97 (s, 3H) 3.82-3.78 (m, 2H), 2.96-2.88 (m, 2H), 2.11-2.01 (m, 2H), 1.91-1.82 (s, 2H), 1.21 (s, 9H).

Example 23

1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide

I-160

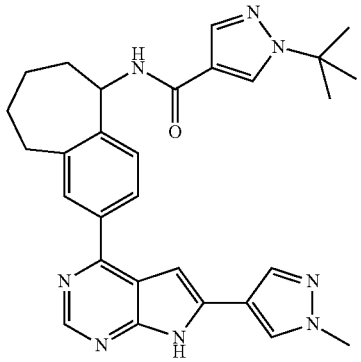

1. Synthesis of (E)-5-(3-bromophenyl)pent-4-enoic acid

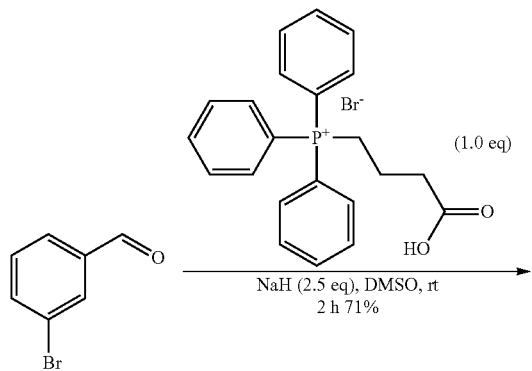

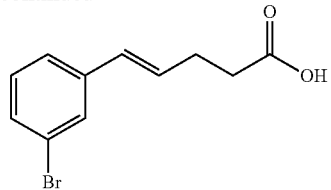

To a solution of (3-carboxypropyl)triphenylphosphonium (428 g, 1 mol) in dry DMSO (1 L) was added NaH (60% in oil, 100 g, 2.5 mol) by portions at 0° C. The reaction was stirred at room temperature for 30 min and then 3-bromobenzaldehyde (184 g, 1 mol) was added dropwise. The mixture was stirred at room temperature for an additional 2 h and then poured into water (2 L) and extracted with ethyl acetate (500 mL×3). The aqueous solution was acidified with conc. HCl and extracted with ethyl acetate (800 mL×3). The combined organic layer was washed with brine (100 mL×3). The organic layer was dried over sodium sulfate and concentrated under reduced pressure. The residue was purified by silica gel column (PE/EA=2:1) to give (E)-5-(3-bromophenyl)pent-4-enoic acid (180 g, yield: 71%) as a pale yellow solid. ¹H NMR (400 MHz, CDCl₃) δ: 7.48 (s, 1H), 7.33 (d, J=7.6 Hz, 1H), 7.23 (d, J=8.0 Hz, 1H), 7.15 (t, J=8.0 Hz, 1H), 6.39-6.35 (m, 1H), 6.23-6.19 (m, 1H), 2.55-2.53 (m, 4H); ESI-MS (M+1)⁺: 254.9.

2. Synthesis of 5-(3-bromophenyl)pentanoic acid

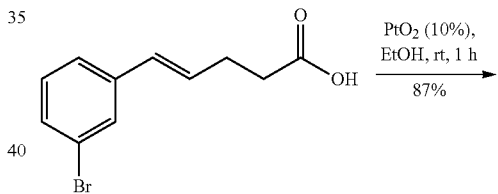

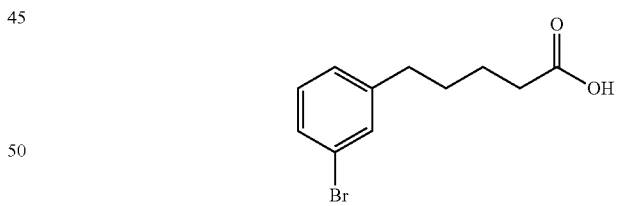

To a solution of (E)-5-(3-bromophenyl)pent-4-enoic acid (24.0 g, 94 mmol) in ethanol (200 mL) was added PtO₂ (1.2 g, 5% wt). The mixture was stirred for 1 h under hydrogen atmosphere. After filtration through Celite, the filtrate was concentrated to give target compound 5-(3-bromophenyl)pentanoic acid (21.0 g, yield: 87%) as a yellow solid, which was used to next step without further purification. ¹H NMR (400 MHz, CD₃OD) δ: 7.24 (s, 1H), 7.21-7.18 (m, 1H), 7.06-7.03 (m, 2H), 2.50 (t, J=6.8 Hz, 2H), 2.20 (t, J=6.8 Hz, 2H), 1.53-1.51 (m, 4H); ESI-MS (M+1)⁺: 256.9.

3. Synthesis of 2-bromo-6,7,8,9-tetrahydro-5H-benzo[7]annulen-5-one

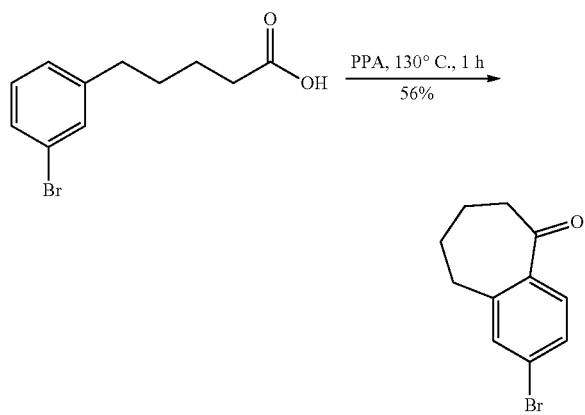

A mixture of 5-(3-bromophenyl)pentanoic acid (21 g, 82 mmol) in PPA (50 mL) was stirred at 130° C. for 1 h. After cooling down, the mixture was basified to pH=7-8 with NaOH (1 N). The mixture was extracted with ethyl acetate (200 mL×2). The combined organic layer was dried over anhydrous sodium sulfate and concentrated under reduced pressure. The residue was purified by silica gel column (PE/EA=20:1) to give 2-bromo-6,7,8,9-tetrahydro-5H-benzo[7]annulen-5-one (11.0 g, yield: 56%) as a colorless oil. $^1$H NMR (400 MHz, CDCl$_3$) δ: 7.59 (d, J=8.4 Hz, 1H), 7.43 (d, J=8.4 Hz, 1H), 7.38 (s, 1H), 2.89 (t, J=6.8 Hz, 2H), 2.72 (t, J=6.0 Hz, 2H), 1.90-1.79 (m, 4H); ESI-MS (M+H)$^+$: 239.0.

4. Synthesis of 2-bromo-6,7,8,9-tetrahydro-5H-benzo[7]annulen-5-amine

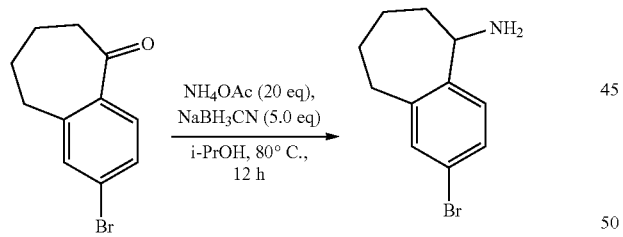

To a solution of 2-bromo-6,7,8,9-tetrahydro-5H-benzo[7]annulen-5-one (30 g, 126 mmol) in $^i$PrOH (500 mL), NH$_4$OAc (190 g, 2.5 mol) and NaBH$_3$CN (40 g, 630 mmol) were added. The mixture was stirred at 80° C. for 12 h. After cooling down, the mixture was basified to pH>12 with NaOH (1 N) and extracted with DCM (200 mL×2). The combined organic layers were dried over sodium sulfate and concentrated under reduced pressure. The residue was treated with HCl/dioxane (4 M) to give 2-bromo-6,7,8,9-tetrahydro-5H-benzo[7]annulen-5-amine (25 g, yield: 83%) as a white solid. $^1$H NMR (400 MHz, CD$_3$OD) δ: 7.27 (dd, J$_1$=8.4 Hz, J$_1$=2.4 Hz, 1H), 7.22 (d, J=2.8 Hz, 1H), 7.16 (d, J=8.4 Hz, 1H), 4.15-4.13 (m, 1H), 2.80-2.74 (m, 2H), 1.92-1.73 (m, 4H), 1.50-1.43 (m, 1H), 1.32-1.19 (m, 1H); ESI-MS (M−16)$^+$: 223.0.

5. Synthesis of tert-butyl (2-bromo-6,7,8,9-tetrahydro-5H-benzo[7]annulen-5-yl)carbamate

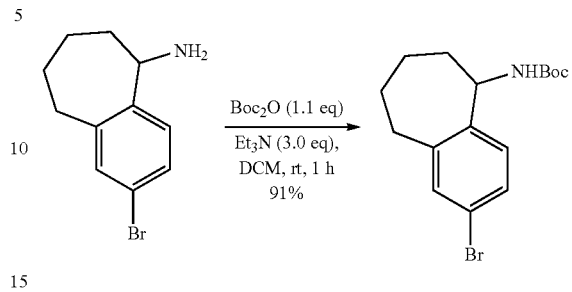

To a solution of 2-bromo-6,7,8,9-tetrahydro-5H-benzo[7]annulen-5-amine (50.0 g, 18.2 mmol) in DCM (500 mL) were added TEA (55.0 g, 54.5 mmol) and (Boc)$_2$O (43.6 g, 20 mmol) at 0° C. The mixture was stirred for 1 h at rt, washed with citric acid solution, sat. NaHCO$_3$ solution and brine. The organic layer was dried over sodium sulfate and concentrated under reduced pressure. The residue was purified by silica gel column (PE/EA=10:1) to give tert-butyl (2-bromo-6,7,8,9-tetrahydro-5H-benzo[7]annulen-5-yl)carbamate (56.0 g, yield: 91%) as a white solid. ESI-MS (M+H)$^+$: 340.1.

6. The preparation of tert-butyl (2-(4,4,5,5-tetramethyl-1,3,2-dioxaborolan-2-yl)-6,7,8,9-tetrahydro-5H-benzo[7]annulen-5-yl)carbamate

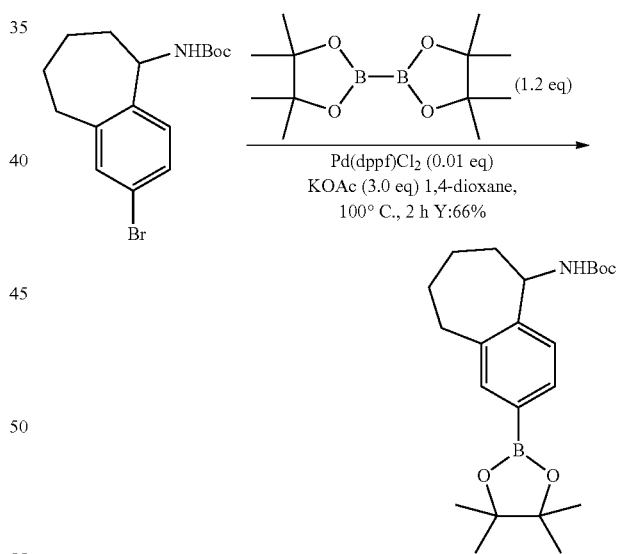

To a solution of tert-butyl (2-bromo-6,7,8,9-tetrahydro-5H-benzo[7]annulen-5-yl)carbamate (56.0 g, 16.5 mmol) in anhydrous 1,4-dioxane (500 mL) were added bis(pinacolato)diboron (50.0 g, 19.8 mmol), KOAc (49.0 g, 0.5 mol) and Pd(dppf)Cl$_2$DCM (1.5 g, 1.66 mmol) under nitrogen atmosphere. The mixture was stirred at 100° C. for 6 h under nitrogen atmosphere. After cooling down to rt, the mixture was diluted with ethyl acetate (200 mL) and filtered by Celite. The filtrate was washed with brine (200 mL×2), dried over sodium sulfate, and concentrated under reduced pressure. The residue was purified by silica gel column (PE/

EA=10:1) to give tert-butyl (2-(4,4,5,5-tetramethyl-1,3,2-dioxaborolan-2-yl)-6,7,8,9-tetrahydro-5H-benzo[7]annulen-5-yl)carbamate (40.0 g, yield: 66%) as a white solid. ¹H NMR (400 MHz, CDCl₃) δ: 7.63 (d, J=7.6 Hz, 1H), 7.54 (s, 1H), 7.24 (d, J=7.6 Hz, 1H), 4.97-4.90 (m, 2H), 2.91-2.81 (m, 2H), 1.90-1.61 (m, 6H), 1.49 (s, 9H), 1.26 (s, 12H); ESI-MS (M+H)⁺: 388.3.

7. Synthesis of tert-butyl (2-(6-(1-methyl-1H-pyrazol-4-yl)-7H-pyrrolo[2,3-d]pyrimidin-4-yl)-6,7,8,9-tetrahydro-5H-benzo[7]annulen-5-yl)carbamate

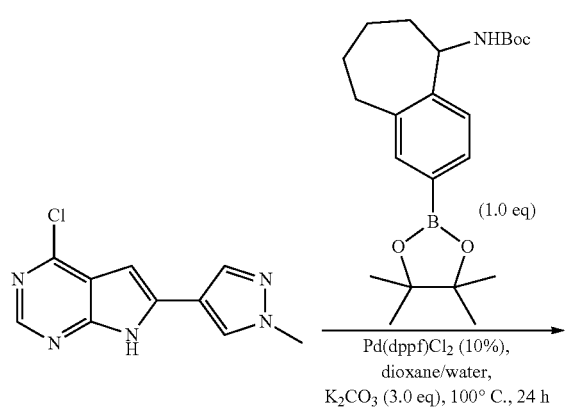

To a mixture of 4-chloro-6-(1-methyl-1H-pyrazol-4-yl)-7H-pyrrolo[2,3-d]pyrimidine (2.33 g, 10 mmol) and tert-butyl (2-(4,4,5,5-tetramethyl-1,3,2-dioxaborolan-2-yl)-6,7,8,9-tetrahydro-5H-benzo[7]annulen-5-yl)carbamate (3.87 g, 10 mmol) in dioxane/water (40 mL, 5:1), K₂CO₃ (2.76 g, 20 mmol) and Pd(dppf)Cl₂·DCM (408 mg, 0.5 mmol) was added. The mixture was stirred at 100° C. for 24 h under N₂. After cooling down, the mixture was filtered through a Celite pad. The filtrate was concentrated and purified by silica gel column (DCM:MeOH=30:1) to give tert-butyl (2-(6-(1-methyl-1H-pyrazol-4-yl)-7H-pyrrolo[2,3-d]pyrimidin-4-yl)-6,7,8,9-tetrahydro-5H-benzo[7]annulen-5-yl)carbamate (1.83 g, yield: 40%) as a brown solid. ESI-MS (M+H)⁺: 459.2. ¹H NMR (400 MHz, DMSO-d6) δ: 12.94 (s, 1H), 8.74 (s, 1H), 8.30 (s, 1H), 8.10 (s, 1H), 8.03 (d, J=8.0 Hz, 1H), 7.97 (s, 1H), 7.40 (d, J=8.0 Hz, 1H), 7.09 (d, J=1.6 Hz, 1H), 4.81 (t, J=8.8 Hz, 1H), 3.92 (s, 3H) 3.33-2.88 (m, 2H), 1.91-1.78 (m, 4H), 1.58-1.55 (m, 1H), 1.56 (s, 9H), 1.34-1.32 (m, 2H).

8. Synthesis of 2-(6-(1-methyl-1H-pyrazol-4-yl)-7H-pyrrolo[2,3-d]pyrimidin-4-yl)-6,7,8,9-tetrahydro-5H-benzo[7]annulen-5-amine

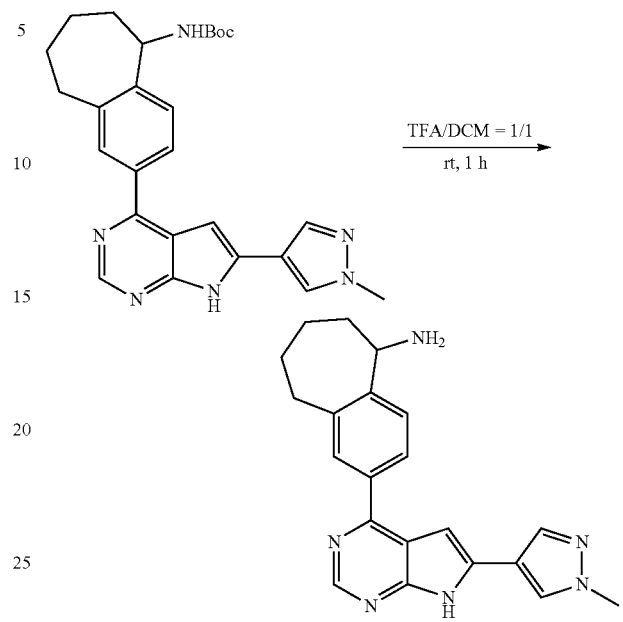

Synthesis of 2-(6-(1-methyl-1H-pyrazol-4-yl)-7H-pyrrolo[2,3-d]pyrimidin-4-yl)-6,7,8,9-tetrahydro-5H-benzo[7]annulen-5-amine was similar to that of 6-(6-(1-methyl-1H-pyrazol-4-yl)-7H-pyrrolo[2,3-d]pyrimidin-4-yl)-1,2,3,4-tetrahydronaphthalen-1-amine. The crude product (830 mg, yield: 87%) was used in the next step without further purification. ESI-MS (M+H)⁺: 359.2.

9. Synthesis of 1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide

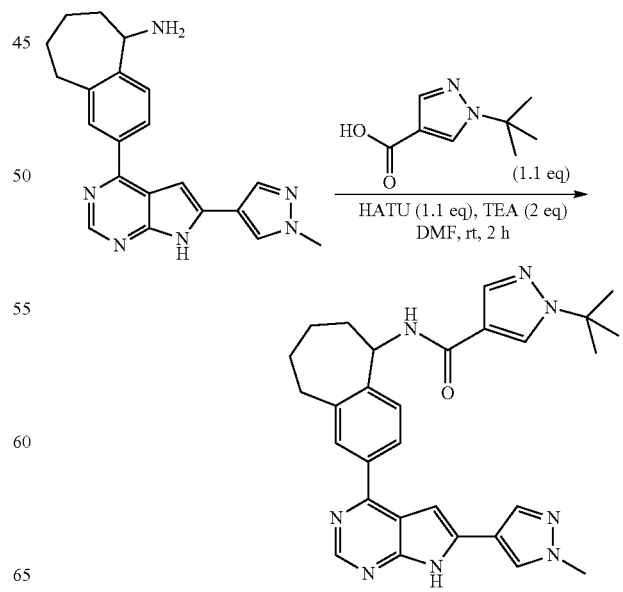

Synthesis of 1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide was similar to that of 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide. The crude was purified by prep-HPLC (MeCN/H$_2$O with 0.05% NH$_4$OH as mobile phase) to give 1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide (70 mg, yield: 47%) as a pale yellow solid. ESI-MS (M+H)$^+$:509.3. $^1$H NMR (400 MHz, CD$_3$OD) δ: 8.74-8.65 (m, 2H), 8.40 (s, 1H), 8.14 (s, 1H), 8.09 (s, 1H), 8.01 (s, 1H), 7.92-7.84 (m, 2H), 7.47 (d, J=8.4 Hz, 1H), 6.96 (s, 1H), 5.47-5.36 (m, 1H), 3.98 (s, 3H), 3.18-3.01 (m, 2H), 2.15-1.79 (m, 5H), 1.66 (s, 9H), 1.55-1.41 (m, 1H).

Example 24

2-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)thiazole-5-carboxamide

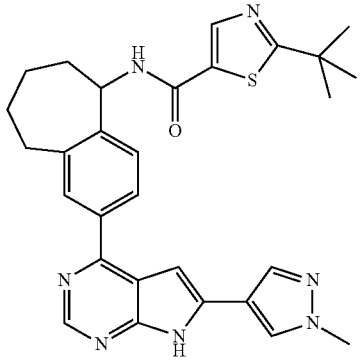

I-161

Synthesis of 2-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)thiazole-5-carboxamide was similar to that of 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide. The crude was purified by prep-HPLC (MeCN/H$_2$O with 0.05% NH$_4$OH as mobile phase) to give 2-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)thiazole-5-carboxamide (64 mg, yield: 21%) as a pale yellow solid. ESI-MS (M+H)$^+$:526.2. $^1$H NMR (400 MHz, d$_6$-DMSO) δ: 12.48 (s, 1H), 9.16 (d, J=8.0 Hz, 1H), 8.73 (s, 1H), 8.52 (s, 1H), 8.27 (s, 1H), 8.07 (s, 1H), 8.05-7.94 (m, 2H), 7.40 (d, J=7.6 Hz, 1H), 7.07 (s, 1H), 5.27 (t, J=8.8 Hz, 1H), 3.90 (s, 3H), 3.09-2.93 (m, 2H), 2.07-1.69 (m, 6H), 1.42 (s, 9H).

Example 25

3-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)pyrrolidine-1-carboxamide

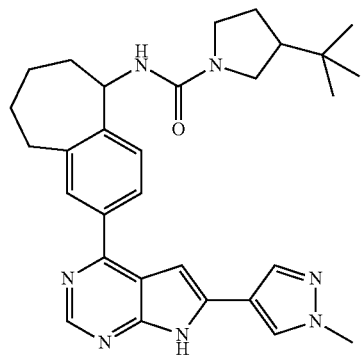

I-162

Synthesis of 3-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)pyrrolidine-1-carboxamide was similar to that of 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide. The crude was purified by prep-HPLC (MeCN/H$_2$O with 0.05% NH$_4$OH as mobile phase) to give 3-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)pyrrolidine-1-carboxamide (56 mg, yield: 26%) as a yellow solid. ESI-MS (M+H)$^+$:512.3. $^1$H NMR (400 MHz, CD$_3$OD) δ: 8.67 (s, 1H), 8.08 (s, 1H), 7.97 (s, 1H), 7.86-7.80 (m, 2H), 7.45 (dd, J=6.4 Hz, J=7.6 Hz, 1H), 6.87 (d, J=1.6 Hz, 1H), 5.18 (t, J=10.4 Hz, 1H), 3.95 (s, 3H), 3.71-3.52 (m, 2H), 3.39-3.35 (m, 1H), 3.23-3.14 (m, 1H), 3.07-2.94 (m, 2H), 2.16-2.12 (m, 1H), 2.04-1.90 (m, 5H), 1.80-1.73 (m, 2H), 1.43-1.40 (m, 1H), 0.99 (s, 9H).

Example 26

3-isopropoxy-N-(2-(6-(1-methyl-7H-pyrazol-4-yl)-7H-pyrrolo[2,3-d]pyrimidin-4-yl)-6,7,8,9-tetrahydro-5H-benzo[7]annulen-5-yl)azetidine-1-carboxamide

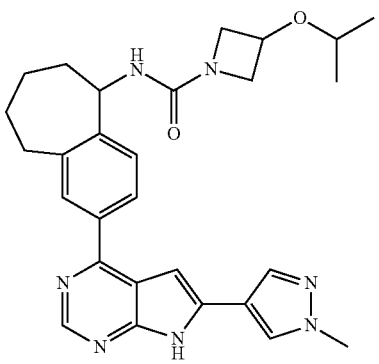

I-163

Synthesis of 3-isopropoxy-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide was similar to that of 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide. The crude product was purified by prep-HPLC (MeCN/H$_2$O with 0.05% NH$_4$HCO$_3$ as mobile phrase) to give 3-isopropoxy-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide (200 mg, yield: 47%) as a yellow solid. ESI-MS (M+H)$^+$: 500.1. $^1$H NMR (400 MHz, CD$_3$OD) δ: 8.70 (s, 1H), 8.14 (s, 1H), 8.01 (s, 1H), 7.90 (d, J=8.0 Hz, 1H), 7.84 (s, 1H), 7.46 (d, J=8.0 Hz, 1H), 6.94-6.90 (m, 1H), 5.13-5.09 (m, 1H), 4.50-4.48 (m, 1H), 4.30-4.22 (m, 2H), 3.98 (s, 3H), 3.92-3.84 (m, 2H), 3.74-3.67 (m, 1H), 3.11-2.98 (m, 2H), 2.04-1.92 (m, 4H), 1.76-1.68 (m, 1H), 1.49-1.35 (m, 1H), 1.19 (d, J=6.0 Hz, 6H).

Example 27

3-(tert-butoxy)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide

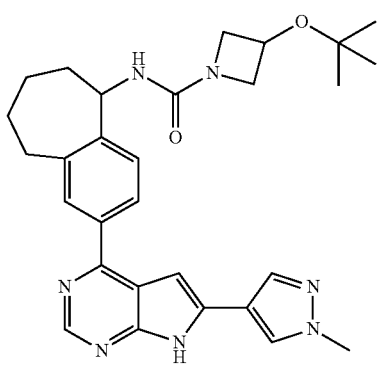

I-164

Synthesis of 3-(tert-butoxy)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide was similar to that of 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide. The crude was purified by prep-HPLC (MeCN/H$_2$O with 0.05% NH$_4$OH as mobile phase) to give 3-(tert-butoxy)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide (117 mg, yield: 41%) as a yellow solid. ESI-MS (M+H)$^+$:514.3. $^1$H NMR (400 MHz, CD$_3$OD) δ: 8.68 (s, 1H), 8.09 (s, 1H), 7.98 (s, 1H), 7.87-7.80 (m, 2H), 7.45 (d, J=8.0 Hz, 1H), 6.88 (s, 1H), 5.10 (d, J=10.4 Hz, 1H), 4.63-4.59 (m, 1H), 4.29-4.21 (m, 2H), 3.96 (s, 3H), 3.93-3.83 (m, 2H), 3.03-2.99 (m, 2H), 2.02-1.89 (m, 4H), 1.75-1.69 (m, 1H), 1.42-1.39 (m, 1H), 1.23 (s, 9H).

Example 28

Protocol for Human B Cell Stimulation

Human B cells are purified from 150 ml of blood. Briefly, the blood is diluted 1/2 with PBS and centrifuged through a Ficoll density gradient. The B cells are isolated from the mononuclear cells by negative selection using the B cell isolation kit II from Milenyi (Auburn, Calif.). 50,000 B cells per well are then stimulated with 10 g/ml of goat F(ab')2 anti-human IgM antibodies (Jackson ImmunoResearch Laboratories, West Grove, Pa.) in a 96-well plate. Compounds are diluted in DMSO and added to the cells. Final concentration of DMSO is 0.5%. Proliferation is measured after 3 days using Promega CellTiter-Glo (Madison, Wis.).

Example 29

In Vitro BTK Kinase Assay: BTK-POLYGAT-LS Assay

The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 μL aliquot of a ATP/peptide master mix (final concentration; ATP 1 μM, polyGAT 100 nM) in kinase buffer (10 mM Tris-HCl pH 7.5, 10 mM MgCl$_2$, 20 μM Na$_3$PO$_4$, 5 mM DTT, 0.01% Triton X-100, and 0.2 mg/ml casein) is added to each well. Next, 1 μL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 μL of a 50 mM EDTA solution. Aliquots (5 μL) of the kinase reaction are transferred to a low volume white 384 well plate (Corning 3674), and 5 μL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-27 herein, supra. Compounds have an activity designated as "A" provided an IC$_{50}$<10 nM; compounds having an activity designated as "B" provided an IC$_{50}$ of 10-99 nM; compounds having an activity designated as "C" provided an IC$_{50}$ of 100-999 nM; and compounds having an activity designated as "D" provided an IC$_{50}$ of 1,000-10,000 nM; and compounds having an activity designated as "E" provided an IC$_{50}$ of >10,000 nM. In some instances where a compound tested has activity "E", other structurally similar compounds beyond the measurable limits of the assay are not included in Table 1.

TABLE 1

Inhibitory Data for Exemplary Compounds

| Compound tested | IC50 (10 uMATP) uM |
|---|---|
| I-1 | A |
| I-2 | A |
| I-3 | B |

TABLE 1-continued

Inhibitory Data for Exemplary Compounds

| Compound tested | IC50 (10 uMATP) uM |
|---|---|
| I-4 | B |
| I-5 | B |
| I-6 | B |
| I-7 | D |
| I-9 | D |
| I-10 | B |
| I-11 | A |
| I-12 | C |
| I-13 | B |
| I-14 | B |
| I-15 | B |
| I-16 | B |
| I-17 | B |
| I-18 | A |
| I-19 | A |
| I-20 | A |
| I-21 | A |
| I-22 | A |
| I-23 | A |
| I-24 | B |
| I-25 | A |
| I-26 | A |
| I-27 | B |
| I-28 | B |
| I-29 | B |
| I-30 | A |
| I-31 | A |
| I-32 | A |
| I-33 | A |
| I-34 | A |
| I-35 | A |
| I-36 | A |
| I-37 | A |
| I-38 | A |
| I-39 | A |
| I-40 | A |
| I-41 | A |
| I-42 | A |
| I-43 | A |
| I-44 | A |
| I-45 | B |
| I-46 | A |
| I-47 | A |
| I-48 | A |
| I-49 | A |
| I-50 | A |
| I-51 | A |
| I-52 | A |
| I-53 | A |
| I-54 | C |
| I-55 | B |
| I-56 | C |
| I-57 | D |
| I-58 | C |
| I-59 | D |
| I-60 | E |
| I-61 | B |
| I-62 | B |
| I-63 | D |
| I-64 | E |
| I-65 | B |
| I-66 | C |
| I-67 | C |
| I-68 | C |
| I-69 | B |
| I-70 | C |
| I-71 | B |
| I-72 | C |
| I-73 | B |
| I-74 | C |
| I-75 | D |
| I-76 | A |
| I-77 | A |
| I-78 | A |
| I-79 | B |
| I-80 | B |
| I-81 | C |
| I-82 | C |
| I-83 | D |
| I-84 | C |
| I-85 | A |
| I-86 | B |
| I-87 | A |
| I-88 | B |
| I-89 | A |
| I-90 | C |
| I-91 | B |
| I-92 | C |
| I-93 | B |
| I-95 | C |
| I-96 | B |
| I-97 | B |
| I-98 | A |
| I-99 | A |
| I-100 | A |
| I-101 | C |
| I-102 | A |
| I-103 | C |
| I-104 | C |
| I-105 | C |
| I-106 | B |
| I-107 | A |
| I-108 | B |
| I-109 | C |
| I-110 | B |
| I-111 | A |
| I-112 | A |
| I-113 | A |
| I-114 | A |
| I-115 | A |
| I-116 | A |
| I-117 | A |
| I-118 | A |
| I-119 | A |
| I-120 | A |
| I-121 | A |
| I-122 | B |
| I-123 | B |
| I-124 | B |
| I-125 | B |
| I-126 | B |
| I-127 | B |
| I-128 | B |
| I-129 | B |
| I-130 | B |
| I-131 | C |
| I-132 | B |
| I-133 | B |
| I-134 | B |
| I-135 | B |
| I-136 | B |
| I-137 | B |
| I-138 | B |
| I-139 | B |
| I-140 | C |
| I-141 | C |
| I-142 | C |
| I-143 | C |
| I-144 | C |
| I-145 | C |
| I-146 | C |
| I-147 | D |
| I-148 | D |
| I-149 | D |
| I-150 | D |
| I-151 | D |
| I-152 | D |
| I-153 | B |

TABLE 1-continued

Inhibitory Data for Exemplary Compounds

| Compound tested | IC50 (10 uMATP) uM |
|---|---|
| I-154 | E |
| I-155 | D |
| I-156 | A |
| I-157 | A |
| I-158 | A |
| I-159 | A |
| I-160 | A |
| I-161 | A |
| I-162 | A |
| I-163 | A |
| I-164 | A |

Example 30

In Vitro Inhibition of BTK Activity in Mouse Whole Blood

Anti-rabbit MSD plates (Meso Scale Discovery, Rockville, Md.) are coated with 35 uL/well of rabbit anti-BTK C82B8 (Cell Signaling Technology, Danvers, Mass.) diluted 1:50 in PBS. Plates are incubated for 2 hours±1 hour at room temp, shaking (setting 3-5) or ON at 4° C. Plates are blocked with MSD Blocker A (Meso Scale Discovery, Rockville, Md.) using 3% MSD Blocker A in TBST. Coated plates are first washed 3× with 250 uL/well TBST followed by addition of 200 uL/well 3% Blocker A/TBST. Plates are blocked for >2 hour at RT, shaking or ON at 4° C.

Whole blood is collected from DBA/1 mice in 16×100 sodium heparin tubes (Becton Dickinson, Cat No. 367874). Blood from multiple DBA/1 mice is pooled. 96 uL of whole blood per well is aliquotted into a 96-round bottom plate changing tips each time. 4 uL diluted test compound is added to each sample, mixed, and incubated for 30 min at 37° C.

For serial dilutions of test compound, 1000× plate is produced with serial dilutions of test compound in 100% DMSO. Ten dilutions, done 1:3, starting at 10 mM are created by: adding 15 uL of test compound at 10 mM in 100% DMSO to well Al; adding 10 uL 100% DMSO to wells A2-A12; diluting 5 uL from well A1 to well A2 and mixing; continuing 1:3 serial dilutions, changing tips between transfers, to well A10. Wells A11 and A12 contain 100% DMSO without test compound.

For dilution 1, a 1:40 plate is created. Using a 12-well multi-channel pipette, each concentration of test compound or DMSO is diluted 1:40 by adding 2 uL from each well of 1000× stock plate to 78 uL water and mixing.

For dilution 2, test compound or DMSO are added to whole blood by diluting 1:25. Using a 12-well multi-channel pipette, 4 uL from 1:40 plate (B) is added to 96 uL whole blood and mixed.

The final concentration of test compounds are shown below. The concentration of DMSO is 0.1% final in each well.

Lysing buffer used to lyse whole blood is prepared as follows. A 10× Lysis buffer is prepared using 1500 mM NaCl; 200 mM Tris, pH 7.5; 10 mM EDTA; 10 mM EGTA; and 10% Triton-X-100. The 10× Lysis buffer is diluted to 1× in dH$_2$O, and complete lysing buffer (+/− phosphatase inhibitors) is prepared as follows:

|  | +PPi (mL) | −PPi (mL) |
|---|---|---|
| 1X Lysis buffer | 10 | 10 |
| 500 mM PMSF in DMSO | 0.02 | 0.02 |
| Phosphatase Inhibitor 3 | 0.1 | |
| Phosphatase Inhibitor 2 | 0.1 | |
| Protease Inhibitor (cOmplete) (1 tablet for 10 mL) | 1 tablet | 1 tablet |
| PhosStop (1 tablet for 10 mL) | 1 tablet | |
| Sodium Orthovanadate (Na$_3$VO$_4$) (50 uM final) | 0.1 | |
| Sodium Fluoride (NaF) (10 mM final) | 0.005 | |
| 1% Deoxycholate (0.25% final) | 2.5 | 2.5 |

100 uL of complete lysing buffer (+/− phosphatase inhibitors) is added to each well, and mixed well by pipetting up and down a few times. Wells 1-10 and 12 received 1× Lysis buffer containing phosphatase inhibitors (+PPi) and well 11 receive 1× Lysis buffer without phosphatase inhibitors (−PPi). Samples are incubated for 1 hour on ice or at 4° C. Samples are mixed again at half time point for complete lysing.

Blocking buffer is washed off blocked MSD plates with 250 uL TBST per well 3 times. 100-150 uL of whole blood lysates is added to each well of the coated and blocked MSD plates followed by incubation overnight in a cold room with shaking.

The plates are then washed 4 times with 250 μL TBST per well. Biotinylated phospho-tyrosine mouse mAb (pY100, Cell Signaling Technology, Danvers, Mass.) was diluted 1:125 in 1% Blocker A. Mouse anti-BTK mAb (Fitzgerald Industries International, Acton, Mass.) is diluted 1:900 in 1% Blocker A. 35 μL of diluted pY100 or diluted anti-BTK mAb is added to each well and incubated for 2 hours at room temperature, shaking.

Plates are then washed 3 times with 250 uL TBST/well. 35 uL of 1:500 Streptavidin-Sulfo-Tag labeled antibody in 3% Blocker A is added to each well. For anti-BTK, 35 uL of 1:500 anti-mouse-Tag labeled antibody in 3% Blocker A is added to each well. Plates are incubated for 1 hour at RT, shaking.

To develop and read the plates, 1× Read Buffer in dH$_2$O is prepared from 4× stock. Plates are washed 3 times with 250 uL TBST/well. 150 uL of 1×MSD Read Buffer is added to each well. Plates are read in a SECTOR Imager 6000 (Meso Scale Discovery, Rockville, Md.).

Materials

| ITEM | VENDOR | CATALOG NO. |
|---|---|---|
| Anti-rabbit MSD plates | MSD | L45RA-1 |
| Rabbit anti-BTK (C82B8) | Cell Signaling | 3533S |
| PBS | Media Prep | |

| | 1 | 2 | 3 | 4 | 5 | 6 | 7 | 8 | 9 | 10 | (+PPi) 11 | (−PPi) 12 |
|---|---|---|---|---|---|---|---|---|---|---|---|---|
| A | 10000 nM | 3333 nM | 1111 nM | 370 nM | 123 nM | 41 nM | 14 nM | 5 nM | 2 nM | 0.5 nM | 0 nM | 0 nM |
| B | 10000 nM | 3333 nM | 1111 nM | 370 nM | 123 nM | 41 nM | 14 nM | 5 nM | 2 nM | 0.5 nM | 0 nM | 0 nM |
| C | 10000 nM | 3333 nM | 1111 nM | 370 nM | 123 nM | 41 nM | 14 nM | 5 nM | 2 nM | 0.5 nM | 0 nM | 0 nM |

-continued

| ITEM | VENDOR | CATALOG NO. |
|---|---|---|
| MSD Blocker A | MSD | R93BA-4 |
| TBST (1xTBS/0.1% Tween20) | Media Prep | |
| 10X Lysing Buffer | Media Prep | |
| PMSF in DMSO (500 mM) | Media Prep | |
| Phosphatase Cocktail Inhibitor 3 | Sigma Aldrich | P0044-5ML |
| Phosphatase Cocktail Inhibitor 2 | Sigma Aldrich | P5726-1ML |
| cOmplete Mini | Roche | 11 836 153 001 |
| PhosStop Inhibitor | Roche | 04 906 837 001 |
| Sodium Orthovanadate 100 mM | Media Prep | |
| Sodium Fluoride 1M | Media Prep | |
| 1% Deoxycholate | Media Prep | |
| pTyr 100 ms mAb biotinylated | Cell Signaling | 9417S |
| Streptavidin Sulfo-Tag | MSD | R32AD-1 |
| MSD Read Buffer 4X | MSD | R92TC-1 |
| Costar 96-round bottom | Costar/Fisher | 3799 |
| Mouse anti-BTK (7F12H4) | Fitzgerald | 10R-1929 |
| Anti-mouse Sulfo-Tag | MSD | R32AC-5 |

Results

FIG. 1 depicts pBTK levels in mouse whole blood after being contacted with indicated concentrations of Compound A. Heparinized whole blood from DBA/2 mice were pooled, aliquoted in a 96-well plate and "spiked" with the indicated final concentration of Compound A. Two additional wells, used for controls, were spiked with no drug. The final concentration of DMSO was held constant at 0.1% for all wells including controls. Samples were incubated for 30 min at 37° C. Drug "spiked" wells and one of the DMSO control wells (+PPi) were lysed in lysis buffer containing protease and phosphatase inhibitors. The remaining DMSO control well (−PPi) was lysed in the same solution except the phosphatase inhibitors were excluded. The lysed whole blood was transferred to an MSD plate and total BTK was captured. After removing unbound material by washing, tyrosine phosphorylated BTK was detected with an anti-phosphotyrosine antibody. The +PPi sample serves as the high control for maximal ECL signal and the −PPi serves as the low control for minimal ECL signal. As shown in FIG. 1, Compound A inhibited BTK phosphorylation in a dose dependent manner.

A best-fit curve was calculated in Prism and the drug concentration that produces a 50% inhibition of BTK phosphorylation ($IC_{50}$) was estimated from the curve by interpolation. The $IC_{50}$ value was determined to be 443 nM and the $R^2$ value was 0.84.

Example 31

PK/PD Correlation in DBA1 Mice

Mice were dosed orally (PO) with test compound in CMC-Tween and killed by $CO_2$ asphyxiation at various times after dosing. Heparinized whole blood was immediately collected by cardiac puncture and split into two samples. One sample was used to quantify the amount of test compound present and the other was lysed in MSD lysis buffer in the presence of phosphatase inhibitors. Heparinized whole blood from cardiac punctures of vehicle (CMC-Tween) dosed mice are lysed either in the presence (high control) or absence (low control) of phosphatase inhibitors. Lysed whole blood samples were analyzed for phospho-BTK as described above. The percent inhibition of phospho-BTK in each whole blood sample from dosed mice was calculated as follows: (1−((pBTK(x+PPi)−pBTK(vehicle−PPi))/(pBTK(vehicle+PPi))))*100, where pBTK(x+PPi) is the ECL signal for whole blood from each test compound-treated mouse, pBTK(vehicle−PPi) is the average ECL signal of whole blood from vehicle-treated mice lysed in the absence of phosphatase inhibitors (low control) and pBTK (vehicle+PPi) is the average ECL signal of whole blood from vehicle-treated mice lysed in the presence of phosphatase inhibitors (high control).

Results

Figure 2:
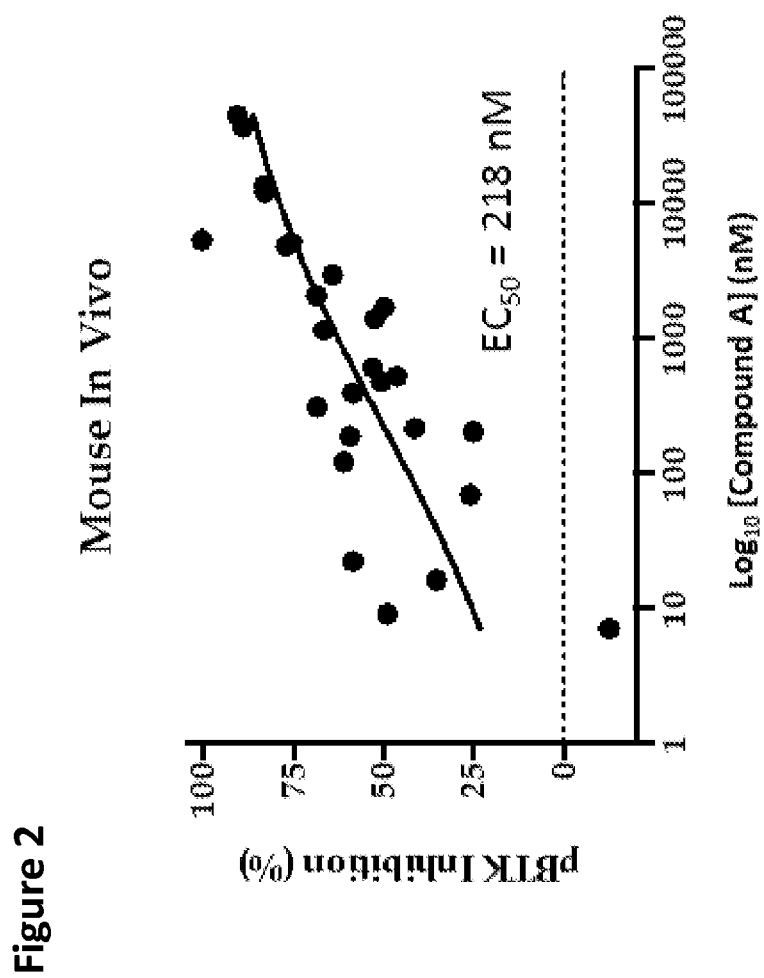
FIG. 2 is a graph of percent inhibition of phosphorylated BTK measured in murine whole blood relative to concentration of test agent Compound A administered orally.

Mice were dosed orally with either vehicle, 0.1, 0.3, 1, 3, 10 or 30 mg drug/kg body weight and killed after one hour. FIG. 2 depicts PK/PD correlation for Compound A. Heparinized whole blood from individual mice was used to quantify the amount of Compound A in the plasma and to determine the level of phospho-BTK in whole blood. Each dot represents an individual mouse. Data was graphed as % inhibition of phospho-BTK versus plasma concentration of Compound A in Prism and a best-fit curve was fitted with the maximum inhibition set at 100% and minimum set at 0%. The best-fit curve was used to determine the in vivo $EC_{50}$. The $EC_{50}$ value was determined to be 218 nm, with a Hill slope of 0.35 and $R^2$ value of 0.61.

Example 32

In Vitro PD Assay in Whole Blood

Heparinized venous blood was purchased from Bioreclamation, Inc. or SeraCare Life Sciences and shipped overnight. Whole blood was aliquoted into 96-well plate and "spiked" with serial dilutions of test compound in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (−PPi, low control). All of the lysed whole blood samples were subjected to the total BTK capture and phosphotyrosine detection method described in Example 30. ECL values were graphed in Prism and a best-fit curve with restrictions on the maximum and minimum defined by the +PPi high and −PPi low controls was used to estimate the test compound concentration that results in 50% inhibition of ECL signal by interpolation.

Table 2 shows the activity of selected compounds in the pBTK assay, wherein each compound number corresponds to the compound numbering set forth in Examples 1-27 herein, supra. Compounds have an activity designated as "A" provided an $IC_{50}$<500 nM; compounds having an activity designated as "B" provided an $IC_{50}$ of 500-1499 nM; compounds having an activity designated as "C" provided an $IC_{50}$ of 1500-10000 nM; and compounds having an activity designated as "D" provided an $IC_{50}$ of >10,000 nM. In some instances where a compound tested has activity "D", other structurally similar compounds beyond the measurable limits of the assay are not included in Table 2.

TABLE 2 pBTK Inhibitory Data for Exemplary Compounds

| Compound tested | pBTK IC50 uM |
|---|---|
| I-1 | C |
| I-2 | C |
| I-16 | C |
| I-18 | A |
| I-19 | A |

TABLE 2-continued pBTK Inhibitory Data for Exemplary Compounds

| Compound tested | pBTK IC50 uM |
|---|---|
| I-20 | A |
| I-21 | A |
| I-22 | A |
| I-25 | B |
| I-26 | A |
| I-30 | C |
| I-31 | B |
| I-32 | A |
| I-34 | A |
| I-35 | B |
| I-36 | A |
| I-39 | A |
| I-40 | A |
| I-41 | B |
| I-42 | A |
| I-43 | B |
| I-44 | B |
| I-45 | C |
| I-46 | A |
| I-47 | A |
| I-48 | A |
| I-49 | B |
| I-52 | A |
| I-78 | C |
| I-85 | C |
| I-87 | C |
| I-89 | C |
| I-98 | D |
| I-100 | C |
| I-112 | A |
| I-113 | C |
| I-115 | B |
| I-116 | C |
| I-119 | C |
| I-122 | C |

Example 33

In Vitro PD Assay in Whole Blood from Healthy Donors or SLE Patients

Methods

Heparinized venous blood from healthy controls (HC) was obtained from in-house donors. Blood from a patient diagnosed with Systemic Lupus Erythematosis (SLE) was purchased from Bioreclamation, Inc. and shipped overnight. The assay was carried out as described above in Example 32, using Compound A as a test drug compound.

Results

Figure 3A:
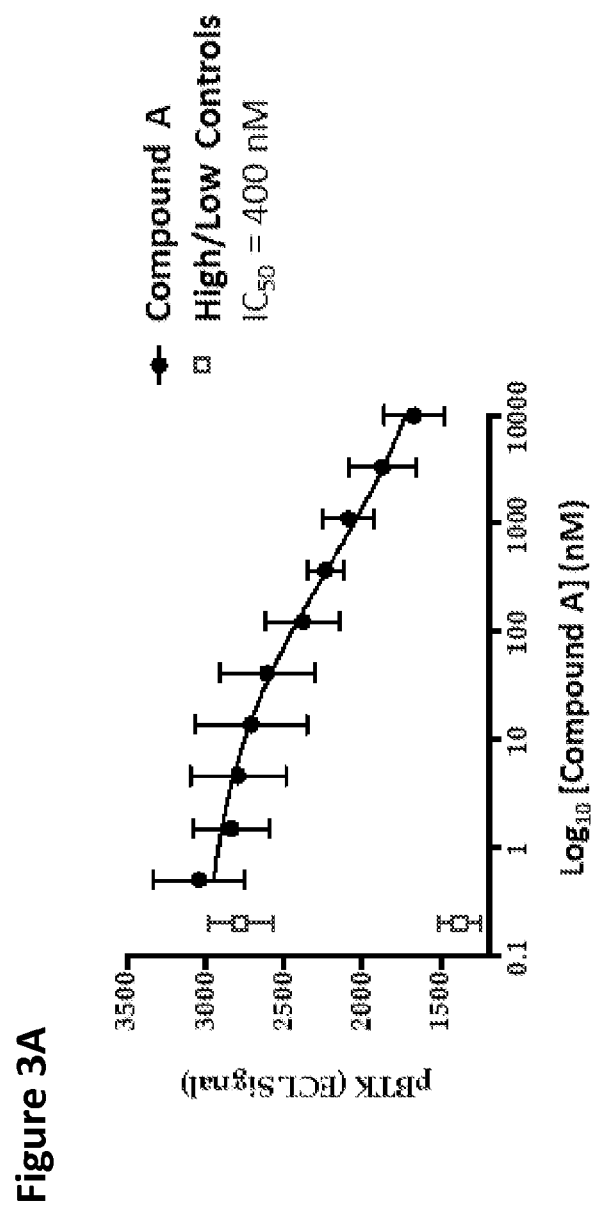
FIG. 3A is a graph depicting $IC_{50}$ for test agent Compound A after contacting whole blood from a healthy control.

FIG. 3A depicts drug-mediated inhibition of BTK phosphorylation assessed in whole blood from a healthy control. The estimated concentration of Compound A that inhibits 50% of ECL signal ($IC_{50}$) was determined to be 400 nM, with an $R^2$ value of 0.75.

Figure 3B:
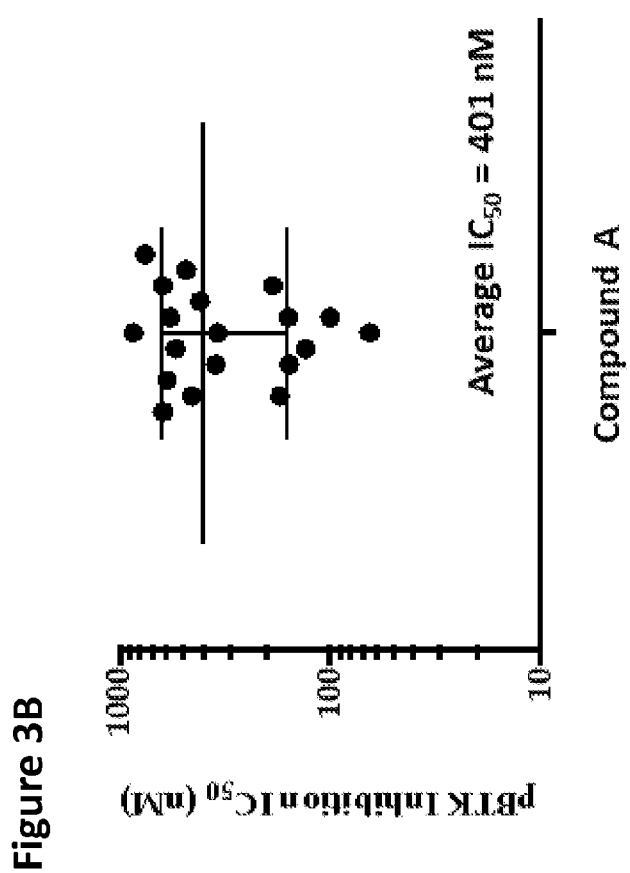
FIG. 3B is a graph depicting $IC_{50}$ for test agent Compound A after contacting whole blood from 19 healthy controls.

FIG. 3B depicts $IC_{50}$ values from 19 HC. Each symbol represents data derived from whole blood from a HC. The bar represents the average $IC_{50}$ value of 401 nM.

Figure 3C:
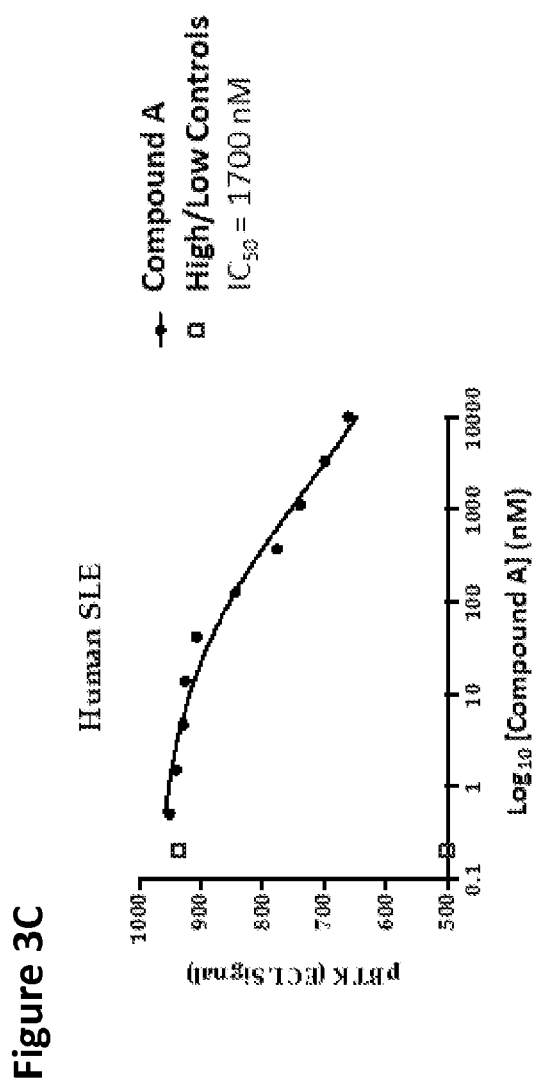
FIG. 3C is a graph depicting $IC_{50}$ for test agent Compound A after contacting whole blood from a SLE patient.

FIG. 3C depicts drug-mediated inhibition of BTK phosphorylation assessed in whole blood from a SLE patient. The estimated concentration of Compound A that inhibits 50% of ECL signal ($IC_{50}$) was determined to be 1700 nM, with an $R^2$ value of 0.98.

Example 34

In Vitro PD Assay in Whole Blood from Cynomolgus Monkey

Methods

Heparinized venous blood from a Cynomolgus monkey was purchased from Bioreclamation, Inc. and shipped overnight. Whole blood was aliquoted into 96-well plate and "spiked" with serial dilutions of Compound A in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (−PPi, low control). All of the lysed whole blood samples were subjected to the total BTK capture and phosphotyrosine detection method described in Example 30. ECL values were graphed in Prism and a best-fit curve with restrictions on the maximum and minimum defined by the +PPi high and −PPi low controls was used to estimate the drug concentration that results in 50% inhibition of ECL signal by interpolation.

Results

Figure 4:
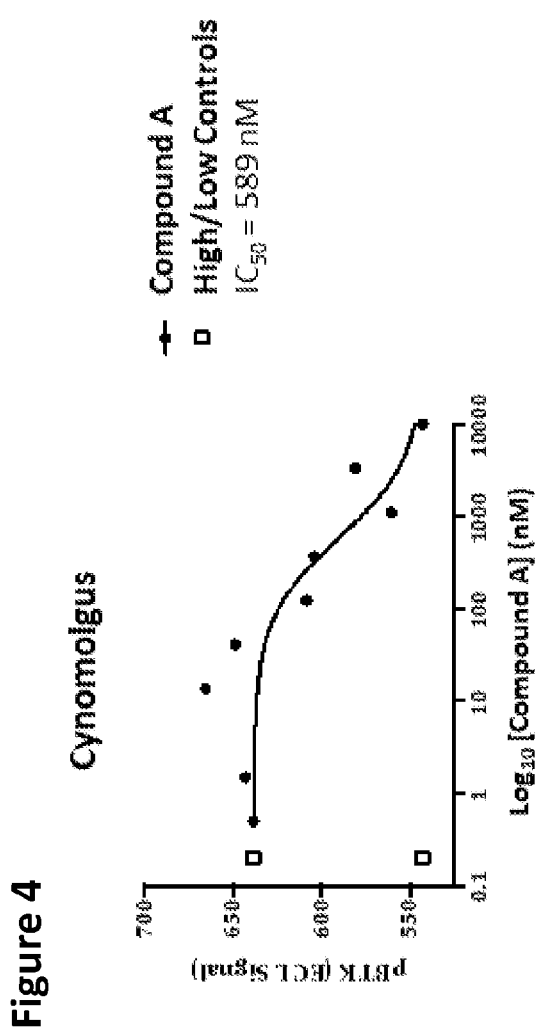
FIG. 4 is a graph depicting drug-mediated inhibition of BTK phosphorylation assessed in whole blood from a Cynomolgus monkey.

FIG. 4 depicts drug-mediated inhibition of BTK phosphorylation assessed in whole blood from a Cynomolgus monkey. The estimated concentration of Compound A that inhibits 50% of ECL signal ($IC_{50}$) was determined to be 589 nM, with an $R^2$ value of 0.23.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of formula II-b:

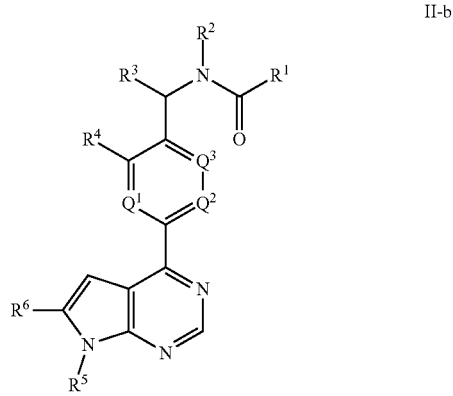

or a pharmaceutically acceptable salt thereof, wherein:
$Q^1$, $Q^2$ and $Q^3$ are CH;
$R^1$ is an optionally substituted group selected from thiazolyl, thiadiazolyl and imidazolyl, wherein $R^1$ is optionally substituted with one or more $R^{10}$;
$R^2$ is H or $C_{1-6}$ aliphatic;

$R^3$ is selected from H, halogen, —C(O)N(R)$_2$, —C(O)OR, —C(O)R, and C$_{1-6}$ aliphatic, wherein the C$_{1-6}$ aliphatic group is optionally substituted with hydroxyl;

$R^4$ is selected from H, halogen, —NO$_2$, —CN, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, and C$_{1-6}$ aliphatic, wherein said C$_{1-6}$ aliphatic is optionally substituted with one or more $R^{40}$;

or $R^3$ and $R^4$ together with their intervening atoms form fused Ring A selected from fused 5- to 7-membered monocyclic carbocycle, fused 5- to 7-membered monocyclic heterocycle having 1-2 heteroatoms selected from oxygen, nitrogen, or sulfur, wherein said fused Ring A is optionally substituted with one or more $R^{40}$;

each $R^5$ is selected from H and C$_{1-6}$ aliphatic;

$R^6$ is selected from H, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur, are optionally substituted with one or more $R^{60}$; or $R^5$ and $R^6$, taken together with their intervening atoms, form a fused 5- to 7-membered monocyclic carbocycle or fused 5- to 7-membered monocyclic heterocycle having 1-2 heteroatoms selected from oxygen, nitrogen, or sulfur; wherein said monocyclic carbocycle or heterocycle is optionally substituted with one or more $R^{60}$; and each R is independently hydrogen or C$_{1-6}$ aliphatic, phenyl, 3- to 8-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said C$_{1-6}$ aliphatic, phenyl, 3- to 7-membered saturated or partially unsaturated carbocyclyl ring, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, are optionally substituted with one or more $R^{60}$; or two R groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, wherein said ring is optionally substituted with one or more $R^{60}$;

each $R^{10}$ is independently selected from halogen, —OR$^{10a}$, C$_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, wherein said C$_{1-6}$aliphatic, 3- to 5-membered saturated or partially unsaturated carbocyclyl, 3- to 5-membered saturated or partially unsaturated monocyclic heterocyclyl having 1-2 heteroatoms selected from oxygen, nitrogen, or sulfur, are optionally substituted with one or more $R^{15}$;

each $R^{15}$ is independently selected from halogen and —OR$^{15a}$;

$R^{10a}$ is C$_{1-6}$alkyl;

$R^{15a}$ is C$_{1-6}$alkyl;

each $R^{40}$ is independently selected from halogen, 4- to 6-membered monocyclic heterocyclyl, —N(R$^{40a}$)$_2$, —N(R$^{40a}$)C(O)(R$^{40b}$), —N(R$^{40a}$)C(O)$_2$(R$^{40a}$), —OR$^{40a}$, —SR$^{40a}$, and —C(O)$_2$R$^{40a}$;

each $R^{40a}$ is independently selected from H and C$_{1-6}$alkyl; or two $R^{40a}$ groups on the same nitrogen are taken together with their intervening atoms to form a ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;

each $R^{40b}$ is independently selected from C$_{2-6}$alkenyl and 5- or 6-membered heterocyclyl having 1-2 heteroatoms selected from oxygen, nitrogen, or sulfur, wherein said 5- or 6-membered heterocyclyl having 1-2 heteroatoms selected from oxygen, nitrogen, or sulfur, is optionally substituted with one or more $R^{45}$;

$R^{45}$ is C$_{1-6}$alkyl;

each $R^{60}$ is independently selected from C$_{1-6}$alkyl, —OR$^{60a}$, —N(R$^{60a}$)$_2$, —C(O)N(R$^{60a}$)$_2$; —C(O)$_2$R$^{60a}$; —C(O)R$^{60b}$, 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, wherein said 3- to 6-membered saturated or partially unsaturated monocyclic carbocyclyl, 3- to 6-membered saturated or partially unsaturated monocyclic heterocyclyl having 1-2 heteroatoms selected from oxygen, nitrogen, or sulfur, and 3- to 10-membered heterocyclyalkyl having 1-4 heteroatoms selected from oxygen, nitrogen, or sulfur, are optionally substituted with one or more $R^{65}$;

$R^{60a}$ is selected from H and C$_{1-6}$alkyl; or two $R^{60a}$ groups are taken together with their intervening atoms to form a 3- to 6-membered heterocyclyl having 1-2 heteroatoms selected from oxygen, nitrogen, or sulfur;

$R^{60b}$ is 5- or 6-membered monocyclic heterocyclyl;

each $R^{65}$ is independently selected from C$_{1-6}$alkyl, —OR$^{65a}$, —N(R$^{65a}$)$_2$, —C(O)$_2$R$^{65a}$, —S(O)$_2$R$^{65b}$, and —S(O)$_2$(NR$^{65a}$)$_2$;

$R^{65a}$ is selected from H and C$_{1-6}$alkyl; and $R^{65b}$ is C$_{1-6}$alkyl.

2. The compound of claim 1, wherein $R^1$ is thiazolyl and $R^{10}$ is a C$_{1-6}$aliphatic optionally substituted with one or more $R^{15}$, wherein $R^{15}$ is halogen.

3. The compound of claim 1, wherein $R^2$ is hydrogen.

4. The compound of claim 3, wherein $R^3$ is hydrogen or C$_{1-6}$ aliphatic optionally substituted with hydroxyl.

5. The compound of claim 3, wherein $R^3$ is —C(O)N(R)$_2$, —C(O)N(R)$_2$, —C(O)OR, or $C_{1-6}$ aliphatic optionally substituted with hydroxyl.

6. The compound of claim 4, wherein $R^4$ is halogen, —OR, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or $C_{1-6}$ aliphatic optionally substituted with one or more $R^{40}$.

7. The compound of claim 3, wherein $R^3$ and $R^4$, together with their intervening atoms, form fused Ring A optionally substituted with one or more $R^{40}$.

8. The compound of claim 1, wherein $R^5$ is hydrogen.

9. The compound of claim 1, wherein $R^6$ is selected from H, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, and 5- to 6-membered heteroaryl having 1-4 heteroatoms selected from oxygen, nitrogen, or sulfur, wherein said phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heterocyclyl having 1-4 heteroatoms selected from oxygen, nitrogen, or sulfur, and 5- to 6-membered heteroaryl having 1-4 heteroatoms selected from oxygen, nitrogen, or sulfur, are optionally substituted with one or more $R^{60}$.

10. The compound of claim 1, wherein the compound is of formula IV-b, V-b, VI-b, VII-b or VII-e, or a pharmaceutically acceptable salt thereof:

IV-b

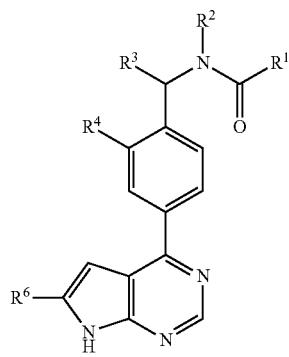

V-b

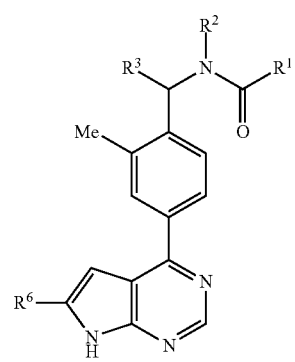

VI-b

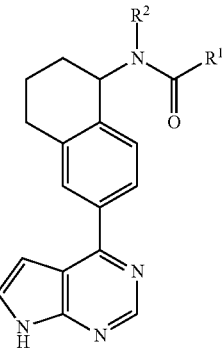

VII-b

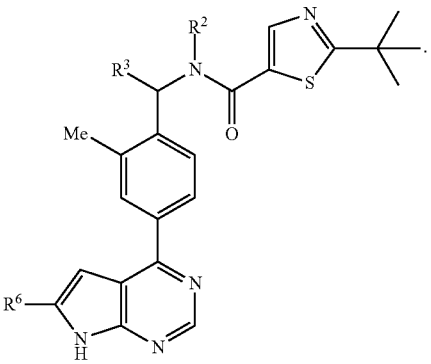

11. The compound of claim 1, wherein the compound is selected from one of the following compounds, or a pharmaceutically acceptable salt thereof:

I-19

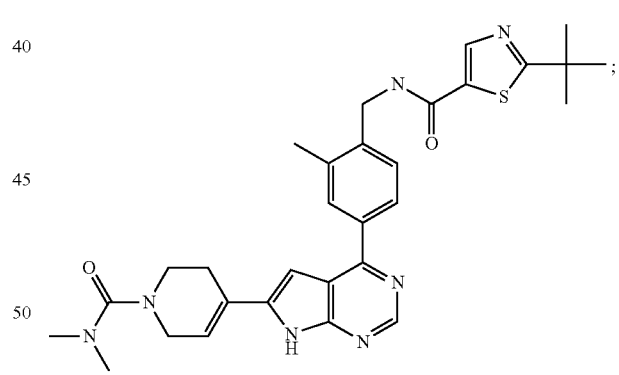

I-20

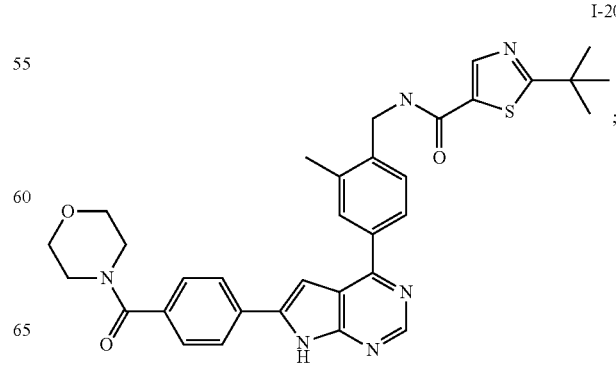

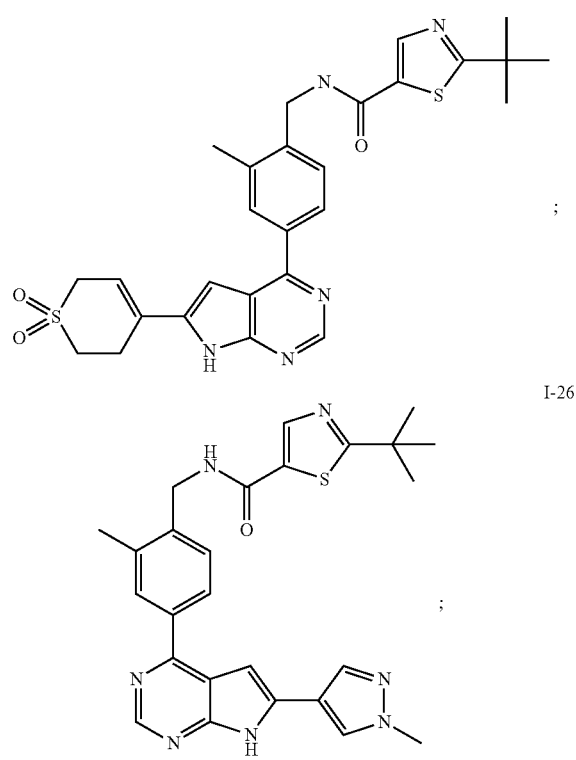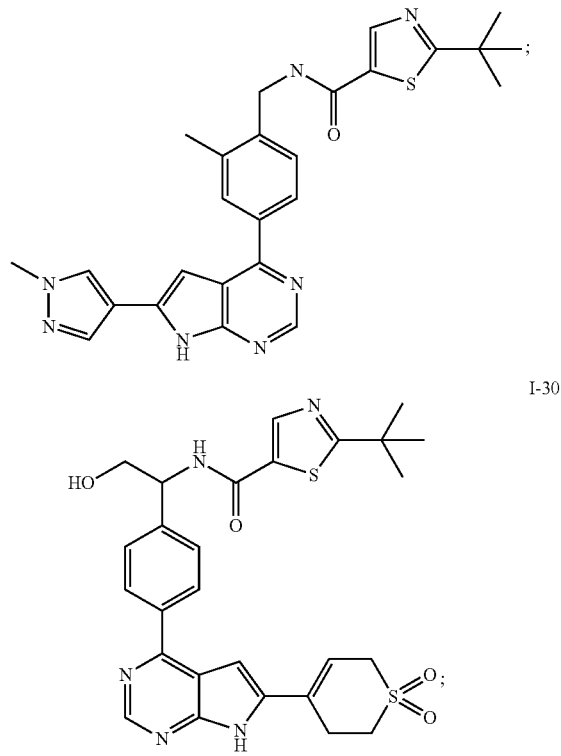

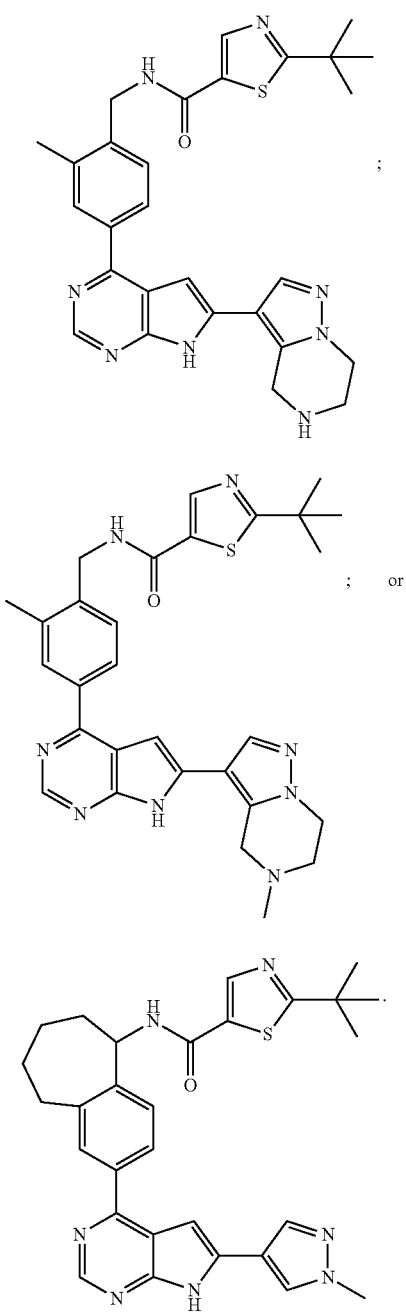

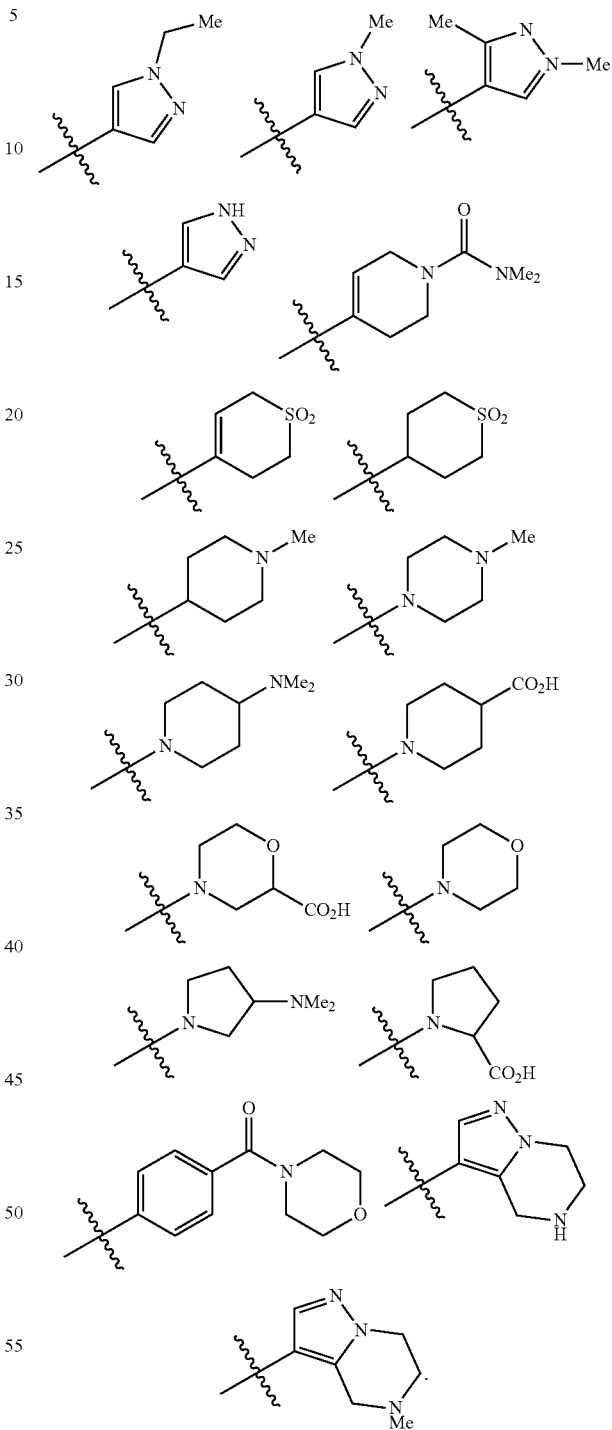

12. A pharmaceutical composition comprising a compound of claim 1, and a pharmaceutically acceptable excipient.

13. The compound of claim 10, wherein $R^2$ in formula IV-b, V-b, or VI-b is hydrogen; $R^3$ in formula IV-b, V-b or VII-b is hydrogen, methyl or hydroxymethyl; $R^4$ in formula IV-b is $C_{1-6}$aliphatic optionally substituted with one or more $R^{40}$, wherein $R^{40}$ is halogen; or $R^3$ and $R^4$, in formula IV-b, together with their intervening atoms, form fused Ring A optionally substituted with one or more $R^{40}$, wherein ring A is fused 5- to 7-membered monocyclic carbocycle.

14. The compound of claim 13, wherein $R^6$ is selected from the following:

15. The compound of claim 14, wherein the compound is of formula VII-b, or VII-e, or a pharmaceutically acceptable salt thereof:

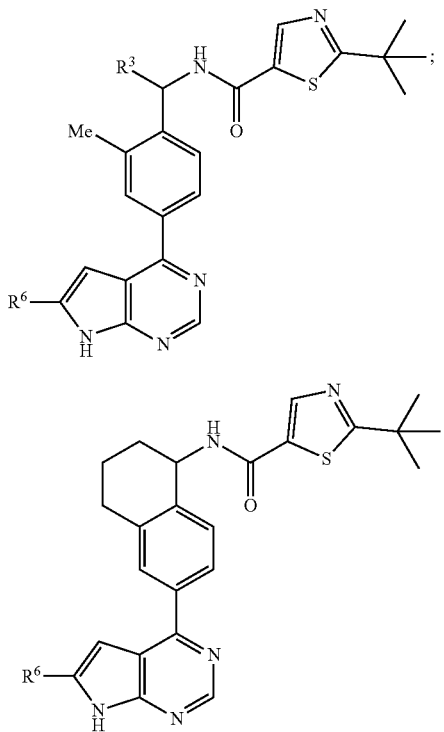

16. A compound selected from:
5-(tert-butyl)-N-(2-methyl-4-(7H-pyrrolo[2,3-d]pyrimidin-4-yl)benzyl)picolinamide,
4-(tert-butyl)-N-(2-methyl-4-(7H-pyrrolo[2,3-d]pyrimidin-4-yl)benzyl)benzamide,
N-(4-(7H-pyrrolo[2,3-d]pyrimidin-4-yl)-2-(trifluoromethyl)benzyl)-4-(tert-butyl)benzamide,
N-(4-(7H-pyrrolo[2,3-d]pyrimidin-4-yl)-2-(trifluoromethyl)benzyl)-5-(tert-butyl)picolinamide,
5-(tert-butyl)-N-(2-chloro-4-(7H-pyrrolo[2,3-d]pyrimidin-4-yl)benzyl)picolinamide,
5-(tert-butyl)-N-(2-cyano-4-(7H-pyrrolo[2,3-d]pyrimidin-4-yl)benzyl)picolinamide,
5-(tert-butyl)-N-(2-carbamoyl-4-(7H-pyrrolo[2,3-d]pyrimidin-4-yl)benzyl)picolinamide,
4-(tert-butyl)-N-(2-cyano-4-(7H-pyrrolo[2,3-d]pyrimidin-4-yl)benzyl)benzamide,
4-(tert-butyl)-N-(2-carbamoyl-4-(7H-pyrrolo[2,3-d]pyrimidin-4-yl)benzyl)benzamide,
4-(tert-butyl)-N-(2-ethyl-4-(7H-pyrrolo[2,3-d]pyrimidin-4-yl)benzyl)benzamide,
5-(tert-butyl)-N-(2-ethyl-4-(7H-pyrrolo[2,3-d]pyrimidin-4-yl)benzyl)picolinamide,
tert-butyl 2-methyl-4-(4,4,5,5-tetramethyl-1,3,2-dioxaborolan-2-yl)benzylcarbamate,
5-(tert-butyl)-N-(2-chloro-5-fluoro-4-(7H-pyrrolo[2,3-d]pyrimidin-4-yl)benzyl)picolinamide,
N-(6-(7H-pyrrolo[2,3-d]pyrimidin-4-yl)-1,2,3,4-tetrahydronaphthalen-1-yl)-4-(tert-butyl)benzamide,
N-(6-(7H-pyrrolo[2,3-d]pyrimidin-4-yl)-1,2,3,4-tetrahydronaphthalen-1-yl)-5-(tert-butyl)picolinamide,
N-(6-(7H-pyrrolo[2,3-d]pyrimidin-4-yl)-1,2,3,4-tetrahydronaphthalen-1-yl)-4,5,6,7-tetrahydrobenzo[b]thiophene-2-carboxamide,
N-(6-(7H-pyrrolo[2,3-d]pyrimidin-4-yl)-1,2,3,4-tetrahydronaphthalen-1-yl)-4,5,6,7-tetrahydrobenzo[d]thiazole-2-carboxamide,
5-(tert-butyl)-N-(4-(6-(1-(dimethylcarbamoyl)-1,2,3,6-tetrahydropyridin-4-yl)-5H-pyrrolo[3,2-d]pyrimidin-4-yl)-2-methylbenzyl)thiazole-2-carboxamide,
2-(tert-butyl)-N-(4-(6-(1-(dimethylcarbamoyl)-1,2,3,6-tetrahydropyridin-4-yl)-7H-pyrrolo[2,3-d]pyrimidin-4-yl)-2-methylbenzyl)thiazole-5-carboxamide,
methyl 4-(4-(4-((2-(tert-butyl)thiazole-5-carboxamido)methyl)-3-methylphenyl)-7H-pyrrolo[2,3-d]pyrimidin-6-yl)benzoate,
2-(tert-butyl)-N-(4-(6-(1,1-dioxido-3,6-dihydro-2H-thiopyran-4-yl)-7H-pyrrolo[2,3-d]pyrimidin-4-yl)-2-methylbenzyl)thiazole-5-carboxamide,
2-(tert-butyl)-N-(4-(6-(1,1-dioxido-3,6-dihydro-2H-thiopyran-4-yl)-5H-pyrrolo[3,2-d]pyrimidin-4-yl)-2-methylbenzyl)thiazole-5-carboxamide,
2-(tert-butyl)-N-(4-(6-(1,1-dioxidotetrahydro-2H-thiopyran-4-yl)-5H-pyrrolo[3,2-d]pyrimidin-4-yl)-2-methylbenzyl)thiazole-5-carboxamide,
2-(tert-butyl)-N-(4-(6-(1,1-dioxidotetrahydro-2H-thiopyran-4-yl)-5-methyl-5H-pyrrolo[3,2-d]pyrimidin-4-yl)-2-methylbenzyl)thiazole-5-carboxamide,
2-(tert-butyl)-N-(2-methyl-4-(6-(1-methylpiperidin-4-yl)-5H-pyrrolo[3,2-d]pyrimidin-4-yl)benzyl)thiazole-5-carboxamide,
2-(tert-butyl)-N-(2-methyl-4-(6-(1-methyl-1H-pyrazol-4-yl)-7H-pyrrolo[2,3-d]pyrimidin-4-yl)benzyl)thiazole-5-carboxamide,
2-(tert-butyl)-N-(2-methyl-4-(7-methyl-6-(1-methyl-1H-pyrazol-4-yl)-7H-pyrrolo[2,3-d]pyrimidin-4-yl)benzyl)thiazole-5-carboxamide,
2-(tert-butyl)-N-(4-(6-(1,3-dimethyl-1H-pyrazol-4-yl)-7-methyl-7H-pyrrolo[2,3-d]pyrimidin-4-yl)-2-methylbenzyl)thiazole-5-carboxamide,
2-(tert-butyl)-N-(1-(4-(6-(1,1-dioxido-3,6-dihydro-2H-thiopyran-4-yl)-5H-pyrrolo[3,2-d]pyrimidin-4-yl)phenyl)-2-hydroxyethyl)thiazole-5-carboxamide,
2-(tert-butyl)-N-(1-(4-(6-(1,1-dioxido-3,6-dihydro-2H-thiopyran-4-yl)-7H-pyrrolo[2,3-d]pyrimidin-4-yl)phenyl)-2-hydroxyethyl)thiazole-5-carboxamide,
2-(tert-butyl)-N-(2-hydroxy-1-(2-methyl-4-(6-(1-methyl-1H-pyrazol-4-yl)-7H-pyrrolo[2,3-d]pyrimidin-4-yl)phenyl)ethyl)thiazole-5-carboxamide,
N-(2-hydroxy-1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide,
N-(2-methyl-4-(6-(1-methyl-1H-pyrazol-4-yl)-7H-pyrrolo[2,3-d]pyrimidin-4-yl)benzyl)-6,7-dihydro-4H-thieno[3,2-c]pyran-2-carboxamide,
2-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)thiazole-5-carboxamide,
N-(6-(6-(1-methyl-1H-pyrazol-4-yl)-7H-pyrrolo[2,3-d]pyrimidin-4-yl)-1,2,3,4-tetrahydronaphthalen-1-yl)-6,7-dihydro-4H-thieno[3,2-c]pyran-2-carboxamide,
5-(tert-butyl)-N-(2-methyl-4-(6-(1-methyl-1H-pyrazol-4-yl)-5H-pyrrolo[3,2-d]pyrimidin-4-yl)benzyl)thiazole-2-carboxamide,
2-(tert-butyl)-N-(6-(6-(1-methyl-1H-pyrazol-4-yl)-5H-pyrrolo[3,2-d]pyrimidin-4-yl)-1,2,3,4-tetrahydronaphthalen-1-yl)thiazole-5-carboxamide,
2-(tert-butyl)-N-(2-methyl-4-(5-methyl-6-(1-methyl-1H-pyrazol-4-yl)-5H-pyrrolo[3,2-d]pyrimidin-4-yl)benzyl)thiazole-5-carboxamide,
2-(tert-butyl)-N-(4-(6-(1,3-dimethyl-1H-pyrazol-4-yl)-5H-pyrrolo[3,2-d]pyrimidin-4-yl)-2-methylbenzyl)thiazole-5-carboxamide, 5-(tert-butyl)-N-(4-(6-(1-ethyl-1H-pyrazol-4-yl)-5H-pyrrolo[3,2-d]pyrimidin-4-yl)-2-methylbenzyl)thiazole-2-carboxamide,
N-(4-(6-(1H-pyrazol-4-yl)-5H-pyrrolo[3,2-d]pyrimidin-4-yl)-2-methylbenzyl)-5-(tert-butyl)thiazole-2-carboxamide,
N-(2-methyl-4-(6-(1-methyl-1H-pyrazol-4-yl)-5H-pyrrolo[3,2-d]pyrimidin-4-yl)benzyl)-6,7-dihydro-4H-thieno[3,2-c]pyran-2-carboxamide,
3-isopropoxy-N-(2-methyl-4-(6-(1-methyl-1H-pyrazol-4-yl)-5H-pyrrolo[3,2-d]pyrimidin-4-yl)benzyl)azetidine-1-carboxamide,
2-(tert-butyl)-N-(2-hydroxy-1-(2-methyl-4-(6-(1-methyl-1H-pyrazol-4-yl)-5H-pyrrolo[3,2-d]pyrimidin-4-yl)phenyl)ethyl)thiazole-5-carboxamide,
N-(2-hydroxy-1-(2-methyl-4-(6-(1-methyl-1H-pyrazol-4-yl)-5H-pyrrolo[3,2-d]pyrimidin-4-yl)phenyl)ethyl)-6,7-dihydro-4H-thieno[3,2-c]pyran-2-carboxamide,
2-(tert-butyl)-N-(1-(2-methyl-4-(6-(1-methyl-1H-pyrazol-4-yl)-5H-pyrrolo[3,2-d]pyrimidin-4-yl)phenyl)ethyl)thiazole-5-carboxamide,
2-(tert-butyl)-N-(2-methyl-4-(8-(4-methylpiperazin-1-yl)-7H-purin-6-yl)benzyl)thiazole-5-carboxamide,
2-(tert-butyl)-N-(2-methyl-4-(8-morpholino-7H-purin-6-yl)benzyl)thiazole-5-carboxamide,
2-(tert-butyl)-N-(4-(8-(4-(dimethylamino)piperidin-1-yl)-7H-purin-6-yl)-2-methylbenzyl)thiazole-5-carboxamide,
2-(tert-butyl)-N-(4-(8-(3-(dimethylamino)pyrrolidin-1-yl)-7H-purin-6-yl)-2-methylbenzyl)thiazole-5-carboxamide,
1-(6-(4-((2-(tert-butyl)thiazole-5-carboxamido)methyl)-3-methylphenyl)-7H-purin-8-yl)pyrrolidine-3-carboxylic acid,
1-(6-(4-((2-(tert-butyl)thiazole-5-carboxamido)methyl)-3-methylphenyl)-7H-purin-8-yl)piperidine-4-carboxylic acid,
2-(tert-butyl)-N-(4-(8-(3-(dimethylamino)azetidin-1-yl)-7H-purin-6-yl)-2-methylbenzyl)thiazole-5-carboxamide,
2-(tert-butyl)-N-(2-methyl-4-(8-(1-methylpiperidin-4-yl)-7H-purin-6-yl)benzyl)thiazole-5-carboxamide,
1-(6-(4-((2-(tert-butyl)thiazole-5-carboxamido)methyl)-3-methylphenyl)-7H-purin-8-yl)pyrrolidine-2-carboxylic acid,
N-(4-(7H-pyrrolo[2,3-d]pyrimidin-4-yl)benzyl)-5,6,7,8-tetrahydroisoquinoline-3-carboxamide,
N-(4-(7H-pyrrolo[2,3-d]pyrimidin-4-yl)benzyl)-5,6,7,8-tetrahydroquinoline-2-carboxamide,
N-(4-(7H-pyrrolo[2,3-d]pyrimidin-4-yl)benzyl)-6,7-dihydro-5H-pyrrolo[1,2-a]imidazole-2-carboxamide,
N-(4-(7H-pyrrolo[2,3-d]pyrimidin-4-yl)benzyl)-2,3-dihydro-1H-indene-2-carboxamide,
N-(4-(7H-pyrrolo[2,3-d]pyrimidin-4-yl)benzyl)benzo[b]thiophene-2-carboxamide,
N-(4-(7H-pyrrolo[2,3-d]pyrimidin-4-yl)benzyl)-4,5,6,7-tetrahydrobenzo[d]thiazole-2-carboxamide,
N-(4-(7H-pyrrolo[2,3-d]pyrimidin-4-yl)benzyl)-5-chloro-4-(trifluoromethyl)picolinamide,
N-(4-(7H-pyrrolo[2,3-d]pyrimidin-4-yl)benzyl)-5,6,7,8-tetrahydroimidazo[1,2-a]pyridine-2-carboxamide,
N-(4-(7H-pyrrolo[2,3-d]pyrimidin-4-yl)benzyl)-4,5,6,7-tetrahydrobenzo[b]thiophene-2-carboxamide, N-(4-(7H-pyrrolo[2,3-d]pyrimidin-4-yl)benzyl)-4-(trifluoromethyl)benzamide,
N-(4-(7H-pyrrolo[2,3-d]pyrimidin-4-yl)benzyl)-6-(tert-butyl)nicotinamide,
N-(4-(7H-pyrrolo[2,3-d]pyrimidin-4-yl)benzyl)-5-(tert-butyl)picolinamide,
N-(4-(7H-pyrrolo[2,3-d]pyrimidin-4-yl)benzyl)isoindoline-2-carboxamide,
N-((5-(7H-pyrrolo[2,3-d]pyrimidin-4-yl)pyridin-2-yl)methyl)-4-(tert-butyl)benzamide,
N-((5-(7H-pyrrolo[2,3-d]pyrimidin-4-yl)pyridin-2-yl)methyl)-4,5,6,7-tetrahydrobenzo[b]thiophene-2-carboxamide,
N-((6-(1H-pyrrolo[2,3-b]pyridin-4-yl)pyridin-3-yl)methyl)-5-(tert-butyl)picolinamide,
N-((6-(1H-pyrrolo[2,3-b]pyridin-4-yl)pyridin-3-yl)methyl)-4,5,6,7-tetrahydrobenzo[b]thiophene-2-carboxamide,
(R)—N-(1-(4-(7H-pyrrolo[2,3-d]pyrimidin-4-yl)phenyl)ethyl)-4,5,6,7-tetrahydrobenzo[d]thiazole-2-carboxamide,
(S)—N-(1-(4-(7H-pyrrolo[2,3-d]pyrimidin-4-yl)phenyl)ethyl)-4,5,6,7-tetrahydrobenzo[d]thiazole-2-carboxamide,
2-(tert-butyl)-N-(2-methyl-4-(6-(4,5,6,7-tetrahydropyrazolo[1,5-a]pyrazin-3-yl)-7H-pyrrolo[2,3-d]pyrimidin-4-yl)benzyl)thiazole-5-carboxamide hydrochloride,
N-(1-(2-methyl-4-(7H-pyrrolo[2,3-d]pyrimidin-4-yl)phenyl)ethyl)-4,5,6,7-tetrahydrobenzo[d]thiazole-2-carboxamide,
N-(1-(2-methyl-4-(7H-pyrrolo[2,3-d]pyrimidin-4-yl)phenyl)ethyl)-4,5,6,7-tetrahydrobenzo[b]thiophene-2-carboxamide,
N-(1-(4-(7H-pyrrolo[2,3-d]pyrimidin-4-yl)-2-(trifluoromethyl)phenyl)ethyl)-4,5,6,7-tetrahydrobenzo[d]thiazole-2-carboxamide,
N-(1-(4-(7H-pyrrolo[2,3-d]pyrimidin-4-yl)-2-(trifluoromethyl)phenyl)ethyl)-4,5,6,7-tetrahydrobenzo[b]thiophene-2-carboxamide,
(R)—N-(6-(7H-pyrrolo[2,3-d]pyrimidin-4-yl)-1,2,3,4-tetrahydronaphthalen-1-yl)-4,5,6,7-tetrahydrobenzo[b]thiophene-2-carboxamide,
N-(7-(7H-pyrrolo[2,3-d]pyrimidin-4-yl)isochroman-4-yl)-5-(tert-butyl)picolinamide,
N-(7-(7H-pyrrolo[2,3-d]pyrimidin-4-yl)isochroman-4-yl)-4-(tert-butyl)benzamide,
N-(4-(1H-pyrazolo[3,4-d]pyrimidin-4-yl)benzyl)-4-(tert-butyl)benzamide,
N-(2-methyl-4-(1H-pyrazolo[3,4-d]pyrimidin-4-yl)benzyl)-4,5,6,7-tetrahydrobenzo[b]thiophene-2-carboxamide,
(R)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide,
(S)—N-(6-(1H-Pyrazolo[3,4-d]pyrimidin-4-yl)-1,2,3,4-tetrahydronaphthalen-1-yl)-4,5,6,7-tetrahydrobenzo[b]thiophene-2-carboxamide,
N-(6-(1H-pyrazolo[3,4-d]pyrimidin-4-yl)-1,2,3,4-tetrahydronaphthalen-1-yl)-4-(tert-butyl)benzamide,
(S)—N-(6-(7H-Pyrrolo[2,3-d]pyrimidin-4-yl)-1,2,3,4-tetrahydronaphthalen-1-yl)-4,5,6,7-tetrahydrobenzo[b]thiophene-2-carboxamide,
N-(6-(1H-pyrazolo[3,4-d]pyrimidin-4-yl)-1,2,3,4-tetrahydronaphthalen-1-yl)-4-chloro-3-fluorobenzamide,
N-(6-(1H-pyrazolo[3,4-d]pyrimidin-4-yl)-1,2,3,4-tetrahydronaphthalen-1-yl)-3-fluoro-4-(trifluoromethyl)benzamide,
N-(6-(1H-pyrazolo[3,4-d]pyrimidin-4-yl)-1,2,3,4-tetrahydronaphthalen-1-yl)-3-chloro-4-(trifluoromethyl)benzamide, N-(6-(1H-pyrazolo[3,4-d]pyrimidin-4-yl)-1,2,3,4-tetrahydronaphthalen-1-yl)-3,4-dichlorobenzamide, N-(6-(1H-pyrazolo[3,4-d]pyrimidin-4-yl)-1,2,3,4-tetrahydronaphthalen-1-yl)-5,6-dihydro-4H-cyclopenta[b]thiophene-2-carboxamide, N-(6-(1H-pyrazolo[3,4-d]pyrimidin-4-yl)-1,2,3,4-tetrahydronaphthalen-1-yl)-4,5-dimethylthiazole-2-carboxamide, N-(6-(1H-pyrazolo[3,4-d]pyrimidin-4-yl)-1,2,3,4-tetrahydronaphthalen-1-yl)-4-isopropylthiazole-2-carboxamide, N-(6-(1H-pyrazolo[3,4-d]pyrimidin-4-yl)-1,2,3,4-tetrahydronaphthalen-1-yl)-4-(trifluoromethyl)benzamide, N-(6-(1H-pyrazolo[3,4-d]pyrimidin-4-yl)-1,2,3,4-tetrahydro naphthalen-1-yl) -4-(tert-butyl) thiazole-2-carboxamide, (R)—N-(6-(1H-pyrazolo[3,4-d]pyrimidin-4-yl)-1,2,3,4-tetrahydronaphthalen-1-yl)-4-(tert-butyl)thiazole-2-carboxamide, (R)—N-(6-(1H-pyrazolo[3,4-d]pyrimidin-4-yl)-1,2,3,4-tetrahydronaphthalen-1-yl)-4-(tert-butyl)thiazole-2-carboxamide, N-(6-(1H-pyrazolo[3,4-d]pyrimidin-4-yl)-1,2,3,4-tetrahydronaphthalen-1-yl)-1-methyl-1H-benzo[d]imidazole-2-carboxamide, 2-(tert-butyl)-N-(2-methyl-4-(6-(5-methyl-4,5,6,7-tetrahydropyrazolo[1,5-a]pyrazin-3-yl)-7H-pyrrolo[2,3-d]pyrimidin-4-yl)benzyl)thiazole-5-carboxamide, N-(6-(1H-pyrazolo[3,4-d]pyrimidin-4-yl)-1,2,3,4-tetrahydronaphthalen-1-yl)-5-(tert-butyl)-1,3,4-thiadiazole-2-carboxamide, N-(6-(1H-pyrazolo[3,4-d]pyrimidin-4-yl)-1,2,3,4-tetrahydronaphthalen-1-yl)-4-(tert-butyl)cyclohexanecarboxamide, trans-N—((R)-6-(1H-pyrazolo[3,4-d]pyrimidin-4-yl)-1,2,3,4-tetrahydronaphthalen-1-yl)-4-(trifluoromethyl)cyclohexanecarboxamide, N-(6-(1H-pyrazolo[3,4-d]pyrimidin-4-yl)-1,2,3,4-tetrahydronaphthalen-1-yl)benzo[d]thiazole-2-carboxamide, N-(6-(1H-pyrazolo[3,4-d]pyrimidin-4-yl)-1,2,3,4-tetrahydronaphthalen-1-yl)-4,5,6,7-tetrahydrobenzo[b]thiophene-2-carboxamide, N-(4-(1H-pyrazolo[3,4-d]pyrimidin-4-yl)-2-(trifluoromethyl)benzyl)-4,5,6,7-tetrahydrobenzo[d]thiazole-2-carboxamide, N-((3-fluoro-5-(1H-pyrazolo[3,4-d]pyrimidin-4-yl)pyridin-2-yl)methyl)-4,5,6,7-tetrahydrobenzo[b]thiophene-2-carboxamide, N-((3-fluoro-5-(1H-pyrazolo[3,4-b]pyridin-4-yl)pyridin-2-yl)methyl)-4,5,6,7-tetrahydrobenzo[b]thiophene-2-carboxamide, 4-(tert-butyl)-N-(4-(6-(4-(morpholine-4-carbonyl)phenyl)-7H-pyrrolo[2,3-d]pyrimidin-4-yl)benzyl)benzamide, 2-(tert-butyl)-N-(1-(2-methyl-4-(6-(1-methyl-1H-pyrazol-4-yl)-7H-pyrrolo[2,3-d]pyrimidin-4-yl)phenyl)ethyl)thiazole-5-carboxamide, N-(1-(2-methyl-4-(6-(1-methyl-1H-pyrazol-4-yl)-7H-pyrrolo[2,3-d]pyrimidin-4-yl)phenyl)ethyl)-6,7-dihydro-4H-thieno[3,2-c]pyran-2-carboxamide, 2-(tert-butyl)-N-(1-(4.-(6-(1-methyl-1H-pyrazol-4-yl)-5H-pyrrolo[3,2-d]pyrimidin-4-yl)phenyl)ethyl)thiazole-5-carboxamide, 2-(tert-butyl)-N-(2-methyl-4-(5H-pyrrolo[3,2-d]pyrimidin-4-yl)benzyl)thiazole-5-carboxamide, N-(2-methyl-4-(5H-pyrrolo[3,2-d]pyrimidin-4-yl)benzyl)-4,5,6,7-tetrahydrobenzo[b]thiophene-2-carboxamide, N-((4-methyl-6-(1H-pyrazolo[3,4-b]pyridin-4-yl)pyridin-3-yl)methyl)-4,5,6,7-tetrahydrobenzo[b]thiophene-2-carboxamide, N-((2-methyl-6-(1H-pyrazolo[3,4-b]pyridin-4-yl)pyridin-3-yl)methyl)-4,5,6,7-tetrahydrobenzo[b]thiophene-2-carboxamide, 4,5,6,7-tetrahydro-benzothiazole-2-carboxylic acid 2-methyl-4-(1H-pyrazolo[3,4-d]pyrimidin-4-yl)-benzylamide, N-(6-(1H-pyrazolo[3,4-d]pyrimidin-4-yl)-1,2,3,4-tetrahydronaphthalen-1-yl)benzo[b]thiophene-2-carboxamide, N-(1-(2-methyl-4-(1H-pyrazolo[3,4-d]pyrimidin-4-yl)phenyl)ethyl)-4,5,6,7-tetrahydrobenzo[b]thiophene-2-carboxamide, N-(4-(7H-pyrrolo[2,3-d]pyrimidin-4-yl)-2-(trifluoromethyl)benzyl)-4,5,6,7-tetrahydrobenzo[d]thiazole-2-carboxamide, N-(1-(2-methyl-4-(5H-pyrrolo[3,2-d]pyrimidin-4-yl)phenyl)ethyl)-4,5,6,7-tetrahydrobenzo[b]thiophene-2-carboxamide, 4-(6-(4-((2-(tert-butyl)thiazole-5-carboxamido)methyl)-3-methylphenyl)-7H-purin-8-yl)morpholine-2-carboxylic acid, N-((3-methyl-5-(1H-pyrazolo[3,4-d]pyrimidin-4-yl)pyridin-2-yl)methyl)-4,5,6,7-tetrahydrobenzo[b]thiophene-2-carboxamide, N-((3-methyl-5-(1H-pyrrolo[2,3-b]pyridin-4-yl)pyridin-2-yl)methyl)-4,5,6,7-tetrahydrobenzo[b]thiophene-2-carboxamide, N-(1-(2-methyl-4-(1H-pyrazolo[3,4-d]pyrimidin-4-yl)phenyl)ethyl)-4,5,6,7-tetrahydrobenzo[d]thiazole-2-carboxamide, 2-(tert-butyl)-N-(1-(2-methyl-4-(1H-pyrazolo[3,4-d]pyrimidin-4-yl)phenyl)ethyl)thiazole-5-carboxamide, N-(6-(5H-pyrrolo[3,2-d]pyrimidin-4-yl)-1,2,3,4-tetrahydronaphthalen-1-yl)-2-(tert-butyl)thiazole-5-carboxamide, N-(6-(1H-pyrazolo[3,4-d]pyrimidin-4-yl)-1,2,3,4-tetrahydronaphthalen-1-yl)-5,6-dihydro-4H-cyclopenta[d]thiazole-2-carboxamide, N-(6-(1H-pyrazolo[3,4-d]pyrimidin-4-yl)-1,2,3,4-tetrahydronaphthalen-1-yl)-5-(tert-butyl)picolinamide, N-(1-(4-(1H-pyrazolo[3,4-d]pyrimidin-4-yl)phenyl)-2-hydroxyethyl)-4,5,6,7-tetrahydrobenzo[b]thiophene-2-carboxamide, 2-(tert-butyl)-N-(2-methyl-4-(2-(4-methylpiperazin-1-yl)thiazolo[4,5-d]pyrimidin-7-yl)benzyl)thiazole-5-carboxamide, 2-(tert-butyl)-N-(1-(2-methyl-4-(5H-pyrrolo[3,2-d]pyrimidin-4-yl)phenyl)ethyl)thiazole-5-carboxamide, N-(1-(4-(1H-pyrazolo[3,4-d]pyrimidin-4-yl)-2-(trifluoromethyl)phenyl)ethyl)-4,5,6,7-tetrahydrobenzo[b]thiophene-2-carboxamide, N-(6-(1H-pyrazolo[3,4-d]pyrimidin-4-yl)-1,2,3,4-tetrahydronaphthalen-1-yl)-6,6-dimethyl-4,5,6,7-tetrahydrobenzo[d]thiazole-2-carboxamide, N-(6-(1H-pyrazolo[3,4-d]pyrimidin-4-yl)-1,2,3,4-tetrahydronaphthalen-1-yl)-4,5,6,7-tetrahydrobenzo[d]thiazole-2-carboxamide, 2-(6-(1H-pyrazolo[3,4-d]pyrimidin-4-yl)-1,2,3,4-tetrahydronaphthalen-1-yl)-6-cyclopropyl-8-fluoroisoquinolin-1(2H)-one, N-((3-methyl-5-(1H-pyrazolo[3,4-b]pyridin-4-yl)pyridin-2-yl)methyl)-4,5,6,7-tetrahydrobenzo[b]thiophene-2-carboxamide, N-((3-methyl-5-(5H-pyrrolo[3,2-d]pyrimidin-4-yl)pyridin-2-yl)methyl)-4,5,6,7-tetrahydrobenzo[b]thiophene-2-carboxamide, N-(6-(1H-pyrazolo[3,4-d]pyrimidin-4-yl)-1,2,3,4-tetrahydronaphthalen-1-yl)-6-(tert-butyl)nicotinamide, N-(1-(4-(1H-pyrazolo[3,4-d]pyrimidin-4-yl)phenyl)propyl)-4,5,6,7-tetrahydrobenzo[b]thiophene-2-carboxamide, (R)—N-(3-(1H-pyrazolo[3,4-b]pyridin-4-yl)-5,6,7,8-tetrahydroquinolin-8-yl)-2-(tert-butyl)thiazole-5-carboxamide, N-(1-(4-(1H-pyrazolo[3,4-d]pyrimidin-4-yl)-2-(trifluoromethyl)phenyl)ethyl)-4,5,6,7-tetrahydrobenzo[d]thiazole-2-carboxamide, N-(6-(1H-pyrazolo[3,4-d]pyrimidin-4-yl)-1,2,3,4-tetrahydronaphthalen-1-yl)-5-(trifluoromethyl)picolinamide, N-(1-(4-(1H-pyrazolo[3,4-d]pyrimidin-4-yl)phenyl)-2-methylpropyl)-4,5,6,7-tetrahydrobenzo[b]thiophene-2-carboxamide, N-(6-(1H-pyrazolo[3,4-d]pyrimidin-4-yl)-1,2,3,4-tetrahydronaphthalen-1-yl)-4-(tert-butyl)picolinamide, N-(1-(4-(1H-pyrazolo[3,4-d]pyrimidin-4-yl)phenyl)-2-amino-2-oxoethyl)-4,5,6,7-tetrahydrobenzo[b]thiophene-2-carboxamide, (S)—N-(3-(1H-pyrazolo[3,4-b]pyridin-4-yl)-5,6,7,8-tetrahydroquinolin-8-yl)-2-(tert-butyl)thiazole-5-carboxamide, N-((3-methyl-5-(7H-pyrrolo[2,3-d]pyrimidin-4-yl)pyridin-2-yl)methyl)-4,5,6,7-tetrahydrobenzo[b]thiophene-2-carboxamide, N-(5-(7H-pyrrolo[2,3-d]pyrimidin-4-yl)-2,3-dihydro-1H-inden-1-yl)-4-(tert-butyl)benzamide, 1-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)-1H-pyrazole-4-carboxamide, 3-(tert-butyl)-N-(6-(6-(1-methyl-1H-pyrazol-4-yl)-7H-pyrrolo[2,3-d]pyrimidin-4-yl)-1,2,3,4-tetrahydronaphthalen-1-yl)pyrrolidine-1-carboxamide, 3-isopropoxy-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide, 3-(tert-butoxy)-N-(6-(6-(1-methyl-1H-pyrazol-4-yl)-7H-pyrrolo[2,3-d]pyrimidin-4-yl)-1,2,3,4-tetrahydronaphthalen-1-yl)azetidine-1-carboxamide, 1-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)-1H-pyrazole-4-carboxamide, 2-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)thiazole-5-carboxamide, 3-(tert-butyl)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)pyrrolidine-1-carboxamide, 3-isopropoxy-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide, and 3-(tert-butoxy)-N-(2-(6-(1-methyl-1H-pyrazol-4-yl)-7H-pyrrolo[2,3-d]pyrimidin-4-yl)-6,7,8,9-tetrahydro-5H-benzo[7]annulen-5-yl)azetidine-1-carboxamide, or a pharmaceutically acceptable salt thereof.

\* \* \* \* \*